US012752012B2

(12) United States Patent
Lei et al.

(10) Patent No.: US 12,752,012 B2
(45) Date of Patent: Oct. 6, 2026

(54) EGFR DEGRADERS AND ASSOCIATED METHODS OF USE

(71) Applicant: BeiGene Switzerland GmbH, Basel (CH)

(72) Inventors: Bailin Lei, Beijing (CN); Huaqing Liu, Beijing (CN); Songzhe Han, Beijing (CN); Zhiwei Wang, Beijing (CN)

(73) Assignee: BeOne Medicines I GmbH, Basel (CH)

(*) Notice: Subject to any disclaimer, the term of this patent is extended or adjusted under 35 U.S.C. 154(b) by 371 days.

(21) Appl. No.: 18/497,586

(22) Filed: Oct. 30, 2023

(65) Prior Publication Data

US 2024/0131167 A1 Apr. 25, 2024

Related U.S. Application Data

(63) Continuation of application No. PCT/CN2022/090342, filed on Apr. 29, 2022.

(51) Int. Cl.
*A61K 47/55* (2017.01)
*A61K 47/54* (2017.01)

(52) U.S. Cl.
CPC ............ *A61K 47/55* (2017.08); *A61K 47/545* (2017.08)

(58) Field of Classification Search
CPC ...................................................... A61K 47/55
See application file for complete search history.

(56) References Cited

U.S. PATENT DOCUMENTS

| | | | |
|---|---|---|---|
| 2013/0225527 | A1 | 8/2013 | Wang |
| 2014/0066406 | A1 | 3/2014 | Wang |
| 2016/0045607 | A1 | 2/2016 | Crew |
| 2017/0008904 | A1 | 1/2017 | Crew |
| 2018/0050021 | A1 | 2/2018 | Ciulli |
| 2018/0072711 | A1 | 3/2018 | Crew |
| 2019/0106417 | A1 | 4/2019 | Gray |

FOREIGN PATENT DOCUMENTS

| | | | |
|---|---|---|---|
| CN | 101374818 | A | 2/2009 |
| CN | 102105150 | A | 6/2011 |
| CN | 103153064 | A | 6/2013 |
| CN | 107257800 | A | 10/2017 |
| CN | 109422733 | A | 3/2019 |
| CN | 109912655 | A | 6/2019 |
| CN | 109928956 | A | 6/2019 |
| CN | 110357889 | A | 10/2019 |
| CN | 110684015 | A | 1/2020 |
| CN | 110753693 | A | 2/2020 |
| CN | 110818690 | A | 2/2020 |
| CN | 112079866 | A | 12/2020 |
| CN | 114286678 | A | 4/2022 |
| WO | 2002020740 | A2 | 3/2002 |
| WO | 2012051587 | A1 | 4/2012 |
| WO | 2014108452 | A1 | 7/2014 |
| WO | 2016105518 | A1 | 6/2016 |
| WO | 2016146985 | A1 | 9/2016 |
| WO | 2016149668 | A1 | 9/2016 |
| WO | 2016197032 | A1 | 12/2016 |
| WO | 2016197114 | A1 | 12/2016 |
| WO | 2017011590 | A1 | 1/2017 |
| WO | 2017030814 | A1 | 2/2017 |
| WO | 2017079267 | A1 | 5/2017 |
| WO | 2017182418 | A1 | 10/2017 |
| WO | 2017197036 | A1 | 11/2017 |
| WO | 2017197046 | A1 | 11/2017 |
| WO | 2017197051 | A1 | 11/2017 |
| WO | 2017197056 | A1 | 11/2017 |
| WO | 2017201449 | A1 | 11/2017 |
| WO | 2017204445 | A2 | 11/2017 |
| WO | 2018071606 | A1 | 4/2018 |
| WO | 2018119441 | A1 | 6/2018 |
| WO | 2019015655 | A1 | 1/2019 |
| WO | 2019040274 | A1 | 2/2019 |
| WO | 2019042444 | A1 | 3/2019 |
| WO | 2019060742 | A1 | 3/2019 |
| WO | 2019113071 | A1 | 6/2019 |
| WO | 2019114770 | A1 | 6/2019 |
| WO | 2019121562 | A1 | 6/2019 |
| WO | 2019133531 | A1 | 7/2019 |
| WO | 2019149922 | A1 | 8/2019 |
| WO | 2019183523 | A1 | 9/2019 |
| WO | 2019190259 | A1 | 10/2019 |
| WO | 2019196812 | A1 | 10/2019 |
| WO | 2020010210 | A1 | 1/2020 |
| WO | 2020051564 | A1 | 3/2020 |
| WO | 2020051572 | A1 | 3/2020 |
| WO | 2020113233 | A1 | 6/2020 |
| WO | 2020200291 | A1 | 10/2020 |
| WO | 2020216371 | A1 | 10/2020 |
| WO | 2020253862 | A1 | 12/2020 |

(Continued)

OTHER PUBLICATIONS

Ardley, H.C. et al., "E3 ubiquitin ligases," Essays Biochemistry, 41: 15-30, 2005.

Cermakova, K. et al., "Next-Generation Drugs and Probes for Chromatin Biology: From Targeted Protein Degradation to Phase Separation," Molecules, 23(1958):26 pages, 2018.

Chen, Y. et al., "The cullin 4A/B-DDB1-cereblon E3 ubiquitin ligase complex mediates the degradation of CLC-1 chloride channels," Scientific Reports, 5(10667):1-13, 2015.

Chu, T. T. et al., "Specific knockdown of endogenous tau protein by peptide-directed ubiquitin-proteasome degradation", Cell Chemical Biology, 23(4):453-461, 2016.

(Continued)

*Primary Examiner* — John S Kenyon

(74) *Attorney, Agent, or Firm* — Foley & Lardner LLP

(57) ABSTRACT

Provided herein are novel bifunctional compounds formed by conjugating EGFR inhibitor moieties with E3 ligase Ligand moieties, which function to recruit targeted proteins to E3 ubiquitin ligase for degradation. The disclosure also provides pharmaceutically acceptable compositions comprising compounds and methods for the treatment of EGFR mutant-related cancers.

26 Claims, No Drawings

(56) References Cited

FOREIGN PATENT DOCUMENTS

| | | | |
|---|---|---|---|
| WO | 2021011871 | A1 | 1/2021 |
| WO | 2021011913 | A1 | 1/2021 |
| WO | 2021023233 | A1 | 2/2021 |
| WO | 2021036922 | A1 | 3/2021 |
| WO | 2021057882 | A1 | 4/2021 |
| WO | 2021073498 | A1 | 4/2021 |
| WO | 2021123087 | A1 | 6/2021 |
| WO | 2021127190 | A1 | 6/2021 |
| WO | 2021127283 | A2 | 6/2021 |
| WO | 2021127561 | A1 | 6/2021 |
| WO | 2021133809 | A1 | 7/2021 |
| WO | 2021168074 | A1 | 8/2021 |
| WO | 2021173677 | A1 | 9/2021 |
| WO | 2021178920 | A1 | 9/2021 |
| WO | 2021208918 | A1 | 10/2021 |
| WO | 2021216440 | A1 | 10/2021 |
| WO | 2022012622 | A1 | 1/2022 |
| WO | 2022012623 | A1 | 1/2022 |
| WO | 2022063106 | A1 | 3/2022 |
| WO | 2022068849 | A1 | 4/2022 |
| WO | 2022171123 | A1 | 8/2022 |
| WO | 2022228556 | A1 | 11/2022 |

OTHER PUBLICATIONS

Chung Hyo Kang et al., "Induced protein degradation of anaplastic lymphoma kinase (ALK) by proteolysis targeting chimera (PROTAC)", Biochemical and Biophysical Research Communications, 505(2):542-547, 2018, Abstract.

Crews, Craig M. et al., "Inducing Protein Degradation as a Therapeutic Strategy," J. Med. Chem., 61(2):403-404, 2018.

Extended European Search Report dated Feb. 3, 2025 issued for European Pat. App. No. 22795025 (8 pages).

Grice, G. L. et al., "The Proteasome Distinguishes between Heterotypic and Homotypic Lysine-11-Linked Polyubiquitin Chains," Cell Rep., 12(4):545-553, 2015.

He, Kailun, et al., "Discovery and biological evaluation of proteolysis targeting chimeras (PROTACs) as an EGFR degraders based on osimertinib and lenalidomide", Bioorganic & Medicinal Chemistry Letters, 30(12):127167, 2020.

International Search Report and Written Opinion for PCT/CN2021/121563 mailed on Dec. 30, 2021 (11 pages).

International Search Report and Written Opinion for PCT/CN2022/075651 issued May 9, 2022 (14 pages).

International Search Report and Written Opinion for PCT/CN2022/090342 issued on Jul. 27, 2022 (18 pages).

Komander, D. et al., "The Ubiquitin Code," Annu. Rev. Biochem., 81:203-229, 2012.

Konduri et al., "EGFR fusions as novel therapeutic targets in lung cancer", Cancer Discovery, 6(6):601-611, 2016.

Lebraud, H. et al., "Protein degradation by in-cell self-assembly of proteolysis targeting chimeras," ACS Central Science, 2(12):927-934, 2016.

Lebraud, H. et al., "Protein degradation: a validated therapeutic strategy with exciting prospects," Essays Biochem., 61(5):517-527, 2017.

Lim, K. M. H. et al., "Dynamic Kinetic Resolution in Rhodium-Catalyzed Asymmetric Arylation of Phospholene Oxides", Journal of the American Chemical Society, 139(24):8122-8125, 2017.

Liu, S. et al., "Targeted selective degradation of Bruton's tyrosine kinase by PROTACs", Medicinal Chemistry Research, 29:802-808, 2020.

Lochmuller, C. H. et al., "Chromatographic Resolution of Enantiomers," Journal of Chromatography, 113:283-302, 1975.

Lu, J. et al., "Hijacking the E3 Ubiquitin ligase cereblon to efficiently target BRD4," Chemistry and Biology, 22(6):755-763, 2015.

Lu, X. et al., "Targeting EGFRL858R/T790M and EGFRL858R/T790M/C797S resistance mutations in NSCLC: Current developments in medicinal chemistry," Medicinal Research Reviews, 38(5):1550-1581, 2018.

Maemondo, M. et al., "Gefitinib or chemotherapy for non-small-cell lung cancer with mutated EGFR," New England Journal of Medicine, 362(25):2380-2388, 2010.

Matyskiela, M. E. et al., "SALL4 mediates teratogenicity as a thalidomide-dependent cereblon substrate," Nature Chemical Biology, 14(10):981-987, 2018.

Neklesa, T. K. et al., "Targeted protein degradation by PROTACs," Pharmacology & Therapeutics, 174:138-144, 2017.

Ottis, P. et al., "Assessing Different E3 Ligases for Small Molecule Induced Protein Ubiquitination and Degradation," ACS Chem. Biol., 12(10):2570-2578, 2017.

Ottis, P. et al., "Proteolysis-Targeting Chimeras: Induced Protein Degradation as a Therapeutic Strategy," ACS Chem. Biol., 12(4):892-898, 2017.

Pav, O. et al., "Novel phosphanucleoside analogs of dideoxynucleosides", Tetrahedron, 73: 5220-5228, 2017.

Qin, C. et al., "Discovery of QCA570 as an exceptionally potent and efficacious proteolysis targeting chimera (PROTAC) degrader of the bromodomain and extra-terminal (BET) proteins capable of inducing complete and durable tumor regression", Journal of Medicinal Chemistry, 61(15):6685-6704, 2018.

Qu, X. et al., "Effective degradation of EGFRL858R+T790M mutant proteins by CRBN-based PROTACs through both proteosome and autophagy/lysosome degradation systems," European Journal of Medicinal Chemistry, 218(113328):1-14, 2021.

Sainan, A. et al., "Small-molecule PROTACs: An emerging and promising approach for the development of targeted therapy drugs", EBioMedicine, 36:552-562, 2018.

Sakamoto, Kathleen M., "Chimeric molecules to target proteins for ubiquitination and degradation," Methods Enzymol., 399:833-847, 2005.

Sakamoto, Kathleen M., "Protacs: chimeric molecules that target proteins to the Skp1-Cullin-F box complex for ubiquitination and degradation," Proc Natl Acad Sci USA, 98(15):8554-8559, 2001.

Spradlin, J. N. et al., "Harnessing the anti-cancer natural product nimbolide for targeted protein degradation," Nat. Chem. Biol, 15(7):747-755, 2019.

Sun, N. et al., "Development of a Brigatinib degrader (SIAIS117) as a potential treatment for ALK positive cancer resistance", European Journal of Medicinal Chemistry, vol. 193, 7 pages, 2020.

Sun, Y. et al., "PROTAC-induced BTK degradation as a novel therapy for mutated Btk C481S induced ibrutinib-resistant B-cell malignancies", Cell Research, 28(7):779-781, 2018.

Sun, Y. et al., "Degradation of Bruton's tyrosine kinase mutants by PROTACs for potential treatment of ibrutinib-resistant non-Hodgkin lymphomas", Leukemia, 33:2105-2110, 2019.

Swatek, K. N. et al., "Ubiquitin modifications," Cell Research, 26(4):399-422, 2016.

Thress, K. S. et al., "Acquired EGFR C797S mutation mediates resistance to AZD9291 in non-small cell lung cancer harboring EGFR T790M," Nature Medicine, 21(6):560-562, 2015.

Tinworth, C. P. et al., "PROTAC-mediated degradation of Bruton's tyrosine kinase is inhibited by covalent binding", ACS Chemical Biology, 14(3):342-347, 2019.

Toure, M. et al., "Small-Molecule PROTACS: New Approaches to Protein Degradation," Angew. Chem. Int. Ed., 55(6):1966-1973, 2016.

Winter, G. E. et al., "Phthalimide conjugation as a strategy for in vivo target protein degradation," Science, 348(6241):1376-1381, 2015.

Xu, Y. et al., "Acquired resistance of lung adenocarcinoma to EGFR-tyrosine kinase inhibitors gefitinib and erlotinib," Cancer Biology & Therapy, 9(8):572-582, 2010.

Yarden, Y. et al., "Untangling the ErbB signalling network," Nature Reviews Molecular Cell Biology, 2(2):127-137, 2001.

Yewale, C. et al., "Epidermal growth factor receptor targeting in cancer: a review of trends and strategies", Biomaterials, 34(34):8690-8707, 2013.

Zhang, H. et al., "Design, synthesis and biological evaluation of novel EGFR PROTACs targeting Del19/T790M/C797S mutation," ACS Medicinal Chemistry Letters, 13:278-283, 2022.

(56) References Cited

OTHER PUBLICATIONS

Zhang, H. et al., "Discovery of potent epidermal growth factor receptor (EGFR) degraders by proteolysis targeting chimera (PROTAC)", European Journal of Medicinal Chemistry, 189, p. 112061, 2020.
Zhang, X. et al., "Design and synthesis of selective degraders of EGFRL858R/T790M mutant", European Journal of Medicinal Chemistry, 192, p. 112199, 2020.
Zhang, X. et al., "Electrophilic PROTACs that degrade nuclear proteins by engaging DCAF16", Nat. Chem. Biol., 15(7):737-746, 2019.
Foreign Search Report on European Patent Application No. 22795025.0, dated Feb. 3, 2025.

EGFR DEGRADERS AND ASSOCIATED METHODS OF USE

FIELD OF THE INVENTION

Provided herein are novel bifunctional compounds formed by conjugating EGFR inhibitor moieties with E3 ligase Ligand moieties, which function to recruit targeted proteins to E3 ubiquitin ligase for degradation. The disclosure also provides pharmaceutically acceptable compositions comprising compounds and methods for the treatment of EGFR mutant-related cancers.

BACKGROUND OF THE INVENTION

Proteolysis targeting chimera (PROTAC) consists of two covalently linked protein-binding molecules: one capable of engaging an E3 ubiquitin ligase, and another that binds to the protein of interest (POI) a target meant for degradation (Sakamoto K M et al., *Proc. Natl. Acad Sci.* 2001, 98: 8554-9; Sakamoto K. M. et al., *Methods Enzymol.* 2005, 399:833-847.). Rather than inhibiting the target protein's enzymatic activity, recruitment of the E3 ligase to the specific unwanted proteins results in ubiquitination and subsequent degradation of the target protein by the proteasome. The whole process of ubiquitination and proteasomal degradation is known as the ubiquitin-proteasome pathway (UPP) (Ardley H. et al., *Essays Biochem.* 2005, 41, 15-30; Komander D. et al., *Biochem.* 2012, 81, 203-229; Grice G. L. et al., *Cell Rep.* 2015, 12, 545-553; Swatek K. N. et al., *Cell Res.* 2016, 26, 399-422). Proteasomes are protein complexes which degrade unneeded, misfolded or abnormal proteins into small peptides to maintain health and productivity of the cells. Ubiquitin ligases, also called an E3 ubiquitin ligase, directly catalyze the transfer of ubiquitin from the E2 to the target protein for degradation. Although the human genome encodes over 600 putative E3 ligases, only a limited number of E3 ubiquitin ligases have been widely applied by small molecule PROTAC technology: cereblon (CRBN), Von Hippel-Lindau (VHL), mouse double minute 2 homologue (MDM2) and cellular inhibitor of apoptosis protein (cIAP) (Philipp O. et al., *Chem. Biol.* 2017, 12, 2570-2578), recombinant Human Ring Finger Protein 114 (RNF114) (Spradlin, J. N. et al. *Nat. Chem. Biol.* 2019, 15, 747-755) and DDB1 And CUL4 Associated Factor 16 (DCAF16) (Zhang, X. et al. *Nat. Chem. Biol.* 2019, 15, 737-746). For example, cereblon (CRBN) forms an E3 ubiquitin ligase complex with damaged DNA binding protein 1 (DDB1) and Cullin-4A (CUL4A) to ubiquitinate a number of other proteins followed by the degradation via proteasomes. (Yi-An Chen, et al., Scientific Reports 2015, 5, 1-13). Immunomodulatory drugs (IMiDs), including thalidomide, lenalidomide, and pomalidomide, function as monovalent promoters of PPIs by binding to the cereblon (CRBN) subunit of the $CRL4A^{CRBN}$ E3 ligase complex and recruiting neosubstrate proteins. (Matyskiela, M. E. et al., *Nat Chem Biol* 2018, 14, 981-987.) As a consequence, the ability of thalidomide, and its derivatives, to recruit CRBN has been widely applied in proteolysis-targeting chimeras (PROTACs) related studies (Christopher T. et al. *ACS Chem. Biol.* 2019, 14, 342-347; Honorine L. et al. *ACS Cent. Sci.* 2016, 2, 927-934). PROTACs have great potential to eliminate protein targets that are "undruggable" by traditional inhibitors or are non-enzymatic proteins. (Chu T T. et al., *Cell Chem Biol.* 2016; 23:453-461. Qin C. et al., *J Med Chem* 2018; 61: 6685-6704. Winter G E. et al., *Science* 2015; 348:1376-1381.) In the recent years, PROTACs as useful modulators promote the selective degradation of a wide range of target proteins have been reported in antitumor studies. (Lu J. et al., *Chem Biol.* 2015; 22(6):755-763; Ottis P. et al., *Chem Biol.* 2017: 12(4):892-898. Crews C. M. et al., *J Med Chem.* 2018; 61(2):403-404; Neklesa T. K. et al., *Pharmacol Ther.* 2017, 174:138-144. Cermakova K. et al., *Molecules,* 2018.23(8). An S. et al., *EBioMedicine,* 2018. Lebraud H. et al., *Essays Biochem.* 2017; 61(5): 517-527. Sun Y. H. et al., *Cell Res.* 2018; 28:779-81; Toure M. et al., *Angew Chem Int Ed Engl.* 2016:55(6):1966-1973; Yonghui Sun et al., *Leukemia*, volume 33, pages 2105-2110(2019); Shaodong Liu et al., *Medicinal Chemistry Research*, volume 29, pages 802-808(2020); and has been disclosed or discussed in patent publications, e.g., US20160045607, US20170008904, US20180050021, US20180072711, WO2002020740, WO2014108452, WO2016146985, WO2016149668, WO2016197032, WO2016197114, WO2017011590, WO2017030814, WO2017079267, WO2017182418, WO2017197036, WO2017197046, WO2017197051, WO2017197056, WO2017201449, and WO2018071606.

Epidermal growth factor receptor (EGFR) that belongs to the ErbB family is a transmembrane receptor tyrosine kinase (RTK), which plays a fundamentally key role in cell proliferation, differentiation, and motility (Y. Yarden, et al., *Nat. Rev. Mol. Cell Biol.* 2001; 2:127-137.). Homo- or heterodimerization of EGFR and other ErbB family members activates cytoplasmic tyrosine kinase domains to initiate intracellular signaling. Overexpression or activating mutations of EGFR are associated the development of many types of cancers, such as pancreatic cancer, breast cancer, glioblastoma multiforme, head and neck cancer, and non-small cell lung cancer (Yewale C., et al. *Biomaterials.* 2013, 34 (34): 8690-8707.). The activating mutations in the EGFR tyrosine kinase domain (L858R mutation and exon-19 deletion) have been identified as oncogenic drivers for NSCLC (Konduri, K., et al. *Cancer Discovery* 2016, 6 (6), 601-611.). The first-generation EGFR tyrosine kinase inhibitors (EGFR-TKIs) gefitinib and erlotinib have approved for NSCLC patients with EGFR activation mutations (M. Maemondo. *N. Engl. J. Med* 362 (2010) 2380-2388.). Although most patients with EGFR mutant NSCLC respond to these therapies, patients typically develop resistance after an average of one year on treatment. There are several mechanisms of acquired resistance to gefitinib and erlotinib, including a secondary threonine 790 to methionine 790 mutation (T790M), is also called "gatekeeper" T790M mutation (Xu Y., et al. *Cancer Biol Ther.* 2010, 9 (8): 572-582.). Therefore, the second-generation EGFR-TKIs afatinib and the third-generation EGFR-TKIs osimertinib (AZD9291) were developed as irreversible EGFR inhibitors that bind to Cys797 for the treatment of patients with T790M mutation. In particular, osimertinib that largely spares WvT EGFR has achieved greater clinical response rate in NSCLC patients with EGFR T790M. However, several recent studies have reported a tertiary Cys797 to Ser797 (C797S) point mutation with osimertinib clinical therapy (Thress K S. et al. *Nat. Med* 2015, 21 (6): 560-562.). There is a need for drugs which can overcome EGFR (C797S) resistance obstacle in non-small cell lung cancer (NSCLC). EGFR-Targeting PROTACs serve as a potential strategy to overcome drug resistance mediated by these mutants, which has been disclosed or discussed in patent publications, e.g. WO2018119441, WO2019149922, WO2019183523, WO2019121562, US20190106417 and WO202173498.

Although, a number of EGFR-targeting PROTACs which were designed to degrade EGFR mutant proteins have been published (Zhang X., et al. *Eur. J. Med Chem.* 2020, 192, 112199. Zhang H. et al. *Eur. J. Med Chem.* 2020, 189, 112061. Lu X, *Med Res. Rev.* 2018, 38(5):1550-1581. He K., et al. *Bioorg. Med Chem. Lett.* 2020, 15, 127167.). Most of the published molecules are based on first, second, and third generation of EGFR inhibitors. However, there were no data which showed those EGFR-Targeting PROTACs degrading all the main EGFR mutations, Such as Del19, L858R, Del19/T790M, L858R, T790M, Del19/T790M/C797S, L858R/T790M/C797S.

The present application provides novel bifunctional compounds and compositions for the treatment of serious diseases.

SUMMARY OF THE INVENTION

Aspect 1. A compound of Formula (X):

(X)

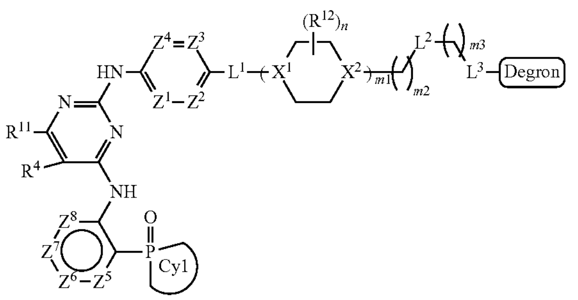

or an N-oxide thereof, or a pharmaceutically acceptable salt thereof, or a stereoisomer thereof, or a deuterated analog thereof, wherein:

Cyl is a 4- to 7-membered saturated or partially unsaturated ring including P═O shown in Formula (X), said ring comprising 0-3 additional heteroatoms independently selected from nitrogen, oxygen or sulfur in addition to P═O; said ring is optionally substituted with at least one substituent $R^{1c}$;

$R^{1c}$ is selected from hydrogen, halogen, —$C_{1-8}$alkyl, —$C_{2-8}$alkenyl, —$C_{2-8}$alkynyl, $C_3$-$C_8$cycloalkyl, 3- to 8-membered heterocyclyl, $C_6$-$C_{12}$aryl, 5- to 12-membered heteroaryl, —CN, —$OR^{1d}$, —$COR^{1d}$, —$CO_2R^{1d}$, —$CONR^{1d}R^{1e}$, —$NR^{1d}R^{1e}$, —$NR^{1d}COR^{1e}$ or —$NR^{1d}CO_2R^{1e}$, wherein each of —$C_{1-8}$alkyl, —$C_{2-8}$alkenyl, —$C_{2-8}$alkynyl, $C_3$-$C_8$cycloalkyl, 3- to 8-membered heterocyclyl, $C_6$-$C_{12}$aryl or 5- to 12-membered heteroaryl is optionally substituted with at least one substituent $R^{1f}$;

$R^{1d}$, $R^{1e}$ and $R^{1f}$ are each independently selected from hydrogen, hydroxy, —$C_{1-8}$alkyl, —$C_{2-8}$alkenyl, —$C_{2-8}$alkynyl, or $C_3$-$C_8$cycloalkyl;

$Z^5$ is selected from —$CR^2$, or N;

$Z^6$ is selected from —$CR^3$, or N;

$Z^7$ is selected from —$CR^9$, or N;

$Z^8$ is selected from —$CR^{10}$, or N;

$R^2$ and $R^3$ are each independently selected from hydrogen, halogen, —$C_{1-8}$alkyl, —$C_{2-8}$alkenyl, —$C_{2-8}$ alkynyl, $C_3$-$C_8$cycloalkyl, 3- to 8-membered heterocyclyl, $C_6$-$C_{12}$aryl, 5- to 12-membered heteroaryl, —CN, —$OR^{2a}$, —$SO_2R^{2a}$, —$SO_2NR^{2a}R^{2b}$, —$COR^{2a}$, —$CO_2R^{2a}$, —$CONR^{2a}R^{2b}$, —$NR^{2a}R^{2b}$, —$NR^{2a}COR^{2b}$, —$NR^{2a}CO_2R^{2b}$, or —$NR^{2a}SO_2R^{2b}$, wherein each of —$C_{1-8}$alkyl, —$C_{2-8}$alkenyl, —$C_{2-8}$alkynyl, $C_3$-$C_8$cycloalkyl, 3- to 8-membered heterocyclyl, $C_6$-$C_{12}$aryl or 5- to 12-membered heteroaryl is optionally substituted with at least one substituent $R^{2d}$; or $R^2$ and $R^3$ together with the carbon atoms to which they are attached, form a 5-6 membered saturated or partially or completely unsaturated (preferably completely unsaturated, i.e., aromatic) ring, said ring comprising 0-3 heteroatoms independently selected from nitrogen, oxygen or sulfur; said ring is optionally substituted with at least one substituent $R^{2e}$;

$R^{2e}$, at each of its occurrences, is independently hydrogen, halogen, —$C_{1-8}$alkyl, —$C_{2-8}$alkenyl, —$C_{2-8}$ alkynyl, —$C_{1-8}$alkoxy, —$C_3$-$C_8$cycloalkyl, oxo, 3- to 8-membered heterocyclyl, $C_6$-$C_{12}$aryl, 5- to 12-membered heteroaryl, —CN, —$SO_2R^{2a}$, —$SO_2NR^{2a}R^{2b}$, —$COR^{2a}$, —$CO_2R^{2a}$, —$CONR^{2a}R^{2b}$, —$NR^{2a}R^{2b}$, —$NR^{2a}COR^{2b}$, —$NR^{2a}CO_2R^{2b}$ or —$NR^{2a}SO_2R^{2b}$, wherein each of —$C_{1-8}$alkyl, —$C_{2-8}$alkenyl, —$C_{2-8}$alkynyl, —$C_{1-8}$ alkoxy, $C_3$-$C_8$cycloalkyl, 3- to 8-membered heterocyclyl, $C_6$-$C_{12}$aryl or 5- to 12-membered heteroaryl is optionally substituted with at least one substituent $R^{2d}$;

$R^{2a}$ and $R^{2b}$ are each independently selected from hydrogen, —$C_{1-8}$alkyl, —$C_{2-8}$alkenyl, —$C_{2-8}$alkynyl, $C_{1-8}$alkoxy-$C_{1-8}$alkyl-, $C_3$-$C_8$cycloalkyl, 3- to 8-membered heterocyclyl, $C_6$-$C_{12}$aryl or 5- to 12-membered heteroaryl; or $R^{2a}$ and $R^{2b}$ together with the carbon atoms to which they are attached, form a 5-6 membered saturated or partially or completely unsaturated (preferably completely unsaturated, i.e., aromatic) ring, said ring comprising 0-3 heteroatoms independently selected from nitrogen, oxygen or sulfur; said ring is optionally substituted with at least one substituent $R^{2d}$;

$R^{2d}$, at each of its occurrences, is independently halogen, —OH, —$C_{1-8}$alkyl, —$C_{1-8}$alkoxy, $C_{1-8}$alkoxy-$C_{1-8}$alkyl-, oxo, —$C_{2-8}$alkenyl, —$C_{2-8}$alkynyl, —$C_3$-$C_8$cycloalkyl, 3- to 8-membered heterocyclyl, —$C_6$-$C_{12}$aryl, or 5- to 12-membered heteroaryl;

$R^4$ is selected from hydrogen, halogen, —$C_{1-8}$alkyl, —$C_{2-8}$alkenyl, —$C_{2-8}$alkynyl, —$C_{1-8}$alkoxy, —$C_3$-$C_8$cycloalkyl, 3- to 8-membered heterocyclyl, —$C_6$-$C_{12}$aryl, 5- to 12-membered heteroaryl, —CN, —$SO_2R^{4a}$, —$SO_2NR^{4a}R^{4b}$, —$COR^{4a}$, —$CO_2R^{4a}$, —$CONR^{4a}R^{4b}$, —$NR^{4a}R^{4b}$, —$NR^{4a}COR^{4b}$, —$NR^{4a}CO_2R^{4b}$, or —$NR^{4a}SO_2R^{4b}$, wherein each of —$C_{1-8}$alkyl, —$C_{2-8}$alkenyl, —$C_{2-8}$alkynyl, —$C_{1-8}$ alkoxy, —$C_3$-$C_8$cycloalkyl, 3- to 8-membered heterocyclyl, —$C_6$-$C_{12}$aryl or 5- to 12-membered heteroaryl is optionally substituted with halogen, —$C_{1-8}$ alkoxy, —$C_{1-8}$alkyl, —$C_{2-8}$alkenyl, —$C_{2-8}$alkynyl, —$C_3$-$C_8$cycloalkyl, 3- to 8-membered heterocyclyl, $C_6$-$C_{12}$aryl, 5- to 12-membered heteroaryl, oxo, —CN, —$OR^{4c}$, —$SO_2R^{4c}$, —$SO_2NR^{4c}R^{4d}$, —$COR^{4c}$, —$CO_2R^{4c}$, —$CONR^{4c}R^{4d}$, —$NR^{4c}R^{4d}$, —$NR^{4c}COR^{4d}$, —$NR^{4c}CO_2R^{4d}$, or —$NR^{4c}SO_2R^{4d}$;

$R^{4a}$, $R^{4b}$, $R^{4c}$ and $R^{4d}$ are each independently hydrogen, —$C_{1-8}$alkyl, —$C_{2-8}$alkenyl, —$C_{2-8}$alkynyl, $C_3$-$C_8$cycloalkyl, 3- to 8-membered heterocyclyl, —$C_6$-$C_{12}$aryl, or 5- to 12-membered heteroaryl; or $R^4$ and $R^{11}$ together with the carbon atoms to which they are attached, form a 5-6 membered saturated or partially or completely unsaturated (preferably completely unsaturated, i.e., aromatic) ring, said ring comprising 0-3 heteroatoms independently selected from nitrogen, oxygen or sulfur; said ring is optionally substituted with at least one substituent $R^{4e}$;

$R^{4e}$, at each of its occurrences, is independently hydrogen, halogen, —$C_{1-8}$alkyl, —$C_{2-8}$alkenyl, —$C_{2-8}$ alkynyl, —$C_{1-8}$alkoxy, —$C_3$-$C_8$cycloalkyl, oxo, 3- to 8-membered heterocyclyl, $C_6$-$C_{12}$aryl, 5- to 12-membered heteroaryl, —CN, —$SO_2R^{4f}$, —$SO_2NR^{4f}R^{4g}$, —$COR^{4f}$, —$CO_2R^{4f}$, —$CONR^{4f}R^{4g}$, —$NR^{4f}R^{4g}$, —$NR^{4f}COR^{4g}$, —$NR^{4f}CO_2R^{4g}$ or —$NR^{4f}SO_2R^{4g}$, wherein each of —$C_{1-8}$alkyl, —$C_{2-8}$alkenyl, —$C_{2-8}$alkynyl, —$C_{1-8}$ alkoxy, $C_3$-$C_8$cycloalkyl, 3- to 8-membered heterocyclyl, $C_6$-$C_{12}$aryl or 5- to 12-membered heteroaryl is optionally substituted with at least one substituent $R^{4h}$;

$R^{4f}$ and $R^{4g}$ are each independently selected from hydrogen, —$C_{1-8}$alkyl, —$C_{2-8}$alkenyl, —$C_{2-8}$alkynyl, $C_{1-8}$alkoxy-$C_{1-8}$alkyl-, $C_3$-$C_8$cycloalkyl, 3- to 8-membered heterocyclyl, $C_6$-$C_{12}$aryl or 5- to 12-membered heteroaryl;

$R^{4h}$, at each of its occurrences, is independently halogen, —OH, —$C_{1-8}$alkyl, —$C_{1-8}$alkoxy, $C_{1-8}$alkoxy-$C_{1-8}$alkyl-, —$C_{2-8}$alkenyl, —$C_{2-8}$alkynyl, —$C_3$-$C_8$cycloalkyl, 3- to 8-membered heterocyclyl, —$C_6$-$C_{12}$aryl, or 5- to 12-membered heteroaryl;

$R^9$, $R^{10}$, $R^{11}$ and $R^{12}$ are each independently selected from hydrogen, halogen, —$C_{1-8}$alkyl, —$C_{2-8}$alkenyl, —$C_{2-8}$alkynyl, —$NR^{9a}R^{9b}$, —$OR^{9a}$, oxo, —$C_3$-$C_8$cycloalkyl, 3- to 8-membered heterocyclyl, —$C_6$-$C_{12}$aryl, 5- to 12-membered heteroaryl, or —CN, wherein each of —$C_{1-8}$alkyl, —$C_{2-8}$alkenyl, —$C_{2-8}$alkynyl, —$C_3$-$C_8$cycloalkyl, 3- to 8-membered heterocyclyl, —$C_6$-$C_{12}$aryl, or 5- to 12-membered heteroaryl is optionally substituted with at least one substituent $R^{9c}$; or two $R^{12}$ together with the carbon atoms to which they are attached, form a 3- to 12-membered ring, said ring comprising 0-3 heteroatoms independently selected from nitrogen, oxygen or sulfur, said ring is optionally substituted with at least one substituent $R^{9c}$;

$R^{9a}$ and $R^{9b}$ are each independently selected from hydrogen, —$C_{1-8}$alkyl, —$C_{2-8}$alkenyl, —$C_{2-8}$alkynyl, —$C_3$-$C_8$cycloalkyl, 3- to 8-membered heterocyclyl, —$C_6$-$C_{12}$aryl or 5- to 12-membered heteroaryl, wherein each of said —$C_{1-8}$alkyl, —$C_{2-8}$ alkenyl, —$C_{2-8}$alkynyl, $C_3$-$C_8$cycloalkyl, 3- to 8-membered heterocyclyl, $C_6$-$C_{12}$aryl or 5- to 12-membered heteroaryl is optionally substituted with at least one substituent $R^{9d}$; or $R^{9c}$ and $R^{9d}$ are each independently halogen, hydroxy, —$C_{1-8}$alkyl, —$C_{1-8}$alkoxy, —$C_{2-8}$alkenyl, —$C_{2-8}$ alkynyl, —$C_3$-$C_8$cycloalkyl, 3- to 8-membered heterocyclyl, —$C_6$-$C_{12}$aryl, 5- to 12-membered heteroaryl, —CN or $NR^{9aa}R^{9bb}$, wherein each of said —$C_{1-8}$alkyl, —$C_{1-8}$alkoxy, —$C_{2-8}$alkenyl, —$C_{2-8}$ alkynyl, —$C_3$-$C_8$cycloalkyl, 3- to 8-membered heterocyclyl, —$C_6$-$C_{12}$aryl, 5- to 12-membered heteroaryl is optionally substituted with at least one hydrogen, halogen, hydroxy, —$C_{1-8}$alkyl, —$C_{1-8}$ alkoxy, —CN, —$NH_2$ or oxo, and $R^{9aa}$ and $R^{9bb}$ are each independently hydrogen or $C_{1-8}$alkyl;

$Z^1$, $Z^2$, $Z^3$ and $Z^4$ are each independently selected from —$CR^z$, or N;

$R^Z$, at each of its occurrences, is independently selected from hydrogen, halogen, —$C_{1-8}$alkyl, —$C_{2-8}$alkenyl, —$C_{2-8}$alkynyl, —$NR^{Za}R^{Zb}$, —$OR^{Za}$, —$SR^{Za}$, $C_3$-$C_8$cycloalkyl, 3- to 8-membered heterocyclyl, $C_6$-$C_{12}$aryl, 5- to 12-membered heteroaryl, or CN, wherein each of —$C_{1-8}$alkyl, —$C_{2-8}$alkenyl, —$C_{2-8}$ alkynyl, $C_3$-$C_8$cycloalkyl, 3- to 8-membered heterocyclyl, $C_6$-$C_{12}$aryl, or 5- to 12-membered heteroaryl is optionally substituted with at least one $R^{Zc}$; or when adjacent two $R^z$ together with the carbon atoms to which they are attached, form a 5-6 membered saturated or partially or completely unsaturated (preferably completely unsaturated, i.e., aromatic) ring, said ring comprising 0-3 heteroatoms independently selected from nitrogen, oxygen or sulfur; said ring is optionally substituted with at least one substituent $R^{Zc}$;

$R^{Za}$ and $R^{Zb}$ are each independently selected from hydrogen, —$C_{1-8}$alkyl, —$C_{2-8}$alkenyl, —$C_{2-8}$alkynyl, $C_3$-$C_8$cycloalkyl, 3- to 8-membered heterocyclyl, $C_6$-$C_{12}$aryl, or 5- to 12-membered heteroaryl, wherein each of said —$C_{1-8}$alkyl, —$C_{2-8}$alkenyl, —$C_{2-8}$alkynyl, $C_3$-$C_8$cycloalkyl, 3- to 8-membered heterocyclyl, $C_6$-$C_{12}$aryl, or 5- to 12-membered heteroaryl is optionally substituted with at least one substituent $R^{Zd}$;

$R^{Zc}$ and $R^{Zd}$ are each independently halogen, hydroxy, —$C_{1-8}$alkyl, —$C_{2-8}$alkenyl, —$C_{2-8}$alkynyl, —$C_{1-8}$ alkoxy, $C_{1-8}$alkoxy-$C_{1-8}$alkyl-, —$C_{2-8}$alkenyl, —$C_{2-8}$ alkynyl, $C_3$-$C_8$cycloalkyl, 3- to 8-membered heterocyclyl, $C_6$-$C_{12}$aryl, or 5- to 12-membered heteroaryl;

$L^1$ is selected from a single bond, —O—, —$SO_2$—, —C(O)—, —$NR^{L1a}$—, —$C_3$-$C_8$cycloalkylene-, $*^{L1}$—O—$C_{1-8}$ alkylene-$^{L1}$, $^{L1}C_{1-8}$alkylene-O—$^{L1}$, $*^{L1}$—$SO_2$—$C_{1-8}$alkylene-$**^{L1}$, $*^{L1}$—$C_{1-8}$alkylene-$SO_2$—$**^{L1}$, $*^{L1}$—CO—$C_{1-8}$alkylene-$**^{L1}$, $*^{L1}$—$C_{1-8}$ alklylene-CO—$**^{L1}$, $*^{L1}$—$NR^{L1a}$—$C_{1-8}$ alkylene-$**^{L1}$, $*^{L1}$—$C_{1-8}$alkylene-$NR^{L1a}$—$**^{L1}$, $*^{L1}$—$NR^{L1a}C(O)$—$**^{L1}$, $*^{L1}$—C(O)$NR^{L1a}$—$**^{L1}$, —$C_{1-8}$alkylene-, —$C_{2-8}$alkenylene-, —$C_{2-8}$alkynylene-, —$[O(CR^{L1a}R^{L1b})_{m4}]_{m5}$—,

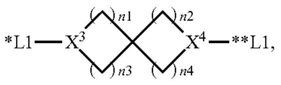

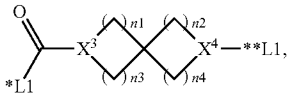

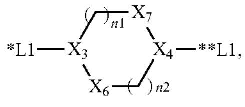

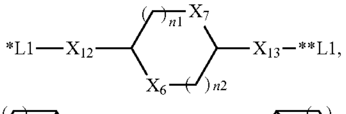

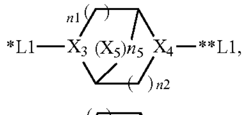

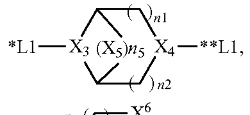

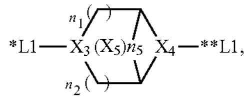

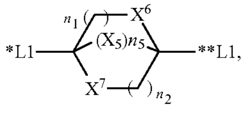

-continued

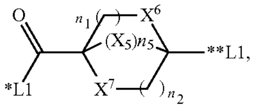, 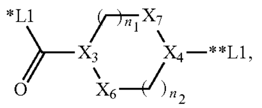

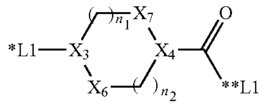 or

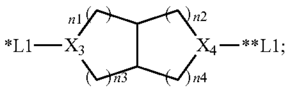

wherein each of said —$C_{1-8}$alkylene, —$C_3$-$C_8$cycloalkylene-, *$^{L1}$—O—$C_{1-8}$ alkylene-**$^{L1}$, *$^{L1}$—$C_{1-8}$alkylene-O—**$^{L1}$, *$^{L1}$—$SO_2$—$C_{1-8}$alkylene-**$^{L1}$, *$^{L1}$—$C_{1-8}$alkylene-$SO_2$—**$^{L1}$, *$^{L1}$—CO—$C_{1-8}$alkylene-**$^{L1}$, *$^{L1}$—$C_{1-8}$ alkylene-CO—**$^{L1}$, *$^{L1}$—$NR^{L1a}$—$C_{1-8}$ alkylene-**$^{L1}$, *$^{L1}$—$C_{1-8}$alkylene-$NR^{L1a}$—**$^{L1}$, —$C_{1-8}$alkylene-, —$C_{2-8}$alkenylene-, —$C_{2-8}$alkynylene-,

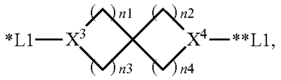

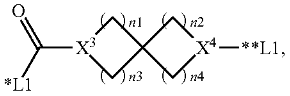 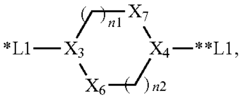

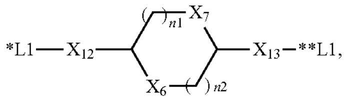

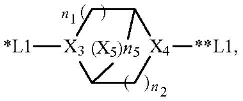 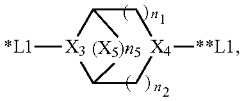

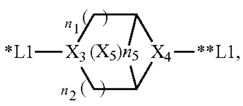 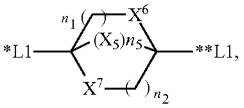

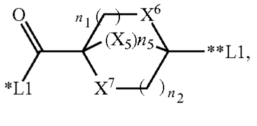 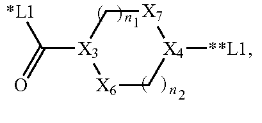

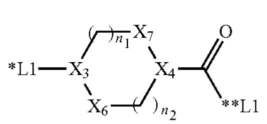 or

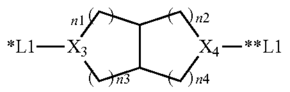

is optionally substituted with at least one $R^{L1c}$;

wherein *$^{L1}$ refers to the position attached to

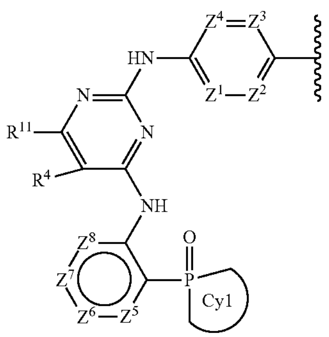

moiety, and **$^{L1}$ refers to the position attached to the

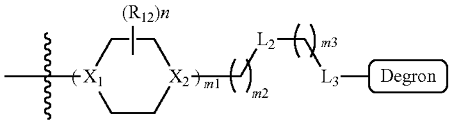

moiety;

$R^{L1a}$ and $R^{L1b}$ are each independently selected from hydrogen, —$C_{1-8}$alkyl, —$C_{2-8}$alkenyl, —$C_{2-8}$alkynyl, $C_3$-$C_8$cycloalkyl, 3- to 8-membered heterocyclyl, $C_6$-$C_{12}$aryl or 5- to 12-membered heteroaryl, wherein each of said —$C_{1-8}$alkyl, —$C_{2-8}$alkenyl, —$C_{2-8}$alkynyl, $C_3$-$C_8$cycloalkyl, 3- to 8-membered heterocyclyl, $C_6$-$C_{12}$aryl or 5- to 12-membered heteroaryl is optionally substituted with at least one substituent $R^{L1d}$;

each of said $R^{L1c}$ and $R^{L1d}$ are independently halogen, hydroxy, —$C_{1-8}$alkyl, —$C_{1-8}$alkoxy, $C_{1-8}$alkoxy-$C_{1-8}$ alkyl-, —$C_{2-8}$alkenyl, —$C_{2-8}$alkynyl, $C_3$-$C_8$cycloalkyl, 3- to 8-membered heterocyclyl, $C_6$-$C_{12}$aryl, 5- to 12-membered heteroaryl or oxo;

$L^2$ is selected from a single bond, —O—, —$SO_2$—, —CO—, —$NR^{L2a}$—, —$C_{1-8}$alkylene, —$C_3$-$C_8$cycloalkylene-, *$^{L2}$—O—$C_{1-8}$ alkylene-$^{L2}$, $^{L2}C_{1-8}$alkylene-O—$^{L2}$, *$^{L2}$—$SO_2$—$C_{1-8}$alkylene-**$^{L2}$, *$^{L2}$—$C_{1-8}$alkylene-$SO_2$—**$^{L2}$, *$^{L2}$—CO—$C_{1-8}$alkylene-**$^{L2}$, *$^{L2}$—$C_{1-8}$alklylene-CO—**$^{L2}$, *$^{L2}$—$NR^{L2a}$—$C_{1-8}$alkylene-**$^{L2}$, *$^{L2}$—$C_{1-8}$alkylene-$NR^{L2a}$—**$^{L2}$, *$^{L2}$—$NR^{L2a}$C(O)—**$^{L2}$, *$^{L2}$—C(O)$NR^{L2a}$—**$^{L2}$, —$C_{1-8}$alkylene-, —$C_{2-8}$alkenylene-, —$C_{2-8}$alkynylene-, —$[O(CR^{L2a}R^{L2b})_{m4}]_{m5}$—,

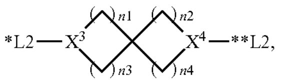

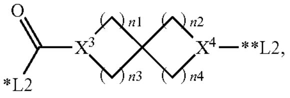 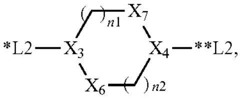

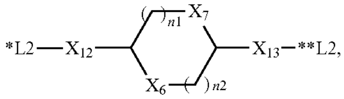

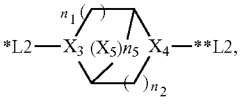 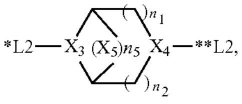

-continued

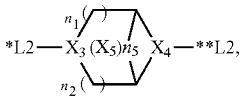

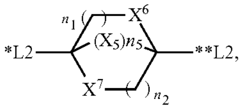

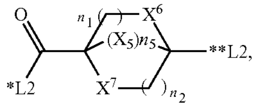

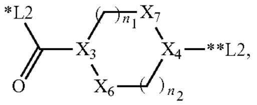

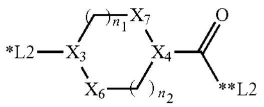

or

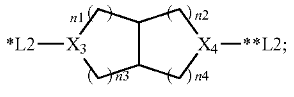

wherein each of said —$C_{1-8}$alkylene, —$C_3$-$C_8$cycloalkylene-, $*^{L2}$—O—$C_{1-8}$ alkylene-$**^{L2}$, $*^{L2}$—$C_{1-8}$alkylene-O—$**^{L2}$, $*^{L2}$—$SO_2$—$C_{1-8}$alkylene-$**^{L2}$, $*^{L2}$—$C_{1-8}$alkylene-$SO_2$—$**^{L2}$, $*^{L2}$—CO—$C_{1-8}$alkylene-$**^{L2}$, $*^{L2}$—$C_{1-8}$ alkylene-CO—$**^{L2}$, $*^{L2}$—$NR^{L2a}$—$C_{1-8}$alkylene-$**^{L2}$, $*^{L2}$—$C_{1-8}$alkylene-$NR^{L2a}$—$**^{L2}$, —$C_{1-8}$alkylene-, —$C_{2-8}$alkenylene-, —$C_{2-8}$alkynylene-,

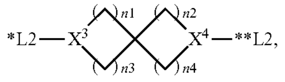

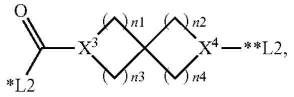

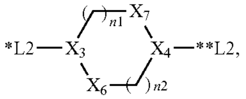

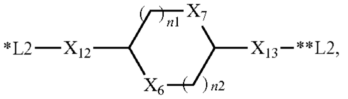

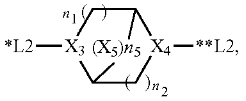

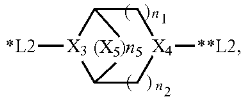

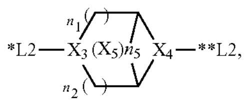

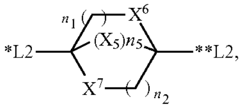

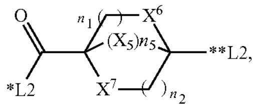

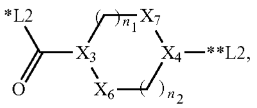

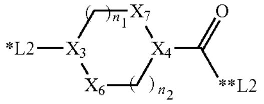

or

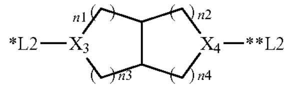

is optionally substituted with at least one substituent $R^{L2c}$;

wherein $*^{L2}$ refers to the position attached to

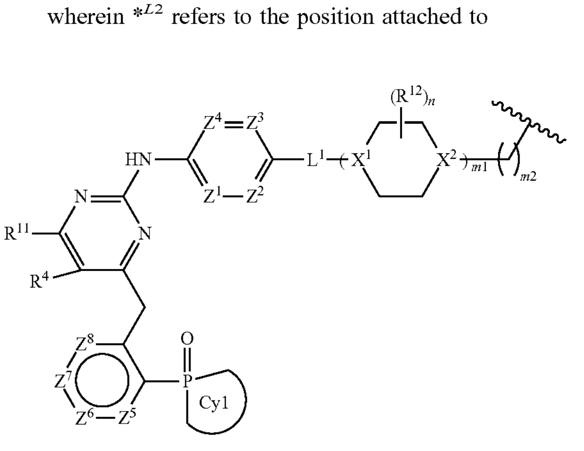

moiety, and $**^{L2}$ refers to the position attached to the

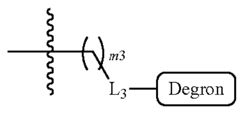

moiety;

$R^{L2a}$ and $R^{L2b}$ are each independently selected from hydrogen, —$C_{1-8}$alkyl, —$C_{2-8}$alkenyl, —$C_{2-8}$alkynyl, $C_3$-$C_8$cycloalkyl, 3- to 8-membered heterocyclyl, $C_6$-$C_{12}$aryl or 5- to 12-membered heteroaryl, wherein each of said —$C_{1-8}$alkyl, —$C_{2-8}$alkenyl, —$C_{2-8}$alkynyl, $C_3$-$C_8$cycloalkyl, 3- to 8-membered heterocyclyl, $C_6$-$C_{12}$aryl or 5- to 12-membered heteroaryl is optionally substituted with at least one substituent $R^{L2d}$;

each of said $R^{L2c}$ and $R^{L2d}$ are independently halogen, hydroxy, —$C_{1-8}$alkyl, —$C_{1-8}$alkoxy, $C_{1-8}$alkoxy-$C_{1-8}$ alkyl-, —$C_{2-8}$alkenyl, —$C_{2-8}$alkynyl, $C_3$-$C_8$cycloalkyl, 3- to 8-membered heterocyclyl, $C_6$-$C_{12}$aryl, 5- to 12-membered heteroaryl or oxo;

$L^3$ is selected from a single bond, —O—, —$SO_2$—, —CO—, —$NR^{L3a}$—, —$C_{1-8}$alkylene, —$C_3$-$C_8$cycloalkylene-, $*^{L3}$—O—$C_{1-8}$ alkylene-$^{L3}$, $^{L3}C_{1-8}$alkylene-O—$^{L3}$, $*^{L3}$—$SO_2$—$C_{1-8}$alkylene-$**^{L3}$, $*^{L3}$—$C_{1-8}$alkylene-$SO_2$—$**^{L3}$, $*^{L3}$—CO—$C_{1-8}$alkylene-$**^{L3}$, $*^{L3}$—$C_{1-8}$alklylene-CO—$**^{L3}$, $*^{L3}$—$NR^{L3a}$—$C_{1-8}$alkylene-$**^{L3}$, $*^{L3}$—$C_{1-8}$alkylene-$NR^{L3a}$—$**^{L3}$, $*^{L3}$—$NR^{L3a}$C(O)—$**^{L3}$, $*^{L3}$—C(O)$NR^{L3a}$—$**^{L3}$, —$C_{1-8}$alkylene-, —$C_{2-8}$alkenylene-, —$C_{2-8}$alkynylene-, —$[O(CR^{L3a}R^{L3b})_{m4}]_{m5}$—,

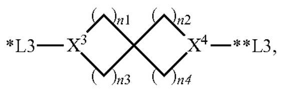

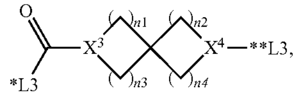

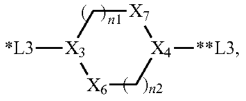

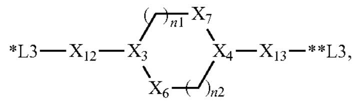

-continued

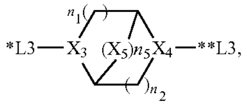
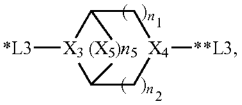
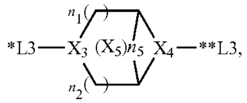
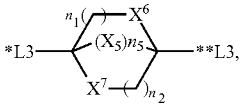
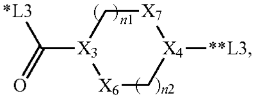
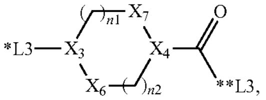
or
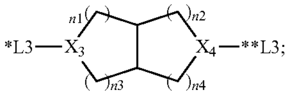

wherein each of said $-C_{1-8}$alkylene, $-C_3$-$C_8$cycloalkylene-, $*^{L3}-O-C_{1-8}$ alkylene-$**^{L3}$, $*^{L3}-C_{1-8}$alkylene-O$-**^{L3}$, $*^{L3}-SO_2-C_{1-8}$alkylene-$**^{L3}$, $*^{L3}-C_{1-8}$alkylene-$SO_2-**^{L3}$, $*^{L3}-CO-C_{1-8}$alkylene-$**^{L3}$, $*^{L3}-C_{1-8}$ alkylene-CO$-**^{L3}$, $*^{L3}-NR^{L3a}-C_{1-8}$alkylene-$**^{L3}$, $*^{L3}-C_{1-8}$alkylene-$NR^{L3a}-**^{L3}$, $-C_{1-8}$alkylene-, $-C_{2-8}$alkenylene-, $-C_{2-8}$alkynylene-,

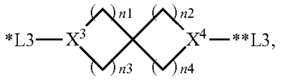
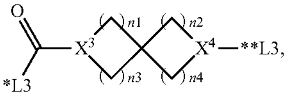
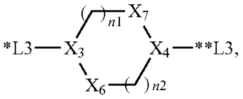
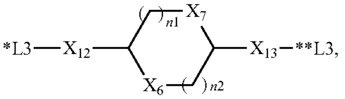
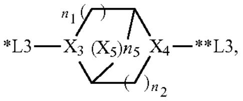
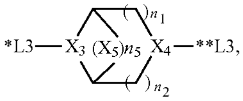
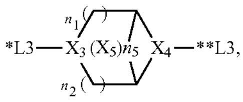
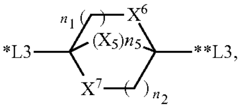
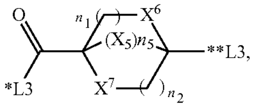
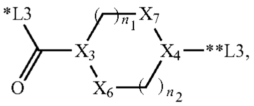
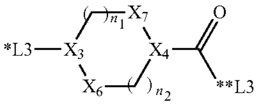
or
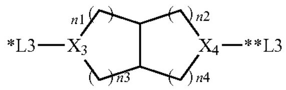

is optionally substituted with at least one substituent $R^{L3c}$;

wherein $*^{L3}$ refers to the position attached to the

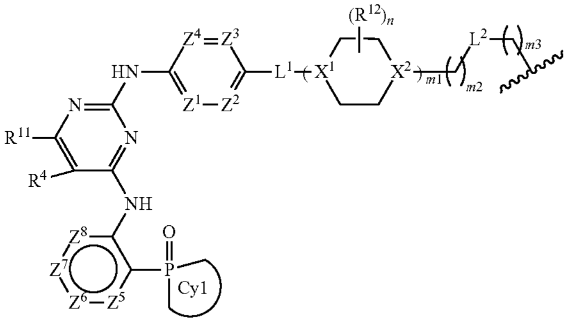

moiety, and $**^{L3}$ refers to the position attached to the

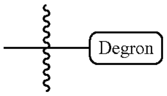

moiety.

$R^{L3a}$ and $R^{L3b}$ are each independently selected from hydrogen, $-C_{1-8}$alkyl, $-C_{2-8}$alkenyl, $-C_{2-8}$alkynyl, $C_3$-$C_8$cycloalkyl, 3- to 8-membered heterocyclyl, $C_6$-$C_{12}$aryl or 5- to 12-membered heteroaryl, wherein each of said $-C_{1-8}$alkyl, $-C_{2-8}$alkenyl, $-C_{2-8}$alkynyl, $C_3$-$C_8$cycloalkyl, 3- to 8-membered heterocyclyl, $C_6$-$C_{12}$aryl or 5- to 12-membered heteroaryl is optionally substituted with at least one substituent $R^{L3d}$;

each of said $R^{L3c}$ and $R^{L3d}$ are independently halogen, hydroxy, $-C_{1-8}$alkyl, $-C_{1-8}$alkoxy, $C_{1-8}$alkoxy-$C_{1-8}$ alkyl-, $-C_{2-8}$alkenyl, $-C_{2-8}$alkynyl, $C_3$-$C_8$cycloalkyl, 3- to 8-membered heterocyclyl, $C_6$-$C_{12}$aryl, 5- to 12-membered heteroaryl or oxo;

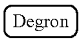

is selected from

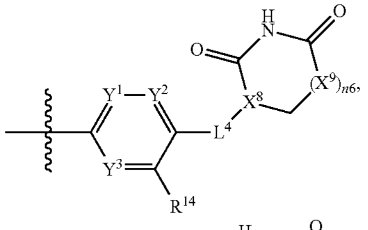
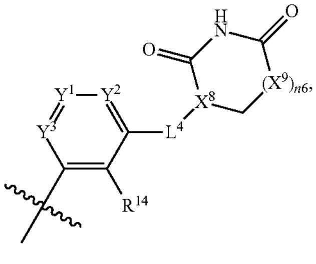

-continued
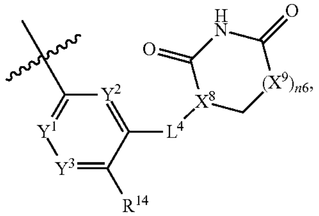
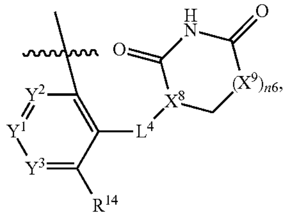
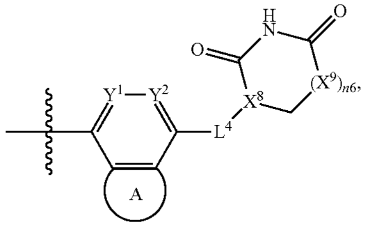
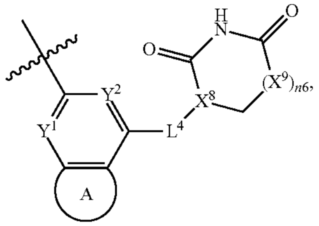
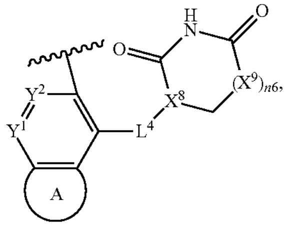
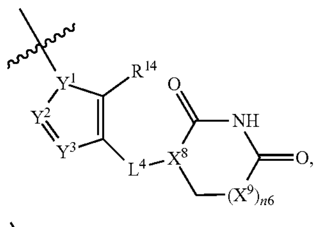
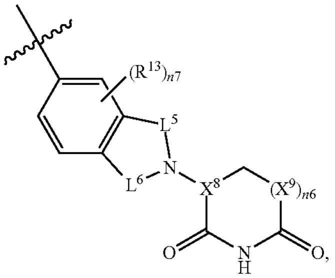
-continued
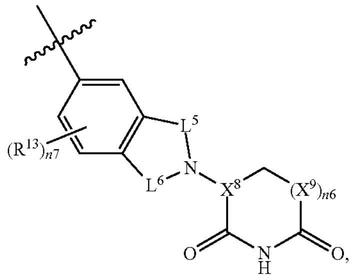
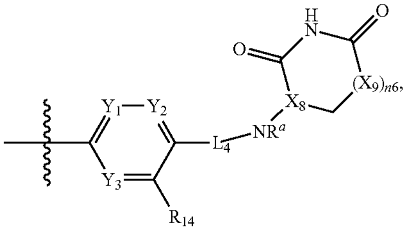
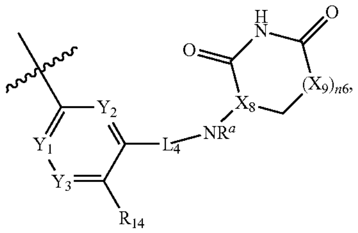
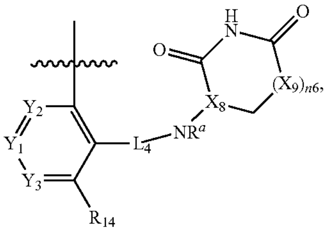
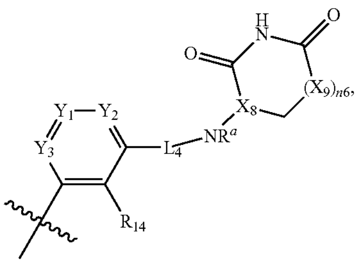
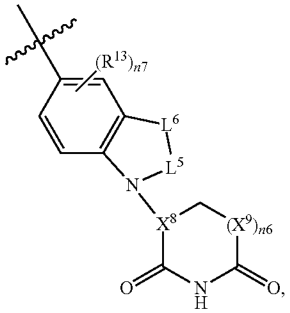

-continued

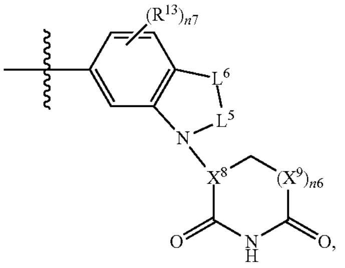

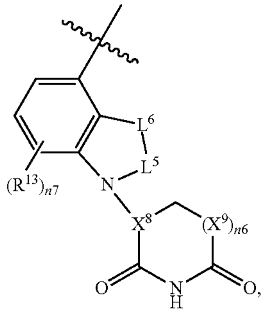

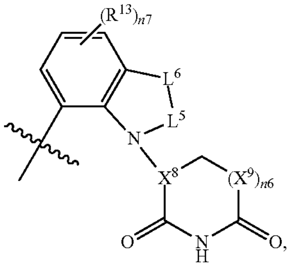

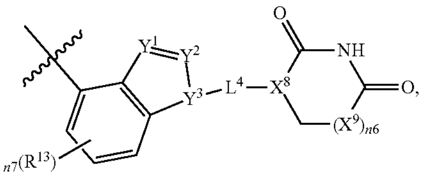

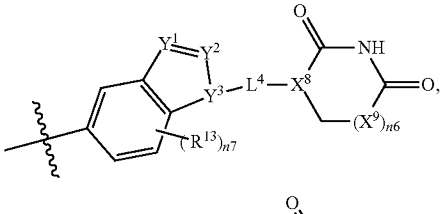

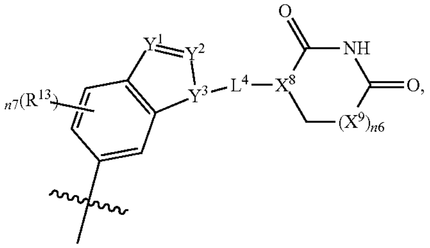

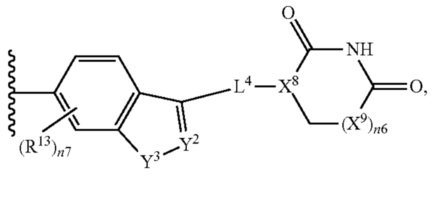

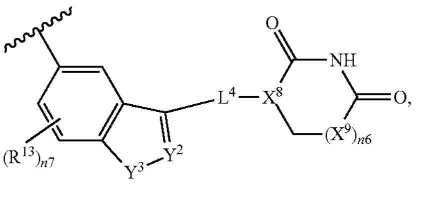

or

-continued

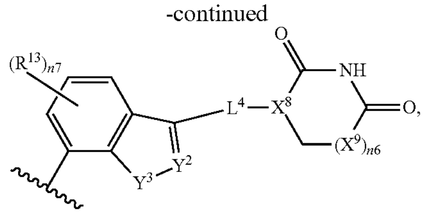

Ring A is selected from 3-12 membered cycloalkyl, 3-12 membered heterocyclyl, aryl, or heteroaryl;

said Ring A is optionally substituted with at least one halogen, oxo, —$C_{1-8}$alkyl, $C_{1-8}$alkoxy-$C_{1-8}$alkyl-, —$C_{2-8}$alkenyl, —$C_{3-8}$alkynyl, $C_3$-$C_8$cycloalkyl, 3- to 8-membered heterocyclyl, $C_6$-$C_{12}$aryl or 5- to 12-membered heteroaryl;

$R^{13}$ and $R^{14}$ are independently selected from hydrogen, halogen, CN, —$C_{1-8}$alkyl, —$C_{2-8}$alkenyl, —$C_{2-8}$alkynyl, —$C_{1-8}$alkoxy, $C_3$-$C_8$cycloalkyl, 3- to 8-membered heterocyclyl, $C_6$-$C_{12}$aryl or 5- to 12-membered heteroaryl; said each —$C_{1-8}$alkyl, —$C_{2-8}$alkenyl, —$C_{2-8}$alkynyl, —$C_{1-8}$alkoxy, $C_3$-$C_8$cycloalkyl, 3- to 8-membered heterocyclyl, $C_6$-$C_{12}$aryl or 5- to 12-membered heteroaryl is optionally substituted with at least one substituent halogen, —$C_{1-8}$alkyl, $C_{1-8}$alkoxy-$C_{1-8}$alkyl-, —$C_{2-8}$ alkenyl, —$C_{2-8}$alkynyl, $C_3$-$C_8$cycloalkyl, 3- to 8-membered heterocyclyl, $C_6$-$C_{12}$aryl or 5- to 12-membered heteroaryl;

$X^1$, $X^2$, $X^3$, $X^4$ and $X^8$ are each independently selected from —$CR^a$, or N;

$X^5$, $X^6$, $X^7$ and $X^9$ are each independently selected from —$NR^a$—, —O—, —S— and —$CR^aR^b$—;

$X^{12}$ and $X^{13}$ are each independently selected from —$NR^a$— and —O—;

$L^4$, $L^5$ and $L^6$ are each independently selected from a single bond, —O—, —$NR^a$—, —$(CR^aR^b)_{n8}$—, —$O(CR^aR^b)_{n8}$—, —$NR^a(CR^aR^b)_{n8}$— or —C(O)—;

$Y^1$, $Y^2$ and $Y^3$ are each independently selected from $CR^a$ or N;

$R^a$ and $R^b$ are each independently selected from hydrogen (H, D or T), halogen, CN, —$C_{1-8}$alkyl, —$C_{1-8}$alkoxy, —$C_{2-8}$alkenyl, —$C_{2-8}$alkynyl, —$C_3$-$C_8$cycloalkyl, 3- to 8-membered heterocyclyl, —$C_6$-$C_{12}$aryl or 5- to 12-membered heteroaryl, wherein each of said —$C_{1-8}$alkyl, —$C_{1-8}$alkoxy, —$C_{2-8}$alkenyl, —$C_{2-8}$alkynyl, —$C_3$-$C_8$cycloalkyl, 3- to 8-membered heterocyclyl, —$C_6$-$C_{12}$aryl or 5- to 12-membered heteroaryl is optionally substituted with at least one substituent halogen, hydroxy, halogen, —$C_{1-8}$alkyl, —$C_{1-8}$alkoxy, —$C_{2-8}$alkenyl, —$C_{2-8}$alkynyl, —$C_3$-$C_8$cycloalkyl, 3- to 8-membered heterocyclyl, —$C_6$-$C_{12}$aryl or 5- to 12-membered heteroaryl; or $R^a$ and $R^b$ together with the carbon atoms to which they are attached, form a 3- to 12-membered ring, said ring comprising 0-3 heteroatoms independently selected from nitrogen, oxygen or sulfur, said ring is optionally substituted with at least one substituent halogen, hydroxy, —$C_{1-8}$alkyl, —$C_{2-8}$alkenyl, —$C_{2-8}$ alkynyl, —$C_{1-8}$alkoxy, —$C_{2-8}$-alkenyl, —$C_{2-8}$ alkynyl, $C_3$-$C_8$cycloalkyl, 3- to 8-membered heterocyclyl, $C_6$-$C_{12}$aryl or 5- to 12-membered heteroaryl;

$m_1$ is 0 or 1;

$m_2$ and $m_3$ are each independently 0, 1, 2, 3, 4, 5, 6, 7 or 8;

$m_4$ and $m_5$ are each independently 0, 1, 2 or 3;

n, $n_1$, $n_2$, $n_3$, $n_4$ and $n_5$ are each independently 0, 1, 2 or 3; and $n_6$ is 0, 1, 2, 3 or 4

$n_7$ is 0, 1, 2 or 3;

$n_8$ is 0, 1, 2, 3, 4, 5, 6.7 or 8.

Aspect 2. The compound of Aspect 1, wherein Cy1 is a 4-, 5-, 6- or 7-membered saturated or partially unsaturated ring including P═O, said ring comprising 0 or 1 additional heteroatom independently selected from nitrogen, oxygen or sulfur in addition to P═O; said ring is optionally substituted with at least one substituent $R^{1c}$;

$R^{1c}$ is selected from hydrogen, —F, —Cl, —Br, —I, methyl, ethyl, propyl, butyl, pentyl, hexyl, cyclopropyl, cyclobutyl, cyclopentyl, cyclohexyl, piperidinyl, piperazinyl, morpholinyl, phenyl, —CN, —$OR^{1d}$, —$COR^{1d}$, —$CO_2R^{1d}$, —$CONR^{1d}R^{1e}$, —$NR^{1d}R^{1e}$, —$NR^{1d}COR^{1e}$ or —$NR^{1d}CO_2R^{1e}$, wherein each of —$C_{1-8}$alkyl, —$C_{2-8}$alkenyl, —$C_{2-8}$alkynyl, $C_3$-$C_8$cycloalkyl, 3- to 8-membered heterocyclyl, $C_6$-$C_{12}$aryl or 5- to 12-membered heteroaryl is optionally substituted with at least one substituent $R^{1f}$;

$R^{1d}$, $R^{1e}$ and $R^{1f}$ are each independently selected from hydrogen, methyl, ethyl, propyl, butyl, pentyl, hexyl, cyclopropyl, cyclobutyl, cyclopentyl, or cyclohexyl.

Aspect 3. The compound of any one of Aspects 1-2, wherein the

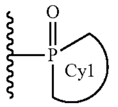

moiety is selected from

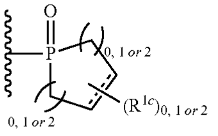

or

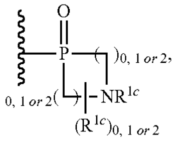

wherein ═══ is a single or double bond.

$R^{1c}$, at each of its occurrences, has the same definition with Aspect 1 or 2.

Aspect 4. The compound of any one of Aspects 1-3, wherein the

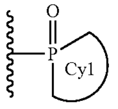 [SMILES: *P(C)(C)=O]

moiety is selected from

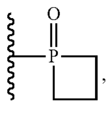,
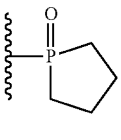,
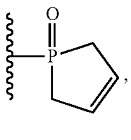,
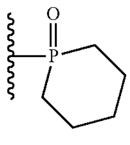
or

-continued

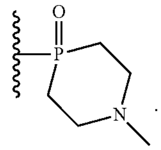.

Aspect 5. The compound of any one of Aspects 1-4, wherein $R^2$ and $R^3$ are each independently selected from hydrogen, —F, —Cl, —Br, —I, methyl, ethyl, propyl, butyl, pentyl, hexyl, heptyl, octyl, cyclopropyl, cyclobutyl, cyclopentyl, cyclohexyl, cycloheptyl, cyclooctyl, 3- to 8-membered heterocyclyl, $C_6$-$C_{12}$aryl, 5- to 12-membered heteroaryl, —CN, —$OR^{2a}$, —$SO_2R^{2a}$, —$SO_2NR^{2a}R^{2b}$, —$COR^{2a}$—, —$CO_2R^{2a}$, —$CONR^{2a}R^{2b}$, —$NR^{2a}R^{2b}$, —$NR^{2a}COR^{2b}$, —$NR^{2a}CO_2R^{2b}$, or —$NR^{2a}SO_2R^{2b}$, wherein each of methyl, ethyl, propyl, butyl, pentyl, hexyl, heptyl, octyl, cyclopropyl, cyclobutyl, cyclopentyl, cyclohexyl, cycloheptyl, cyclooctyl, 3- to 8-membered heterocyclyl, $C_6$-$C_{12}$aryl or 5- to 12-membered heteroaryl is optionally substituted with at least one substituent $R^{2d}$.

$R^{2a}$ and $R^{2b}$ are each independently selected from hydrogen, methyl, ethyl, propyl, butyl, pentyl, hexyl, heptyl, octyl, methoxyl, ethoxyl, propoxyl, butoxyl, pentoxyl, hexoxyl, heptyloxyl, octyloxyl, $C_{1-8}$alkoxy-$C_{1-8}$alkyl-, cyclopropyl, cyclobutyl, cyclopentyl, cyclohexyl, cycloheptyl, cyclooctyl, 3- to 8-membered heterocyclyl, phenyl or 5- to 12-membered heteroaryl;

$R^{2d}$, at each of its occurrences, is independently halogen, —OH, methyl, ethyl, propyl, butyl, pentyl, hexyl, heptyl, octyl, cyclopropyl, cyclobutyl, cyclopentyl, cyclohexyl, cycloheptyl, cyclooctyl, 3- to 8-membered heterocyclyl, phenyl, or 5- to 12-membered heteroaryl.

Aspect 6. The compound of any one of Aspects 1-5, wherein $R^2$ and $R^3$ are each independently selected from hydrogen, halogen, methyl, ethyl, propyl, butyl, pentyl, hexyl, heptyl or octyl, preferable selected from —H, —F, —Cl, —Br, —I, —$CH_3$, —$CH_2CH_3$, —$CH_2CH_2CH_3$, —$CH(CH_3)_2$, —$CH_2CH_2CH_2CH_3$, —$CH(CH_3)CH_2CH_3$, —$CH_2CH(CH_3)_2$, or —$C(CH_3)_3$.

Aspect 7. The compound of any one of Aspects 1-4, wherein $Z^5$ is —$CR^2$ and $Z^6$ is —$CR^3$, wherein $R^2$ and $R^3$ together with the carbon atoms to which they are attached, form a 5 or 6 membered unsaturated (preferred aromatic) ring, said ring comprising 0, 1 or 2 heteroatoms independently selected from nitrogen, oxygen or sulfur; said ring is optionally substituted with at least one substituent $R^{2e}$;

$R^{2e}$, at each of its occurrences, is independently hydrogen, —F, —Cl, —Br, —I, methyl, ethyl, propyl, butyl, pentyl, hexyl, heptyl, octyl, methoxyl, ethoxyl, propoxyl, butoxyl, pentoxyl, hexoxyl, heptyloxyl, octyloxyl, cyclopropyl, cyclobutyl, cyclopentyl, cyclohexyl, cycloheptyl, cyclooctyl or oxo, wherein each of methyl, ethyl, propyl, butyl, pentyl, hexyl, heptyl, octyl, methoxyl, ethoxyl, propoxyl, butoxyl, pentoxyl, hexoxyl, heptyloxyl, octyloxyl, cyclopropyl, cyclobutyl, cyclopentyl, cyclohexyl, cycloheptyl or cyclooctyl is optionally substituted with at least one substituent $R^{2d}$;

$R^{2d}$, at each of its occurrences, is independently —F, —Cl, —Br, —I, —OH, methyl, ethyl, propyl, butyl, pentyl, hexyl, heptyl, octyl, methoxyl, ethoxyl, propoxyl, butoxyl, pentoxyl, hexoxyl, heptyloxyl, octyloxyl, cyclopropyl, cyclobutyl, cyclopentyl, cyclohexyl, cycloheptyl, cyclooctyl or phenyl.

Aspect 8. The compound of any one of Aspects 1-7, wherein the

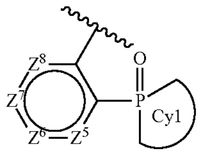

moiety is

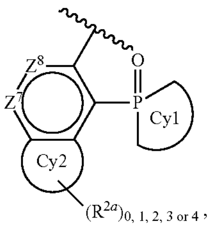

wherein Cy2 is a 5-6 membered unsaturated (preferred aromatic) or saturated ring, said ring comprising 0-3 heteroatoms independently selected from nitrogen, oxygen or sulfur;

preferable, the

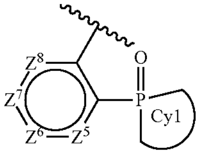

moiety is

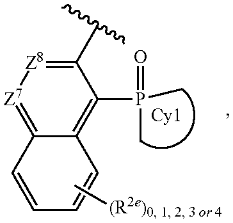

,

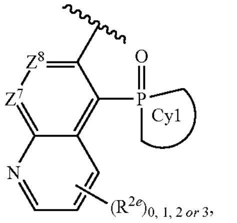

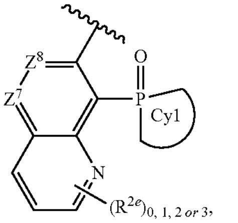

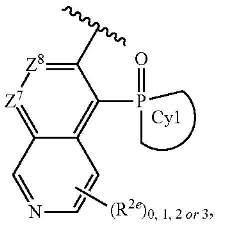

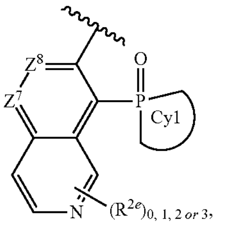

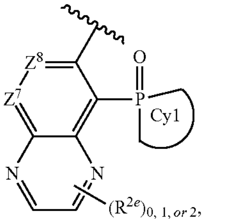

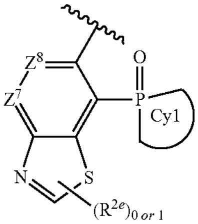

,

-continued

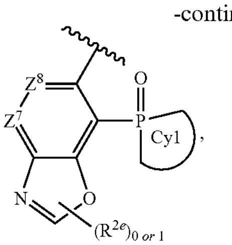

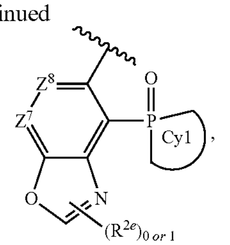

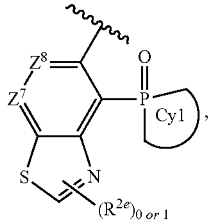

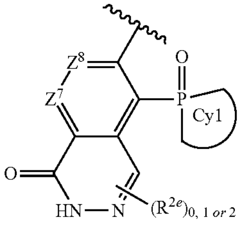

or

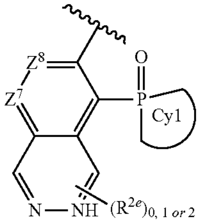

wherein $R^{2e}$, $Z^7$, and $Z^8$ are defined as in Aspect 1.

Aspect 9. The compound any of Aspects 1-8, wherein $R^{2e}$ at each of its occurrences, is independently hydrogen, —F, —Cl, —Br, —I, methyl, ethyl, propyl, butyl, pentyl, hexyl, heptyl, octyl, methoxyl, ethoxyl, propoxyl, butoxyl, pentoxyl, hexoxyl, heptyloxyl, octyloxyl, cyclopropyl, cyclobutyl, cyclopentyl, cyclohexyl, cycloheptyl, cyclooctyl or oxo, wherein each of methyl, ethyl, propyl, butyl, pentyl, hexyl, heptyl, octyl, methoxyl, ethoxyl, propoxyl, butoxyl, pentoxyl, hexoxyl, heptyloxyl, octyloxyl, cyclopropyl, cyclobutyl, cyclopentyl, cyclohexyl, cycloheptyl or cyclooctyl is optionally substituted with at least one substituent $R^{2d}$;

$R^{2d}$, at each of its occurrences, is independently —F, —Cl, —Br, —I, —OH, methyl, ethyl, propyl, butyl, pentyl, hexyl, heptyl, octyl, methoxyl, ethoxyl, propoxyl, butoxyl, pentoxyl, hexoxyl, heptyloxyl, octyloxyl, cyclopropyl, cyclobutyl, cyclopentyl, cyclohexyl, cycloheptyl, cyclooctyl or phenyl.

Aspect 10. The compound any one of Aspects 1-9, wherein $R^{2e}$ at each of its occurrences, is independently hydrogen, —F, —Cl, —Br, —I, $—CH_3$, $—CH_2CH_3$, $—CH_2CH_2CH_3$, $—CH(CH_3)_2$, $—CH_2CH_2CH_2CH_3$, $—CH(CH_3)CH_2CH_3$, $—CH_2CH(CH_3)_2$, $—C(CH_3)_3$,

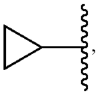

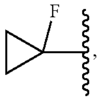

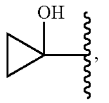

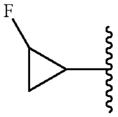

or

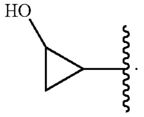

Aspect 11. The compound of one of Aspects 1-10, wherein the

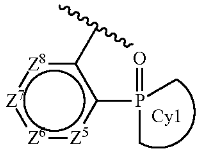
moiety is
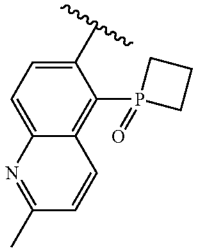,
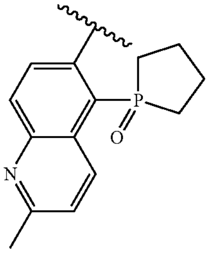,
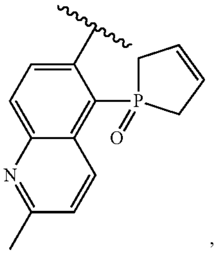,
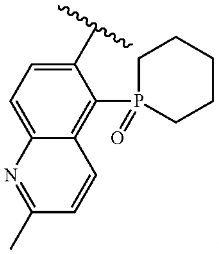,
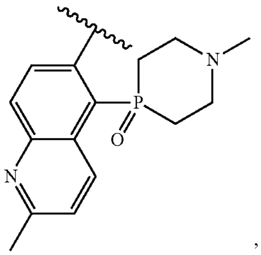,
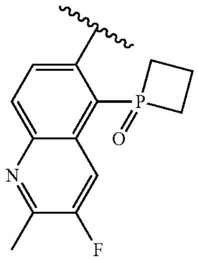,
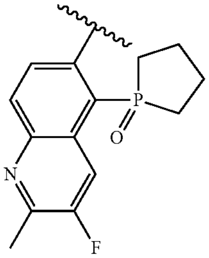,
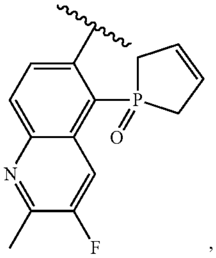,
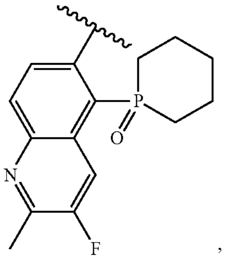,
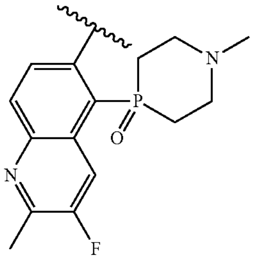,
-continued
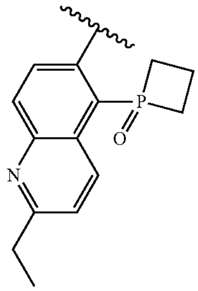,
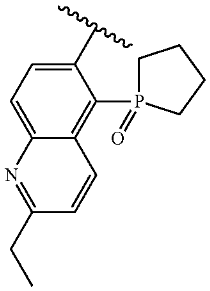,
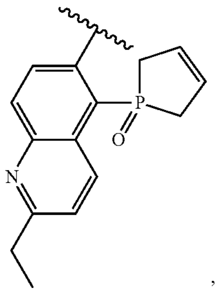,
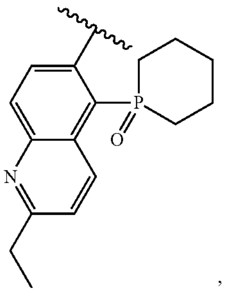,
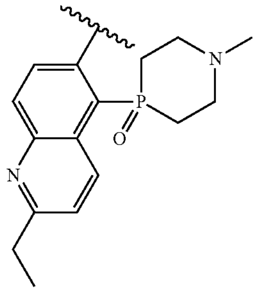,
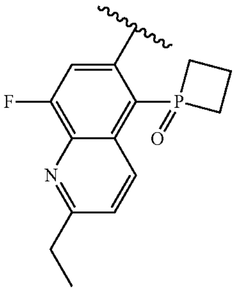,
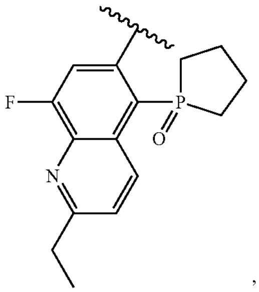,
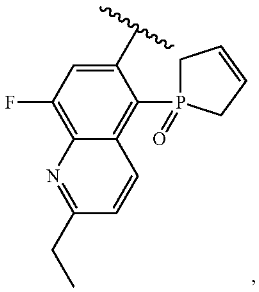,
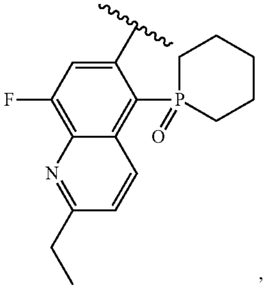, -continued
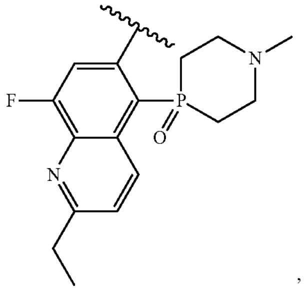
,
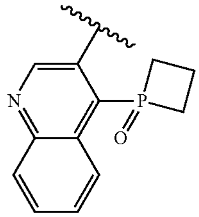
,
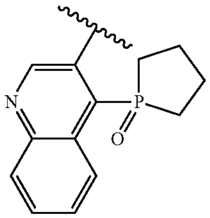
,
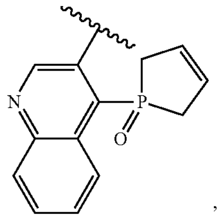
,
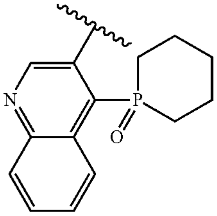
,
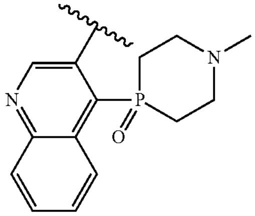
,
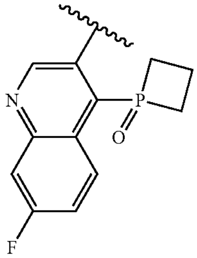
,
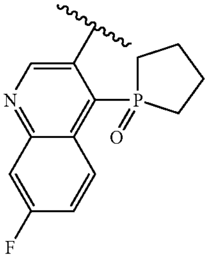
,
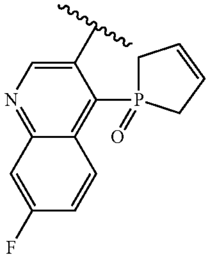
,
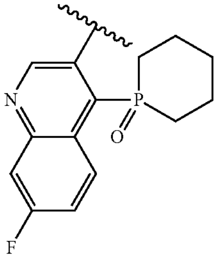
,
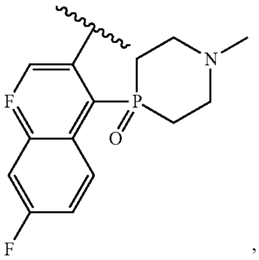
,
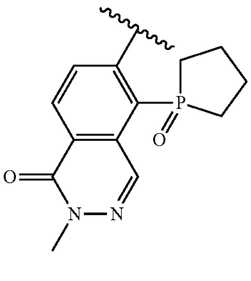
,
-continued
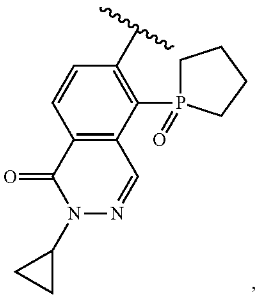
,
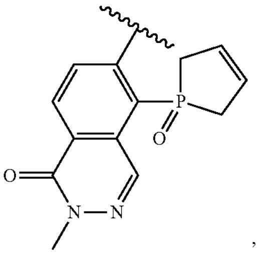
,
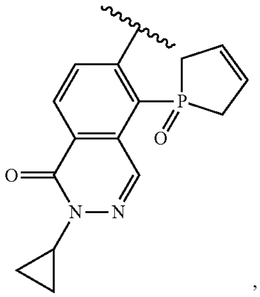
,
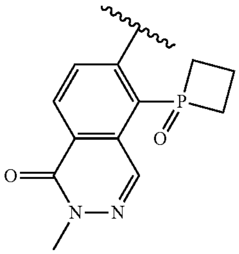
,
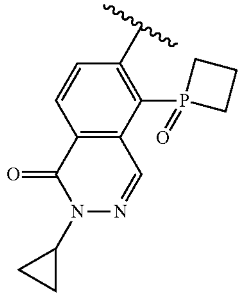
,
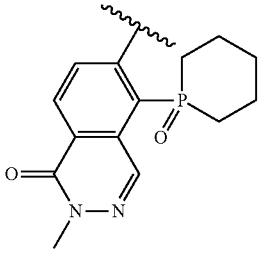
,
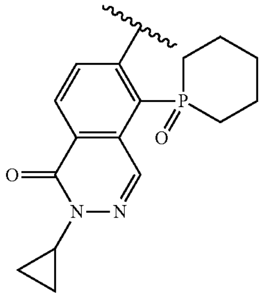
,
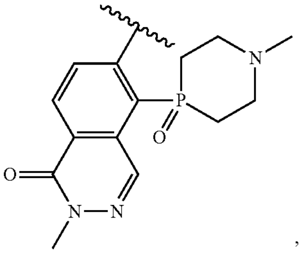
, -continued

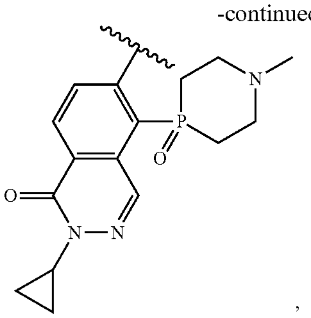

,

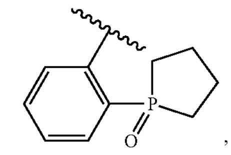

,

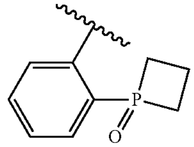

,

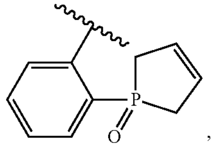

,

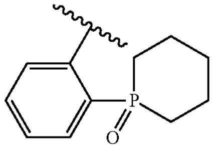

or

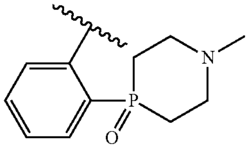

.

Aspect 12. The compound of any one of Aspects 1-11, wherein $R^9$, $R^{10}$, $R^{11}$ and $R^{12}$ are each independently selected from hydrogen, —F, —Cl, —Br, —I, methyl, ethyl, propyl, butyl, pentyl, hexyl, heptyl, octyl, methoxyl, ethoxyl, propoxyl, butoxyl, pentoxyl, hexoxyl, heptyloxyl, octyloxyl, cyclopropyl, cyclobutyl, cyclopentyl, cyclohexyl, cycloheptyl, cyclooctyl, —$NH_2$ or oxo, wherein each of methyl, ethyl, propyl, butyl, pentyl, hexyl, heptyl, octyl, methoxyl, ethoxyl, propoxyl, butoxyl, pentoxyl, hexoxyl, heptyloxyl, octyloxyl, cyclopropyl, cyclobutyl, cyclopentyl, cyclohexyl, cycloheptyl, cyclooctyl is optionally substituted with at least one substituent $R^{9c}$; or two $R^{12}$ together with the carbon atoms to which they are attached, form a 3, 4, 5, 6, 7 or 8-membered ring, said ring comprising 0, 1, 2 or 3 heteroatoms independently selected from nitrogen, oxygen or sulfur; said ring is optionally substituted with at least one substituent $R^{9c}$;

$R^{9c}$ is independently —F, —Cl, —Br, —I, hydroxy, methyl, ethyl, propyl, butyl, pentyl, hexyl, heptyl, octyl, methoxyl, ethoxyl, propoxyl, butoxyl, pentoxyl, hexoxyl, heptyloxyl, octyloxyl, cyclopropyl, cyclobutyl, cyclopentyl, cyclohexyl, cycloheptyl, cyclooctyl, —$C_{2-8}$alkenyl, —$C_{2-8}$alkynyl, 3- to 8-membered heterocyclyl, phenyl, 5- to 12-membered heteroaryl, $NH_2$, or —$NHCH_3$.

Aspect 13. The compound of any one of Aspects 1-12, wherein $R^9$, $R^{10}$, $R^{11}$ and $R^{12}$ are each independently selected from hydrogen, F, Cl, Br, —$NH_2$, —$CH_3$, —$C_2H_5$, —$C_3H_7$, —$CH_2F$, —$CHF_2$, —$CF_3$, —$C_4H_9$, —$C_5H_{11}$, —$OCH_3$, —$OC_2H_5$, —$OC_3H_7$, —$OC_4H_9$, —$OC_5H_{11}$, —CN, cyclopropyl or oxo; or two $R^{12}$ together with the carbon atoms to which they are attached, form a 3, 4, 5, 6, 7 or 8-membered ring, said ring comprising 0, 1, 2 or 3 heteroatoms independently selected from nitrogen, oxygen or sulfur; said ring is optionally substituted with at least one substituent —H, —F, —Cl, —Br, —I, methyl, ethyl, propyl, butyl, —$NH_2$, —$NHCH_3$, —OH, —$OCH_3$, —$OC_2H_5$, cyclopropyl, cyclobutyl, cyclopentyl, or cyclohexyl.

Aspect 14. The compound of any one of Aspects 1-13, wherein $R^4$ is selected from —H, —F, —Cl, —Br, —I, —$CH_3$, —$C_2H_5$, —$C_3H_7$, —$C_4H_9$, —$C_5H_{11}$, —$OCH_3$, —$OC_2H_5$, —$OC_3H_7$, —$OC_4H_9$, —$OC_5H_{11}$, cyclopropyl, cyclobutyl, cyclopentyl, cyclohexyl, cycloheptyl, cyclooctyl, phenyl or —CN, wherein each of —$CH_3$, —$C_2H_5$, —$C_3H_7$, —$C_4H_9$, —$C_5H_{11}$, —$OCH_3$, —$OC_2H_5$, —$OC_3H_7$, —$OC_4H_9$, —$OC_5H_{11}$, cyclopropyl, cyclobutyl, cyclopentyl, cyclohexyl, cycloheptyl, cyclooctyl or phenyl is optionally substituted with —F, —Cl, —Br, —I, —$C_{1-8}$alkyl, —$C_{2-8}$ alkenyl, —$C_{2-8}$alkynyl, —$C_3$-$C_8$cycloalkyl, 3- to 8-membered heterocyclyl, $C_6$-$C_{12}$aryl, 5- to 12-membered heteroaryl, oxo, —CN, —$OR^{4c}$, —$SO_2R^{4c}$, —$SO_2NR^{4c}R^{4d}$, —$COR^{4c}$, —$CO_2R^{4c}$, —$CONR^{4c}R^{4d}$, —$NR^{4c}R^{4d}$, —$NR^{4c}COR^{4d}$, —$NR^{4c}CO_2R^{4d}$, or —$NR^{4c}SO_2R^{4d}$;

$R^{4c}$ and $R^{4d}$ are each independently hydrogen, —$C_{1-8}$alkyl, —$C_{2-8}$alkenyl, —$C_{2-8}$alkynyl, $C_3$-$C_8$cycloalkyl, 3- to 8-membered heterocyclyl, $C_6$-$C_{12}$aryl, or 5- to 12-membered heteroaryl.

Aspect 15. The compound of any one of Aspects 1-14, wherein $R^4$ is Selected from —F, —Cl, —Br, —I, —$CH_3$, —$CF_3$, —$CH_2F$, or —$CHF_2$.

Aspect 16. The compound of any one of Aspects 1-15, wherein $L^1$ is selected from a single bond, —O—, —$SO_2$—, —C(O)—, —$NR^{L1a}$—, —$C_{1-8}$alkylene, —$C_3$-$C_8$cycloalkylene-, $*^{L1}$—O—$C_{1-8}$alkylene-$^{L1}$, $^{L1}C_{1-8}$alkylene-O—$^{L1}$, $*^{L1}$—$SO_2$—$C_{1-8}$alkylene-$**^{L1}$, $*^{L1}$—$C_{1-8}$ alkylene-$SO_2$—$**^{L1}$, $*^{L1}$—CO—$C_{1-8}$alkylene-$**^{L1}$, $*^{L1}$—$C_{1-8}$alkylene-CO—$**^{L1}$, $*^{L1}$—$NR^{L1a}$—$C_{1-8}$ alkylene-$**^{L1}$, $*^{L1}$—$C_{1-8}$alkylene-$NR^{L1a}$—$**^{L1}$, $*^{L1}$—$NR^{L1a}C(O)$—$**^{L1}$, $*^{L1}$—$C(O)NR^{L1a}$—$**^{L1}$, —$C_{1-8}$alkylene-, —$C_{2-8}$alkenylene-, —$C_{2-8}$alkynylene-, —$[O(CR^{L1a}R^{L1b})_{m4}]_{m5}$—,

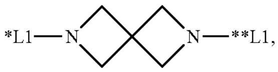

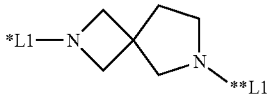

,

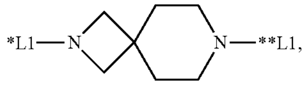

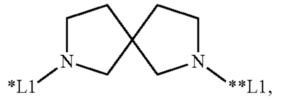

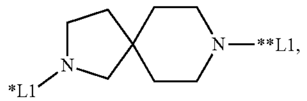

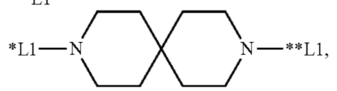

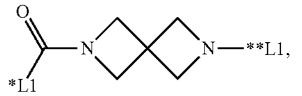

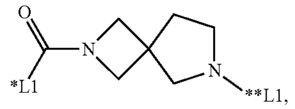

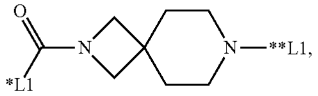

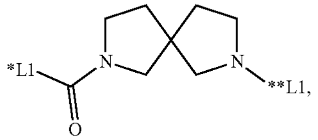

-continued
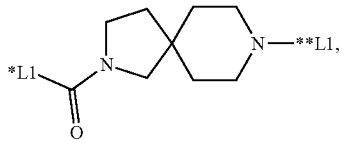
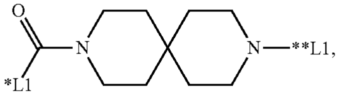
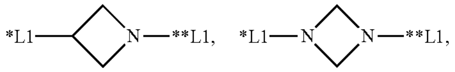
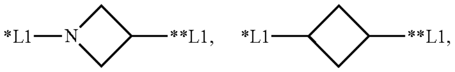
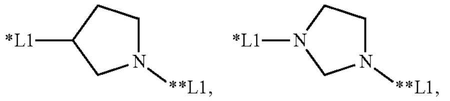
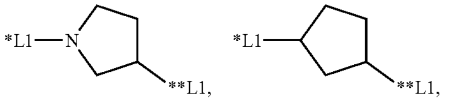
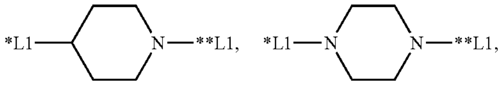
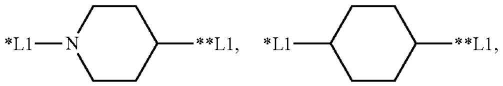
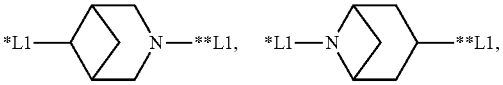
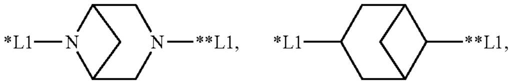
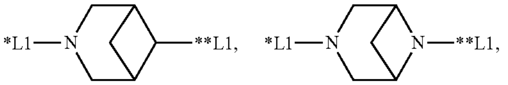
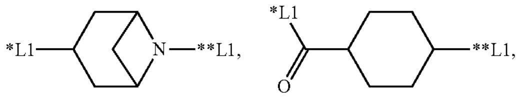
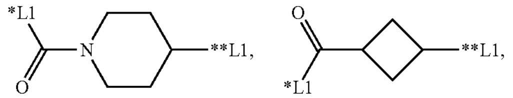
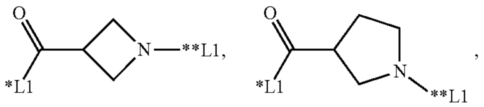
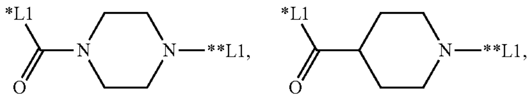
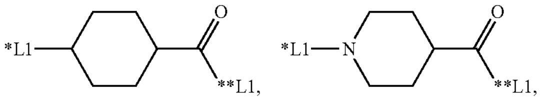
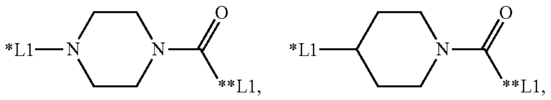
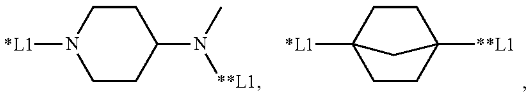
-continued
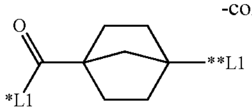
or
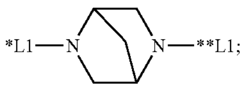
wherein each of said $—C_{1-8}$alkylene, $—C_3$-$C_8$cycloalkylene-, $*^{L1}—O—C_{1-8}$alkylene-$**^{L1}$, $*^{L1}—C_{1-8}$alkylene-O—$**^{L1}$, $*^{L1}—SO_2—C_{1-8}$ alkylene-$**^{L1}$, $*^{L1}—C_{1-8}$alkylene-$SO_2—**^{L1}$, $*^{L1}$—CO—$C_{1-8}$alkylene-$**^{L1}$, $*^{L1}—C_{1-8}$alkylene-CO—$**^{L1}$, $*^{L1}—NR^{L1a}—C_{1-8}$alkylene-$**^{L1}$, $*^{L1}—C_{1-8}$ alkylene-$NR^{L1a}—**^{L1}$, $—C_{1-8}$alkylene-, $—C_{2-8}$ alkenylene-, $—C_{2-8}$alkynylene-,
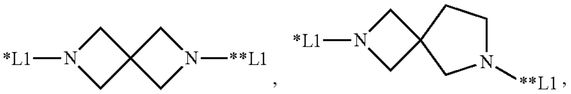
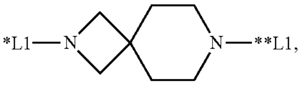
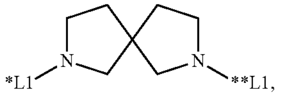
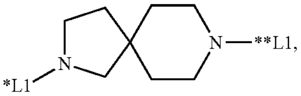
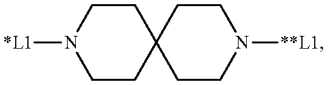
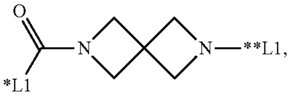
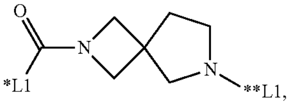
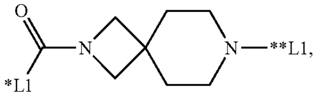
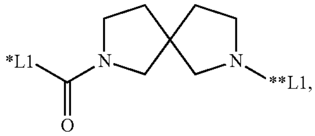
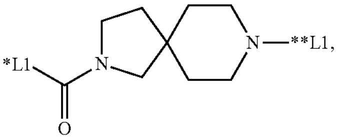
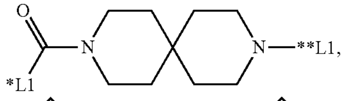
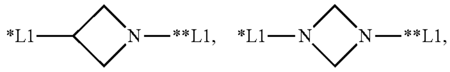
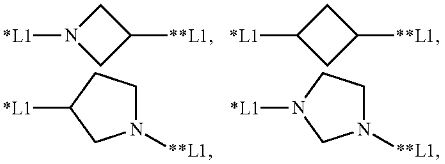

-continued

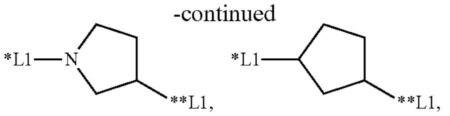
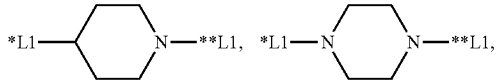
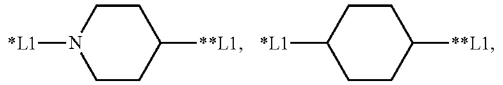
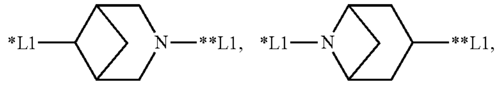
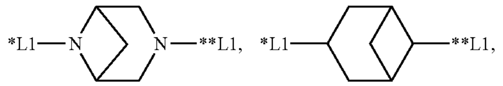
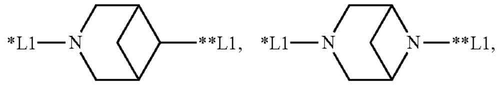
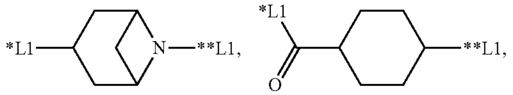
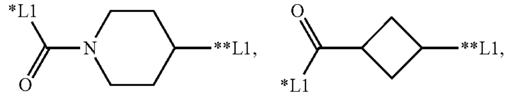
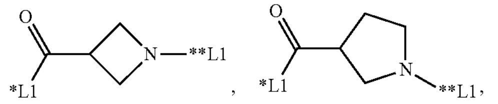
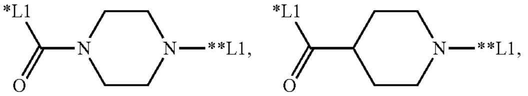
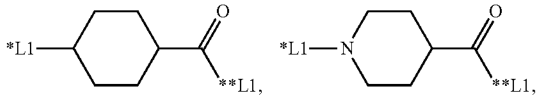
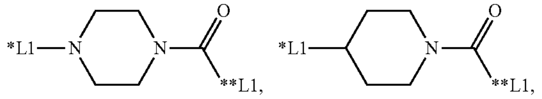
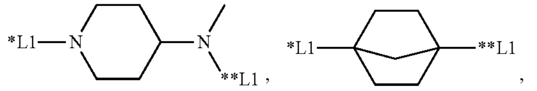
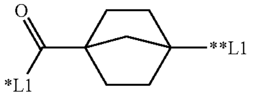

or

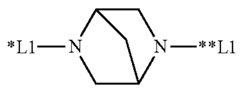

is optionally substituted with at least one $R^L$c;

$R^{L1a}$ and $R^{L1b}$ are each independently selected from hydrogen, methyl, ethyl, propyl, butyl, pentyl, hexyl, heptyl, octyl, vinyl, ethynyl, cyclopropyl, cyclobutyl, cyclopentyl, cyclohexyl, cycloheptyl, cyclooctyl, oxazolidinyl, imidazolidinyl, thiazolidinyl, pyrazolidinyl, morpholinyl, piperidinyl, piperazinyl, oxazinyl, imidazolyl, thiazolyl, oxazolyl, pyridyl, pyrimidinyl, pyrazinyl, pyridazinyl, phenyl, pyrrolyl, imidazolyl, pyrazolyl, thiazolyl, oxazolyl, triazolyl, thiophenyl, furanyl, pyridyl, pyrimidinyl or pyrazinyl, wherein each of said methyl, ethyl, propyl, butyl, pentyl, hexyl, heptyl, octyl, vinyl, ethynyl, cyclopropyl, cyclobutyl, cyclopentyl, cyclohexyl, cycloheptyl, cyclooctyl, oxazolidinyl, imidazolidinyl, thiazolidinyl, pyrazolidinyl, morpholinyl, piperidinyl, piperazinyl, oxazinyl, imidazolyl, thiazolyl, oxazolyl, pyridyl, pyrimidinyl, pyrazinyl, pyridazinyl, phenyl, pyrrolyl, imidazolyl, pyrazolyl, thiazolyl, oxazolyl, triazolyl, thiophenyl, furanyl, pyridyl, pyrimidinyl or pyrazinyl is optionally substituted with at least one substituent $R^{L1d}$;

each of said $R^{L1c}$ and $R^{L1d}$ are independently —F, —Cl, —Br, —I, —OH, methyl, ethyl, propyl, butyl, pentyl, hexyl, heptyl, octyl, vinyl, ethynyl, methoxyl, ethoxyl, propoxyl, butoxyl, pentoxyl, hexoxyl, heptyloxyl, octyloxyl, cyclopropyl, cyclobutyl, cyclopentyl, cyclohexyl, cycloheptyl, cyclooctyl, oxazolidinyl, imidazolidinyl, thiazolidinyl, pyrazolidinyl, morpholinyl, piperidinyl, piperazinyl, oxazinyl, imidazolyl, thiazolyl, oxazolyl, pyridyl, pyrimidinyl, pyrazinyl, pyridazinyl, phenyl, pyrrolyl, imidazolyl, pyrazolyl, thiazolyl, oxazolyl, triazolyl, thiophenyl, furanyl, pyridyl, pyrimidinyl, pyrazinyl or oxo.

Aspect 17. The compound of any one of Aspects 1-16, wherein $L^1$ is selected from a single bond, —$C_{1-8}$alkylene- (preferably —$CH_2$—, —$C_2H_4$—, —$C_3H_6$—), —CO—, —O—, —$N(CH_3)$—, —NH—,

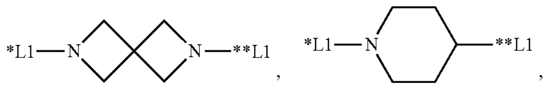
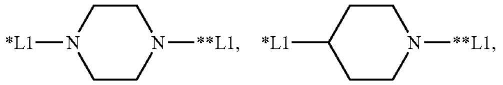
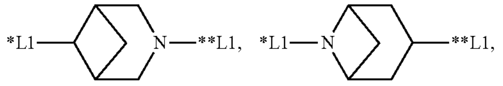
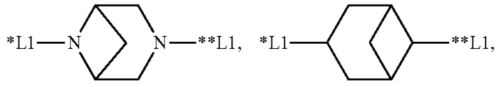
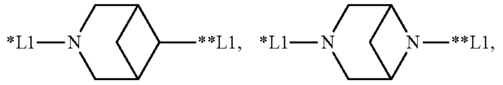
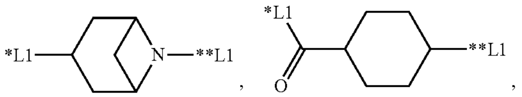
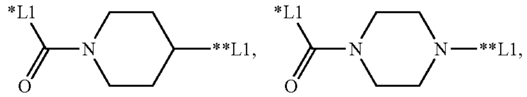
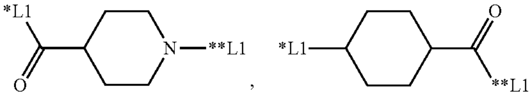
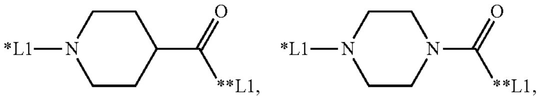
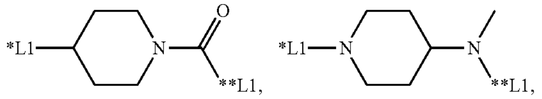
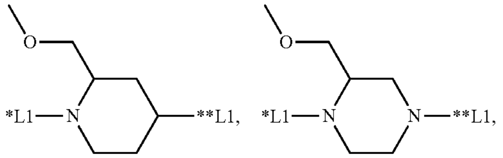

-continued

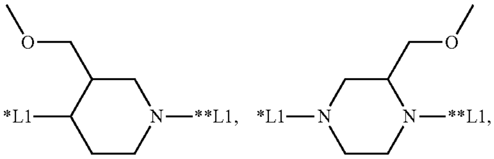

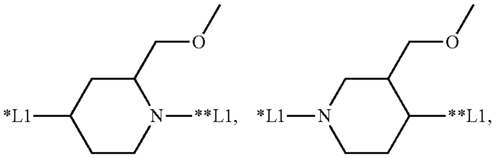

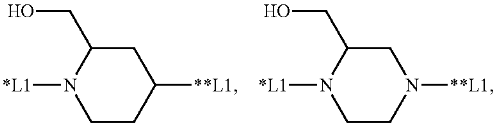

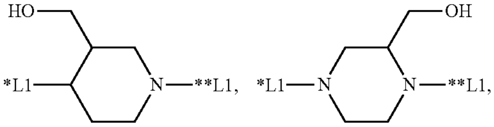

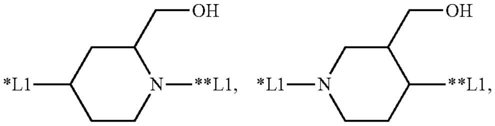

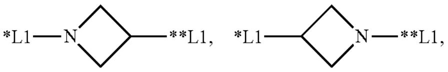

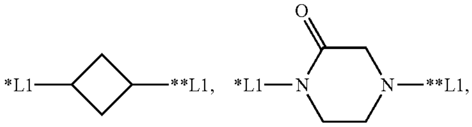

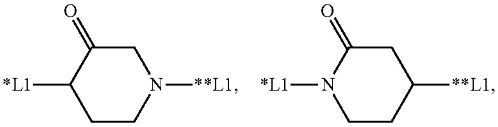

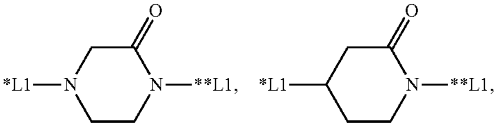

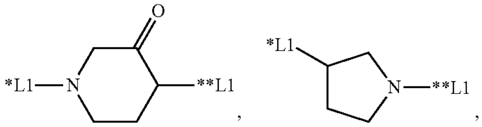

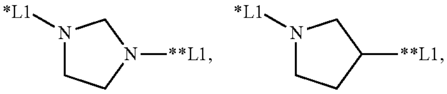

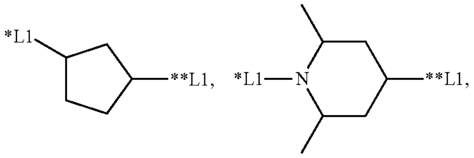

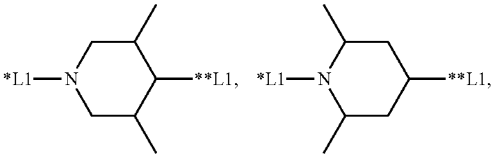

-continued

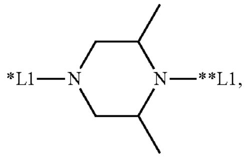, 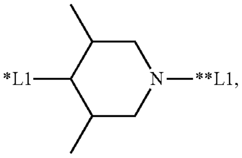,

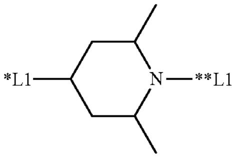, 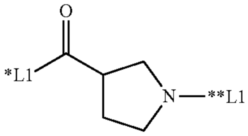,

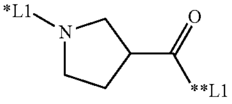, 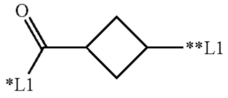,

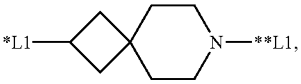,

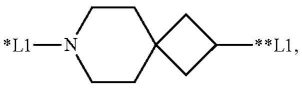, 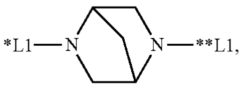,

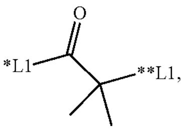, 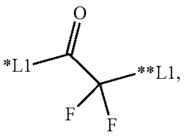, 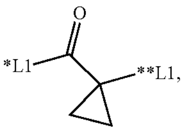,

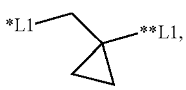, 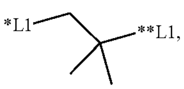, 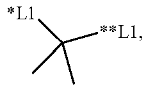,

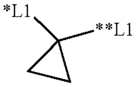, 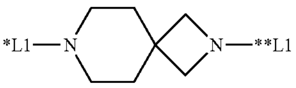,

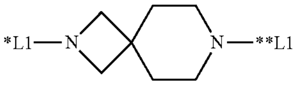, 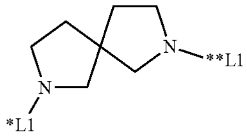,

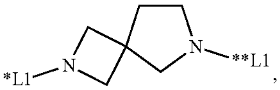, 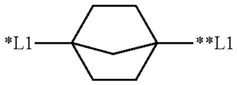,

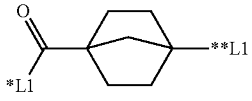 or 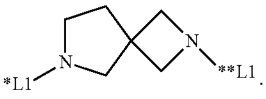.

Aspect 18. The compound of any one of Aspects 1-17, wherein $X^1$ and $X^2$ are each independently selected from —$CR^a$ or N;

wherein $R^a$ is selected from hydrogen, —F, —Cl, —Br, —I, CN, methyl, ethyl, methoxy, ethoxy, or cyclopropyl, wherein each of said methyl, ethyl, methoxy, ethoxy, or cyclopropyl is optionally substituted with at least one substituent —F, —Cl, —Br, —I, hydroxy, methyl, or ethyl, (preferably, $X^1$ and $X^2$ are each independently selected from CH, C(F), $C(CH_3)$ or N);

m1=1 or 0;

$R^{12}$ is hydrogen, oxo, methoxymethyl, hydroxymethyl, —CN or —$CH_3$.

Aspect 19. The compound of any one of Aspects 1-18, wherein m1 is 1; preferably,

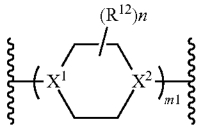

moiety is

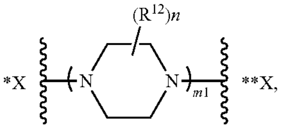

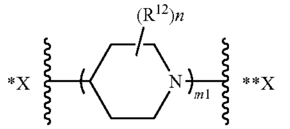 or

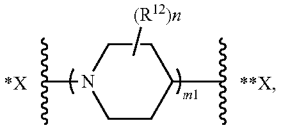

wherein $*^X$ refers to the position attached to

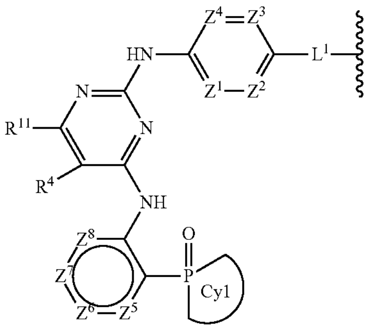

moiety, and $**^X$ refers to the position attached to the

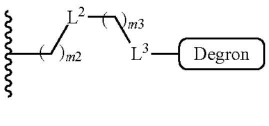

moiety.

Aspect 20. The compound of any one of Aspects 1-19, wherein m1 is 0.

Aspect 21. The compound of any one of Aspects 1-20, wherein

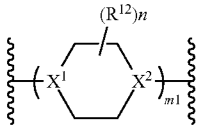

moiety is

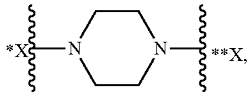 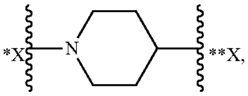

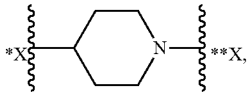 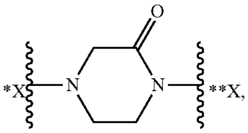

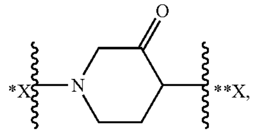 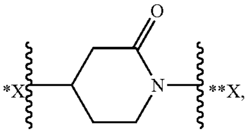

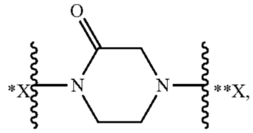 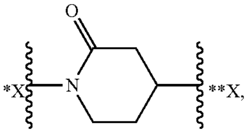

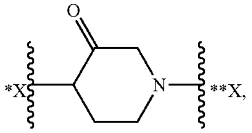 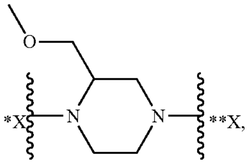

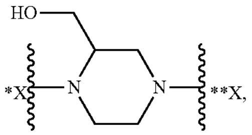 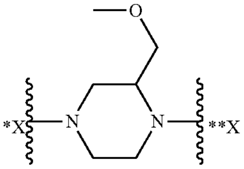 or

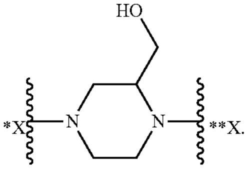

Aspect 22. The compound of any one of Aspects 1-21, wherein m2 is selected from 0, 1, 2, 3, 4 or 5.

Aspect 23. The compound of any one of Aspects 1-24, wherein $L^2$ is selected from a single bond, —O—, —$SO_2$—, —CO—, —$NR^{L2a}$—, —$C_{1-8}$alkylene, —$C_3$-$C_8$cycloalkylene-, $*^{L2}$—O—$C_{1-8}$alkylene-$^{L2}$, $^{L2}C_{1-8}$alkylene-O—$^{L2}$, $*^{L2}$—$SO_2$—$C_{1-8}$alkylene-$**^{L2}$, $*^{L2}$—$C_{1-8}$ alkylene-$SO_2$—$**^{L2}$, $*^{L2}$—CO—$C_{1-8}$alkylene-$**^{L2}$, $*^{L2}$—$C_{1-8}$alkylene-CO—$**^{L2}$, $*^{L2}$—$NR^{L2a}$—$C_{1-8}$ alkylene-$**^{L2}$, $*^{L2}$—$C_{1-8}$alkylene-$NR^{L2a}$—$**^{L2}$, $*^{L2}$—$NR^{L2a}$C(O)—$**^{L2}$, $*^{L2}$—C(O)$NR^{L2a}$—$**^{L2}$, —$C_{1-8}$alkylene-, —$C_{2-8}$alkenylene-, —$C_{2-8}$alkynylene-, —[O$(CR^{L2a}R^{L2b})_{m4}]_{m5}$—,

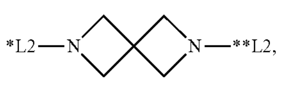 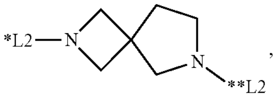,

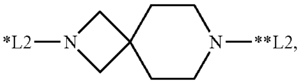

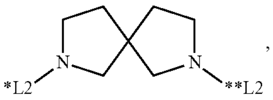, 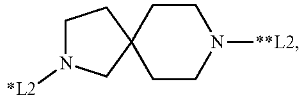

-continued
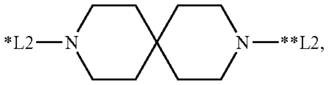
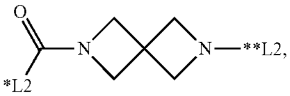
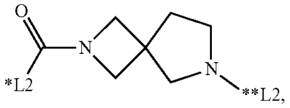
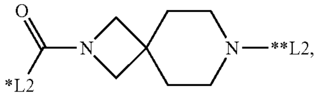
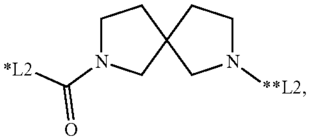
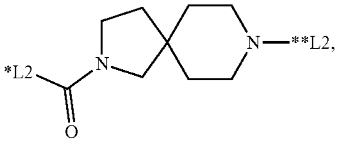
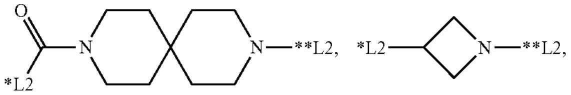
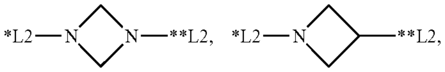
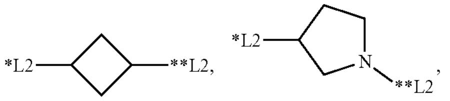
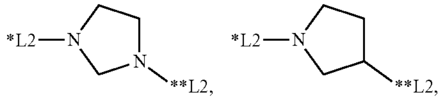
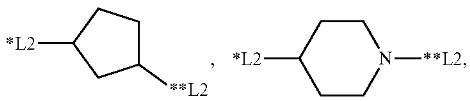
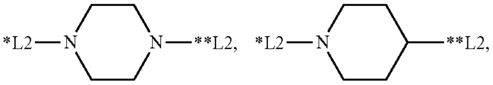
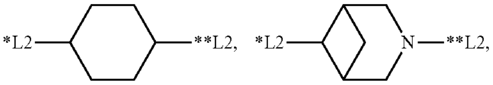
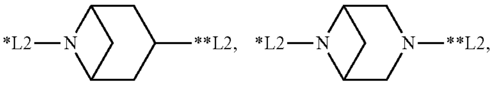
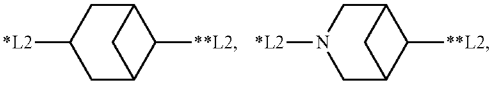
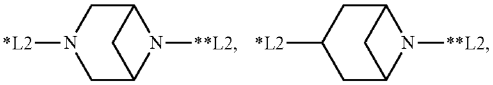
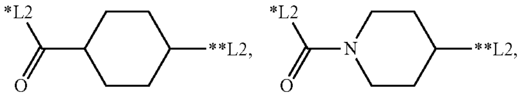
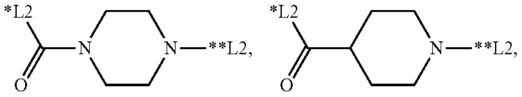
-continued
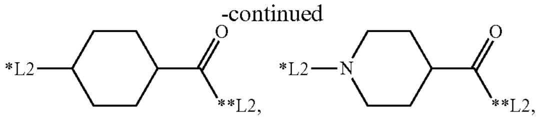
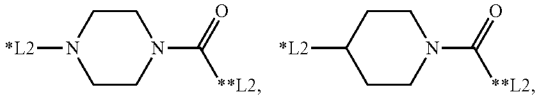
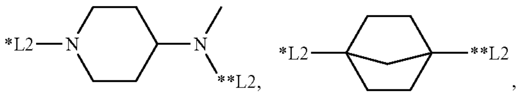
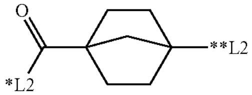 or 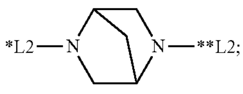
wherein each of said —$C_{1-8}$alkylene, —$C_3$-$C_8$cycloalkylene-, $*^{L2}$—O—$C_{1-8}$alkylene-$**^{L2}$, $*^{L2}$—$C_{1-8}$alkylene-O—$**^{L2}$, $*^{L2}$—$SO_2$—$C_{1-8}$ alkylene-$**^{L2}$, $*^{L2}$—$C_{1-8}$alkylene-$SO_2$—$**^{L2}$, $*^{L2}$—CO—$C_{1-8}$alkylene-$**^{L2}$, $*^{L2}$—$C_{1-8}$alkylene-CO—$**^{L2}$, $*^{L2}$—$NR^{L2a}$—$C_{1-8}$alkylene-$**^{L2}$, $*^{L2}$—$C_{1-8}$ alkylene-$NR^{L2a}$—$**^{L2}$, —$C_{1-8}$alkylene-, —$C_{2-8}$ alkenylene-, —$C_{2-8}$alkynylene-,
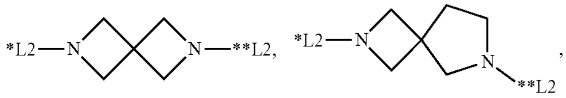
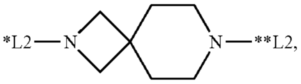
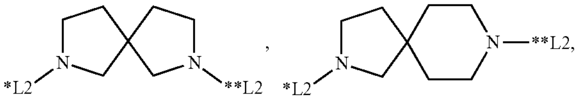
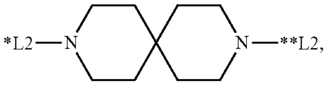
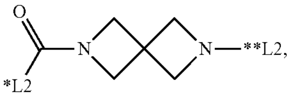
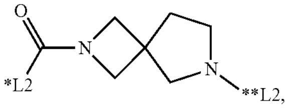
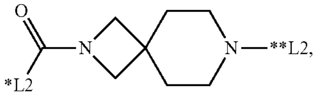
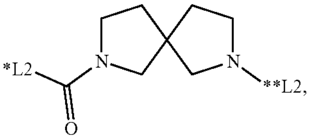
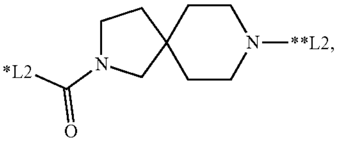
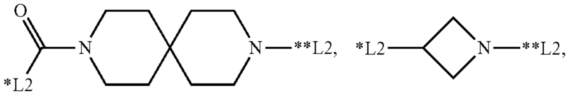

-continued

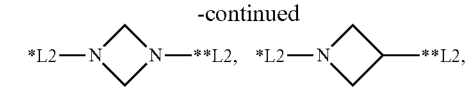
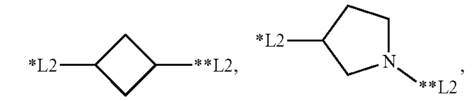
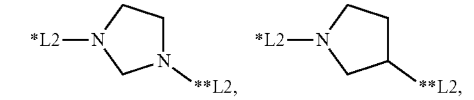
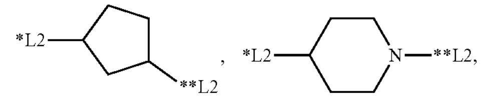
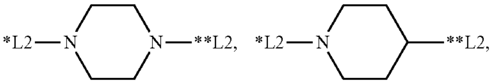
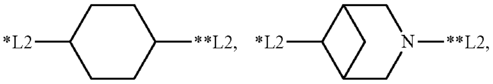
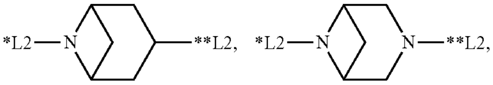
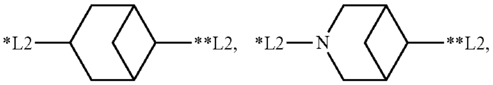
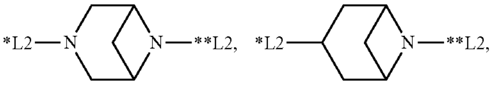
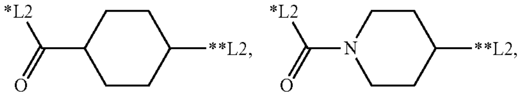
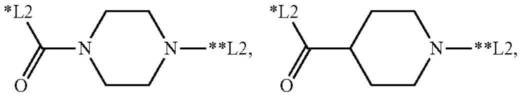
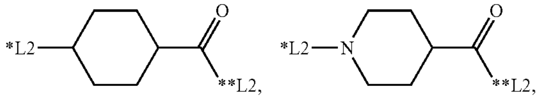
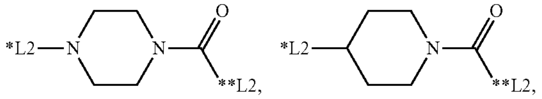
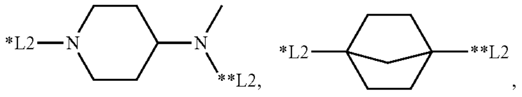
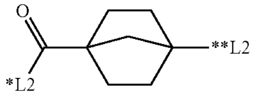
or
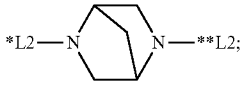

is optionally substituted with at least one substituent $R^{L2c}$;

$R^{L2a}$ and $R^{L2b}$ are each independently selected from hydrogen, methyl, ethyl, propyl, butyl, pentyl, hexyl, heptyl, octyl, vinyl, ethynyl, cyclopropyl, cyclobutyl, cyclopentyl, cyclohexyl, cycloheptyl, cyclooctyl, oxazolidinyl, imidazolidinyl, thiazolidinyl, pyrazolidinyl, morpholinyl, piperidinyl, piperazinyl, oxazinyl, imidazolyl, thiazolyl, oxazolyl, pyridyl, pyrimidinyl, pyrazinyl, pyridazinyl, phenyl, pyrrolyl, imidazolyl, pyrazolyl, thiazolyl, oxazolyl, triazoyl, thiophenyl, furanyl, pyridyl, pyrimidinyl or pyrazinyl, wherein each of said methyl, ethyl, propyl, butyl, pentyl, hexyl, heptyl, octyl, vinyl, ethynyl, cyclopropyl, cyclobutyl, cyclopentyl, cyclohexyl, cycloheptyl, cyclooctyl, oxazolidinyl, imidazolidinyl, thiazolidinyl, pyrazolidinyl, morpholinyl, piperidinyl, piperazinyl, oxazinyl, imidazolyl, thiazolyl, oxazolyl, pyridyl, pyrimidinyl, pyrazinyl, pyridazinyl, phenyl, pyrrolyl, imidazolyl, pyrazolyl, thiazolyl, oxazolyl, triazolyl, thiophenyl, furanyl, pyridyl, pyrimidinyl or pyrazinyl is optionally substituted with at least one substituent $R^{L2d}$;

each of said $R^{L2c}$ and $R^{L2d}$ are independently —F, —Cl, —Br, —I, —OH, methyl, ethyl, propyl, butyl, pentyl, hexyl, heptyl, octyl, vinyl, ethynyl, cyclopropyl, cyclobutyl, cyclopentyl, cyclohexyl, cycloheptyl, cyclooctyl, oxazolidinyl, imidazolidinyl, thiazolidinyl, pyrazolidinyl, morpholinyl, piperidinyl, piperazinyl, oxazinyl, imidazolyl, thiazolyl, oxazolyl, pyridyl, pyrimidinyl, pyrazinyl, pyridazinyl, phenyl, pyrrolyl, imidazolyl, pyrazolyl, thiazolyl, oxazolyl, triazolyl, thiophenyl, furanyl, pyridyl, pyrimidinyl, pyrazinyl or oxo;

Aspect 24. The compound of any one of Aspects 1-23, wherein $L^2$ is selected from a single bond, —$C_{1-8}$alkylene- (preferably —$CH_2$—, —$C_2H_4$—, —$C_3H_6$—), —CO—, —O—, —N($CH_3$)—, —NH—,

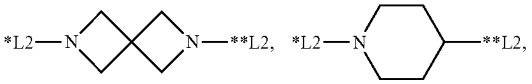
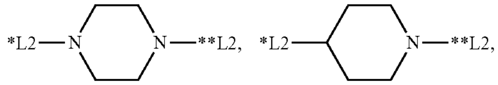
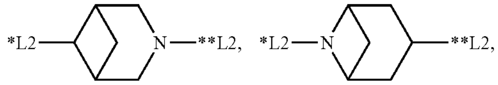
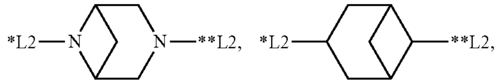
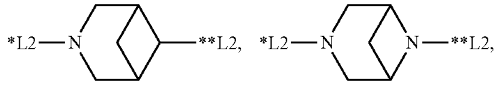
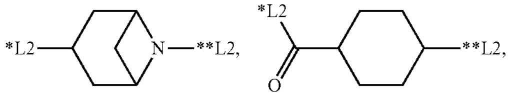
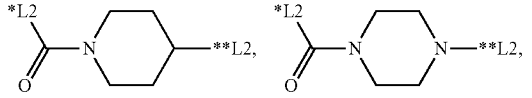
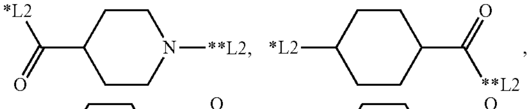
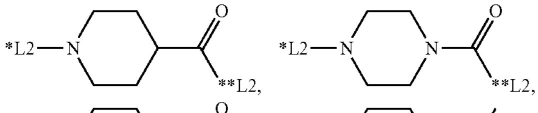
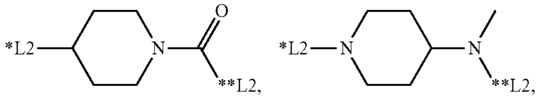
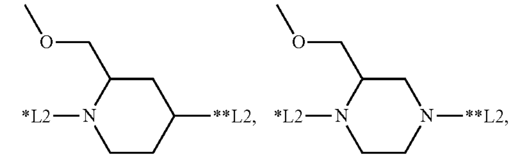

-continued

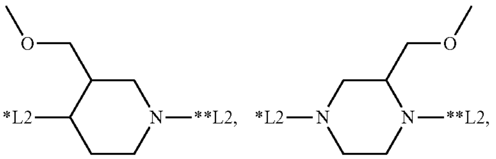
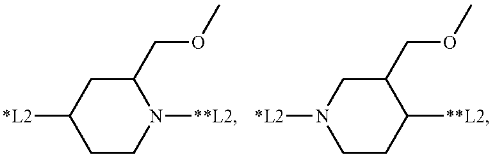
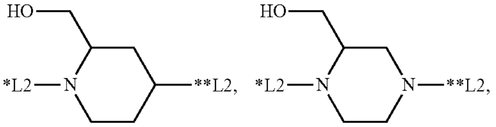
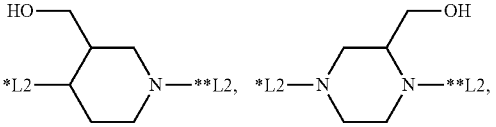
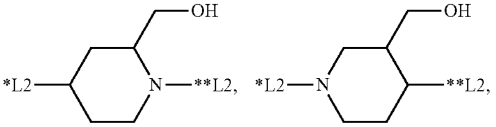
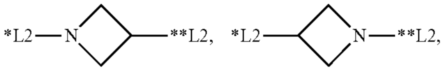
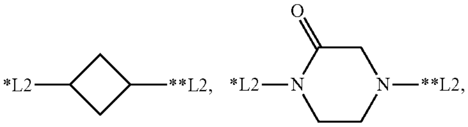
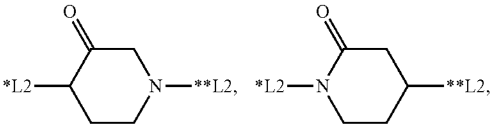
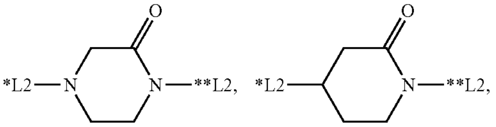
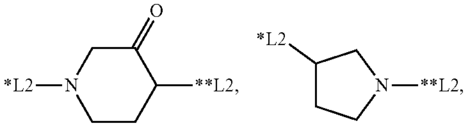
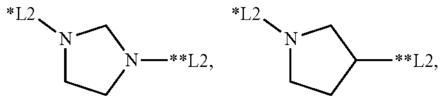
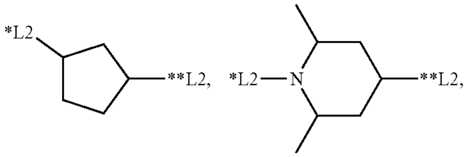
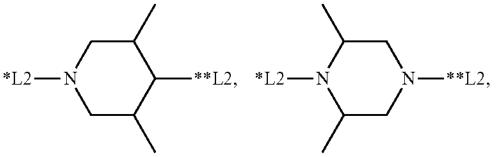

-continued

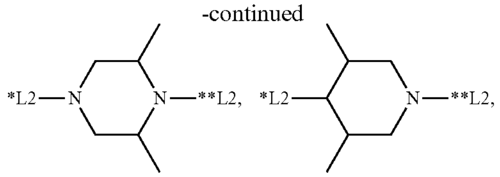
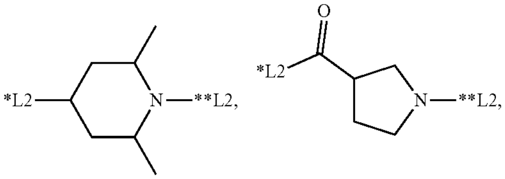
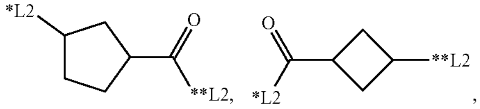
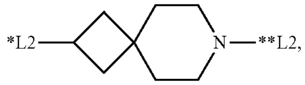
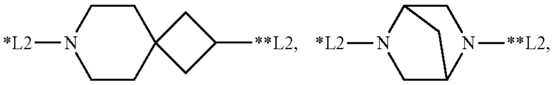
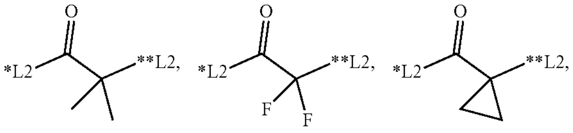
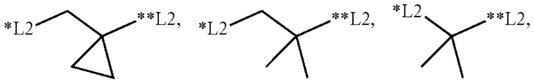
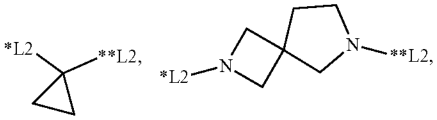
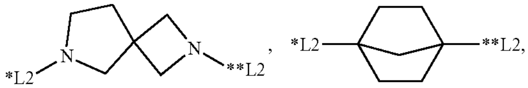
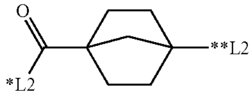
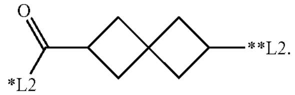

Aspect 25. The compound of any one of Aspects 1-24, wherein m3 is 0, 1, 2, 3, 4, 5 or 6.

Aspect 26. The compound of any one of Aspects 1-25, wherein $L^3$ is selected from a single bond, —O—, —$SO_2$—, —CO—, —$NR^{L3a}$—, —$C_{1-8}$alkylene, —$C_3$-$C_8$cycloalkylene-, $*^{L3}$—O—$C_{1-8}$alkylene-$^{L3}$, $^{L3}C_{1-8}$alkylene-O—$^{L3}$, $*^{L3}$—$SO_2$—$C_{1-8}$alkylene-$**^{L3}$, $*^{L3}$—$C_{1-8}$ alkylene-$SO_2$—$**^{L3}$, $*^{L3}$—CO—$C_{1-8}$alkylene-$**^{L3}$, $*^{L3}$—$C_{1-8}$alkylene-CO—$**^{L3}$, $*^{L3}$—$NR^{L3a}$—$C_{1-8}$ alkylene-$**^{L3}$, $*^{L3}$—$C_{1-8}$alkylene-$NR^{L3a}$—$**^{L3}$, $*^{L3}$—$NR^{L3a}$C(O)—$**^{L3}$, $*^{L3}$—C(O)$NR^{L3a}$—$**^{L3}$, —$C_{1-8}$alkylene-, —$C_{2-8}$alkenylene-, —$C_{2-8}$alkynylene-, —[O$(CR^{L3a}R^{L3b})_{m4}]_{m5}$—,

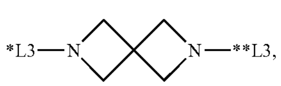
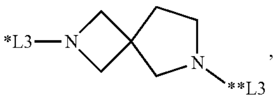

-continued
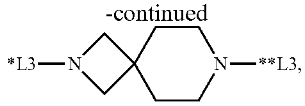
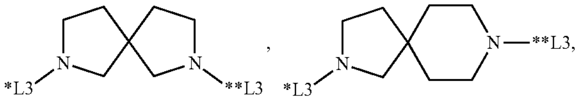
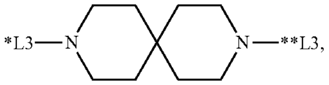
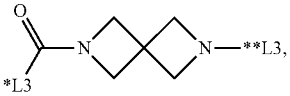
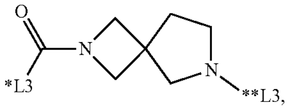
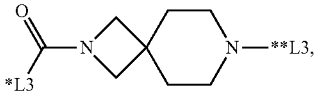
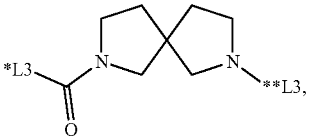
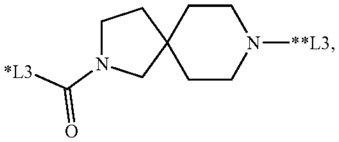
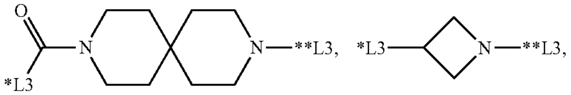
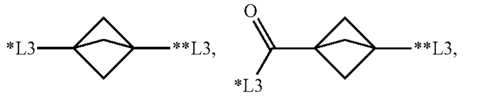
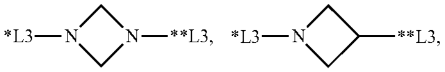
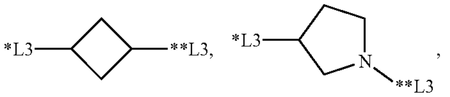
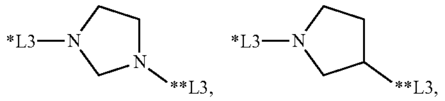
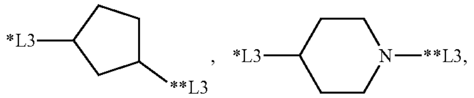
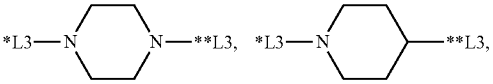
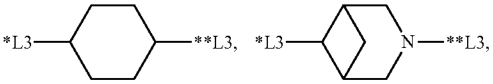
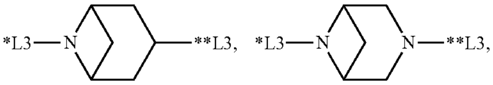
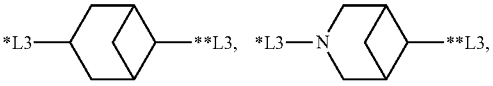
-continued
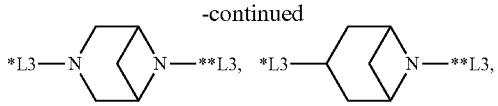
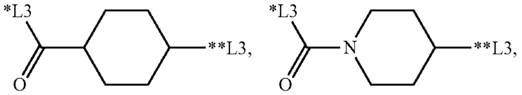
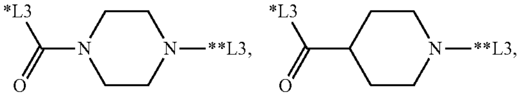
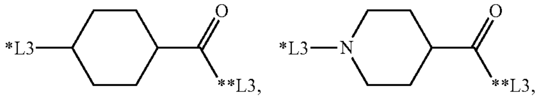
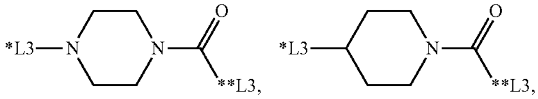
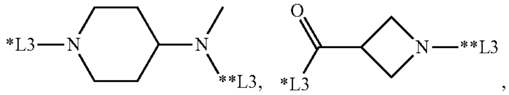
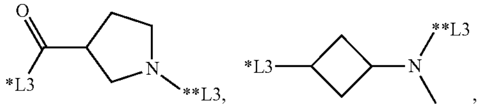
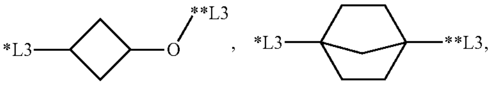
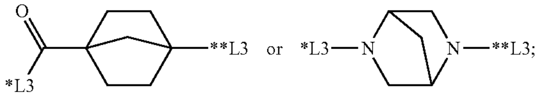
wherein each of said $—C_{1-8}$alkylene, $—C_3$-$C_8$cycloalkylene-, $*^{L3}—O—C_{1-8}$alkylene-$**^{L3}$, $*^{L3}—C_{1-8}$alkylene-O—$**^{L3}$, $*^{L3}—SO_2—C_{1-8}$ alkylene-$**^{L3}$, $*^{L3}—C_{1-8}$alkylene-$SO_2—**^{L3}$, $*^{L3}$—CO—$C_{1-8}$alkylene-$**^{L3}$, $*^{L3}—C_{1-8}$alkylene-CO—$**^{L3}$, $*^{L3}—NR^{L3a}—C_{1-8}$alkylene-$**^{L3}$, $*^{L3}—C_{1-8}$ alkylene-$NR^{L3a}—**^{L3}$, $—C_{1-8}$alkylene-, $—C_{2-8}$ alkenylene-, $—C_{2-8}$alkynylene-,
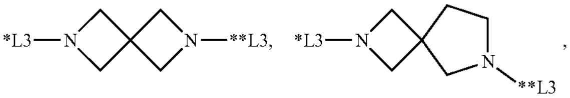
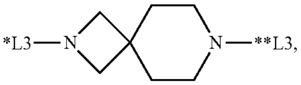
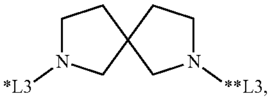
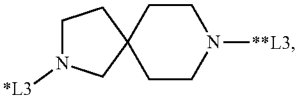
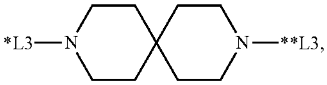
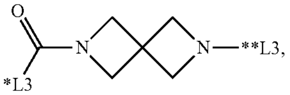

-continued

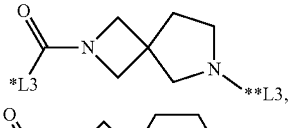

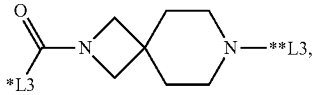

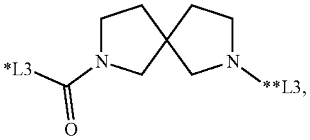

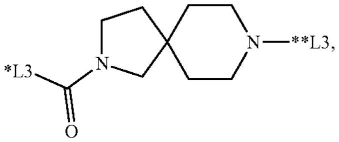

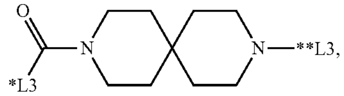

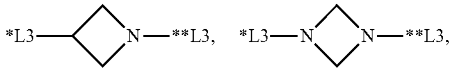

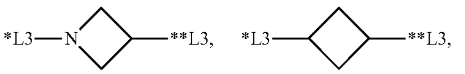

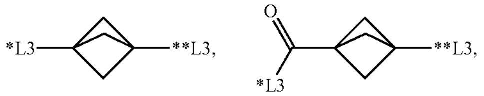

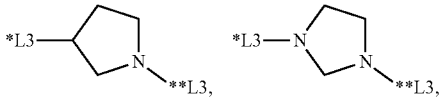

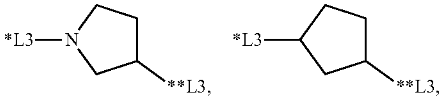

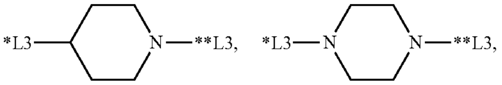

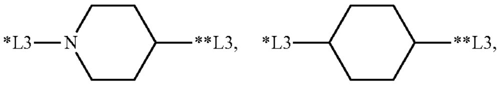

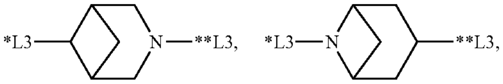

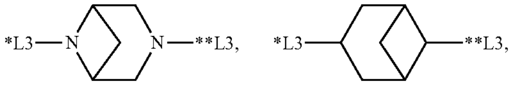

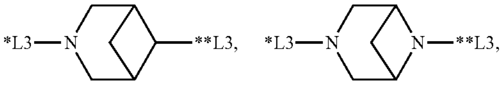

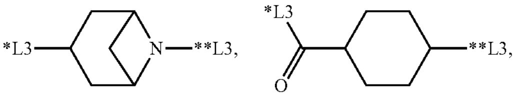

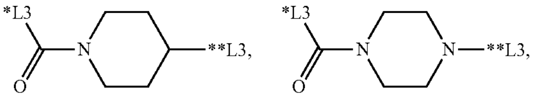

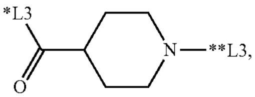

-continued

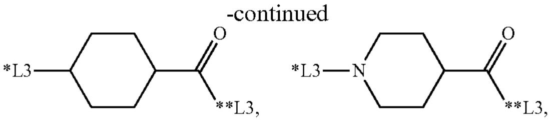

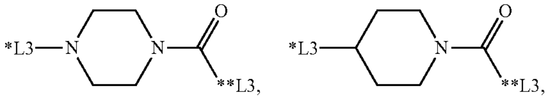

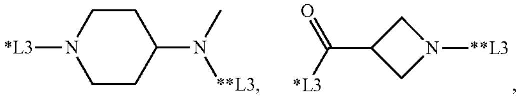

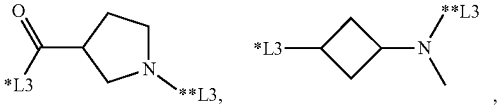

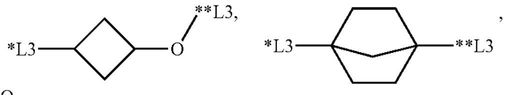

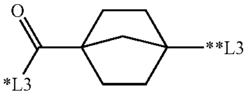

or

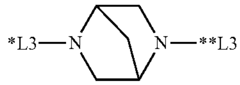

is optionally substituted with at least one substituent $R^{L3c}$;

$R^{L3a}$ and $R^{L3b}$ are each independently selected from hydrogen, methyl, ethyl, propyl, butyl, pentyl, hexyl, heptyl, octyl, vinyl, ethynyl, cyclopropyl, cyclobutyl, cyclopentyl, cyclohexyl, cycloheptyl, cyclooctyl, oxazolidinyl, imidazolidinyl, thiazolidinyl, pyrazolidinyl, morpholinyl, piperidinyl, piperazinyl, oxazinyl, imidazolyl, thiazolyl, oxazolyl, pyridyl, pyrimidinyl, pyrazinyl, pyridazinyl, phenyl, pyrrolyl, imidazolyl, pyrazolyl, thiazolyl, oxazolyl, triazolyl, thiophenyl, furanyl, pyridyl, pyrimidinyl or pyrazinyl, wherein each of said methyl, ethyl, propyl, butyl, pentyl, hexyl, heptyl, octyl, vinyl, ethynyl, cyclopropyl, cyclobutyl, cyclopentyl, cyclohexyl, cycloheptyl, cyclooctyl, oxazolidinyl, imidazolidinyl, thiazolidinyl, pyrazolidinyl, morpholinyl, piperidinyl, piperazinyl, oxazinyl, imidazolyl, thiazolyl, oxazolyl, pyridyl, pyrimidinyl, pyrazinyl, pyridazinyl, phenyl, pyrrolyl, imidazolyl, pyrazolyl, thiazolyl, oxazolyl, triazolyl, thiophenyl, furanyl, pyridyl, pyrimidinyl or pyrazinyl is optionally substituted with at least one substituent $R^{L3d}$;

each of said $R^{L3c}$ and $R^{L3d}$ are independently —F, —Cl, —Br, —I, —OH, methyl, ethyl, propyl, butyl, pentyl, hexyl, heptyl, octyl, vinyl, ethynyl, cyclopropyl, cyclobutyl, cyclopentyl, cyclohexyl, cycloheptyl, cyclooctyl, oxazolidinyl, imidazolidinyl, thiazolidinyl, pyrazolidinyl, morpholinyl, piperidinyl, piperazinyl, oxazinyl, imidazolyl, thiazolyl, oxazolyl, pyridyl, pyrimidinyl, pyrazinyl, pyridazinyl, phenyl, pyrrolyl, imidazolyl, pyrazolyl, thiazolyl, oxazolyl, triazolyl, thiophenyl, furanyl, pyridyl, pyrimidinyl, pyrazinyl or oxo.

Aspect 27. The compound of any one of Aspects 1-26, wherein $L^3$ is selected from single bond, —$C_{1-8}$alkylene- (preferably —$CH_2$—, —$C_2H_4$—, —$C_3H_6$—), —CO—, —O—, —$N(CH_3)$—, —NH—,

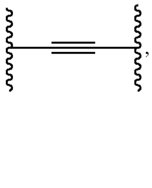,

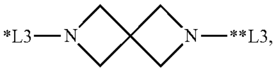

-continued
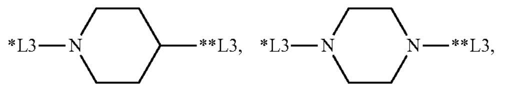
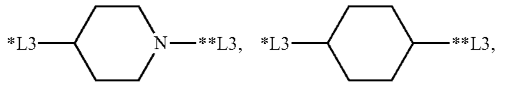
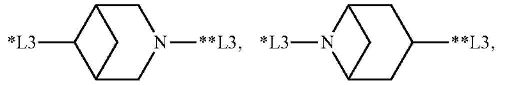
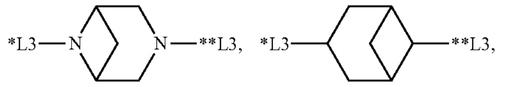
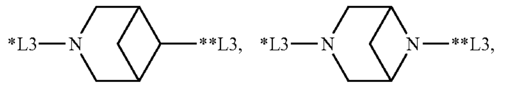
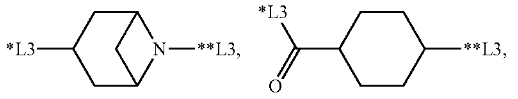
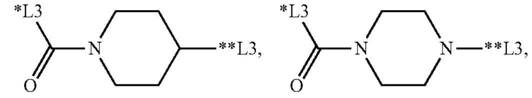
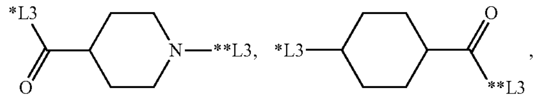
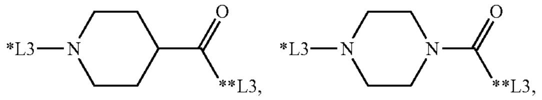
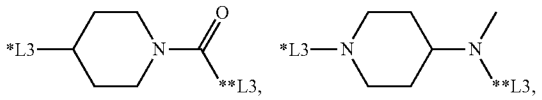
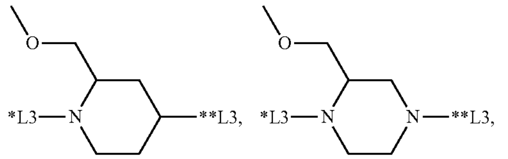
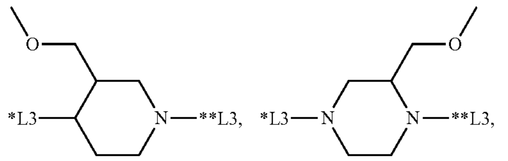
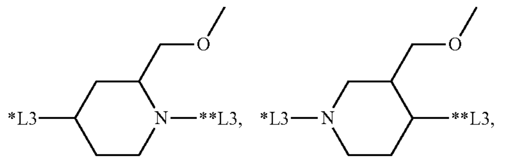
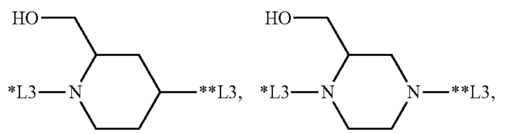
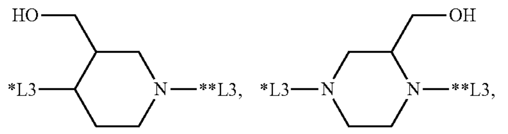
-continued
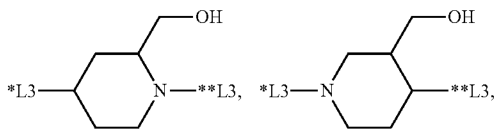
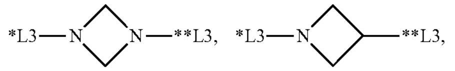
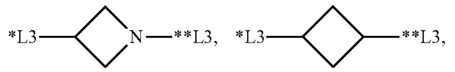
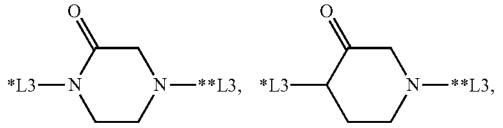
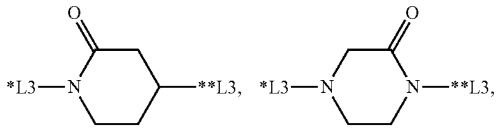
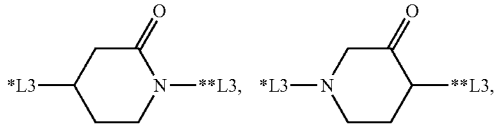
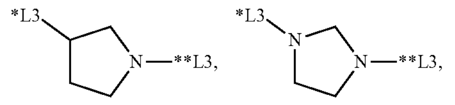
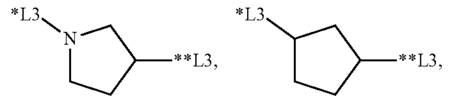
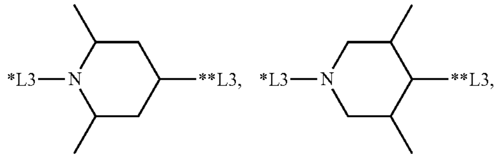
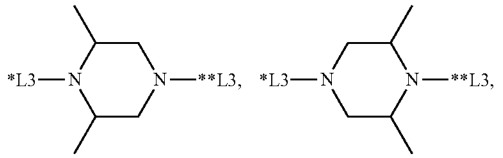
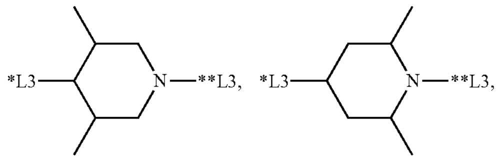
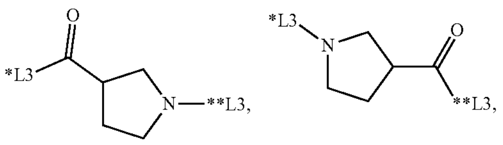
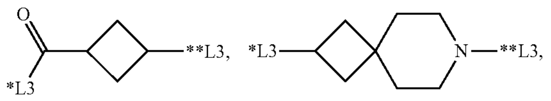
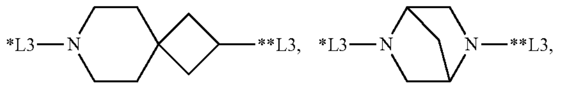

-continued
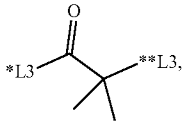, 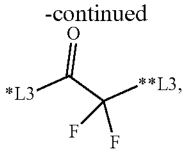, 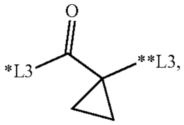, 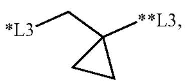, 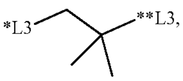, 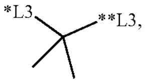, 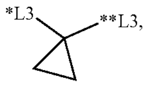, 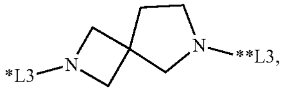, 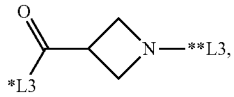, 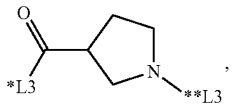, 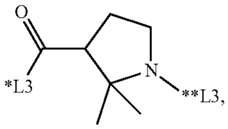, 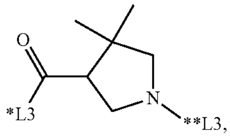, 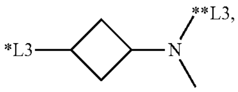, 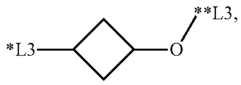, 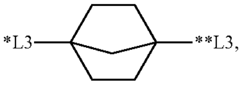, 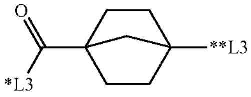 or 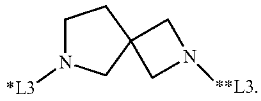.
Aspect 28. The compound of any one of Aspects 1-27, wherein
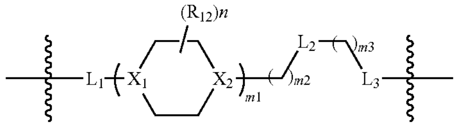
is selected from $-CH_2CH_2-$,
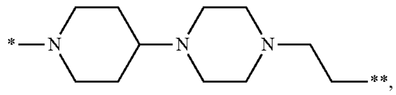,
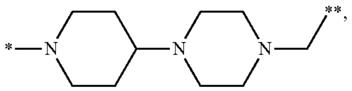,
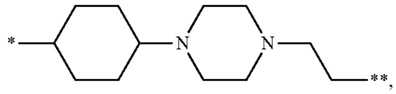,
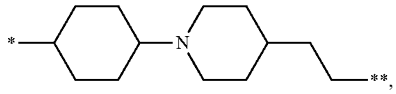,
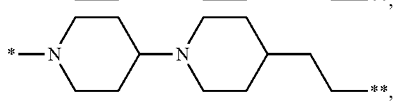,
-continued
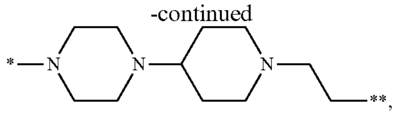,
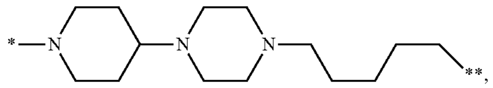,
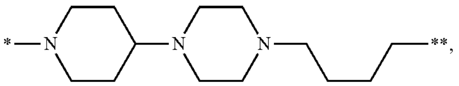,
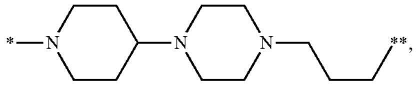,
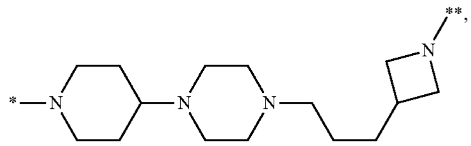,
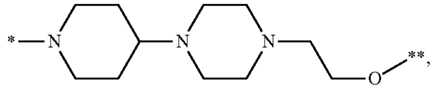,
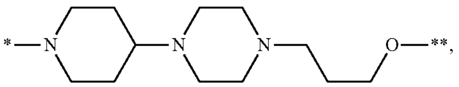,
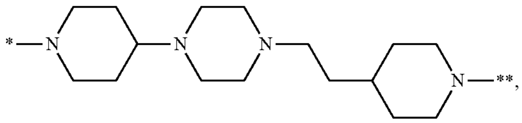,
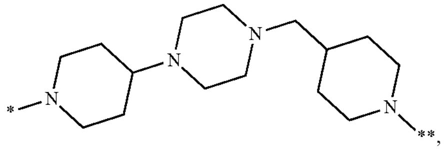,
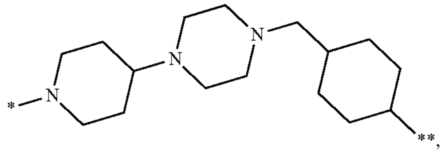,
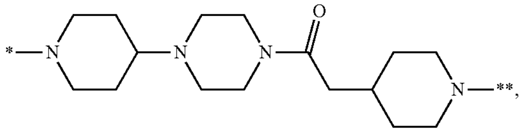,
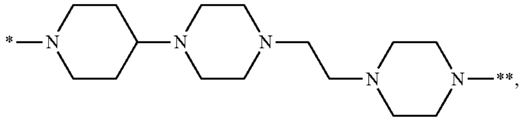,
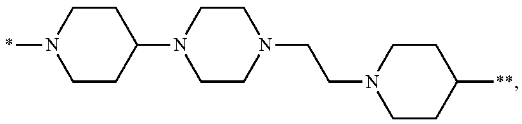,
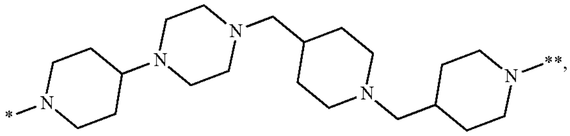,
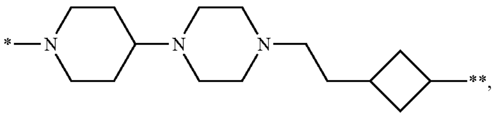, -continued
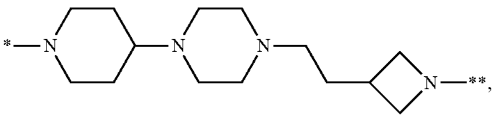
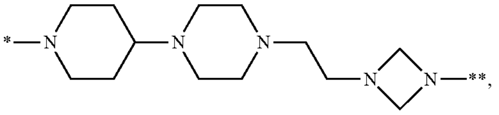
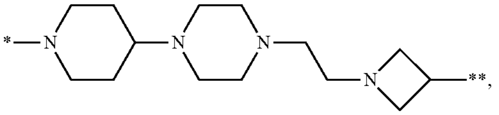
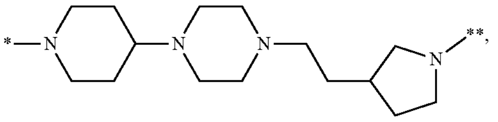
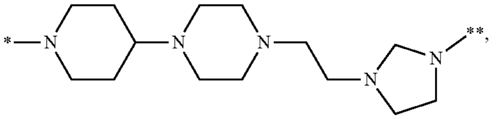
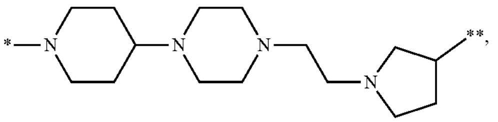
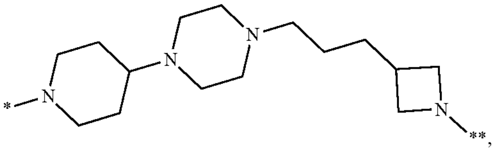
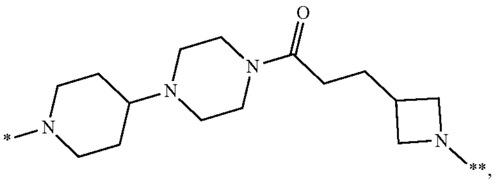
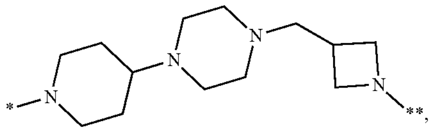
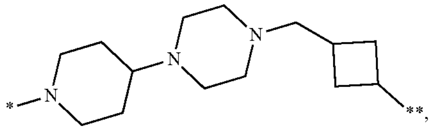
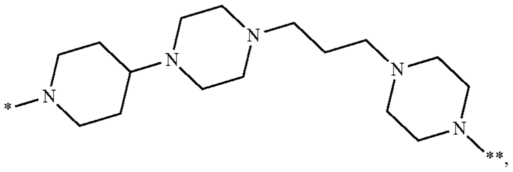
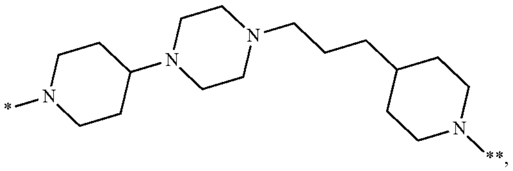
-continued
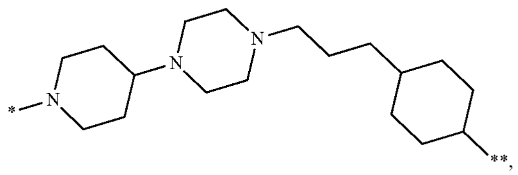
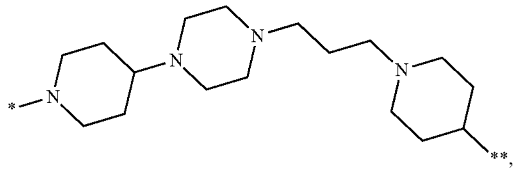
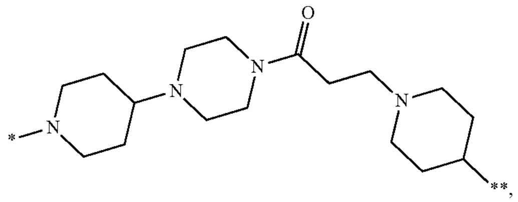
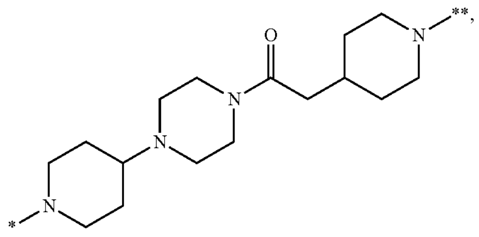
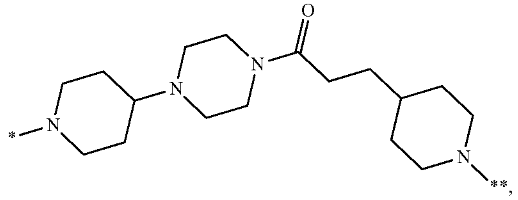
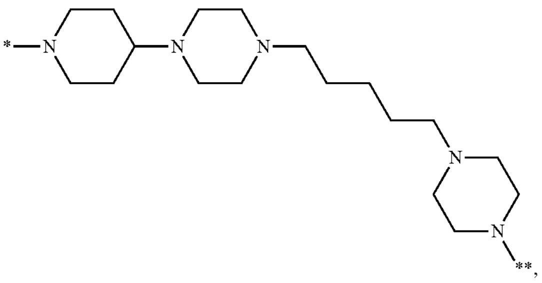
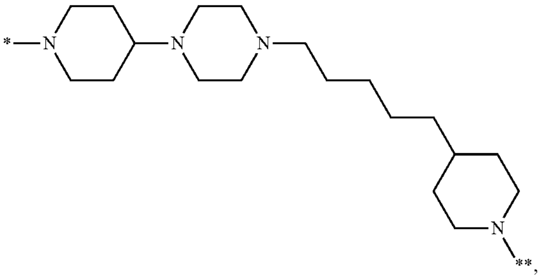

-continued
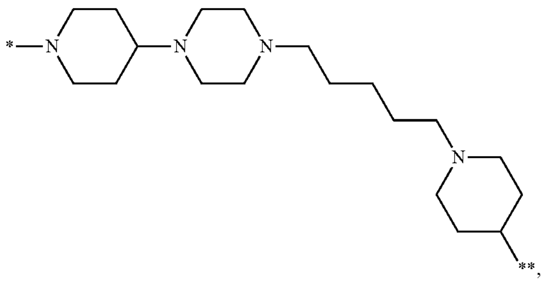
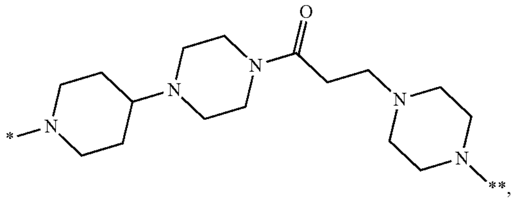
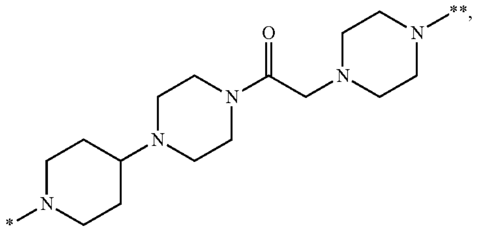
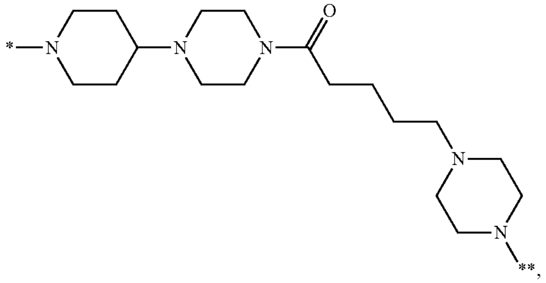
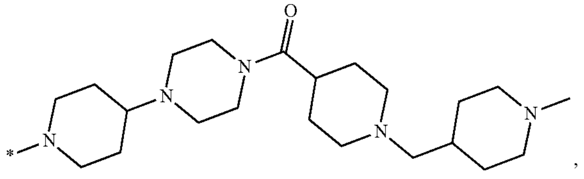
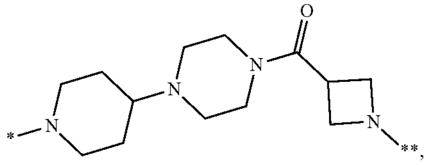
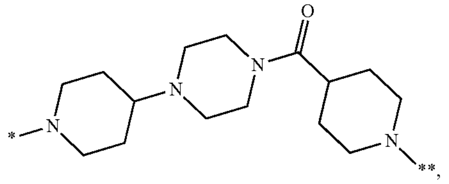
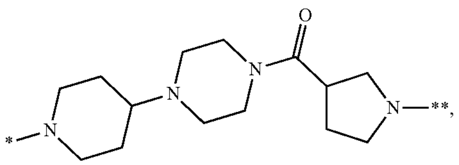
-continued
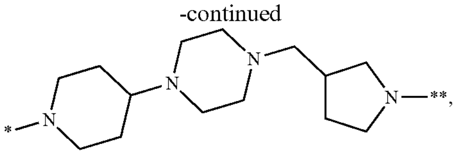
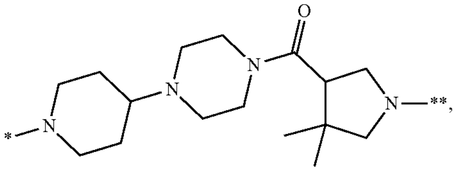
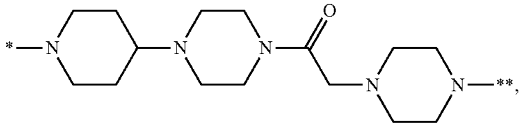
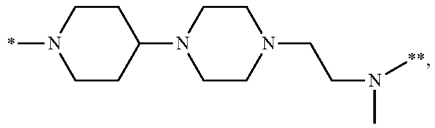
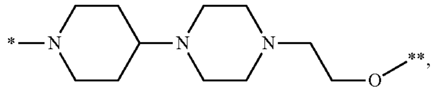
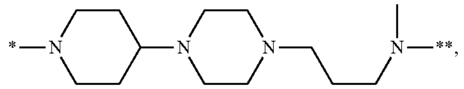
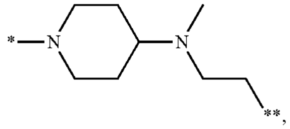
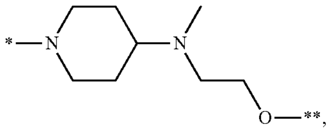
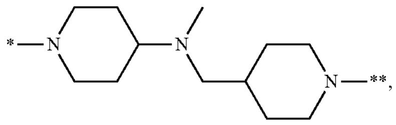
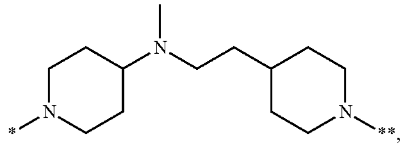
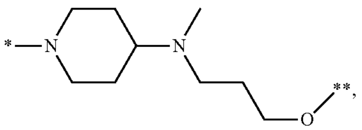
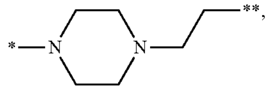
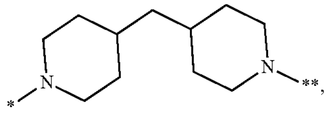
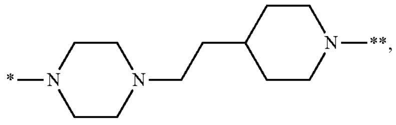

-continued
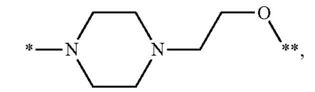
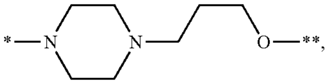
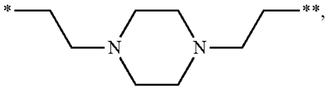
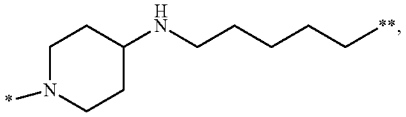
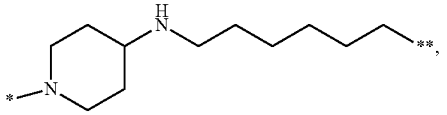
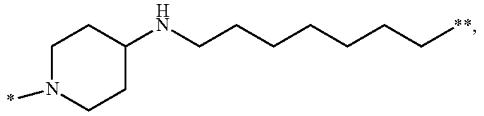
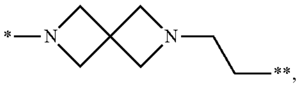
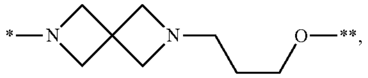
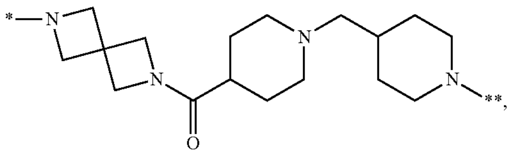
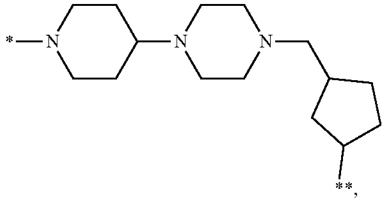
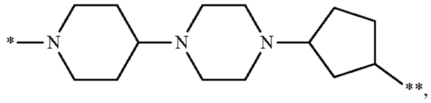
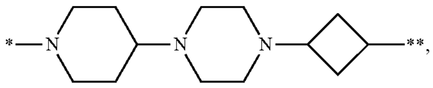
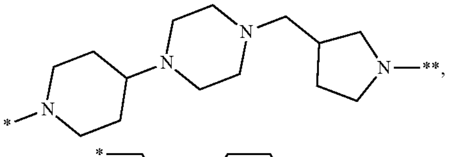
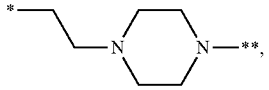
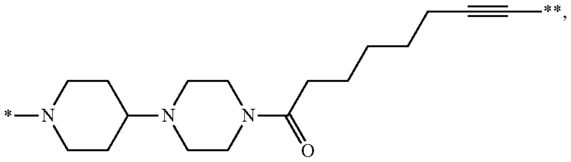
-continued
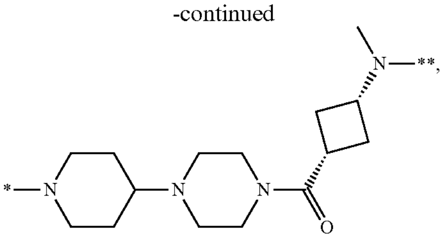
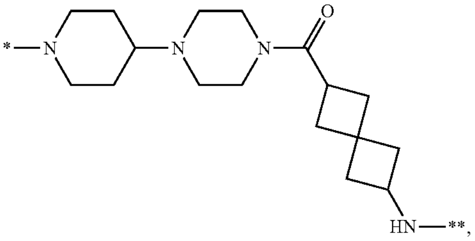
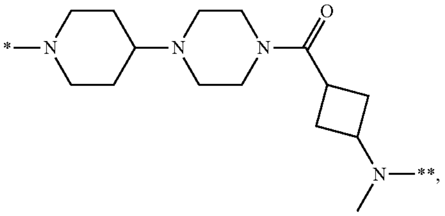
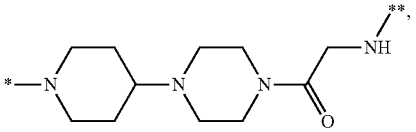
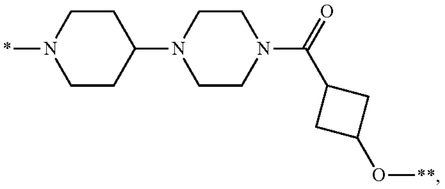
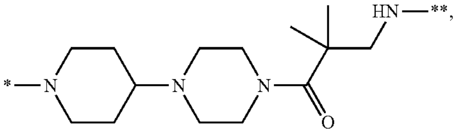
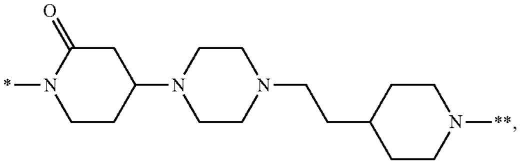
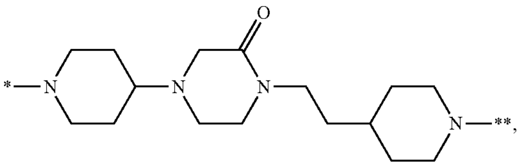
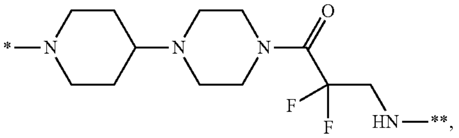
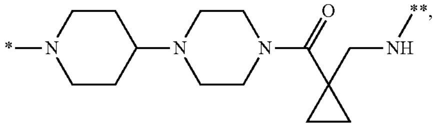

-continued
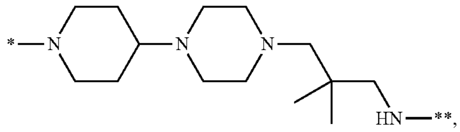
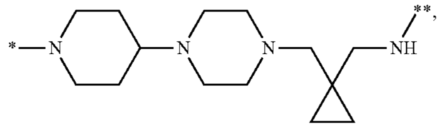
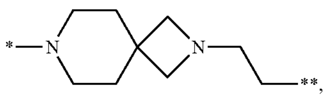
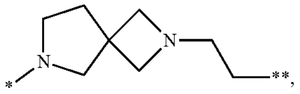
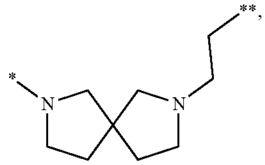
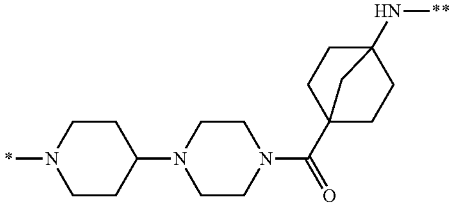
or
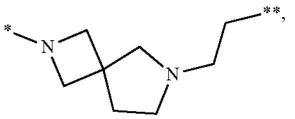
wherein * refers to the position attached to
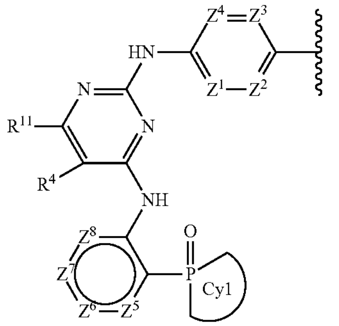
moiety, and ** refers to the position attached to the
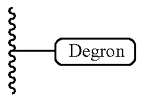
moiety.
Aspect 29. The compound of any one of Aspects 1-28, wherein
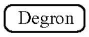
is selected from
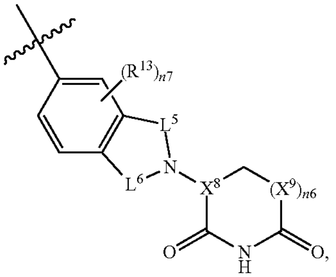
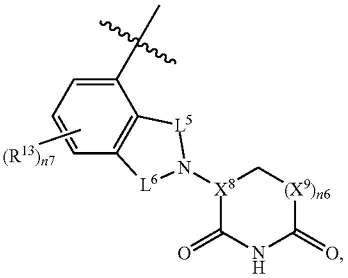
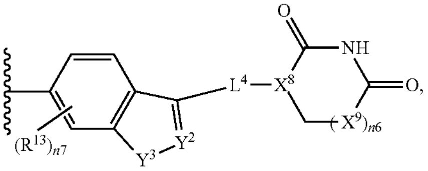
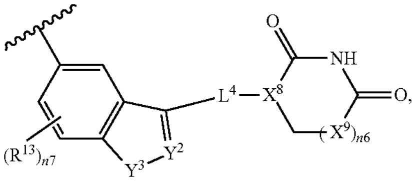
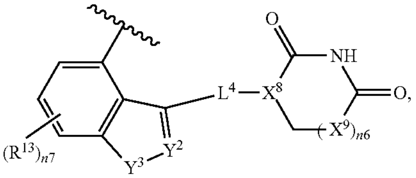
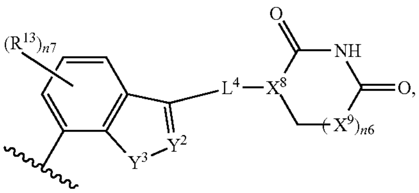

-continued

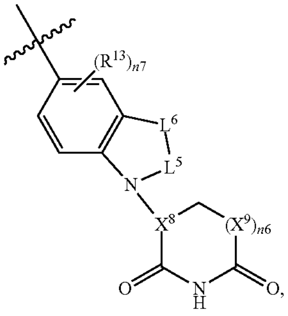

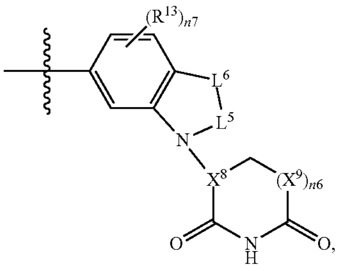

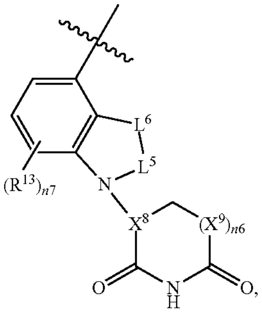

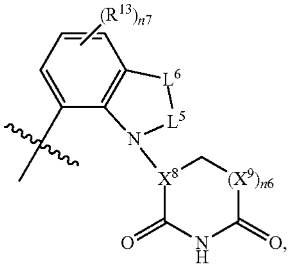

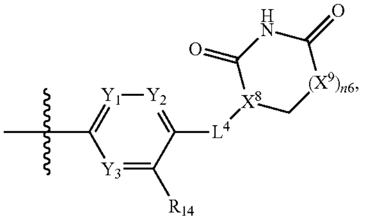

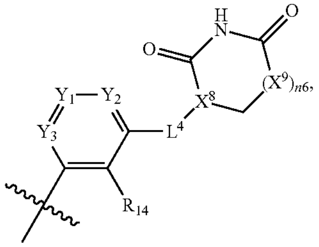

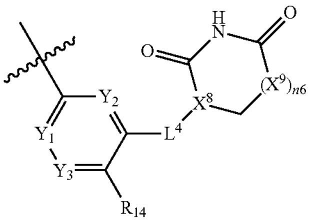

or

-continued

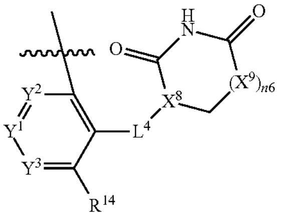

$R^{14}$ is independently selected from hydrogen, halogen, $-C_{1-8}$alkyl, $-C_{1-8}$alkoxy, or CN; said each $-C_{1-8}$ alkyl, or $-C_{1-8}$alkoxy is optionally substituted by one or more halogen or $-C_{1-8}$alkyl, preferably $R^{14}$ is independently selected from H, F, Cl, Br, I, $CH_3$, $-OCH_3$, $CH_2F$, CN, $CHF_2$, or $CF_3$;

$X^8$ is independently selected from CH, CD, $C(CH_3)$, $C(C_2H_5)$, $C(C_3H_7)$, C(CN) or N;

$L^4$ is independently selected from a single bond,

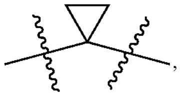 [SMILES: *C1(*)CC1]

—O—, —NH—, $-CH_2-$, —CHF—, or $-CF_2-$;

$Y^1$, $Y^2$, and $Y^3$ are each independently selected from $CR^a$ or N;

$X^9$ is $CH_2$;

$R^a$ is each independently selected from hydrogen, halogen, $-C_{1-8}$alkyl, or $-C_{1-8}$alkoxy, wherein each of said $-C_{1-8}$alkyl or $-C_{1-8}$alkoxy is optionally substituted with at least one or more halogen, hydroxy, halogen, $-C_{1-8}$alkyl, or $-C_{1-8}$alkoxy; and n6 is independently 0, 1 or 2.

Aspect 30. The compound of any one of Aspects 1-29, wherein

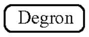

is

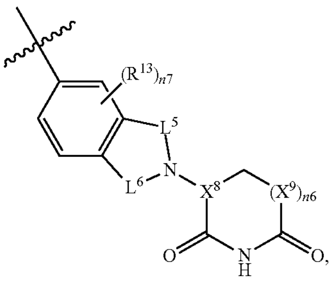

-continued
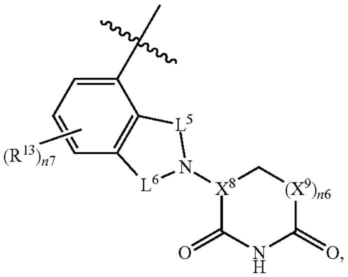
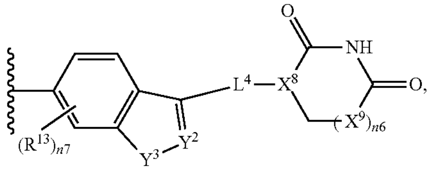
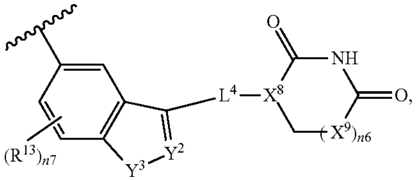
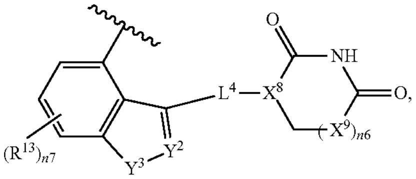
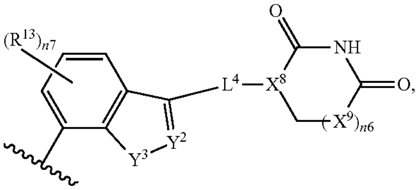
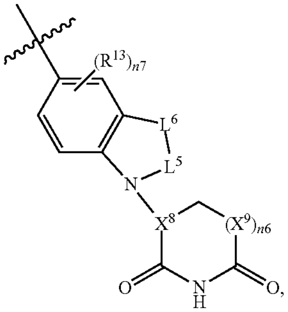
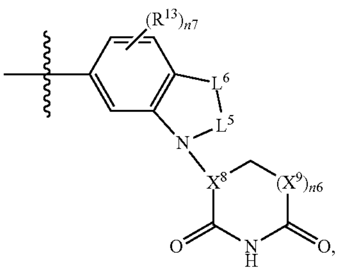
-continued
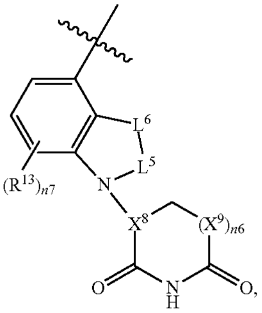
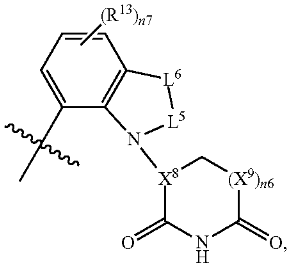
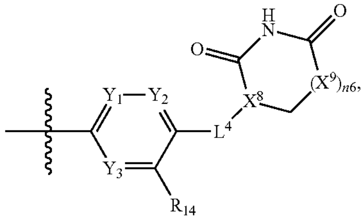
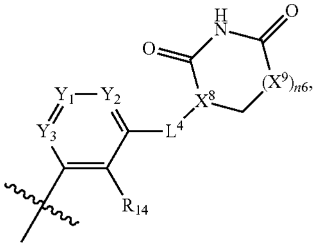
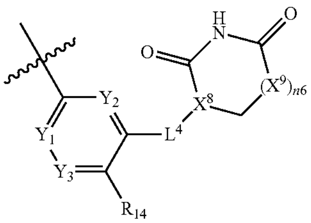
or
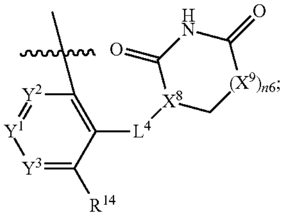
Wherein $L^5$ and $L^6$ is independently selected from a single bond,
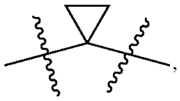 [SMILES: *C1(*)CC1]
—O—, —NH—, —NMe-, —$N(CH_2CH_3)$—, —$CH_2$—, —CHF—, —$CF_2$—, —$C(CH_3)_2$— or —CO— (preferably $L^5$ is —CO— or —$CH_2$—, and $L^6$ is

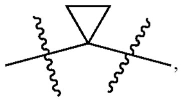 [SMILES: *C1(*)CC1]
—O—, —NH—, —NMe-, —$N(CH_2CH_3)$—, —$CH_2$—, —CHF—, —$CF_2$—, —$C(CH_3)_2$— or —CO—);
$X^9$ is $CH_2$;
each $R^{13}$ is independently selected from hydrogen, —F, —Cl, —Br, —I, CN, —$C_{1-8}$alkyl, or —$C_{1-8}$alkoxy;
$n_6$ is 0 or 1; and
$n_7$ is 0, 1 2.
Aspect 31. The compound of any one of Aspects 1-30, wherein
Degron
is selected from
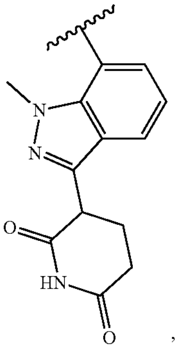
,
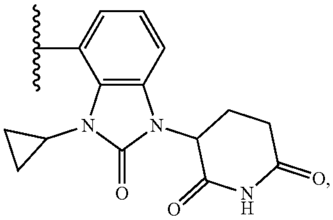
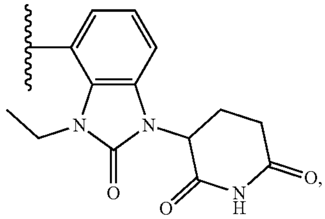
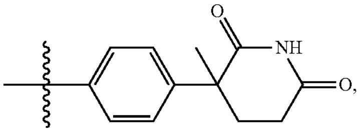
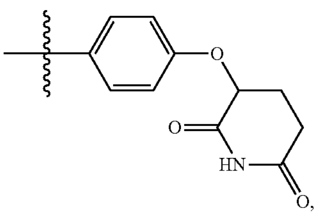
-continued
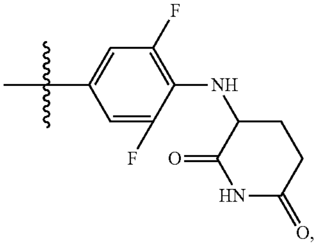
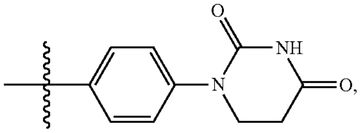
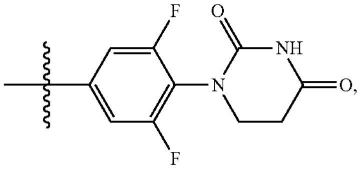
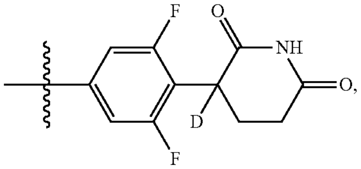
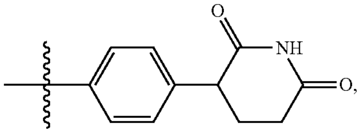
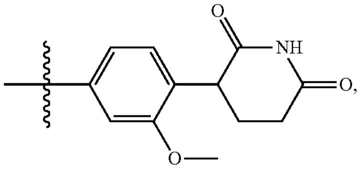
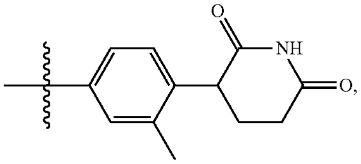
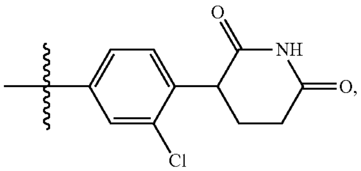
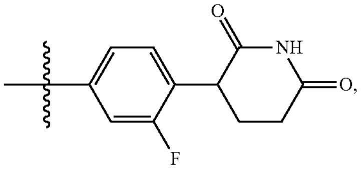
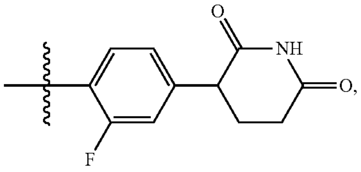

-continued
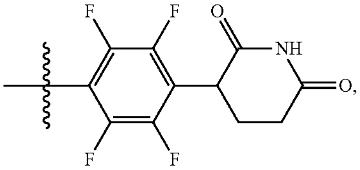
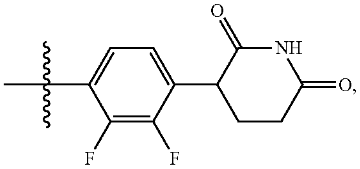
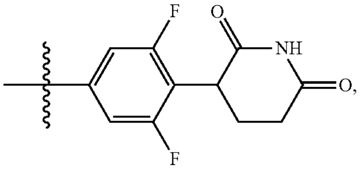
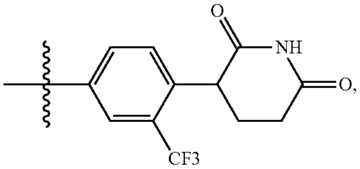
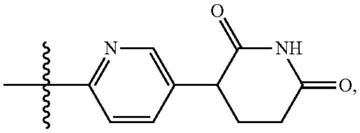
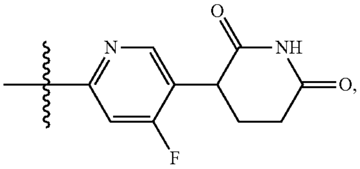
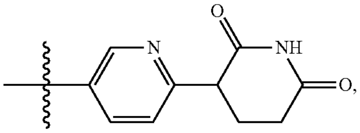
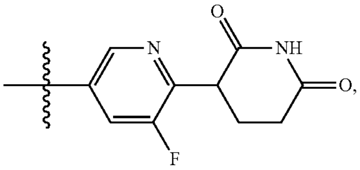
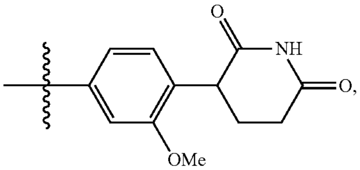
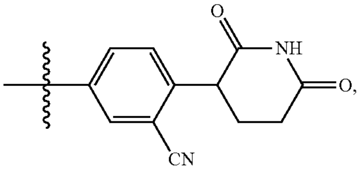
-continued
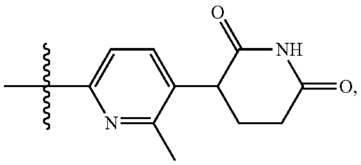
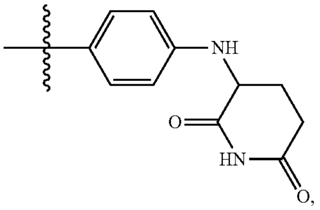
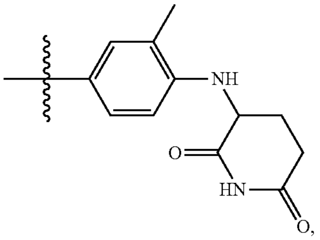
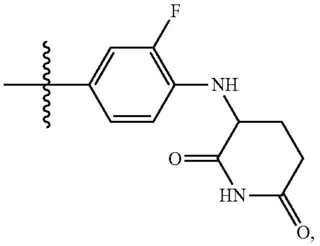
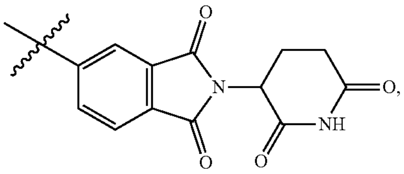
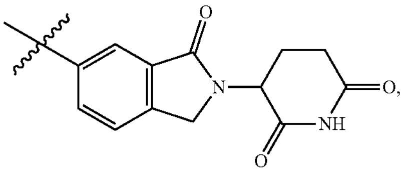
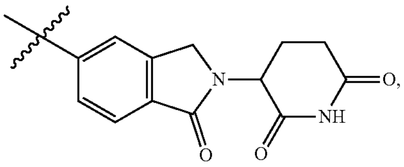
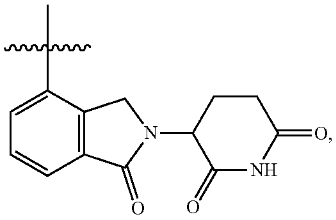

-continued
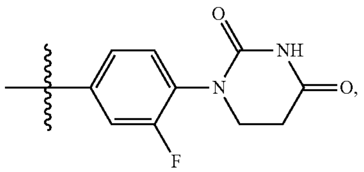
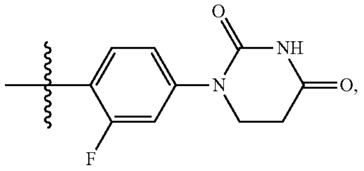
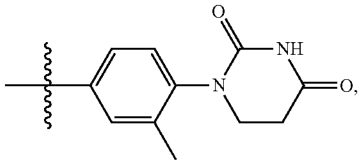
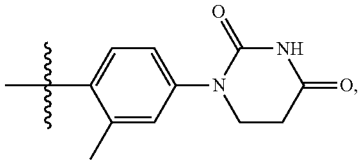
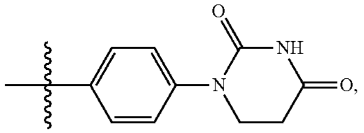
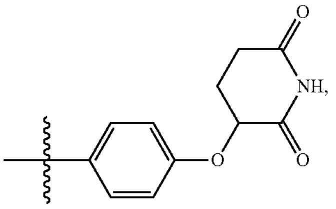
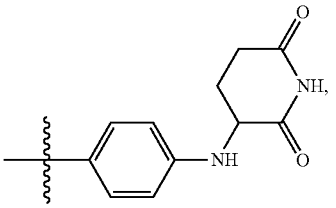
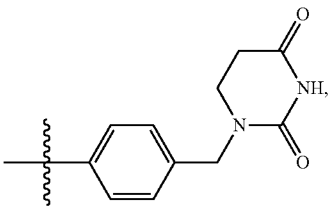
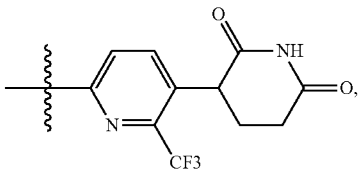
-continued
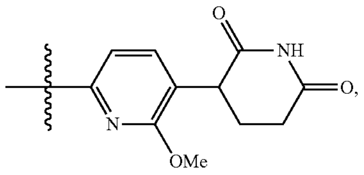
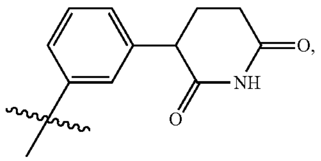
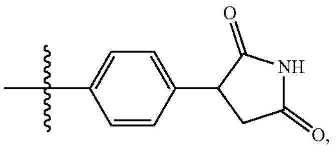
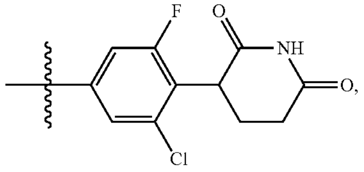
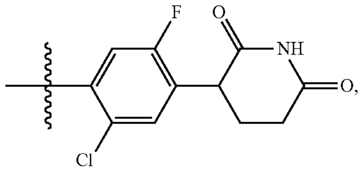
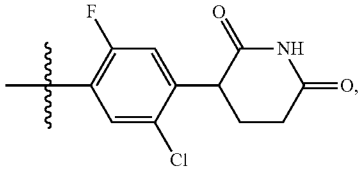
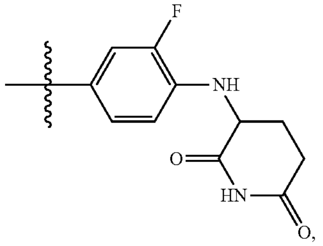
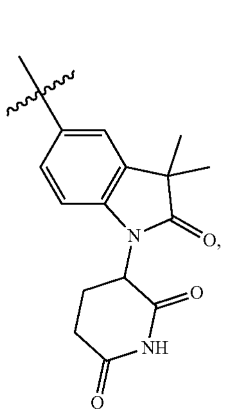
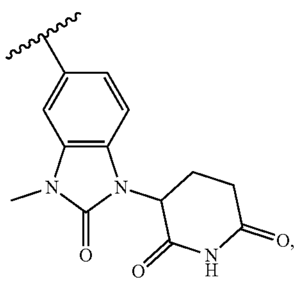

-continued
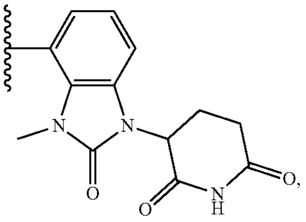
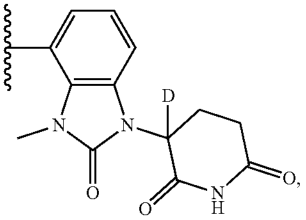
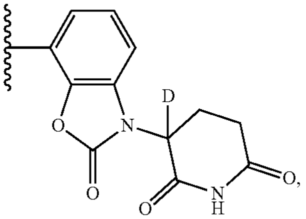
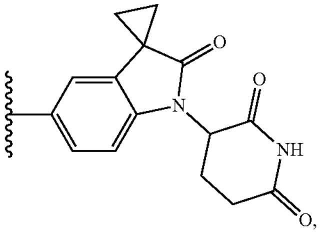
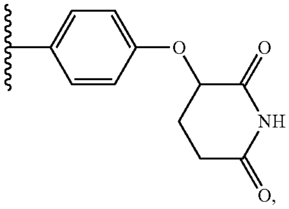
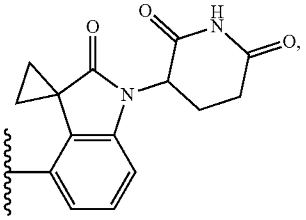
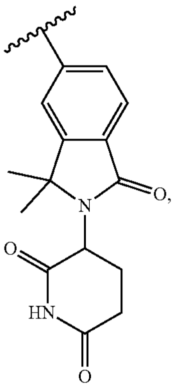
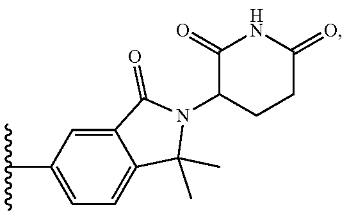
-continued
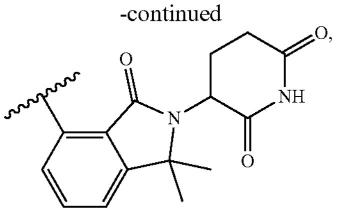
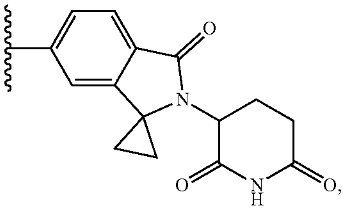
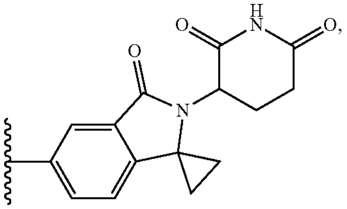
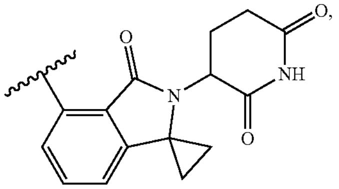
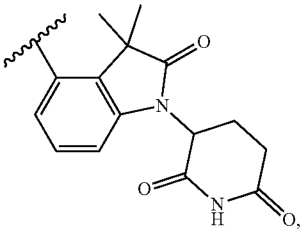
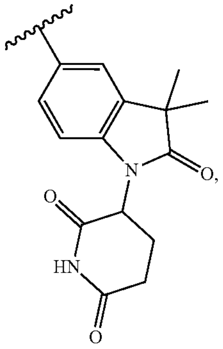
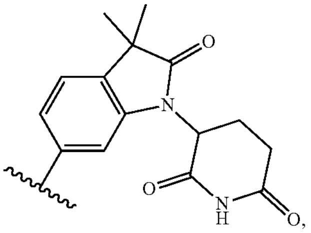
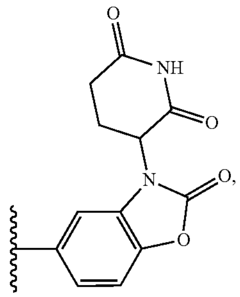
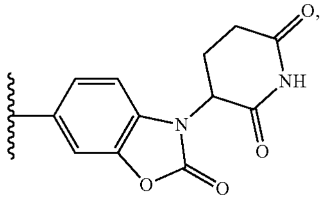

-continued
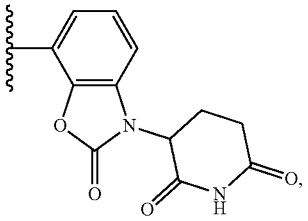
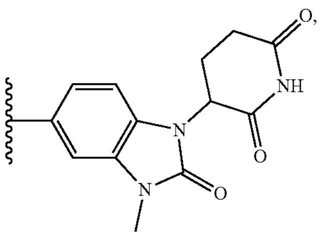
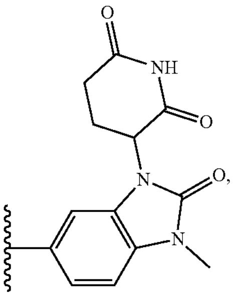
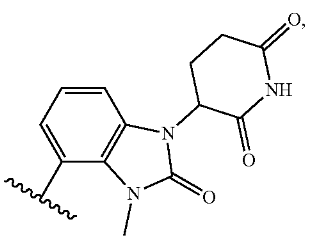
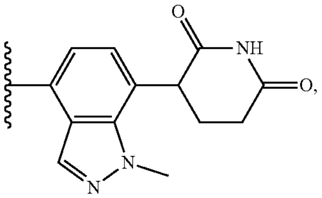
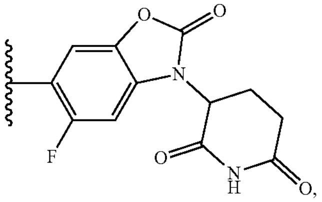
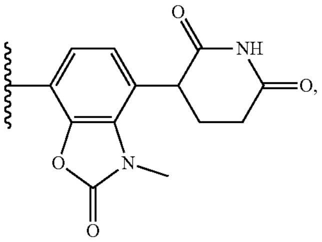
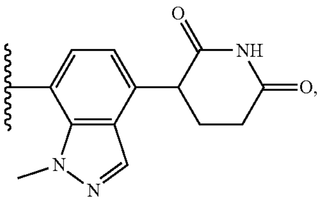
-continued
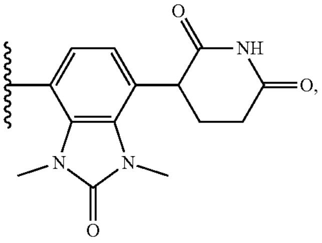
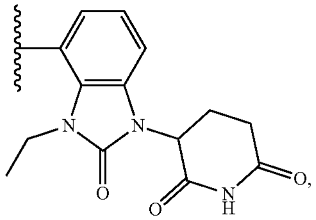
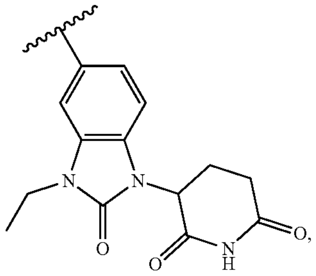
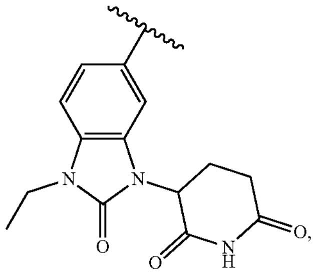
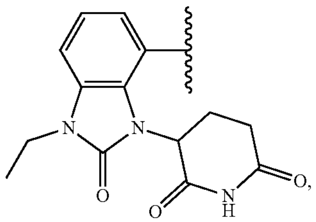
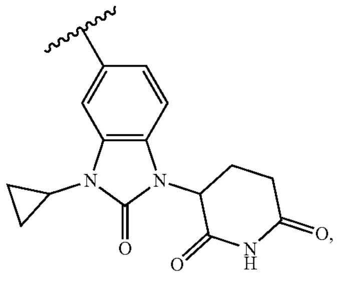

-continued

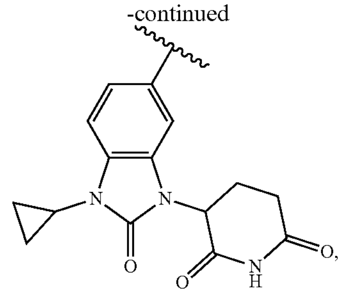

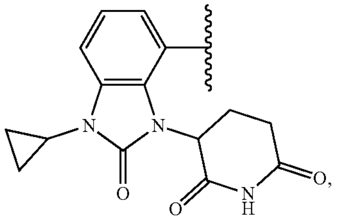

or

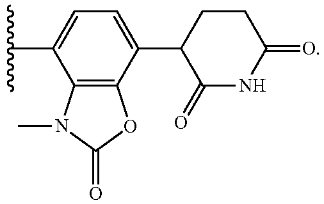

Aspect 32. The compound of any one of Aspects 1-31, wherein $Z^1$, $Z^2$, $Z^3$ and $Z^4$ are each independently —$CR^z$;

$R^Z$, at each of its occurrences, is independently selected from hydrogen, —F, —Cl, —Br, —I, methyl, ethyl, propyl, butyl, pentyl, hexyl, heptyl, octyl, —$NR^{Za}R^{Zb}$, —$OR^{Za}$, —$SR^{Za}$, cyclopropyl, cyclobutyl, cyclopentyl, cyclohexyl, cycloheptyl, cyclooctyl, 3- to 8-membered heterocyclyl, phenyl, 5- to 12-membered heteroaryl, or CN, wherein each of methyl, ethyl, propyl, butyl, pentyl, hexyl, heptyl, octyl, cyclopropyl, cyclobutyl, cyclopentyl, cyclohexyl, cycloheptyl, cyclooctyl, 3- to 8-membered heterocyclyl, phenyl, or 5- to 12-membered heteroaryl is optionally substituted with at least one $R^{Ze}$;

$R^{Za}$ and $R^{Zb}$ are each independently selected from hydrogen, methyl, ethyl, propyl, butyl, pentyl, hexyl, heptyl, octyl, —$C_{2-8}$alkenyl, —$C_{2-8}$alkynyl, cyclopropyl, cyclobutyl, cyclopentyl, cyclohexyl, cycloheptyl, cyclooctyl, 3- to 8-membered heterocyclyl, phenyl or 5- to 12-membered heteroaryl, wherein each of said hydrogen, methyl, ethyl, propyl, butyl, pentyl, hexyl, heptyl, octyl, —$C_{2-8}$alkenyl, —$C_{2-8}$alkynyl, cyclopropyl, cyclobutyl, cyclopentyl, cyclohexyl, cycloheptyl, cyclooctyl, 3- to 8-membered heterocyclyl, phenyl or 5- to 12-membered heteroaryl is optionally substituted with at least one substituent $R^{Zd}$;

$R^{Zc}$ and $R^{Zd}$ are each independently —F, —Cl, —Br, —I, hydroxy, methyl, ethyl, propyl, butyl, pentyl, hexyl, heptyl, octyl, —$C_{1-8}$alkoxy, —$C_{2-8}$alkenyl, —$C_{2-8}$ alkynyl, cyclopropyl, cyclobutyl, cyclopentyl, cyclohexyl, cycloheptyl, cyclooctyl, 3- to 8-membered heterocyclyl, phenyl, or 5- to 12-membered heteroaryl.

Aspect 33. The compound of any one of Aspects 1-32, wherein $R^z$ is independently selected from H, —$CH_3$, —$C_2H_5$, F, —$CH_2F$, —$CHF_2$, —$CF_3$, —$OCH_3$, —$OC_2H_5$, —$C_3H_7$, —$OCH_2F$, —$OCHF_2$, —$OCH_2CF_3$, —$OCF_3$, —$SCF_3$, —$CF_3$, cyclopropyl or —$CH(OH)CH_3$.

Aspect 34. The compound of any one of Aspects 1-33, wherein the deuterium substitution is on degron, preferable, deuterium substitution is on $X^8$.

Aspect 35. The compound of any one of Aspects 1-34, wherein the compound is selected from

1

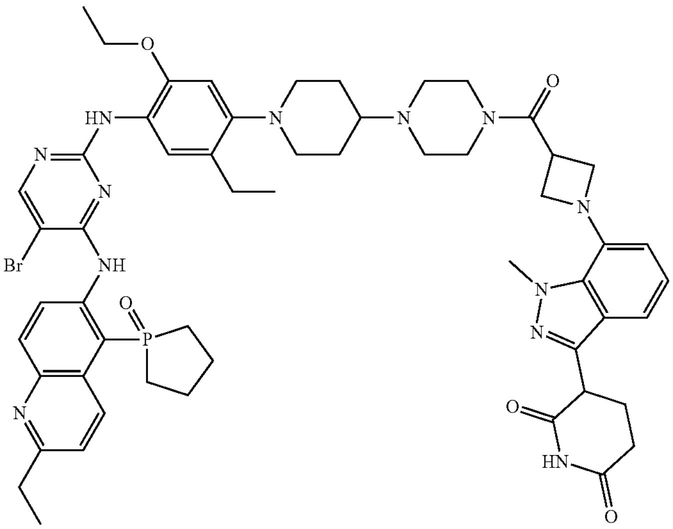

-continued
2
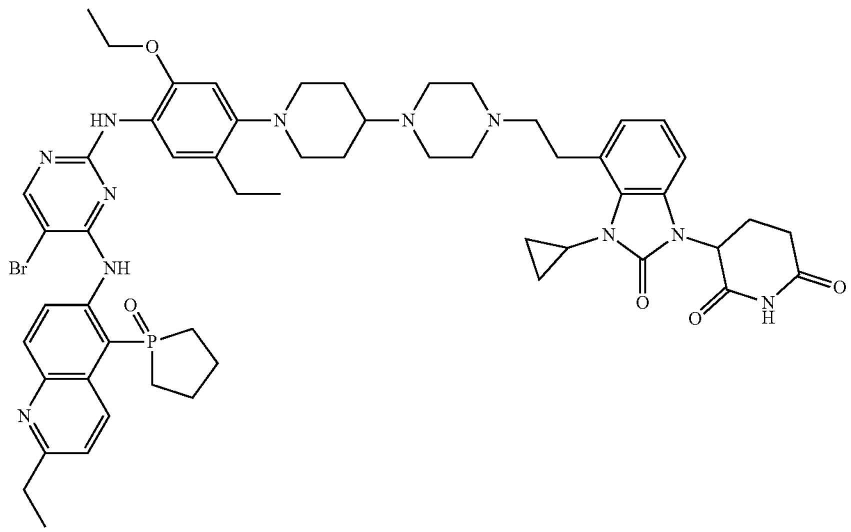
3
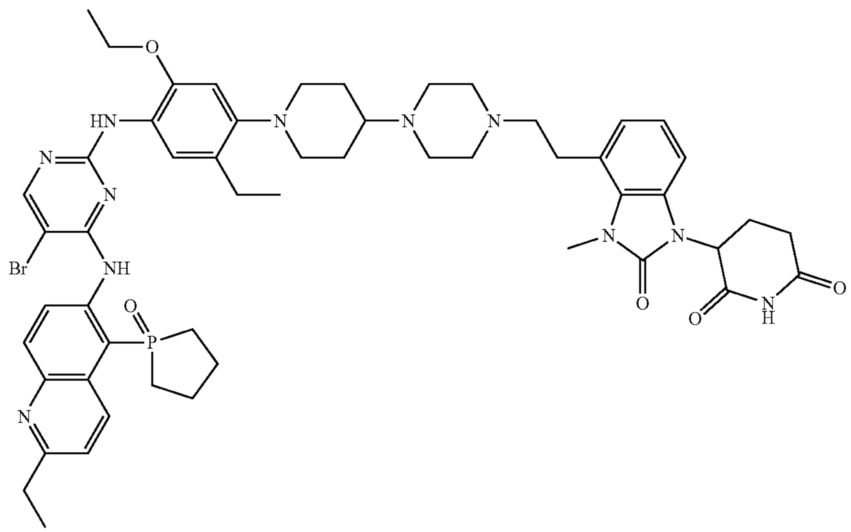
4
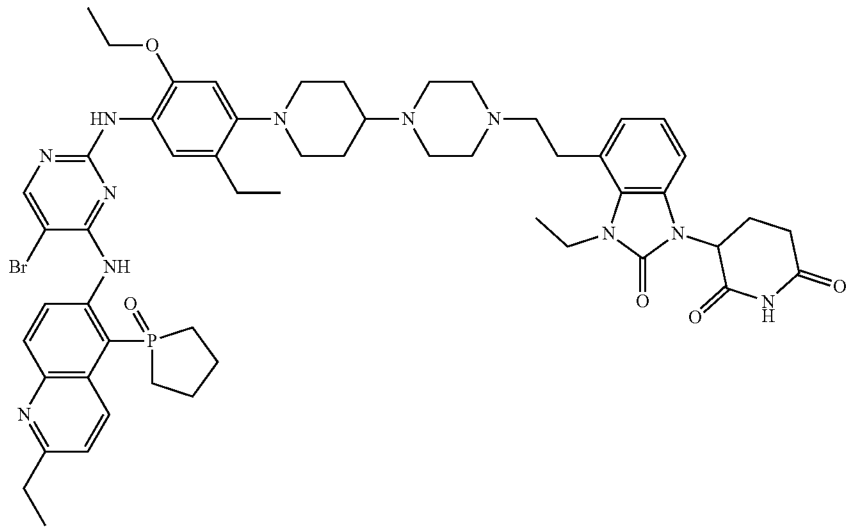

-continued
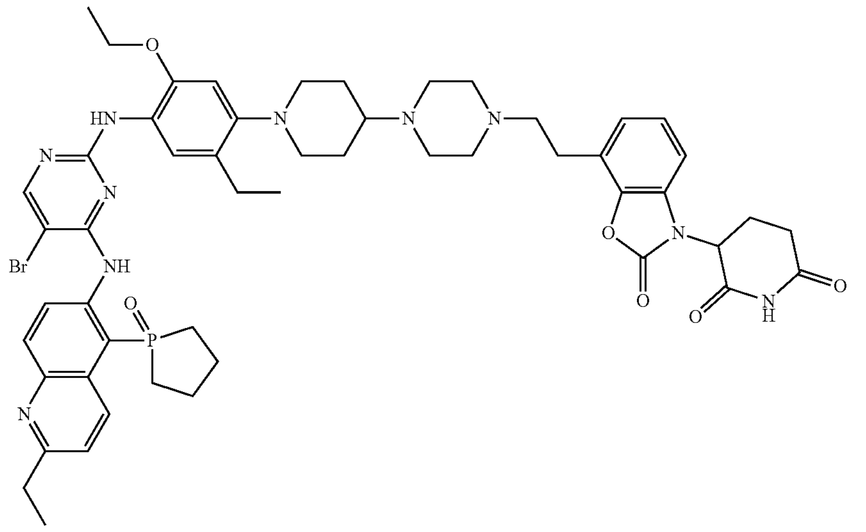
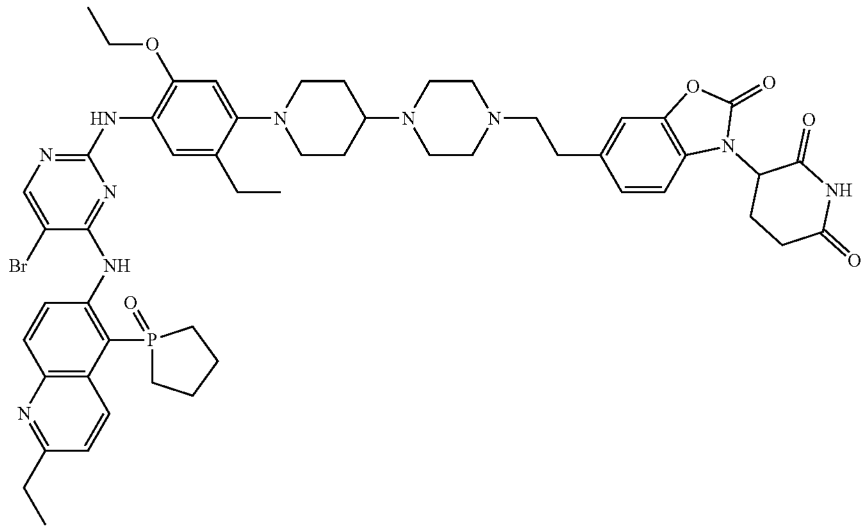
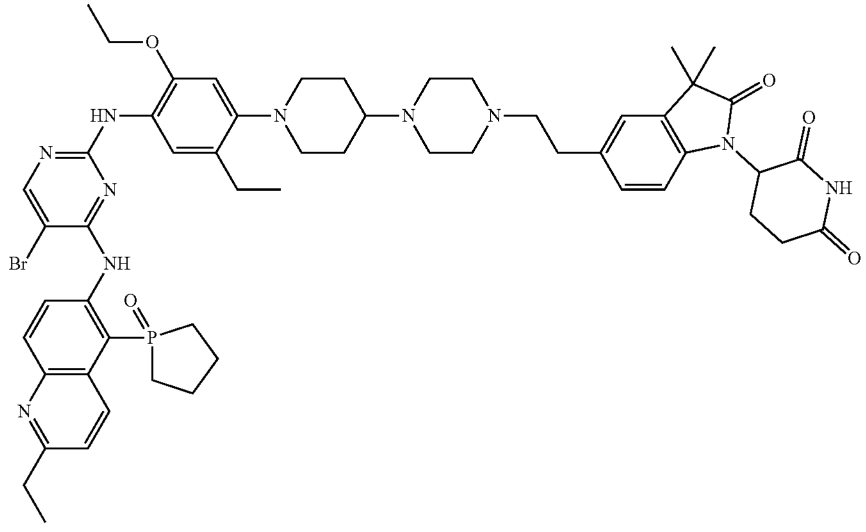

-continued
8
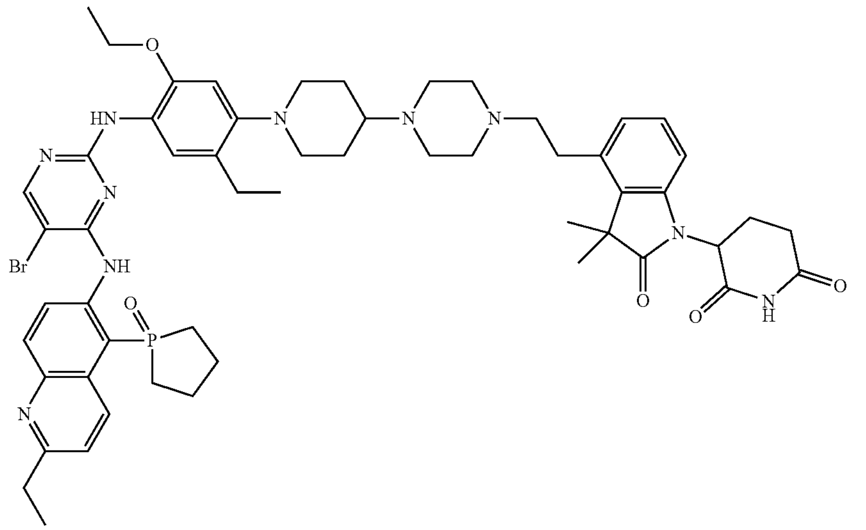
9
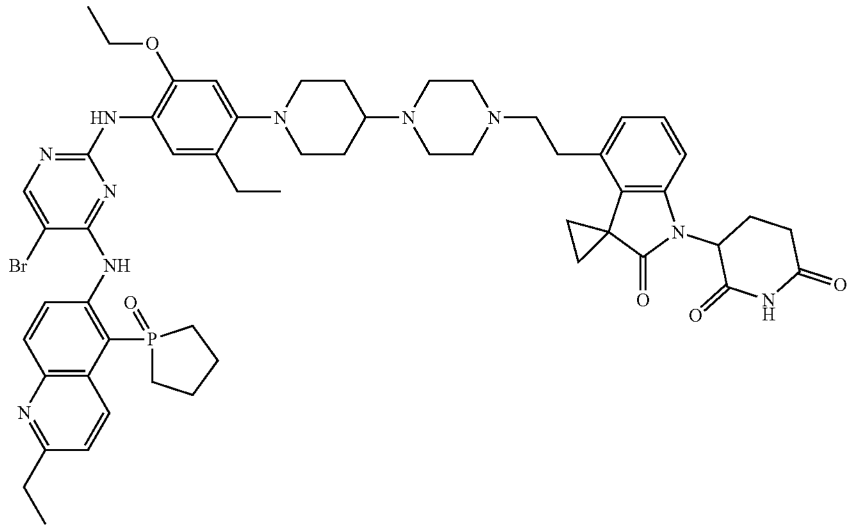
10
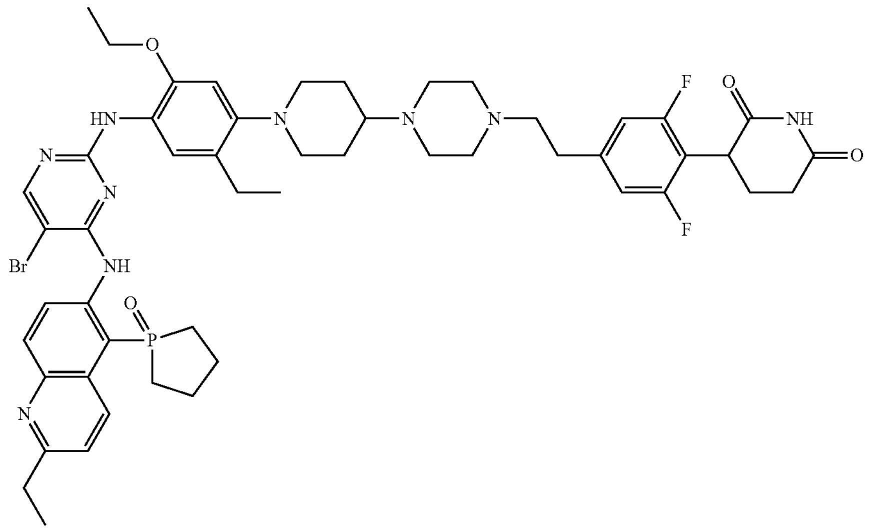

-continued
11
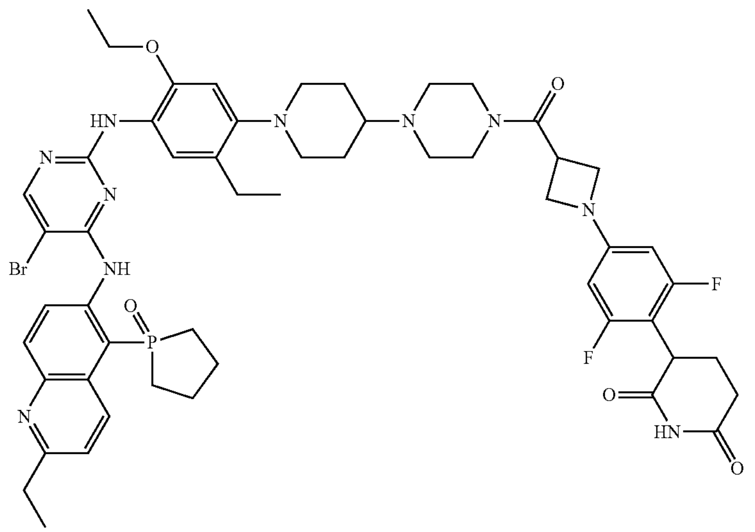
12
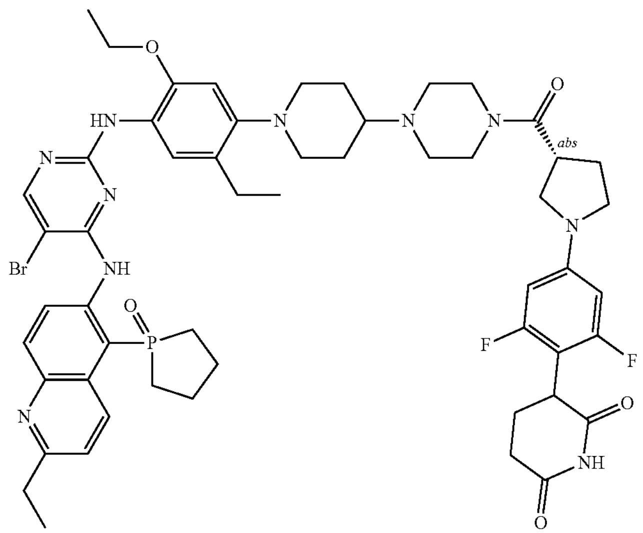
13
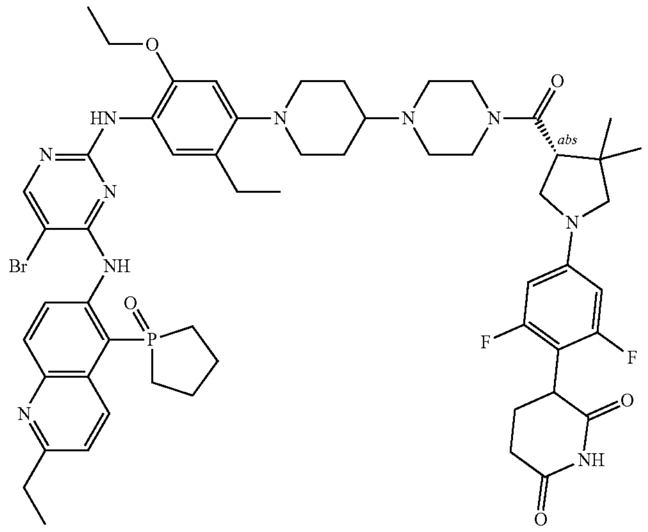

-continued
14
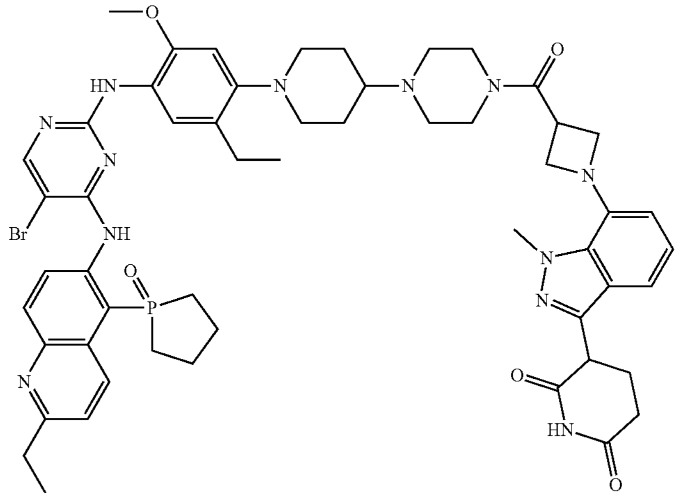
15
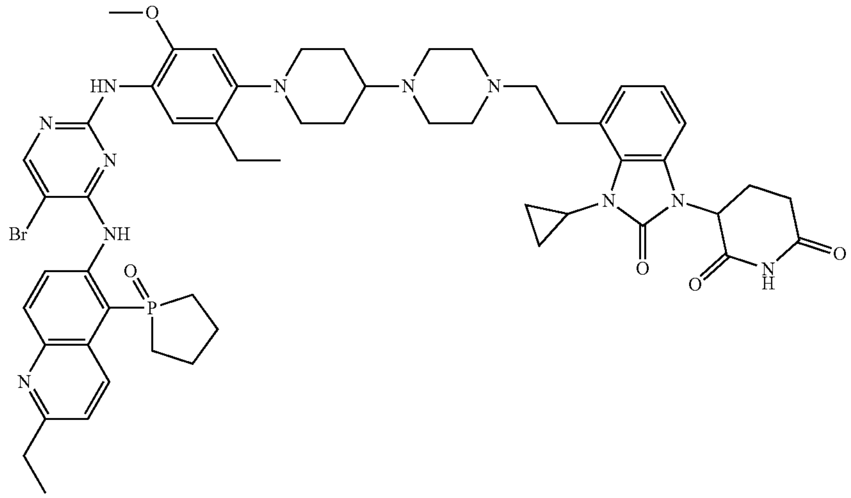
16
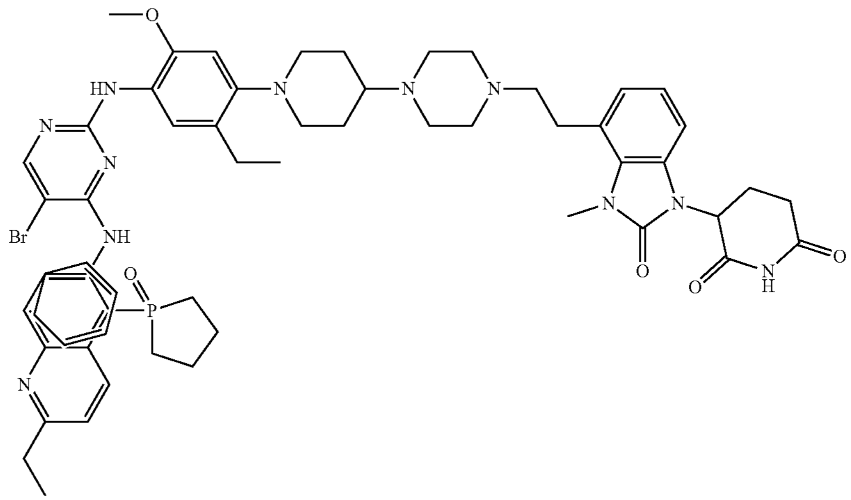

-continued
17
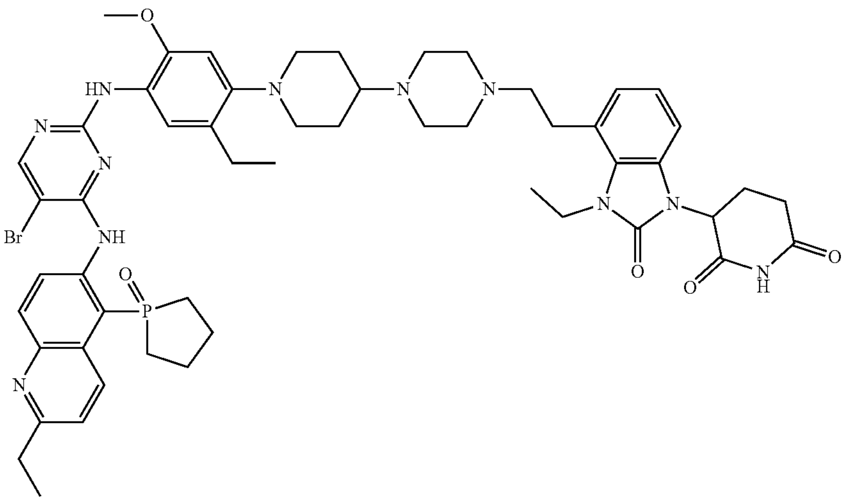
18
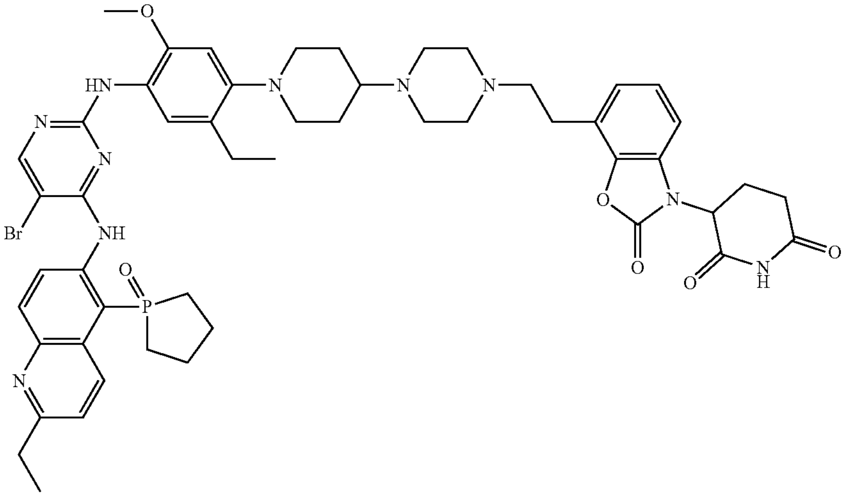
19
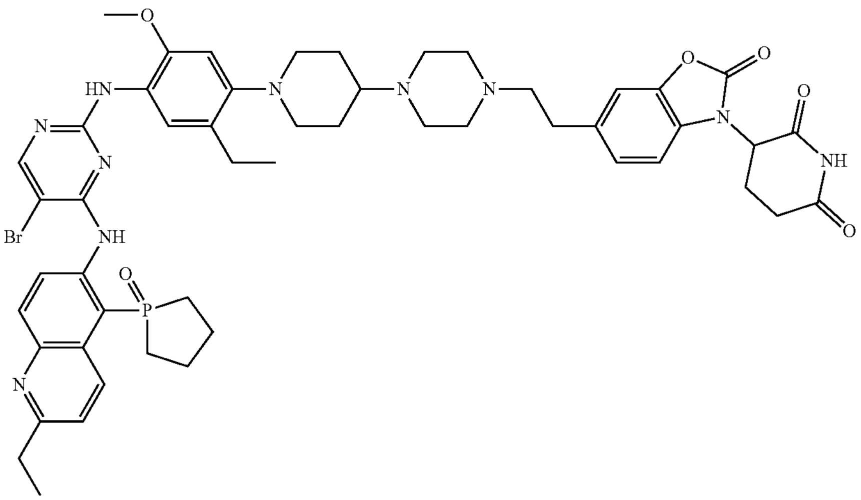

-continued
20
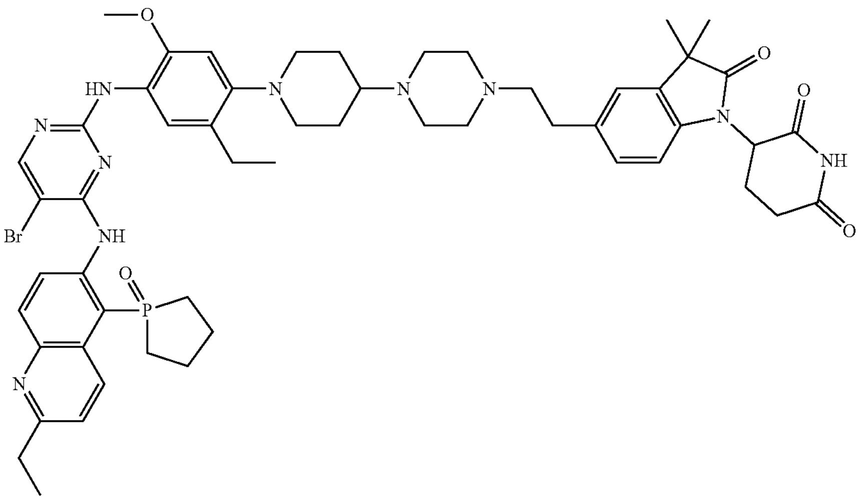
21
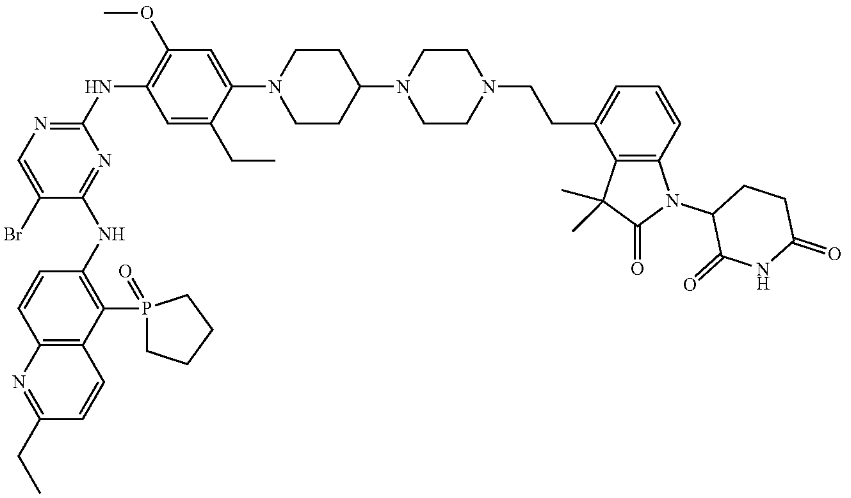
22
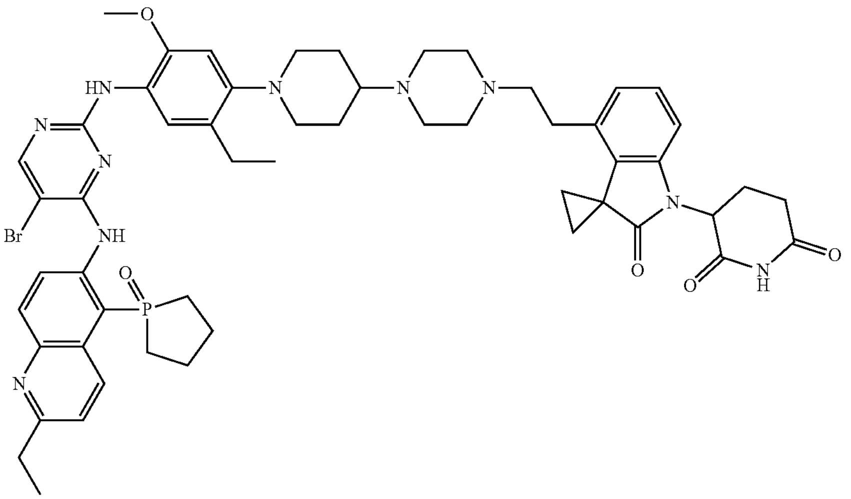

-continued
23
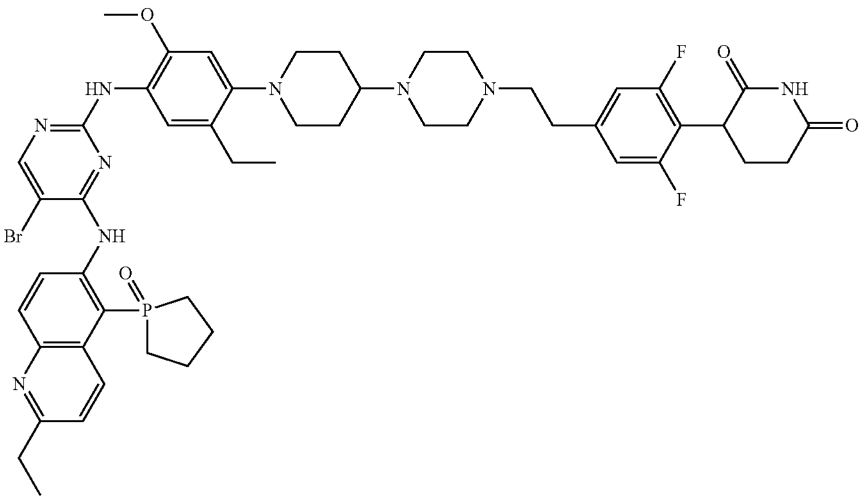
24
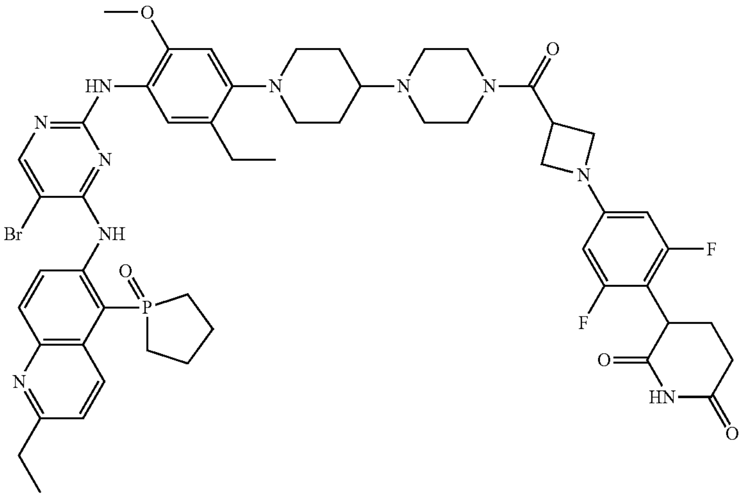
25
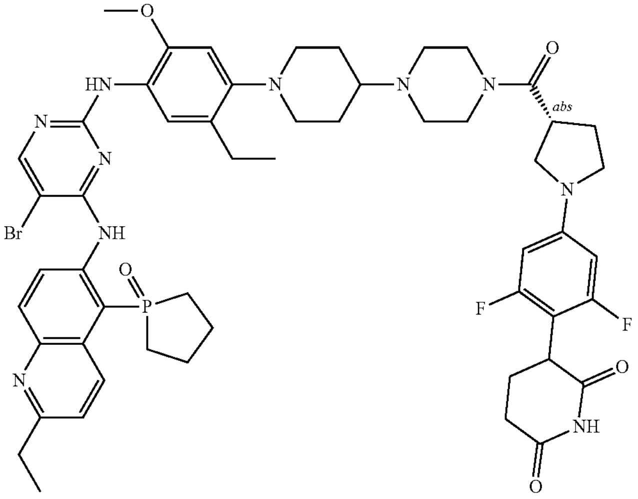

-continued
26
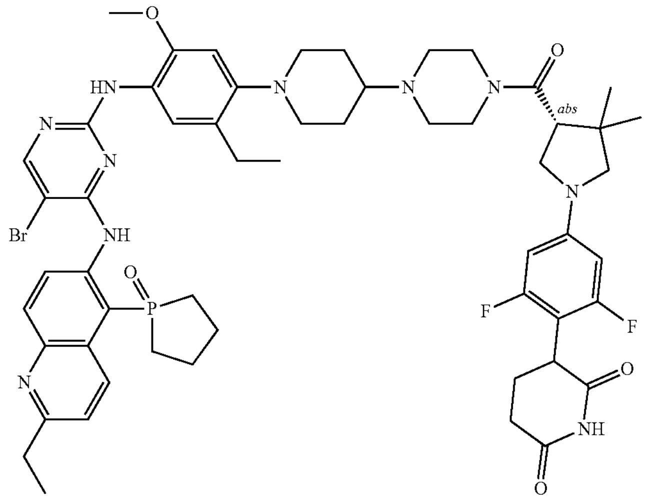
27
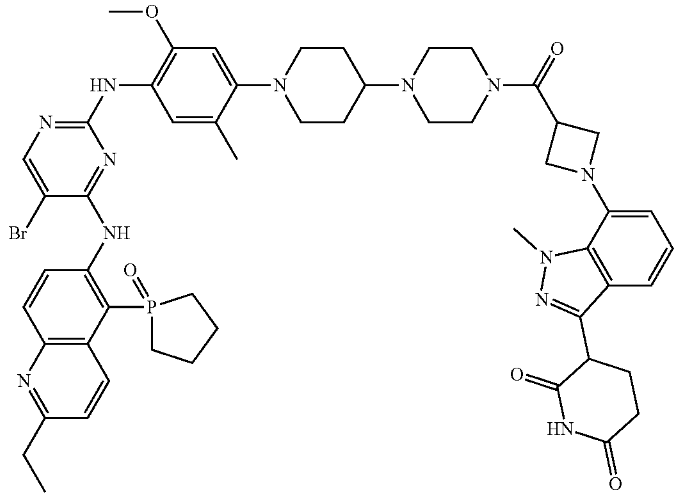
28
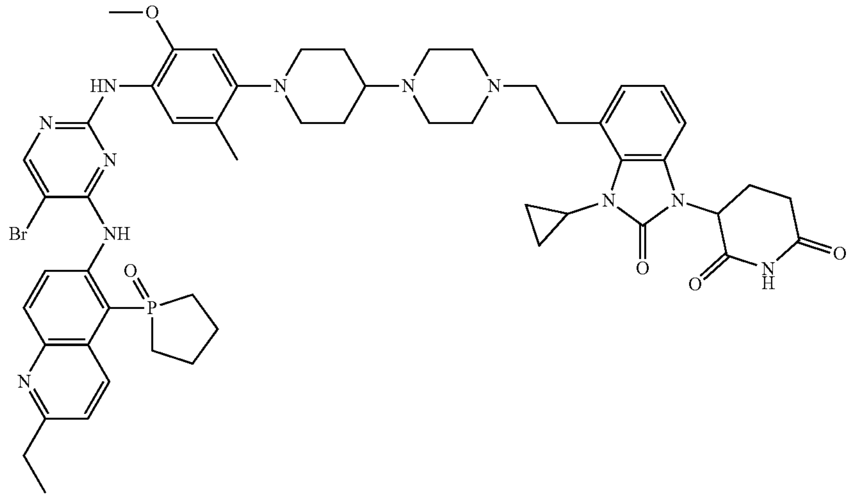

-continued
29
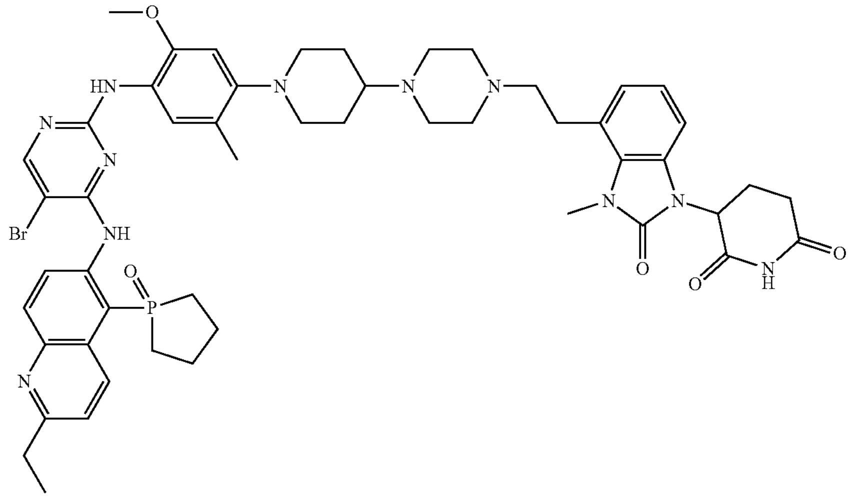
30
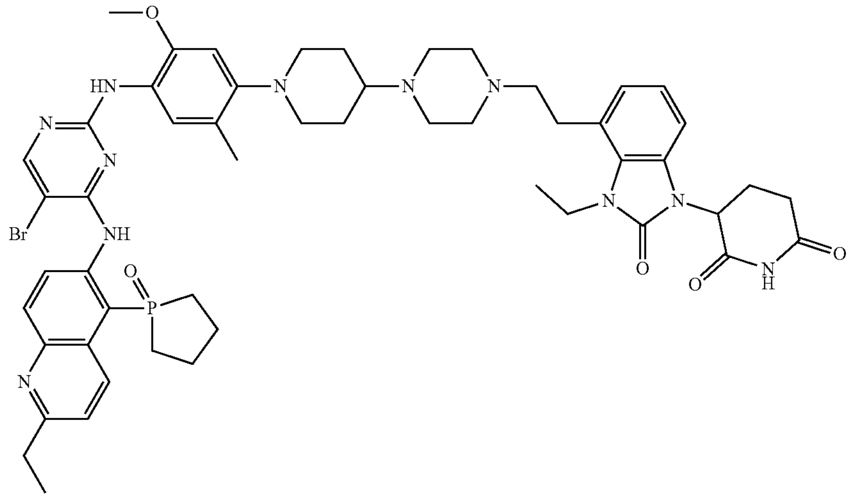
31
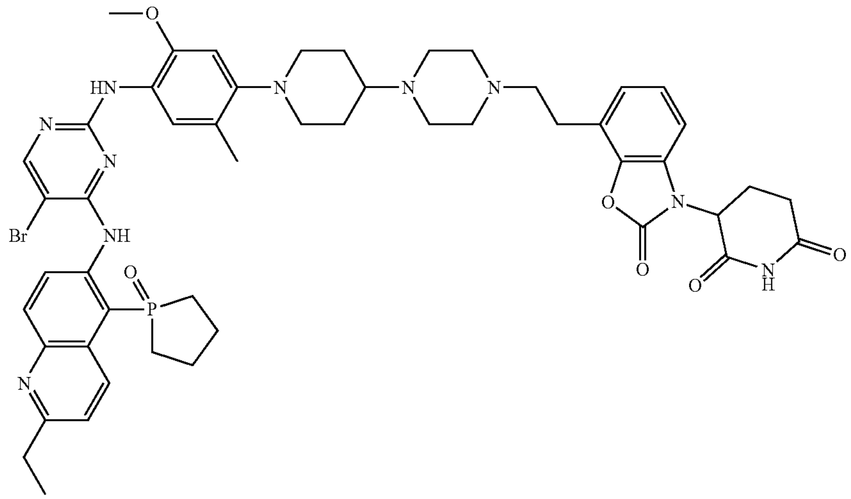

-continued
32
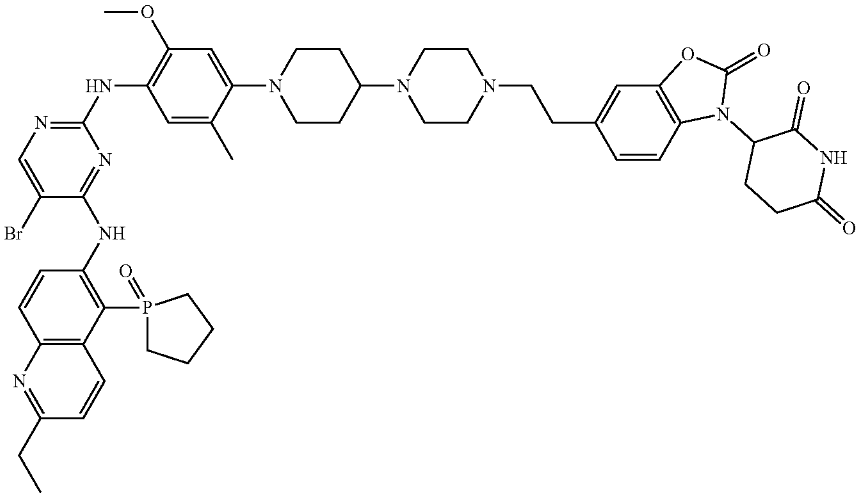
33
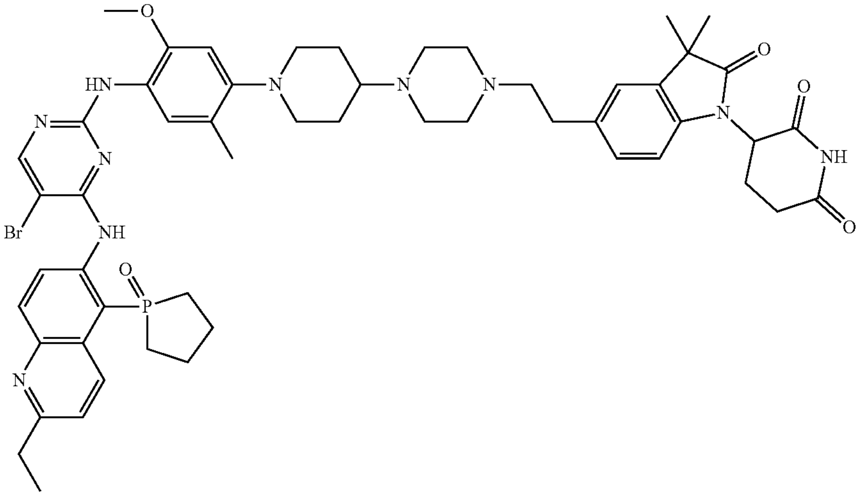
34
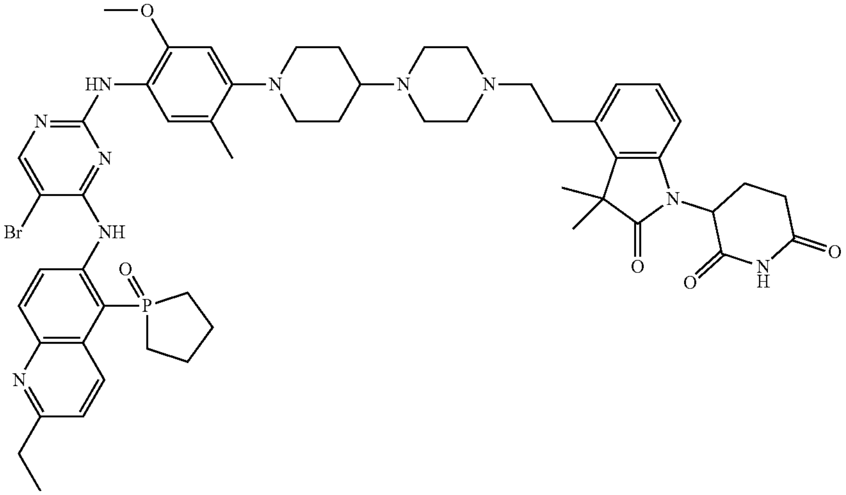

-continued
35
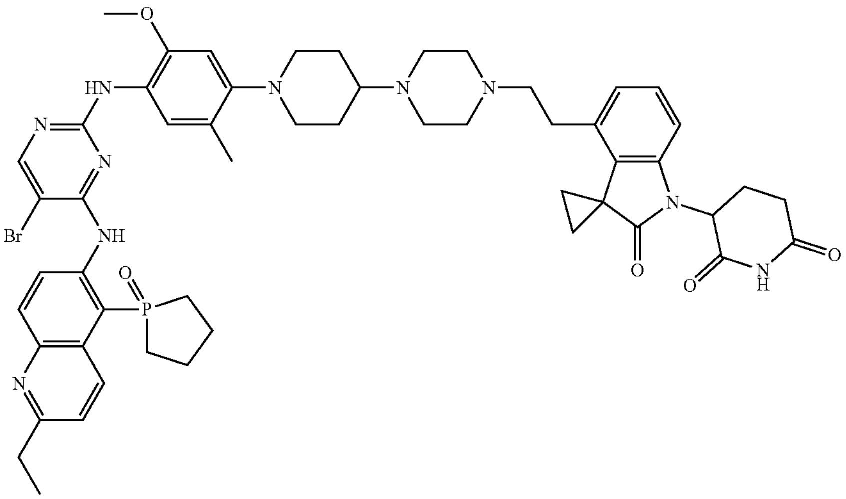
36
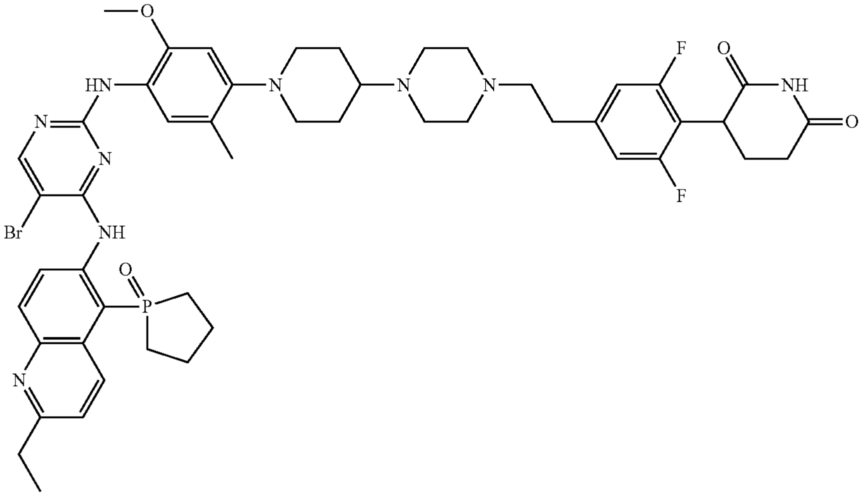
37
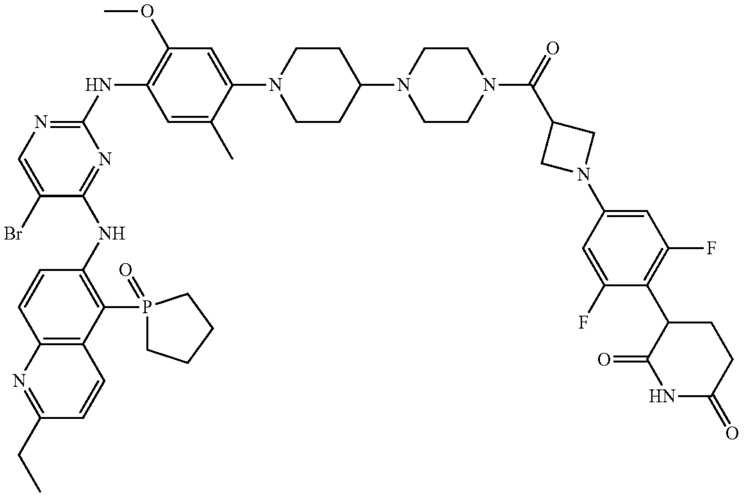

-continued
38
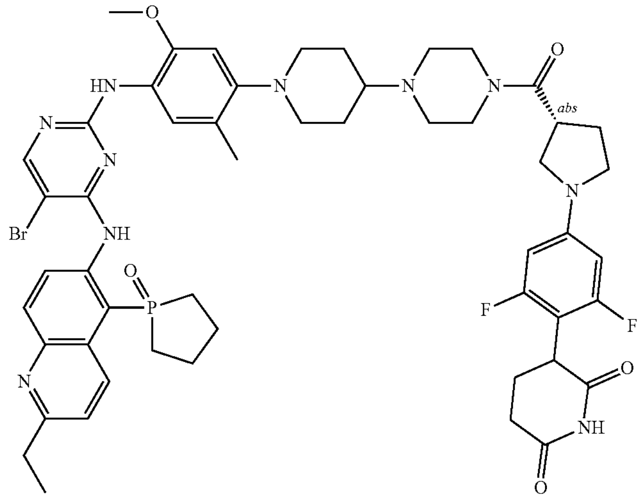
39
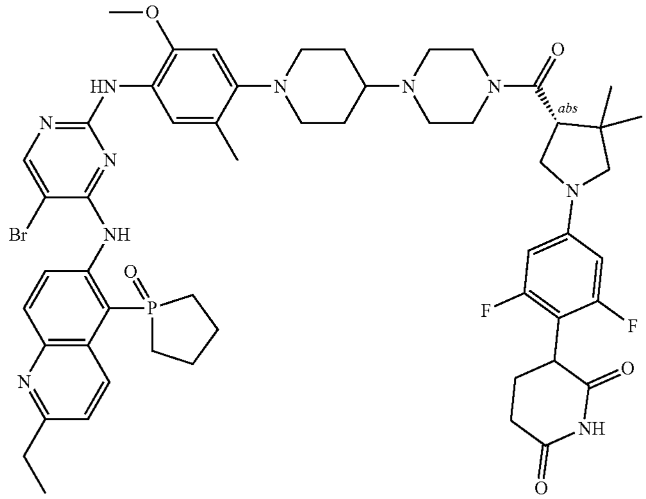
40
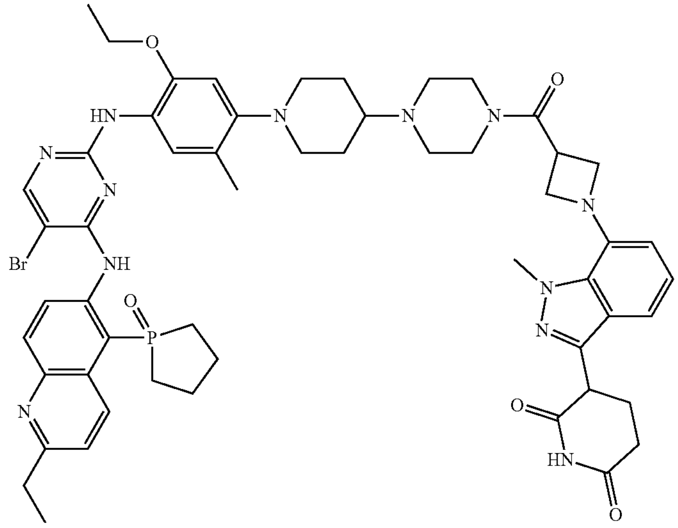

-continued
41
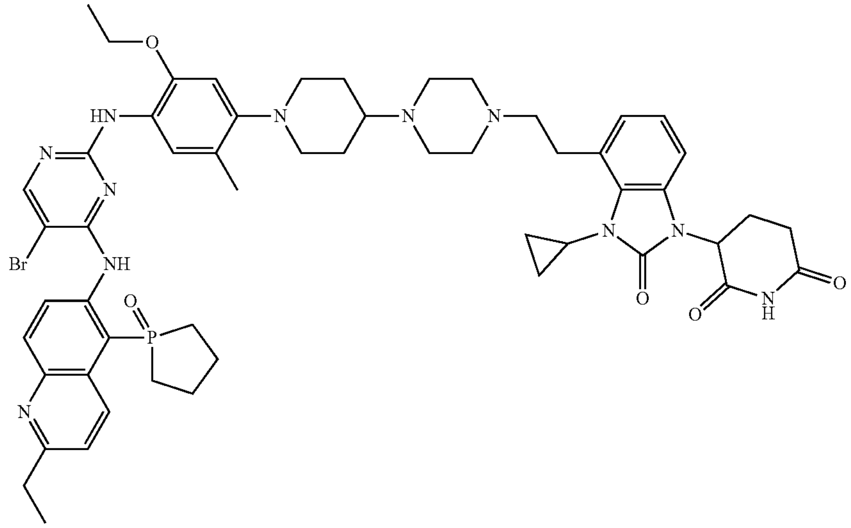
42
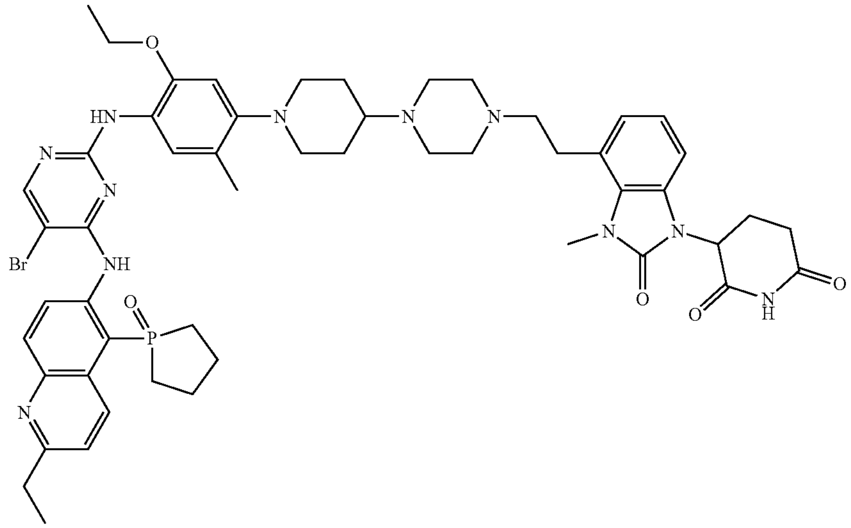
43
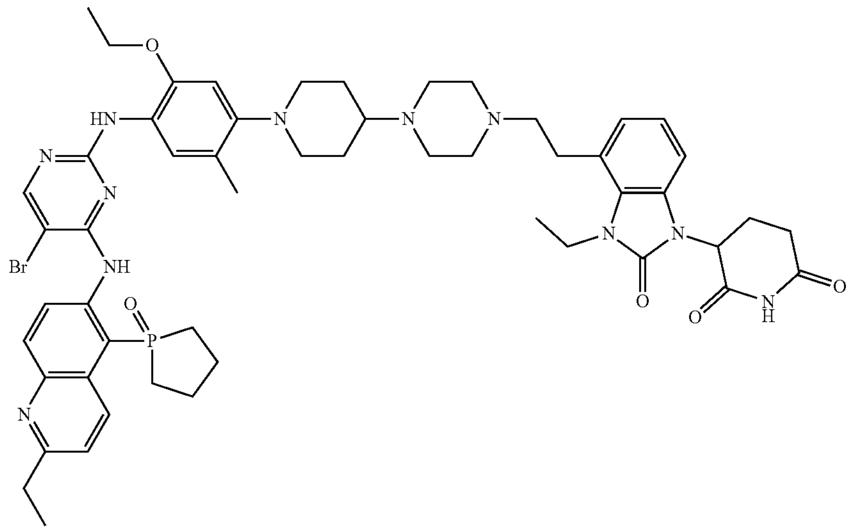

-continued
44
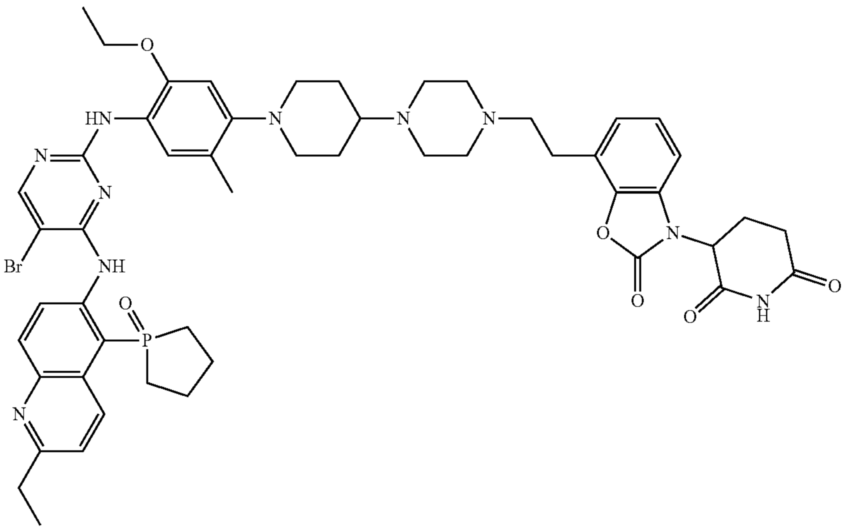
45
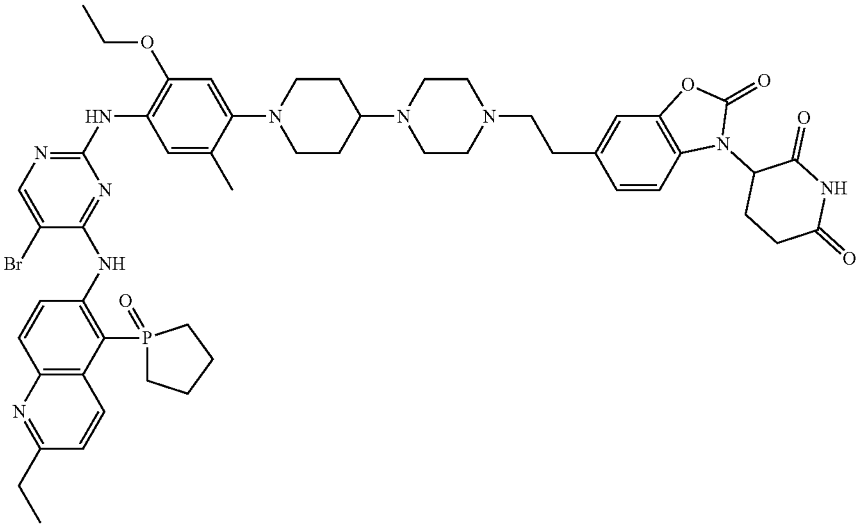
46
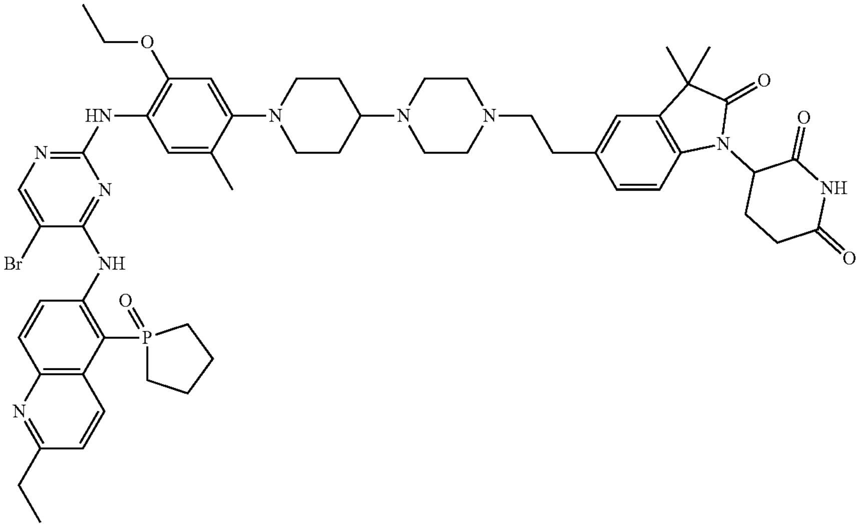

-continued
47
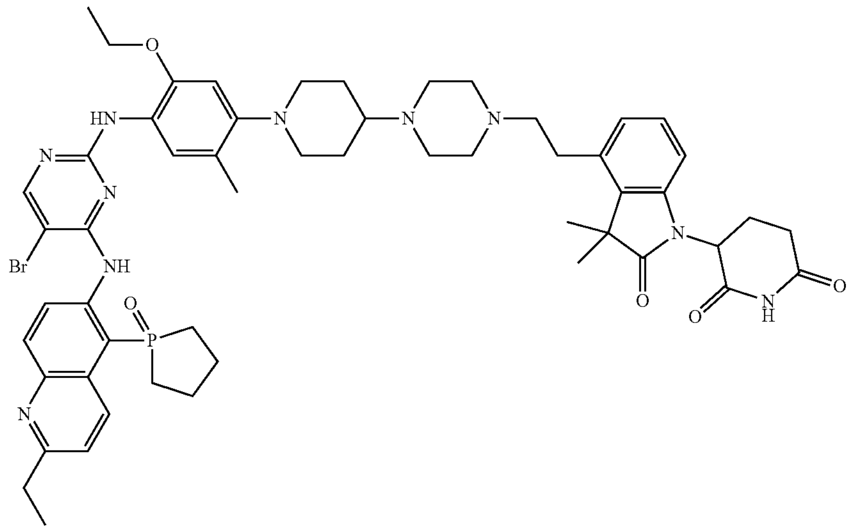
48
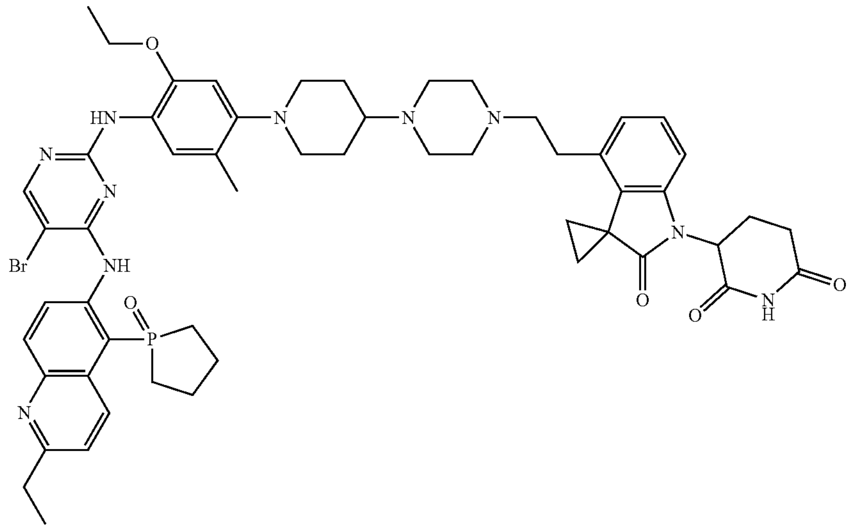
49
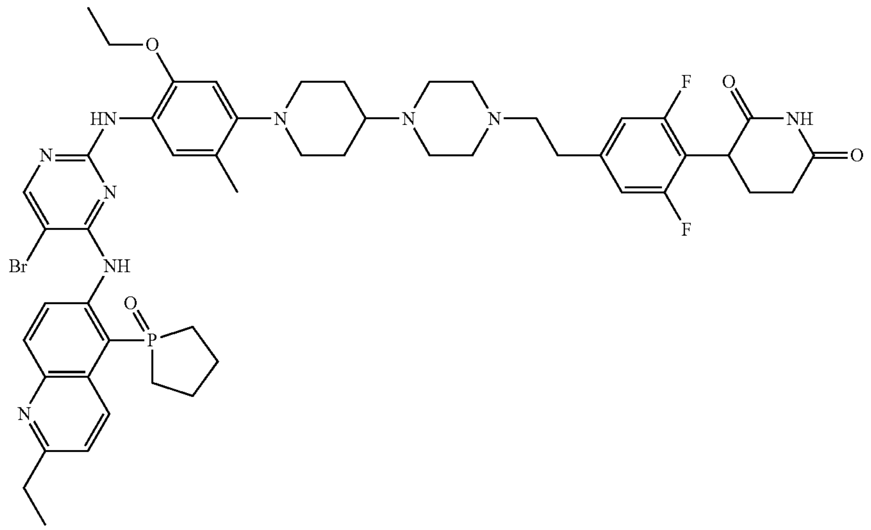

-continued
50
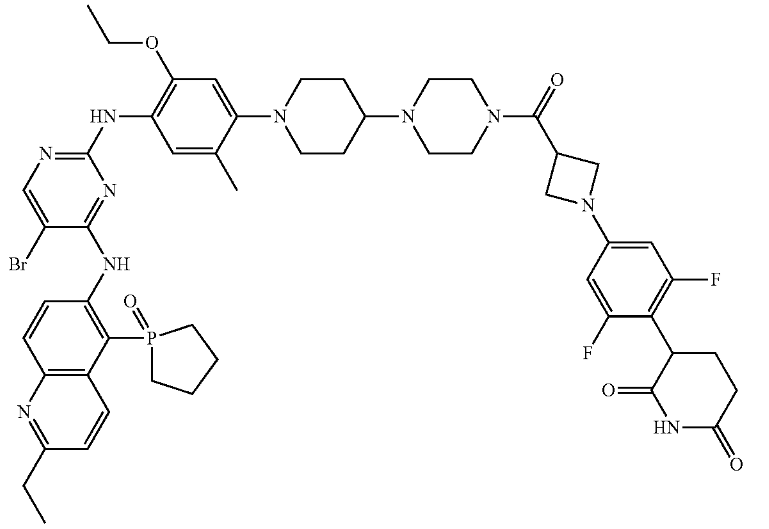
51
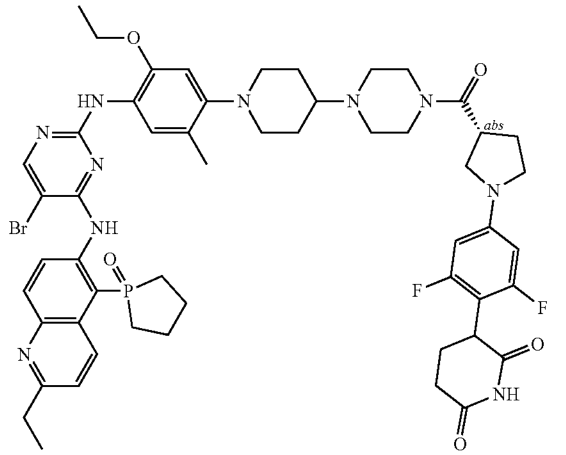
52
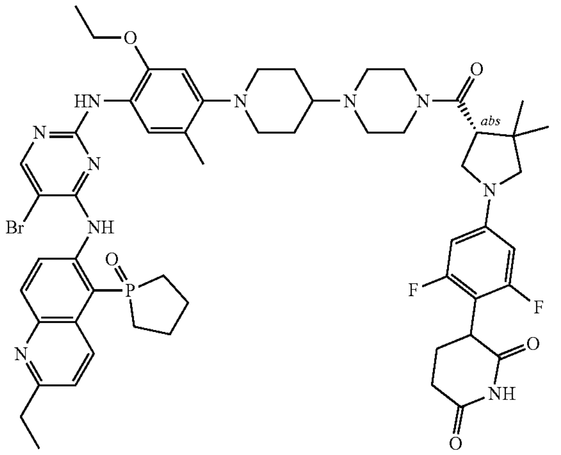
53
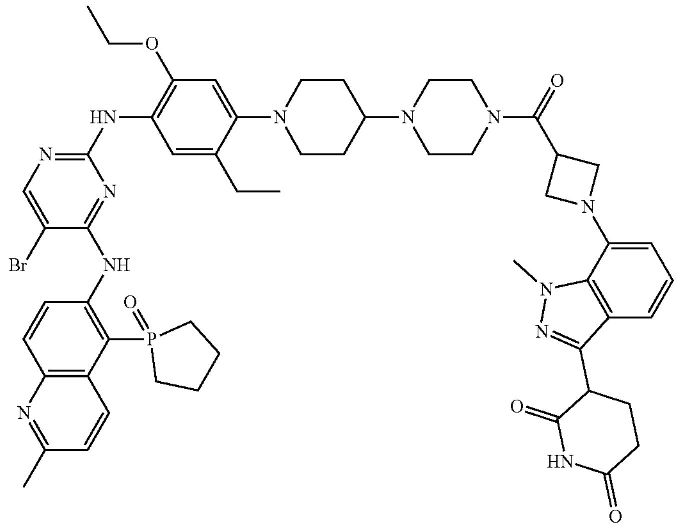

-continued
54
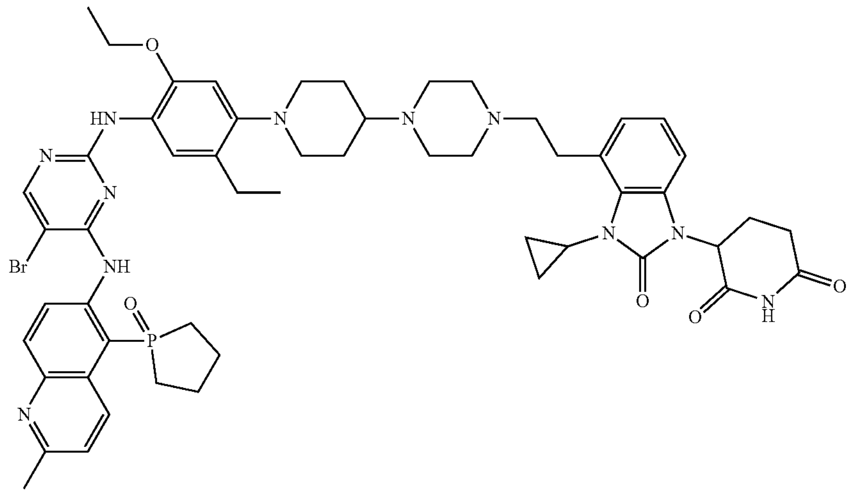
55
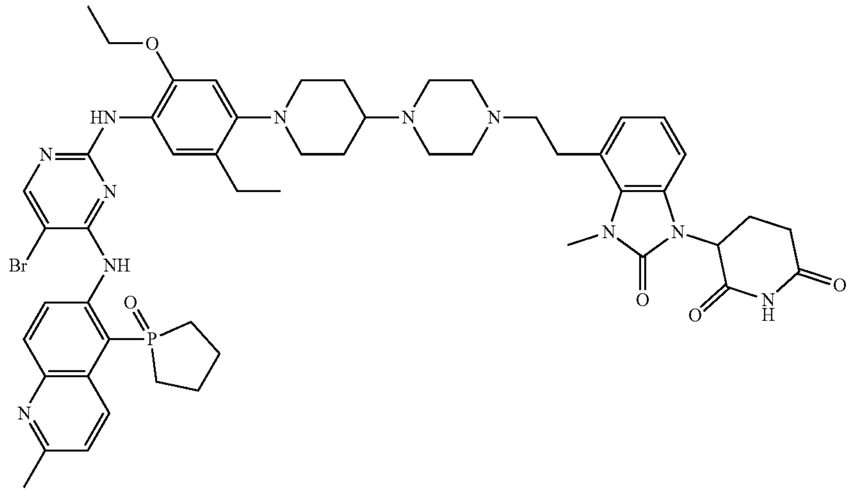
56
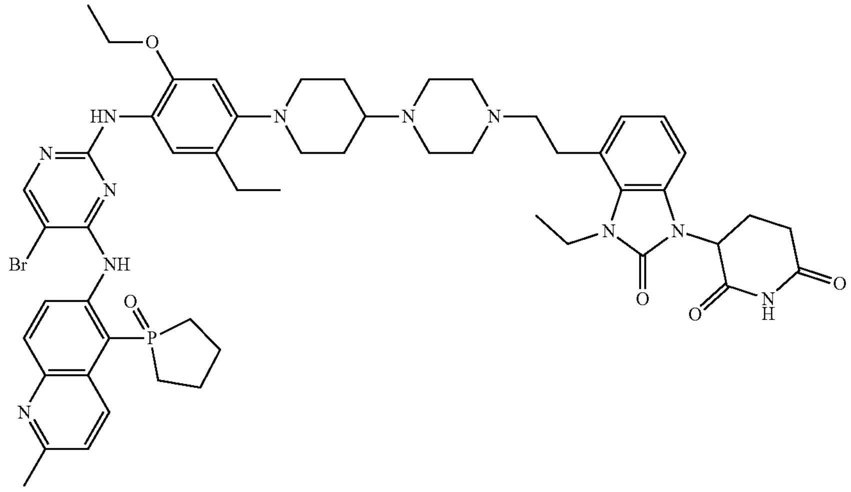

-continued
57
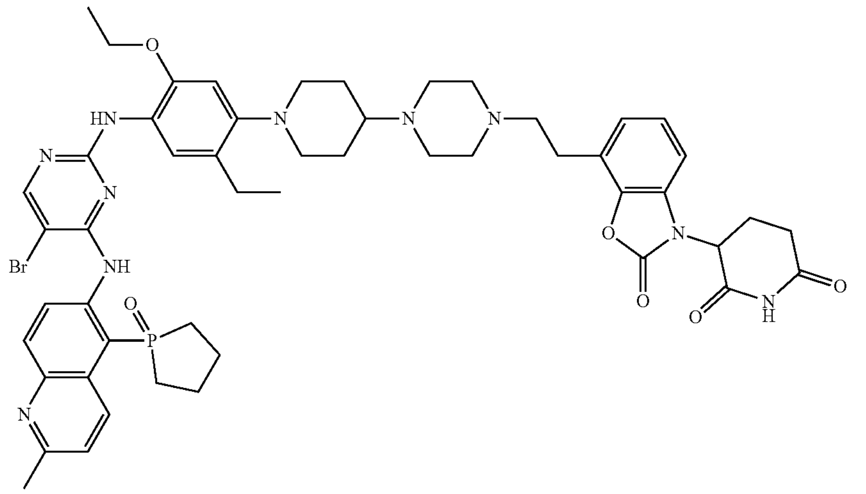
58
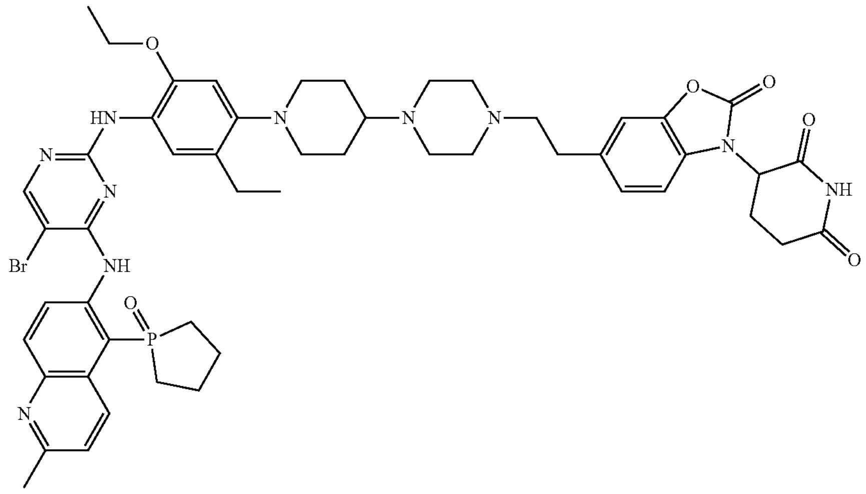
59
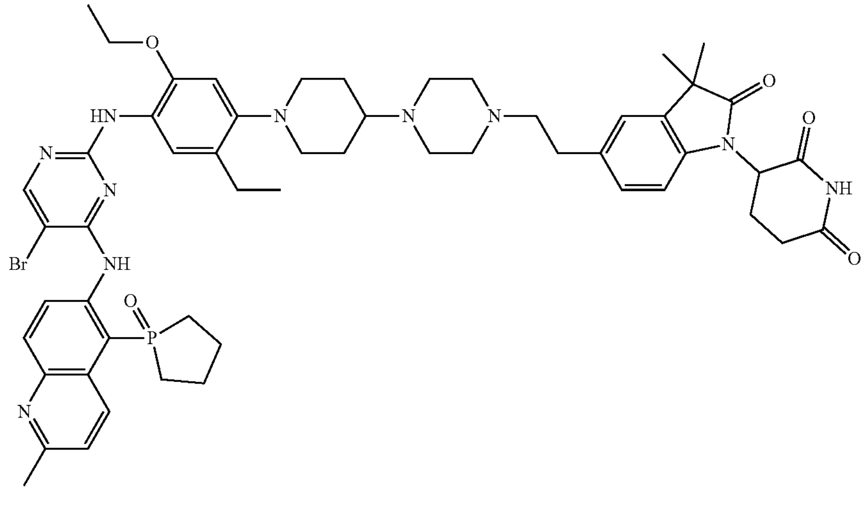

-continued
60
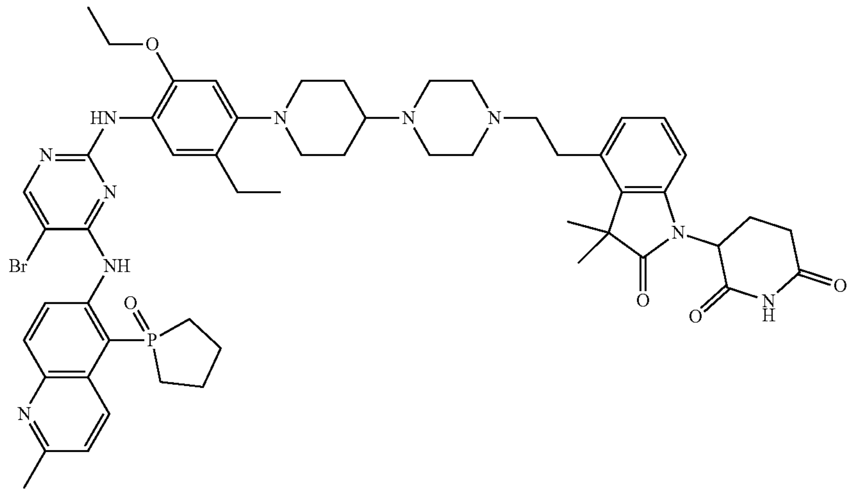
61
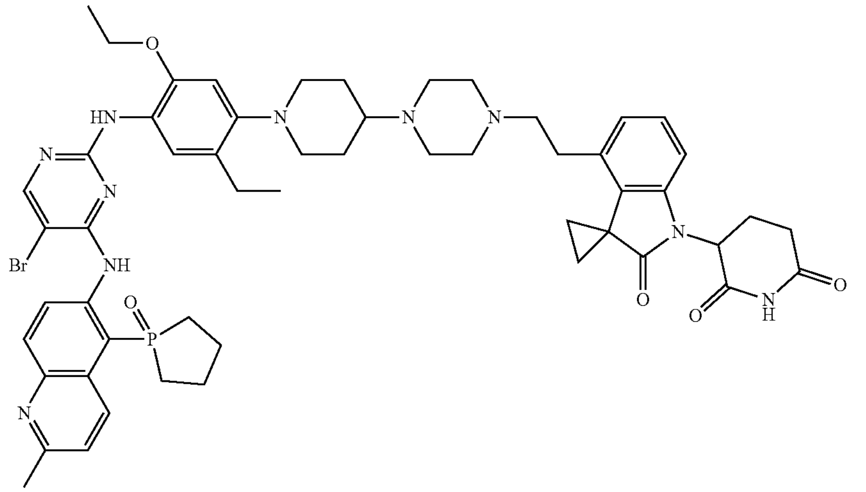
62
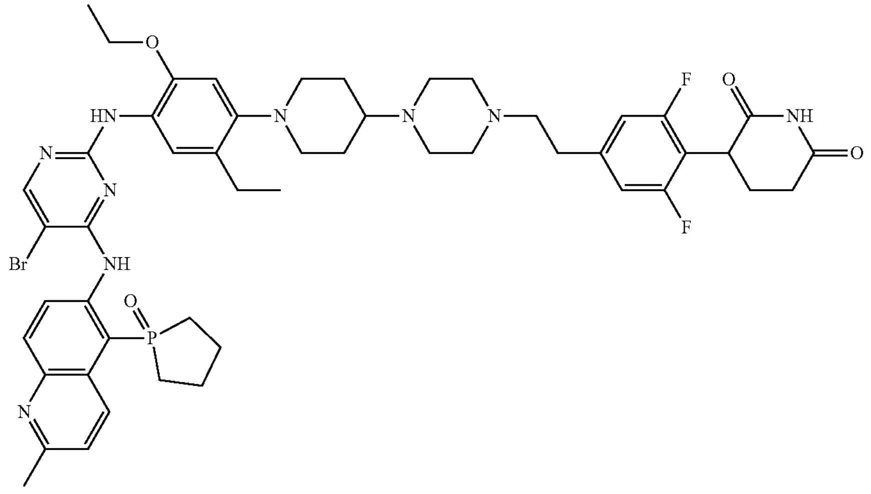

-continued
63
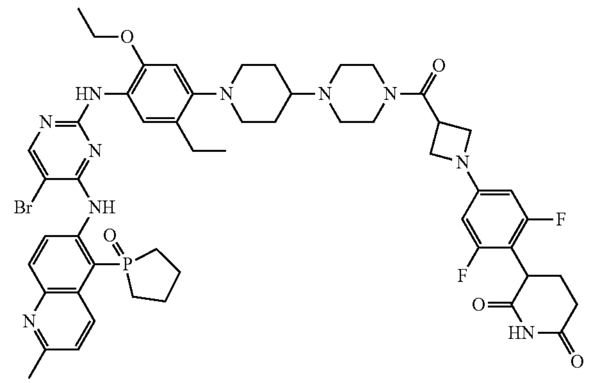
64
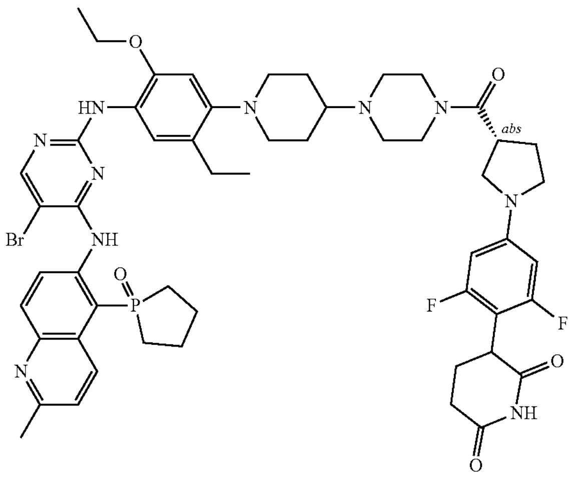
65
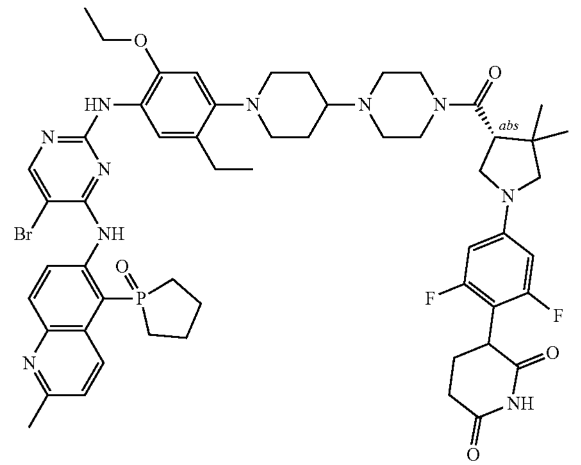
66
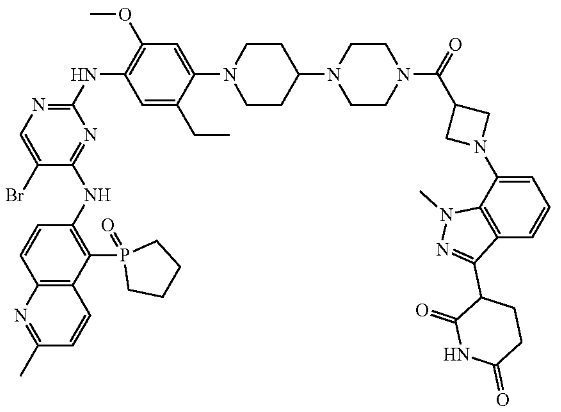
67
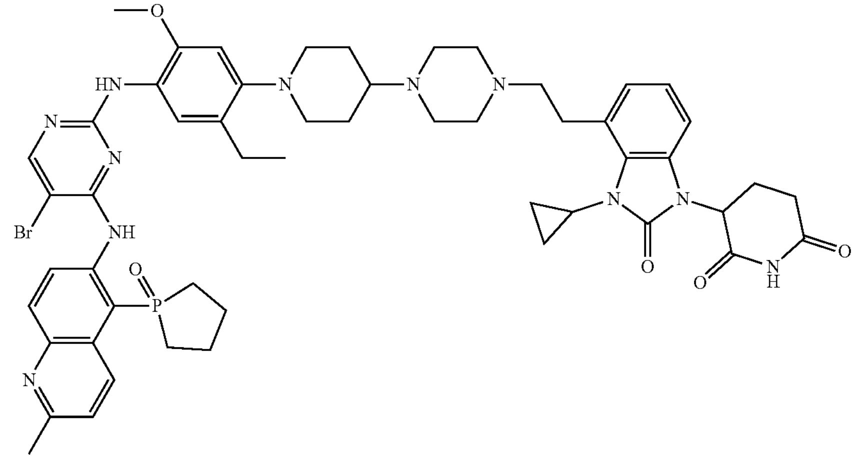

-continued
68
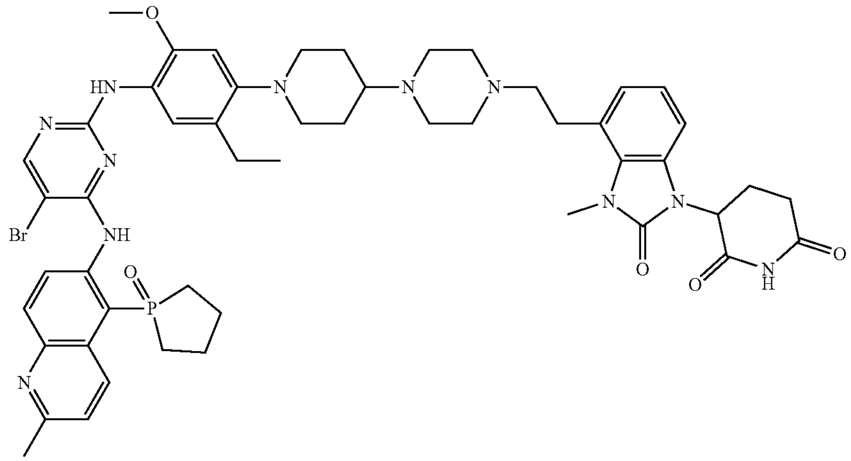
69
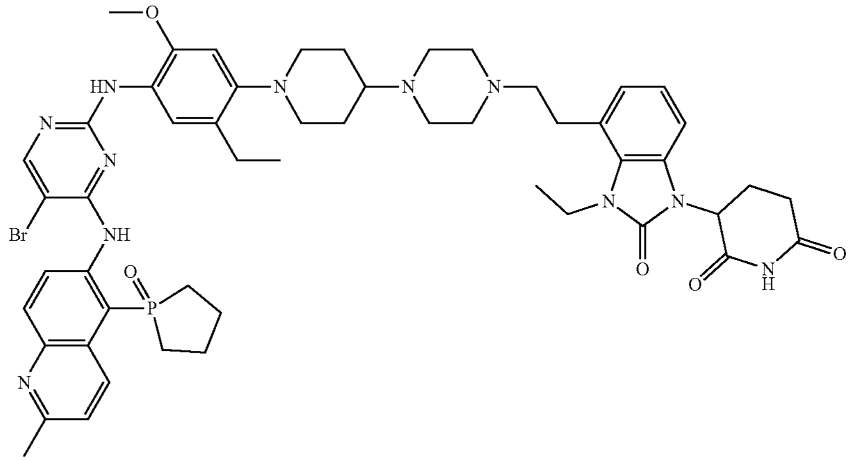
70
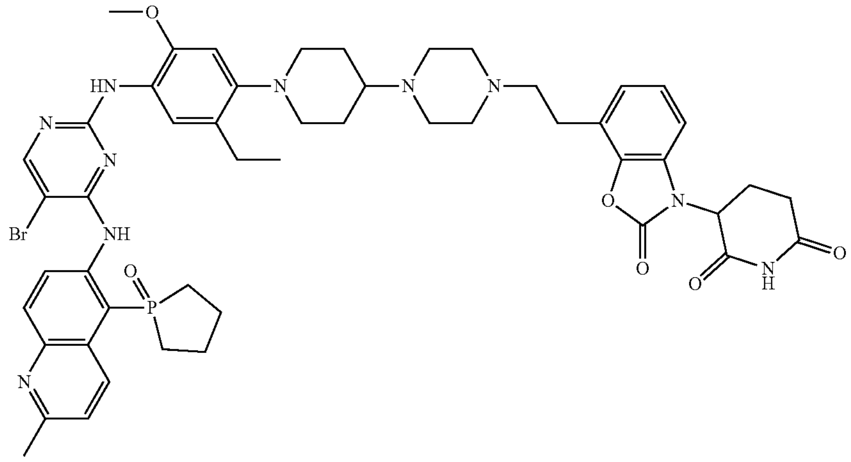

-continued
71
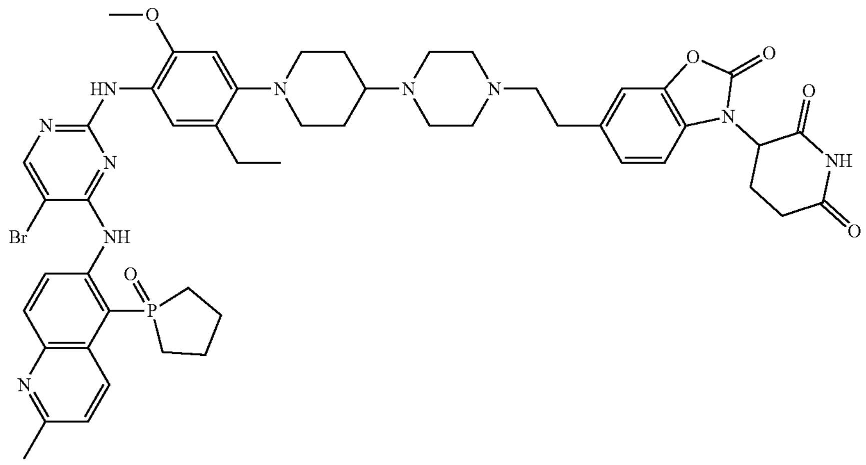
72
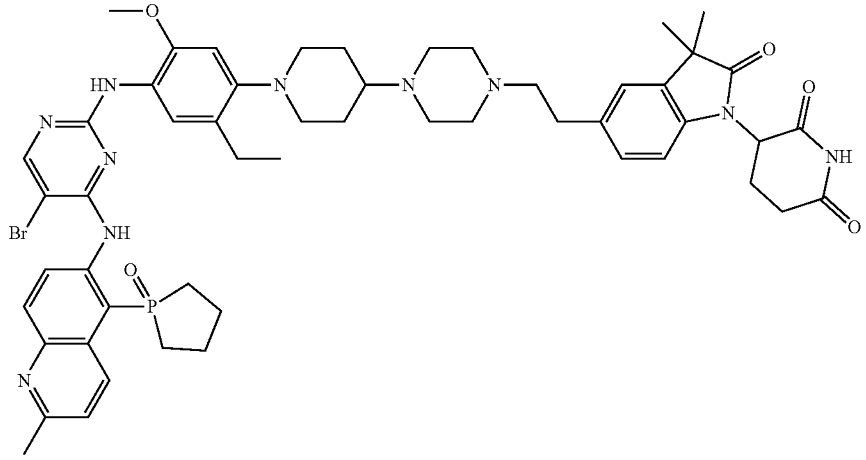
73
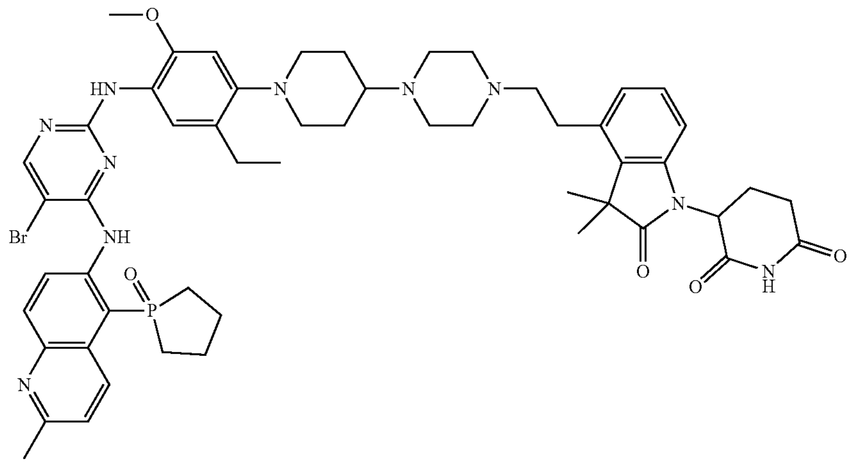

-continued
74
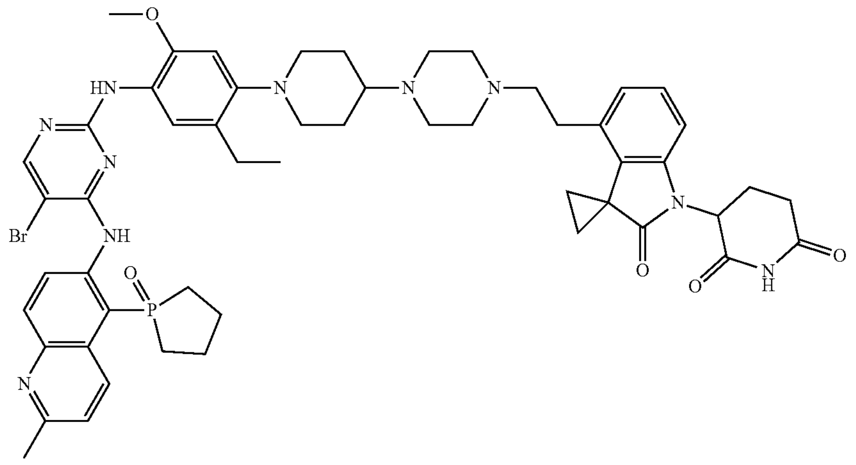
75
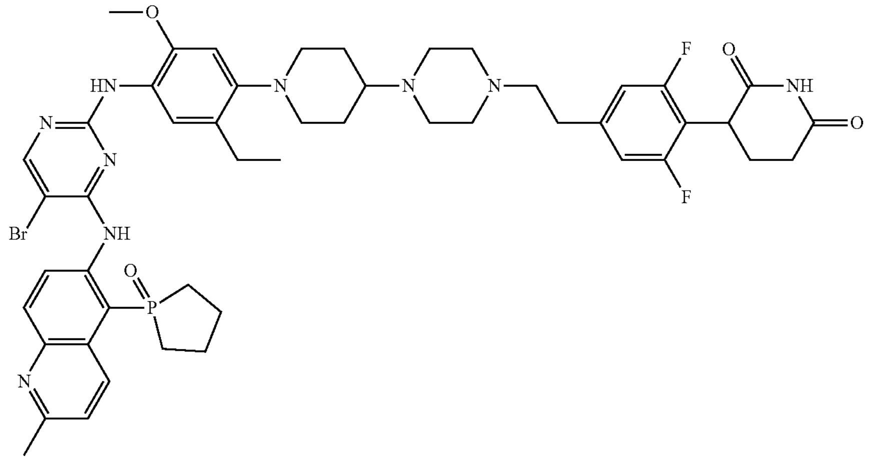
76
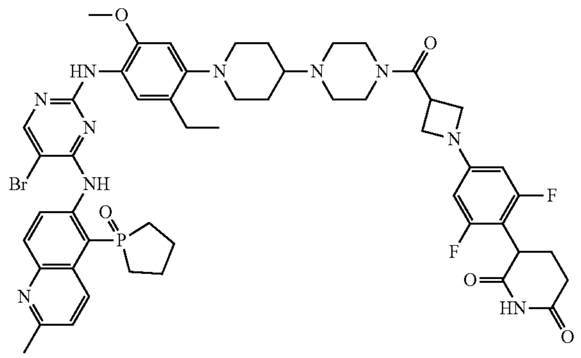
77
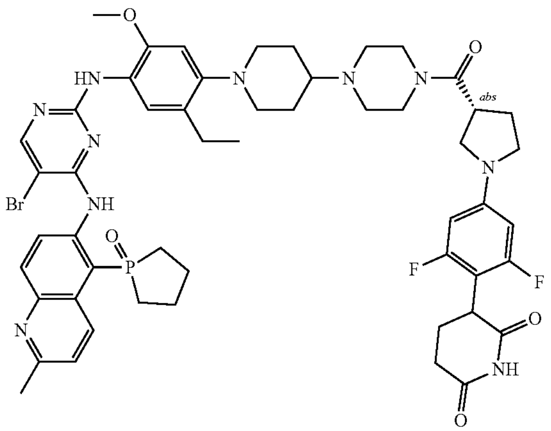

-continued
78
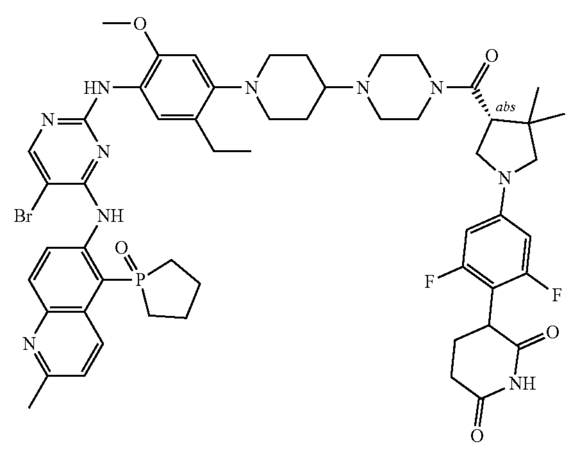
79
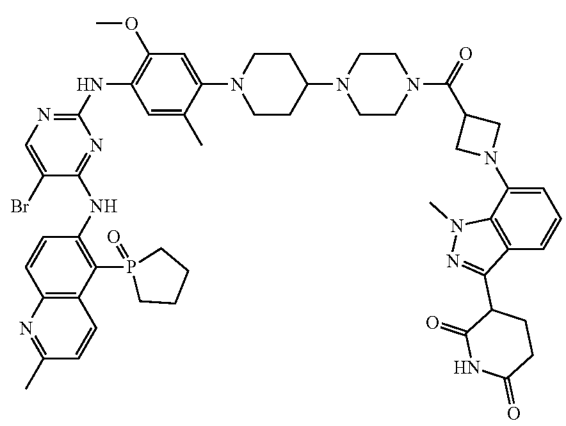
80
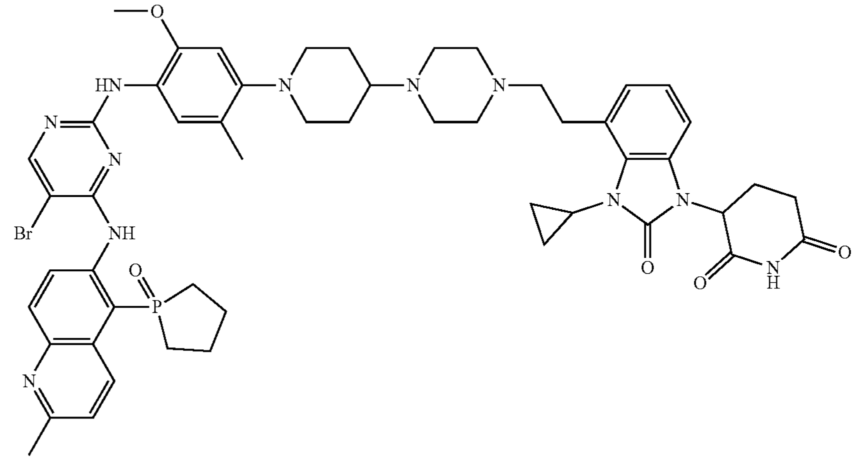
81
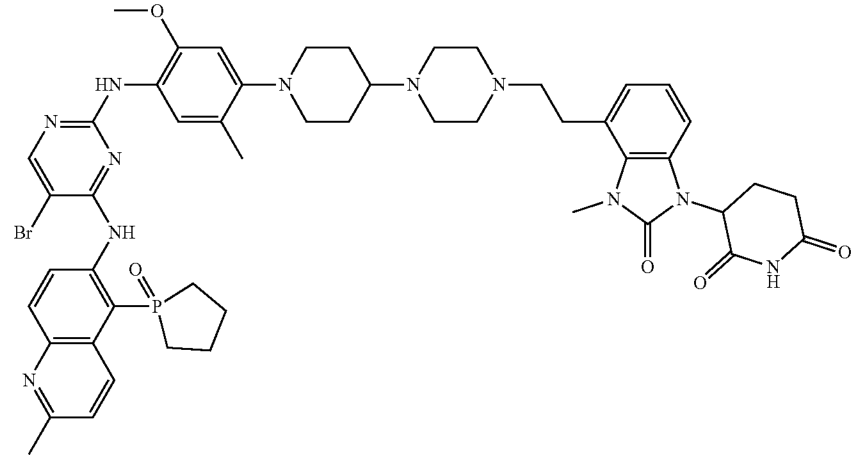

-continued
82
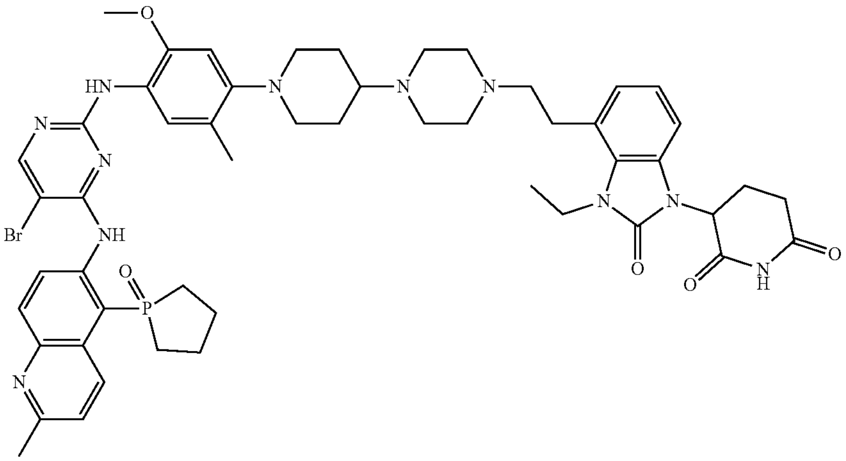
83
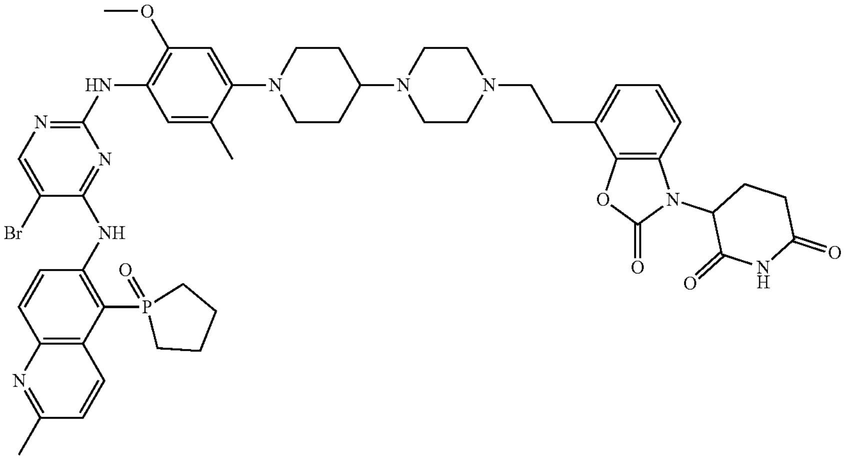
84
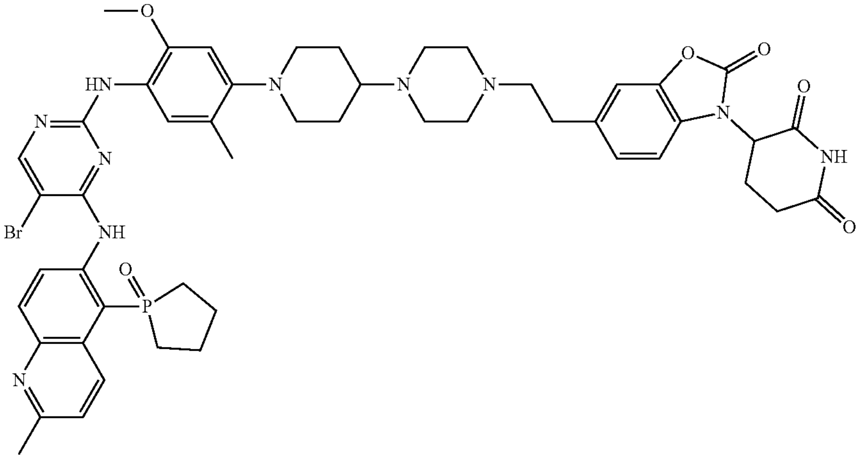

-continued
85
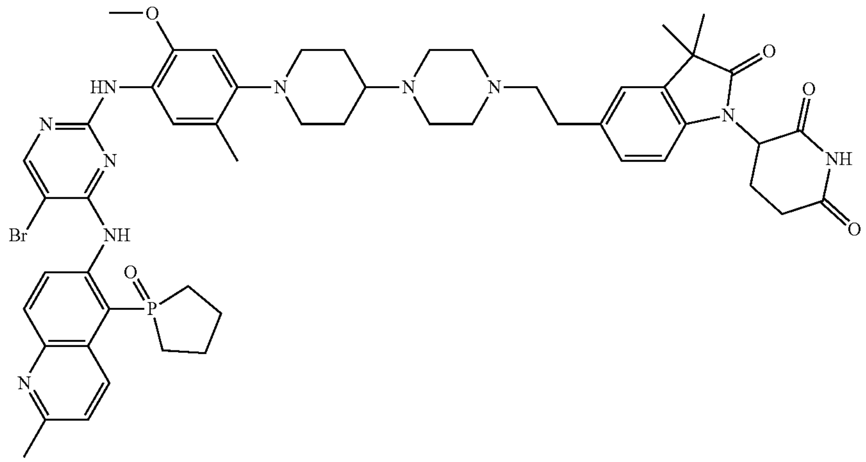
86
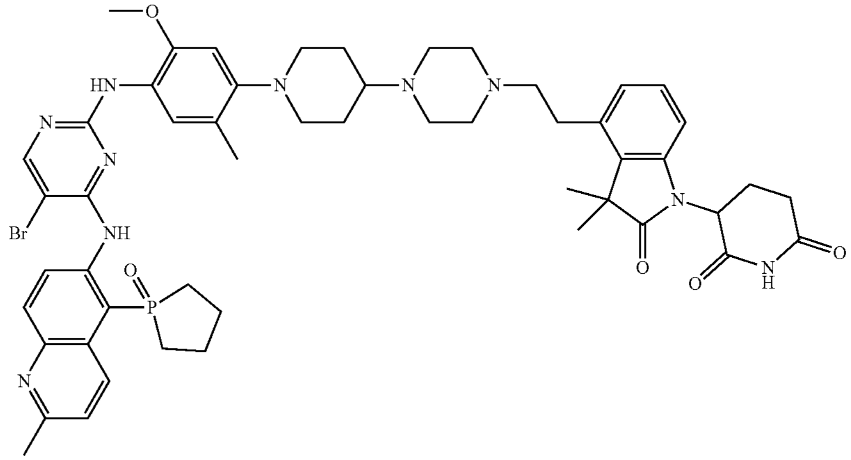
87
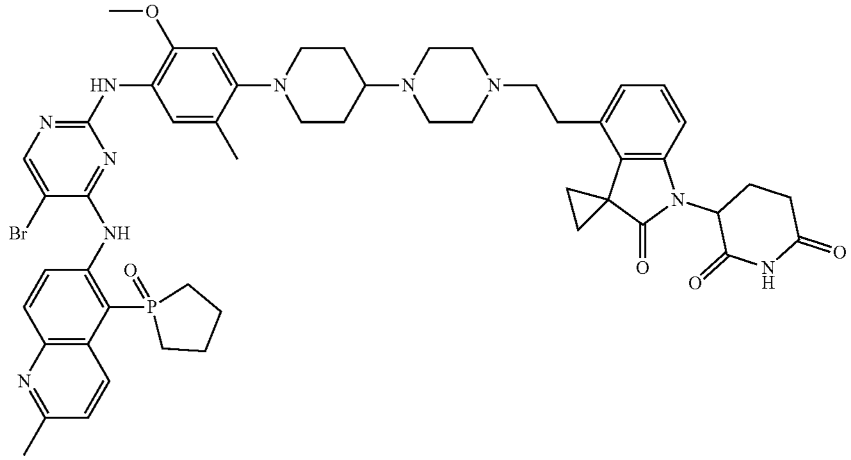

-continued
88
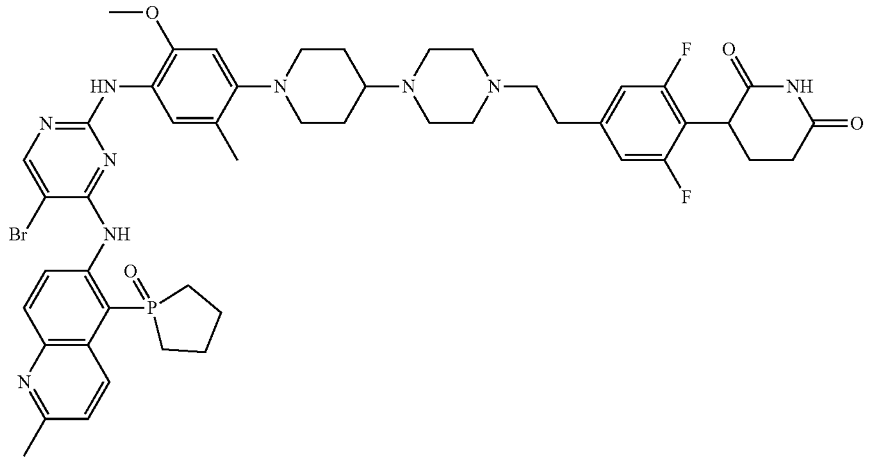
89
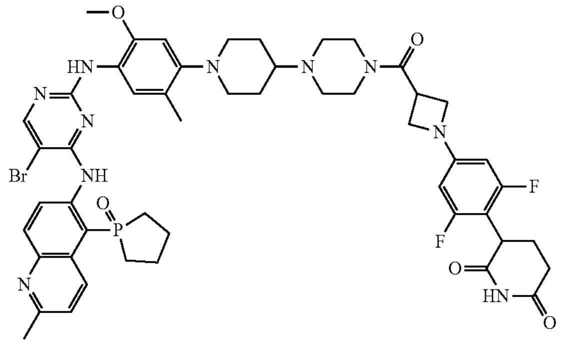
90
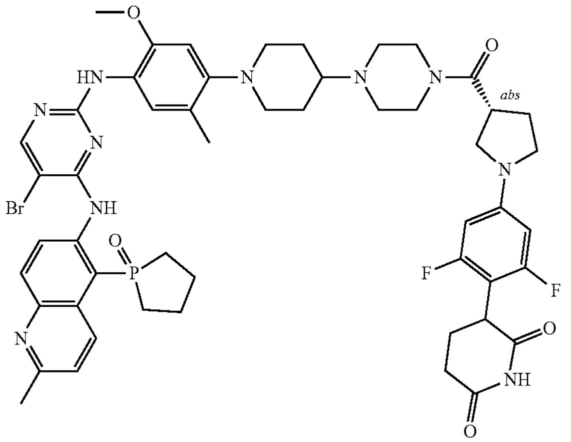
91
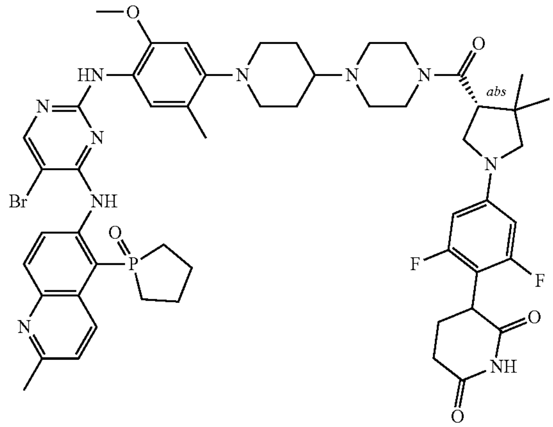
92
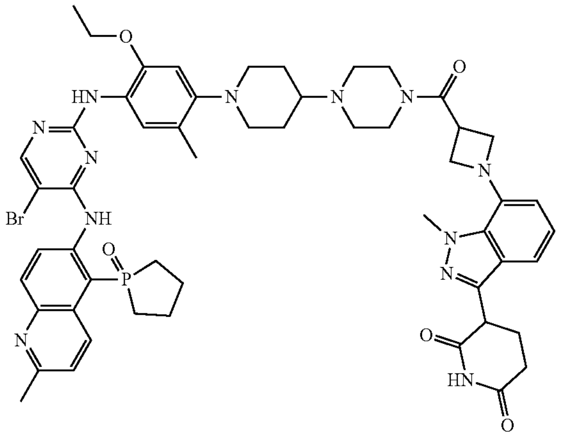

-continued
93
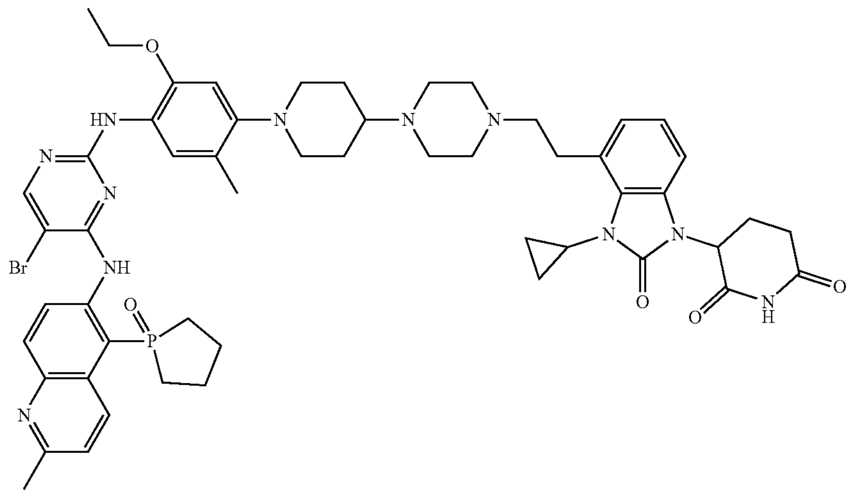
94
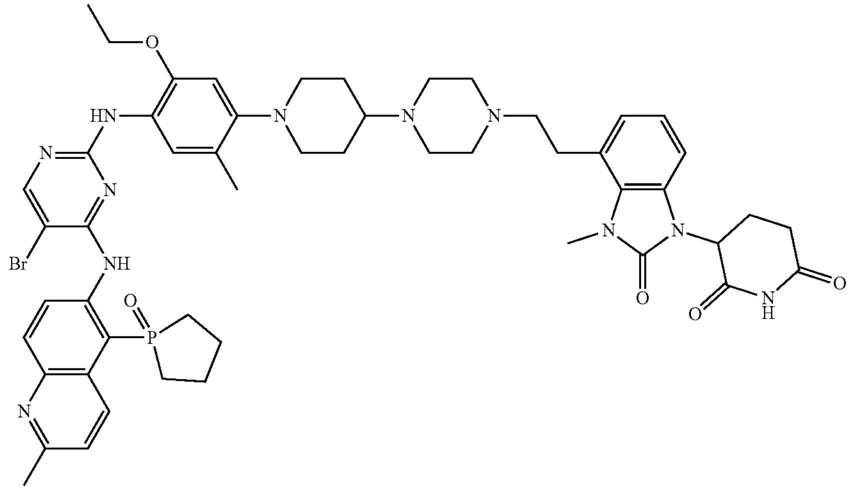
95
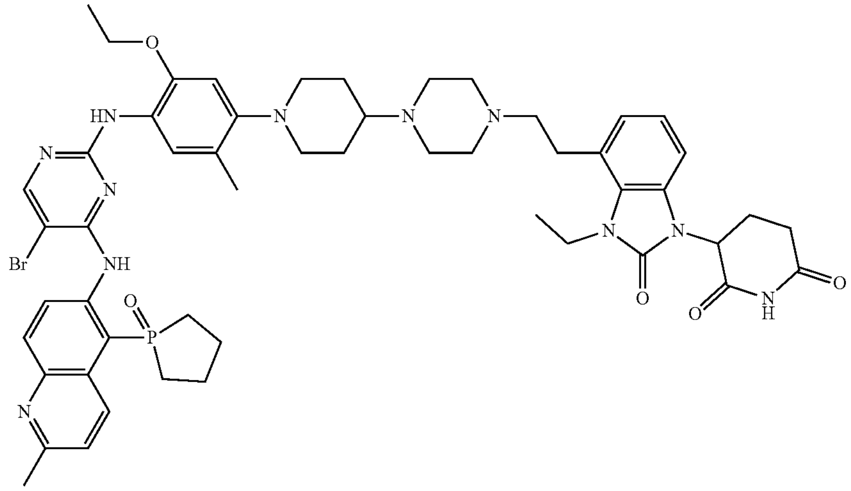

-continued
96
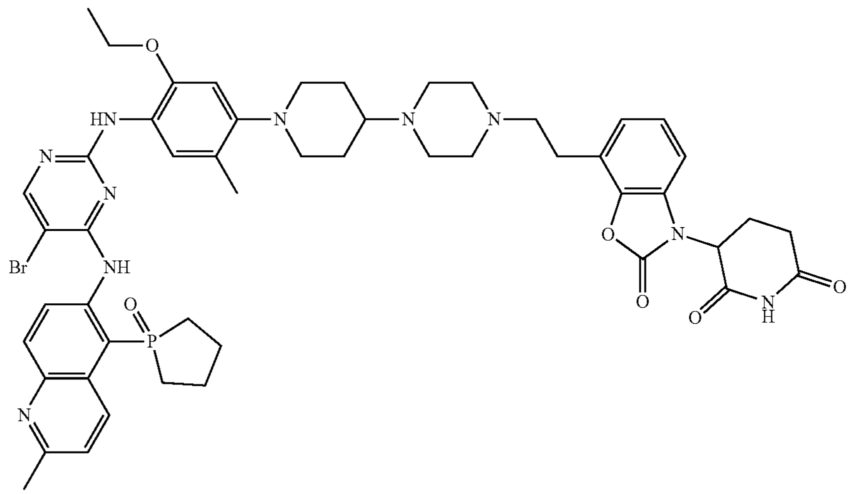
97
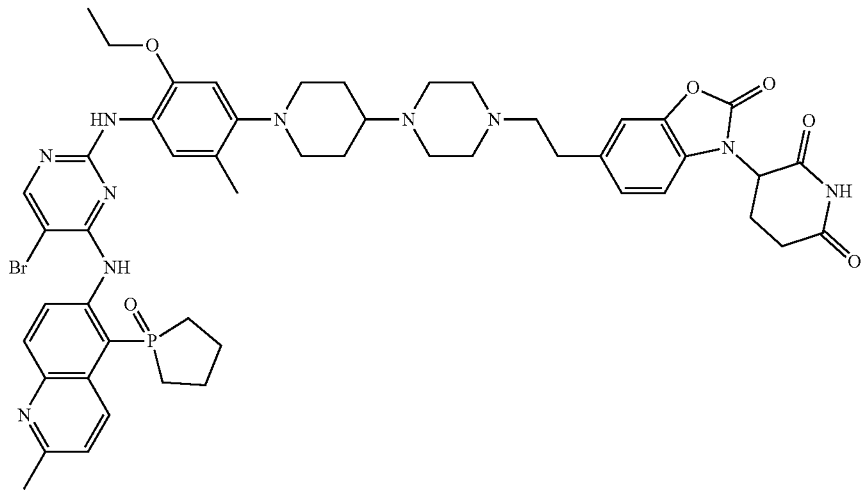
98
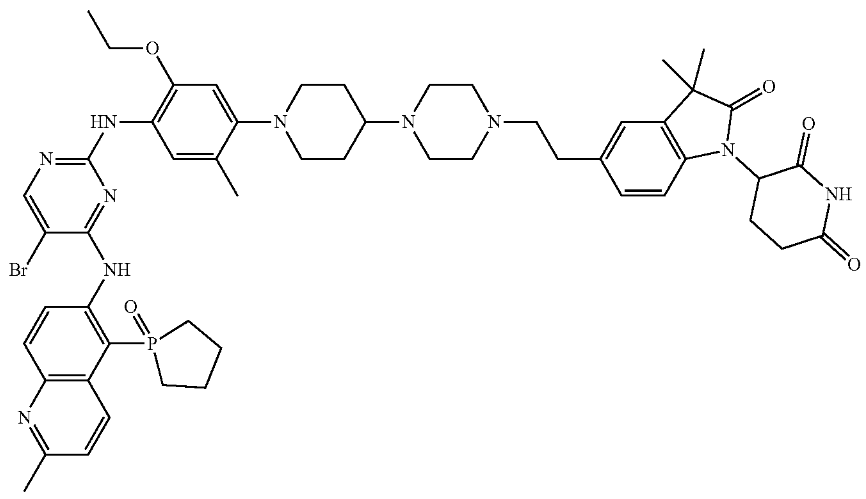

-continued
99
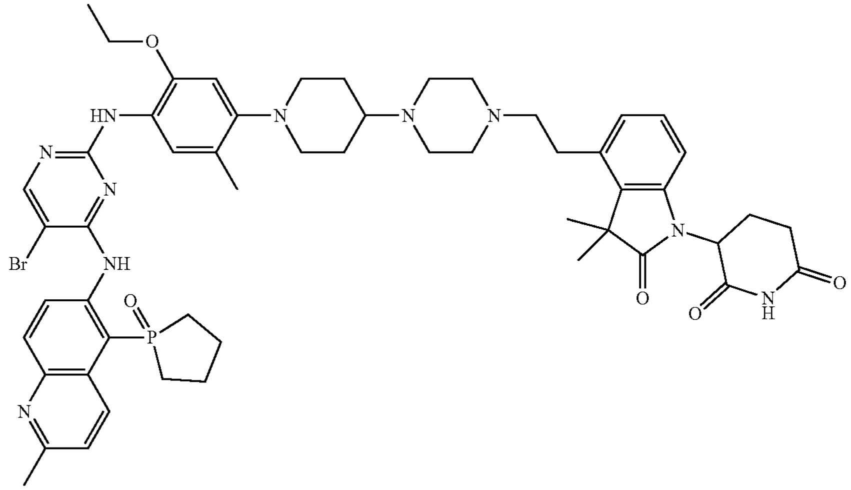
100
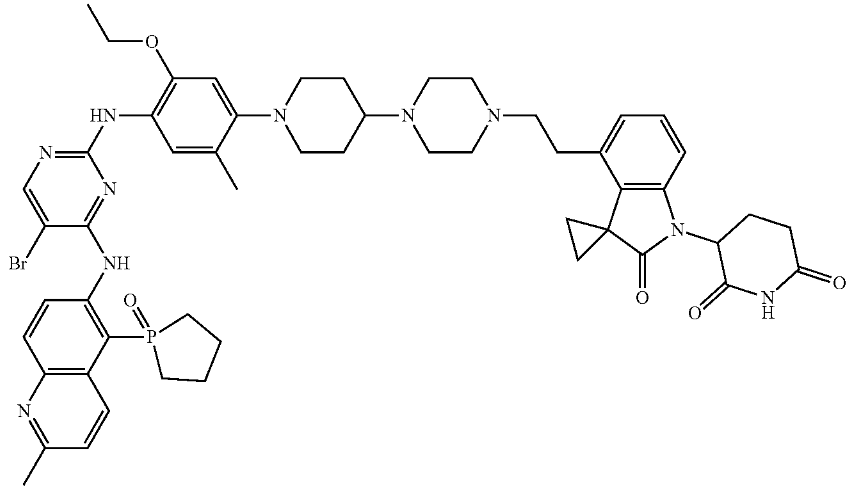
101
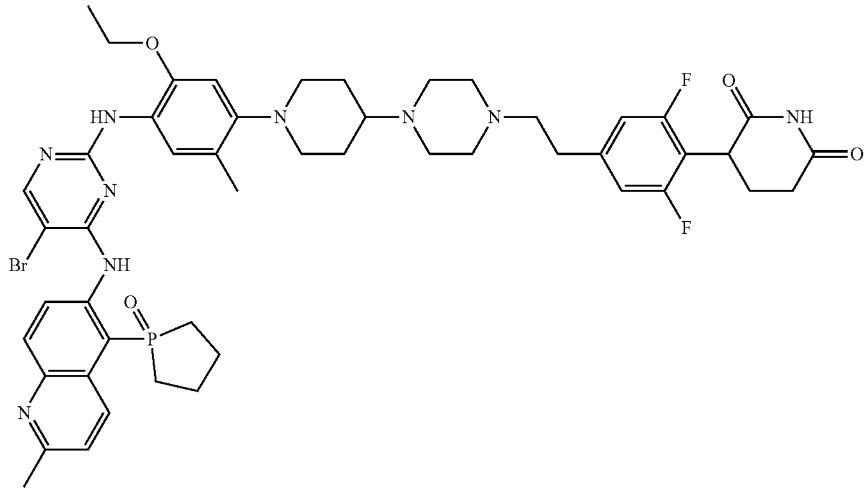

-continued
102
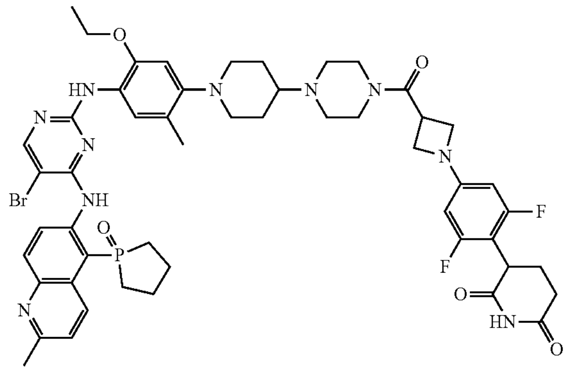
103
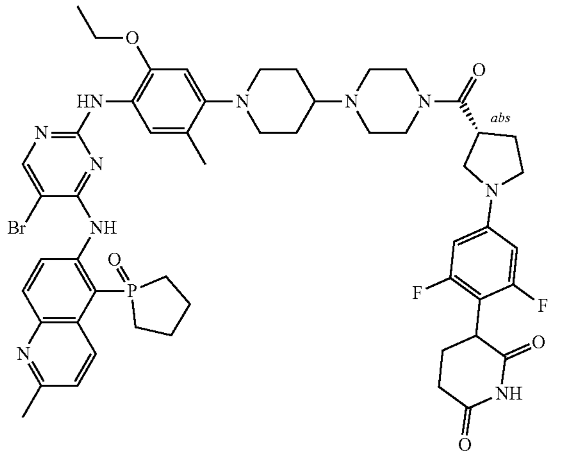
104
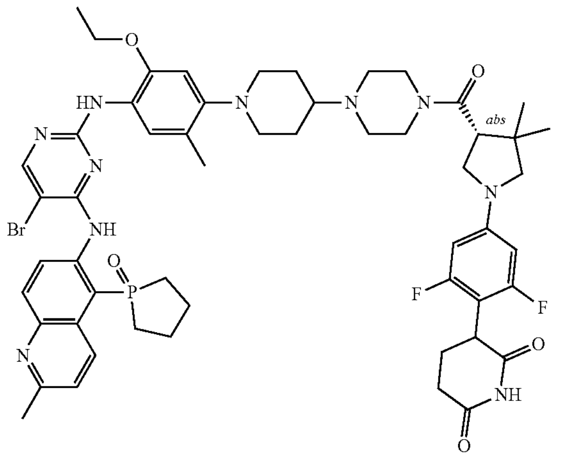
105
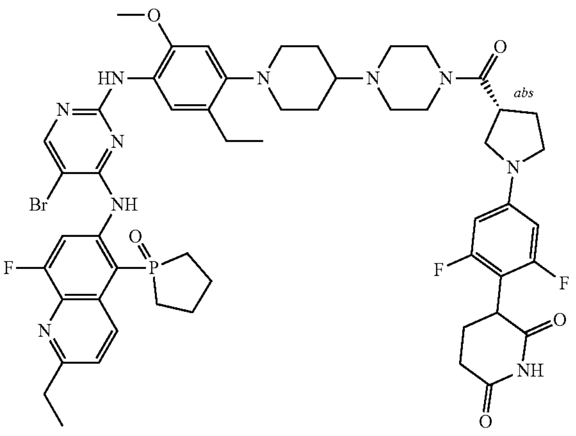
106
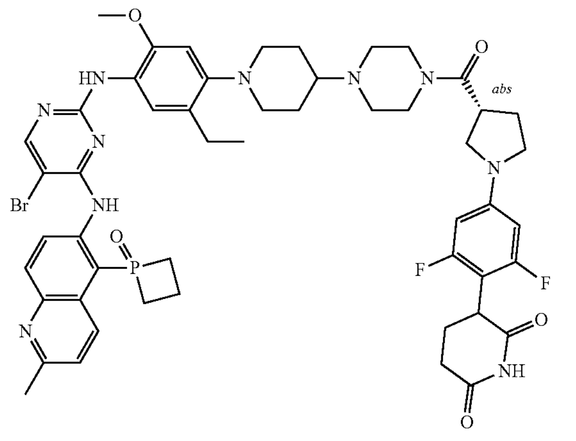
107
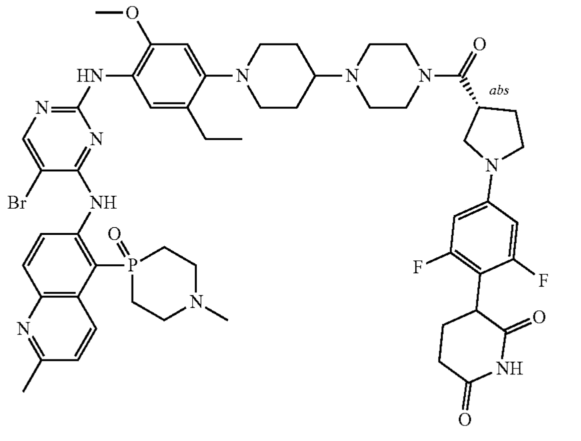

-continued
108
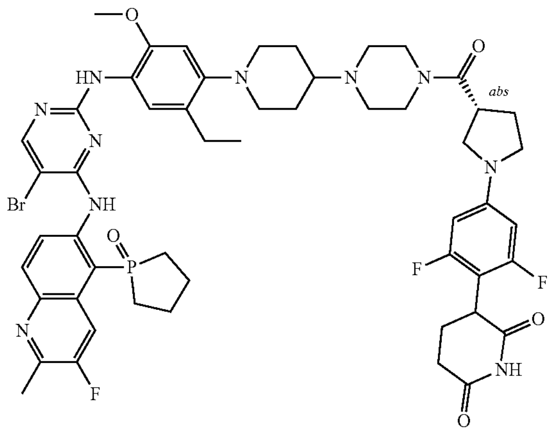
109
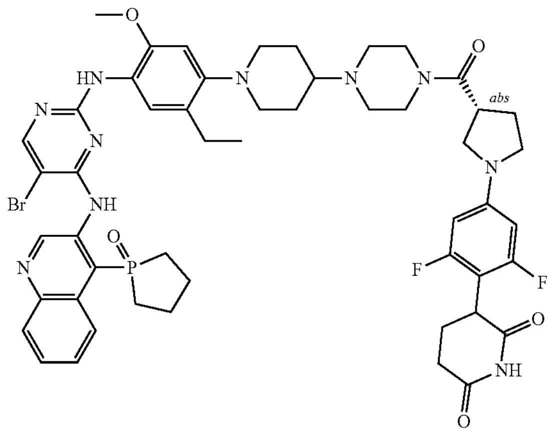
110
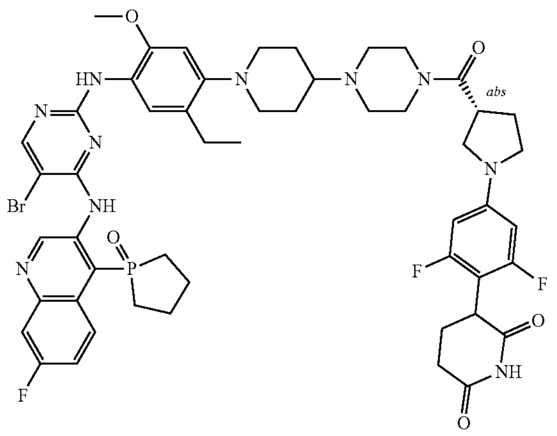
111
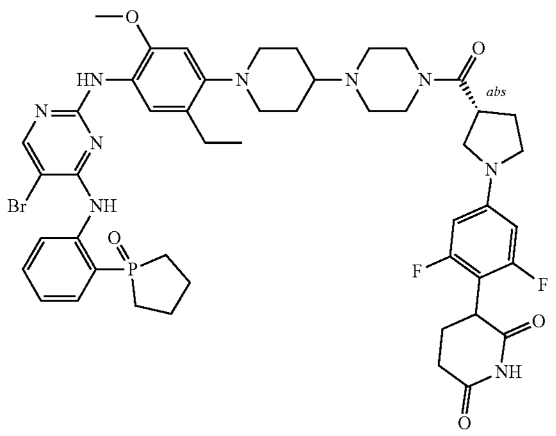
112
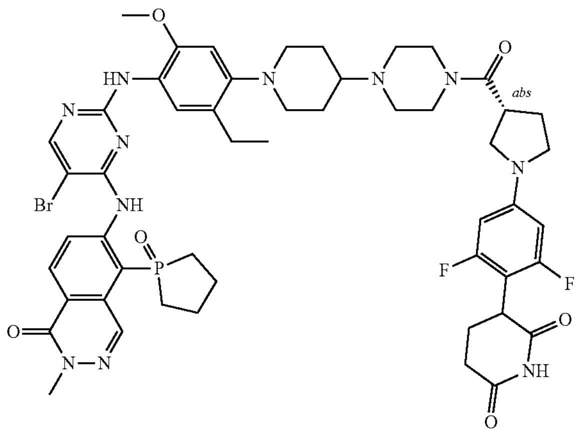
113
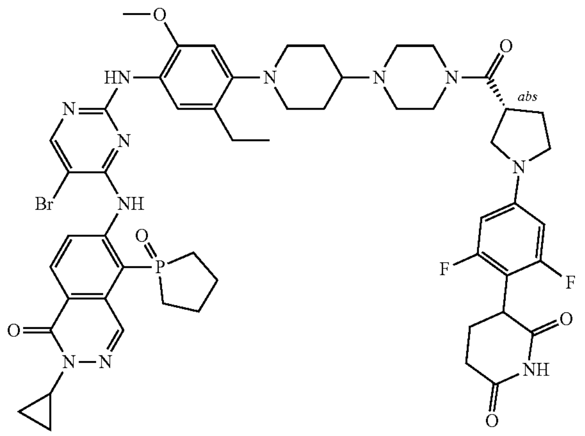

-continued
114
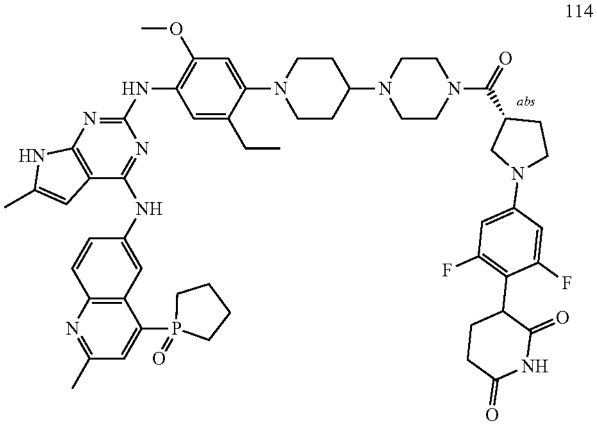
115
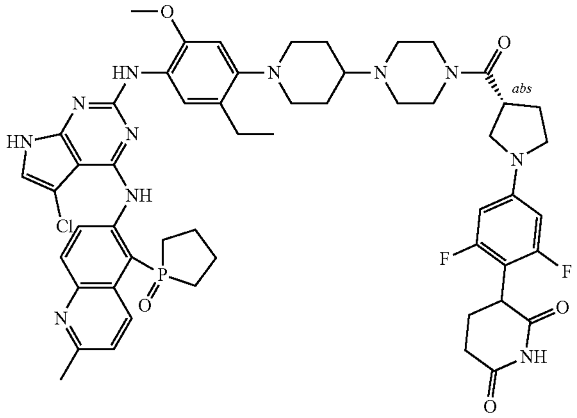
116
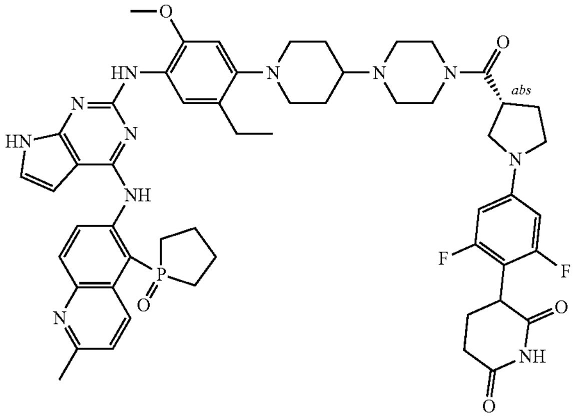
117
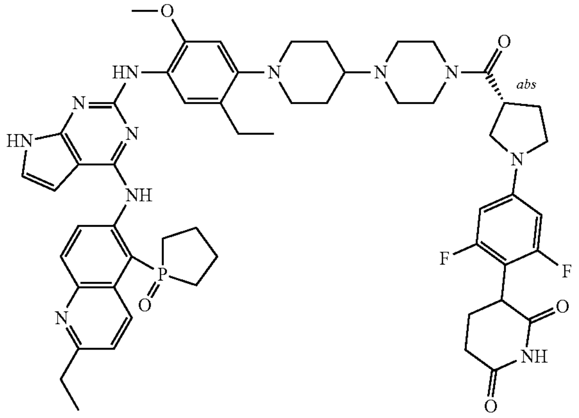
118
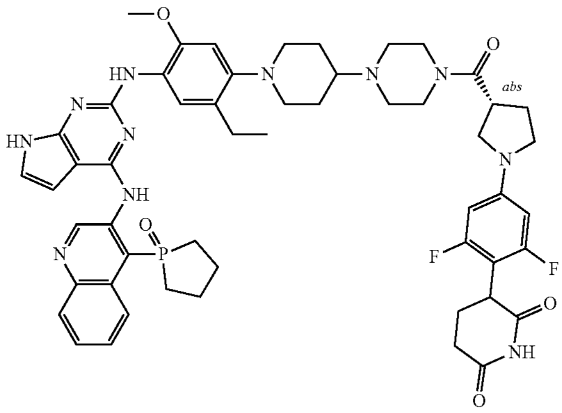
119
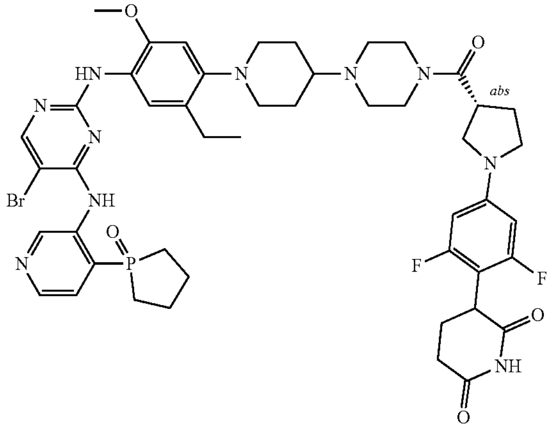

-continued
120
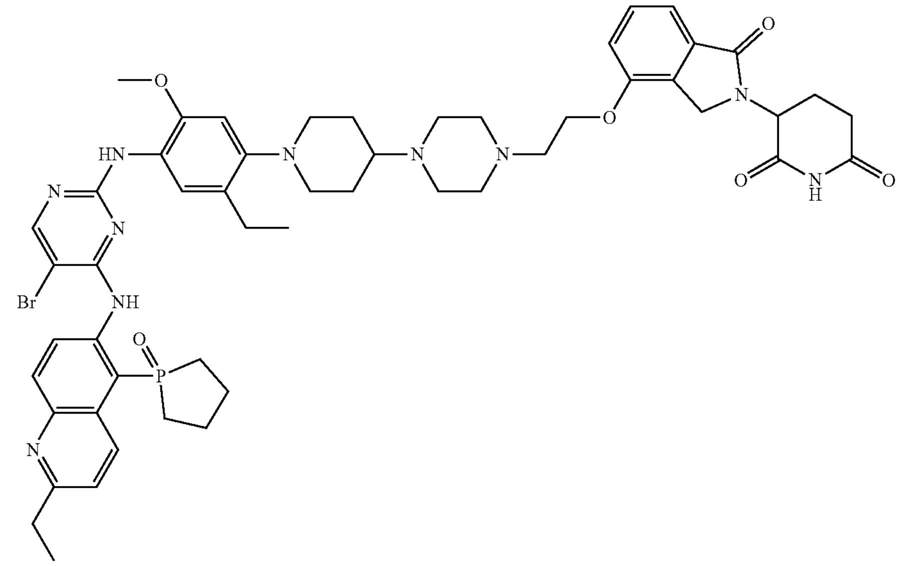
121
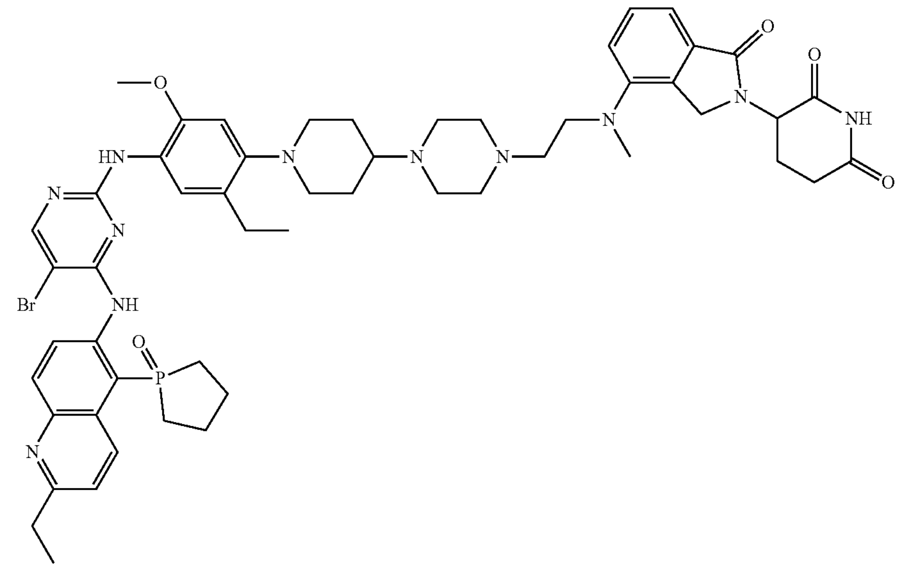
122
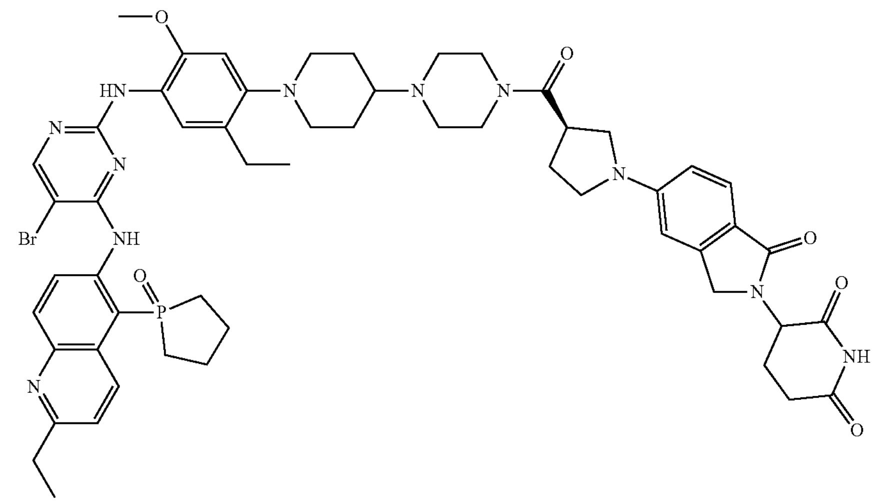

-continued
123
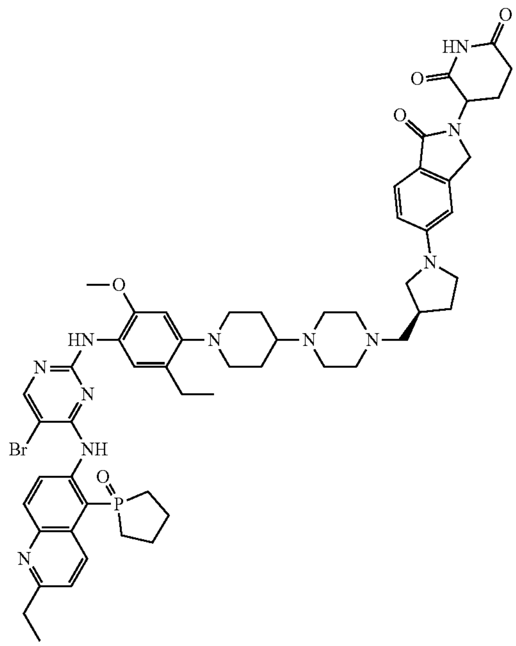
124
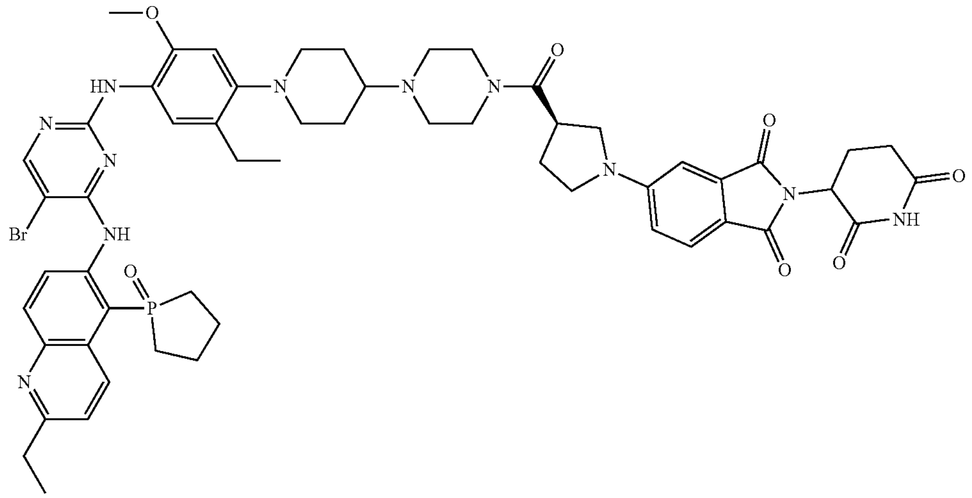
125
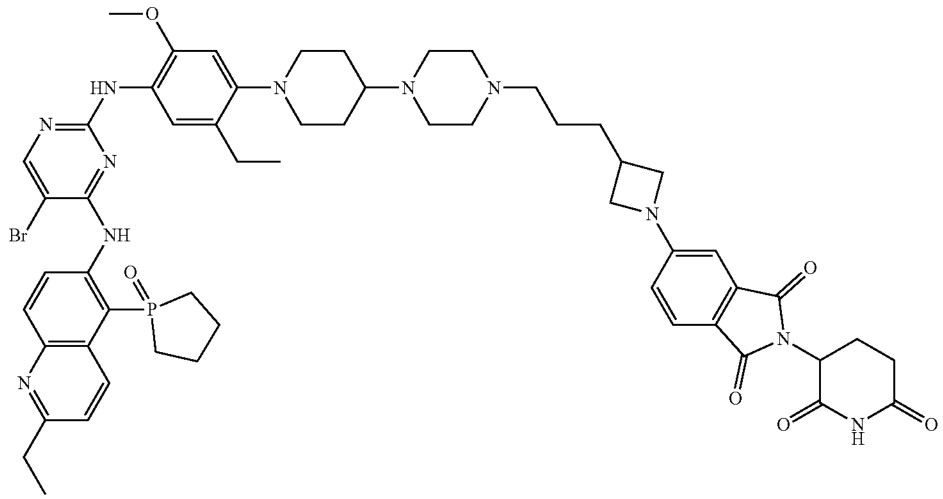

-continued
126
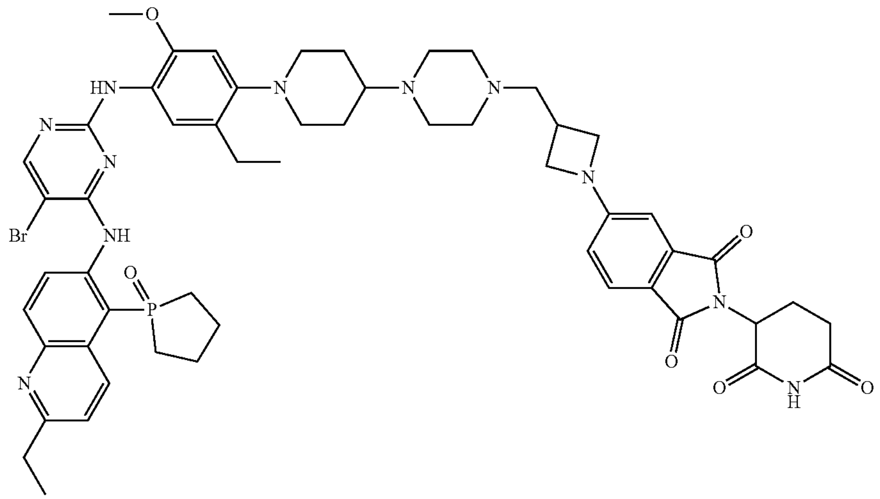
127
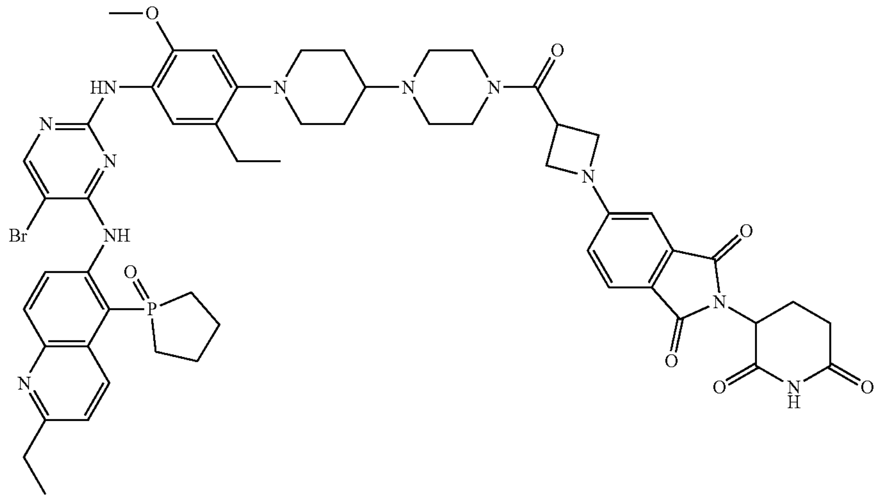
128
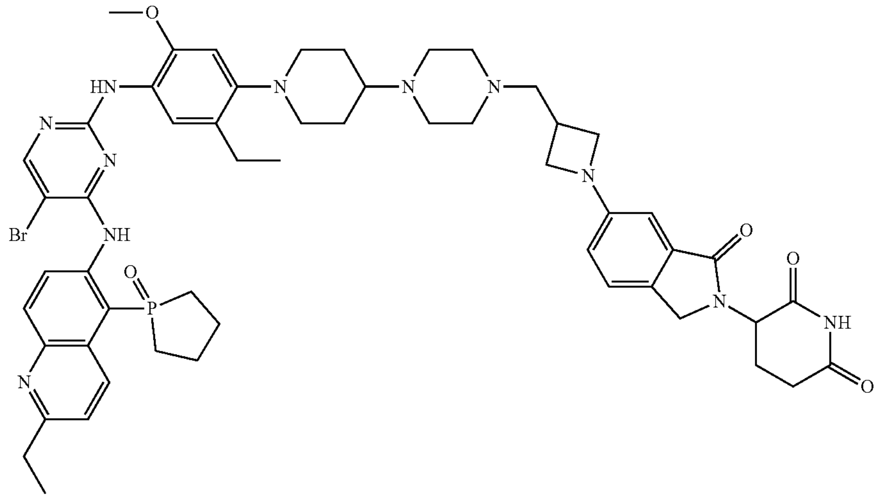

-continued
129
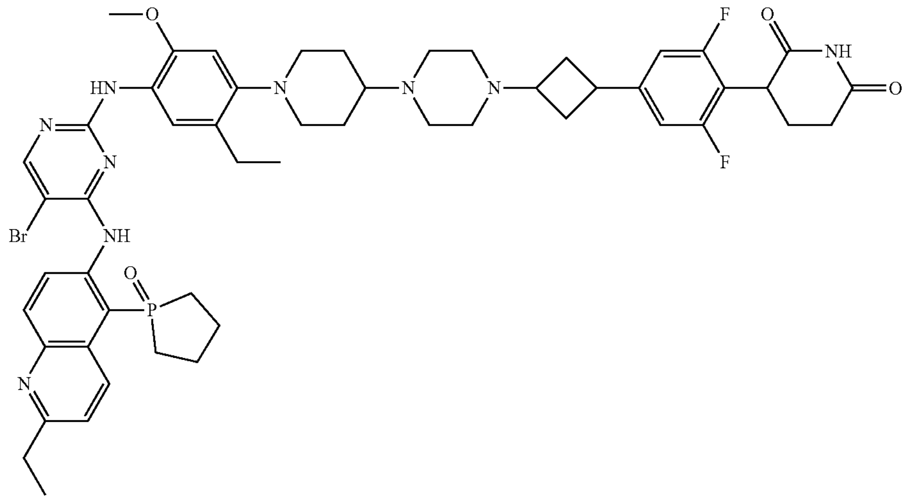
130
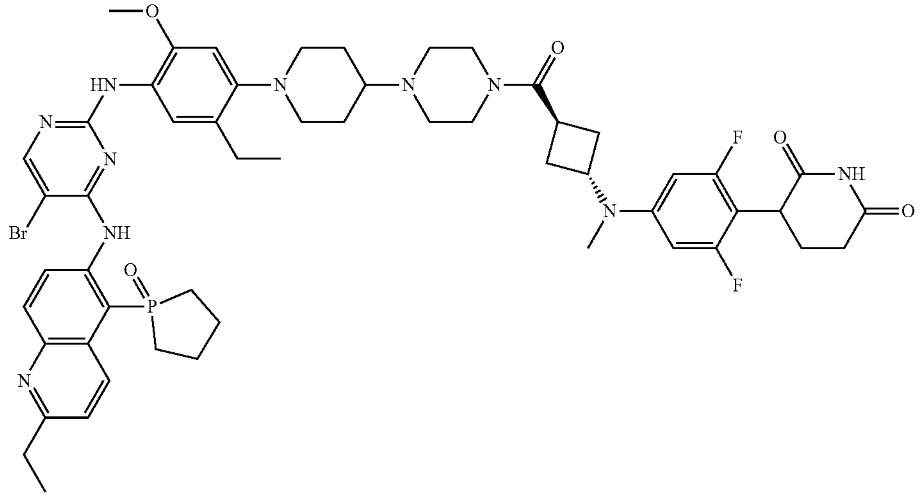
131
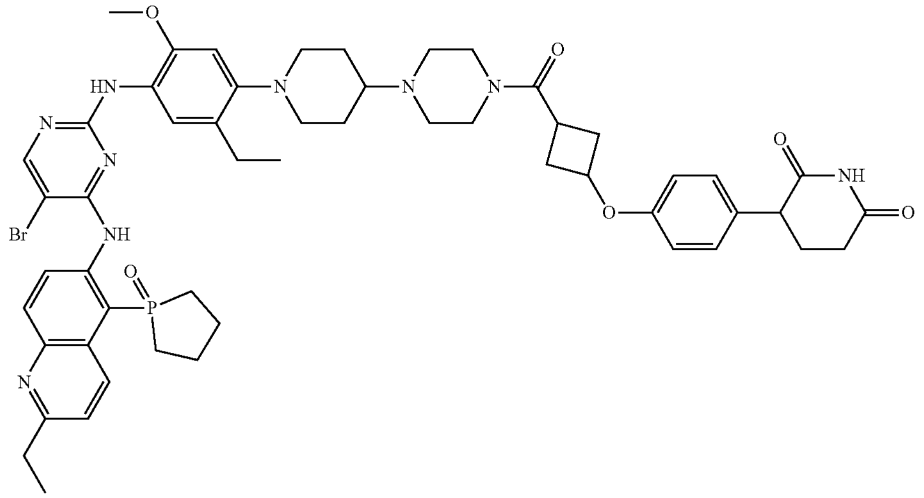

-continued
132
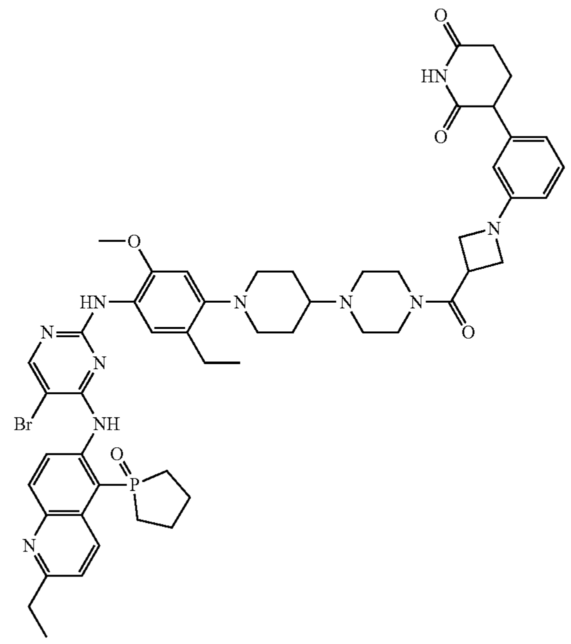
133
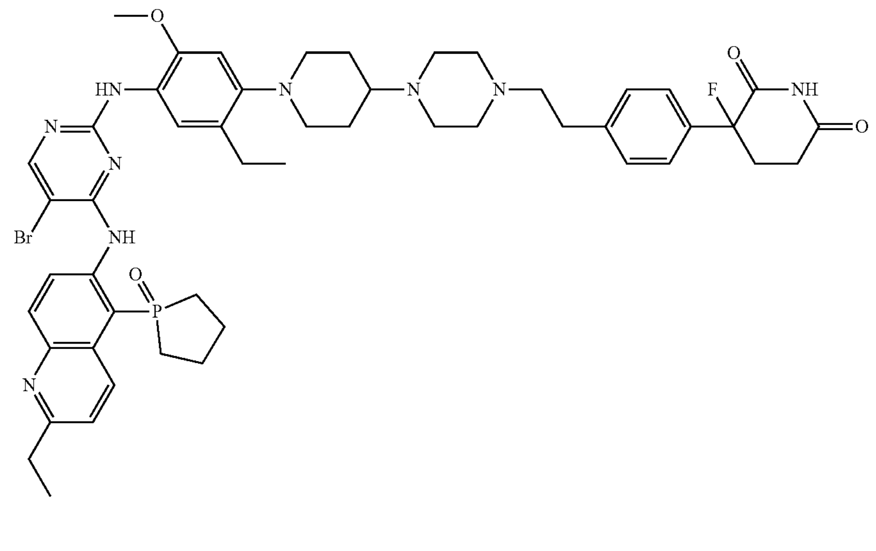

-continued
134
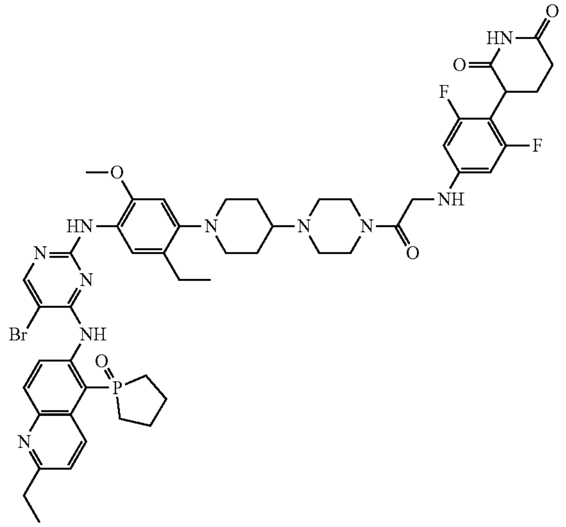
136
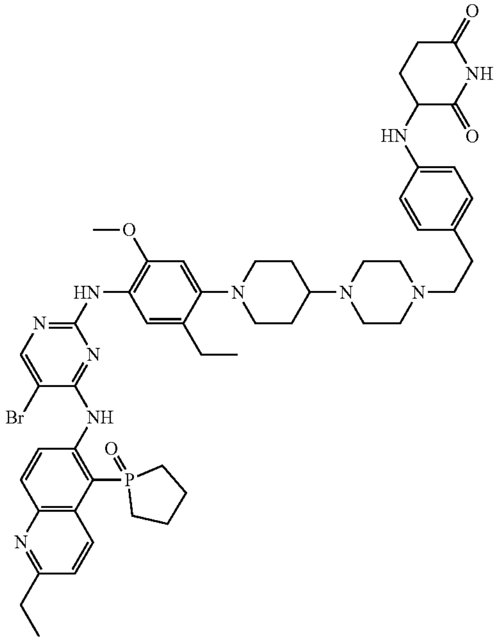
137
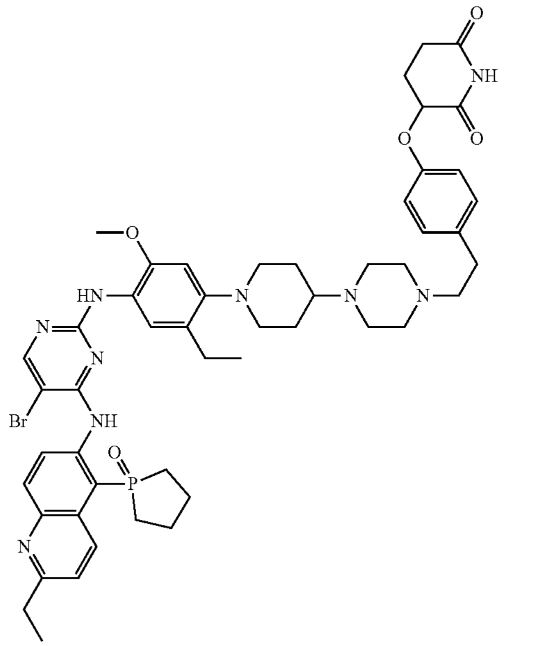

-continued
138
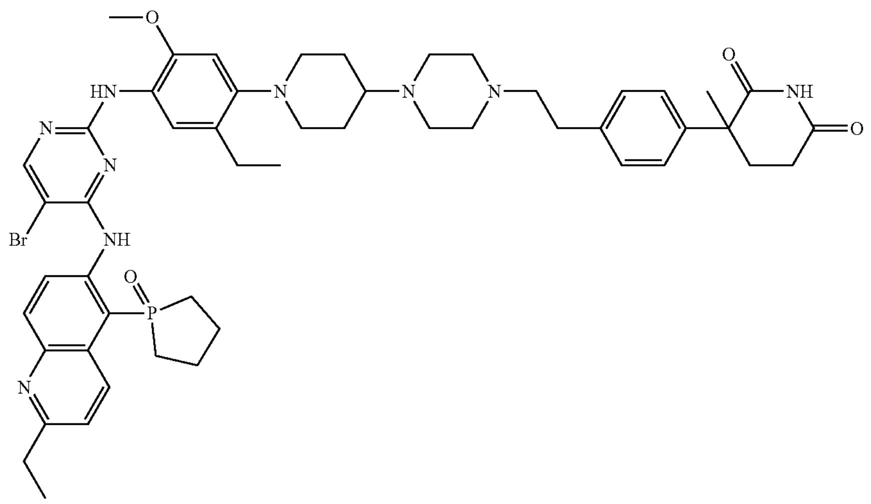
140
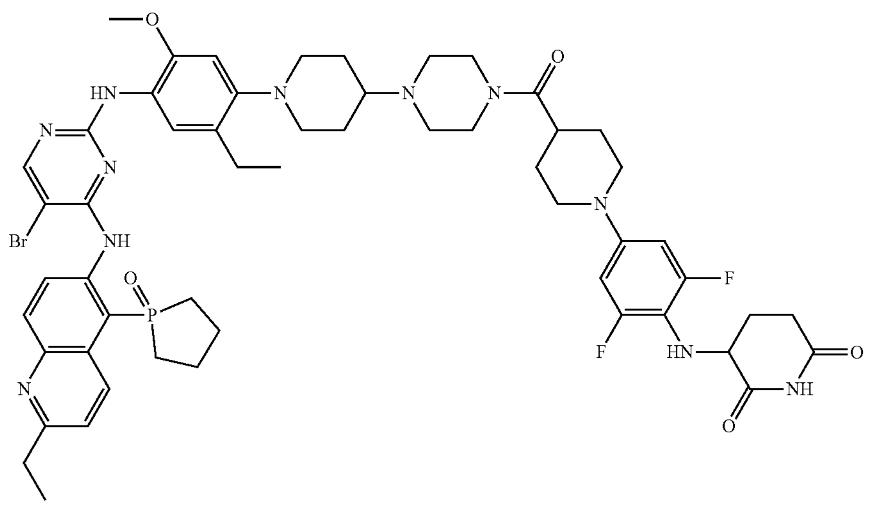
141
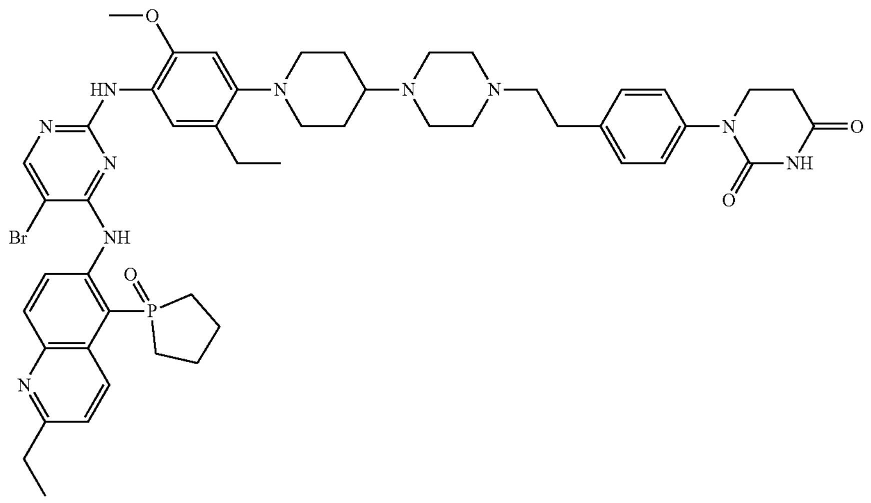

-continued
142
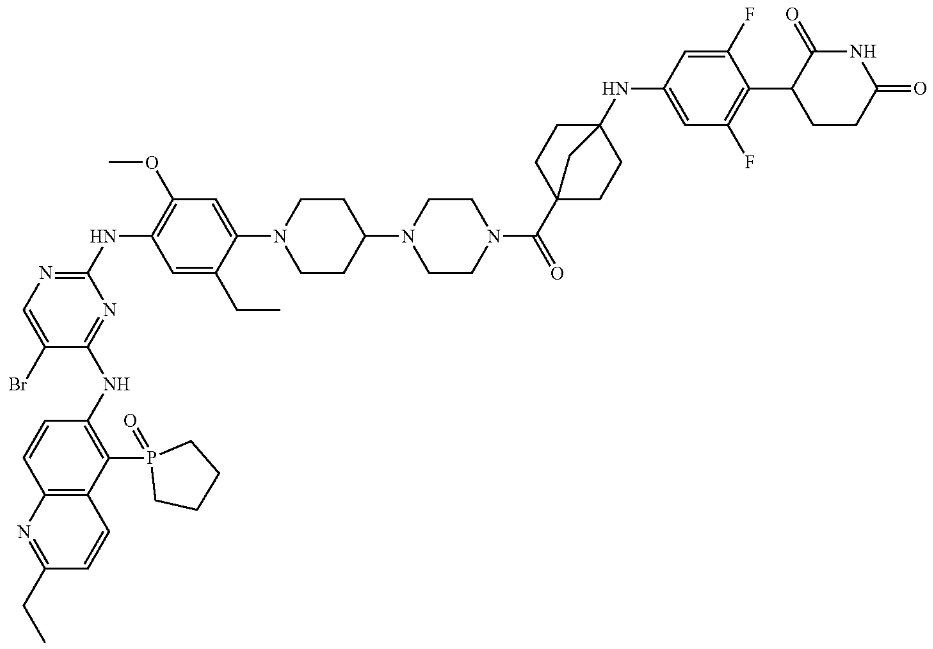
143
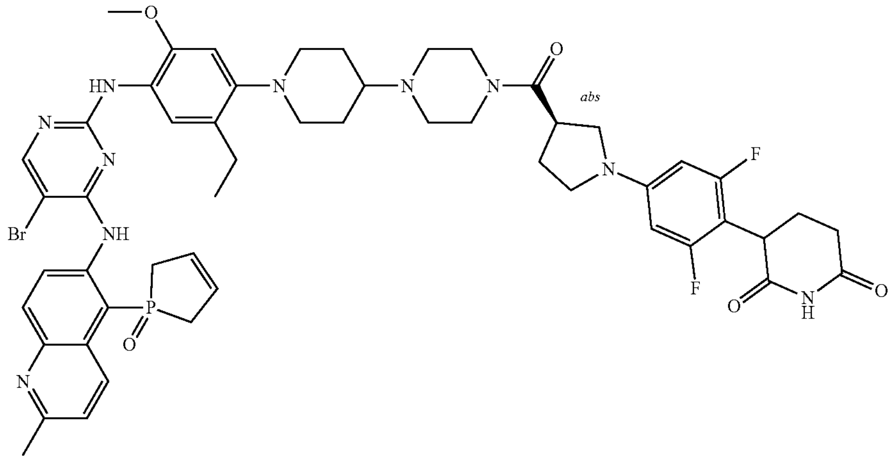
144
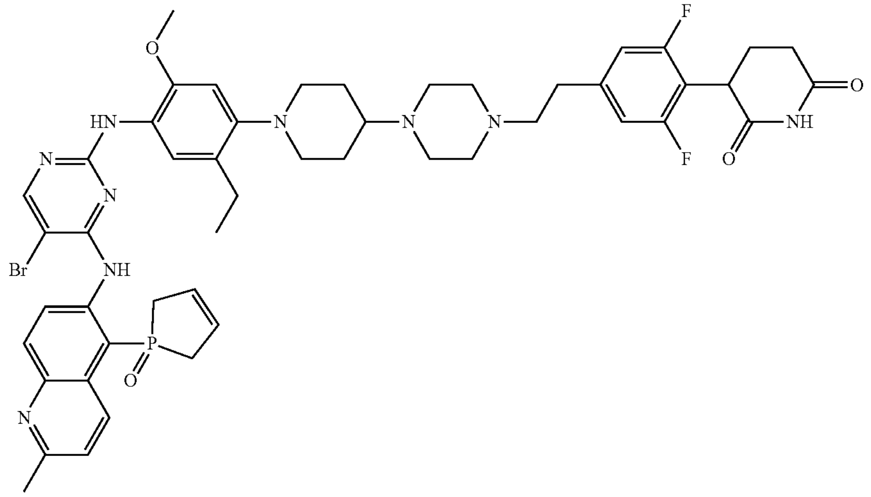

-continued
145
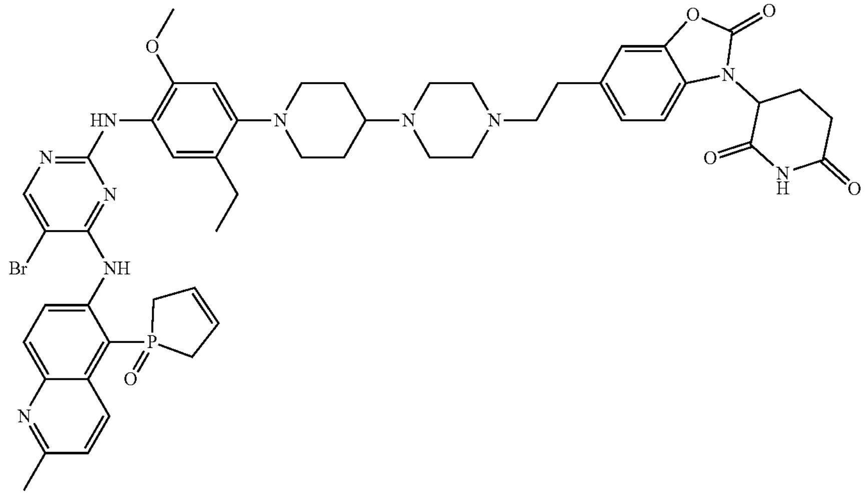
146
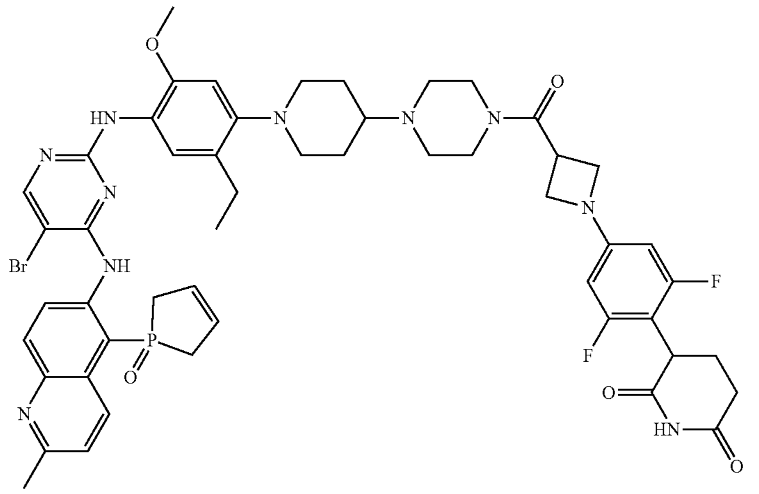
147
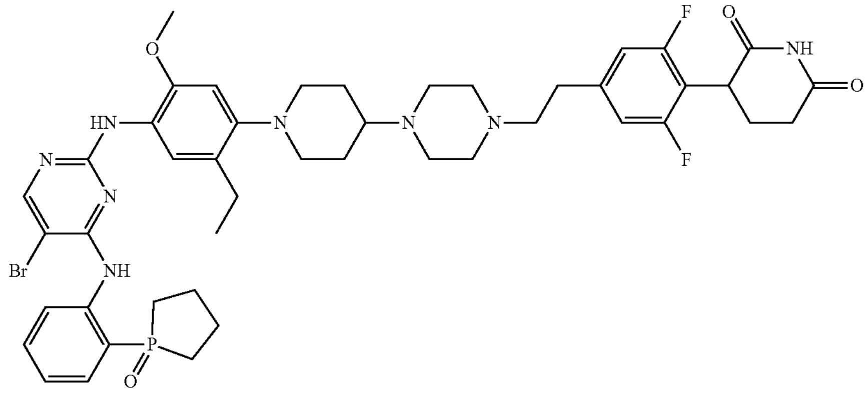

-continued
148
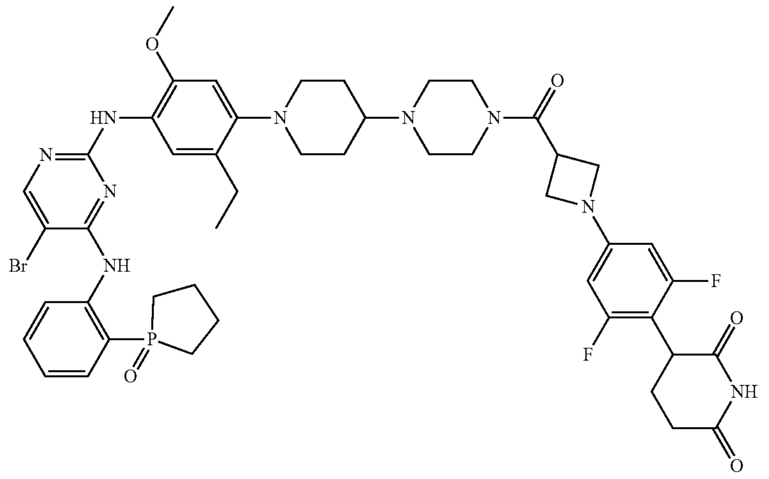
149
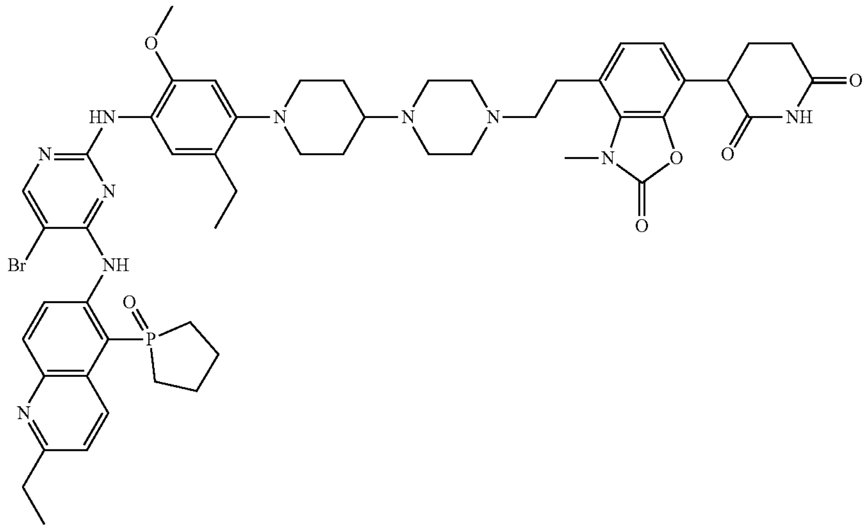
150
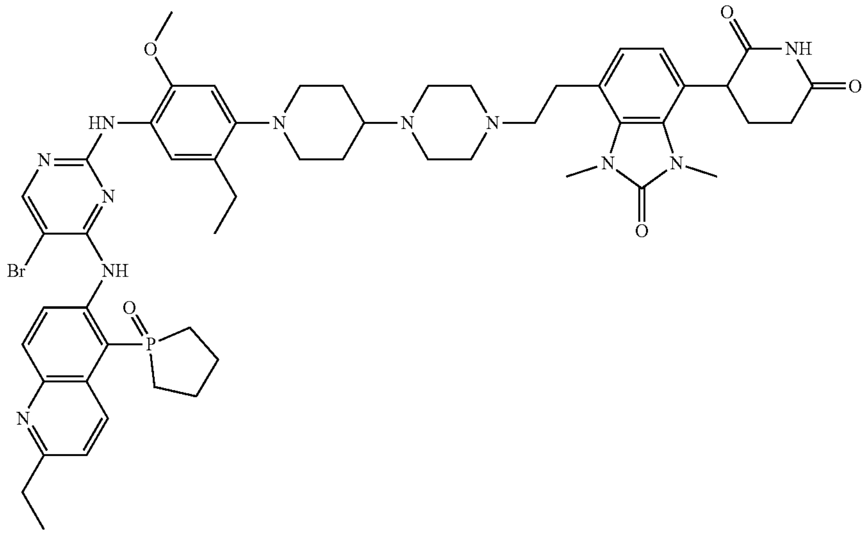

-continued
151
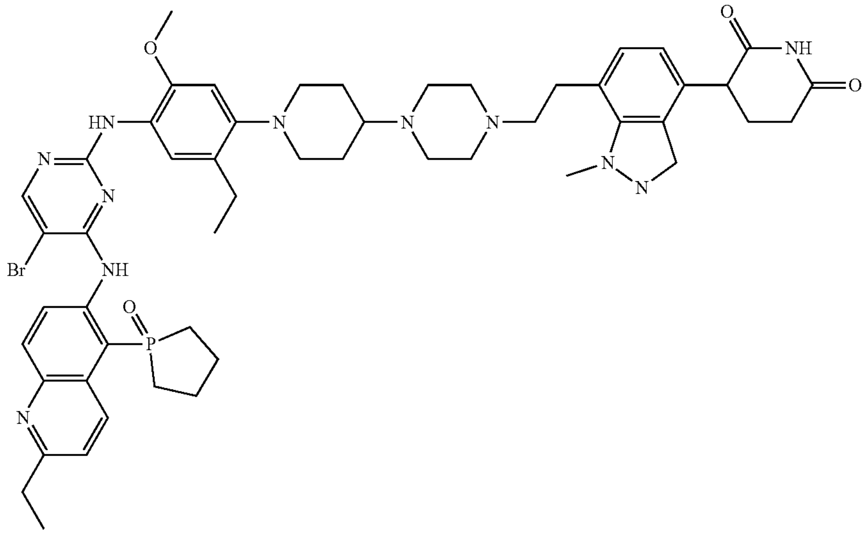
152
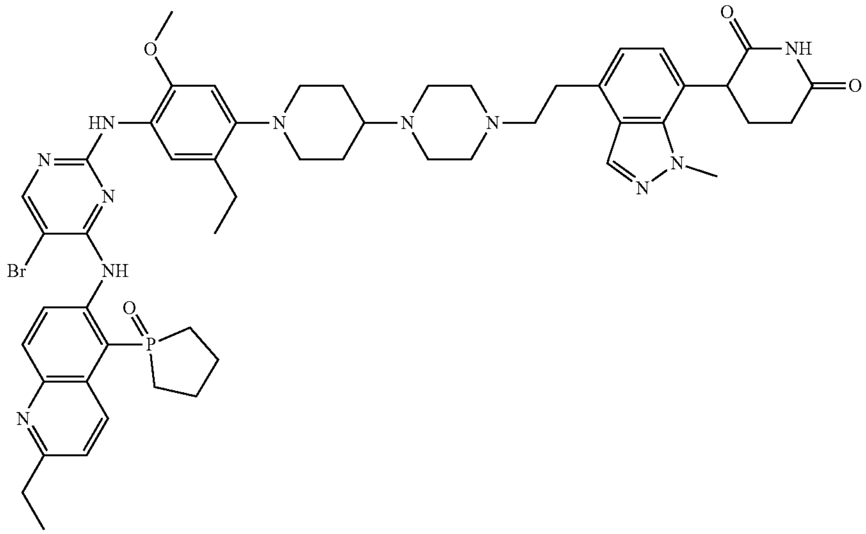
153
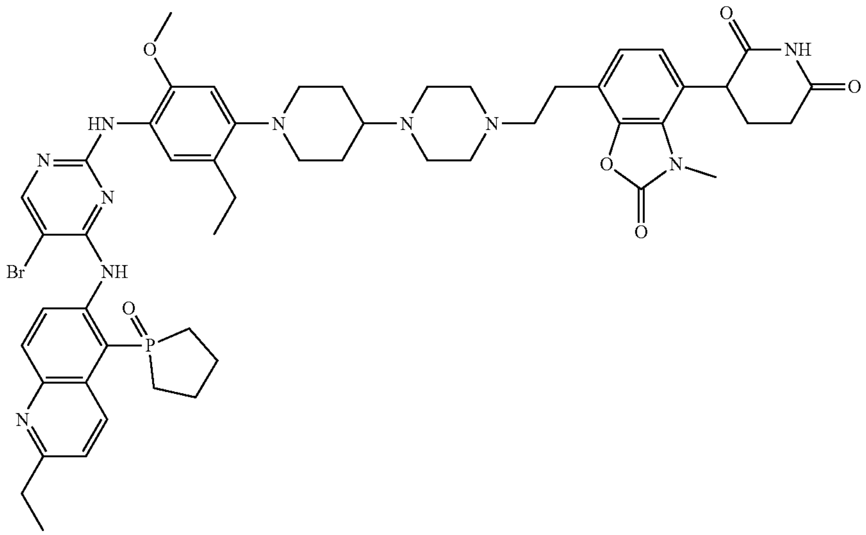

-continued
154
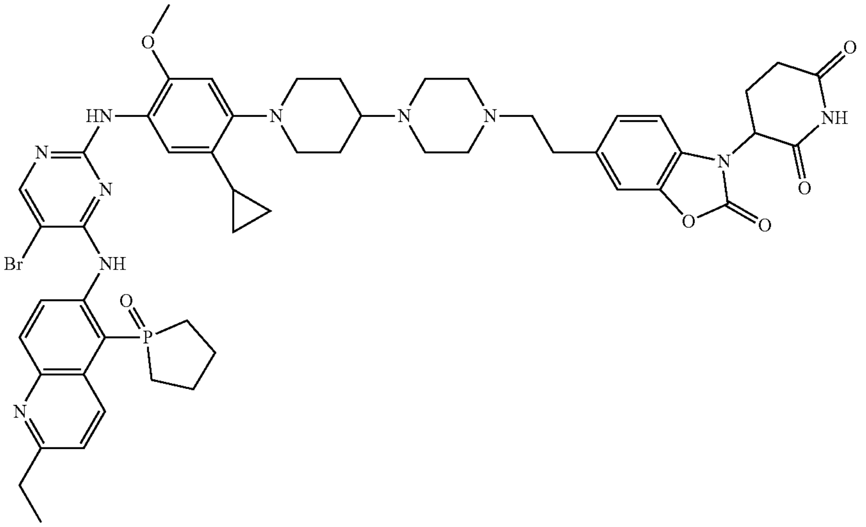
155
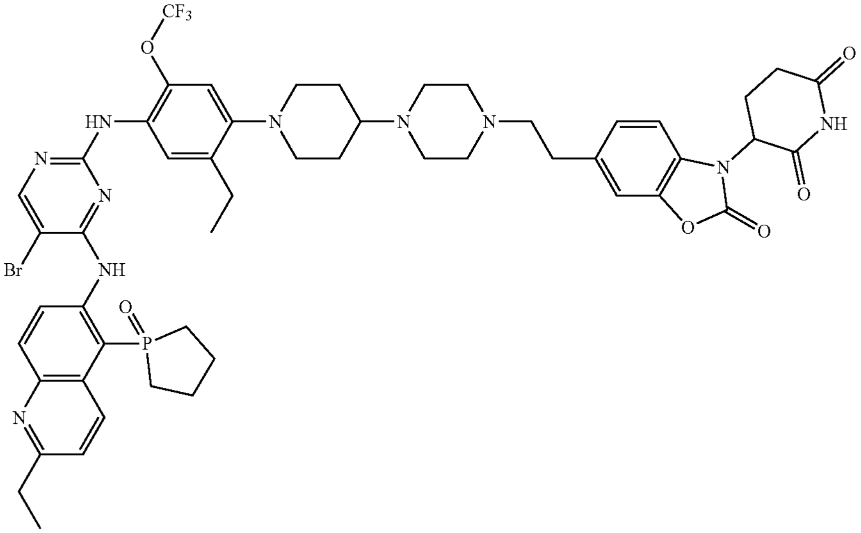
156
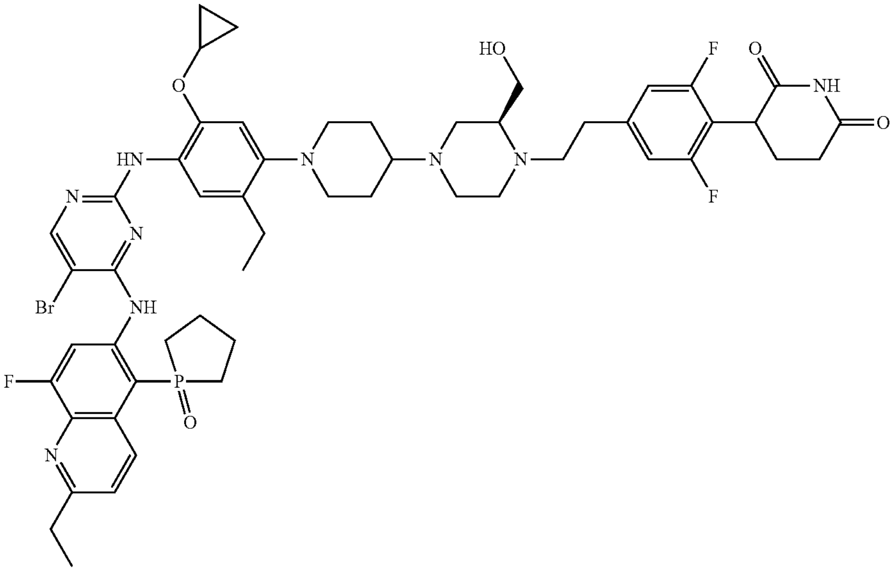

-continued

156

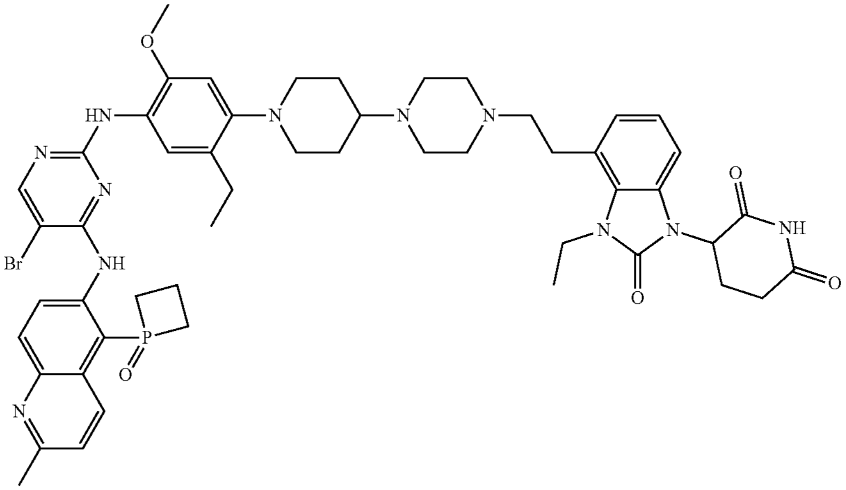

157

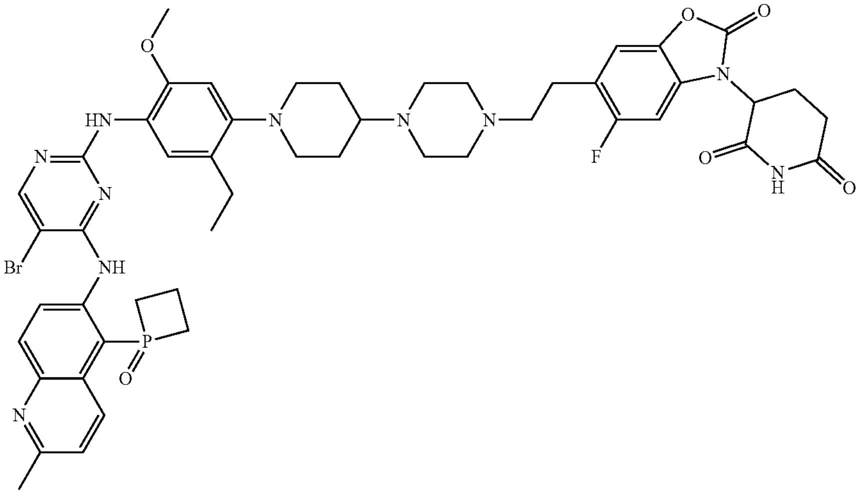

Aspect 36. A pharmaceutical composition comprising a compound of any one of Aspects 1-35 or a pharmaceutically acceptable salt, stereoisomer, tautomer or prodrug thereof, together with a pharmaceutically acceptable excipient.

Aspect 37. A method of decreasing EGFR activity by inhibition and/or degradation, which comprises administering to an individual the compound according to any one of Aspects 1-35, or a pharmaceutically acceptable salt thereof, including the compound of formula (I) or the specific compounds exemplified herein.

Aspect 38. The method of Aspect 37, wherein the disease is selected from cancer, preferred pancreatic cancer, breast cancer, glioblastoma multiforme, head and neck cancer, or non-small cell lung cancer.

Aspect 39. Use of a compound of any one of Aspects 1-35 or a pharmaceutically acceptable salt, stereoisomer, tautomer or prodrug thereof in the preparation of a medicament for treating a disease that can be affected by EGFR modulation.

Aspect 40. The use of Aspect 39, wherein the disease is cancer, preferred pancreatic cancer, breast cancer, glioblastoma multiforme, head and neck cancer, or non-small cell lung cancer.

Aspect 41. A method of treating a disease or disorder in a patient comprising administering to the patient a therapeutically effective amount of the compound any one of Aspects 1-35, or a pharmaceutically acceptable salt thereof as a EGFR kinase inhibitor and/or degrader, wherein the disease or disorder is associated with inhibition of EGFR.

Aspect 42. The method of Aspect 41, wherein the disease is selected from cancer, preferred pancreatic cancer, breast cancer, glioblastoma multiforme, head and neck cancer, or non-small cell lung cancer.

DETAILED DESCRIPTION OF THE INVENTION

The following terms have the indicated meanings throughout the specification:

Unless specifically defined elsewhere in this document, all other technical and scientific terms used herein have the meaning commonly understood by one of ordinary skill in the art to which this invention belongs.

The following terms have the indicated meanings throughout the specification:

As used herein, including the appended claims, the singular forms of words such as "a". "an", and "the", include their corresponding plural references unless the context clearly indicates otherwise.

The term "or" is used to mean, and is used interchangeably with, the term "and/or" unless the context clearly dictates otherwise.

The term "alkyl" includes a hydrocarbon group selected from linear and branched, saturated hydrocarbon groups comprising from 1 to 18, such as from 1 to 12, further such as from 1 to 10, more further such as from 1 to 8, or from 1 to 6, or from 1 to 4, carbon atoms. Examples of alkyl groups comprising from 1 to 6 carbon atoms (i.e., $C_1$a alkyl) include, but not limited to, methyl, ethyl, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), 1,1-dimethylethyl or t-butyl ("t-Bu"), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl and 3,3-dimethyl-2-butyl groups.

The term "propyl" includes 1-propyl or n-propyl ("n-Pr"), 2-propyl or isopropyl ("i-Pr").

The term "butyl" includes 1-butyl or n-butyl ("n-Bu"), 2-methyl-1-propyl or isobutyl ("i-Bu"), 1-methylpropyl or s-butyl ("s-Bu"), 1,1-dimethylethyl or t-butyl ("t-Bu").

The term "pentyl" includes 1-pentyl, 2-pentyl, 3-pentyl, 2-methyl-2-butyl, 3-methyl-2-butyl, 3-methyl-1-butyl, 2-methyl-1-butyl.

The term "hexyl" includes 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl and 3,3-dimethyl-2-butyl.

The term "alkylene" refers to a divalent alkyl group by removing two hydrogen from alkane. Alkylene includes but not limited to methylene, ethylene, propylene, and so on.

The term "halogen" includes fluoro (F), chloro (Cl), bromo (Br) and iodo (I).

The term "alkenyl" includes a hydrocarbon group selected from linear and branched hydrocarbon groups comprising at least one C═C double bond and from 2 to 18, such as from 2 to 8, further such as from 2 to 6, carbon atoms. Examples of the alkenyl group, e.g., $C_{2-6}$, alkenyl, include, but not limited to ethenyl or vinyl, prop-1-enyl, prop-2-enyl, 2-methylprop-1-enyl, but-1-enyl, but-2-enyl, but-3-enyl, buta-1,3-dienyl, 2-methylbuta-1,3-dienyl, hex-1-enyl, hex-2-enyl, hex-3-enyl, hex-4-enyl, and hexa-1,3-dienyl groups.

The term "alkenylene" refers to a divalent alkenyl group by removing two hydrogen from alkene.

Alkenylene includes but not limited to, vinylidene, butenylene, and so on.

The term "alkynyl" includes a hydrocarbon group selected from linear and branched hydrocarbon group, comprising at least one C≡C triple bond and from 2 to 18, such as 2 to 8, further such as from 2 to 6, carbon atoms. Examples of the alkynyl group, e.g., $C_{2-6}$ alkynyl, include, but not limited to ethynyl, 1-propynyl, 2-propynyl (propargyl), 1-butynyl, 2-butynyl, and 3-butynyl groups.

The term "alkynylene" refers to a divalent alkynyl group by removing two hydrogen from alkyne. Alkenylene includes but not limited to ethynylene and so on.

The term "cycloalkyl" includes a hydrocarbon group selected from saturated cyclic hydrocarbon groups, comprising monocyclic and polycyclic (e.g., bicyclic and tricyclic) groups including fused, bridged or spiro cycloalkyl.

For example, the cycloalkyl group may comprise from 3 to 12, such as from 3 to 10, further such as 3 to 8, further such as 3 to 6, 3 to 5, or 3 to 4 carbon atoms. Even further for example, the cycloalkyl group may be selected from monocyclic group comprising from 3 to 12, such as from 3 to 10, further such as 3 to 8, 3 to 6 carbon atoms. Examples of the monocyclic cycloalkyl group include cyclopropyl, cyclobutyl, cyclopentyl, cyclohexyl, cycloheptyl, cyclooctyl, cyclononyl, cyclodecyl, cycloundecyl, and cyclododecyl groups. In particular, examples of the saturated monocyclic cycloalkyl group, e.g., $C_{3-8}$cycloalkyl, include, but not limited to cyclopropyl, cyclobutyl, cyclopentyl, cyclohexyl, cycloheptyl, and cyclooctyl groups. In a preferred embodiment, the cycloalkyl is a monocyclic ring comprising 3 to 6 carbon atoms (abbreviated as $C_{3-6}$ cycloalkyl), including but not limited to, cyclopropyl, cyclobutyl, cyclopentyl, and cyclohexyl. Examples of the bicyclic cycloalkyl groups include those having from 7 to 12 ring atoms arranged as a fused bicyclic ring selected from [4,4], [4,5], [5,5], [5,6] and [6,6] ring systems, or as a bridged bicyclic ring selected from bicyclo[2.2.1]heptane, bicyclo[2.2.2]octane, and bicyclo[3.2.2]nonane. Further Examples of the bicyclic cycloalkyl groups include those arranged as a bicyclic ring selected from [5,6] and [6,6] ring systems.

The term "spiro cycloalkyl" includes a cyclic structure which contains carbon atoms and is formed by at least two rings sharing one atom.

The term "fused cycloalkyl" includes a bicyclic cycloalkyl group as defined herein which is saturated and is formed by two or more rings sharing two adjacent atoms.

The term "bridged cycloalkyl" includes a cyclic structure which contains carbon atoms and is formed by two rings sharing two atoms which are not adjacent to each other. The term "7 to 10 membered bridged cycloalkyl" includes a cyclic structure which contains 7 to 12 carbon atoms and is formed by two rings sharing two atoms which are not adjacent to each other.

Examples of fused cycloalkyl, fused cycloalkenyl, or fused cycloalkynyl include but are not limited to bicyclo[1.1.0]butyl, bicyclo[2.1.0]pentyl, bicyclo[3.1.0]hexyl, bicyclo[4.1.0]heptyl, bicyclo[3.3.0]octyl, bicyclo[4.2.0]octyl, decalin, as well as benzo 3 to 8 membered cycloalkyl, benzo $C_{4-6}$ cycloalkenyl, 2,3-dihydro-1H-indenyl, 1H-indenyl, 1, 2, 3, 4-tetralyl, 1,4-dihydronaphthyl, etc. Preferred embodiments are 8 to 9 membered fused rings, which refer to cyclic structures containing 8 to 9 ring atoms within the above examples.

The term "aryl" used alone or in combination with other terms includes a group selected from:

- 5- and 6-membered carbocyclic aromatic rings, e.g., phenyl;
- bicyclic ring systems such as 7 to 12 membered bicyclic ring systems, wherein at least one ring is carbocyclic and aromatic, e.g., naphthyl and indanyl; and,
- tricyclic ring systems such as 10 to 15 membered tricyclic ring systems wherein at least one ring is carbocyclic and aromatic, e.g., fluorenyl.

The terms "aromatic hydrocarbon ring" and "aryl" are used interchangeably throughout the disclosure herein. In some embodiments, a monocyclic or bicyclic aromatic hydrocarbon ring has 5 to 10 ring-forming carbon atoms (i.e., $C_{5-10}$ aryl). Examples of a monocyclic or bicyclic aromatic hydrocarbon ring includes, but not limited to, phenyl, naphth-1-yl, naphth-2-yl, anthracenyl, phenanthrenyl, and the like. In some embodiments, the aromatic hydrocarbon ring is a naphthalene ring (naphth-1-yl or naphth-2-yl) or phenyl ring. In some embodiments, the aromatic hydrocarbon ring is a phenyl ring.

Specifically, the term "bicyclic fused aryl" includes a bicyclic aryl ring as defined herein. The typical bicyclic fused aryl is naphthalene.

The term "heteroaryl" includes a group selected from:

5-, 6- or 7-membered aromatic, monocyclic rings comprising at least one heteroatom, for example, from 1 to 4, or, in some embodiments, from 1 to 3, in some embodiments, from 1 to 2, heteroatoms, selected from nitrogen (N), sulfur (S) and oxygen (O), with the remaining ring atoms being carbon;

7- to 12-membered bicyclic rings comprising at least one heteroatom, for example, from 1 to 4, or, in some embodiments, from 1 to 3, or, in other embodiments, 1 or 2, heteroatoms, selected from N, O, and S, with the remaining ring atoms being carbon and wherein at least one ring is aromatic and at least one heteroatom is present in the aromatic ring; and 11- to 14-membered tricyclic rings comprising at least one heteroatom, for example, from 1 to 4, or in some embodiments, from 1 to 3, or, in other embodiments, 1 or 2, heteroatoms, selected from N. O, and S, with the remaining ring atoms being carbon and wherein at least one ring is aromatic and at least one heteroatom is present in an aromatic ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1. When the heteroaryl group contains more than one heteroatom ring member, the heteroatoms may be the same or different. The nitrogen atoms in the ring(s) of the heteroaryl group can be oxidized to form N-oxides.

Specifically, the term "bicyclic fused heteroaryl" includes a 7- to 12-membered, preferably 7- to 10-membered, more preferably 9- or 10-membered fused bicyclic heteroaryl ring as defined herein. Typically, a bicyclic fused heteroaryl is 5-membered/5-membered, 5-membered/6-membered, 6-membered/6-membered, or 6-membered/7-membered bicyclic. The group can be attached to the remainder of the molecule through either ring.

"Heterocyclyl", "heterocycle" or "heterocyclic" are interchangeable and include a non-aromatic heterocyclyl group comprising one or more heteroatoms selected from nitrogen, oxygen or optionally oxidized sulfur as ring members, with the remaining ring members being carbon, including monocyclic, fused, bridged, and spiro ring, i.e., containing monocyclic heterocyclyl, bridged heterocyclyl, spiro heterocyclyl, and fused heterocyclic groups.

The term "at least one substituent" disclosed herein includes, for example, from 1 to 4, such as from 1 to 3, further as 1 or 2, substituents, provided that the theory of valence is met. For example. "at least one substituent F" disclosed herein includes from 1 to 4, such as from 1 to 3, further as 1 or 2, substituents F.

The term "divalent" refers to a linking group capable of forming covalent bonds with two other moieties. For example, "a divalent cycloalkyl group" refers to a cycloalkyl group obtained by removing two hydrogen from the corresponding cycloalkane to form a linking group, the term "divalent aryl group", "divalent heterocycyl group" or "divalent heteroaryl group" should be understood in a similar manner.

Compounds disclosed herein may contain an asymmetric center and may thus exist as enantiomers. "Enantiomers" refer to two stereoisomers of a compound which are non-superimposable mirror images of one another. Where the compounds disclosed herein possess two or more asymmetric centers, they may additionally exist as diastereomers. Enantiomers and diastereomers fall within the broader class of stereoisomers. All such possible stereoisomers as substantially pure resolved enantiomers, racemic mixtures thereof, as well as mixtures of diastereomers are intended to be included. All stereoisomers of the compounds disclosed herein and/or pharmaceutically acceptable salts thereof are intended to be included. Unless specifically mentioned otherwise, reference to one isomer applies to any of the possible isomers. Whenever the isomeric composition is unspecified, all possible isomers are included.

When compounds disclosed herein contain olefinic double bonds, unless specified otherwise, such double bonds are meant to include both E and Z geometric isomers.

When compounds disclosed herein contain a di-substituted cyclic ring system, substituents found on such ring system may adopt cis and trans formations. Cis formation means that both substituents are found on the upper side of the 2 substituent placements on the carbon, while trans would mean that they were on opposing sides. For example, the di-substituted cyclic ring system may be cyclohexyl or cyclobutyl ring.

It may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed ("SMB") and preparative thin or thick layer chromatography, as well as techniques of small scale thin layer and flash chromatography. One skilled in the art could select and apply the techniques most likely to achieve the desired separation.

"Diastereomers" refer to stereoisomers of a compound with two or more chiral centers but which are not mirror images of one another. Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column.

A single stereoisomer, e.g., a substantially pure enantiomer, may be obtained by resolution of the racemic mixture using a method such as formation of diastereomers using optically active resolving agents (Eliel, E and Wilen, S *Stereochemistry of Organic Compounds*. New York: John Wiley & Sons, Inc., 1994; Lochmuller, C. H., et al. "*Chromatographic resolution of enantiomers: Selective review.*" *J. Chromatogr.,* 113(3) (1975): pp, 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: Wainer, Irving W., Ed *Drug Stereochemistry: Analytical Methods and Pharmacology*. New York: Marcel Dekker, Inc., 1993.

Some of the compounds disclosed herein may exist with different points of attachment of hydrogen, referred to as tautomers. For example, compounds including carbonyl —$CH_2C(O)$— groups (keto forms) may undergo tautomerism to form hydroxyl —CH═C(OH)— groups (enol forms). Both keto and enol forms, individually as well as mixtures thereof, are also intended to be included where applicable.

"Prodrug" refers to a derivative of an active agent that requires a transformation within the body to release the active agent. In some embodiments, the transformation is an enzymatic transformation. Prodrugs are frequently, although not necessarily, pharmacologically inactive until converted to the active agent.

"Pharmaceutically acceptable salts" refer to those salts which are, within the scope of sound medical judgment, suitable for use in contact with the tissues of humans and lower animals without undue toxicity, irritation, allergic response and the like, and are commensurate with a reasonable benefit/risk ratio. A pharmaceutically acceptable salt may be prepared in situ during the final isolation and purification of the compounds disclosed herein, or separately by reacting the free base function with a suitable organic acid or by reacting the acidic group with a suitable base. The term also includes salts of the stereoisomers (such as enantiomers and/or diastereomers), tautomers and prodrugs of the compound of the invention.

In addition, if a compound disclosed herein is obtained as an acid addition salt, the free base can be obtained by basifying a solution of the acid salt. Conversely, if the product is a free base, an addition salt, such as a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used without undue experimentation to prepare non-toxic pharmaceutically acceptable addition salts.

The terms "administration", "administering", "treating" and "treatment" herein, when applied to an animal, human, experimental subject, cell, tissue, organ, or biological fluid, mean contact of an exogenous pharmaceutical, therapeutic, diagnostic agent, or composition to the animal, human, subject, cell, tissue, organ, or biological fluid. Treatment of a cell encompasses contact of a reagent to the cell, as well as contact of a reagent to a fluid, where the fluid is in contact with the cell. The term "administration" and "treatment" also means in vitro and ex vivo treatments, e.g., of a cell, by a reagent, diagnostic, binding compound, or by another cell. The term "subject" herein includes any organism, preferably an animal, more preferably a mammal (e.g., rat, mouse, dog, cat, and rabbit) and most preferably a human.

The term "effective amount" or "therapeutically effective amount" refers to an amount of the active ingredient, such as compound that, when administered to a subject for treating a disease, or at least one of the clinical symptoms of a disease or disorder, is sufficient to affect such treatment for the disease, disorder, or symptom. The term "therapeutically effective amount" can vary with the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be apparent to those skilled in the art or can be determined by routine experiments. In some embodiments, "therapeutically effective amount" is an amount of at least one compound and/or at least one stereoisomer, tautomer or prodrug thereof, and/or at least one pharmaceutically acceptable salt thereof disclosed herein effective to "treat" as defined herein, a disease or disorder in a subject. In the case of combination therapy, the term "therapeutically effective amount" refers to the total amount of the combination objects for the effective treatment of a disease, a disorder or a condition.

The term "disease" refers to any disease, discomfort, illness, symptoms or indications, and can be interchangeable with the term "disorder" or "condition".

Throughout this specification and the claims which follow, unless the context requires otherwise, the term "comprise", and variations such as "comprises" and "comprising" are intended to specify the presence of the features thereafter, but do not exclude the presence or addition of one or more other features. When used herein the term "comprising" can be substituted with the term "containing", "including" or sometimes "having".

Throughout this specification and the claims which follow, the term "$C_{n-m}$~" indicates a range which includes the endpoints, wherein n and m are integers and indicate the number of carbons. Examples include $C_{1-8}$, $C_{1-6}$, and the like.

Unless specifically defined elsewhere in this document, all other technical and scientific terms used herein have the meaning commonly understood by one of ordinary skill in the art to which this invention belongs.

EXAMPLES

The examples below are intended to be purely exemplary and should not be considered to be limiting in any way. Efforts have been made to ensure accuracy with respect to numbers used (for example, amounts, temperature, etc.), but some experimental errors and deviations should be accounted for. Unless indicated otherwise, temperature is in degrees Centigrade. Reagents were purchased from commercial suppliers such as Sigma-Aldrich, Alfa Aesar, or TCI, and were used without further purification unless indicated otherwise. Unless indicated otherwise, the reactions set forth below were performed under a positive pressure of nitrogen or argon or with a drying tube in anhydrous solvents; the reaction flasks were fitted with rubber septa for the introduction of substrates and reagents via syringe; and glassware was oven dried and/or heat dried.

$^1$H NMR spectra were recorded on an Agilent instrument operating at 400 MHz. $^1$HNMR spectra were obtained using $CDCl_3$, $CD_2Cl_2$, $CD_3OD$, $D_2O$, $d_6$-DMSO, $d_6$-acetone or $(CD_3)_2CO$ as solvent and tetramethylsilane (0.00 ppm) or residual solvent ($CDCl_3$: 7.25 ppm; $CD_3OD$: 3.31 ppm; $D_2O$: 4.79 ppm; $d_6$-DMSO: 2.50 ppm; $d_6$-acetone: 2.05; $(CD_3)_3CO$: 2.05) as the reference standard. When peak multiplicities are reported, the following abbreviations are used: s (singlet), d (doublet), t (triplet), q (quartet), qn (quintuplet), sx (sextuplet), m (multiplet), br (broadened), dd (doublet of doublets), dt (doublet of triplets). Coupling constants, when given, are reported in Hertz (Hz).

LCMS-1: LC-MS spectrometer (Agilent 1260 Infinity) Detector: MWD (190-400 nm), Mass detector: 6120 SQ Mobile phase: A: water with 0.1% Formic acid, B: acetonitrile with 0.1% Formic acid Column: Poroshell 120 EC-C18, 4.6×50 mm, 2.7 pm Gradient method: Flow: 1.8 mL/min Time (min) A (%) B (%)

| Time (min) | A(%) | B(%) |
|---|---|---|
| 0.00 | 95 | 5 |
| 1.5 | 5 | 95 |
| 2.0 | 5 | 95 |
| 2.1 | 95 | 5 |
| 3.0 | 95 | 5 |

LCMS, LCMS-3: LC-MS spectrometer (Agilent 1260 Infinity II) Detector: MWD (190400 nm). Mass detector: G6125C SQ Mobile phase: A: water with 0.1% Formic acid, B: acetonitrile with 0.1% Formic acid Column: Poroshell 120 EC-C18, 4.6×50 mm, 2.7 pm Gradient method: Flow: 1.8 mL/min Time (min) A (%) B (%)

| Time (min) | A(%) | B(%) |
|---|---|---|
| 0.00 | 95 | 5 |
| 1.5 | 5 | 95 |

-continued

| Time (min) | A(%) | B(%) |
|---|---|---|
| 2.0 | 5 | 95 |
| 2.1 | 95 | 5 |
| 3.0 | 95 | 5 |

LCMS-2: LC-MS spectrometer (Agilent 1290 Infinity II) Detector: MWD (190-400 nm). Mass detector: G6125C SQ Mobile phase: A: water with 0.1% Formic acid, B: acetonitrile with 0.1% Formic acid Column: Poroshell 120 EC-C18, 4.6×50 mm, 2.7 pm Gradient method: Flow: 1.2 mL/min Time (min) A (%) B (%)

| Time (min) | A(%) | B(%) |
|---|---|---|
| 0.00 | 90 | 10 |
| 1.5 | 5 | 95 |
| 2.0 | 5 | 95 |
| 2.1 | 90 | 10 |
| 3.0 | 90 | 10 |

Preparative HPLC was conducted on a column (150×21.2 mm ID, 5 pm, Gemini NXC 18) at a flow rate of 20 ml/min, injection volume 2 ml, at room temperature and UV Detection at 214 nm and 254 nm.

In the following examples, the abbreviations below are used:

| | |
|---|---|
| $(BPin)_2$ | 4,4,4',4',5,5,5',5'-Octamethyl-2,2'-bi-1,3,2-dioxaborolane |
| $Ac_2O$ | acetic anhydride |
| AcCl | Acetyl chloride |
| ACN or MeCN | Acetonitrile |
| AcOH or HOAc | Acetic acid |
| AcONa or NaOAc | Sodium acetate |
| Aq | Aqueous |
| BINAP | (±)-2,2'-Bis(diphenylphosphino)-1,1'-BINAPhthyl |
| Bn | benzyl |
| BnBr | Benzyl Bromide |
| Boc | t-Butyloxy carbonyl |
| C: 40691-33-6 | dichlorobis(tri-o-tolylphosphine)palladium(II) |
| Cbz | Benzyloxycarbonyl |
| CDI | 1,1'-Carbonyldiimidazole |
| DCM | Dichloromethane |
| Con. | Concentrated |
| DavePhos | 2'-(Dicyclohexylphosphino)-N,N-dimethyl-2-biphenylamine |
| DBU | 1,8-diazabicyclo[5.4.0]undec-7-ene |
| DCE | dichloroethane |
| DHP | 3,4-Dihydro-2H-pyran |
| DIBAL-H | Diisobutylaluminium hydride |
| DIEA or DIPEA | N,N-diisopropylethylamine |
| DMAc | N,N-Dimethylacetamide |
| DMAP | 4-N,N-dimethylaminopyridine |
| DMP | Dess-Martin periodinane |
| DMF | N,N-Dimethylformamide |
| DMSO | Dimethyl sulfoxide |
| Dppf | 1,1''-bis(diphenylphosphino)ferrocene |
| EA or EtOAc | Ethyl acetate |
| EtOH | ethanol |
| FA | Formic acid |
| h or hr | Hour |
| HATU | 2-(7-Azabenzotriazol-1-yl)-N,N,N',N'-tetramethyluronium hexafluorophosphate |
| HBTU | O-(7-Benzotriazole-1-yl)-N,N,N',N'-tetramethyluronium hexafluorophosphate |
| Hex | Hexane |
| HPLC | High Performance Liquid Chromatography |
| HOVEYDA-Grubbs catalyst | (1,3-Bis-(2,4,6-trimethylpheny1)-2-imidazolidinylidene)dichloro(o-isopropylphenylMethylene)ruthenium |
| hrs | hours |
| IBX | 2-lodoxybenzoic acid |
| IPA | 2-propanol |
| i-PrOH | Isopropyl alcohol |

-continued

| | |
|---|---|
| KHMDS | Potassium bis(trimethylsilyl)amide |
| LiHMDS | Lithium bis(trimethylsilyl)amide |
| KOAc or AcOK | Potassium Acetate |
| MeCN or ACN | Acetonitrile |
| MeOH | Methanol |
| Min | Minutes |
| ms or MS | Mass spectrum |
| MsCl | Methanesulfonyl chloride |
| MsOH | Methanesulfonic acid |
| MTBE | Methyl tert-butyl ether |
| NMP | 1-Methyl-2-pyrrolidinone |
| o/n | overnight |
| Pd(dppf)$Cl_2$ | [1,1'-Bis(diphenylphosphino)ferrocene]dichloropalladium(II) |
| $Pd_2(dba)_3$ | Tris(dibenzylideneacetone)dipalladium |
| PE | Petroleum ether |
| PhMe | Toluene |
| PMB | 4-Methoxybenzyl |
| PPA | Polyphosphoric acid |
| R.T. or r.t. | Room temperature |
| Rt | Retention time |
| SEMCl | 2-(TrimethylsilyD)ethoxymethyl chloride |
| STAB | Sodium Triacetoxyborohydride;Sodium triacetoborohydride |
| Sat. | saturated |
| TBAF | Tetra-butyl ammonium fluoride |
| TBDPS | tert-Butyldiphenylsilyl |
| TBS | tert-Butyldimethylsilyl |
| TBSCl | tert-Butyldimethylsilyl chloride |
| $Ti(OiPr)_4$ | Titanium tetraisopropanolate |
| T3P | Propylphosphonic anhydride |
| t-Bu | tert-butyl |
| t-BuOH | tert-Butanol |
| t-BuONa | Sodium tert-butoxide |
| t-BuOK | Potassium tert-butoxide |
| TEA | Triethy lamine |
| $Tf_2O$ | Triflic anhydride |
| TFA | Trifluoroacetic acid |
| THF | Tetrahydrofuran |
| TLC | Thin layer chromatography |
| TMSOK | Potassium trimethylsilanolate |
| Ts | para-Toluenesulfonyl |
| TsCl | 4-Toluenesulfonyl chloride |
| TsOH | p-toluenesulfonic acid |
| TsOH,Py | Pyridinium toluene-4-sulphonate |
| Xphos or X-phos | 2-Dicyclohexylphosphino-2',4',6'-triisopropylbiphenyl |
| XantPhos | 4,5-Bis(diphenylphosphino)-9,9-dimethylxanthene |
| RBF | round-bottomed flask |

Example 77: 3-(4-((R)-3-(4-(1-(4-((5-bromo-4-((2-methyl-5-(1-oxidophospholan-1-yl)quinolin-6-yl)amino)pyrimidin-2-yl)amino)-2-ethyl-5-methoxyphenyl)piperidin-4-yl)piperazine-1l-carbonyl)pyrrolidin-1-yl)-2,6-difluorophenyl)piperidine-2,6-dione

Step 1: 1-(6-amino-2-methylquinolin-5 yl)phospholane 1-oxide

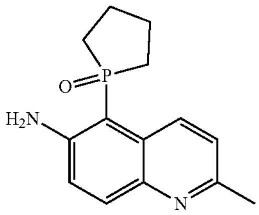 [SMILES: Cc1ccc2c(P3(=O)CCCC3)c(N)ccc2n1]

To a solution of 1-((6-amino-2-methylquinolin-5-yl)-2,5-dihydrophosphole 1-oxide (800 mg, 3.1 mmol) in MeOH (20 mL) was added Pd/C (10%, wet, 100 mg). The resulting solution was stirred for 12 h at room temperature under $H_2$ atmosphere (1-2 atm). Pd/C was filtered out, the filtrate was evaporated to dryness. 1-(6-amino-2-methylquinolin-5-yl)phospholane 1-oxide (720 mg, 89.3%) was obtained and used to the next step without further purification. $[M+H]^+=$ 261.1.

Step 2: 1-(6-((5-bromo-2-chloropyrimidin-4-yl)amino)-2-methylquinolin-5-yl)phospholane 1-oxide

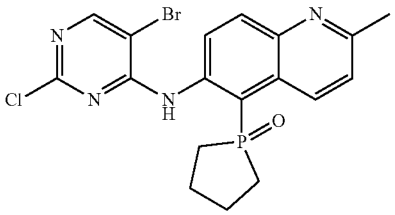 [SMILES: Cc1ccc2c(P3(=O)CCCC3)c(Nc3nc(Cl)ncc3Br)ccc2n1]

To a solution of 1-(6-amino-2-methylquinolin-5-yl)phospholane 1-oxide (720 mg, 2.8 mmol) in THF (20 mL) was added 5-bromo-2,4-dichloropyrimidine (1.6 g, 6.9 mmol) at 0° C. And then LiHMDS (1 M, 5.5 mL, 5.5 mmol) was added to the reaction mixture at 0° C. The mixture was stirred at 20° C., for 3 hrs. Water (10 mL) was poured into the mixture, which was further extracted with DCM (20 mL×3). The combined organic phase was washed with brine (20 mL), dried over $Na_2SO_4$, filtered and concentrated in vacuum. The residue was purified by column chromatography (DCM/MeOH=10/1 to 5/1) to afford 1-(6-((5-bromo-2-chloropyrimidin-4-yl)amino)-2-methylquinolin-5-yl)phospholane 1-oxide (680 mg, 54.4%). $[M+H]^+$=451.0.

Step 3: tert-butyl 4-(1-(2-bromo-5-methoxy-4-nitrophenyl)piperidin-4-yl)piperazine-1-carboxylate

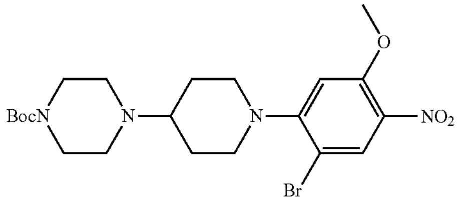 [SMILES: COc1cc(N2CCC(N3CCN(C(=O)OC(C)(C)C)CC3)CC2)c(Br)cc1[N+](=O)[O-]]

A mixture of 1-bromo-2-fluoro-4-methoxy-5-nitrobenzene (4 g, 16 mmol), tert-butyl 4-(piperidin-4-yl)piperazine-1-carboxylate (6.4 g, 24 mmol), $K_2CO_3$ (4.4 g, 32 mmol) in DMF (50 mL) was stirred in a flask at 80° C. overnight. The reaction mixture was allowed to cool down to room temperature. The resulting mixture was diluted with water and extracted with EtOAc (3×500 mL). The combined organic layers were washed with brine (500 mL), dried over anhydrous $Na_2SO_4$. After filtration, the filtrate was concentrated under reduced pressure. The residue was purified by silica gel column chromatography, eluted with PE/EtOAc (1:1) to afford the product (7 g, 90%). $[M+H]^+$=499.1.

Step 4: tert-butyl 4-(1-(5-methoxy-4-nitro-2-vinylphenyl)piperidin-4-yl)piperazine-1-carboxylate

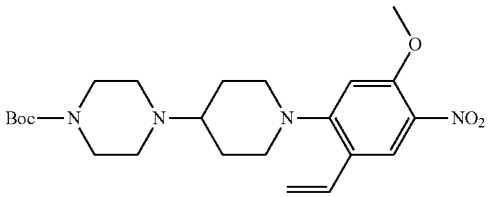 [SMILES: C=Cc1cc([N+](=O)[O-])c(OC)cc1N1CCC(N2CCN(C(=O)OC(C)(C)C)CC2)CC1]

A mixture of tert-butyl 4-(1-(2-bromo-5-methoxy-4-nitrophenyl)piperidin-4-yl)piperazine-1-carboxylate (7 g, 14 mmol), 4,4,5,5-tetramethyl-2-vinyl-1,3,2-dioxaborolane (4.3 g, 28 mmol), $Pd(dppf)Cl_2$ (1.1 g, 1.4 mmol) and $K_3PO_4$ (8.9 g, 42 mmol) in DMF (160 mL) and water (20 mL) was stirred in a flask at 90° C. under nitrogen atmosphere for 16 hrs. The reaction mixture was allowed to cool down to room temperature. The resulting mixture was extracted with EtOAc (3×1000 mL). The combined organic layers were washed with brine (50) mL), dried over anhydrous $Na_2SO_4$. After filtration, the filtrate was concentrated under reduced pressure. The residue was purified by silica gel column chromatography, eluted with PE/EtOAc (1:1) to afford the product (5 g, 80%). $[M+H]^+$=447.0.

Step 5: tert-butyl 4-(1-(4-amino-2-ethyl-5-methoxyphenyl)piperidin-4-yl)piperazine-1-carboxylate

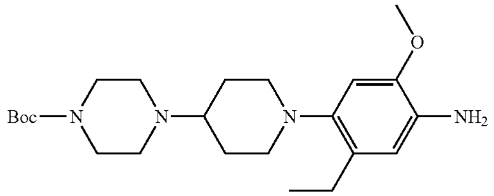 [SMILES: CCc1cc(N)c(OC)cc1N1CCC(N2CCN(C(=O)OC(C)(C)C)CC2)CC1]

To a stirred solution of tert-butyl 4-(1-(5-methoxy-4-nitro-2-vinylphenyl)piperidin-4-yl)piperazine-1-carboxylate (5 g, 11.2 mmol) in MeOH (100 mL) and DCM (20.00 mL) was added Pd/C (wet, 10%) (1 g) under nitrogen atmosphere. The resulting mixture was stirred for 16 hrs at room temperature under hydrogen atmosphere. The resulting mixture was filtered, the filter cake was washed with $DCM/CH_3OH$ (10:1, 200 mL). The filtrate was concentrated under reduced pressure to afford the product (4.0 g, 85.3%). $[M+H]^+$=419.1.

Step 6: 1-(6-(5-bromo-2-((5-ethyl-2-methoxy-4-(4-(piperazin-1-yl)piperidin-1-yl)phenyl)amino)pyrimidin-4-yl)amino)-2-methylquinolin-5-yl)phospholane 1-oxide

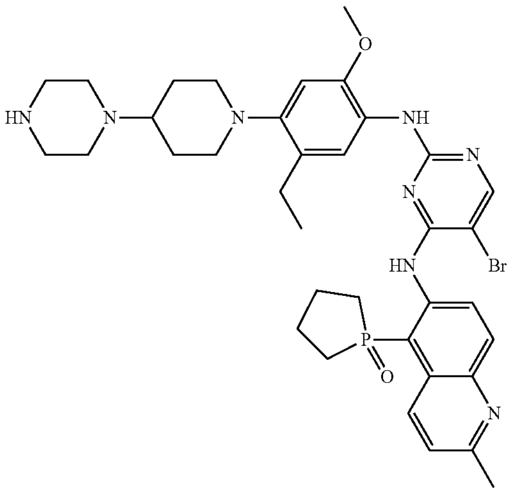 [SMILES: CCc1cc(Nc2ncc(Br)c(Nc3ccc4nc(C)ccc4c3P3(=O)CCCC3)n2)c(OC)cc1N1CCC(N2CCNCC2)CC1]

To a solution of 1-(6-((5-bromo-2-chloropyrimidin-4-yl)amino)-2-methylquinolin-5-yl)phospholane 1-oxide (680 mg, 1.5 mmol) in n-BuOH (20 mL) was added tert-butyl 4-(1-(4-amino-2-ethyl-5-methoxyphenyl)piperidin-4-yl)piperazine-1-carboxylate (633 mg, 1.5 mmol) at 20° C. 4-methylbenzenesulfonic acid (774 mg, 4.5 mmol) was added to the reaction mixture at 20° C. Then the mixture was stirred at 90° C. for 15 hrs. The reaction mixture was evaporated to dryness, water (20 mL) was poured into the mixture. Then the mixture was adjusted to pH=8 with sat. aq. $NaHCO_3$ solution and extracted with DCM (20 mL×3). The organic phase was washed with brine (30 mL), dried over $Na_2SO_4$, filtered, and concentrated in vacuum. The residue was purified by column chromatography (DCM/MeOH=10/1 to 5/1) to afford 1-(6-((5-bromo-2-((5-ethyl-2-methoxy-4-(4-(piperazin-1-yl)piperidin-1-yl)phenyl)amino)pyrimidin-4-yl)amino)-2-methylquinolin-5-yl)phospholane 1-oxide (580 mg, 52.3%). $[M+H]^+$=733.3.

Step 7: 2,6-bis(benzyloxy)-3-(4,4,5,5-tetramethyl-1,3,2-dioxaborolan-2-yl)pyridine

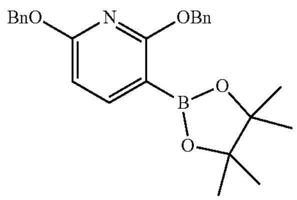 [SMILES: CC1(C)OB(c2ccc(OCc3ccccc3)nc2OCc2ccccc2)OC1(C)C]

A mixture of 2,6-bis(benzyloxy)-3-bromopyridine (15 g, 40.65 mmol) and 4,4,4',4',5,5,5',5'-octamethyl-2,2'-bi(1,3,2-dioxaborolane) (12.6 g, 49.61 mmol), Pd(dppf)$Cl_2$ (3.32 g, 4.07 mmol), KOAc (12 g, 122.45 mmol) in dioxane (200 mL) was stirred overnight at 100° C. under nitrogen atmosphere. The resulting mixture was filtered, the filter cake was washed with MeOH and DCM. The filtrate was concentrated under reduced pressure. The residue was purified by silica gel column chromatography, eluted with PE/EtOAc (8:1) to afford the product (9.00 g, 53%). $[M+H]^+$=418.3.

Step 8: 2,6-bis(benzyloxy)-3-(4-bromo-2,6-difluorophenyl)pyridine

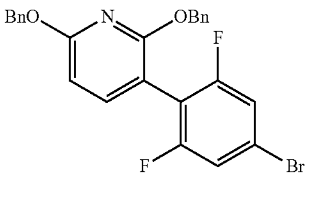 [SMILES: Fc1cc(Br)cc(F)c1-c1ccc(OCc2ccccc2)nc1OCc1ccccc1]

A mixture of 2,6-bis(benzyloxy)-3-(4,4,5,5-tetramethyl-1,3,2-dioxaborolan-2-yl)pyridine (9.00 g, 21.56 mmol) and 5-bromo-1,3-difluoro-2-iodobenzene (6.88 g, 21.57 mmol), $K_2CO_3$ (10.43 g, 75.48 mmol), Pd(dppf)$Cl_2$ (789 mg, 1.078 mmol) in dioxane (90 mL) and $H_2O$ (30 mL) was stirred for 16 h at 100° C. under nitrogen atmosphere. The resulting mixture was extracted with EtOAc (50 mL×3). The combined organic layers were washed with brine, dried over anhydrous $Na_2SO_4$. After filtration, the filtrate was concentrated under reduced pressure. The residue was purified by silica gel column chromatography, eluted with PE/EtOAc (5:1) to afford the product (4 g, 38%). $[M+H]^+$=482.4.

Step 9: methyl (R)-1-(4-(2,6-bis(benzyloxyl)pyridin-3-yl)-3,5-difluorophenyl)pyrrolidine-3-carboxylate

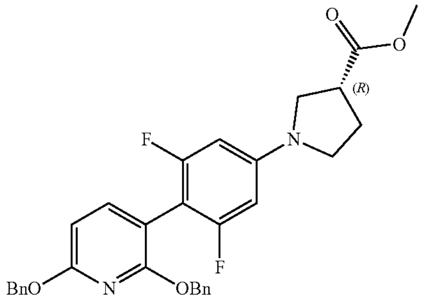

To a solution of 2,6-bis(benzyloxy)-3-(4-bromo-2,6-difluorophenyl)pyridine (1 g, 2.07 mmol), methyl (R)-pyrrolidine-3-carboxylate hydrochloride (495 mg, 3 mmol) and $Cs_2CO_3$ (1.95 g, 6 mmol) in 10 mL DMSO, $Pd_2(dba)_3$ (183 mg, 0.2 mmol) and Xantphos (231 mg, 0.4 mmol) was added wider $N_2$ atmosphere. The mixture was stirred at 90° C. for 16 hours under $N_2$ atmosphere. After LCMS showed the reaction was completed. The mixture was diluted with EtOAc (100 mL) and washed with brine (100 mL×2). The organic phase was dried over $Na_2SO_4$, filtered and concentrated in vacuum. The residue was purified by silica column chromatography (PE:EA=10:1) to afford product (740 mg, 67.4% yield). $[M+H]^+$=530.8.

Step 10: (R)-1-(4-(2,6-bis(benzyloxy)pyridin-3-yl)-3,5-difluorophenyl)pyrrolidine-3-carboxylic acid

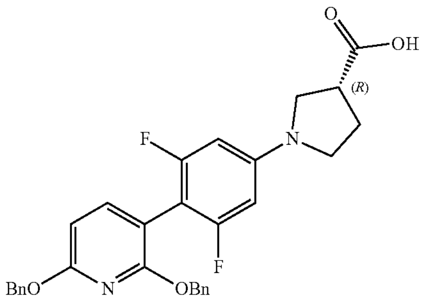

To a solution of methyl (R)-1-(4-(2,6-bis(benzyloxy)pyridin-3-yl)-3,5-difluorophenyl)pyrrolidine-3-carboxylate (740 mg, 1.4 mmol) in 10 mL THF. LiOH·$H_2O$ (84 mg, 2 mmol) in 2 mL water was added. The mixture was stirred at 25° C. for 2 hours. After LCMS showed the reaction was completed. The mixture was concentrated in vacuum. The residue was adjust pH<5 with 1 N HCl and extracted with 50 mL EtOAc. The organic phase was dried over $Na_2SO_4$, filtered and concentrated in vacuum to afford product (700 mg, 96.9% yield). $[M+H]^+$=516.8.

Step 11: (3R)-1-(4-(2,6-dioxopiperidin-3-yl)-3,5-difluorophenyl)pyrrolidine-3-carboxylic acid

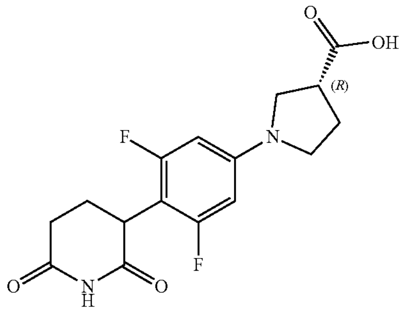

To a solution of (R)-1-(4-(2,6-bis(benzyloxy)pyridin-3-yl)-3,5-difluorophenyl)pyrrolidine-3-carboxylic acid (700 mg, 1.35 mmol) in 5 mL DCM and 30 mL MeOH, 350 mg Pd/C was added. The mixture was stirred at 30° C. for 16 hours under $H_2$ atmosphere. After LCMS showed the reaction was completed and the mixture was filtered. The organic phase was concentrated in vacuum to afford product (350 mg, 76.7% yield). $[M+H]^+$=338.8.

Step 12: 3-(4-((R)-3-(4-(1-(4-((5-bromo-4-((2-methyl-5-(1-oxidophospholan-1-yl)quinolin-6-yl)amino)pyrimidin-2-yl)amino)-2-ethyl-5-methoxyphenyl)piperidin-4-yl)piperazine-1-carbonyl)pyrrolidin-1-yl)-2,6-difluorophenyl)piperidine-2,6-dione

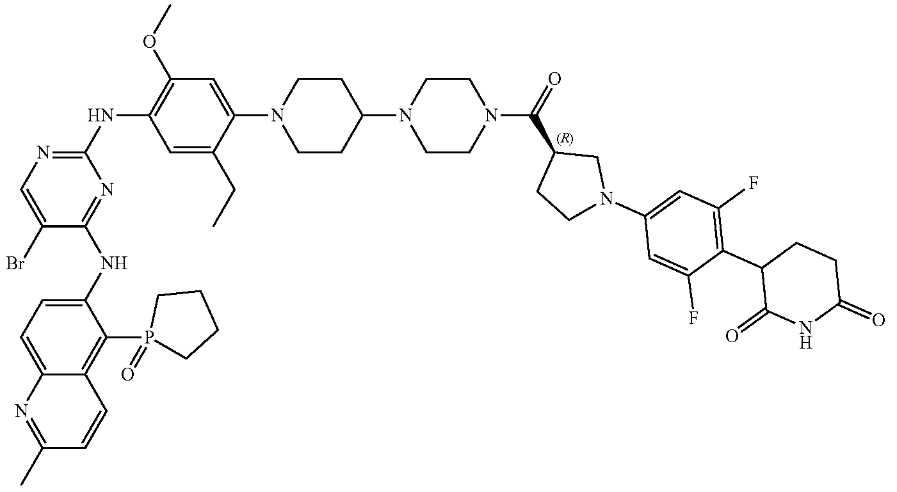

To a solution of 1-(6-((5-bromo-2-((5-ethyl-2-methoxy-4-(4-(piperazin-1-yl)piperidin-1-yl)phenyl)amino)pyrimidin-4-yl)amino)-2-methylquinolin-5-yl)phospholane-1-oxide (50 mg, 0.07 mmol), (3R)-1-(4-(2,6-dioxopiperidin-3-yl)-3,5-difluorophenyl)pyrrolidine-3-carboxylic acid (35 mg, 0.1 mmol) and DIEA (26 mg, 0.2 mmol) in 10 mL DCM, 50% w.t. $T_3P$ in EtOAc solution (64 mg, 0.1 mmol) was added. The mixture was stirred at 25° C. for 16 hours. When LCMS showed the reaction was completed, the mixture was quenched with water (10 mL). The organic phase was concentrated in vacuum and purified by prep-HPLC with C-18 column chromatography (0.1% FA in water: acetonitrile=90:10~50:50 gradient elution) to afford product (18.2 mg, 25.3% yield). $^1$H NMR (500 MHz, DMSO) δ 11.31 (s, 1H), 10.84 (s, 1H), 8.32 (s, 1H), 8.22 (s, 1H), 8.03 (s, 1H), 7.94 (dd, J=13.9, 9.3 Hz, 2H), 7.29-7.47 (m, 2H), 6.75 (s, 1H), 6.18 (dd, J=44.0, 21.4 Hz, 4H), 4.02 (dd, J=12.5, 4.9 Hz, 1H), 3.78 (s, 3H), 3.43-3.56 (m, 7H), 3.24-3.28 (m, 4H), 2.94-3.04 (m, 4H), 2.73-2.88 (m, 3H), 2.52-2.71 (m, 9H), 2.47-2.49 (m, 1H), 2.23-2.43 (m, 3H), 2.02-2.21 (m, 3H), 1.89-2.00 (m, 1H), 1.83 (d, J=10.4 Hz, 2H), 1.49-1.63 (m, 2H), 0.78 (s, 3H). $[M+H]^+$=1053.4.

Example 147: 3-(4-(2-(4-(1-(4-((5-bromo-4-((2-(1-oxidophospholan-1-yl)phenyl)amino)pyrimidin-2-yl)amino)-2-ethyl-5-methoxyphenyl)piperidin-4-yl)piperazin-1-yl)ethyl)-2,6-difluorophenyl)piperidine-2,6-dione Step 1: diallylphosphine oxide

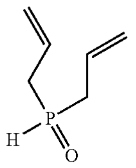

To a solution of allylmagnesium bromide (310 mL, 1M in $Et_2O$, 0.35 mol) in $Et_2O$ (200 mL) was added diethyl phosphonate (12 g dissolved in $Et_2O$, 87 mmol) dropwise in 30 min at −20 degrees C. the reaction solution was stirred for 30 min at this temperature, then allowed the temperature rise to room temperature naturally. Then the mixture was stirred at 100° C. for 14 hrs. The reaction was quenched by the addition of Sat.$NH_4Cl$, extracted with $Et_2O$ (100 mL×2), combined the organic layer and washed with brine, dried over anhydrous $Na_2SO_4$, after filtration, the filtrate was concentrated under reduced pressure to afford the product (3.1 g, 27.2%). $[M+H]^+$=131.1.

Step 2: diallyl(2-aminophenyl)phosphine oxide

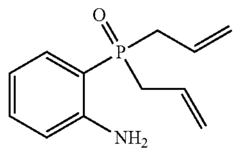

To a solution of 2-iodoaniline (2 g, 9.1 mmol) and diallylphosphine oxide (2.4 g, 18.3 mmol) in dioxane (50 mL) was added $K_3PO_4$ (4.8 g, 22.7 mmol), then $Pd(OAc)_2$ (205 mg, 0.91 mmol) and Xantphos (528 mg, 0.91 mmol) were added to the mixture at 20° C. The suspension was degassed under vacuum and purged with $N_2$ three times. Then the mixture was stirred at 100° C. for 4 hrs. The mixture was filtered and concentrated in vacuum. The residue was purified by column chromatography (DCM/MeOH=20/1 to 10/1) to afford diallyl(2-aminophenyl)phosphine oxide (1.2 g, 60%). $[M+H]^+$=222.1.

Step 3: 1-(2-aminophenyl)-2,5-dihydrophosphole 1-oxide

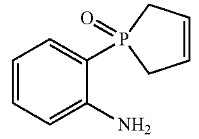 [SMILES: Nc1ccccc1P1(=O)CC=CC1]

To a solution of diallyl(2-aminophenyl)phosphine oxide (1.2 g, 5.4 mmol) in DCM (200 mL) was added Grubbs $2^{nd}$ generation catalyst (918 mg, 1.1 mmol). The reaction mixture was stirred for 16 h at room temperature. The mixture was concentrated in vacuum. The residue was purified by column chromatography (DCM/MeOH=20/1 to 10/1) to afford 1-(2-aminophenyl)-2,5-dihydrophosphole 1-oxide (750 mg, 71.4%). m/z $[M+H]^+$=194.1.

Step 4: 1-(2-aminophenyl)phospholane 1-oxide

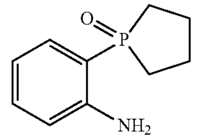

To a solution of 1-(2-aminophenyl)-2,5-dihydrophosphole 1-oxide (750 mg, 3.9 mmol) in MeOH (20 mL) was added Pd/C (10%, wet, 100 mg). The resulting solution was stirred for 12 h at room temperature under $H_2$ atmosphere (1-2 atm). Pd/C was filtered out, the filtrate was evaporated to dryness, 1-(2-aminophenyl)phospholane 1-oxide (720 mg, 95%) was obtained and used to the next step without further purification. m/z $[M+H]^+$=196.1.

Step 5: 1-(2-(5-bromo-2-chloropyrimidin-4-yl) amino)phenyl)phospholane 1-oxide

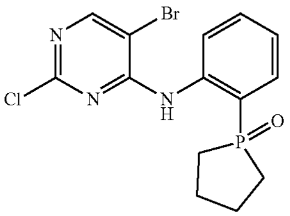 [SMILES: O=P1(c2ccccc2Nc2nc(Cl)ncc2Br)CCCC1]

To a solution of 1-(2-aminophenyl)phospholane 1-oxide (720 mg, 3.7 mmol) in THF (15 mL) was added 5-bromo-2,4-dichloropyrimidine (2.1 g, 9.2 mmol) at 0° C. And then LiHMDS (1 M, 7.4 mL, 7.4 mmol) was added to the reaction mixture at 0° C. The mixture was stirred at 20° C. for 3 hrs. Water (10 mL) was poured into the mixture, which was further extracted with DCM (20 mL×3). The combined organic phase was washed with brine (20 mL), dried over $Na_2SO_4$, filtered and concentrated in vacuum. The residue was purified by column chromatography (DCM/MeOH=10/1 to 5/1) to afford 1-(2-((5-bromo-2-chloropyrimidin-4-yl)amino)phenyl)phospholane 1-oxide (620 mg, 43%). $[M+H]^+$=386.0.

Step 6: 1-(2-((5-bromo-2-((5-ethyl-2-methoxy-4-(4-(piperazin-1-yl)piperidin-1-yl)phenyl)amino)pyrimidin-4-yl amino)phenyl)phospholane 1-oxide

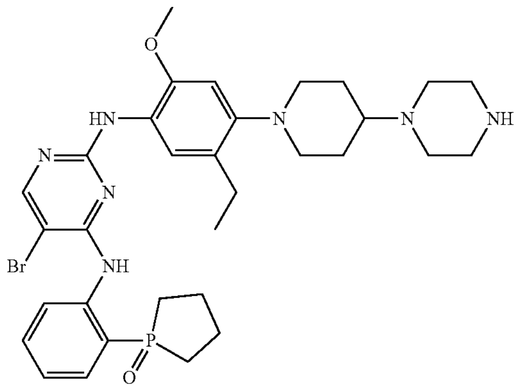 [SMILES: CCc1cc(Nc2ncc(Br)c(Nc3ccccc3P3(=O)CCCC3)n2)c(OC)cc1N1CCC(N2CCNCC2)CC1]

To a solution of 1-(2-((5-bromo-2-chloropyrimidin-4-yl) amino)phenyl)phospholane 1-oxide (620 mg, 1.6 mmol) in n-BuOH (20 mL) was added tert-butyl 4-(1-(4-amino-2-ethyl-5-methoxyphenyl)piperidin-4-yl)piperazine-1-carboxylate (671 mg, 1.6 mmol) at 20° C. 4-methylbenzenesulfonic acid (826 mg, 4.8 mmol) was added to the reaction mixture at 20° C. Then the mixture was stirred at 90° C. for 15 hrs. The reaction mixture was evaporated to dryness, water (20 mL) was poured into the mixture. Then the mixture was adjusted to pH=8 with sat. aq. $NaHCO_3$ solution and extracted with DCM (20 mL×3). The organic phase was washed with brine (30 mL), dried over $Na_2SO_4$, filtered and concentrated in vacuum. The residue was purified by column chromatography (DCM/MeOH=10/1 to 5/1) to afford 1-(2-((5-bromo-2-((5-ethyl-2-methoxy-4-(4-(piperazin-1-yl)piperidin-1-yl)phenyl)amino)pyrimidin-4-yl) amino)phenyl)phospholane 1-oxide (510 mg, 47.7%). [M+H]+=668.2.

Step 7: ethyl 2-(3,5-difluoro-4-nitrophenyl)acetate

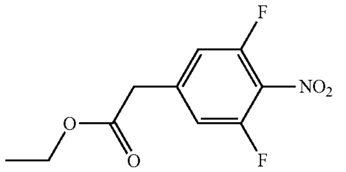 [SMILES: CCOC(=O)Cc1cc(F)c([N+](=O)[O-])c(F)c1]

A solution of 1,3-difluoro-2-nitrobenzene (50.0 g, 314.4 mmol) in NMP (300 mL) were cooled to −20° C. under $N_2$ atmosphere. Then a mixture of ethyl 2-chloroacetate (65.5 g, 534.7 mmol) and t-BuOK (121.0 g, 1.08 mol) in NMP (50 mL) was added slowly at −10° C. to −20° C. over 2 h. After being stirred for 2 h, the reaction was quenched by pouring into 1M HCl (200 mL) and ice-water. The mixture was extracted with EA (300 mL×3). The combined organic layer was washed by brine, dried with $Na_2SO_4$. The solution was concentrated in vacuum and the residue was purified by silica gel column chromatography (PE/EA=200/1 to 100/1) to provide product (13.7 g, 18%). $^1$H NMR (400 MHz, $CDCl_3$) $\delta_H$ 7.06 (d, J=8.4 Hz, 2H), 4.20 (q, J=7.2 Hz, 2H), 3.65 (s, 2H), 1.28 (t, J=7.2 Hz, 3H).

Step 8: ethyl 2-(4-amino-3,5-difluorophenyl)acetate

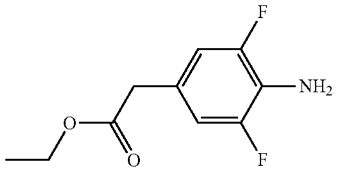

To a solution of ethyl 2-(3,5-difluoro-4-nitrophenyl)acetate (13.7 g, 56 mmol) in MeOH (150 mL) was added 10% Pd/C (1.5 g) at r.t. The mixture was stirred at r.t under $H_2$ atmosphere for 5 h. Filtrated on vacuum to remove Pd/C and concentrated in vacuum to provide the product (12.2 g), which was used in next step without further purification. $^1$H NMR (400 MHz, DMSO_d$_6$) $\delta_H$ 6.82 (d, J=8.0 Hz, 2H), 5.69 (s, 2H), 4.06 (q, J=7.2 Hz, 2H), 3.52 (s, 2H), 1.17 (t, J=7.2 Hz, 3H). $[M+H]^+$=216.4.

Step 9: ethyl 2-(3,5-difluoro-4-iodophenyl)acetate

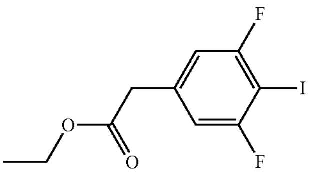

A solution of ethyl 2-(4-amino-3,5-difluorophenyl)acetate (12.2 g, 56 mmol) in MeCN (150 mL) was cooled to 0° C. under $N_2$ atmosphere and CuI (21.2 g, 112 mmol) was added. After stirring for 10 min, tert-butylnitrite (11.5 g, 112 mmol) was added dropwise over 30 min. Then the mixture was stirred at r.t for overnight. The reaction was quenched by pouring into water and extracted with EA (300 mL×3). All organic layers were combined and washed by brine, dried with $Na_2SO_4$. The solution was concentrated in vacuum and the residue was purified by silica gel column chromatography (PE/EA=500/1 to 100/1) to provide the product (8.8 g, 48%). $[M+H]^+$=326.5.

Step 10: ethyl 2-(4-(2,6-bis(benzyloxy)pyridin-3-yl)-3,5-difluorophenyl)acetate

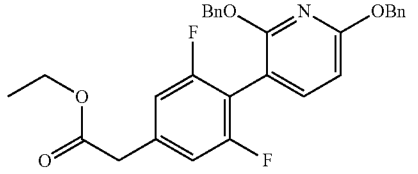 [SMILES: CCOC(=O)Cc1cc(F)c(-c2ccc(OCc3ccccc3)nc2OCc2ccccc2)c(F)c1]

To a solution of ethyl 2-(3,5-difluoro-4-iodophenyl)acetate (8.8 g, 27.0 mmol) in a mixed solvent of 1,4-dioxane/$H_2O$ (100 mL/20 mL) were added $K_2CO_3$ (9.3 g, 67.4 mmol), 2,6-bis(benzyloxy)-3-(4,4,5,5-tetramethyl-1,3,2-dioxaborolan-2-yl)pyridine (14.6 g, 35.0 mol) and Pd(dppf)$Cl_2$ (2.9 g, 4.0 mmol) under $N_2$ atmosphere. The resulting solution was stirred for 6 h at 100° C. The mixture was diluted with water (300 mL) and extracted with EA (300 mL×3). All organic layers were combined and washed with brine (300 mL), dried over $Na_2SO_4$. The solution was concentrated in vacuum and the residue was purified by silica gel column chromatography (PE/EA=200/1) to give the product (8.2 g, 62%). $^1$H NMR (40) MHz, $CDCl_3$) &a 7.49 (d, J=8.0 Hz, 1H), 7.40-7.24 (m, 10H), 6.90 (d, J=8.0 Hz, 2H), 6.47 (d, J=8.0 Hz, 1H), 5.38 (s, 2H), 5.33 (s, 2H), 4.19 (q, J=7.2 Hz, 2H), 3.61 (s, 2H), 1.28 (t, J=7.2 Hz, 3H).

Step 11: 2-(4-(2,6-bis(benzyloxy)pyridin-3-yl)-3,5-difluorophenyl)ethanol

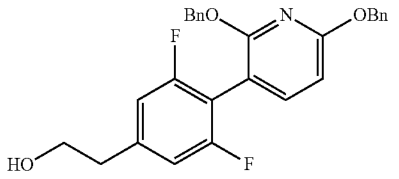 [SMILES: OCCc1cc(F)c(-c2ccc(OCc3ccccc3)nc2OCc2ccccc2)c(F)c1]

A solution of ethyl 2-(4-(2,6-bis(benzyloxy)pyridin-3-yl)-3,5-difluorophenyl)acetate (8.2 g, 16.7 mol) in THF (100 mL) was cooled to 0° C. under $N_2$ atmosphere and 1.5 M DIBAL-H (45 mL, 67.5 mol) in THF was added dropwise over 30 min. Then the mixture was stirred at r.t for 2 h. The reaction was quenched by pouring into water and extracted with EA (300 mL×3). All organic layers were combined and washed by brine, dried with $Na_2SO_4$. The solution was concentrated in vacuum and the residue was purified by column chromatography (PE/EA=10/1 to 3/1) to provide the product (6.6 g, 88%). $^1$H NMR (400 MHz, $CDCl_3$) $\delta_H$ 7.49 (d, J=8.0 Hz, 1H), 7.42-7.25 (m, 9H), 6.84 (d, J=8.0 Hz, 2H), 6.47 (d, J=8.0 Hz, 1H), 5.38 (s, 2H), 5.33 (s, 2H), 3.90 (m, 2H), 2.87 (t, J=6.4 Hz, 2H). $[M+H]^+$=448.3.

Step 12: 3-(2,6-difluoro-4-(2-hydroxyethyl phenyl)piperidine-2,6-dione

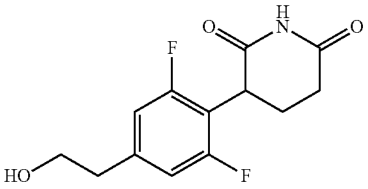 [SMILES: O=C1CCC(c2c(F)cc(CCO)cc2F)C(=O)N1]

To a solution of 2-(4-(2,6-bis(benzyloxy)pyridin-3-yl)-3,5-difluorophenyl)ethanol (6.6 g, 14.7 mmol) in DCM (150 mL) was added TFA (50 mL). After stirred overnight, the mixture was concentrated in vacuo. The residue was dissolved in MeOH (200 mL) and 10% Pd/C (1.0 g) was added. The resulted mixture was stirred for 2 days at r.t under $H_2$ atmosphere. The mixture was filtered and the filtrate was concentrated to give a residue which was purified by reversed flash C18 chromatography (ACN/water=0% to 30%) to give the title compound (2.1 g, 53%). $[M+H]^+$=270.1.

Step 13: 2-(4-(2,6-dioxopiperidin-3-yl)-3,5-difluorophenyl)acetaldehyde

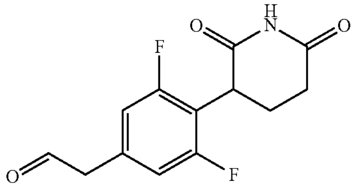 [SMILES: O=CCc1cc(F)c(C2CCC(=O)NC2=O)c(F)c1]

A mixture of 3-(2,6-difluoro-4-(2-hydroxyethyl)phenyl) piperidine-2,6-dione (86.4 mg, 0.32 mmol) and IBX (132 mg, 0.47 mmol) in DMSO (10 mL) was stirred in a flask at room temperature overnight. The reaction was quenched with water and the mixture was extracted with EtOAc, washed three times with saturated aqueous NaCl and twice with saturated aqueous $NaHCO_3$. The organic layer was dried over anhydrous Na2SO4 and evaporated in vacuum to afford the product (61 mg, 71%). $[M+H]^+$=268.1.

Step 14: 3-(4-(2-(4-(1-(4-((5-bromo-4-((2-(1-oxidophospholan-1-yl)phenyl)amino)pyrimidin-2-yl) amino)-2-ethyl-5-methoxyphenyl)piperidin-4-yl) piperazin-1-yl)ethyl)-2,6-difluorophenyl)piperidine-2,6-dione

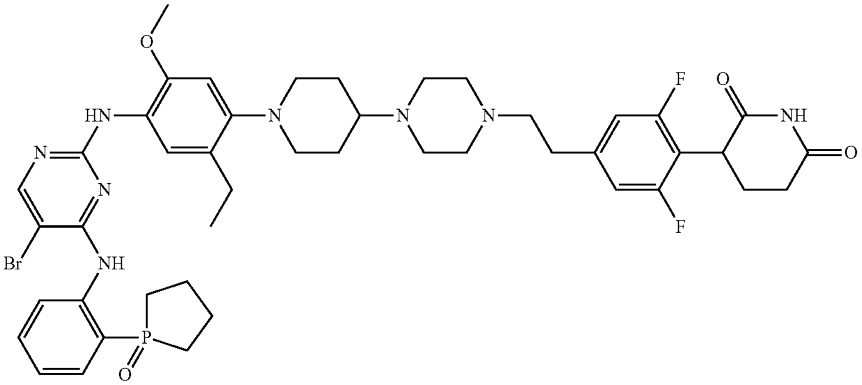 [SMILES: CCc1cc(Nc2ncc(Br)c(Nc3ccccc3P3(=O)CCCC3)n2)c(OC)cc1N1CCC(N2CCN(CCc3cc(F)c(C4CCC(=O)NC4=O)c(F)c3)CC2)CC1]

To a solution of 1-(2-((5-bromo-2-((5-ethyl-2-methoxy-4-(4-(piperazin-1-yl)piperidin-1-yl)phenyl)amino)pyrimidin-4-yl)amino)phenyl)phospholane 1-oxide (50 mg, 0.075 mmol) in DCM (3 mL) was added 2-(4-(2,6-dioxopiperidin-3-yl)-3,5-difluorophenyl)acetaldehyde (40 mg, 0.15 mmol) at 20° C. The mixture was stirred at 20° C. for 1 hr and STAB (32 mg, 0.15 mmol) was added. Then the mixture was stirred at 20° C. for 2 hrs. Water (10 mL) was poured into the mixture. Then the mixture was extracted with DCM (20 mL). The organic phase was washed with brine (10 mL), dried over $Na_2SO_4$, filtered and concentrated in vacuum. The residue was purified by prep-HPLC (C-18 column chromatography (0.1% FA in water:acetonitrile=90:10~60:40 gradient elution) to afford the product (17.7 mg, 17.6%). $^1$H NMR (500 MHz, DMSO) δ 10.88 (s, 1H), 10.50 (s, 1H), 8.15 (d, J=27.9 Hz, 2H), 7.98 (s, 1H), 7.42 (dd, J=13.4, 7.7 Hz, 1H), 7.36 (s, 1H), 7.30 (t, J=7.6 Hz, 1H), 7.10 (t, J=7.4 Hz, 1H), 6.96 (d, J=10.2 Hz, 2H), 6.69 (s, 1H), 4.13 (dd, J=12.6, 5.0 Hz, 1H), 3.69 (s, 3H), 2.92 (d, J=10.8 Hz, 2H), 2.65-2.80 (m, 6H), 2.46-2.60 (m, 6H), 2.21-2.41 (m, 6H), 1.73-2.10 (m, 13H), 1.39-1.60 (m, 2H), 0.85-1.02 (m, 3H). $[M+H]^+$=919.3.

Example 62: 3-(4-(2-(4-(1-(4-((5-bromo-4-((2-methyl-5-(1-oxidophospholan-1-yl)quinolin-6-yl)amino)pyrimidin-2-yl)amino)-5-ethoxy-2-ethylphenyl)piperidin-4-yl)piperazin-1-yl)ethyl)-2,6-difluorophenyl)piperidine-2,6-dione Step 1: 4-ethoxy-1-ethyl-2-fluorobenzene

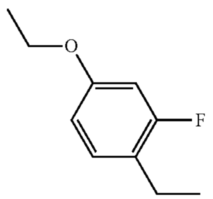

To a solution of 4-ethyl-3-fluorophenol (35 g, 0.25 mol) in DMF (200 mL) was added $K_2CO_3$ (69, 0.5 mol). EtI (50.7 g, 0.32 mol). The mixture was stirred at 20-30° C. for 18 hours. The reaction was quenched by $H_2O$ (200 mL) and extracted with EA (150 mL*2). The organic phase was combined and washed with brine (300 mL*3). The organic phase was concentrated and purified by a silica gel column, eluted with PE (100%) to give product (35 g, yield: 83.3%). $[M+H]^+$=169.2.

Step 2: 1-ethoxy-7-ethyl-5-fluoro-2-nitrobenzene

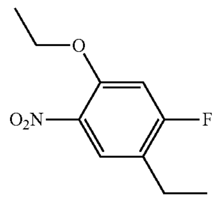

To a solution of 4-ethoxy-1-ethyl-2-fluorobenzene (35 g, 0.2 mol) in $Ac_2O$ (100 mL) was added conc. $HNO_3$ (25.2 g, 0.26 mol, 65%) dropwise at 0° C. The mixture was stirred at r.t. for 2 hs. The reaction was quenched with $Na_2CO_3$ solution (500 mL). Product was isolated by filtration. (25 g, yield: 58.7%). $^1$H NMR (500 MHz, d-DMSO) δ 7.90 (d, J=8.0 Hz, 1H), 7.26 (d, J=12.0 Hz, 1H), 4.2 (q, J=7.0 Hz, 2H), 2.60 (q, J=7.5 Hz, 2H), 1.33 (t, J=7.0 Hz, 3H), 1.15 (t, J=7.5 Hz, 3H).

Step 3: tert-butyl 4-(1-(5-ethoxy-2-ethyl-4-nitrophenyl)piperidin-4-yl)piperazine-1-carboxylate

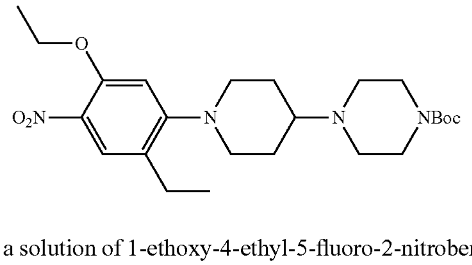

To a solution of 1-ethoxy-4-ethyl-5-fluoro-2-nitrobenzene (20 g, 94 mmol) in DMF (300 mL) was added tert-butyl 4-(piperidin-4-yl)piperazine-1-carboxylate (30 g, 112 mmoL), $K_2CO_3$ (32 g, 235 mmol). The mixture was stirred at 120° C. for 28 hours. The mixture was poured into ice water. The product was isolated by filtration. (20 g, yield: 46.1%). $[M+H]^+$=: 463.2. $^1$H NMR (500 MHz, d-DMSO) δ 7.74 (s, 1H), 6.73 (s, 1H), 4.19 (q, J=7.0 Hz, 2H), 3.30 (br, 4H), 3.23 (d, J=11.0 Hz, 2H), 2.71 (t, J=11.5 Hz, 2H), 2.57 (q, J=7.5 Hz, 2H), 2.47 (br, 4H), 2.39 (t, J=11.0 Hz, 1H), 1.84 (d, J=11.5 Hz, 2H), 1.58 (q, J=10.5 Hz, 2H), 1.39 (s, 9H), 1.34 (t, J=7.5 Hz, 3H), 1.19 (t, J=7.5 Hz, 3H).

Step 4: tert-butyl 4-(1-(4-amino-5-ethoxy-2-ethylphenyl piperidin-4-yl)piperazine-1-carboxylate

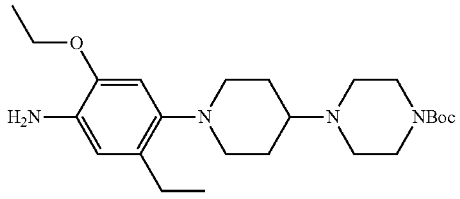 [SMILES: CCOc1cc(N2CCC(N3CCN(C(=O)OC(C)(C)C)CC3)CC2)c(CC)cc1[N+](=O)[O-]]

To a solution of tert-butyl 4-(1-(5-ethoxy-2-ethyl-4-nitrophenyl)piperidin-4-yl)piperazine-1-carboxylate (20 g, 94 mmol) in THF (150 mL) was added Pd/C (2 g). The mixture was stirred at r.t. under $H_2$ (1 atm) for 48 hs. The solid was filtered off. The filtrate was concentrated for next step directly without further operation. $[M+H]^+$=433.4.

Step 5: 1-(6-((5-bromo-2-((2-ethoxy-5-ethyl-4-(4-piperazin-1-yl)piperidin-1-yl)phenyl)amino)pyrimidin-4-yl)amino)-2-methylquinolin-5-yl)phospholane 1-oxide

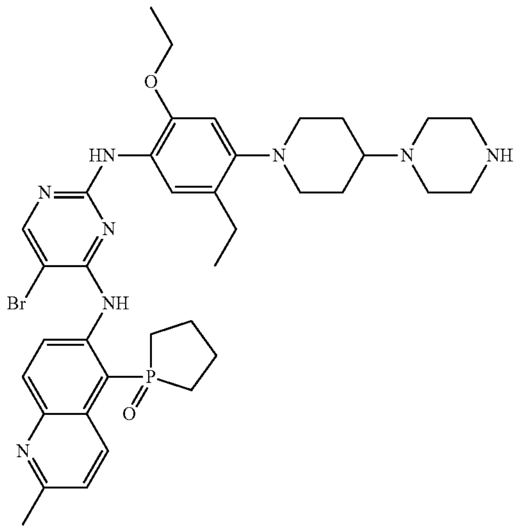 [SMILES: CCOc1cc(N2CCC(N3CCNCC3)CC2)c(CC)cc1Nc1ncc(Br)c(Nc2ccc3nc(C)ccc3c2P2(=O)CCCC2)n1]

The titled compound was synthesized in a manner similar to that in Example 77 Step 6 from 1-(6-((5-bromo-2-chloropyrimidin-4-yl)amino)-2-methylquinolin-5-yl)phospholane 1-oxide and tert-butyl 4-(1-(4-amino-5-ethoxy-2-ethylphenyl)piperidin-4-yl)piperazine-1-carboxylate. $[M+H]^+$=747.2.

Step 6: 3-(4-(2-(4-(1-(4-((5-bromo-4-((2-methyl-5-(1-oxidophospholan-1-yl)quinolin-6-yl)amino)pyrimidin-2-yl amino)-5-ethoxy-2-ethylphenyl)piperidin-4-yl)piperazin-1-yl)ethyl)-2,6-difluorophenyl) piperidine-2,6-dione

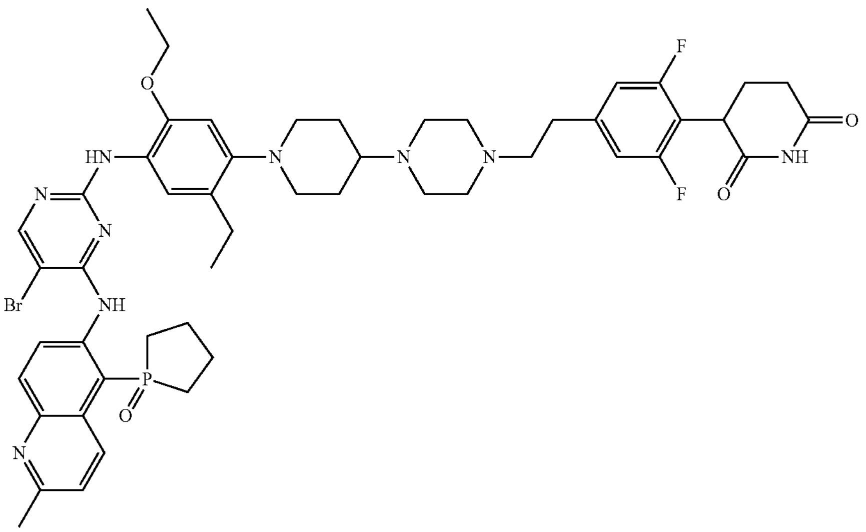 [SMILES: CCOc1cc(N2CCC(N3CCN(CCc4cc(F)c(C5CCC(=O)NC5=O)c(F)c4)CC3)CC2)c(CC)cc1Nc1ncc(Br)c(Nc2ccc3nc(C)ccc3c2P2(=O)CCCC2)n1]

The titled compound was synthesized in a manner similar to that in Example 147 Step 14 from 1-(6-((5-bromo-2-((2-ethoxy-5-ethyl-4-(4-(piperazin-1-yl)piperidin-1-yl)phenyl) amino)pyrimidin-4-yl)amino)-2-methylquinolin-5-yl)phospholane 1-oxide and 2-(4-(2,6-dioxopiperidin-3-yl)-3,5-difluorophenyl)acetaldehyde. $^{1}$H NMR (500 MHz, DMSO) δ 10.88 (s, 1H), 10.48 (s, 1H), 8.65 (d, J=8.7 Hz, 1H), 8.17 (s, 1H), 7.89-7.94 (m, 2H), 7.74 (s, 1H), 7.42 (dd, J=13.2, 8.5 Hz, 1H), 7.32 (s, 11H), 6.95 (d, J=10.0 Hz, 2H), 6.59 (s, 1H), 4.13 (dd, J=12.6, 5.0 Hz, 1H), 3.93 (q, J=7.0 Hz, 2H), 2.64-2.83 (m, 5H), 2.60 (s, 3H), 2.44-2.55 (m, 8H), 2.28-2.40 (m, 4H), 1.80-2.21 (m, 14H), 1.73 (d, J=10.9 Hz, 2H), 1.32-1.48 (m, 2H), 1.21 (t, J=6.9 Hz, 3H), 0.47 (s, 3H). $[M+H]^+$=998.4.

Example 68: 3-(4-(2-(4-(1-(4-((5-bromo-4-((2-methyl-5-(1-oxidophospholan-1-yl)quinolin-6-yl) amino)pyrimidin-2-yl)amino)-2-ethyl-5-methoxyphenyl)piperidin-4-yl)piperazin-1-yl)ethyl)-3-methyl-2-oxo-2,3-dihydro-1H-benzo[d]imidazol-1-yl)piperidine-2,6-dione Step 1: 7-bromo-1-methyl-1,3-dihydro-2H-benzo[d] imidazol-2-one

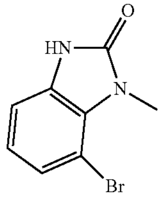

To a solution of 6-bromo-N1-methylbenzene-1,2-diamine (4 g, 19.9 mmol) in $CH_3CN$ (50 mL) was added CDI (6.4 g, 39.8 mmol). The resulting solution was stirred for 6 h at 90° C. under nitrogen atmosphere. The solid was collected by filtration. This was resulted in 7-bromo-1-methyl-1,3-dihydro-2H-benzo[d]imidazol-2-one (4.1 g, 90.7%). $[M+H]^+$=227.0.

Step 2: 3-(4-bromo-3-methyl-2-oxo-2,3-dihydro-1H-benzo[d]imidazol-1-yl)-1-(4-methoxybenzyl) piperidine-2,6-dione

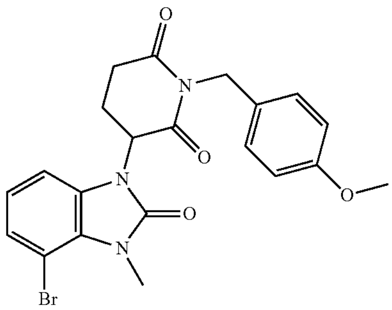 [SMILES: COc1ccc(CN2C(=O)CCC(n3c(=O)n(C)c4c(Br)cccc43)C2=O)cc1]

To a solution of 7-bromo-1-methyl-1,3-dihydro-2H-benzo[d]imidazol-2-one (600 mg, 2.6 mmol) in THF (10 mL) was added t-BuOK (1M in THF, 3.2 mL, 3.1 mmol) dropwise in 10 min at 0° C., the reaction solution was stirred for 30 min at this temperature, then to this was added 1-(4-methoxybenzyl)-2,6-dioxopiperidin-3-yl trifluoromethanesulfonate (1.1 g, 2.9 mmol) in THF (5 mL) dropwise in 10 min. The resulting solution was stirred for 2 h at 0-10° C. The reaction was quenched by the addition of sat.aq. $NH_4Cl$ solution, extracted with EtOAc (10 mL×3), combined the organic layer, and washed with brine, dried over anhydrous $Na_2SO_4$, after filtration, the filtrate was concentrated under reduced pressure. The residue was purified by a silica gel column, eluted with PE/EtOAc (1:1) to afford product (910 mg, 75.2%). $[M+H]^+$=458.1.

Step 3: 3-(4-bromo-3-methyl-2-oxo-2,3-dihydro-1H-benzo[d]imidazol-1-yl)piperidine-2,6-dione

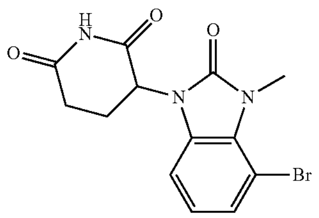 [SMILES: Cn1c(=O)n(C2CCC(=O)NC2=O)c2cccc(Br)c21]

3-(4-bromo-3-methyl-2-oxo-2,3-dihydro-1H-benzo[d]imidazol-1-yl)-1-(4-methoxybenzyl)piperidine-2,6-dione (800 mg, 1.75 mmol) was dissolved in $MeSO_2H$/toluene (2 mL/6 mL). The resulting mixture was stirred for 3 h at 100° C. Solvent was removed and the residue was poured into ice/water. The solid was collected by filtration. 3-(4-bromo-3-methyl-2-oxo-2,3-dihydro-1H-benzo[d]imidazol-1-yl)piperidine-2,6-dione was obtained (510 mg, 86.4%). $[M+H]^+$=338.1.

Step 4: (E)-3-(4-(2-ethoxyvinyl)-3-methyl-2-oxo-2,3-dihydro-1H-benzo[d]imidazol-1-yl)piperidine-2,6-dione

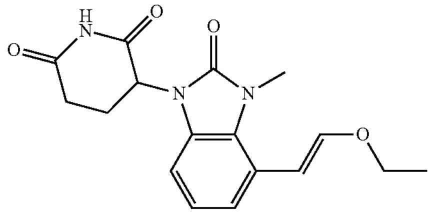 [SMILES: CCO/C=C/c1cccc2c1n(C)c(=O)n2C1CCC(=O)NC1=O]

To a stirred solution of 3-(4-bromo-3-methyl-2-oxo-2,3-dihydro-1H-benzo[d]imidazol-1-yl)piperidine-2,6-dione (250 mg, 0.74 mmol) and (E)-2-(2-ethoxyvinyl)-4,4,5,5-tetramethyl-1,3,2-dioxaborolane (176 mg, 0.89 mmol) in DMF/$H_2O$ (8 mL/2 mL) were added Pd(dtbpf)$Cl_2$ (48 mg, 0.074 mmol) and CsF (225 mg, 1.48 mmol). The resulting mixture was stirred for 2 h at 80° C. under nitrogen atmosphere. The reaction solution was diluted with water, extracted with EtOAc (10 mL×3). The organic layer was washed with water and brine, dried over anhydrous $Na_2SO_4$ which was evaporated to dryness. The residue was purified by a silica gel column, eluted with PE/EtOAc=1:1 to afford the product. (180 mg, 73.8%). m/z $[M+H]^+$=330.2.

Step 5: 2-(1-(2,6-dioxopiperidin-3-yl)-3-methyl-2-oxo-2,3-dihydro-1H-benzo[d]imidazol-4-yl)acetaldehyde

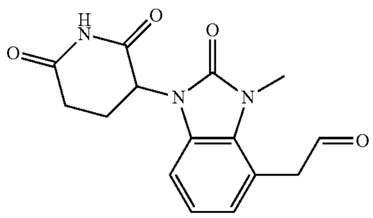 [SMILES: Cn1c(=O)n(C2CCC(=O)NC2=O)c2cccc(CC=O)c21]

(E)-3-(4-(2-ethoxyvinyl)-3-methyl-2-oxo-2,3-dihydro-1H-benzo[d]imidazol-1-yl)piperidine-2,6-dione (180 mg, 0.55 mmol) was dissolved in HCOOH (2 mL). The resulting solution was stirred for 2 h at room temperature. The reaction solution was evaporated to dryness to afford product (125 mg, 75.3%) which was used directly in the next step. m/z $[M+H]^+$=302.1.

Step 6: 3-(4-(2-(4-(1-(4-((5-bromo-4-((2-methyl-5-(1-oxidophospholan-1-yl)quinolin-6-yl)amino)pyrimidin-2-yl)amino)-2-ethyl-5-methoxyphenyl)piperidin-4-yl)piperazin-1-yl)ethyl)-3-methyl-2-oxo-2,3-dihydro-1H-benzo[d]imidazol-1-yl)piperidine-2,6-dione

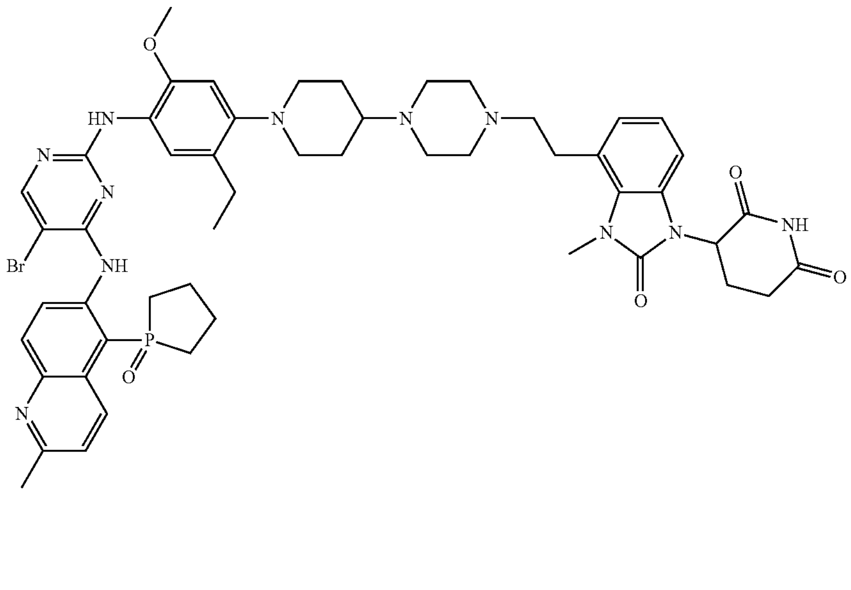 [SMILES: CCc1cc(Nc2ncc(Br)c(Nc3ccc4nc(C)ccc4c3P3(=O)CCCC3)n2)c(OC)cc1N1CCC(N2CCN(CCc3cccc4c3n(C)c(=O)n4C3CCC(=O)NC3=O)CC2)CC1]

The titled compound was synthesized in a manner similar to that in Example 147 Step 14 from 1-(6-((5-bromo-2-((5-ethyl-2-methoxy-4-(4-(piperazin-1-yl)piperidin-1-yl)phenyl)amino)pyrimidin-4-yl)amino)-2-methylquinolin-5-yl) phospholane 1-oxide and 2-(1-(2,6-dioxopiperidin-3-yl)-3-methyl-2-oxo-2,3-dihydro-1H-benzo[d]imidazol-4-yl) acetaldehyde. $^1$H NMR (500 MHz, DMSO) δ 11.02 (s, 1H), 10.60 (s, 1H), 8.58 (d, J=8.0 Hz, 11H), 8.16-8.24 (m, 11H), 7.97 (s, 1H), 7.89 (d, J=9.1 Hz, 11H), 7.80 (s, 11H), 7.42 (d, J=8.9 Hz, 1H), 7.29 (s, 1H), 6.94-6.78 (m, 3H), 6.63 (s, 1H), 5.30 (dd, J=12.7, 5.4 Hz, 1H), 3.69 (s, 3H), 3.51 (s, 3H), 2.94-3.04 (m, 3H), 2.80-2.85 (m, 4H), 2.45-2.70 (m, 15H), 1.82-2.31 (m, 12H), 1.74-1.76 (m, 2H), 1.41-1.47 (m, 2H), 0.54 (s, 3H). $[M+H]^+$=1018.4.

Example 71: 3-(6-(2-(4-(1-(4-((5-bromo-4-((2-methyl-5-(1-oxidophospholan-1-yl)quinolin-6-yl)amino)pyrimidin-2-yl)amino)-2-ethyl-5-methoxyphenyl)piperidin-4-yl)piperazin-1-yl)ethyl)-2-oxobenzo[d]oxazol-3(2H)-yl)piperidine-2,6-dione

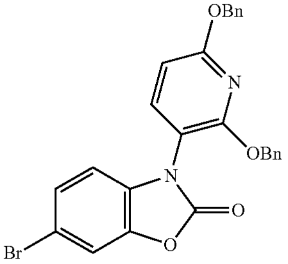 [SMILES: O=c1oc2cc(Br)ccc2n1-c1ccc(OCc2ccccc2)nc1OCc1ccccc1]

To a solution of 6-bromobenzo[d]oxazol-2(3H)-one (30.0 g, 140 mmol), 2,6-bis(benzyloxy)-3-(4,4,5,5-tetramethyl-1,3,2-dioxaborolan-2-yl)pyridine (61 g, 147 mml), and $Cu(OAc)_2$ (25.5 g, 140 mmol) in dry 1,4-dioxane (500 ml), were added pyridine (33.3 mL, 420 mmol), and activated 4 Å molecular sieve (20 g).

The mixture was stirred at 80° C. under the atmosphere of oxygen for 48 hours. After being cooled to rt, the mixture was diluted with ethyl acetate (1500 mL), and filtered through a pad of celite. The filtrate was washed with water (500 mL), and brine (3×500 mL), then dried over anhydrous sodium sulfate, concentrated under reduced pressure. The residue was purified by silica column chromatography (PE/DCM, 30%-50%) to afford crude product, which is further purified by trituration with PE to afford the target product (25.3 g, 35.8%). $[M+H]^+$=503.1.

Step 2: 6-(2-(benzyloxy)ethyl)-3-(2,6-bis(benzyloxy)pyridin-3-yl)benzo[d]oxazol-2(3H)-one

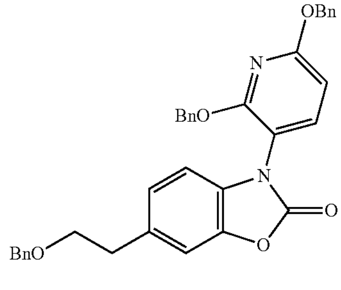 [SMILES: O=c1oc2cc(CCOCc3ccccc3)ccc2n1-c1ccc(OCc2ccccc2)nc1OCc1ccccc1]

A 500 mL three-neck round-bottomed flask equipped with a magnetic stirrer, were charged with 3-(2,6-bis(benzyloxy)pyridin-3-yl)-6-bromobenzo[d]oxazol-2(3H)-one (20 g, 39.7 mmol), ((2-bromoethoxy)methyl)benzene (15.4 g, 71.5 mmol). $NiI_2$ (2.48 g, 7.94 mmol), picolinimidamide hydrochloride (1.23 g, 7.94 mmol). NaI (2.98 g, 19.8 mmol), and Mn (6.55 g, 119 mmol). The mixture was degassed under vacuum and purged with $N_2$ for three times. Dry DMAc (300 mL) was added into the round-bottomed flask by a syringe, the mixture was degassed under vacuum and purged with $N_2$ once more. A solution of TFA (0.89 mL, 11.9 mmol) in DMAc (5 mL) was added into the round-bottomed flask by a syringe. The resulting mixture was stirred at 100° C. till complete conversion (confirmed by LCMS, ~5 hours). After being cooled to rt, the mixture was diluted with ethyl acetate (1.5 L), then filtered through a pad of celite. The filtrate was washed with brine (5×500 mL), dried over anhydrous $Na_2SO_4$ and concentrated under reduced pressure. The residue was purified by silica column chromatography (PE/EA, 10%-20%) to afford crude product (8.00 g, 36.1%). $[M+H]^+$= 559.4.

Step 3: 3-(6-(2-hydroxyethyl)-2-oxobenzo[d]oxazol-3(2H)-yl)piperidine-2,6-dione

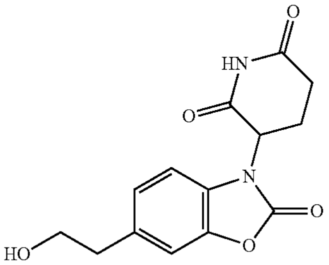 [SMILES: O=C1CCC(n2c(=O)oc3cc(CCO)ccc32)C(=O)N1]

To a solution of 6-(2-(benzyloxy)ethyl)-3-(2,6-bis(benzyloxy)pyridin-3-yl)benzo[d]oxazol-2(3H)-one (8.00 g, 14.3 mmol) in THF/EtOH (200 mL/200 mL), was added Pd/C (10 wt %, 5.00 g). The mixture was degassed under reduced pressure and purged with $H_2$ for five times, and stirred under $H_2$ at 50° C. overnight. After being cooled to rt, the mixture was diluted with EtOH/DCM (200 ml/400 mL), and sonicated in an ultrasonic washer for 5 minutes, then filtered through a pad of celite. The filtrate was concentrated under reduced pressure. Precipitate was observed during evaporation, then it was collected by filtration, and dried under vacuum to afford the first part of product (2.50 g). The filtrate was concentrated under reduced pressure and purified by silica column chromatography (PE/EA=1:1) to afford the other part of target product (0.80 g). Totally 3.30 g product was obtained (79.7%). $[M+H]^+$=291.2.

Step 3: 2-(3-(2,6-dioxopiperidin-3-yl)-2-oxo-2,3-dihydrobenzo[d]oxazol-6-yl)acetaldehyde

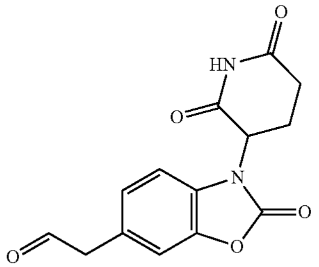 [SMILES: O=CCc1ccc2c(c1)oc(=O)n2C1CCC(=O)NC1=O]

The titled compound was synthesized in a manner similar to that in Example 147 Step 13 from 3-(6-(2-hydroxyethyl)-2-oxobenzo[d]oxazol-3(2H)-yl)piperidine-2,6-dione and IBX. $[M+H]^+$=289.1.

Step 4: 3-(6-(2-(4-(1-(4-((5-bromo-4-((2-methyl-5-(1-oxidophospholan-1-yl)quinolin-6-yl)amino)pyrimidin-2-yl)amino)-2-ethyl-5-methoxyphenyl)piperidin-4-yl)piperazin-1-yl)ethyl)-2-oxobenzo[d]oxazol-3(2H)-yl)piperidine-2,6-dione

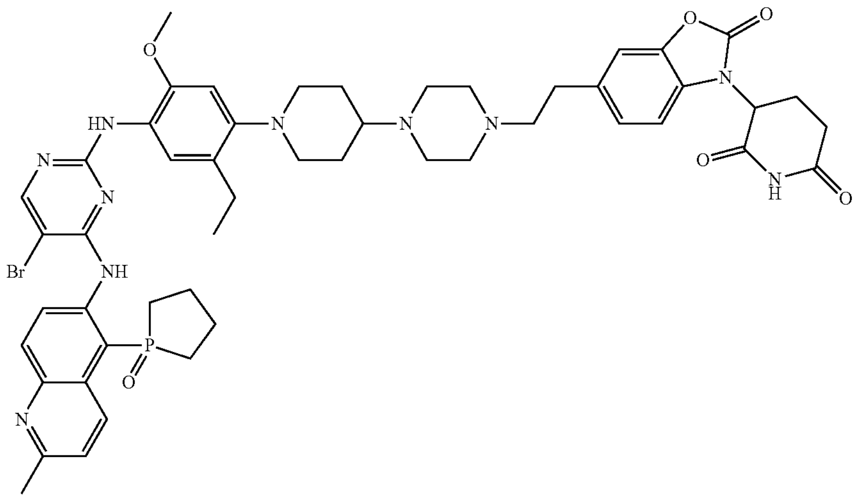 [SMILES: CCc1cc(Nc2ncc(Br)c(Nc3ccc4nc(C)ccc4c3P3(=O)CCCC3)n2)c(OC)cc1N1CCC(N2CCN(CCc3ccc4c(c3)oc(=O)n4C3CCC(=O)NC3=O)CC2)CC1]

The titled compound was synthesized in a manner similar to that in Example 147 Step 14 from 1-(6-((5-bromo-2-((5-ethyl-2-methoxy-4-(4-(piperazin-1-yl)piperidin-1-yl)phenyl)amino)pyrimidin-4-yl)amino)-2-methylquinolin-5-yl)phospholane 1-oxide and 2-(3-(2,6-dioxopiperidin-3-yl)-2-oxo-2,3-dihydrobenzo[d]oxazol-6-yl)acetaldehyde. $^1$H NMR (500 MHz, DMSO) δ 11.14 (s, 1H), 10.60 (s, 1H), 8.57 (d, J=8.8 Hz, 1H), 8.15 (s, 1H), 7.98 (s, 1H), 7.89 (d, J=9.1 Hz, 1H), 7.80 (s, 1H), 7.42 (d, J=8.9 Hz, 1H), 7.29 (s, 1H), 7.22 (s, 1H), 7.09 (d, J=8.1 Hz, 1H), 7.00 (d, J=8.1 Hz, 1H), 6.62 (s, 1H), 5.28 (dd, J=12.9, 5.2 Hz, 1H), 3.68 (s, 3H), 2.74-2.89 (m, 3H), 2.47-2.72 (m, 13H), 2.30-2.42 (m, 5H), 1.87-2.17 (m, 13H), 1.72-1.74 (m, 2H), 1.40-1.46 (m, 2H), 0.54 (s, 3H). $[M+H]^+$=1005.4.

Example 73: 3-(4-(2-(4-(1-(4-((5-bromo-4-((2-methyl-5-(1-oxidophospholan-1-yl)quinolin-6-yl)amino)pyrimidin-2-yl)amino)-2-ethyl-5-methoxy-phenyl)piperidin-4-yl)piperazin-1-yl)ethyl)-3,3-dimethyl-2-oxoindolin-1-yl)piperidine-2,6-dione Step 1: N-(2,6-bis(benzyloxy)pyridin-3-yl)-2-(2,6-dibromophenyl)acetamide

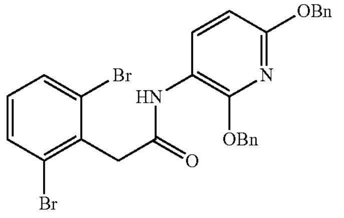 [SMILES: O=C(Cc1c(Br)cccc1Br)Nc1ccc(OCc2ccccc2)nc1OCc1ccccc1]

Into a 100-mL round-bottom flask, (2,6-dibromophenyl) acetic acid (0.85 g, 2.892 mmol). DMF (35 mL), 2,6-bis (benzyloxy)pyridin-3-amine hydrochloride (1.0 g, 2.916 mmol), DIEA (2.0 mL, 11.654 mmol) and HATU (1.3 g, 3.499 mmol) were added. The resulting solution was stirred overnight at room temperature. The resulting solution was diluted with $H_2O$ The solids were collected by filtration. The solid was washed with MeOH to afford 1.5 g (89.08%) product which was used in next step without further purification. $[M+H]^+$=581.1.

Step 2: 1-(2,6-bis(benzyloxy)pyridin-3-yl)-4-bromoindolin-2-one

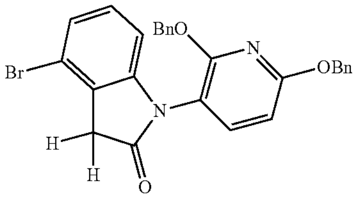 [SMILES: O=C1Cc2c(Br)cccc2N1c1ccc(OCc2ccccc2)nc1OCc1ccccc1]

Into a 50-mL round-bottom flask purged and maintained with an inert atmosphere of nitrogen, was added N-[2,6-bis (benzyloxy)pyridin-3-yl]-2-(2,6-dibromophenyl) acetamide (580 mg, 0.996 mmol), NMP (15 mL). $K_2CO_3$ (688 mg, 4.978 mmol), acetylacetone (200 mg, 1.998 mmol) and CuCl (99 mg, 1.000 mmol). The resulting solution was stirred for 1.5 hr at 85° C. The reaction mixture was cooled to room temperature. The resulting solution was diluted with EtOAc. The resulting solution was extracted with brine and the organic layers combined and dried over anhydrous sodium sulfate and concentrated under vacuum. The residue was applied onto a silica gel column with DCM/EA (6:1) to afford 403 mg (80.1%) of desired product. $[M+H]^+$=501.2.

Step 3: 1-(2,6-bis(benzyloxyl)pyridin-3-yl)-4-bromo-3,3-dimethylindolin-2-one

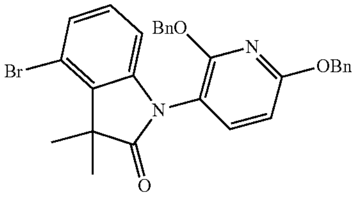 [SMILES: CC1(C)C(=O)N(c2ccc(OCc3ccccc3)nc2OCc2ccccc2)c2cccc(Br)c21]

Into a 50-mL round-bottom flask, was added 1-[2,6-bis (benzyloxy)pyridin-3-yl]-4-bromo-3H-indol-2-one (500 mg, 0.997 mmol). DMF (15 mL), NaH (189 mg, 5.0 mol). The resulting solution was stirred for 0.5 hr at room temperature. And then $CH_3I$ (850 mg, 5.988 mmol) was added to the mixture at room temperature. The reaction was stirred overnight at room temperature. The resulting solution was diluted with EA. The pH value of the solution was adjusted to <7 with 2N HCl. The resulting mixture was extracted with ethyl acetate and the organic layers combined. The organic layer was washed with brine, dried over anhydrous sodium sulfate, and concentrated under vacuum. The residue was applied onto a silica gel column with DCM/PE (3:1) to afford 401 mg (75%) of desired product. $[M+H]^+$=529.2.

Step 4: ethyl 2-(1-(2,6-bis(benzyloxy)pyridin-3-yl)-3,3-dimethyl-2-oxoindolin-4-yl) acetate

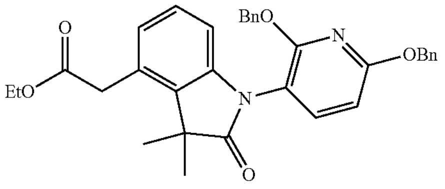 [SMILES: CCOC(=O)Cc1cccc2c1C(C)(C)C(=O)N2c1ccc(OCc2ccccc2)nc1OCc1ccccc1]

Into a 30-mL microwave vial #1 purged and maintained with an inert atmosphere of nitrogen, was placed zinc powder (490 mg, 7.555 mmol), THF (8 mL), TMSCl (41 mg, 0.377 mmol). The resulting solution was stirred for 10 min at room temperature. And then ethyl bromoacetate (630 mg, 3.778 mmol) was added to the mixture. The resulting solution was stirred for 1.5 hrs at 60° C. Into a 100-mL 3-necked round-bottom flask, purged and maintained with an inert atmosphere of nitrogen, was placed 1-[2,6-bis (benzyloxy)pyridin-3-yl]-4-bromo-3,3-dimethylindol-2-one (1 g, 1.889 mmol), THF (17 mL), Xphos (180 mg, 0.378 mmol), $Pd_2(dba)_3$ (170 mg, 0.189 mmol). To the above mixture was added the solution in vial #1 by a syringe through a millipore filter. The resulting solution was allowed to react for an additional 3 hrs at 60° C. The resulting solution was diluted with EtOAc. The pH value of the solution was adjusted to <7 with 2N HCl. The resulting solution was extracted with ethyl acetate and the organic layers combined and dried over anhydrous sodium sulfate and concentrated under vacuum. The residue was applied onto a silica gel column with EA/PE (1:2) to afford 810 mg (78.9%) of desired product. $[M+H]^+$=537.2.

Step 5: [1-[2,6-bis(benzyloxy)pyridin-3]-yl-3,3-dimethyl-2-oxoindol-4-yl]acetic acid

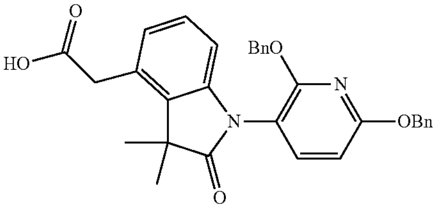 [SMILES: CC1(C)C(=O)N(c2ccc(OCc3ccccc3)nc2OCc2ccccc2)c2cccc(CC(=O)O)c21]

Into a 50-mL round-bottom flask, was placed ethyl 2-[1-[2,6-bis(benzyloxy)pyridine-3-yl]-3,3-dimethyl-2-oxoindol-4-yl]acetate (740 mg, 1.379 mmol), THF (10 mL), $H_2O$ (1 mL), NaOH (276 mg, 6.901 mmol). The resulting solution was stirred for 3 hr at 65° C. The pH value of the solution was adjusted to <7 with 2N HCl (1 mL). The resulting solution was extracted with ethyl acetate and the organic layers combined and concentrated under vacuum to afford 502 mg (71.29%) of desired product which was used in next step without further purification. $[M+H]^+$=509.2.

Step 6: 1-[2,6-bis(benzyloxy)pyridin-3-yl]-4-(2-hydroxyethyl)-3,3-dimethylindol-2-one

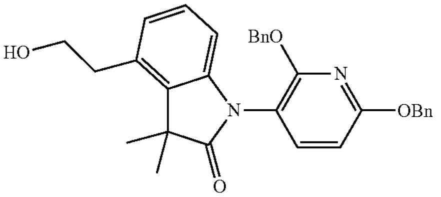 [SMILES: CC1(C)C(=O)N(c2ccc(OCc3ccccc3)nc2OCc2ccccc2)c2cccc(CCO)c21]

Into a 50-mL round-bottom flask, was placed [1-[2,6-bis(benzyloxy)pyridin-3-yl]-3,3-dimethyl-2-oxoindol-4-yl]acetic acid (600 mg, 1.180 mmol), THF (15 mL). And then $BH_3$ (1M in THF, 6 mL) was added dropwise to the mixture at room temperature. The resulting solution was stirred for 5 hr at room temperature. The reaction was then quenched by the addition of MeOH (10 mL). The resulting mixture was concentrated under vacuum to afford the crude residue which was purified with EA/PE (1:1) to afford 400 mg (68.5%) of desired product. $[M+H]^+$=495.2.

Step 7: 3-[4-(2-hydroxyethyl)-3,3-dimethyl-2-oxoindol-1-yl]piperidine-2,6-dione

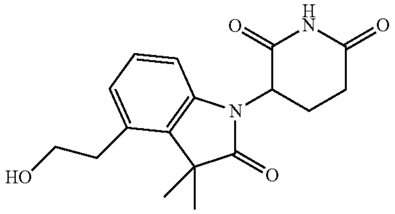 [SMILES: CC1(C)C(=O)N(C2CCC(=O)NC2=O)c2cccc(CCO)c21]

Into a 100-mL round-bottom flask, was placed 1-[2,6-bis(benzyloxy)pyridin-3-yl]-4-(2-hydroxyethyl)-3,3-dimethylindol-2-one (400 mg, 0.809 mmol). EtOH (15 mL), THF (15 mL), AcOH (0.50 mL), Pd/C (400 mg, 10% wt) at hydrogen atmosphere. The resulting solution was stirred overnight at 50° C. and the solids were filtered out. The organic phase was concentrated under vacuum to afford 213 mg (83.37%) of desired product $[M+H]^+$=317.1.

Step 8: 2-(1-(2,6-dioxopiperidin-3-yl)-3,3-dimethyl-2-oxoindolin-4-yl)acetaldehyde

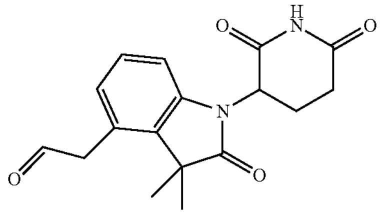 [SMILES: CC1(C)C(=O)N(C2CCC(=O)NC2=O)c2cccc(CC=O)c21]

The titled compound was synthesized in a manner similar to that in Example 147 Step 13 from 3-[4-(2-hydroxyethyl)-3,3-dimethyl-2-oxoindol-1-yl]piperidine-2,6-dione and IBX. $[M+H]^+$=315.2.

Step 9: 3-(4-(2-(4-(1-(4-((5-bromo-4-((2-methyl-5-(1-oxidophospholan-1-yl)quinolin-6-yl)amino)pyrimidin-2-yl)amino)-2-ethyl-5-methoxyphenyl)piperidin-4-yl)piperazin-1-yl)ethyl)-3,3-dimethyl-2-oxoindolin-1-yl)piperidine-2,6-dione

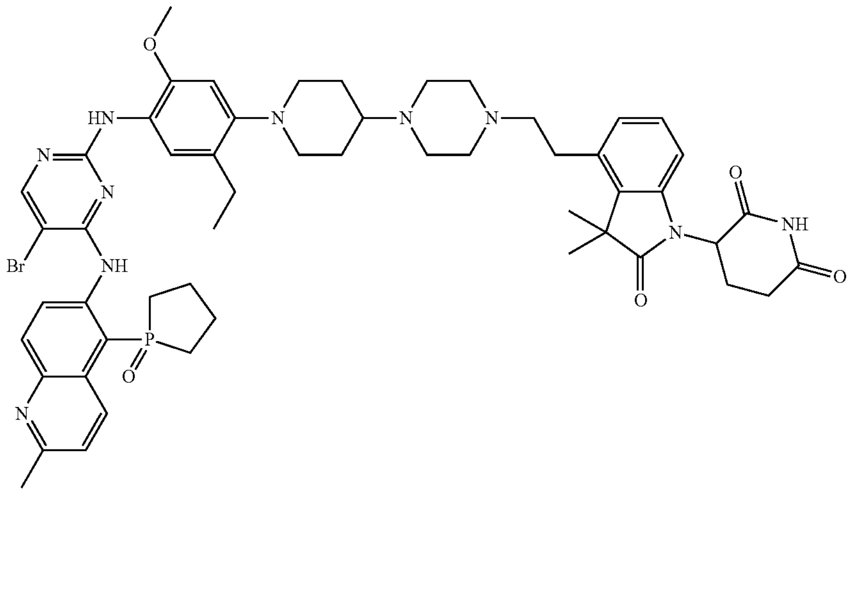 [SMILES: CCc1cc(Nc2ncc(Br)c(Nc3ccc4nc(C)ccc4c3P3(=O)CCCC3)n2)c(OC)cc1N1CCC(N2CCN(CCc3cccc4c3C(C)(C)C(=O)N4C3CCC(=O)NC3=O)CC2)CC1]

The titled compound was synthesized in a manner similar to that in Example 147 Step 14 from 1-(6-((5-bromo-2-((5-ethyl-2-methoxy-4-(4-(piperazin-1-yl)piperidin-1-yl)phenyl)amino)pyrimidin-4-yl)amino)-2-methylquinolin-5-yl) phospholane 1-oxide and 2-(1-(2,6-dioxopiperidin-3-yl)-3, 3-dimethyl-2-oxoindolin-4-yl)acetaldehyde. $^1$H NMR (500 MHz, DMSO) δ 11.07 (s, 1H), 10.68 (s, 1H), 8.64 (d, J=8.8 Hz, 1H), 8.29 (s, 1H), 8.23 (s, 1H), 8.04 (s, 1H), 7.96 (d, J=9.1 Hz, 1H), 7.87 (s, 1H), 7.49 (d, J=8.9 Hz, 1H), 7.36 (s, 1H), 7.17 (t, J=7.8 Hz, 1H), 6.91 (d, J=7.8 Hz, 1H), 6.83 (s, 1H), 6.69 (s, 1H), 5.21 (s, 1H), 3.75 (s, 3H), 2.75-2.94 (m, 6H), 2.51-2.74 (m, 14H), 1.89-2.32 (m, 13H), 1.81 (d, J=10.9 Hz, 2H), 1.51 (dd, J=20.3, 11.3 Hz, 2H), 1.38 (d, J=4.1 Hz, 6H), 0.61 (s, 3H). $[M+H]^+$=1031.4.

Example 75: 3-(4-(2-(4-(1-(4-((5-bromo-4-((2-methyl-5-(1-oxidophospholan-1-yl)quinolin-6-yl)amino)pyrimidin-2-yl)amino)-2-ethyl-5-methoxyphenyl)piperidin-4-yl)piperazin-1-yl)ethyl)-2,6-difluorophenyl)piperidine-2,6-dione

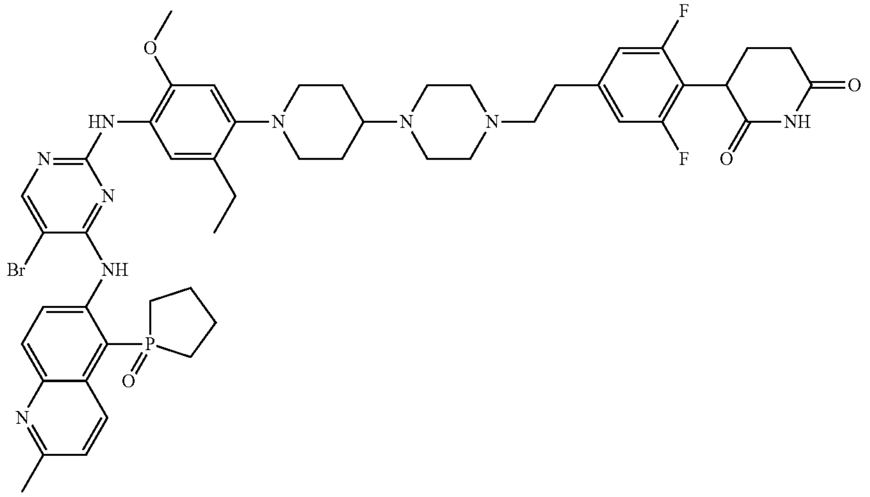 [SMILES: CCc1cc(Nc2ncc(Br)c(Nc3ccc4nc(C)ccc4c3P3(=O)CCCC3)n2)c(OC)cc1N1CCC(N2CCN(CCc3cc(F)c(C4CCC(=O)NC4=O)c(F)c3)CC2)CC1]

The titled compound was synthesized in a manner similar to that in Example 147 Step 14 from 1-(6-((5-bromo-2-((5-ethyl-2-methoxy-4-(4-(piperazin-1-yl)piperidin-1-yl)phenyl)amino)pyrimidin-4-yl)amino)-2-methylquinolin-5-yl) phospholane 1-oxide and 3-(2,6-difluoro-4-(2-hydroxyethyl)phenyl)piperidine-2,6-dione.

$^1$H NMR (500 MHz, DMSO) δ 10.95 (s, 1H), 10.67 (s, 1H), 8.64 (d, J=8.7 Hz, 1H), 8.24 (d, J=11.0 Hz, 1H), 8.04 (s, 1H), 7.96 (d, J=9.1 Hz, 1H), 7.87 (s, 1H), 7.49 (d, J=8.9 Hz, 1H), 7.36 (s, 1H), 7.02 (d, J=10.1 Hz, 2H), 6.69 (s, 1H), 4.20 (dd, J=12.6, 5.0 Hz, 1H), 3.75 (s, 3H), 2.51-2.92 (m, 16H), 2.36-2.48 (m, 4H), 1.88-2.30 (m, 14H), 1.80 (d, J=10.9 Hz, 2H), 1.50 (dd, J=20.2, 11.3 Hz, 2H), 0.61 (s, 3H). $[M+H]^+$=984.3.

Example 76: 3-(4-(3-(4-(1-(4-((5-bromo-4-((2-methyl-5-(1-oxidophospholan-1-yl)quinolin-6-yl)amino)pyrimidin-2-yl)amino)-2-ethyl-5-methoxyphenyl)piperidin-4-yl)piperazine-1-carbonyl)azetidin-1-yl)-2,6-difluorophenyl)piperidine-2,6-dione

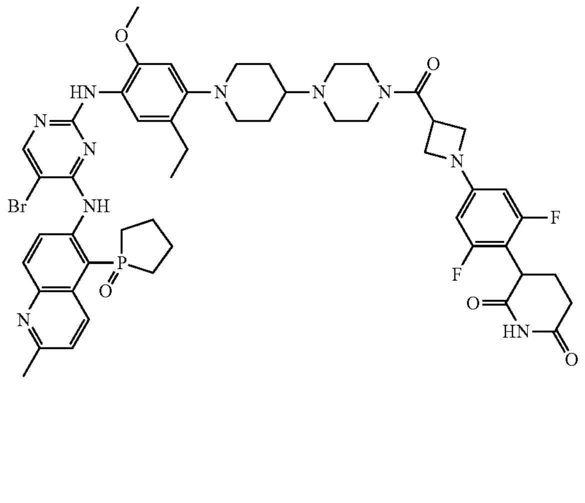 [SMILES: CCc1cc(Nc2ncc(Br)c(Nc3ccc4nc(C)ccc4c3P3(=O)CCCC3)n2)c(OC)cc1N1CCC(N2CCN(C(=O)C3CN(c4cc(F)c(C5CCC(=O)NC5=O)c(F)c4)C3)CC2)CC1]

The titled compound was synthesized in a procedure similar to Example 77.

$^1$H NMR (500 MHz, DMSO) δ 10.86 (s, 1H), 10.67 (s, 1H), 8.65 (s, 1H), 8.22 (s, 1H), 8.04 (s, 1H), 7.96 (d, J=9.0 Hz, 1H), 7.86 (s, 1H), 7.49 (d, J=8.9 Hz, 1H), 7.37 (s, 1H), 6.69 (s, 1H), 6.17 (d, J=11.1 Hz, 2H), 4.03 (t, J=7.4 Hz, 3H), 3.91 (t, J=6.1 Hz, 2H), 3.79-3.86 (m, 1H), 3.75 (s, 3H), 3.48 (s, 2H), 2.87-2.89 (m, 2H), 2.72-2.82 (m, 1H), 2.56-2.71 (m, 5H), 2.51-2.54 (m, 4H), 2.45-2.49 (m, 3H), 2.31-2.39 (m, 1H), 2.17-2.26 (m, 2H), 1.87-2.16 (m, 10H), 1.79 (d, J=10.8 Hz, 2H), 1.53 (dd, J=20.4, 11.3 Hz, 2H), 0.61 (s, 3H). $[M+H]^+$=1039.4.

Example 111: 3-(4-((R)-3-(4-(1-(4-((5-bromo-4-((2-(1-oxidophospholan-1-yl)phenyl)amino)pyrimidin-2-yl)amino)-2-ethyl-5-methoxyphenyl)piperidin-4-yl)piperazine-1-carbonyl)pyrrolidin-1-yl)-2,6-difluorophenyl)piperidine-2,6-dione

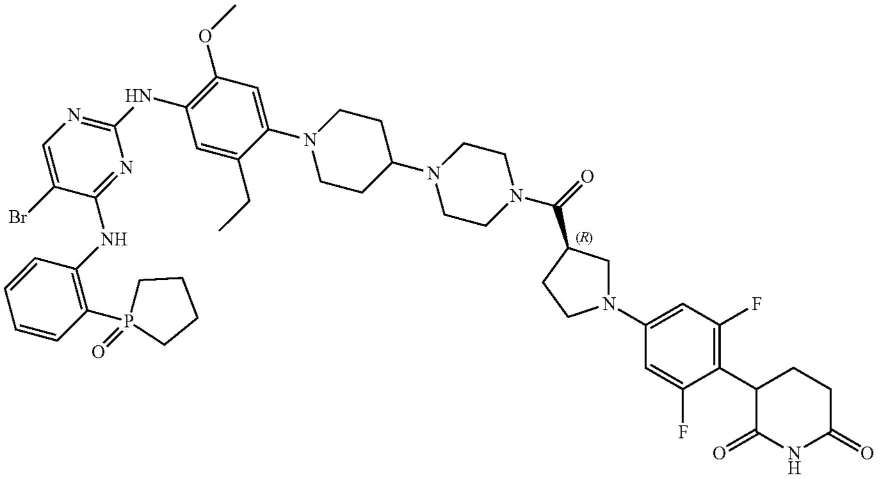

The titled compound was synthesized in a manner similar to that in Example 77 Step 12 from 1-(2-(5-bromo-2-((5-ethyl-2-methoxy-4-(4-(piperazin-1-yl)piperidin-1-yl)phenyl)amino)pyrimidin-4-yl)amino)phenyl)phospholane 1-oxide and (3R)-1-(4-(2,6-dioxopiperidin-3-yl)-3,5-difluorophenyl)pyrrolidine-3-carboxylic acid. $^1$H NMR (500 MHz, DMSO) δ 10.78 (s, 1H), 10.50 (s, 11H), 8.19 (d, J=12.7 Hz, 11H), 8.12 (s, 11H), 7.99 (s, 11H), 7.29-7.39 (m, 3H), 7.10 (t, J=7.3 Hz, 11H), 6.69 (s, 1H), 6.16 (d, J=12.2 Hz, 2H), 3.95 (dd, J=12.5, 4.9 Hz, 1H), 3.69 (s, 3H), 3.37-3.49 (m, 7H), 3.16-3.27 (in, 6H), 2.93-2.95 (m, 2H), 2.47-2.76 (m, 5H), 2.19-2.36 (m, 2H), 1.78-2.13 (m, 14H), 1.50-1.56 (m, 2H), 0.94 (t, J=7.4 Hz, 3H). $[M+H]^+$=988.3.

Example 143: 3-(4-(R)-3-(4-(1-(4-((5-bromo-4-((2-methyl-5-(1-oxido-2,5-dihydrophosphol-1-yl)quinolin-6-yl)amino)pyrimidin-2-yl)amino)-2-ethyl-5-methoxyphenyl)piperidin-4-yl)piperazine-1-carbonyl)pyrrolidin-1-yl)-2,6-difluorophenyl)piperidine-2,6-dione Step 1: 5-iodo-2-methylquinolin-6-amine

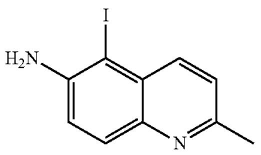

To a solution of 2-methylquinolin-6-amine (5.3 g, 33.5 mmol) in HOAc (60 mL) was added IC1 (6.5 g, 40.3 mmol) at 20° C. Then the mixture was stirred at 20° C. for 1 hr. The reaction solution was concentrated under vacuum. Then the mixture was adjusted to pH=8 with sat. aq. $NaHCO_3$ solution and extracted with DCM (150 mL). The organic phase was washed with brine (50 mL), dried over $Na_2SO_4$, filtered and concentrated in vacuum, 5-iodo-2-methylquinolin-6-amine (8 g, 83.7%) was obtained. $[M+H]^+$=285.0.

Step 2: diallyl(6-amino-2-methylquinolin-5-yl)phosphine oxide

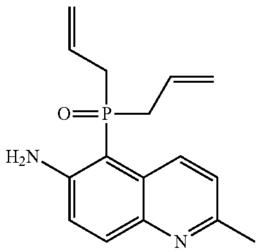 [SMILES: C=CCP(=O)(CC=C)c1c(N)ccc2nc(C)ccc12]

To a solution of 5-iodo-2-methylquinolin-6-amine (4 g, 14 mmol) and diallylphosphine oxide (3.6 g, 28 mmol) in dioxane (80 mL) was added $K_3PO_4$ (7.4 g, 35 mmol), then $Pd(OAc)_2$ (316 mg, 1.4 mmol) and Xantphos (813 mg, 1.4 mmol) were added to the mixture at 20° C. The suspension was degassed under vacuum and purged with $N_2$ three times. Then the mixture was stirred at 100° C. for 15 hrs. The mixture was filtered and concentrated in vacuum. The residue was purified by column chromatography (DCM/MeOH=20/1 to 10/1) to afford diallyl(6-amino-2-methylquinolin-5-yl)phosphine oxide (2.1 g, 52.2%) as a brown solid. $[M+H]^+$=287.1.

Step 3: N-(5-(diallylphosphoryl)-2-methylquinolin-6-yl)pivalamide

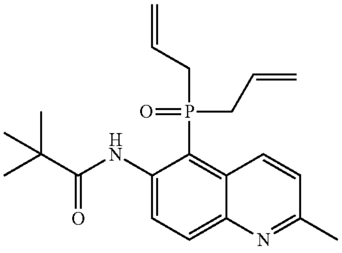 [SMILES: C=CCP(=O)(CC=C)c1c(NC(=O)C(C)(C)C)ccc2nc(C)ccc12]

To a solution of diallyl(6-amino-2-methylquinolin-5-yl) phosphine oxide (2.1 g, 7.3 mmol) in DCM (50 mL) was added TEA (1.85 g, 18.3 mmol), then pivaloyl chloride (1.06 g, 8.8 mmol) was added dropwise in 5 min. The resulting solution was stirred at rt for 3 h. The reaction mixture was diluted with DCM, washed water and brine, dried over anhydrous $Na_2SO_4$. The organic phase was evaporated to dryness to afford N-(5-(diallylphosphoryl)-2-methylquinolin-6-yl)pivalamide. (2.6 g, 95.9%). $[M+H]^+$=371.2.

Step 4: N-(2-methyl-5-(1-oxido-2,5-dihydrophosphol-1-yl)quinolin-6-yl)pivalamide

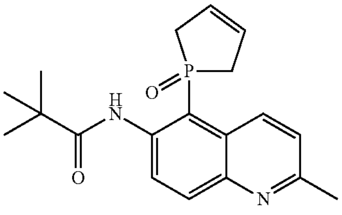 [SMILES: Cc1ccc2c(P3(=O)CC=CC3)c(NC(=O)C(C)(C)C)ccc2n1]

To a solution of N-(5-(diallylphosphoryl)-2-methylquinolin-6-yl)pivalamide (2.6 g, 7.0 mmol) in DCM (200 mL) was added HOVEYDA-Grubbs catalyst (878 mg, 1.4 mmol). The reaction mixture was stirred for 16 h at room temperature. The mixture was concentrated in vacuum. The residue was purified by column chromatography (DCM/MeOH=20/1 to 10/1) to afford N-(2-methyl-5-(l-oxido-2,5-dihydrophosphol-1-yl)quinolin-6-yl)pivalamide (2 g, 83.3%) as a dark-brown solid. $[M+H]^+$=343.2.

Step 5: 1-(6-amino-2-methylquinolin-5-yl)-2,5-dihydrophosphole 1-oxide

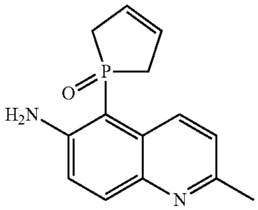 [SMILES: Cc1ccc2c(P3(=O)CC=CC3)c(N)ccc2n1]

N-(2-methyl-5-(1-oxido-2,5-dihydrophosphol-1-yl)quinolin-6-yl)pivalamide (2 g, 5.8 mmol) was dissolved in dioxane (15 mL). HCl (2 M, 15 mL) was added to the reaction mixture. The resulting solution was stirred for 15 h at 100° C. The reaction solution was evaporated to dryness, the reside was dissolved in water, the pH value was adjusted to 8-9 with NaOH (1M), extracted with DCM, then the organic phase was concentrated under vacuum to afford 1-(6-amino-2-methylquinolin-5-yl)-2,5-dihydrophosphole 1-oxide (1.3 g, 86.1%) and used directly to the next step without further purification. $[M+H]^+$=259.1.

Step 6: 1-(6-((5-bromo-2-chloropyrimidin-4-yl)amino)-2-methylquinolin-5-yl)-2,5-dihydrophosphole 1-oxide

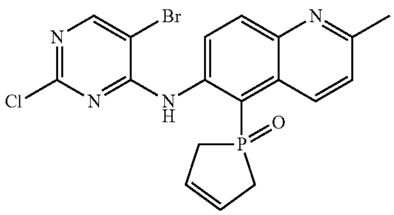 [SMILES: Cc1ccc2c(P3(=O)CC=CC3)c(Nc3nc(Cl)ncc3Br)ccc2n1]

To a solution of 1-(6-amino-2-methylquinolin-5-yl)-2,5-dihydrophosphole 1-oxide (500 mg, 1.9 mmol) in THF (15 mL) was added 5-bromo-2,4-dichloropyrimidine (1.1 g, 4.8 mmol) at 0° C. And then LiHMDS (1 M, 3.8 mL, 3.8 mmol) was added to the reaction mixture at 0° C. The mixture was stirred at 20° C. for 3 hrs. Water (10 mL) was poured into the mixture, which was further extracted with DCM (20 mL×3). The combined organic phase was washed with brine (20 mL), dried over $Na_2SO_4$, filtered and concentrated in vacuum. The residue was purified by column chromatography (DCM/MeOH=10/1 to 5/1) to afford 1-(6-((5-bromo-2-chloropyrimidin-4-yl)amino)-2-methylquinolin-5-yl)-2,5-dihydrophosphole 1-oxide (505 mg, 58.2%). $[M+H]^+$=449.0.

Step 7: 1-(6-((5-bromo-2-((5-ethyl-2-methoxy-4-(4-piperazin-1-yl)piperidin-1-yl)phenyl)amino)pyrimidin-4-yl)amino)-2-methylquinolin-5-yl)-2,5-dihydrophosphole 1-oxide

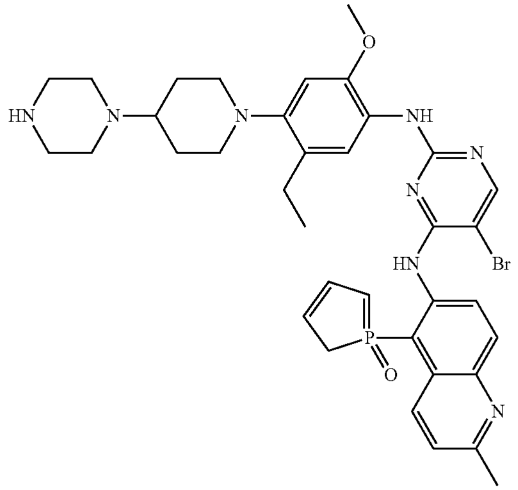

To a solution of 1-(6-((5-bromo-2-chloropyrimidin-4-yl)amino)-2-methylquinolin-5-yl)-2,5-dihydrophosphole 1-oxide (505 mg, 1.1 mmol) in n-BuOH (20 mL) was added tert-butyl 4-(1-(4-amino-2-ethyl-5-methoxyphenyl)piperidin-4-yl)piperazine-1-carboxylate (472 mg, 1.1 mmol) at 20° C. 4-methylbenzenesulfonic acid (568 mg, 3.3 mmol) was added to the reaction mixture at 20° C. Then the mixture was stirred at 90° C. for 15 hrs. The reaction mixture was evaporated to dryness, water (20 mL) was poured into the mixture. Then the mixture was adjusted to pH=8 with sat. aq. $NaHCO_3$ solution and extracted with DCM (20 mL×3). The organic phase was washed with brine (30 mL), dried over $Na_2SO_4$, filtered and concentrated in vacuum. The residue was purified by column chromatography (DCM/MeOH=10/1 to 5/1) to afford the product (485 mg, 58.9%). $[M+H]^+$=731.3.

Step 8: 3-(4-((R)-3-(4-(1-(4-((5-bromo-4-((2-methyl-5-(1-oxido-2,5-dihydrophosphol-1-yl)quinolin-6-yl)amino)pyrimidin-2-yl)amino)-2-ethyl-5-methoxyphenyl)piperidin-4-yl)piperazine-1-carbonyl)pyrrolidin-1-yl-2,6-difluorophenyl)piperidine-2,6-dione

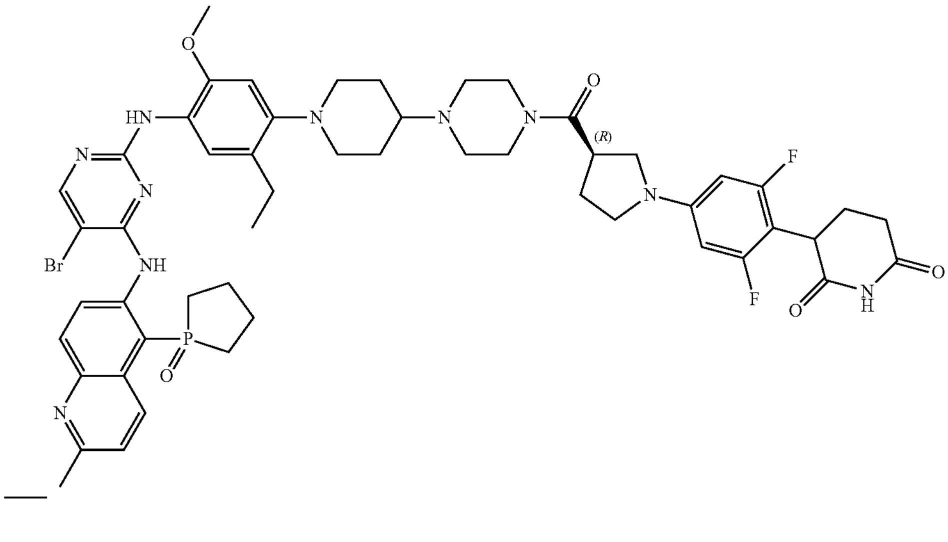

To a solution of 1-(6-((5-bromo-2-((5-ethyl-2-methoxy-4-(4-(piperazin-1-yl)piperidin-1-yl)phenyl)amino)pyrimidin-4-yl)amino)-2-methylquinolin-5-yl)-2,5-dihydrophosphole 1-oxide (50 mg, 0.07 mmol). (3R)-1-(4-(2,6-dioxopiperidin-3-yl)-3,5-difluorophenyl)pyrrolidine-3-carboxylic acid (35 mg, 0.1 mmol) and DIEA (26 mg, 0.2 mmol) in 10 mL DCM, 50% w.t. $T_3P$ in EtOAc solution (64 mg, 0.1 mmol) was added. The mixture was stirred at 25° C. for 16 hours. After LCMS showed the reaction was completed. The mixture was quenched with water (10 mL). The organic phase was concentrated in vacuum and purified by prep-HPLC with C-18 column chromatography (0.1% FA in water:acetonitrile=90:10~50:50 gradient elution) to afford product (20.5 mg, 27.8% yield). $^1$H NMR (500 MHz, DMSO) δ 11.31 (s, 1H), 10.84 (s, 1H), 8.32 (s, 1H), 8.22 (s, 1H), 8.03 (s, 1H), 7.94 (dd, J=13.9, 9.3 Hz, 2H), 7.29-7.47 (m, 2H), 6.75 (s, 1H), 6.11-6.24 (m, 4H), 4.02 (dd, J=12.5, 4.9 Hz, 1H), 3.78 (s, 3H), 3.43-3.56 (m, 7H), 3.23-3.42 (m, 5H), 2.94-3.04 (m, 4H), 2.73-2.88 (m, 3H), 2.53-2.71 (m, 7H), 2.23-2.43 (m, 3H), 2.02-2.21 (m, 3H), 1.89-2.00 (m, 1H), 1.83 (d, J=10.4 Hz, 2H), 1.49-1.63 (m, 2H), 0.78 (s, 3H). $[M+H]^+$=1051.4.

Example 144: 3-(4-(2-(4-(1-(4-((5-bromo-4-((2-methyl-5-(1-oxido-2,5-dihydrophosphol-1-yl)quinolin-6-yl)amino)pyrimidin-2-yl)amino)-2-ethyl-5-methoxyphenyl)piperidin-4-yl)piperazin-1-yl)ethyl)-2,6-difluorophenyl)piperidine-2,6-dione

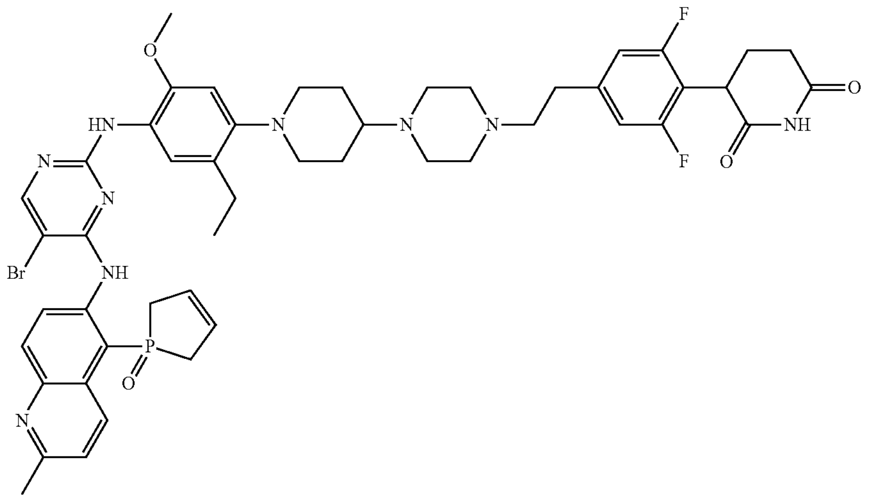

The titled compound was synthesized in a manner similar to that in Example 147 Step 14 from 1-(6-((5-bromo-2-((5-ethyl-2-methoxy-4-(4-(piperazin-1-yl)piperidin-1-yl)phenyl)amino)pyrimidin-4-yl)amino)-2-methylquinolin-5-yl)-2,5-dihydrophosphole 1-oxide and 3-(2,6-difluoro-4-(2-hydroxyethyl)phenyl)piperidine-2,6-dione. $^1$H NMR (500 MHz, DMSO) δ 11.25 (s, 1H), 10.88 (s, 1H), 8.24 (s, 1H), 8.15 (s, 1H), 7.96 (s, 1H), 7.79-7.91 (m, 2H), 7.18-7.43 (m, 2H), 6.95 (d, J=10.1 Hz, 2H), 6.67 (s, 1H), 6.07 (d, J=30.6 Hz, 2H), 4.13 (dd, J=12.6, 5.0 Hz, 1H), 3.69 (s, 3H), 2.85-2.97 (m, 4H), 2.67-2.74 (m, 5H), 2.45-2.63 (m, 10H), 2.21-2.30 (m, 9H), 1.99-2.13 (m, 1H), 1.92-1.94 (m, 1H), 1.76 (d, J=10.9 Hz, 2H), 1.47 (dd, J=20.4, 11.4 Hz, 2H), 0.71 (s, 3H). $[M+H]^+$=982.3.

Example 145: 3-(6-(2-(4-(1-(4-((5-bromo-4-((2-methyl-5-(1-oxido-2,5-dihydrophosphol-1-yl)quinolin-6-yl)amino)pyrimidin-2-yl)amino)-2-ethyl-5-methoxyphenyl)piperidin-4-yl)piperazin-1-yl)ethyl)-2-oxobenzo[d]oxazol-3(2H)-yl)piperidine-2,6-dione

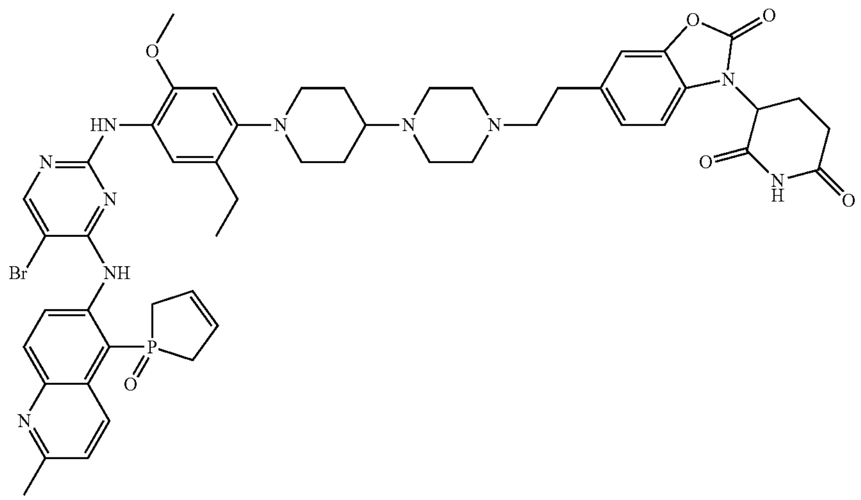

The titled compound was synthesized in a manner similar to that in Example 147 Step 14 from 1-(6-((5-bromo-2-((5-ethyl-2-methoxy-4-(4-(piperazin-1-yl)piperidin-1-yl)phenyl)amino)pyrimidin-4-yl)amino)-2-methylquinolin-5-yl)-2,5-dihydrophosphole 1-oxide and 2-(3-(2,6-dioxopiperidin-3-yl)-2-oxo-2,3-dihydrobenzo[d]oxazol-6-yl)acetaldehyde. $^1$H NMR (500 MHz, DMSO) δ 11.19 (d, J=54.9 Hz, 2H), 8.25 (s, 1H), 8.15 (s, 1H), 7.96 (s, 1H), 7.86 (t, J=9.8 Hz, 2H), 7.31 (dd, J=44.2, 23.7 Hz, 3H), 7.09 (d, J=8.1 Hz, 11H), 7.00 (d, J=8.1 Hz, 11H), 6.67 (s, 1H), 6.07 (d, J=30.6 Hz, 2H), 5.28 (dd, J=12.9, 5.2 Hz, 1H), 3.69 (s, 3H), 2.44-3.02 (m, 23H), 2.21-2.30 (m, 6H), 2.2.01-2.09 (m, 1H), 1.75-1.77 (m, 2H), 1.43-1.50 (m, 2H), 0.71 (s, 3H). $[M+H]^+$=1003.3.

Example 146: 3-(4-(3-(4-(1-(4-((5-bromo-4-((2-methyl-5-(1-oxido-2,5-dihydrophosphol-1-yl)quinolin-6-yl)amino)pyrimidin-2-yl)amino)-2-ethyl-5-methoxyphenyl)piperidin-4-yl)piperazine-1-carbonyl)azetidin-1-yl)-2,6-difluorophenyl)piperidine-2,6-dione

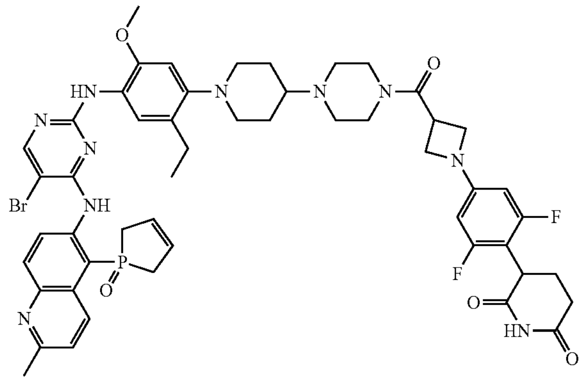 [SMILES: CCc1cc(Nc2ncc(Br)c(Nc3ccc4nc(C)ccc4c3P3(=O)CC=CC3)n2)c(OC)cc1N1CCC(N2CCN(C(=O)C3CN(c4cc(F)c(C5CCC(=O)NC5=O)c(F)c4)C3)CC2)CC1]

The titled compound was synthesized in a procedure similar to Example 77. $^1$H NMR (500 MHz, DMSO) δ 11.24 (s, 1H), 10.79 (s, 1H), 8.25 (s, 1H), 8.16 (s, 1H), 7.96 (s, 1H), 7.87 (dd, J=13.0, 9.4 Hz, 2H), 7.40-7.25 (m, 2H), 6.68 (s, 1H), 6.09 (dd, J=20.9, 14.5 Hz, 4H), 3.97 (t, J=7.6 Hz, 3H), 3.85 (t, J=6.3 Hz, 2H), 3.65-3.79 (m, 4H), 3.42 (s, 2H), 2.86-2.97 (m, 4H), 2.67-2.77 (m, 3H), 2.57-2.62 (m, 5H), 2.43-2.45 (m, 7H), 2.13-2.36 (m, 3H), 2.00-2.04 (m, 11H), 1.83-1.93 (m, 1H), 1.74-1.76 (m, 2H), 1.47-1.53 (m, 2H), 0.71 (s, 3H). $[M+H]^+$=1037.3.

Example 148: 3-(4-(3-(4-(1-(4-((5-bromo-4-((2-(1-oxidophospholan-1-yl)phenyl)amino)pyrimidin-2-yl)amino)-2-ethyl-5-methoxyphenyl)piperidin-4-yl)piperazine-1-carbonyl)azetidin-1-yl)-2,6-difluorophenyl)piperidine-2,6-dione

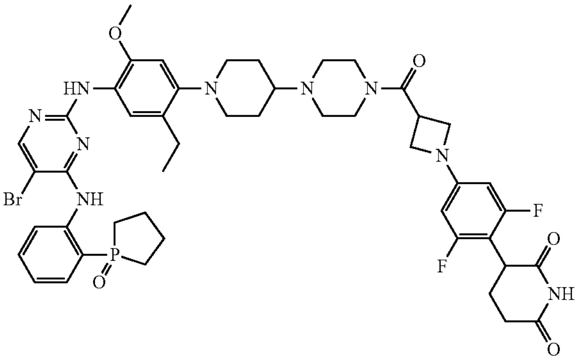 [SMILES: CCc1cc(Nc2ncc(Br)c(Nc3ccccc3P3(=O)CCCC3)n2)c(OC)cc1N1CCC(N2CCN(C(=O)C3CN(c4cc(F)c(C5CCC(=O)NC5=O)c(F)c4)C3)CC2)CC1]

To a solution of 1-(2-((5-bromo-2-((5-ethyl-2-methoxy-4-(4-(piperazin-1-yl)piperidin-1-yl)phenyl)amino)pyrimidin-4-yl)amino)phenyl)phospholane 1-oxide (50 mg, 0.07 mmol), 1-(4-(2,6-dioxopiperidin-3-yl)-3,5-difluorophenyl)azetidine-3-carboxylic acid (synthesized by the similar method of example 77)(33 mg, 0.1 mmol) and DIEA (26 mg, 0.2 mmol) in 10 mL DCM, 50% w.t. $T_3P$ in EtOAc solution (64 mg, 0.1 mmol) was added. The mixture was stirred at 25° C. for 16 hours. After LCMS showed the reaction was completed. The mixture was quenched with water (10 mL). The organic phase was concentrated in vacuum and purified by prep-HPLC with C-18 column chromatography (0.1% FA in water:acetonitrile=90:10-50:50 gradient elution) to afford product (13.9 mg, 19.3% yield). $^1H$ NMR (500 MHz, DMSO) δ 10.84 (s 11H), 10.57 (s, 1H), 8.19 (s, 1H), 8.14 (s, 1H), 8.05 (s, 1H), 7.37-7.51 (m, 3H), 7.17 (t, J=7.3 Hz, 1H), 6.76 (s, 2H), 6.17 (d, J=11.1 Hz, 2H), 4.02-4.05 (m, 3H), 3.80-3.93 (m, 3H), 3.76 (s, 3H), 3.50 (s, 3H), 2.99-3.02 (m, 2H), 2.63-2.81 (m, 3H), 2.54-2.55 (m, 4H), 2.38-2.48 (m, 4H), 1.84-2.13 (m, 12H), 1.56-1.63 (m, 2H), 1.01 (t, J=7.4 Hz, 3H). $[M+H]^+$=974.3.

Cell Degradation

Cell Treatment

1a). BaF3-LTC (L858R/T790M/C797S) cells are seeded at 100000 cells/well in cell culture medium [RPMI1640 (Gibco, phenol red free, Cat #11835-030), 10% heat-inactive FBS, 1% PS (Gibco, Cat #10378)] in Corning 96 well plate (Cat #3799).

1b). On day 1, H1975-clone #28 (Del19/T790M/C797S, homozygous) cells are seeded at 20000 cells/well and 30000 cells/well correspondingly in cell culture medium [RPMI1640 (Gibco, Cat #72400-047), 10% heat-inactive FBS, 1% PS (Gibco, Cat #10378)] in Corning 96 well plate (Cat #3599).

BaF3-LTC (L858R/T790M/C797S) cells are treated with compounds diluted in 0.2% DMSO cell culture medium and incubate for 16 h, 37° C., 5% $CO_2$. H1975-#28 cells are treated with compounds diluted in 0.2% DMSO cell culture medium on day 2, incubate for 16 h, 37° C., 5% $CO_2$, the final concentration of compounds in all assay is start with 10 uM, 4-fold dilution, total 8 doses were included.

HTRF Assay

After 16 h treatment, add HTRF lysis buffer to each well; seal the plate and incubate 1 hour at room temperature on a plate shaker. Once the cells are lysed, 16 μL of cell lysate are transferred to a PE 384-well HTRF detection plate: 4 μL of pre-mixed HTRF antibodies are added to each well; Cover the plate with a plate sealer, spin 1000 rpm for 1 min, Incubate overnight at room temperature; Read on BMG PheraStar with HTRF protocol (337 nm-665 nm-620 nm).

The inhibition (degradation) percentage of the compound was calculated by the following equation:

Inhibition percentage of Compound=100−100×(Signal−low control)/(High control−low control), wherein signal=each test compound group

- Low control=only lysis buffer without cells, indicating that EGFR is completely degraded;
- High control=Cell group with added DMSO and without compound, indicating microplate readings without EGFR degradation;
- Dmax is the maximum percentage of inhibition (degradation).

The $IC_{50}$ ($DC_{50}$) value of a compound can be obtained by fitting the following equation $$Y=\text{Bottom}+(\text{TOP}-\text{Bottom})/(1+((IC_{50}/X)\hat{}\,\text{hillslope}))$$

Wherein, X and Y are known values, and $IC_{50}$. Hillslope, Top and Bottom are the parameters obtained by fitting with software. Y is the inhibition percentage (calculated from the equation), X is the concentration of the compound; $IC_{50}$ is the concentration of the compound when the 50% inhibition is reached. The smaller the $IC_{50}$ value is, the stronger the inhibitory ability of the compound is. Vice versa, the higher the $IC_{50}$ value is, the weaker the ability the inhibitory ability of the compound is; Hillslope represents the slope of the fitted curve, generally around 1*; Bottom represents the minimum value of the curve obtained by data fitting, which is generally 0%±20%. Top represents the maximum value of the curve obtained by data fitting, which is generally 100%±20%. The experimental data were fitted by calculating and analyzing with Dotmatics data analysis software.

TABLE 1

Degradation (BaF3 and H1975 #28) result for Example 68 to Example 148

| | H1975 #28 | | BaF3 | |
|---|---|---|---|---|
| Example | $DC_{50}$(nM) | Dmax (%) | $DC_{50}$(nM) | Dmax (%) |
| 68 | 1.34 | 85.88 | 3.46 | 90.83 |
| 71 | 1.38 | 72.97 | 2.51 | 88.59 |
| 73 | 0.66 | 78.13 | 7.52 | 89.91 |
| 111 | 4.31 | 87.16 | 26.82 | 90.26 |
| 145 | 0.77 | 75.97 | 1.82 | 91.76 |
| 147 | 3.15 | 82.21 | 75.06 | 86.63 |
| 148 | 2.99 | 78.19 | 19.8 | 90.18 |

The foregoing examples and description of certain embodiments should be taken as illustrating, rather than as limiting the present invention as defined by the claims. As will be readily appreciated, numerous variations and combinations of the features set forth above can be utilized without departing from the present invention as set forth in the claims. All such variations are intended to be included within the scope of the present invention. All references cited are incorporated herein by reference in their entireties.

It is to be understood that, if any prior art publication is referred to herein, such reference does not constitute an admission that the publication forms a part of the common general knowledge in the art in any country.

What is claimed is:

1. A compound of Formula (X):

(X)

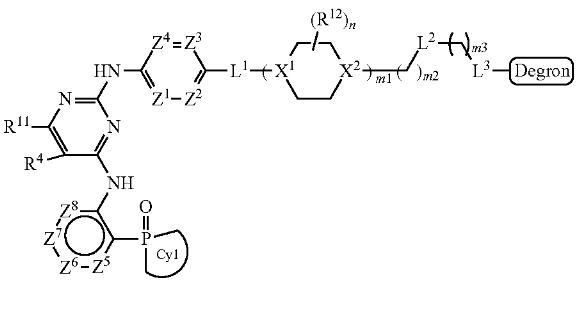

or an N-oxide thereof, or a pharmaceutically acceptable salt thereof, or a stereoisomer thereof, or a deuterated analog thereof, wherein:

Cy1 is a 4- to 7-membered saturated or partially unsaturated ring comprising P═O shown in Formula (X), and 0-3 additional heteroatoms independently selected from nitrogen, oxygen or sulfur in addition to P═O; wherein said ring is optionally substituted with at least one substituent $R^{1c}$;

$R^{1c}$ is selected from hydrogen, halogen, —$C_{1-8}$alkyl, —$C_{2-8}$alkenyl, —$C_{2-8}$alkynyl, $C_3$-$C_8$cycloalkyl, 3- to 8-membered heterocyclyl, $C_6$-$C_{12}$aryl, 5- to 12-membered heteroaryl, —CN, —$OR^{1d}$, —$COR^{1d}$, —$CO_2R^{1d}$, —$CONR^{1d}R^{1e}$, —$NR^{1d}R^{1e}$, —$NR^{1d}COR^{1e}$ or —$NR^{1d}CO_2R^{1e}$, wherein each of —$C_{1-8}$alkyl, —$C_{2-8}$alkenyl, —$C_{2-8}$alkynyl, $C_3$-$C_8$cycloalkyl, 3- to 8-membered heterocyclyl, $C_6$-$C_{12}$aryl or 5- to 12-membered heteroaryl is optionally substituted with at least one substituent $R^{1f}$;

$R^{1d}$, $R^{1e}$ and $R^{1f}$ are each independently selected from hydrogen, hydroxy, —$C_{1-8}$alkyl, —$C_{2-8}$alkenyl, —$C_{2-8}$alkynyl, or $C_3$-$C_8$cycloalkyl;

$Z^5$ is selected from —$CR^2$, or N;

$Z^6$ is selected from —$CR^3$, or N;

$Z^7$ is selected from —$CR^9$, or N;

$Z^8$ is selected from —$CR^{10}$, or N;

$R^2$ and $R^3$ are each independently selected from hydrogen, halogen, —$C_{1-8}$alkyl, —$C_{2-8}$alkenyl, —$C_{2-8}$alkynyl, $C_3$-$C_8$cycloalkyl, 3- to 8-membered heterocyclyl, $C_6$-$C_{12}$aryl, 5- to 12-membered heteroaryl, —CN, —$OR^{2a}$, —$SO_2R^{2a}$, —$SO_2NR^{2a}R^{2b}$, —$COR^{2a}$, —$CO_2R^{2a}$, —$CONR^{2a}R^{2b}$, —$NR^{2a}R^{2b}$, —$NR^{2a}COR^{2b}$, —$NR^{2a}CO_2R^{2b}$, or —$NR^{2a}SO_2R^{2b}$ wherein each of —$C_{1-8}$alkyl, —$C_{2-8}$alkenyl, —$C_{2-8}$alkynyl, $C_3$-$C_8$cycloalkyl, 3- to 8-membered heterocyclyl, $C_6$-$C_{12}$aryl or 5- to 12-membered heteroaryl is optionally substituted with at least one substituent $R^{2d}$; or $R^2$ and $R^3$ together with the carbon atoms to which they are attached, form a 5-6 membered saturated or partially or completely unsaturated ring, said ring comprising 0-3 heteroatoms independently selected from nitrogen, oxygen or sulfur; said ring is optionally substituted with at least one substituent $R^{2e}$;

$R^{2e}$, at each of its occurrences, is independently hydrogen, halogen, —$C_{1-8}$alkyl, —$C_{2-8}$alkenyl, —$C_{2-8}$alkynyl, —$C_{1-8}$alkoxy, —$C_3$-$C_8$cycloalkyl, oxo, 3- to 8-membered heterocyclyl, $C_6$-$C_{12}$aryl, 5- to 12-membered heteroaryl, —CN, —$SO_2R^{2a}$, —$SO_2NR^{2a}R^{2b}$, —$COR^{2a}$, —$CO_2R^{2a}$, —$CONR^{2a}R^{2b}$, —$NR^{2a}R^{2b}$, —$NR^{2a}COR^{2b}$, —$NR^{2a}CO_2R^{2b}$ or —$NR^{2a}SO_2R^{2b}$, wherein each of —$C_{1-8}$alkyl, —$C_{2-8}$alkenyl, —$C_{2-8}$alkynyl, —$C_{1-8}$alkoxy, $C_3$-$C_8$cycloalkyl, 3- to 8-membered heterocyclyl, $C_6$-$C_{122}$aryl or 5- to 12-membered heteroaryl is optionally substituted with at least one substituent $R^{2d}$;

$R^{2a}$ and $R^{2b}$ are each independently selected from hydrogen, —$C_{1-8}$alkyl, —$C_{2-8}$alkenyl, —$C_{2-8}$alkynyl, $C_{1-8}$alkoxy-$C_{1-8}$alkyl-, $C_3$-$C_8$cycloalkyl, 3- to 8-membered heterocyclyl, $C_6$-$C_{12}$aryl or 5- to 12-membered heteroaryl; or $R^{2a}$ and $R^{2b}$ together with the carbon atoms to which they are attached, form a 5-6 membered saturated or partially or completely unsaturated ring, said ring comprising 0-3 heteroatoms independently selected from nitrogen, oxygen or sulfur; said ring is optionally substituted with at least one substituent $R^{2d}$;

$R^{2d}$, at each of its occurrences, is independently halogen, —OH, —$C_{1-8}$alkyl, —$C_{1-8}$alkoxy, $C_{1-8}$alkoxy-$C_{1-8}$alkyl-, oxo, —$C_{2-8}$alkenyl, —$C_{2-8}$alkynyl, —$C_3$-$C_8$cycloalkyl, 3- to 8-membered heterocyclyl, —$C_6$-$C_{12}$aryl, or 5- to 12-membered heteroaryl;

$R^4$ is selected from hydrogen, halogen, —$C_{1-8}$alkyl, —$C_{2-8}$alkenyl, —$C_{2-8}$alkynyl, —$C_{1-8}$alkoxy, —$C_3$-$C_8$cycloalkyl, 3- to 8-membered heterocyclyl, —$C_6$-$C_{12}$aryl, 5- to 12-membered heteroaryl, —CN, —$SO_2R^{4a}$, —$SO_2NR^{4a}R^{4b}$, —$COR^{4a}$, —$CO_2R^{4a}$, —$CONR^{4a}R^{4b}$, —$NR^{4a}R^{4b}$, —$NR^{4a}COR^{4b}$, —$NR^{4a}CO_2R^{4b}$, or —$NR^{4a}SO_2R^{4b}$, wherein each of —$C_{1-8}$alkyl, —$C_{2-8}$alkenyl, —$C_{2-8}$alkynyl, —$C_{1-8}$alkoxy, —$C_3$-$C_8$cycloalkyl, 3- to 8-membered heterocyclyl, —$C_6$-$C_{12}$aryl or 5- to 12-membered heteroaryl is optionally substituted with halogen, —$C_{1-8}$alkoxy, —$C_{1-8}$alkyl, —$C_{2-8}$alkenyl, —$C_2$-8alkynyl, —$C_3$-$C_8$cycloalkyl, 3- to 8-membered heterocyclyl, $C_6$-$C_{12}$aryl, 5- to 12-membered heteroaryl, oxo, —CN, —$OR^{4c}$, —$SO_2R^{4c}$, —$SO_2NR^{4c}R^{4d}$, —$COR^{4c}$, —$CO_2R^{4c}$, —$CONR^{4c}R^{4d}$, —$NR^{4c}R^{4d}$, —$NR^{4c}COR^{4d}$, —$NR^{4c}CO_2R^{4d}$, or —$NR^{4c}SO_2R^{4d}$;

$R^{4a}$, $R^{4b}$, $R^{4c}$ and $R^{4d}$ are each independently hydrogen, —$C_{1-8}$alkyl, —$C_{2-8}$alkenyl, —$C_{2-8}$alkynyl, $C_3$-$C_8$cycloalkyl, 3- to 8-membered heterocyclyl, —$C_6$-$C_{12}$aryl, or 5- to 12-membered heteroaryl; or $R^4$ and $R^{11}$ together with the carbon atoms to which they are attached, form a 5-6 membered saturated or partially or completely unsaturated ring, said ring comprising 0-3 heteroatoms independently selected from nitrogen, oxygen or sulfur; said ring is optionally substituted with at least one substituent $R^{4e}$;

$R^{4c}$, at each of its occurrences, is independently hydrogen, halogen, —$C_{1-8}$alkyl, —$C_{2-8}$alkenyl, —$C_{2-8}$alkynyl, —$C_{1-8}$alkoxy, —$C_3$-$C_8$cycloalkyl, oxo, 3- to 8-membered heterocyclyl, $C_6$-$C_{12}$aryl, 5- to 12-membered heteroaryl, —CN, —$SO_2R^4$, —$SO_2NR^{4f}R^{4g}$, —$COR^{4f}$, —$CO_2R^{4f}$, —$CONR^{4f}R^{4g}$, —$NR^{4f}R^{4g}$, —$NR^{4f}COR^{4g}$, —$NR^4CO_2R^{4g}$ or —$NR^{4f}SO_2R^{4g}$, wherein each of —$C_{1-8}$alkyl, —$C_{2-8}$alkenyl, —$C_{2-8}$alkynyl, —$C_{1-8}$alkoxy, $C_3$-$C_8$cycloalkyl, 3- to 8-membered heterocyclyl, $C_6$-$C_{122}$aryl or 5- to 12-membered heteroaryl is optionally substituted with at least one substituent $R^{4h}$;

$R^{4f}$ and $R^{4g}$ are each independently selected from hydrogen, —$C_{1-8}$alkyl, —$C_2$-8alkenyl, —$C_{2-8}$alkynyl, $C_{1-8}$alkoxy-$C_{1-8}$alkyl-, $C_3$-$C_8$cycloalkyl, 3- to 8-membered heterocyclyl, $C_6$-$C_{12}$aryl or 5- to 12-membered heteroaryl;

$R^{4h}$, at each of its occurrences, is independently halogen, —OH, —$C_{1-8}$alkyl, —$C_{1-8}$alkoxy, $C_{1-8}$alkoxy-$C_{1-8}$alkyl-, —$C_{2-8}$alkenyl, —$C_{2-8}$alkynyl, —$C_3$-$C_8$cycloalkyl, 3- to 8-membered heterocyclyl, —$C_6$-$C_{12}$aryl, or 5- to 12-membered heteroaryl;

$R^9$, $R^{10}$, $R^{11}$ and $R^{12}$ are each independently selected from hydrogen, halogen, —$C_{1-8}$ alkyl, —$C_{2-8}$alkenyl, —$C_{2-8}$alkynyl, —$NR^{9a}R^{9b}$, —$OR^{9a}$, oxo, —$C_3$-$C_8$cycloalkyl, 3- to 8-membered heterocyclyl, —$C_6$-$C_{12}$aryl, 5- to 12-membered heteroaryl, or —CN, wherein each of —$C_{1-8}$alkyl, —$C_2$-8alkenyl, —$C_{2-8}$alkynyl, —$C_3$-$C_8$cycloalkyl, 3- to 8-membered heterocyclyl, —$C_6$-$C_{12}$aryl, or 5- to 12-membered heteroaryl is optionally substituted with at least one substituent $R^{9c}$; or two $R^{12}$ together with the carbon atoms to which they are attached, form a 3- to 12-membered ring, said ring comprising 0-3 heteroatoms independently selected from nitrogen, oxygen or sulfur; said ring is optionally substituted with at least one substituent $R^{9c}$;

$R^{9a}$ and $R^{9b}$ are each independently selected from hydrogen, —$C_{1-8}$alkyl, —$C_{2-8}$alkenyl, —$C_{2-8}$alkynyl, —$C_3$-$C_8$cycloalkyl, 3- to 8-membered heterocyclyl, —$C_6$-$C_{12}$aryl or 5- to 12-membered heteroaryl, wherein each of said —$C_{1-8}$alkyl, —$C_{2-8}$alkenyl, —$C_{2-8}$alkynyl, $C_3$-$C_8$cycloalkyl, 3- to 8-membered heterocyclyl, $C_6$-$C_{12}$aryl or 5- to 12-membered heteroaryl is optionally substituted with at least one substituent $R^{9d}$; or $R^{9c}$ and $R^{9d}$ are each independently halogen, hydroxy, —$C_{1-8}$alkyl, —$C_{1-8}$alkoxy, —$C_{2-8}$alkenyl, —$C_{2-8}$alkynyl, —$C_3$-$C_8$cycloalkyl, 3- to 8-membered heterocyclyl, —$C_6$-$C_{12}$aryl, 5- to 12-membered heteroaryl, —CN or $NR^{9a}R^{9b}$, wherein each of said —$C_{1-8}$alkyl, —$C_{1-8}$alkoxy, —$C_{2-8}$alkenyl, —$C_{2-8}$alkynyl, —$C_3$-$C_8$cycloalkyl, 3- to 8-membered heterocyclyl, —$C_6$-$C_{12}$aryl, 5- to 12-membered heteroaryl is optionally substituted with at least one hydrogen, halogen, hydroxy, —$C_{1-8}$alkyl, —$C_{1-8}$alkoxy, —CN, —$NH_2$ or oxo, and $R^{9a}$ and $R^{9b}$ are each independently hydrogen or $C_{1-8}$alkyl;

$Z^1$, $Z^2$, $Z^3$ and $Z^4$ are each independently selected from —$CR^z$, or N, or wherein $Z^1$, $Z^2$, $Z^3$ and $Z^4$ are each independently —$CR^z$; wherein $R^Z$, at each of its occurrences, is independently selected from hydrogen, —F, —Cl, —Br, —I, methyl, ethyl, propyl, butyl, pentyl, hexyl, heptyl, octyl, —$NR^{Za}R^{Zb}$, —$OR^{Za}$, —$SR^{Za}$, cyclopropyl, cyclobutyl, cyclopentyl, cyclohexyl, cycloheptyl, cyclooctyl, 3- to 8-membered heterocyclyl, phenyl, 5- to 12-membered heteroaryl, or CN, wherein each of methyl, ethyl, propyl, butyl, pentyl, hexyl, heptyl, octyl, cyclopropyl, cyclobutyl, cyclopentyl, cyclohexyl, cycloheptyl, cyclooctyl, 3- to 8-membered heterocyclyl, phenyl, or 5- to 12-membered heteroaryl is optionally substituted with at least one $R^{ZC}$;

$R^{Za}$ and $R^{Zb}$ are each independently selected from hydrogen, methyl, ethyl, propyl, butyl, pentyl, hexyl, heptyl, octyl, —$C_{2-8}$alkenyl, —$C_{2-8}$alkynyl, cyclopropyl, cyclobutyl, cyclopentyl, cyclohexyl, cycloheptyl, cyclooctyl, 3- to 8-membered heterocyclyl, phenyl or 5- to 12-membered heteroaryl, wherein each of said hydrogen, methyl, ethyl, propyl, butyl, pentyl, hexyl, heptyl, octyl, —$C_{2-8}$alkenyl, —$C_{2-8}$alkynyl, cyclopropyl, cyclobutyl, cyclopentyl, cyclohexyl, cycloheptyl, cyclooctyl, 3- to 8-membered heterocyclyl, phenyl or 5- to 12-membered heteroaryl is optionally substituted with at least one substituent $R^{Zd}$; and $R^{Zc}$ and $R^{Zd}$ are each independently —F, —Cl, —Br, —I, hydroxy, methyl, ethyl, propyl, butyl, pentyl, hexyl, heptyl, octyl, —$C_{1-8}$alkoxy, —$C_{2-8}$alkenyl, —$C_{2-8}$alkynyl, cyclopropyl, cyclobutyl, cyclopentyl, cyclohexyl, cycloheptyl, cyclooctyl, 3- to 8-membered heterocyclyl, phenyl, or 5- to 12-membered heteroaryl;

$R^Z$, at each of its occurrences, is independently selected from hydrogen, halogen, —$C_{1-8}$alkyl, —$C_{2-8}$alkenyl, —$C_{2-8}$alkynyl, —$NR^{Za}R^{Zb}$, —$OR^{Za}$, —$SR^{Za}$, $C_3$-$C_8$cycloalkyl, 3- to 8-membered heterocyclyl, $C_6$-$C_{12}$aryl, 5- to 12-membered heteroaryl, or CN, wherein each of —$C_{1-8}$alkyl, —$C_2$-8alkenyl, —$C_{2-8}$alkynyl, $C_3$-$C_8$cycloalkyl, 3- to 8-membered heterocyclyl, $C_6$-$C_{12}$aryl, or 5- to 12-membered heteroaryl is optionally substituted with at least one $R^{Zc}$, or wherein $R^Z$, at each of its occurrences, is independently selected from hydrogen H, —$CH_3$, —$C_2H_5$, F, —$CH_2F$, —$CHF_2$, —$CF_3$, —$OCH_3$, —$OC_2H_5$, —$C_3H_7$, —$OCH_2F$, —$OCHF_2$, —$OCH_2CF_3$, —$OCF_3$, —$SCF_3$, —$CF_3$, cyclopropyl or —CH(OH)$CH_3$; or when adjacent two $R^z$ together with the carbon atoms to which they are attached, form a 5-6 membered saturated or partially or completely unsaturated ring, said ring comprising 0-3 heteroatoms independently selected from nitrogen, oxygen or sulfur; said ring is optionally substituted with at least one substituent $R^{Zc}$;

$R^{Za}$ and $R^{Zb}$ are each independently selected from hydrogen, —$C_{1-8}$alkyl, —$C_{2-8}$alkenyl, —$C_{2-8}$alkynyl, $C_3$-$C_8$cycloalkyl, 3- to 8-membered heterocyclyl, $C_6$-$C_{12}$aryl, or 5- to 12-membered heteroaryl, wherein each of said —$C_{1-8}$alkyl, —$C_{2-8}$alkenyl, —$C_{2-8}$alkynyl, $C_3$-$C_8$cycloalkyl, 3- to 8-membered heterocyclyl, $C_6$-$C_{12}$aryl, or 5- to 12-membered heteroaryl is optionally substituted with at least one substituent $R^{Zd}$;

$R^{Zc}$ and $R^{Zd}$ are each independently halogen, hydroxy, —$C_{1-8}$alkyl, —$C_{2-8}$alkenyl, —$C_{2-8}$alkynyl, —$C_{1-8}$ alkoxy, $C_{1-8}$alkoxy-$C_{18}$alkyl-, —$C_{2-8}$alkenyl, —$C_{2-8}$ alkynyl, $C_3$-$C_8$cycloalkyl, 3- to 8-membered heterocyclyl, $C_6$-$C_{12}$aryl, or 5- to 12-membered heteroaryl;

$L^1$ is selected from a single bond, —O—, —$SO_2$—, —C(O)—, —$NR^{L1}$—, —$C_3$-$C_8$ cycloalkylene-, $*^{L1}$—O—$C_{1-8}$alkylene-$**^{L1}$, $*^{L1}$-$C_{1-8}$alkylene-O—$**^{L1}$, $*^{L1}$—$SO_2$—$C_{1-8}$ alkylene-$**^{L1}$, $*^{L1}$-$C_{1-8}$alkylene-$SO_2$—$**^{L1}$, $*^{L1}$—CO—$C_{1-8}$alkylene-$**^{L1}$, $*^{L1}$-$C_{1-8}$alkylene-CO—$**^{L1}$, $*^{L1}$—$NR^{L1a}$—$C_{1-8}$alkylene-$**^{L1}$, $*^{L1}$—$C_{1-8}$alkylene-$NRL^{1a}$—$**^{L1}$, $*^{L1}$—$NR^{L1a}$C(O)—$**^{L1}$, $*^{L1}$—C(O)$NR^{L1a}$—$**^{L1}$—$C_{1-8}$alkylene-, —$C_{2-8}$alkenylene-, —$C_{2-8}$alkynylene-, —$[O(CR^{L1a}R^{L1b})_{m4}]_{m5}$—,

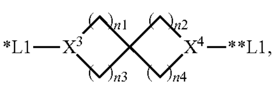,
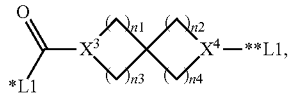,
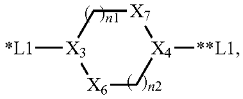,
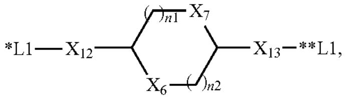,
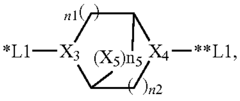,
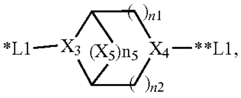,
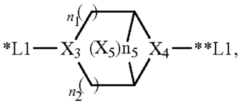,
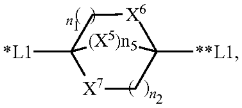,
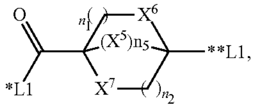,
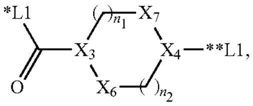,
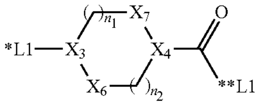
or
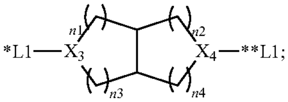;

wherein each of said —$C_{1-8}$alkylene, —$C_3$-$C_8$cycloalkylene-, $*^{L1}$—O—$C_{1-8}$alkylene-$**^{L1}$, *L-$C_{1-8}$alkylene-O—$**^{L1}$, *L-$SO_2$—$C_{1-8}$ alkylene-$**^{L1}$, *L-$C_{1-8}$alkylene-$SO_2$—$**^{L1}$, $*^{L1}$CO—$C_{1-8}$alkylene-** * —$C_{1-8}$alkylene-CO—$**^{L1}$, * —$NR^{L1a}$-$C_{1-8}$alkylene-$**^{L1}$, * —$C_{1-8}$alkylene-$NR^{L1a}$, —$**^{L1}$, —$C_{1-8}$alkylene-, —$C_{2-8}$alkenylene-, —$C_{2-8}$alkynylene-,

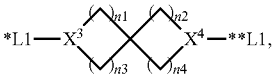
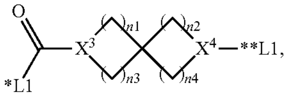
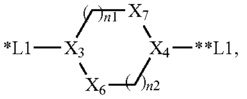
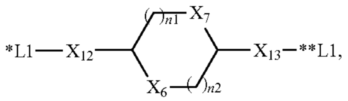
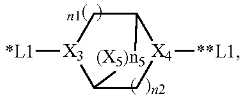
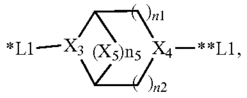
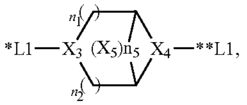
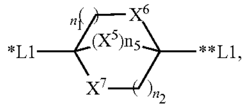
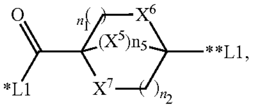
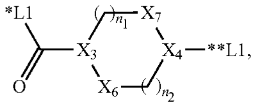
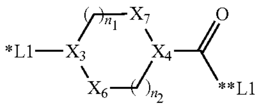
or
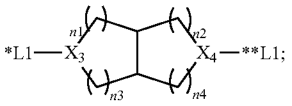

is optionally substituted with at least one $R^{L1c}$, wherein $*^{L1}$ refers to the position attached to

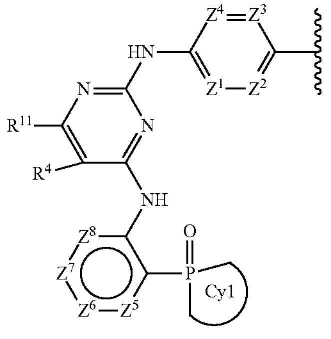

moiety, and $**^{L1}$ refers to the position attached to the

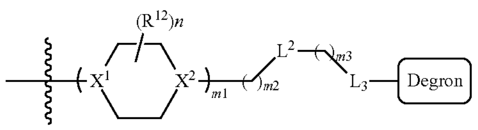

moiety;

$R^{L1a}$ and $R^{L1b}$ are each independently selected from hydrogen, —$C_{1-8}$alkyl, —$C_{2-8}$alkenyl, —$C_{2-8}$alkynyl, $C_3$-$C_8$cycloalkyl, 3- to 8-membered heterocyclyl, $C_6$-$C_{12}$aryl or 5- to 12-membered heteroaryl, wherein each of said —$C_{1-8}$alkyl, —$C_{2-8}$alkenyl, —$C_{2-8}$alkynyl, $C_3$-$C_8$cycloalkyl, 3- to 8-membered heterocyclyl, $C_6$-$C_{12}$aryl or 5- to 12-membered heteroaryl is optionally substituted with at least one substituent $R^{L1d}$;

each of said $R^{L1c}$ and $R^{L1d}$ are independently halogen, hydroxy, —$C_{1-8}$alkyl, —$C_{1-8}$alkoxy, $C_{1-8}$alkoxy-$C_{1-8}$alkyl-, —$C_{2-8}$alkenyl, —$C_{2-8}$alkynyl, $C_3$-$C_8$cycloalkyl, 3- to 8-membered heterocyclyl, $C_6$-$C_{12}$aryl, 5- to 12-membered heteroaryl or oxo;

$L^2$ is selected from a single bond, —O—, —$SO_2$—, —CO—, —$NR^{L2a}$—, —$C_{1-8}$alkylene, —$C_3$-$C_8$cycloalkylene-, $*^{L2}$—O—$C_{1-8}$alkylene-$**^{L2}$, $*^{L2}$-$C_{1-8}$alkylene-O—$**^{L2}$, $*^{L2}$-$SO_2$—$C_{1-8}$alkylene-$**^{L2}$, $*^{L2}$—$C_{1-8}$alkylene-$SO_2$—$**^{L2}$, $*^{L2}$—CO—$C_{1-8}$alkylene-$**^{L2}$, $*^{L2}$—$C_{1-8}$alkylene-CO—$**^{L2}$, $*^{L2}$—$NR^{L2a}C_{1-8}$alkylene-$**^{L2}$, $*^{L2}$—$C_{1-8}$ alkylene-$NR^{L2a}$—$**^{L2}$, $*^{L2}$—$NR^{L2a}$C(O)—$**^{L2}$, $*^{L2}$—C(O)$NR^{L2a}$—$**^{L2}$,

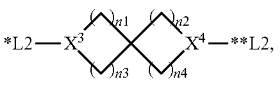
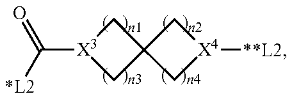
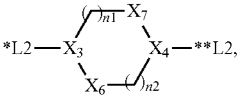
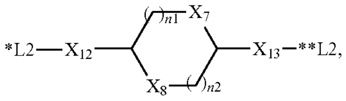
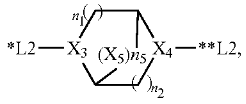
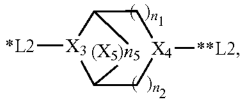
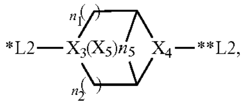
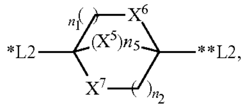
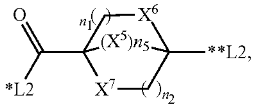
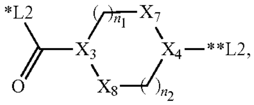
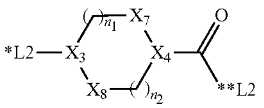
or
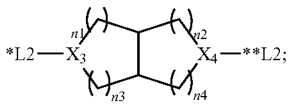

wherein each of said —$C_{1-8}$alkylene, —$C_3$-$C_8$cycloalkylene-, $*^{L2}$—O—$C_{1-8}$alkylene-$**^{L2}$, $*^{L2}$—$C_{1-8}$alkylene-O—$**^{L2}$, $*^{L2}$-$SO_2$—$C_{1-8}$alkylene-$**^{L2}$, $*^{L2}$—$C_{1-8}$alkylene-$SO_2$—$**^{L2}$, $*^{L2}$—CO—$C_{1-8}$alkylene-$**^{L2}$, $*^{L2}$—$C_{1-8}$ alkylene-CO—$**^{L2}$, $*^{L2}$—$NR^{L2a}$—$C_{1-8}$alkylene-$**^{L2}$, $*^{L2}$—$C_{1-8}$alkylene-$NR^{L2a}$, —$**^{L2}$, —$C_{1-8}$alkylene-, —$C_{2-8}$alkenylene-, —$C_{2-8}$alkynylene-,

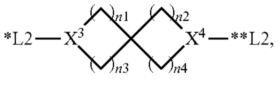
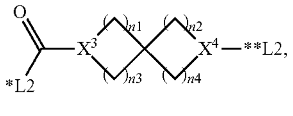

-continued

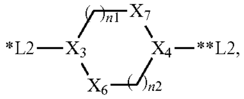

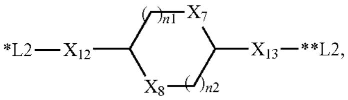

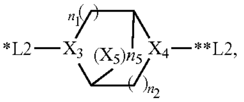

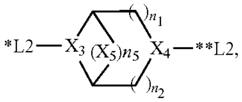

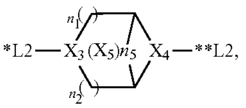

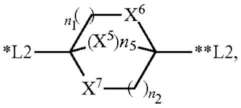

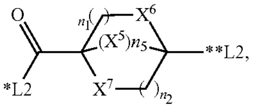

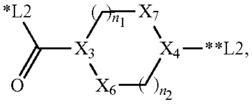

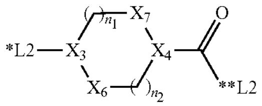
or

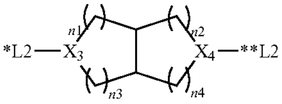

is optionally substituted with at least one substituent $R^{L2c}$;

wherein $*^{L2}$ refers to the position attached to

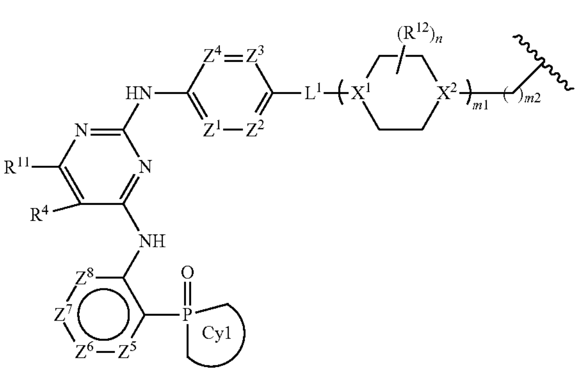

moiety, and $**^{L2}$ refers to the position attached to the

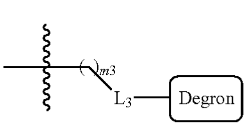

moiety;

$R^{L2a}$ and $R^{L2b}$ are each independently selected from hydrogen, —$C_{1-8}$alkyl, —$C_{2-8}$alkenyl, —$C_{2-8}$alkynyl, $C_3$-$C_8$cycloalkyl, 3- to 8-membered heterocyclyl, $C_6$-$C_{12}$aryl or 5- to 12-membered heteroaryl, wherein each of said —$C_{1-8}$alkyl, —$C_{2-8}$alkenyl, —$C_{2-8}$alkynyl, $C_3$-$C_8$cycloalkyl, 3- to 8-membered heterocyclyl, $C_6$-$C_{12}$aryl or 5- to 12-membered heteroaryl is optionally substituted with at least one substituent $R^{L2}$d;

each of said $R^{L2c}$ and $R^{L2}$d are independently halogen, hydroxy, —$C_{1-8}$alkyl, —$C_{1-8}$alkoxy, $C_{1-8}$alkoxy-$C_{1-8}$alkyl-, —$C_{2-8}$alkenyl, —$C_{2-8}$alkynyl, $C_3$-$C_8$cycloalkyl, 3- to 8-membered heterocyclyl, $C_6$-$C_{12}$aryl, 5- to 12-membered heteroaryl or oxo;

$L^3$ is selected from a single bond, —O—, —$SO_2$—, —CO—, —$NR^{L3a}$, —$C_{1-8}$alkylene, —$C_3$-$C_8$cycloalkylene-, $*^{L3}$-O—$C_{1-8}$alkylene-$**^{L3}$, $*^{L3}$-$C_{1-8}$alkylene-O—$**^{L3}$, $*^{L3}$-$SO_2$—$C_{1-8}$alkylene-$**^{L3}$$*^{L3}$-$C_{1-8}$alkylene-$SO_2$—$**^{L3}$, $*^{L3}$-CO—$C_{1-8}$alkylene-$**^{L3}$, $*^{L3}$-$C_{1-8}$alkylene-CO—$**^{L3}$, $*^{L3}$-$NR^{L3a}$$C_{1-8}$alkylene-$**^{L3}$, $*^{L3}$-$C_{1-8}$alkylene-$NR^{L3a}$—$**^{L3}$, $*^{L3}$-$R^{L3a}$C(O)—$**^{L3}$, $*^{L3}$-C(O)$NR^{L3a}$—$**^{L3}$, —$C_{1-8}$alkylene-, —$C_{2-8}$alkenylene-, —$C_{2-8}$alkynylene-, —$[O(CR^{L3a}R^{L3b})_{m4}]_{m5}$—,

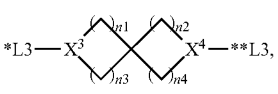

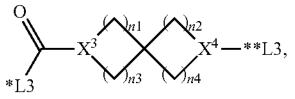

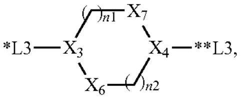

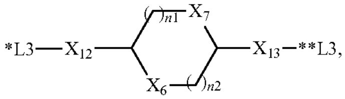

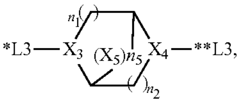

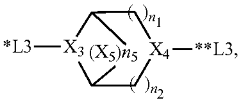

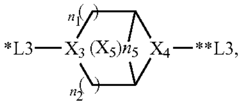

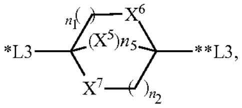

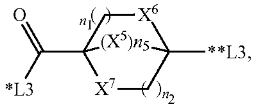

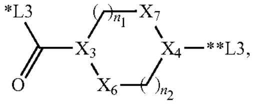

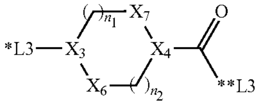
or

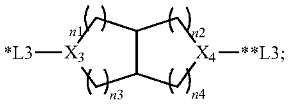

wherein each of said —$C_{1-8}$alkylene, —$C_3$-$C_8$cycloalkylene-, $*^{L3}$-O—$C_{1-8}$alkylene-$**^{L3}$, $*^{L3}$-$C_{1-8}$alkylene-O—$**^{L3}$, $*^{L3}$-$SO_2$—$C_{1-8}$alkylene-$**^{L3}$, $*^{L3}$-$C_{1-8}$alkylene-$SO_2$—$**^{L3}$, $*^{L3}$-CO—$C_{1-8}$alkylene-$**^{L3}$, $*^{L3}$-$C_{1-8}$alkylene-CO—$**^{L3}$, $*^{L3}$$NR^{L3a}$—$C_{1-8}$alkylene-$**^{L3}$, $*^{L3}$-$C_{1-8}$alkylene-$NR^{L3a}$, —$**^{L3}$, —$C_{1-8}$alkylene-, —$C_{2-8}$alkenylene-, —$C_{2-8}$akynylene-,

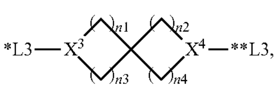

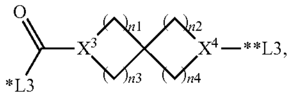

-continued

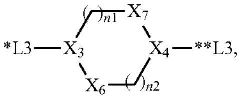
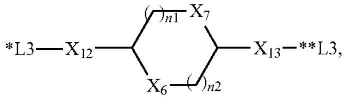
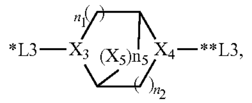
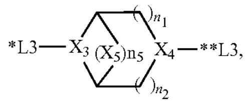
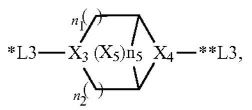
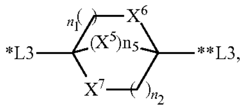
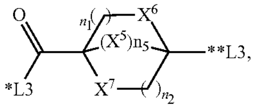
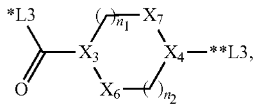
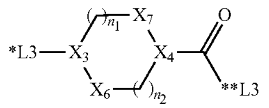
or
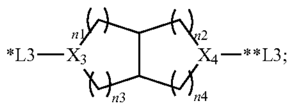

is optionally substituted with at least one substituent $R^{L3c}$;

wherein $*^{L3}$ refers to the position attached to

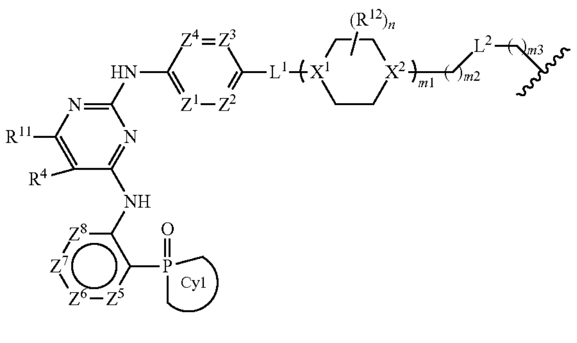

moiety, and $**^{L3}$ refers to the position attached to the

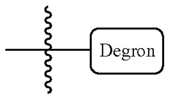

moiety;

$R^{L3a}$ and $R^{L3b}$ are each independently selected from hydrogen, —$C_{1-8}$alkyl, —$C_2$-8alkenyl, —$C_{2-8}$alkynyl, $C_3$-$C_8$cycloalkyl, 3- to 8-membered heterocyclyl, $C_6$-$C_{12}$aryl or 5- to 12-membered heteroaryl, wherein each of said —$C_{1-8}$alkyl, —$C_{2-8}$alkenyl, —$C_{2-8}$alkynyl, $C_3$-$C_8$cycloalkyl, 3- to 8-membered heterocyclyl, $C_6$-$C_{12}$aryl or 5- to 12-membered heteroaryl is optionally substituted with at least one substituent $R^{L3d}$;

each of said $R^{L3c}$ and $R^{L3d}$ are independently halogen, hydroxy, —$C_{1-8}$alkyl, —$C_{1-8}$alkoxy, $C_{1-8}$alkoxy-$C_{1-8}$ alkyl-, —$C_{2-8}$alkenyl, —$C_{2-8}$alkynyl, $C_3$-$C_8$cycloalkyl, 3- to 8-membered heterocyclyl, $C_6$-$C_{12}$aryl, 5- to 12-membered heteroaryl or oxo;

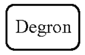

is selected from

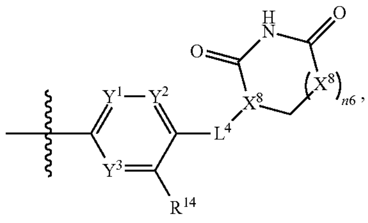
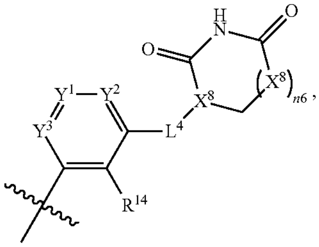
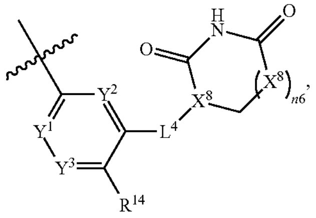
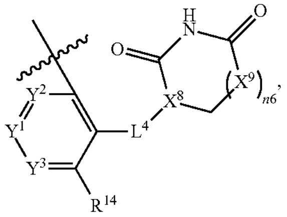
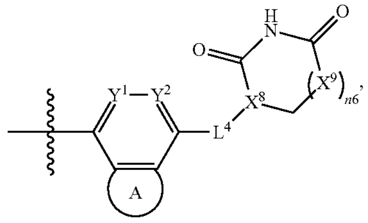
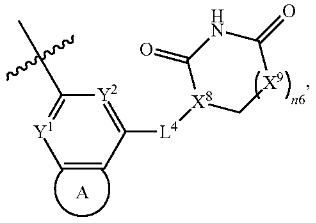

-continued
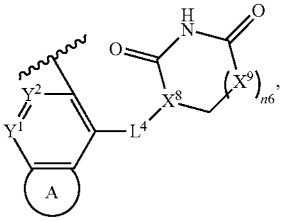
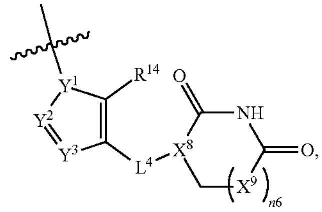
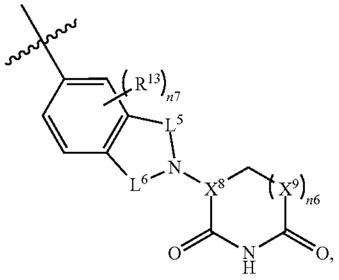
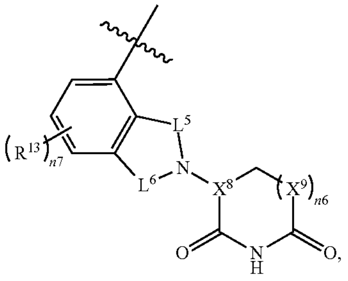
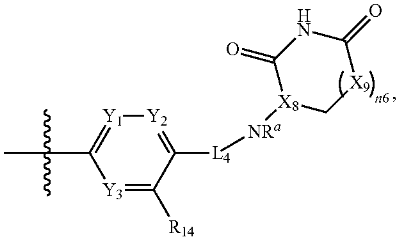
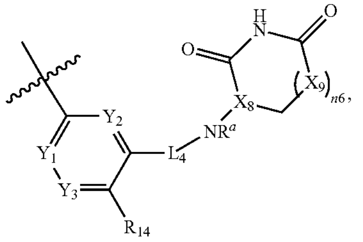
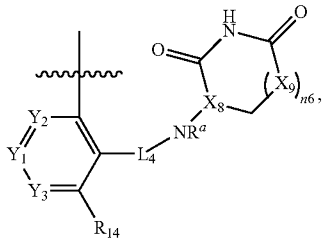
-continued
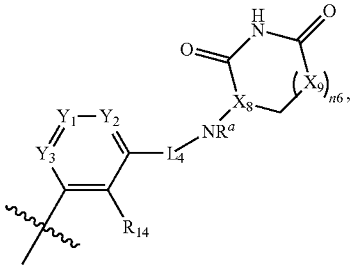
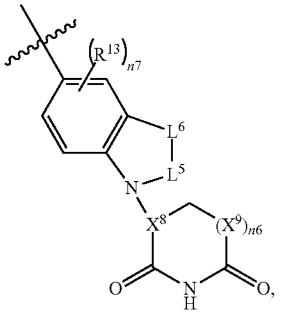
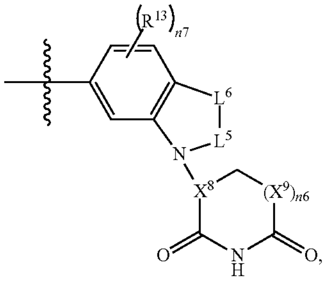
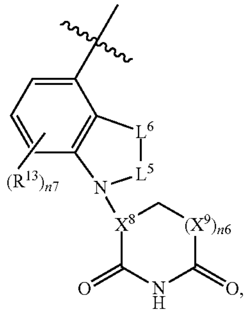
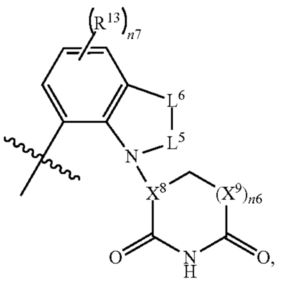
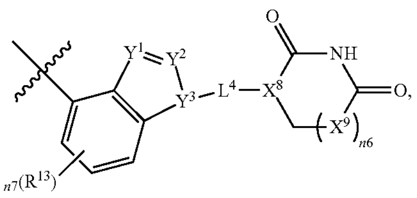

-continued

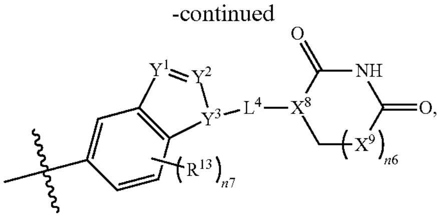

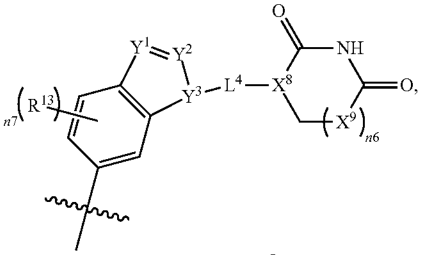

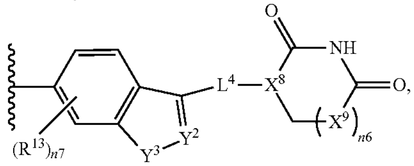

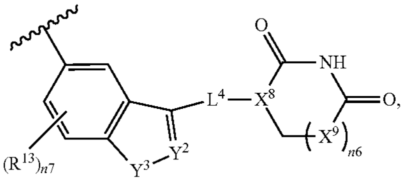

or

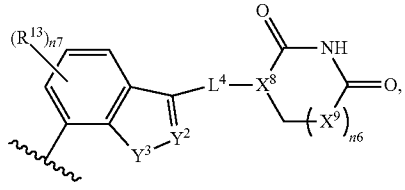

Ring A is selected from 3-12 membered cycloalkyl, 3-12 membered heterocyclyl, aryl, or heteroaryl;

said Ring A is optionally substituted with at least one halogen, oxo, —$C_{1-8}$alkyl, $C_{1-8}$alkoxy-$C_{1-8}$alkyl-, —$C_{2-8}$alkenyl, —$C_{2-8}$alkynyl, $C_3$-$C_8$cycloalkyl, 3- to 8-membered heterocyclyl, $C_6$-$C_{12}$aryl or 5- to 12-membered heteroaryl;

$R^{13}$ and $R^{14}$ are independently selected from hydrogen, halogen, CN, —$C_{1-8}$alkyl, —$C_{2-8}$alkenyl, —$C_{2-8}$alkynyl, —$C_{1-8}$alkoxy, $C_3$-$C_8$cycloalkyl, 3- to 8-membered heterocyclyl, $C_6$-$C_{122}$aryl or 5- to 12-membered heteroaryl; said each —$C_{1-8}$alkyl, —$C_{2-8}$alkenyl, —$C_{2-8}$alkynyl, —$C_{1-8}$alkoxy, $C_3$-$C_8$cycloalkyl, 3- to 8-membered heterocyclyl, $C_6$-$C_{12}$aryl or 5- to 12-membered heteroaryl is optionally substituted with at least one substituent halogen, —$C_{1-8}$alkyl, $C_{1-8}$alkoxy-$C_{1-8}$alkyl-, —$C_{2-8}$ alkenyl, —$C_{2-8}$alkynyl, $C_3$-$C_8$cycloalkyl, 3- to 8-membered heterocyclyl, $C_6$-$C_{12}$aryl or 5- to 12-membered heteroaryl;

$X^1$, $X^2$, $X^3$, $X^4$ and $X^8$ are each independently selected from —$CR^a$, or N;

$X^5$, $X^6$, $X^7$ and $X^9$ are each independently selected from —$NR^a$—, —O—, —S— and —$CR^aR^b$—;

$X^{12}$ and $X^{13}$ are each independently selected from —$NR^a$— and —O—;

$L^4$, $L^5$ and $L^6$ are each independently selected from a single bond, —O—, —$NR^a$—, —$(CR^aR^b)_{n8}$—, —$O(CR^aR^b)_{n8}$—, —$NR^a(CR^aR^b)_{n8}$— or —C(O)—;

$Y^1$, $Y^2$ and $Y^3$ are each independently selected from $CR^a$ or N;

$R^a$ and $R^b$ are each independently selected from hydrogen (H, D or T), halogen, CN, —$C_{1-8}$alkyl, —$C_{1-8}$ alkoxy, —$C_{2-8}$alkenyl, —$C_{2-8}$alkynyl, —$C_3$-$C_8$cycloalkyl, 3- to 8-membered heterocyclyl, —$C_6$-$C_{12}$aryl or 5- to 12-membered heteroaryl, wherein each of said —$C_{1-8}$alkyl, —$C_{1-8}$alkoxy, —$C_{2-8}$alkenyl, —$C_{2-8}$alkynyl, —$C_3$-$C_8$cycloalkyl, 3- to 8-membered heterocyclyl, —$C_6$-$C_{12}$aryl or 5- to 12-membered heteroaryl is optionally substituted with at least one substituent halogen, hydroxy, halogen, —$C_{1-8}$alkyl, —$C_{1-8}$alkoxy, —$C_{2-8}$alkenyl, —$C_{2-8}$alkynyl, —$C_3$-$C_8$cycloalkyl, 3- to 8-membered heterocyclyl, —$C_6$-$C_{12}$aryl or 5- to 12-membered heteroaryl; or $R^a$ and $R^b$ together with the carbon atoms to which they are attached, form a 3- to 12-membered ring, said ring comprising 0-3 heteroatoms independently selected from nitrogen, oxygen or sulfur; said ring is optionally substituted with at least one substituent halogen, hydroxy, —$C_{1-8}$alkyl, —$C_{2-8}$alkenyl, —$C_{2-8}$ alkynyl, —$C_{1-8}$alkoxy, —$C_{2-8}$alkenyl, —$C_{2-8}$alkynyl, $C_3$-$C_8$cycloalkyl, 3- to 8-membered heterocyclyl, $C_6$-$C_{12}$aryl or 5- to 12-membered heteroaryl;

m1 is 0 or 1;

m2 and m3 are each independently 0, 1, 2, 3, 4, 5, 6, 7 or 8;

m4 and m5 are each independently 0, 1, 2 or 3;

n, $n_1$, $n_2$, $n_3$, $n_4$ and $n_5$ are each independently 0, 1, 2 or 3; and $n_6$ is 0, 1, 2, 3 or 4

$n_7$ is 0, 1, 2 or 3;

$n_8$ is 0, 1, 2, 3, 4, 5, 6, 7 or 8; and optionally a deuterium substitution is on degron, and optionally the deuterium substitution is on $X^8$.

2. The compound of claim 1, wherein Cy1 is a 4-, 5-, 6- or 7-membered saturated or partially unsaturated ring comprising P═O, and 0 or 1 additional heteroatom independently selected from nitrogen, oxygen or sulfur in addition to P═O; wherein said ring is optionally substituted with at least one substituent $R^{1c}$;

$R^{1c}$ is selected from hydrogen, —F, —Cl, —Br, —I, methyl, ethyl, propyl, butyl, pentyl, hexyl, cyclopropyl, cyclobutyl, cyclopentyl, cyclohexyl, piperidinyl, piperazinyl, morpholinyl, phenyl, —CN, —$OR^{1d}$, —$COR^{1d}$, —$CO_2R^{1d}$, —$CONR^{1d}R^{1e}$, —$NR^{1d}R^{1e}$, —$NR^{1d}COR^{1e}$ or —$NR^{1d}CO_2R^{1e}$, wherein each of —$C_{1-8}$alkyl, —$C_{2-8}$alkenyl, —$C_{2-8}$alkynyl, $C_3$-$C_8$cycloalkyl, 3- to 8-membered heterocyclyl, $C_6$-$C_{12}$aryl or 5- to 12-membered heteroaryl is optionally substituted with at least one substituent $R^{1f}$;

$R^{1d}$, $R^{1e}$ and $R^{1f}$ are each independently selected from hydrogen, methyl, ethyl, propyl, butyl, pentyl, hexyl, cyclopropyl, cyclobutyl, cyclopentyl, or cyclohexyl.

3. The compound of claim 1, wherein the

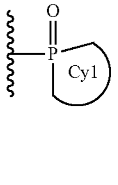 [SMILES: *P(C)(C)=O]

moiety is selected from

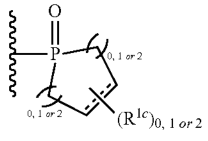
or
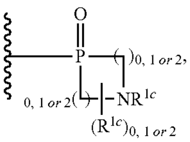

wherein ====== is a single or double bond; and $R^{1c}$, at each of its occurrences, has the same definition as claim 1; and wherein the

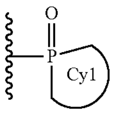

moiety is optionally selected from

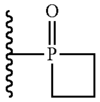
,
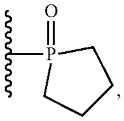
,
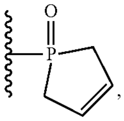
,
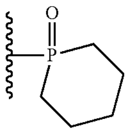
or
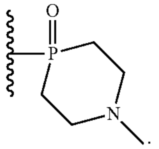
.

4. The compound of claim 1, wherein $R^2$ and $R^3$ are each independently selected from hydrogen, —F, —Cl, —Br, —I, methyl, ethyl, propyl, butyl, pentyl, hexyl, heptyl, octyl, cyclopropyl, cyclobutyl, cyclopentyl, cyclohexyl, cycloheptyl, cyclooctyl, 3- to 8-membered heterocyclyl, $C_6$-$C_{12}$aryl, 5- to 12-membered heteroaryl, —CN, —$OR^{2a}$, —$SO_2R^{2a}$, —$SO_2NR^{2a}R^{2b}$, —$COR^{2a}$, —$C_2R^{2a}$, —$CONR^{2a}R^{2b}$, —$NR^{2a}R^{2b}$, —$NR^{2a}COR^{2b}$, —$NR^{2a}CO_2R^{2b}$, or —$NR^{2a}SO_2R^{2b}$, wherein each of methyl, ethyl, propyl, butyl, pentyl, hexyl, heptyl, octyl, cyclopropyl, cyclobutyl, cyclopentyl, cyclohexyl, cycloheptyl, cyclooctyl, 3- to 8-membered heterocyclyl, $C_6$-$C_{12}$aryl or 5- to 12-membered heteroaryl is optionally substituted with at least one substituent $R^{2d}$, $R^{2a}$ and $R^{2b}$ are each independently selected from hydrogen, methyl, ethyl, propyl, butyl, pentyl, hexyl, heptyl, octyl, methoxyl, ethoxyl, propoxyl, butoxyl, pentoxyl, hexoxyl, heptyloxyl, octyloxyl, $C_{1-8}$alkoxy-$C_{1-8}$alkyl-, cyclopropyl, cyclobutyl, cyclopentyl, cyclohexyl, cycloheptyl, cyclooctyl, 3- to 8-membered heterocyclyl, phenyl or 5- to 12-membered heteroaryl;

$R^{2d}$, at each of its occurrences, is independently halogen, —OH, methyl, ethyl, propyl, butyl, pentyl, hexyl, heptyl, octyl, cyclopropyl, cyclobutyl, cyclopentyl, cyclohexyl, cycloheptyl, cyclooctyl, 3- to 8-membered heterocyclyl, phenyl, or 5- to 12-membered heteroaryl; or wherein $R^2$ and $R^3$ are each independently selected from hydrogen, halogen, methyl, ethyl, propyl, butyl, pentyl, hexyl, heptyl or octyl, or wherein $R^2$ and $R^3$ are each independently selected from selected from —H, —F, —Cl, —Br, —I, —$CH_3$, —$CH_2CH_3$, —$CH_2CH_2CH_3$, —$CH(CH_3)^2$, —$CH_2CH_2CH_2CH_3$, —$CH(CH_3)CH_2CH_3$, —$CH_2CH(CH_3)^2$, and —$C(CH_3)^3$.

5. The compound of claim 1, wherein $Z^5$ is —$CR^2$ and $Z^6$ is —$CR^3$, wherein $R^2$ and $R^3$ together with the carbon atoms to which they are attached, form a 5 or 6 membered unsaturated ring, said ring comprising 0, 1 or 2 heteroatoms independently selected from nitrogen, oxygen or sulfur; said ring is optionally substituted with at least one substituent $R^{2e}$;

$R^{2e}$, at each of its occurrences, is independently hydrogen, —F, —Cl, —Br, —I, methyl, ethyl, propyl, butyl, pentyl, hexyl, heptyl, octyl, methoxyl, ethoxyl, propoxyl, butoxyl, pentoxyl, hexoxyl, heptyloxyl, octyloxyl, cyclopropyl, cyclobutyl, cyclopentyl, cyclohexyl, cycloheptyl, cyclooctyl or oxo, wherein each of methyl, ethyl, propyl, butyl, pentyl, hexyl, heptyl, octyl, methoxyl, ethoxyl, propoxyl, butoxyl, pentoxyl, hexoxyl, heptyloxyl, octyloxyl, cyclopropyl, cyclobutyl, cyclopentyl, cyclohexyl, cycloheptyl or cyclooctyl is optionally substituted with at least one substituent $R^{2d}$;

$R^{2d}$, at each of its occurrences, is independently —F, —Cl, —Br, —I, —OH, methyl, ethyl, propyl, butyl, pentyl, hexyl, heptyl, octyl, methoxyl, ethoxyl, propoxyl, butoxyl, pentoxyl, hexoxyl, heptyloxyl, octyloxyl, cyclopropyl, cyclobutyl, cyclopentyl, cyclohexyl, cycloheptyl, cyclooctyl or phenyl.

6. The compound of claim 1, wherein the

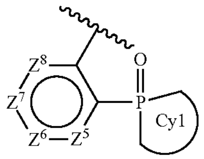

moiety is

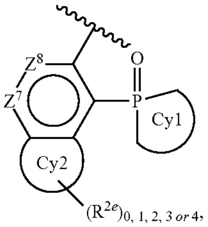
, wherein Cy2 is a 5-6 membered unsaturated or saturated ring, said ring comprising 0-3 heteroatoms independently selected from nitrogen, oxygen or sulfur;

wherein the

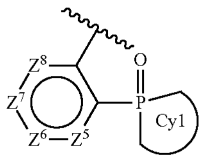

moiety is optionally

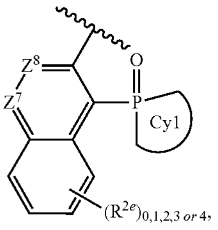 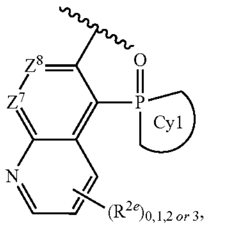

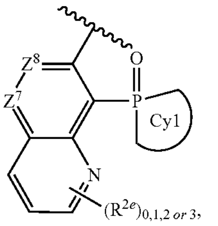 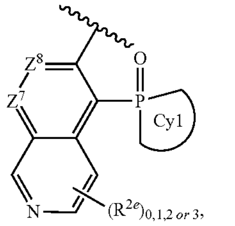

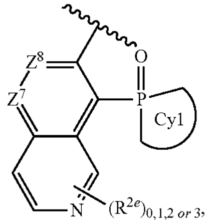 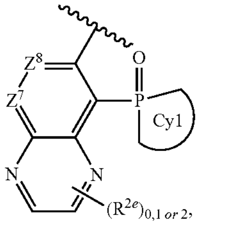

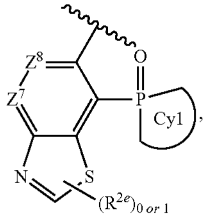 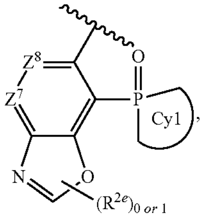

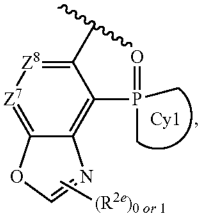 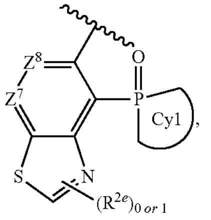

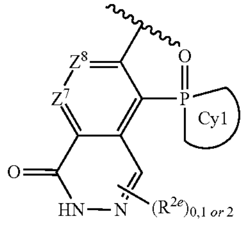 or 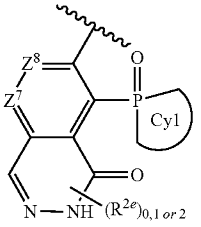

wherein $R^{2e}$, $Z^7$, and $Z^8$ are defined as in claim 1.

7. The compound of claim 1, wherein $R^{2e}$ at each of its occurrences, is independently hydrogen, —F, —Cl, —Br, —I, methyl, ethyl, propyl, butyl, pentyl, hexyl, heptyl, octyl, methoxyl, ethoxyl, propoxyl, butoxyl, pentoxyl, hexoxyl, heptyloxyl, octyloxyl, cyclopropyl, cyclobutyl, cyclopentyl, cyclohexyl, cycloheptyl, cyclooctyl or oxo, wherein each of methyl, ethyl, propyl, butyl, pentyl, hexyl, heptyl, octyl, methoxyl, ethoxyl, propoxyl, butoxyl, pentoxyl, hexoxyl, heptyloxyl, octyloxyl, cyclopropyl, cyclobutyl, cyclopentyl, cyclohexyl, cycloheptyl or cyclooctyl is optionally substituted with at least one substituent $R^{2d}$;

$R^{2d}$, at each of its occurrences, is independently —F, —Cl, —Br, —I, —OH, methyl, ethyl, propyl, butyl, pentyl, hexyl, heptyl, octyl, methoxyl, ethoxyl, propoxyl, butoxyl, pentoxyl, hexoxyl, heptyloxyl, octyloxyl, cyclopropyl, cyclobutyl, cyclopentyl, cyclohexyl, cycloheptyl, cyclooctyl or phenyl; and optionally wherein $R^{2e}$ at each of its occurrences, is independently hydrogen, —F, —Cl, —Br, —I, $—CH_3$, $—CH_2CH_3$, $—CH_2CH_2CH_3$, $—CH(CH_3)^2$, $—CH_2CH_2CH_2CH_3$, $—CH(CH_3)CH_2CH_3$, $—CH_2CH(CH_3)_2$, $—C(CH_3)_3$,

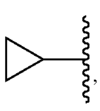, 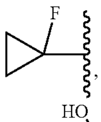, 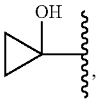, 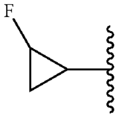 or

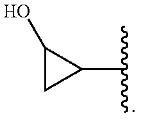.

8. The compound of claim 1, wherein the

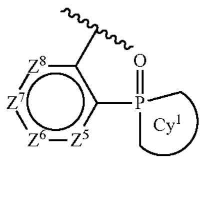

moiety is

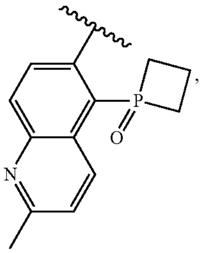, 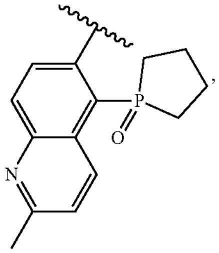,

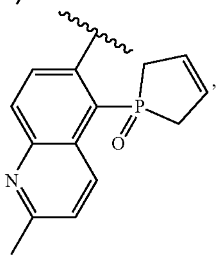, 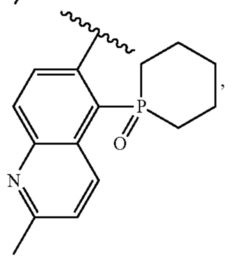,

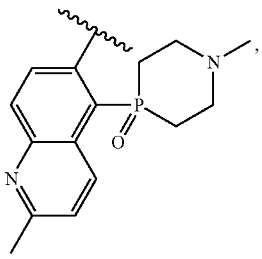, 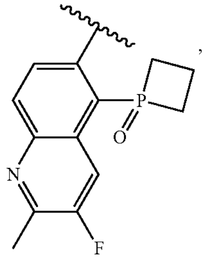,

-continued
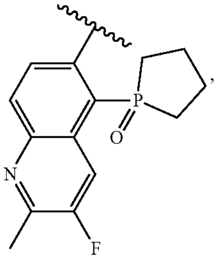,
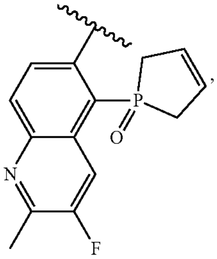,
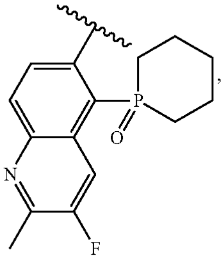,
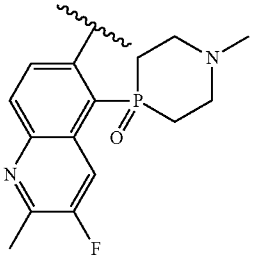,
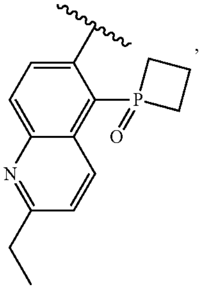,
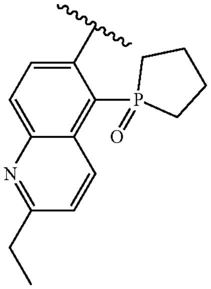,
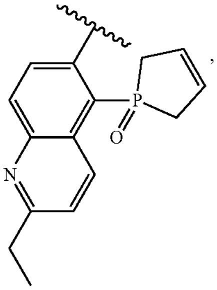,
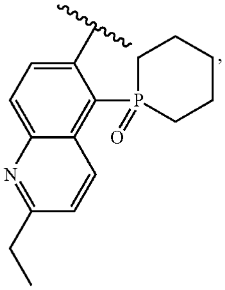,
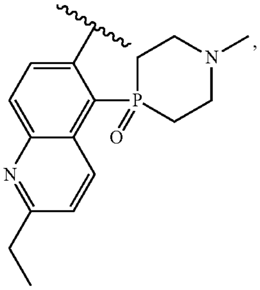,
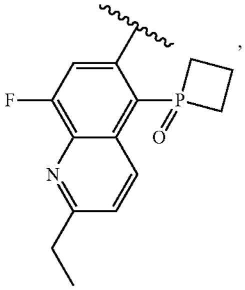,
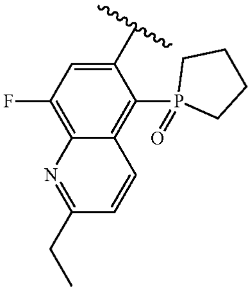,
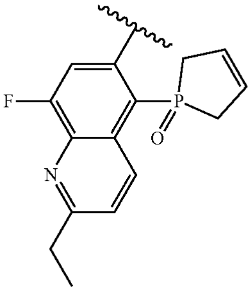,
-continued
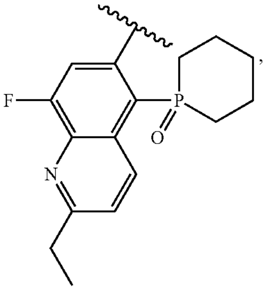,
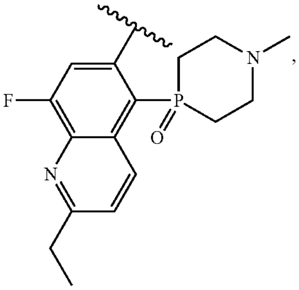,
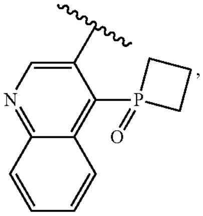,
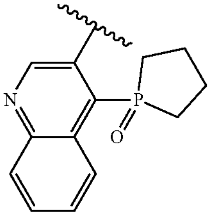,
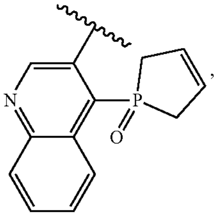,
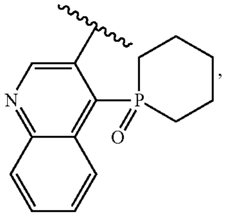,
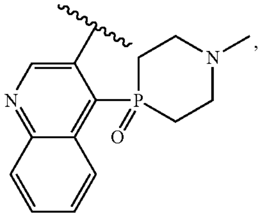,
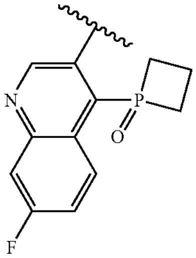,
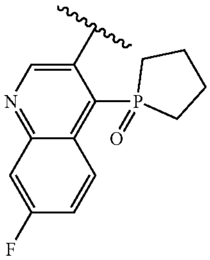,
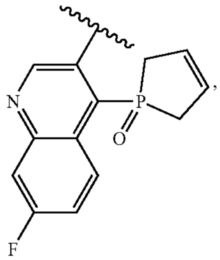,
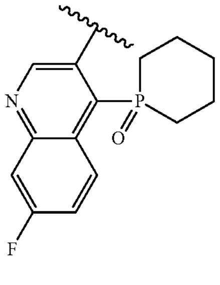,
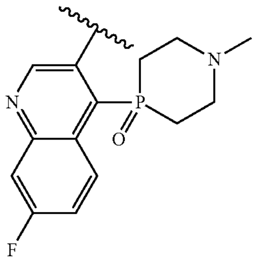, -continued

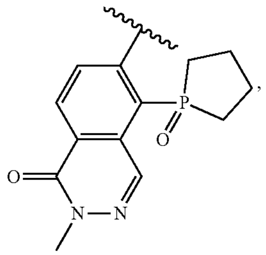

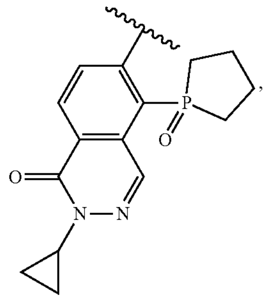

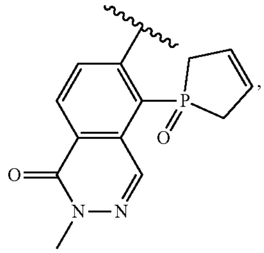

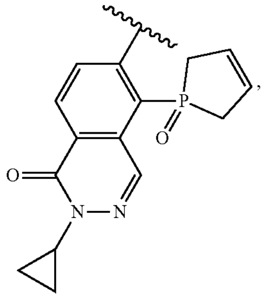

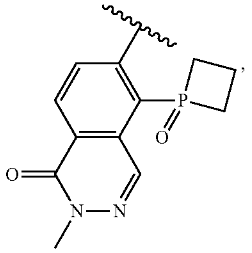

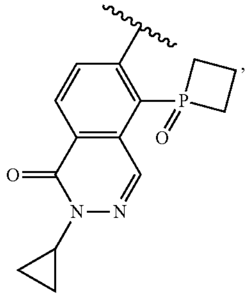

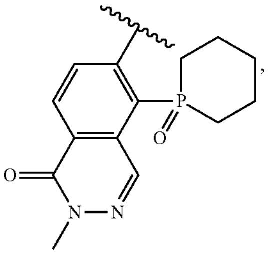

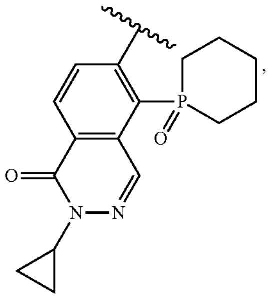

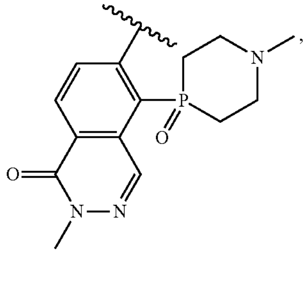

-continued

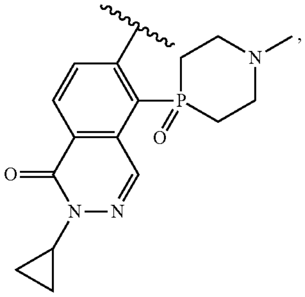

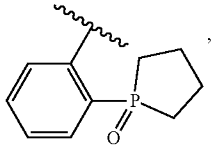

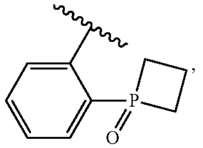

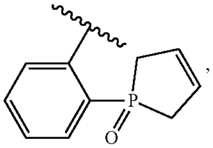

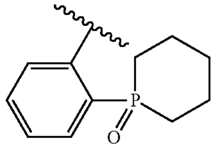

or

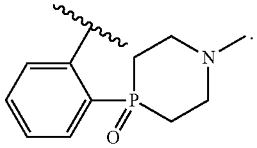

9. The compound of claim 1, wherein $R^9$, $R^{10}$, $R^{11}$ and $R^{12}$ are each independently selected from hydrogen, —F, —Cl, —Br, —I, methyl, ethyl, propyl, butyl, pentyl, hexyl, heptyl, octyl, methoxyl, ethoxyl, propoxyl, butoxyl, pentoxyl, hexoxyl, heptyloxyl, octyloxyl, cyclopropyl, cyclobutyl, cyclopentyl, cyclohexyl, cycloheptyl, cyclooctyl, —$NH_2$ or oxo, wherein each of methyl, ethyl, propyl, butyl, pentyl, hexyl, heptyl, octyl, methoxyl, ethoxyl, propoxyl, butoxyl, pentoxyl, hexoxyl, heptyloxyl, octyloxyl, cyclopropyl, cyclobutyl, cyclopentyl, cyclohexyl, cycloheptyl, cyclooctyl is optionally substituted with at least one substituent $R^{9c}$; or two $R^{12}$ together with the carbon atoms to which they are attached, form a 3, 4, 5, 6, 7 or 8-membered ring, said ring comprising 0, 1, 2 or 3 heteroatoms independently selected from nitrogen, oxygen or sulfur; said ring is optionally substituted with at least one substituent $R^{9c}$;

$R^{9c}$ is independently —F, —Cl, —Br, —I, hydroxy, methyl, ethyl, propyl, butyl, pentyl, hexyl, heptyl, octyl, methoxyl, ethoxyl, propoxyl, butoxyl, pentoxyl, hexoxyl, heptyloxyl, octyloxyl, cyclopropyl, cyclobutyl, cyclopentyl, cyclohexyl, cycloheptyl, cyclooctyl, —$C_{2-8}$alkenyl, —$C_{2-8}$alkynyl, 3- to 8-membered heterocyclyl, phenyl, 5- to 12-membered heteroaryl, $NH_2$, or —$NHCH_3$; and optionally wherein $R^9$, $R^{10}$, $R^{11}$ and $R^{12}$ are each independently selected from hydrogen, F, Cl, Br, —$NH_2$, —$CH_3$, —$C_2H_5$, —$C_3H_7$, —$CH_2F$, —$CHF_2$, —$CF_3$, —$C_4H_9$, —$C_5H_{11}$, —$OCH_3$, —$OC_2H_5$, —$OC_3H_7$, —$OC_4H_9$, —$OC_5H_{11}$, —CN, cyclopropyl or oxo; or two $R^{12}$ together with the carbon atoms to which they are attached, form a 3, 4, 5, 6, 7 or 8-membered ring, said ring comprising 0, 1, 2 or 3 heteroatoms independently selected from nitrogen, oxygen or sulfur; said ring is optionally substituted with at least one substituent —H, —F, —Cl, —Br, —I, methyl, ethyl, propyl, butyl, —$NH_2$, —$NHCH_3$, —OH, —$OCH_3$, —$OC_2H_5$, cyclopropyl, cyclobutyl, cyclopentyl, or cyclohexyl.

10. The compound of claim 1, wherein $R^4$ is selected from —H, —F, —Cl, —Br, —I, —$CH_3$, —$C_2H_5$, —$C_3H_7$, —$C_4H_9$, —$C_5H_{11}$, —$OCH_3$, —$OC_2H_5$, —$OC_3H_7$, —$OC_4H_9$, —$OC_5H_{11}$, cyclopropyl, cyclobutyl, cyclopentyl, cyclohexyl, cycloheptyl, cyclooctyl, phenyl or —CN, wherein each of $—CH_3$, $—C_2H_5$, $—C_3H_7$, $—C_4H_9$, $—C_5H_{11}$, $—OCH_3$, $—OC_2H_5$, $—OC_3H_7$, $—OC_4H_9$, $—OC_5H_{11}$, cyclopropyl, cyclobutyl, cyclopentyl, cyclohexyl, cycloheptyl, cyclooctyl or phenyl is optionally substituted with —F, —Cl, —Br, —I, $—C_{1-8}$alkyl, $—C_{2-8}$alkenyl, $—C_{2-8}$alkynyl, $—C_3$-$C_8$cycloalkyl, 3- to 8-membered heterocyclyl, $C_6$-$C_{12}$aryl, 5- to 12-membered heteroaryl, oxo, —CN, $—OR^{4c}$, $—SO_2R^{4c}$, $—SO_2NR^{4c}R^{4d}$, $—COR^4$c, $—CO_2R^{4c}$, $—CONR^{4c}R^{4d}$, $—NR^{4c}R^{4d}$, $—NR^{4c}COR^{4d}$, $—NR^{4c}CO_2R^{4d}$, or $—NR^{4c}SO_2R^{4d}$;

$R^{4c}$ and $R^{4d}$ are each independently hydrogen, $—C_{1-8}$ alkyl, $—C_{2-8}$alkenyl, $—C_{2-8}$alkynyl, $C_3$-$C_8$cycloalkyl, 3- to 8-membered heterocyclyl, $C_6$-$C_{12}$aryl, or 5- to 12-membered heteroaryl; and optionally wherein $R^4$ is selected from —F, —Cl, —Br, —I, $—CH_3$, $—CF_3$, $—CH_2F$, or $—CHF_2$.

11. The compound of claim 1, wherein $L^1$ is selected from a single bond, —O—, $—SO_2—$, —C(O)—, $—NR^{L1a}—C_{1-8}$ alkylene, $—C_3$-$C_8$cycloalkylene-, $*^{L1}—O—C_{1-8}$ alkylene-$**^{L1}$, $*^{L1}—C_{1-8}$alkylene-O—$**^{L1}$, *L-$SO_2—C_{1-8}$ alkylene-$**^{L1}$, $*^{L1}—C_{1-8}$alkylene-$SO_2$—$**^{L1}*^{L1}$—CO—$C_{1-8}$alkylene-$**^{L1}$, $*^{L1}—C_{1-8}$alkylene-CO—$**^{L1}$, *L-$NR^{L1a}—C_{1-8}$alkylene-$**^{L1}$, $*^{L1}—C_{1-8}$alkylene-$NR^{L1a}—**^{L1}$, $*^{L1}—NR^{L1a}C(O)—**^{L1}$, $*^{L1}$—C(O)$NR^{L1a}—**^{L1}—C_{1-8}$alkylene-, $—C_{2-8}$alkenylene-, $—C_{2-8}$ alkynylene-, $—[O(CR^{L1a}R^{L1b})_{m4}]_{m5}—$,

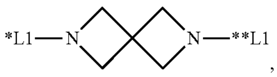
,
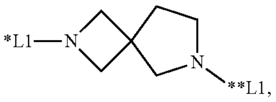
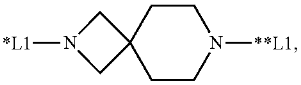
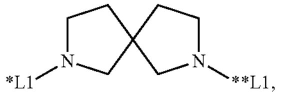
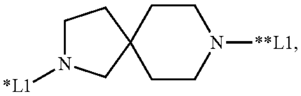
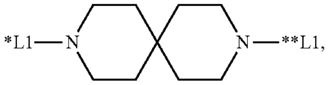
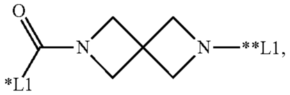
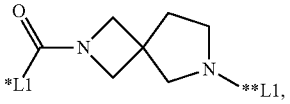
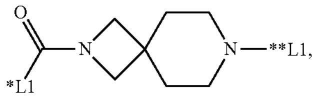
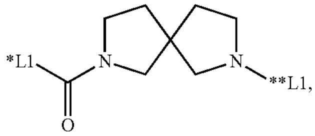
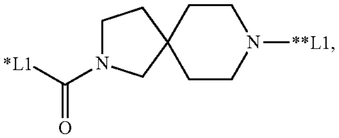

-continued

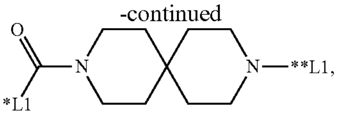
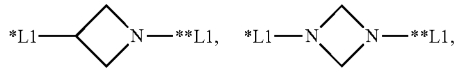
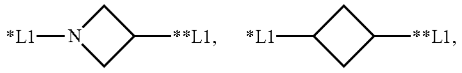
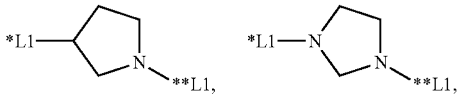
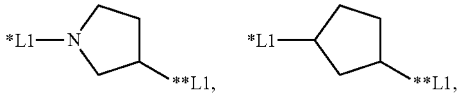
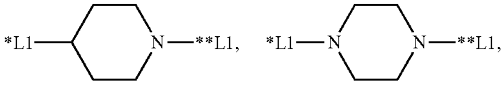
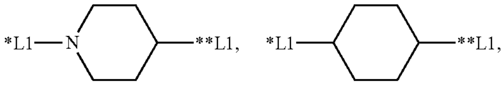
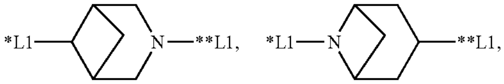
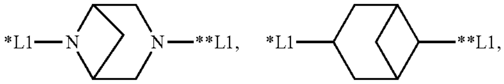
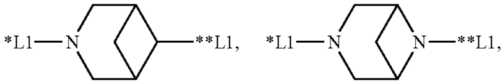
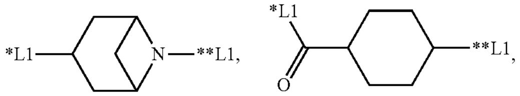
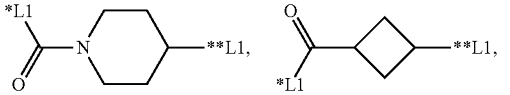
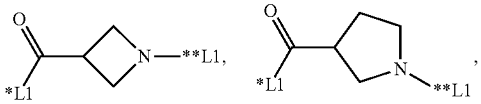
,
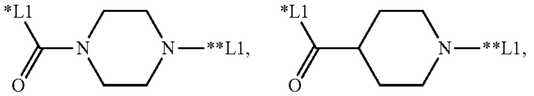
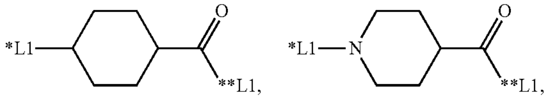
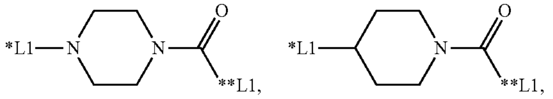
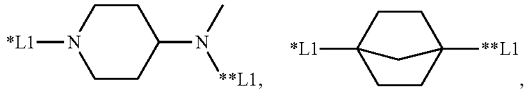
,
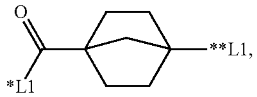
or
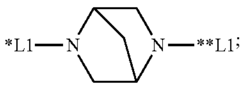
;

wherein each of said $—C_{1-8}$alkylene, $—C_3$-$C_8$cycloalkylene-, $*^{L1}—O—C_{1-8}$alkylene-$**^{L1}$, $*^{L1}—C_{1-8}$alkylene-O—$**^{L1}$, $*^{L1}—SO_2—C_{1-8}$ alkylene-$**^{L1}$, $*^{L1}—C_{1-8}$alkylene-$SO_2—**^{L1}$, $*^{L1}$—

CO—$C_{1-8}$alkylene-$**^{L1}$, $*^{L1}$—$C_{1-8}$alkylene-CO—$**^{L1}$, $*^{L1}$—$NR^{L1a}$—$C_{1-8}$alkylene-$**^{L1}$, $*^{L1}$—$C_{1-8}$ alkylene-$NR^{L1a}$, —$**^{L1}$, —$C_{1-8}$alkylene- —$C_{2-8}$ alkenylene-, —$C_{2-8}$alkynylene-,

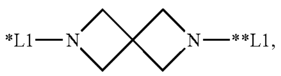
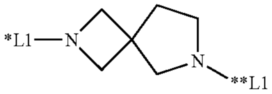
,
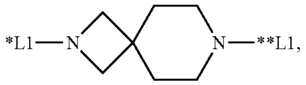
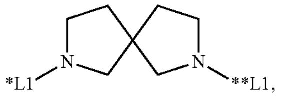
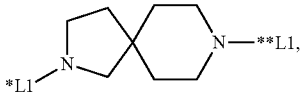
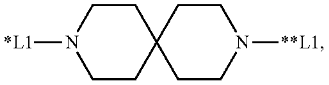
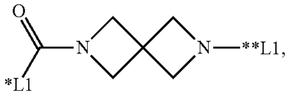
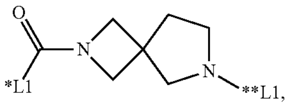
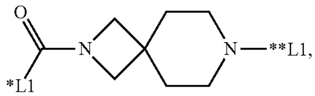
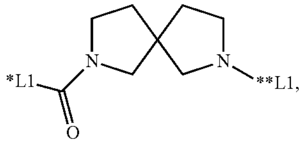
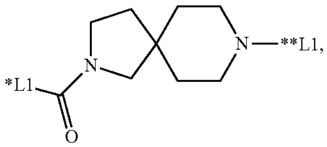
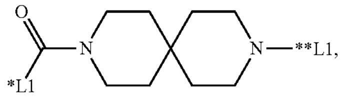
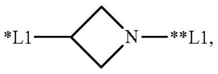
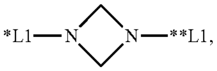
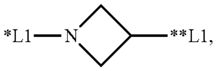
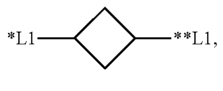
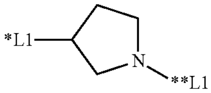
,
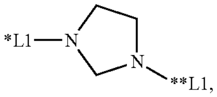
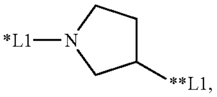
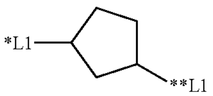
,
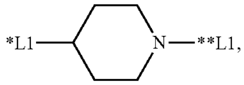
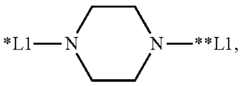
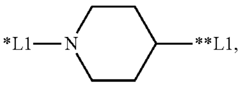

-continued

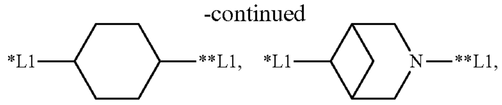
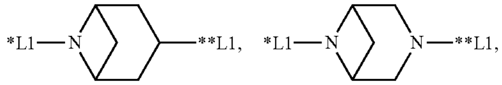
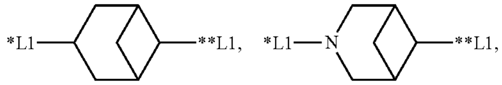
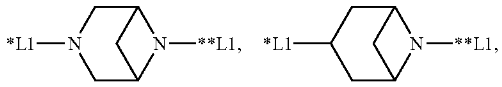
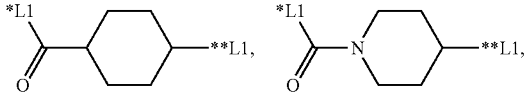
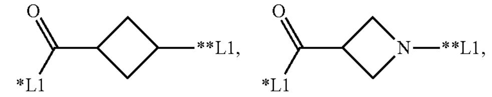
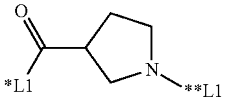
,
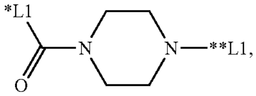
,
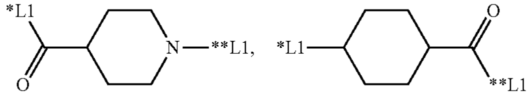
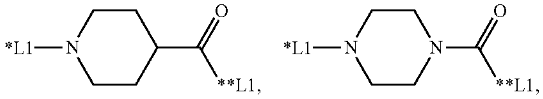
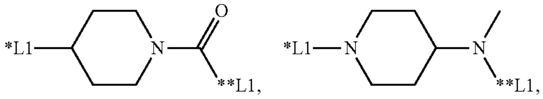
or
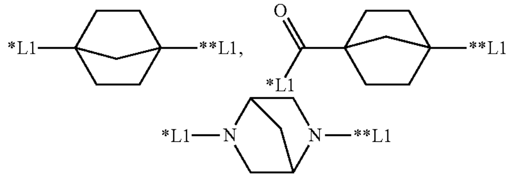

or is optionally substituted with at least one $R^{L1c}$;

$R^{L1a}$ and $R^{L1b}$ are each independently selected from hydrogen, methyl, ethyl, propyl, butyl, pentyl, hexyl, heptyl, octyl, vinyl, ethynyl, cyclopropyl, cyclobutyl, cyclopentyl, cyclohexyl, cycloheptyl, cyclooctyl, oxazolidinyl, imidazolidinyl, thiazolidinyl, pyrazolidinyl, morpholinyl, piperidinyl, piperazinyl, oxazinyl, imidazolyl, thiazolyl, oxazolyl, pyridyl, pyrimidinyl, pyrazinyl, pyridazinyl, phenyl, pyrrolyl, imidazolyl, pyrazolyl, thiazolyl, oxazolyl, triazolyl, thiophenyl, furanyl, pyridyl, pyrimidinyl or pyrazinyl, wherein each of said methyl, ethyl, propyl, butyl, pentyl, hexyl, heptyl, octyl, vinyl, ethynyl, cyclopropyl, cyclobutyl, cyclopentyl, cyclohexyl, cycloheptyl, cyclooctyl, oxazolidinyl, imidazolidinyl, thiazolidinyl, pyrazolidinyl, morpholinyl, piperidinyl, piperazinyl, oxazinyl, imidazolyl, thiazolyl, oxazolyl, pyridyl, pyrimidinyl, pyrazinyl, pyridazinyl, phenyl, pyrrolyl, imidazolyl, pyrazolyl, thiazolyl, oxazolyl, triazolyl, thiophenyl, furanyl, pyridyl, pyrimidinyl or pyrazinyl is optionally substituted with at least one substituent $R^{L1d}$;

each of said $R^{L1c}$ and $R^{L1d}$ are independently —F, —Cl, —Br, —I, —OH, methyl, ethyl, propyl, butyl, pentyl, hexyl, heptyl, octyl, vinyl, ethynyl, methoxyl, ethoxyl, propoxyl, butoxyl, pentoxyl, hexoxyl, heptyloxyl, octyloxyl, cyclopropyl, cyclobutyl, cyclopentyl, cyclohexyl, cycloheptyl, cyclooctyl, oxazolidinyl, imidazolidinyl, thiazolidinyl, pyrazolidinyl, morpholinyl, piperidinyl, piperazinyl, oxazinyl, imidazolyl, thiazolyl, oxazolyl, pyridyl, pyrimidinyl, pyrazinyl, pyridazinyl, phenyl, pyrrolyl, imidazolyl, pyrazolyl, thiazolyl, oxazolyl, triazolyl, thiophenyl, furanyl, pyridyl, pyrimidinyl, pyrazinyl or oxo; or wherein $L^1$ is selected from a single bond, —$C_{1-8}$alkylene-, —CO—, —O—, —N($CH_3$)—, —NH—,

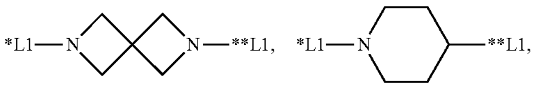
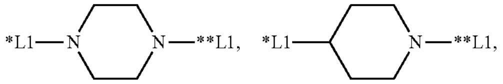
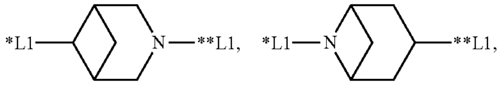
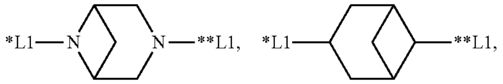
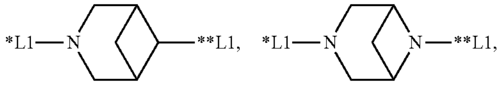
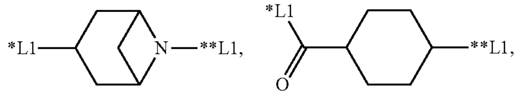
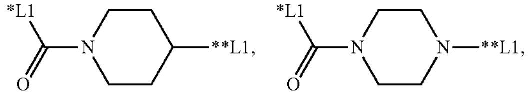
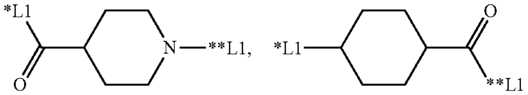
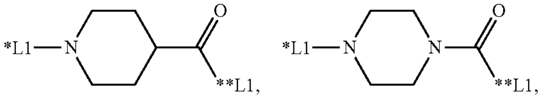
,
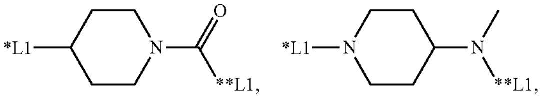
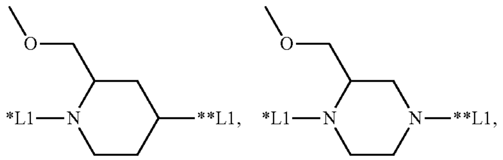
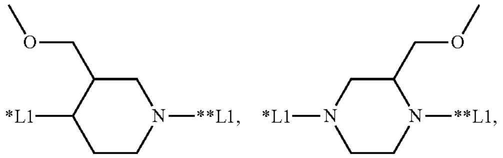
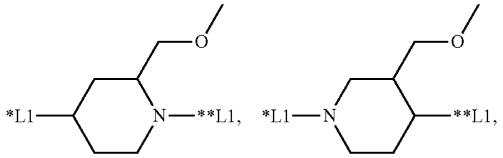

-continued

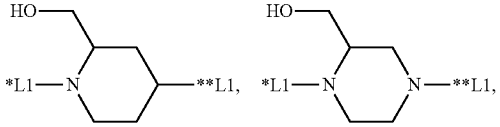
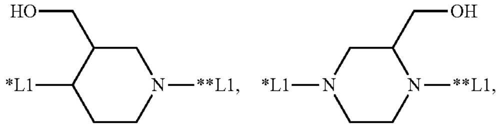
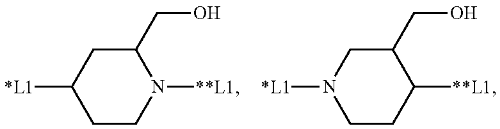
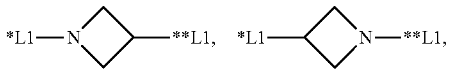
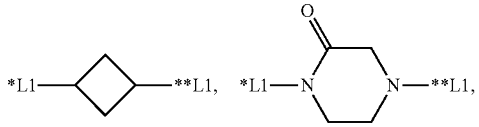
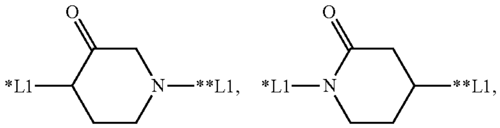
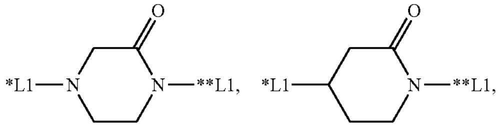
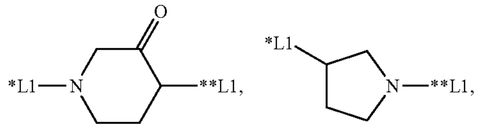
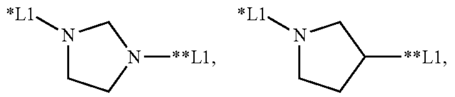
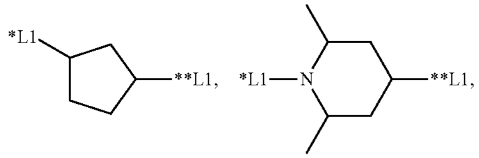
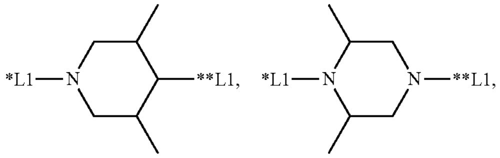
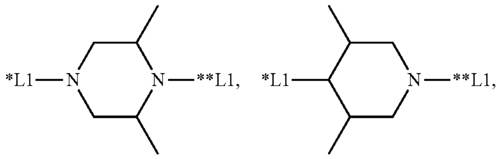
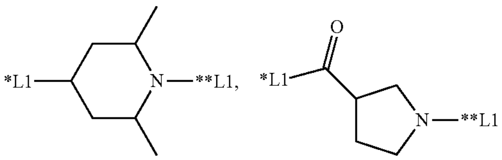
, -continued

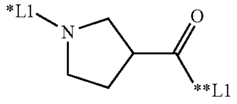
,
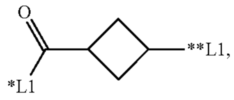

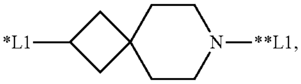

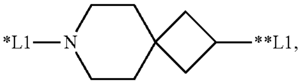

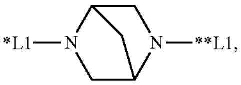
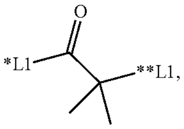

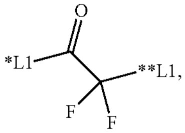
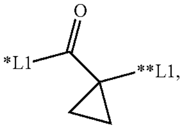
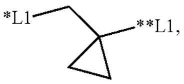

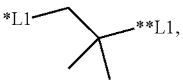
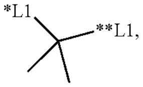
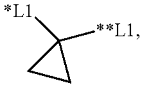

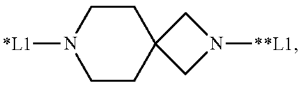

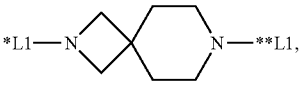
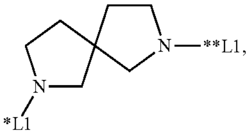

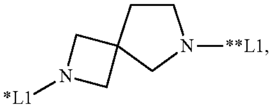
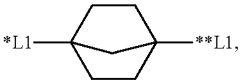

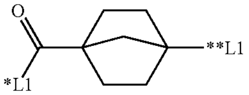
or
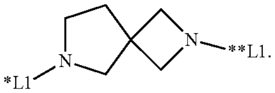

12. The compound of claim 1, wherein $X^1$ and $X^2$ are each independently selected from —$CR^a$ or N;

wherein $R^a$ is selected from hydrogen, —F, —Cl, —Br, —I, CN, methyl, ethyl, methoxy, ethoxy, or cyclopropyl, wherein each of said methyl, ethyl, methoxy, ethoxy, or cyclopropyl is optionally substituted with at least one substituent —F, —Cl, —Br, —I, hydroxy, methyl, or ethyl, ;

m1=1 or 0;

$R^{12}$ is hydrogen, oxo, methoxymethyl, hydroxymethyl, —CN or —$CH_3$.

13. The compound of claim 1, wherein m1 is 1; optionally wherein the

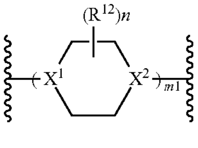

moiety is

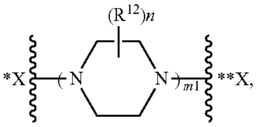
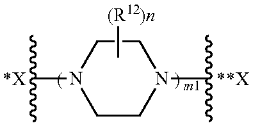
or
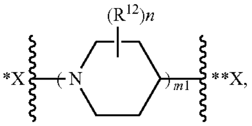

wherein $*^{X}$ refers to the position attached to

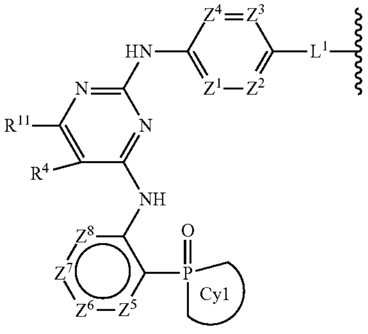

moiety, and $**^{X}$ refers to the position attached to the

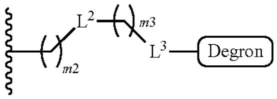

moiety.

14. The compound of claim 1, wherein m1 is 0.

15. The compound of claim 1, wherein

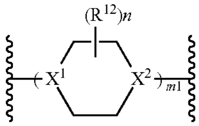

moiety

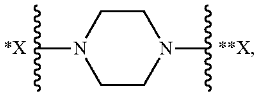
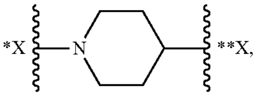

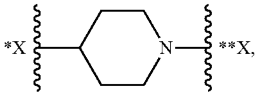
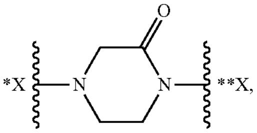

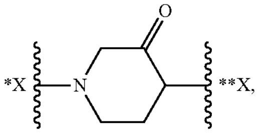
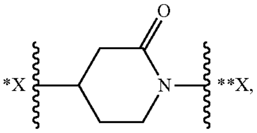

-continued

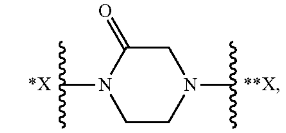
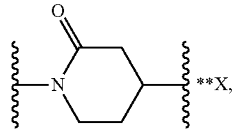
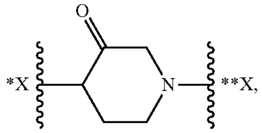
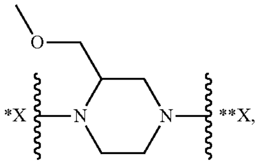
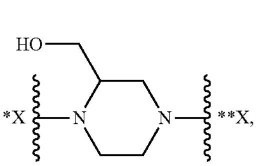
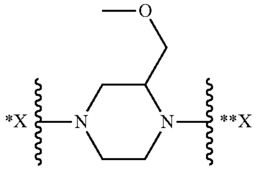
or
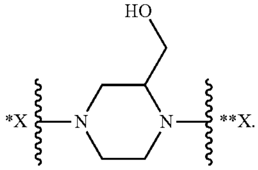

16. The compound of claim 1, wherein m2 is selected from 0, 1, 2, 3, 4 or 5.

17. The compound of claim 1, wherein $L^2$ is selected from a single bond, —O—, —$SO_2$—, —CO—, —$NR^{L2a}$—, —$C_{1-8}$alkylene, —$C_3$-$C_8$cycloalkylene-, $*^{L2}$—O—$C_{1-8}$alkylene-$**^{L2}$, $*^{L2}$—$C_{1-8}$alkylene-O—$**^{L2}$, $*^{L2}$-$SO_2$—$C_{1-8}$ alkylene-$**^{L2}$, $*^{L2}$—$C_{1-8}$alkylene-$SO_2$—$**^{L2}$, $*^{L2}$—CO—$C_{1-8}$alkylene-$**^{L2}$, $*^{L2}$—$C_{1-8}$alkylene-CO—$**^{L2}$, $*^{L2}$—$NR^{L2a}$—$C_{1-8}$alkylene-$**^{L2}$, $*^{L2}$—$C_{1-8}$alkylene-$NR^{L2a}$, —$**^{L2}$, $*^{L2}NR^{L2a}$C(O)—$**^{L2}$, $*^{L2}$—C(O)$NR^{L2a}$-$**^{L2}$, —$C_{1-8}$alkylene-, —$C_{2-8}$alkenylene-, —$C_{2-8}$ alkynylene-, —$[O(CR^{L2a}R^{L2b})_{m4}]_{m5}$—,

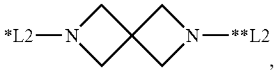
,
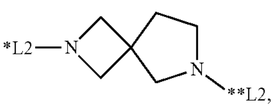
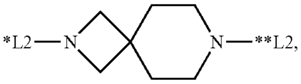
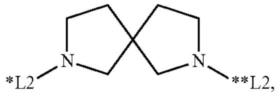
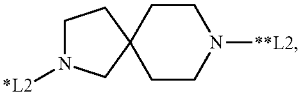
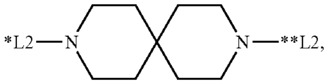
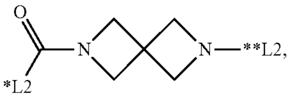
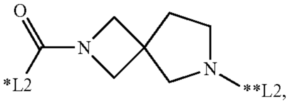

-continued

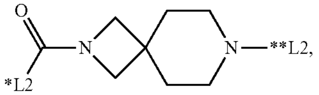
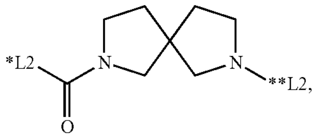
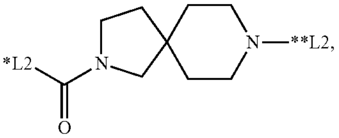
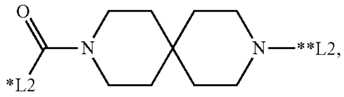
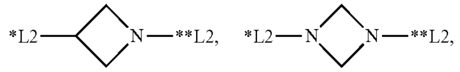
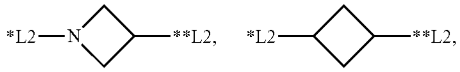
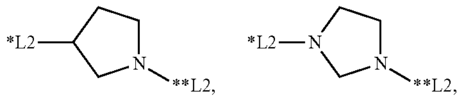
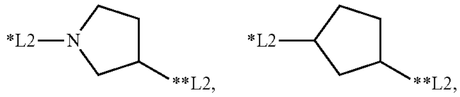
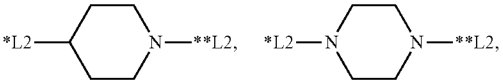
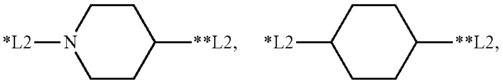
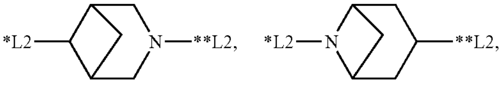
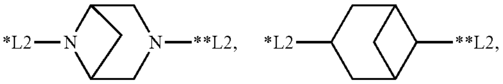
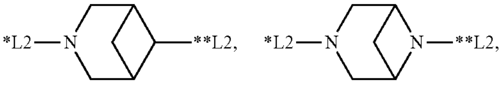
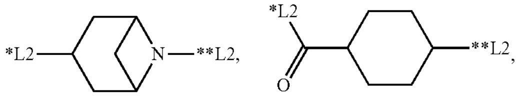
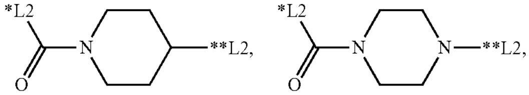
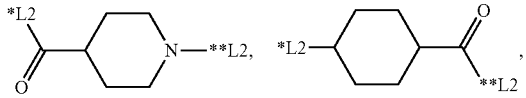
,
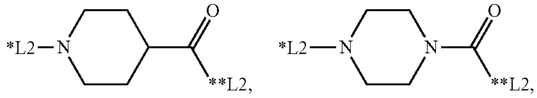
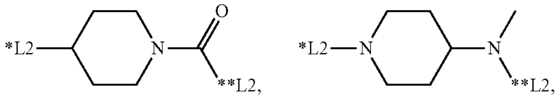

-continued

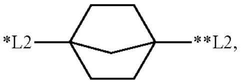
,
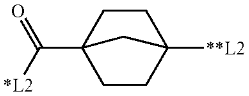
or
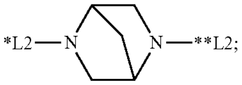
;

wherein each of said $—C_{1-8}$alkylene, $—C_3$-$C_8$cycloalkylene-, $*^{L2}—O—C_{1-8}$alkylene-$**^{L2}$, $*^{L2}—C_{1-8}$alkylene-O—$**^{L2}$, $*^{L2}$-$SO_2—C_{1-8}$ alkylene-$**^{L2}$, $*^{L2}—C_{1-8}$alkylene-$SO_2—**^{L2}$, $*^{L2}$—CO—$C_{1-8}$alkylene-$**^{L2}$, $*^{L2}—C_{1-8}$alkylene-CO—$**^{L2}$, $*^{L2}—NR^{L2a}—C_{1-8}$alkylene-$**^{L2}$, $*^{L2}—C_{1-8}$ alkylene-$NR^{L2a}$, $—**^{L2}$, $—C_{1-8}$alkylene-, $—C_{2-8}$ alkenylene-, $—C_{2-8}$alkynylene-,

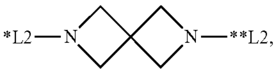
,
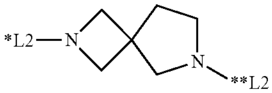
,
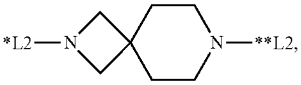
,
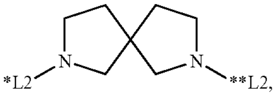
,
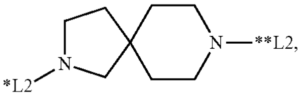
,
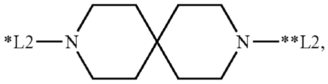
,
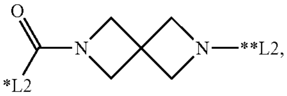
,
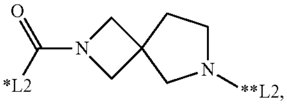
,
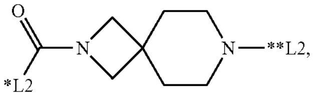
,
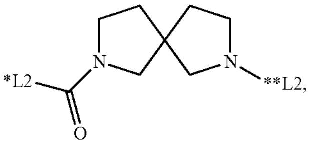
,
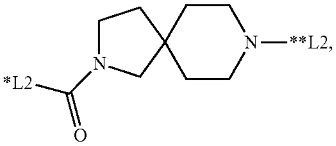
,
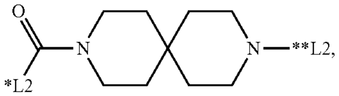
,
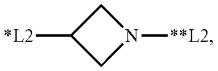
,
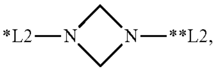
,
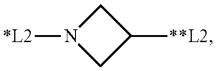
, -continued

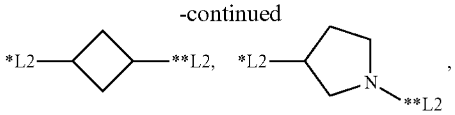
,
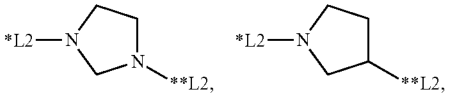
,
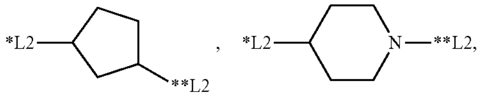
,
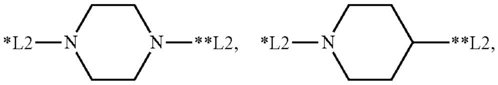
,
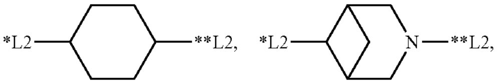
,
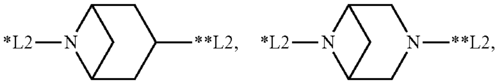
,
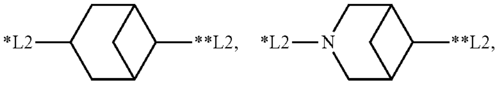
,
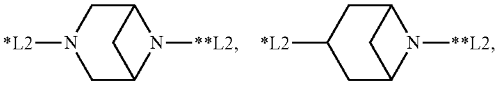
,
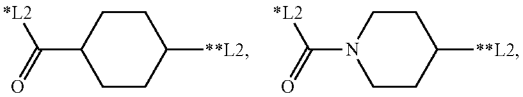
,
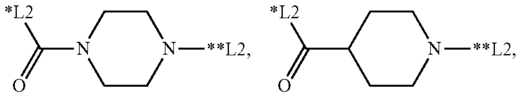
,
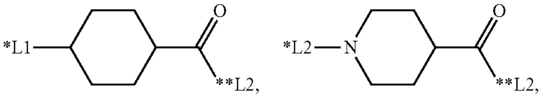
,
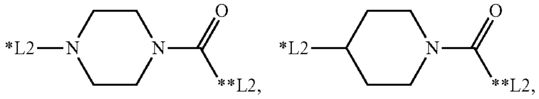
,
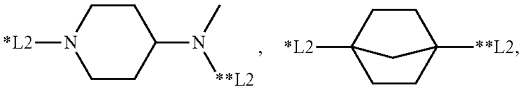
,
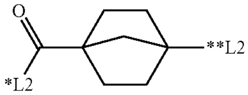
or
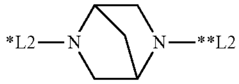

is optionally substituted with at least one substituent $R^{L2c}$;

$R^{L2a}$ and $R^{L2b}$ are each independently selected from hydrogen, methyl, ethyl, propyl, butyl, pentyl, hexyl, heptyl, octyl, vinyl, ethynyl, cyclopropyl, cyclobutyl, cyclopentyl, cyclohexyl, cycloheptyl, cyclooctyl, oxazolidinyl, imidazolidinyl, thiazolidinyl, pyrazolidinyl, morpholinyl, piperidinyl, piperazinyl, oxazinyl, imidazolyl, thiazolyl, oxazolyl, pyridyl, pyrimidinyl, pyrazinyl, pyridazinyl, phenyl, pyrrolyl, imidazolyl, pyrazolyl, thiazolyl, oxazolyl, triazolyl, thiophenyl, furanyl, pyridyl, pyrimidinyl or pyrazinyl, wherein each of said methyl, ethyl, propyl, butyl, pentyl, hexyl, heptyl, octyl, vinyl, ethynyl, cyclopropyl, cyclobutyl, cyclopentyl, cyclohexyl, cycloheptyl, cyclooctyl, oxazolidinyl, imidazolidinyl, thiazolidinyl, pyrazolidinyl, morpholinyl, piperidinyl, piperazinyl, oxazinyl, imidazolyl, thiazolyl, oxazolyl, pyridyl, pyrimidinyl, pyrazinyl, pyridazinyl, phenyl, pyrrolyl, imidazolyl, pyrazolyl, thiazolyl, oxazolyl, triazolyl, thiophenyl, furanyl, pyridyl, pyrimidinyl or pyrazinyl is optionally substituted with at least one substituent $R^{L2d}$;

each of said $R^{L2e}$ and $R^{L2d}$ are independently —F, —Cl, —Br, —I, —OH, methyl, ethyl, propyl, butyl, pentyl, hexyl, heptyl, octyl, vinyl, ethynyl, cyclopropyl, cyclobutyl, cyclopentyl, cyclohexyl, cycloheptyl, cyclooctyl, oxazolidinyl, imidazolidinyl, thiazolidinyl, pyrazolidinyl, morpholinyl, piperidinyl, piperazinyl, oxazinyl, imidazolyl, thiazolyl, oxazolyl, pyridyl, pyrimidinyl, pyrazinyl, pyridazinyl, phenyl, pyrrolyl, imidazolyl, pyrazolyl, thiazolyl, oxazolyl, triazolyl, thiophenyl, furanyl, pyridyl, pyrimidinyl, pyrazinyl or oxo; or wherein $L^2$ is selected from a single bond, $-C_{1-8}$alkylene-, —CO—, —O—, $-N(CH_3)-$, —NH—,

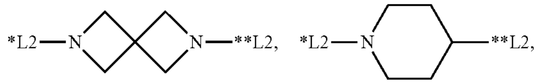
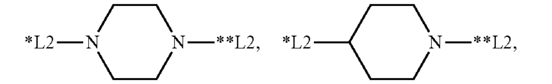
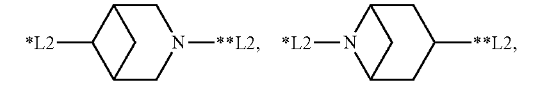
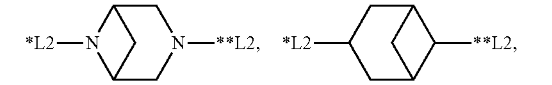
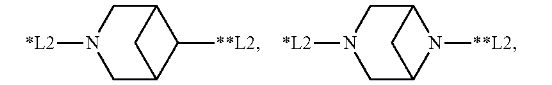
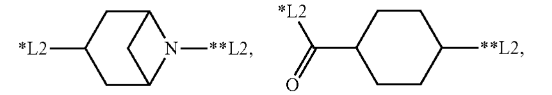
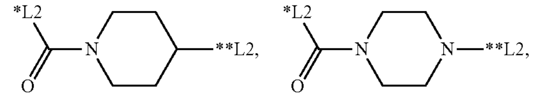
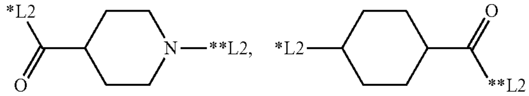
,
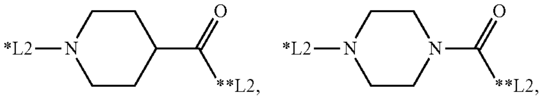
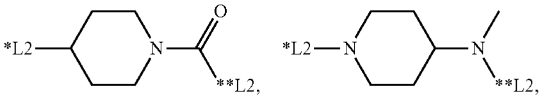
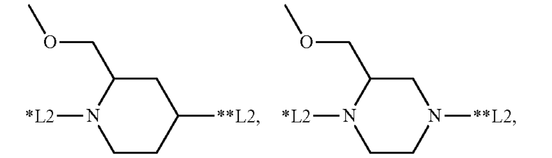
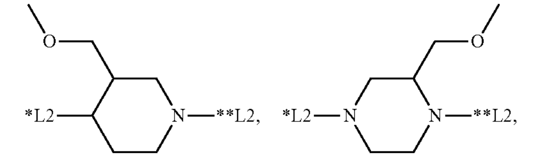

-continued

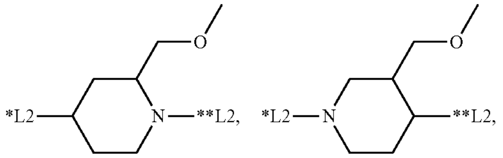
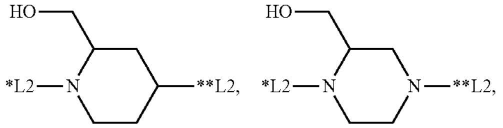
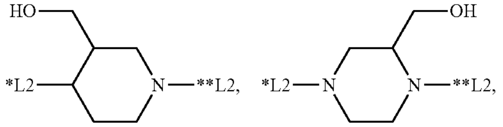
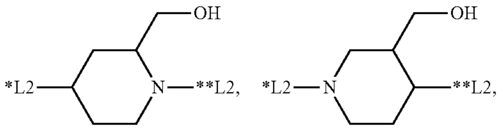
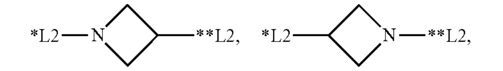
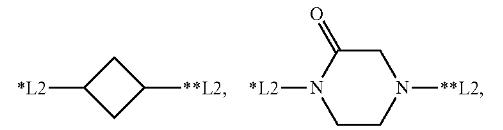
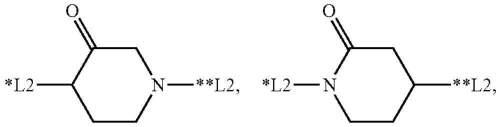
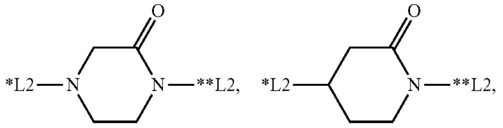
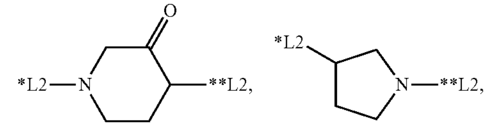
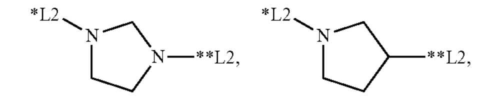
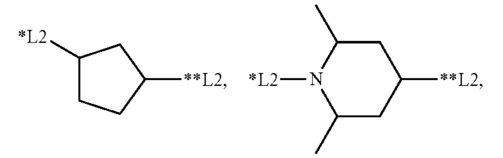
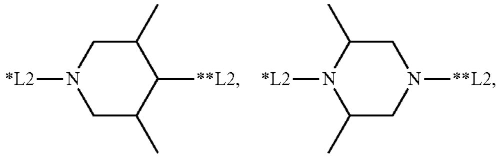
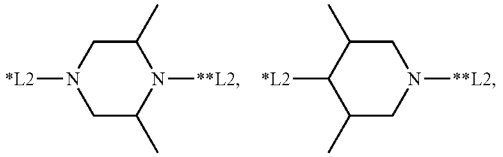

-continued

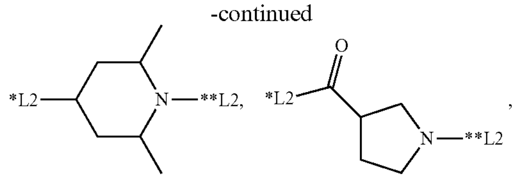
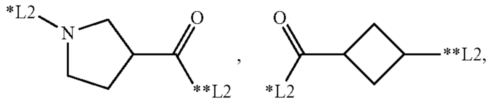
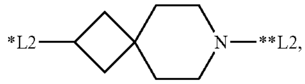
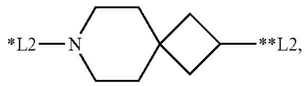
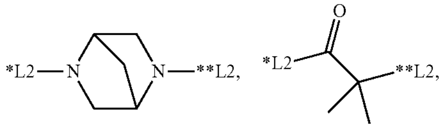
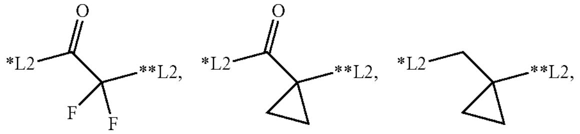
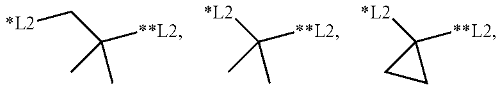
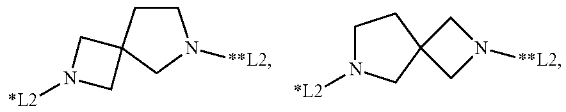
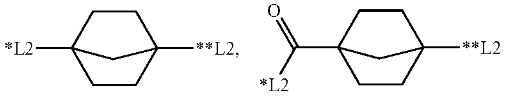
or
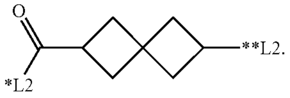

18. The compound of claim 1, wherein $L^3$ is selected from a single bond, —O—, —$SO_2$—, —CO—, —$NR^{L3a}$—$C_{1\text{-}8}$alkylene, —$C_3$-$C_8$cycloalkylene-, $*^{L3}$-O—$C_{1\text{-}8}$ alkylene-$**^{L3}$, $*^{L3}$-$C_{1\text{-}8}$alkylene-O—$**^{L3}$, $*^{L3}$-$SO_2$—$C_{1\text{-}8}$ alkylene-$**^{L3}$, $*^{L3}$-$C_{1\text{-}8}$alkylene-$SO_2$—$**^{L3}$, $*^{L3}$-CO—$C_{1\text{-}8}$ alkylene-$**^{L3}$, $*^{L3}$-$C_{1\text{-}8}$alkylene-CO—$**^{L3}$, $*^{L3}$-$NR^{L3a}$—$C_{1\text{-}8}$alkylene-$**^{L3}$, $*^{L3}$-$C_{1\text{-}8}$alkylene-$NR^{L3a}$—$**^{L3}$, $*^{L3}NR^{L3a}C(O)$—$**^{L3}$, $*^{L3}$-$C(O)NR^{L3a}$-$**^{L3}$, —$C_{1\text{-}8}$ alkylene-, —$C_{2\text{-}8}$alkenylene-, —$C_{2\text{-}8}$alkynylene-, —$[O(CR^{L3a}R^{L3b})_{m4}]_{m5}$—,

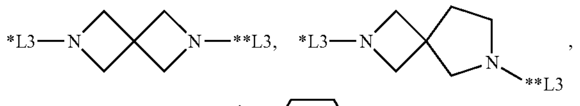
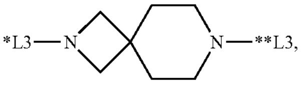
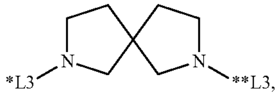

-continued

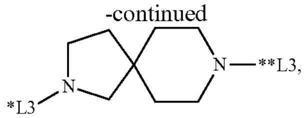
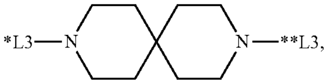
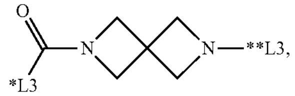
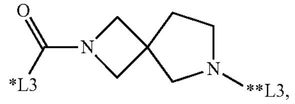
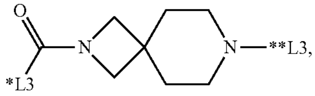
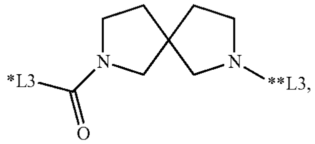
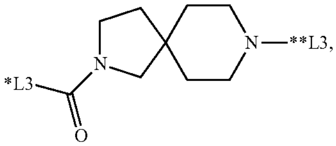
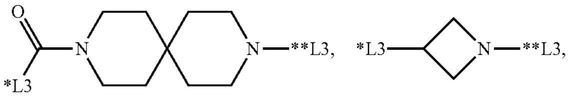
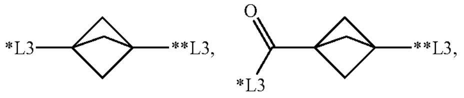
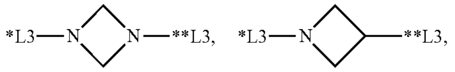
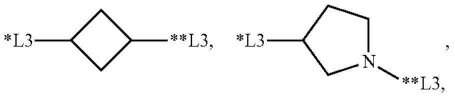
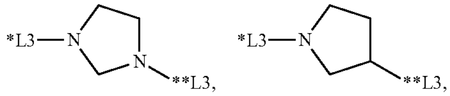
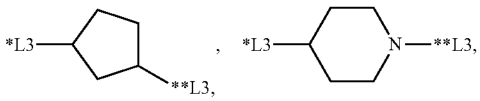
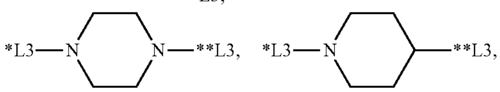
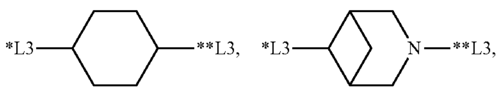
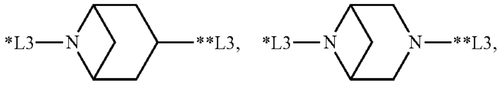
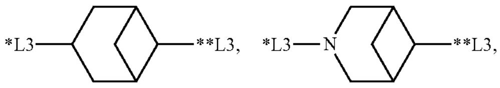
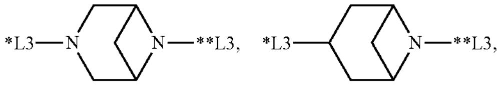

-continued
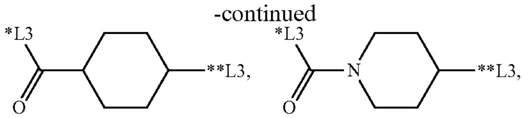
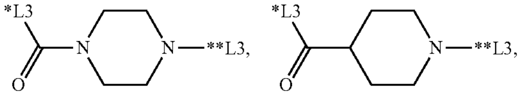
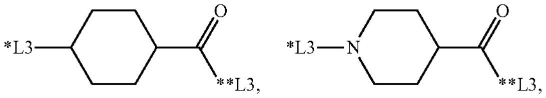
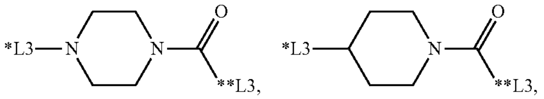
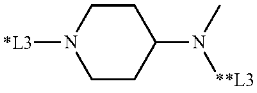
,
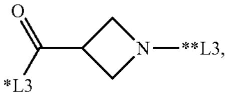
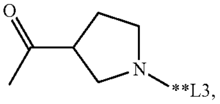
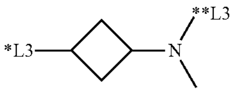
,
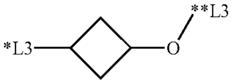
,
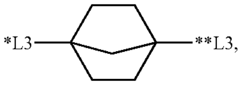
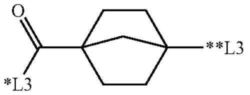
or
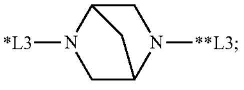
wherein each of said —$C_{1-8}$alkylene, —$C_3$-$C_8$cycloalkylene-, $*^{L3}$-$OC_{1-8}$alkylene-* $*^{L3}$, $*^{L3}$-$C_{1-8}$ alkylene-O—$**^{L3}$, $*^{L3}$-$SO_2$—$C_{1-8}$alkylene-$**^{L3}$, $*^{L3}$-$C_{1-8}$alkylene-$SO_2$—$**^{L3}$, $*^{L3}$-CO—$C_{1-8}$ alkylene-* $*^{L3}$, $*^{L3}$-$C_{1-8}$alkylene-CO—$**^{L3}$, $*^{L3}$-$NR^{L3a}$—$C_{1-8}$alkylene-$**^{L3}$, $*^{L3}$-$C_{1-8}$alkylene-$NR^{L3a}$, —$**^{L3}$, —$C_{1-8}$alkylene-, —$C_{2-8}$alkenylene-, —$C_{2-8}$ alkynylene-,
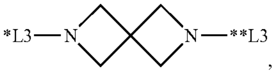
,
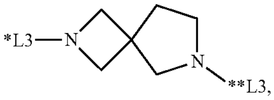
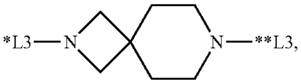
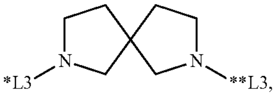
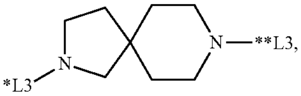
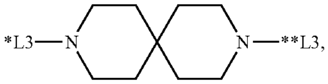
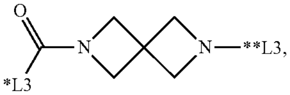
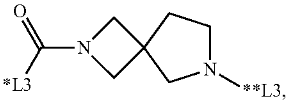
-continued
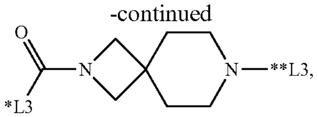
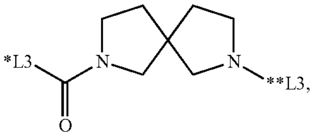
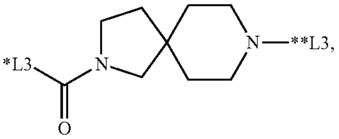
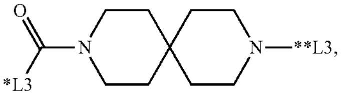
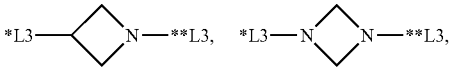
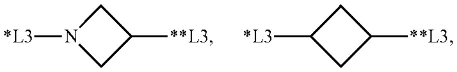
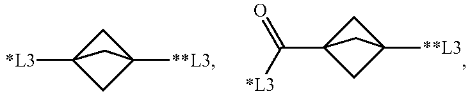
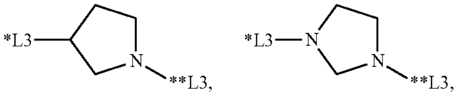
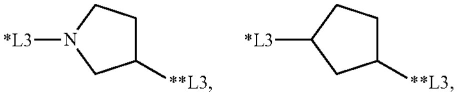
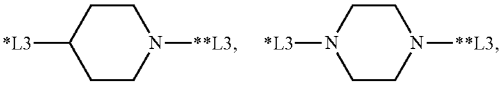
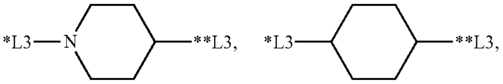
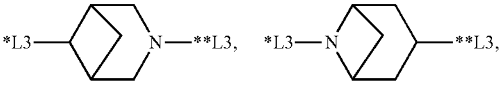
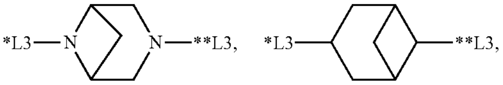
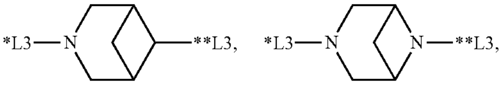
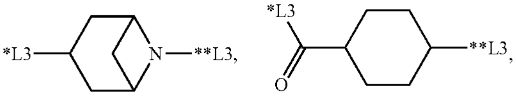
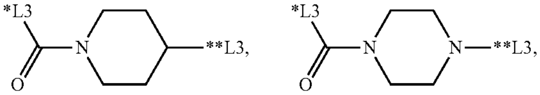
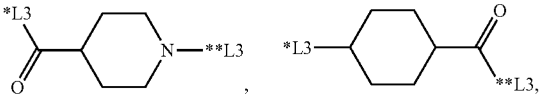
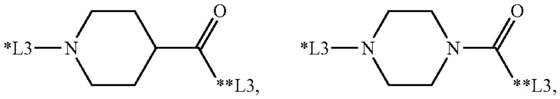

-continued

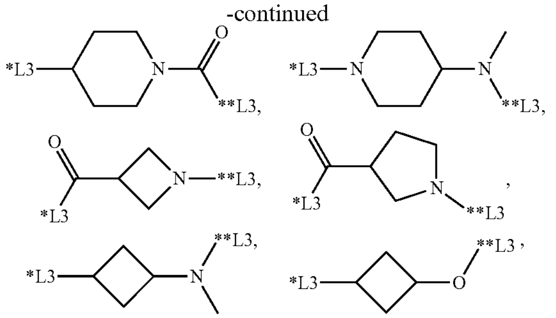

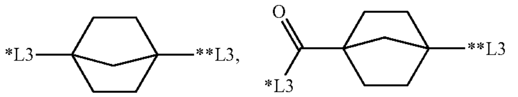

or

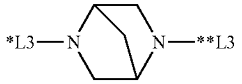

is optionally substituted with at least one substituent $R^{L3c}$, $R^{L3a}$ and $R^{L3b}$ are each independently selected from hydrogen, methyl, ethyl, propyl, butyl, pentyl, hexyl, heptyl, octyl, vinyl, ethynyl, cyclopropyl, cyclobutyl, cyclopentyl, cyclohexyl, cycloheptyl, cyclooctyl, oxazolidinyl, imidazolidinyl, thiazolidinyl, pyrazolidinyl, morpholinyl, piperidinyl, piperazinyl, oxazinyl, imidazolyl, thiazolyl, oxazolyl, pyridyl, pyrimidinyl, pyrazinyl, pyridazinyl, phenyl, pyrrolyl, imidazolyl, pyrazolyl, thiazolyl, oxazolyl, triazolyl, thiophenyl, furanyl, pyridyl, pyrimidinyl or pyrazinyl, wherein each of said methyl, ethyl, propyl, butyl, pentyl, hexyl, heptyl, octyl, vinyl, ethynyl, cyclopropyl, cyclobutyl, cyclopentyl, cyclohexyl, cycloheptyl, cyclooctyl, oxazolidinyl, imidazolidinyl, thiazolidinyl, pyrazolidinyl, morpholinyl, piperidinyl, piperazinyl, oxazinyl, imidazolyl, thiazolyl, oxazolyl, pyridyl, pyrimidinyl, pyrazinyl, pyridazinyl, phenyl, pyrrolyl, imidazolyl, pyrazolyl, thiazolyl, oxazolyl, triazolyl, thiophenyl, furanyl, pyridyl, pyrimidinyl or pyrazinyl is optionally substituted with at least one substituent $R^{L3d}$;

each of said $R^{L3c}$ and $R^{L3d}$ are independently —F, —Cl, —Br, —I, —OH, methyl, ethyl, propyl, butyl, pentyl, hexyl, heptyl, octyl, vinyl, ethynyl, cyclopropyl, cyclobutyl, cyclopentyl, cyclohexyl, cycloheptyl, cyclooctyl, oxazolidinyl, imidazolidinyl, thiazolidinyl, pyrazolidinyl, morpholinyl, piperidinyl, piperazinyl, oxazinyl, imidazolyl, thiazolyl, oxazolyl, pyridyl, pyrimidinyl, pyrazinyl, pyridazinyl, phenyl, pyrrolyl, imidazolyl, pyrazolyl, thiazolyl, oxazolyl, triazolyl, thiophenyl, furanyl, pyridyl, pyrimidinyl, pyrazinyl or oxo; or wherein $L^3$ is selected from a single bond, —$C_{1-8}$alkylene, —CO—, —O—, —$N(CH_3)$—,

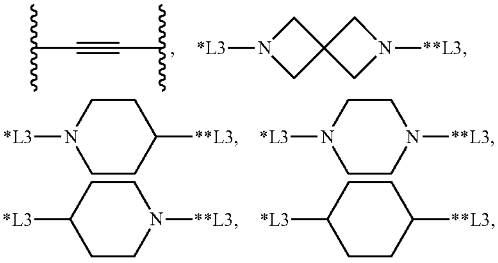

-continued

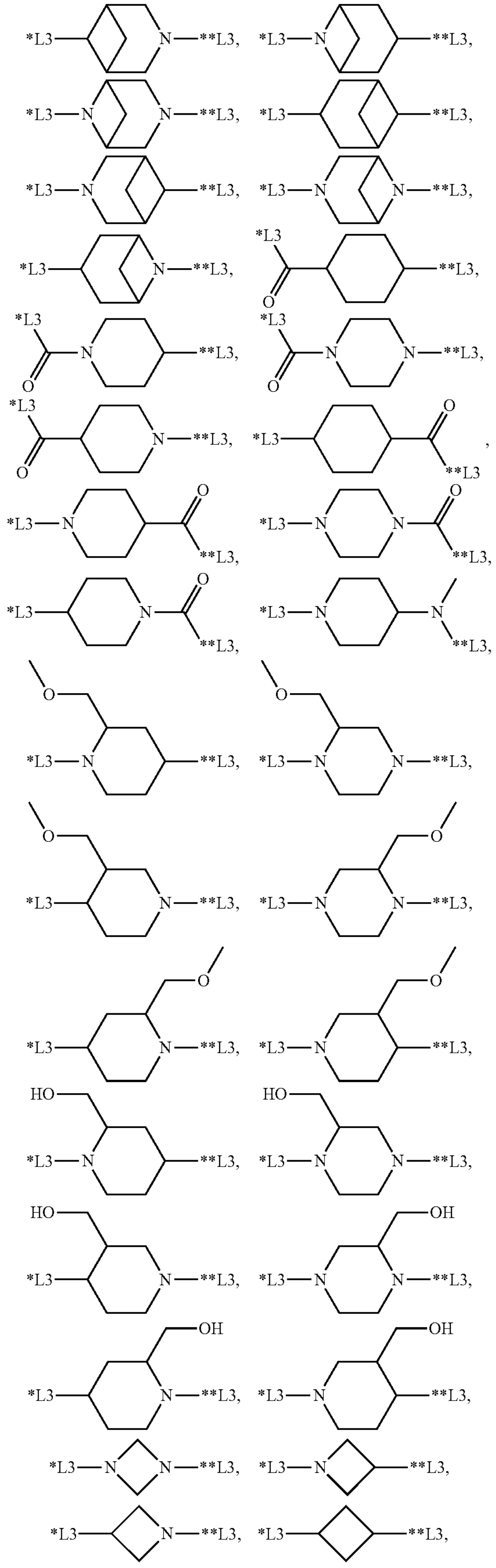

-continued
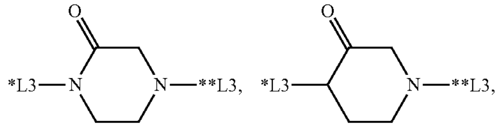
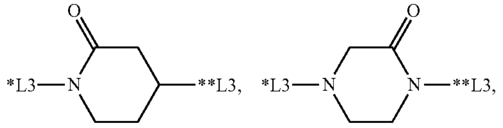
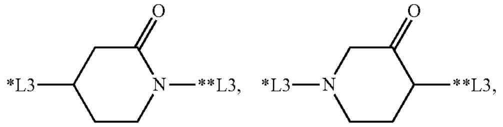
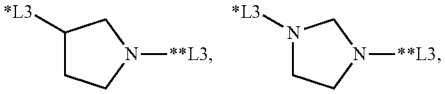
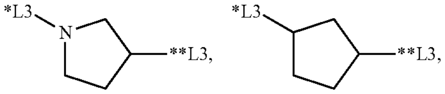
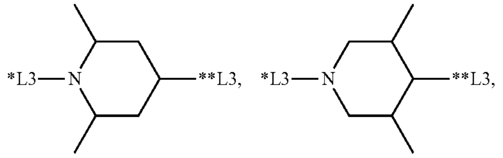
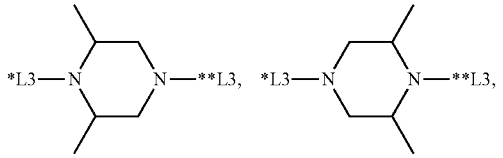
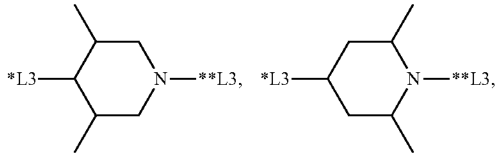
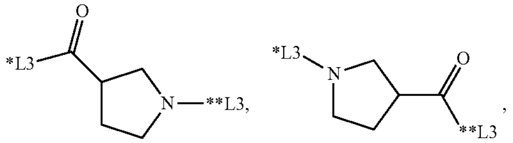
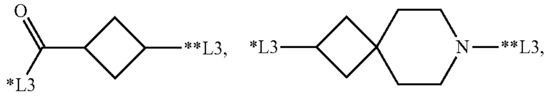
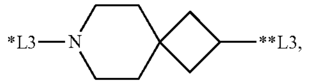
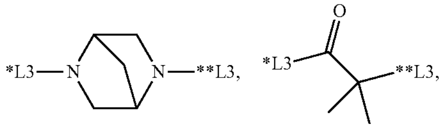
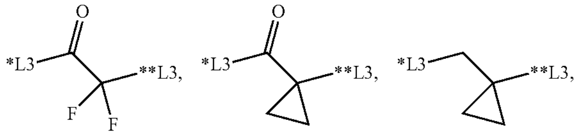
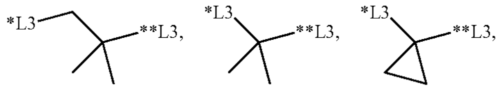
-continued
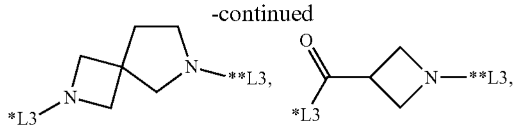
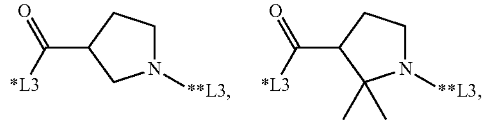
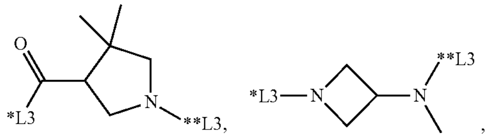
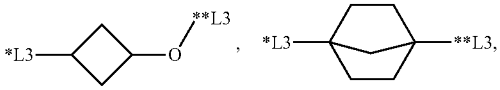
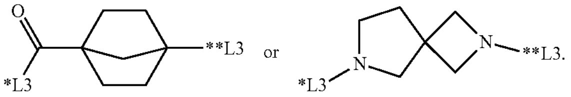
19. The compound of claim 1, wherein
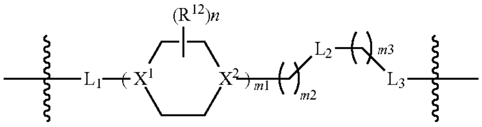
is selected from $—CH_2CH_2—$,
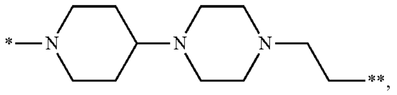
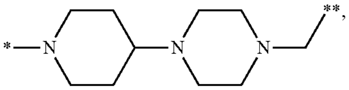
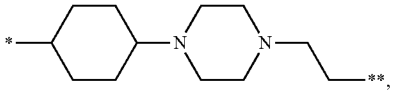
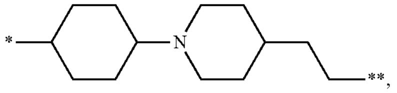
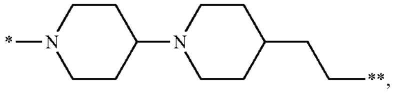
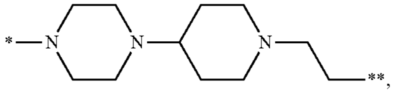
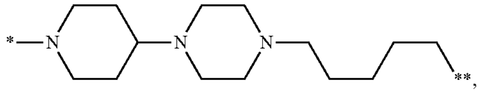
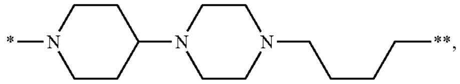
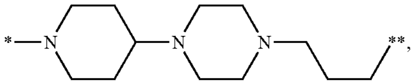

-continued
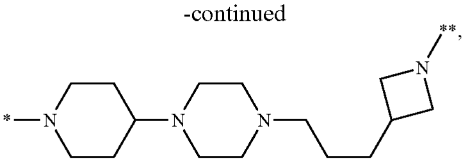
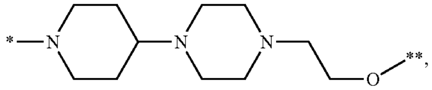
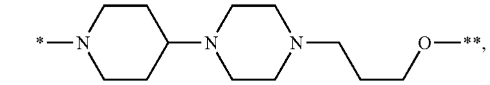
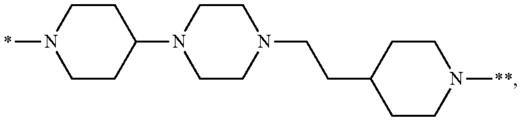
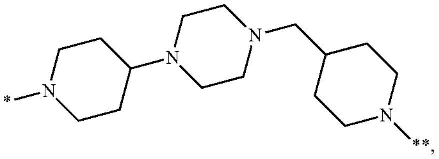
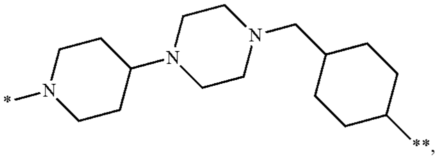
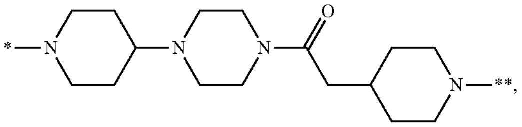
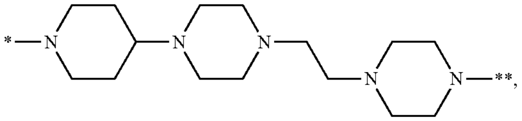
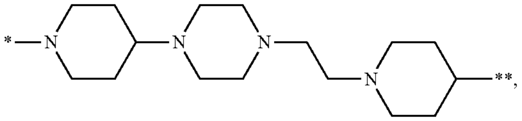
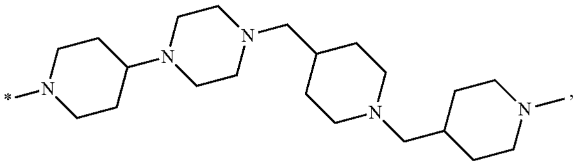
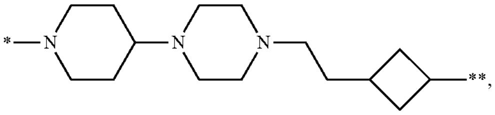
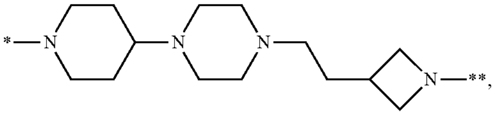
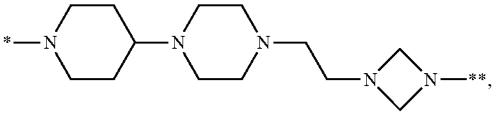
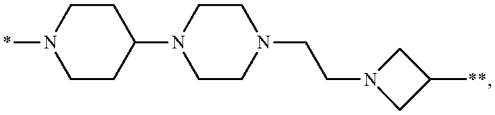
-continued
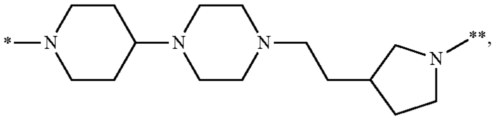
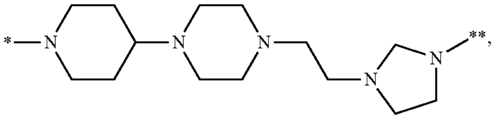
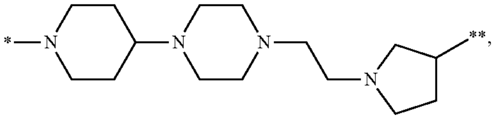
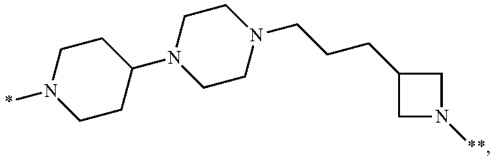
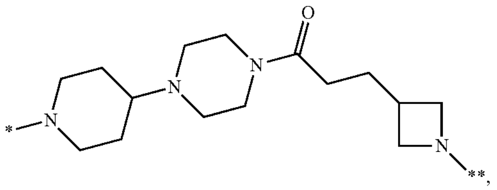
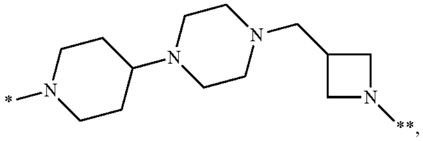
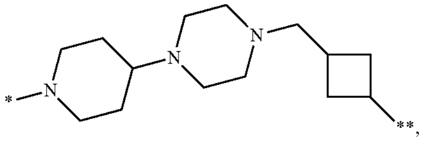
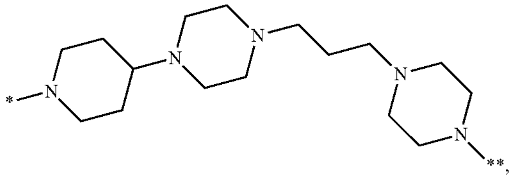
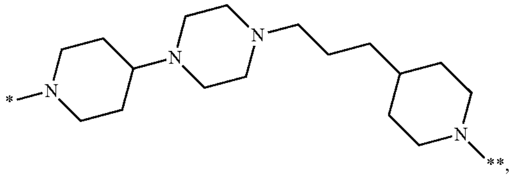
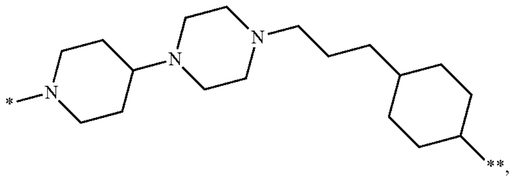
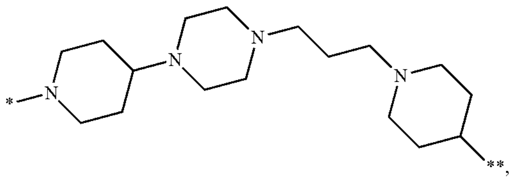

-continued
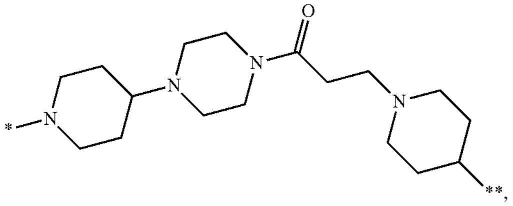
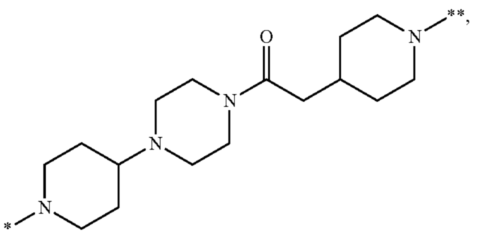
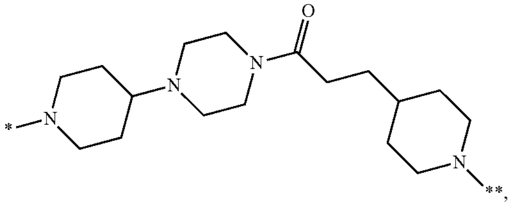
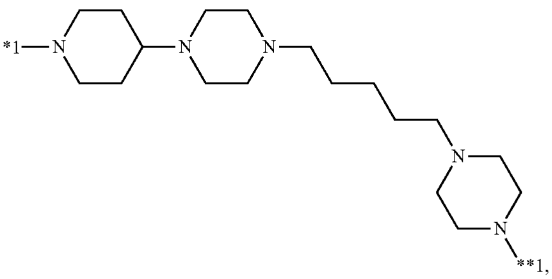
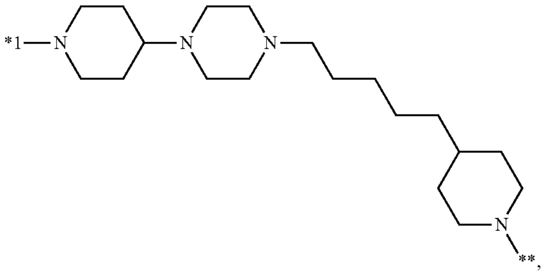
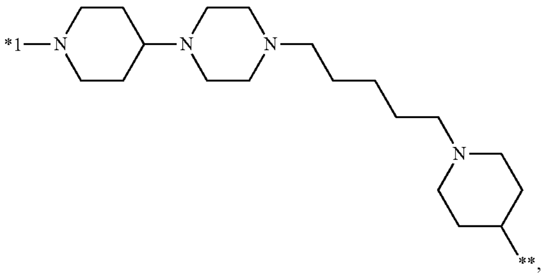
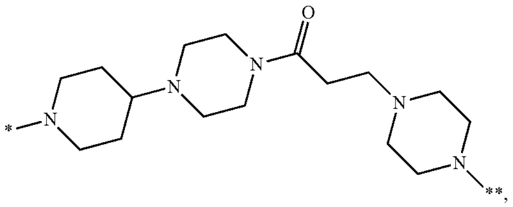
-continued
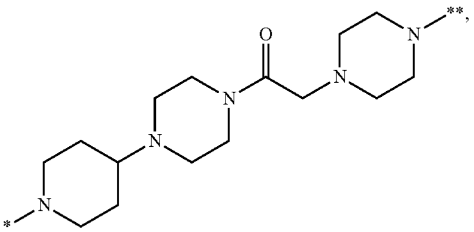
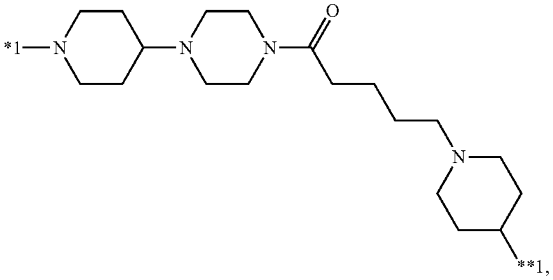
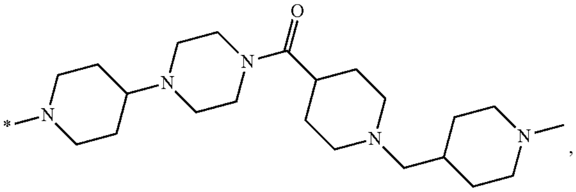
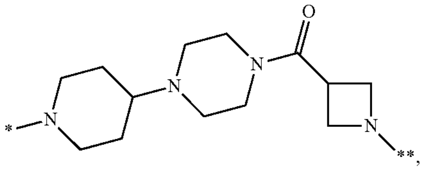
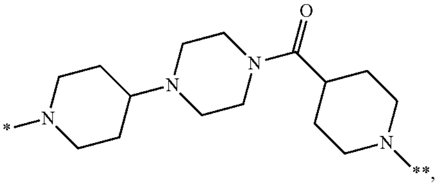
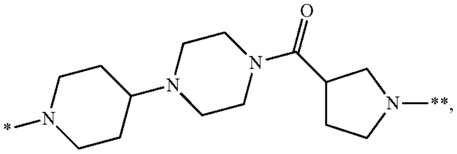
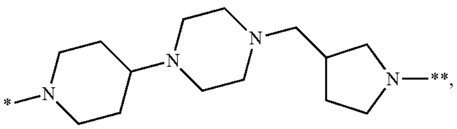
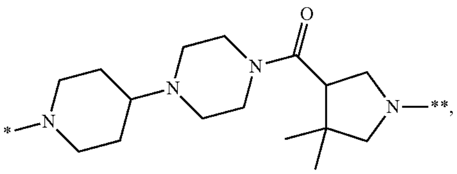
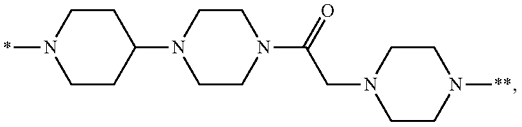

-continued
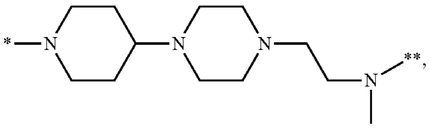
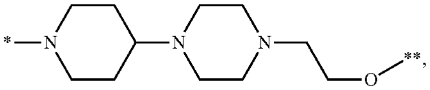
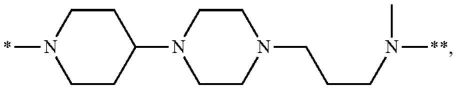
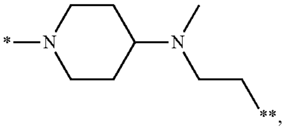
10-4
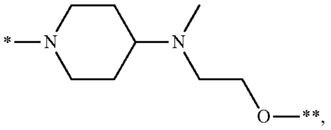
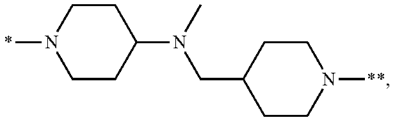
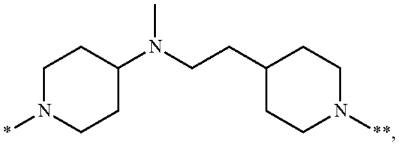
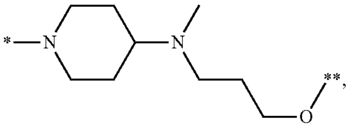
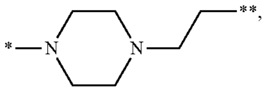
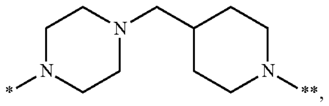
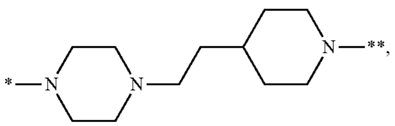
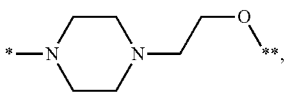
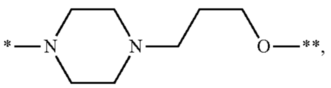
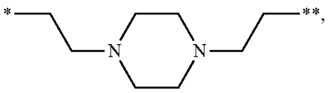
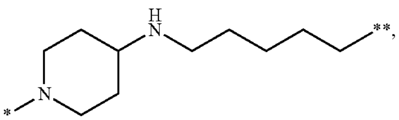
-continued
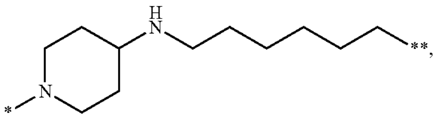
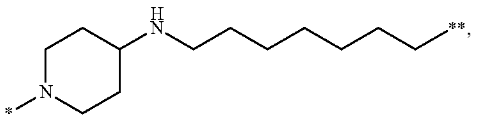
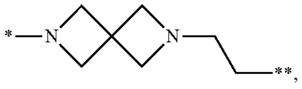
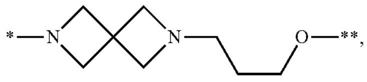
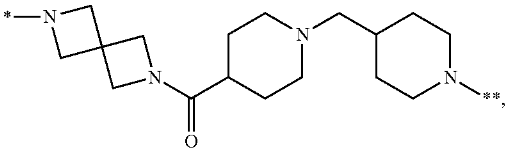
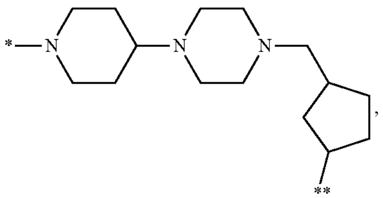
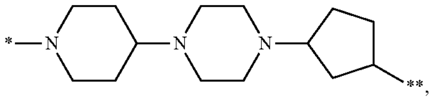
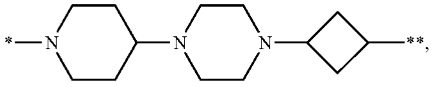
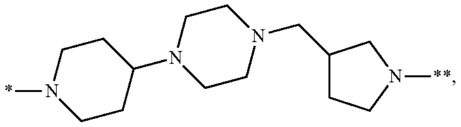
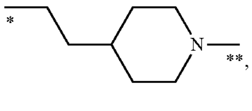
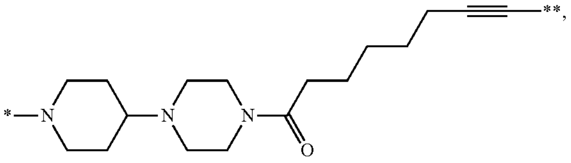
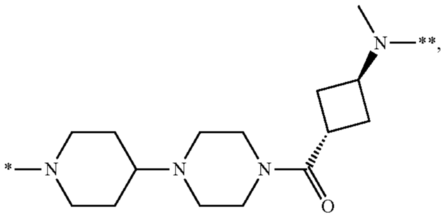

-continued
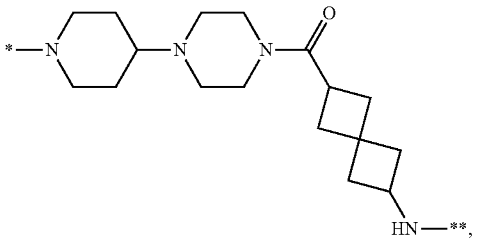
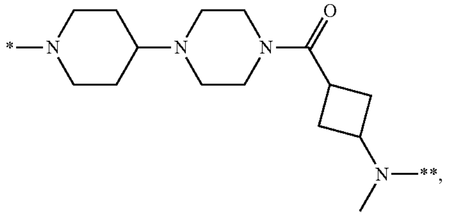
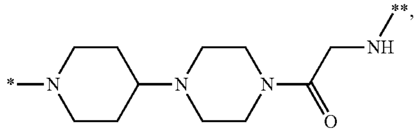
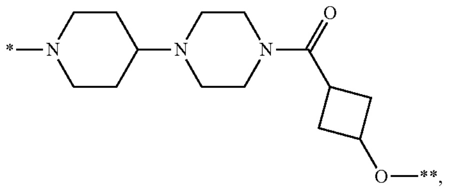
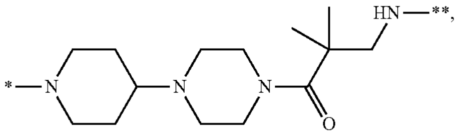
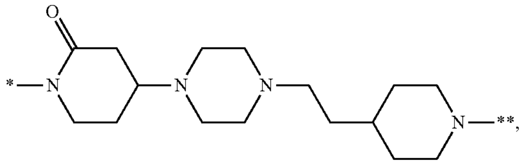
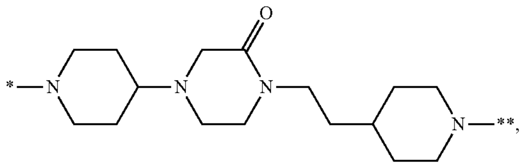
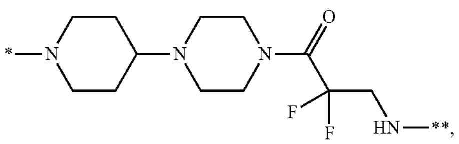
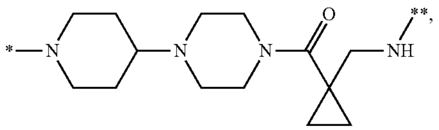
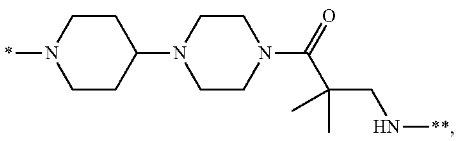
-continued
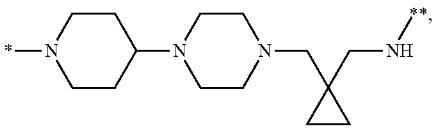
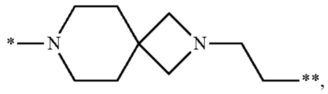
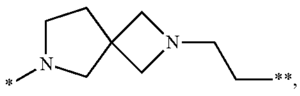
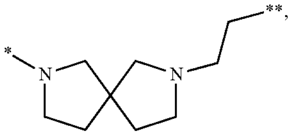
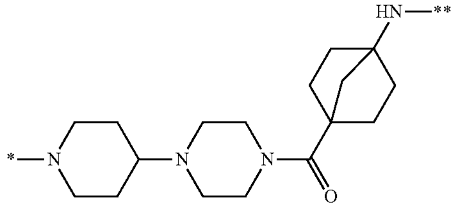
or
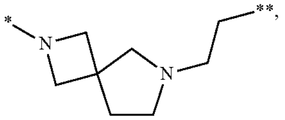
wherein * refers to the position attached to
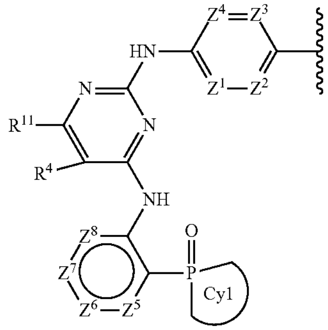
moiety, and ** refers to the position attached to the
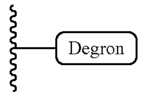
moiety.
20. The compound of claim 1, wherein
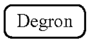

is selected from

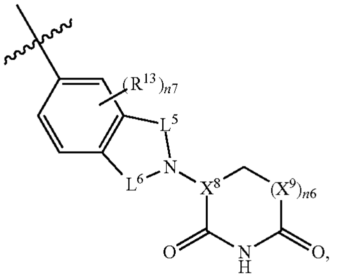

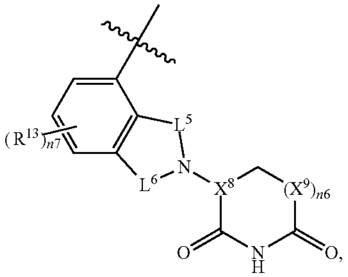

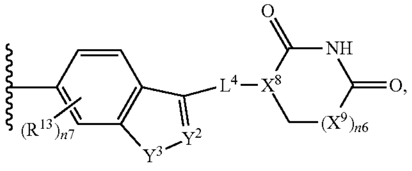

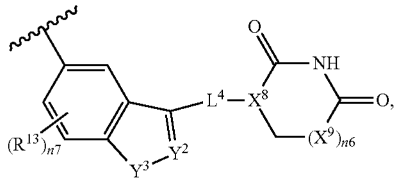

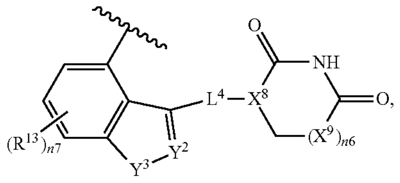

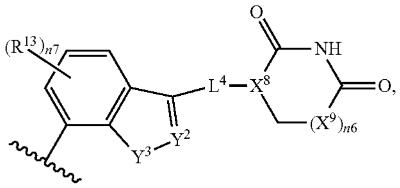

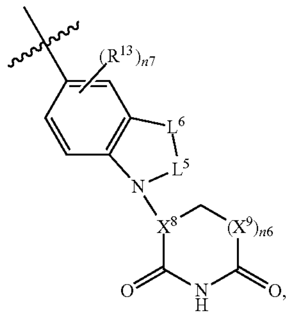

-continued

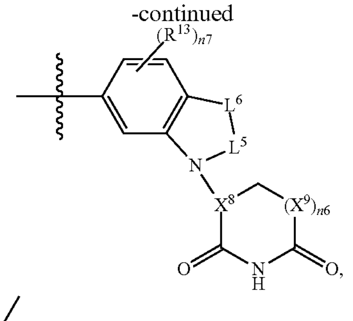

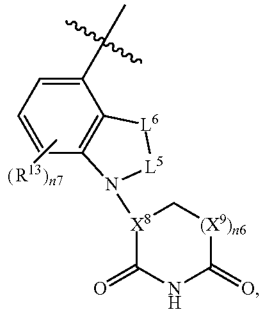

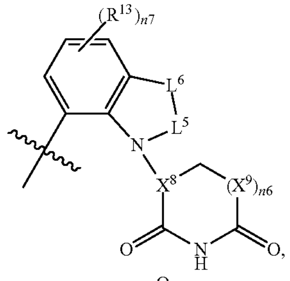

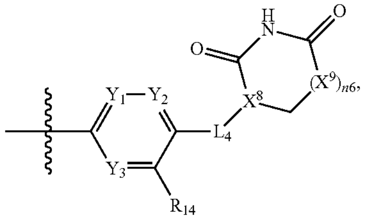

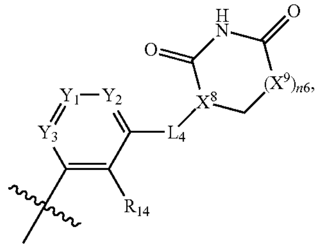

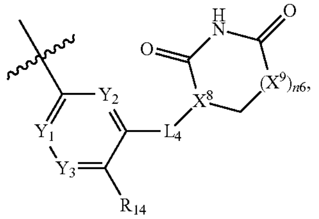

or

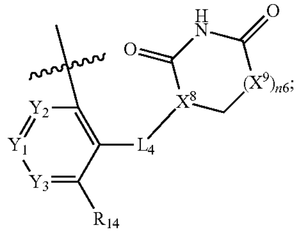

$R^{14}$ is independently selected from hydrogen, halogen, —$C_{1-8}$alkyl, —$C_{1-8}$alkoxy, or CN; said each —$C_{1-8}$ alkyl, or —$C_{1-8}$alkoxy is optionally substituted by one or more halogen or —$C_{1-8}$alkyl; optionally $R^{14}$ is independently selected from H, F, Cl, Br, I, $CH_3$, —$OCH_3$, $CH_2F$, CN, $CHF_2$, or $CF_3$;

$X^8$ is independently selected from CH, CD, $C(CH_3)$, $C(C_2H)$, $C(C_3H_7)$, C(CN) or N;

$L^4$ is independently selected from a single bond,

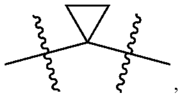 [SMILES: *C1(*)CC1]

,

—O—, —NH—, —$CH_2$—, —CHF—, or —$CF_2$—;

$Y^1$, $Y^2$, and $Y^3$ are each independently selected from $CR^a$ or N;

$X^9$ is $CH_2$;

$R^a$ is each independently selected from hydrogen, halogen, —$C_{1-8}$alkyl, or $C_{1-8}$alkoxy, wherein each of said —$C_{1-8}$alkyl or —$C_{1-8}$alkoxy is optionally substituted with at least one or more halogen, hydroxy, halogen, —$C_{1-8}$alkyl, or —$C_{1-8}$alkoxy; and n6 is independently 0, 1 or 2.

21. The compound of claim 1, wherein

Degron is

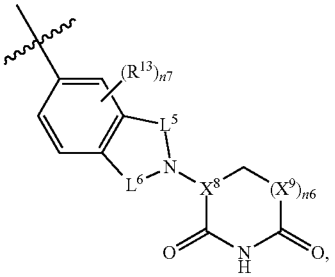

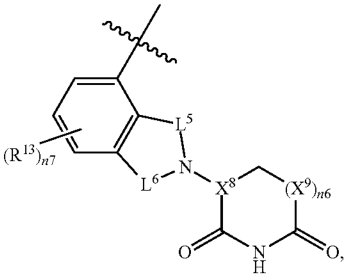

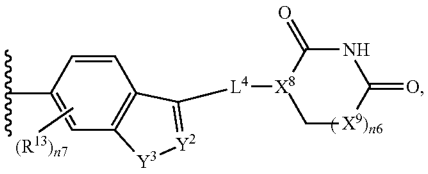

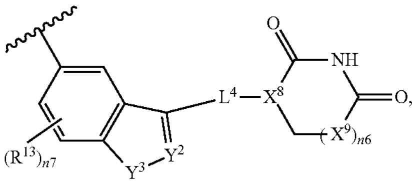

-continued

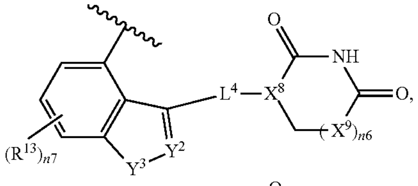

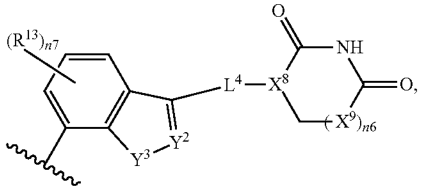

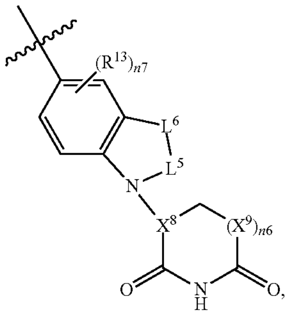

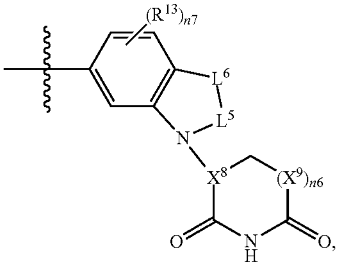

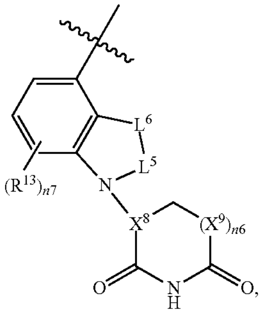

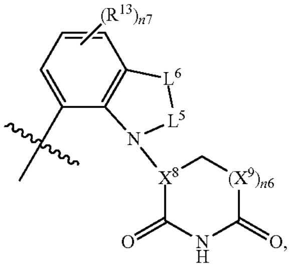

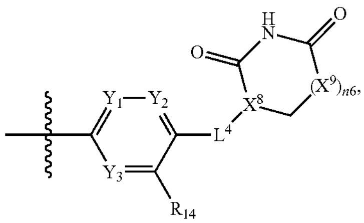

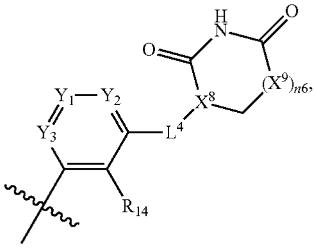

-continued

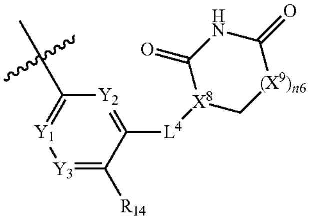

or

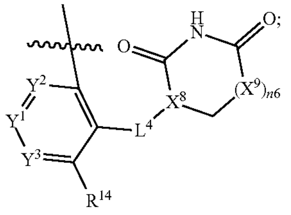

wherein $L^5$ and $L^6$ is independently selected from a single bond,

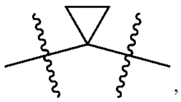 [SMILES: *C1(*)CC1]

,

—O—, —NH—, —NMe-, —$N(CH_2CH_3)$—, —$CH_2$—, —CHF—, —$CF_2$—, —$C(CH_3)^2$— or —CO—, or wherein $L^5$ is —CO— or —$CH_2$—, and $L^6$ is

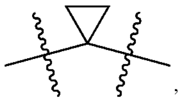 [SMILES: *C1(*)CC1]

,

—O—, —NH—, —NMe-, —$N(CH_2CH_3)$—, —$CH_2$—, —CHF—, —$CF_2$—, —$C(CH_3)^2$— or —CO—;

$X^9$ is $CH_2$;

each $R^{13}$ is independently selected from hydrogen, —F, —Cl, —Br, —I, CN, —$C_{1-8}$alkyl, or —$C_{1-8}$alkoxy;

$n_6$ is 0 or 1; and $n_7$ is 0, 12.

22. The compound of claim 1, wherein

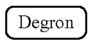

is selected from

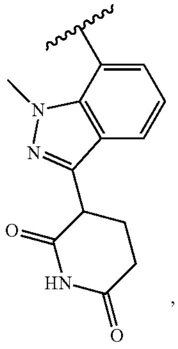

,

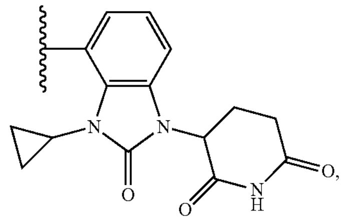

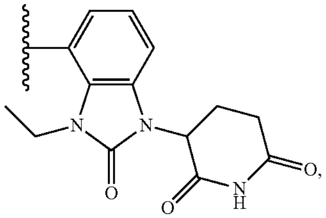

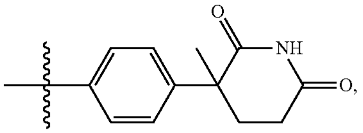

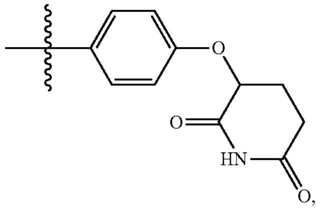

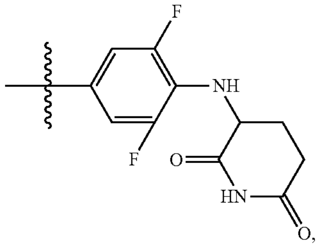

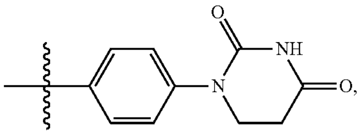

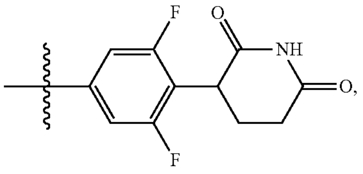

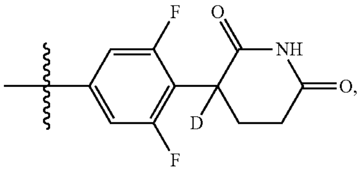

-continued
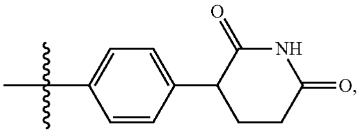
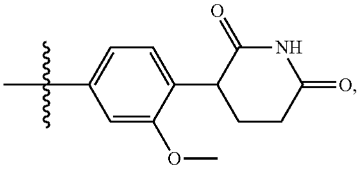
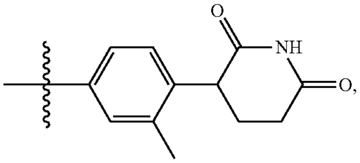
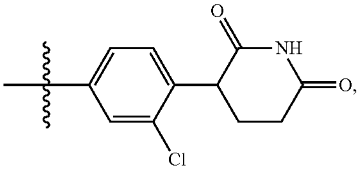
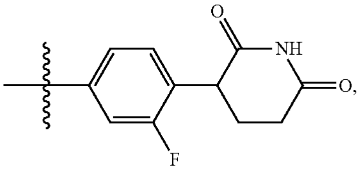
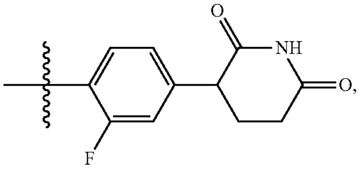
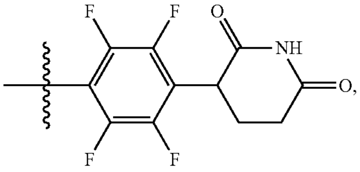
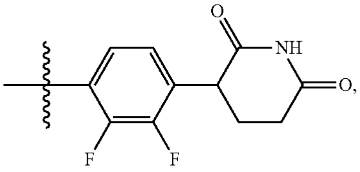
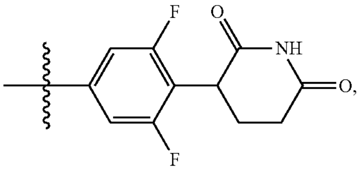
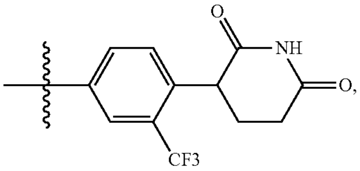
-continued
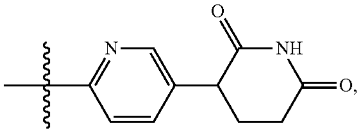
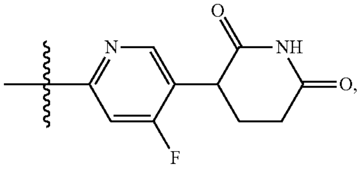
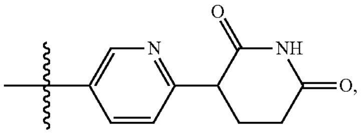
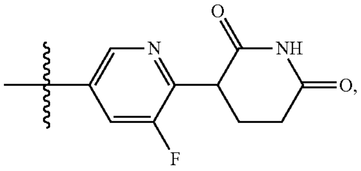
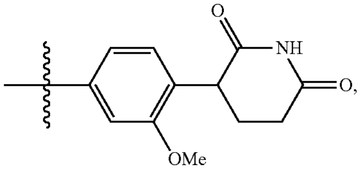
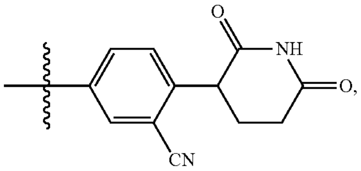
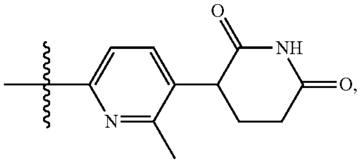
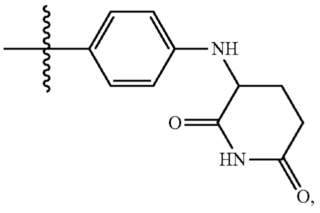
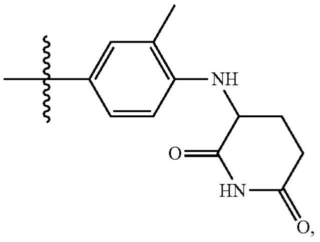

-continued
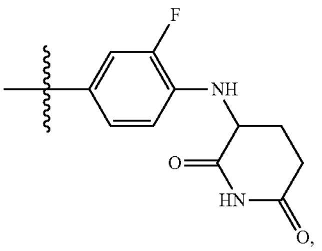
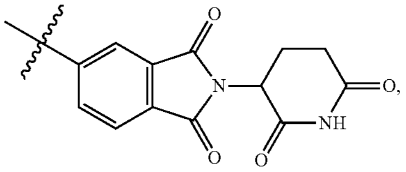
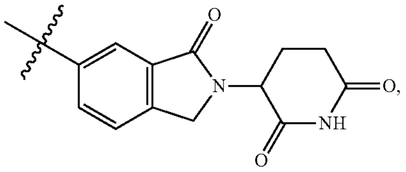
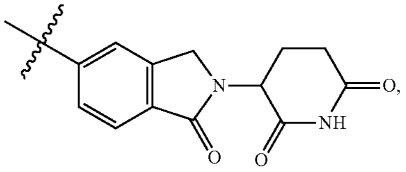
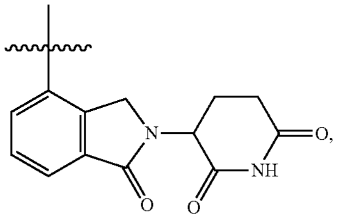
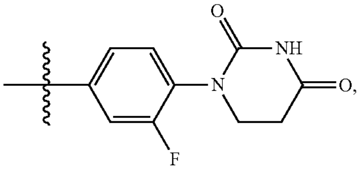
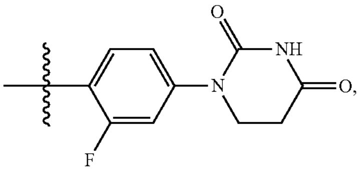
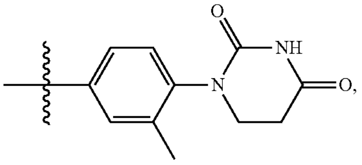
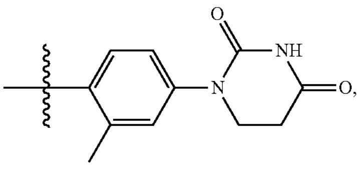
-continued
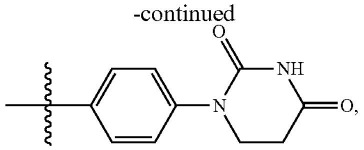
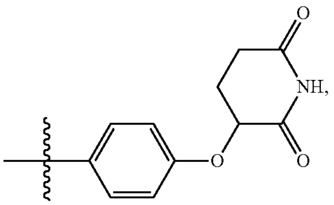
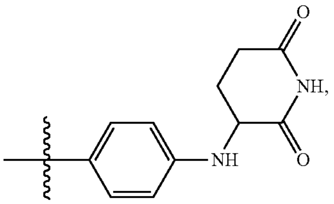
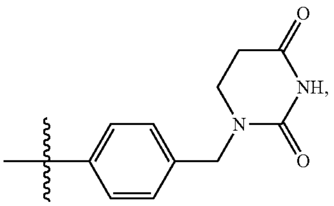
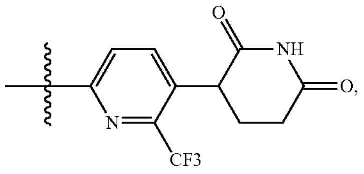
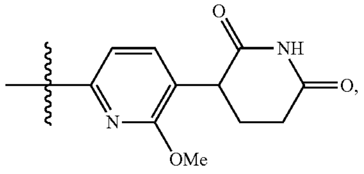
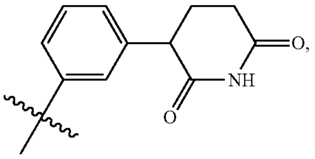
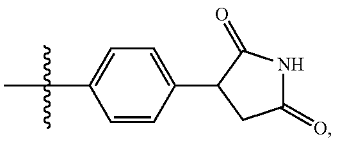
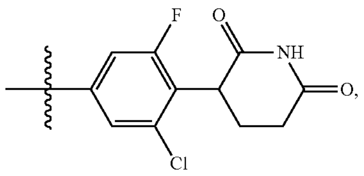
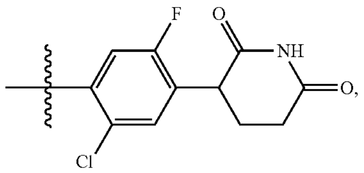

-continued
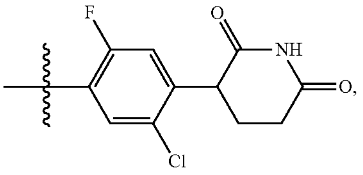
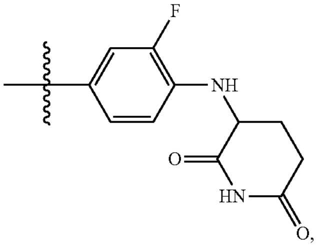
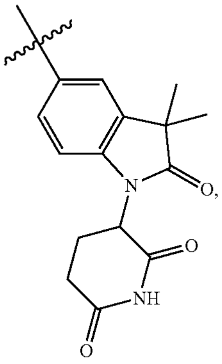
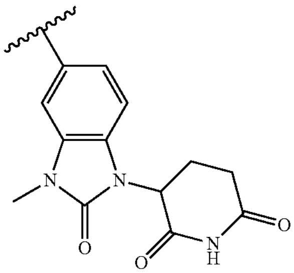
,
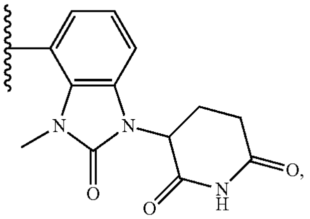
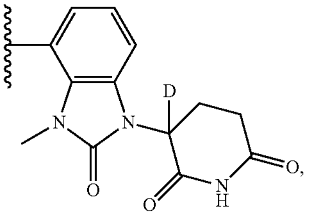
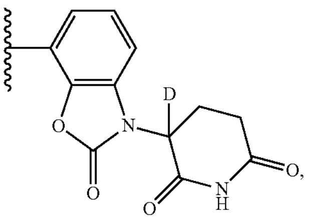
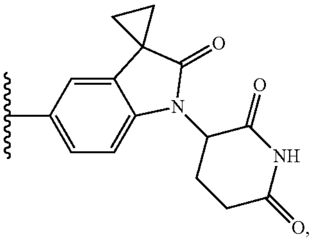
-continued
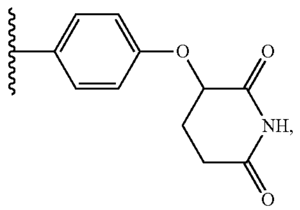
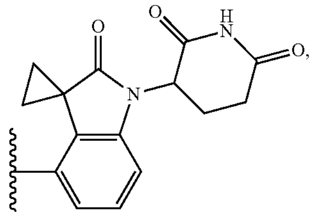
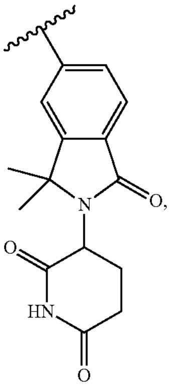
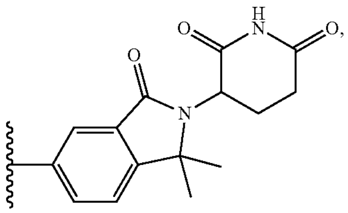
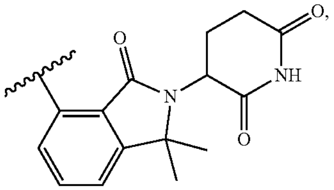
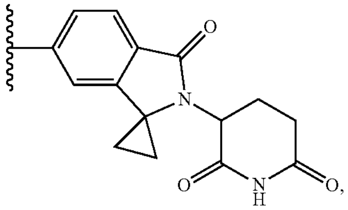
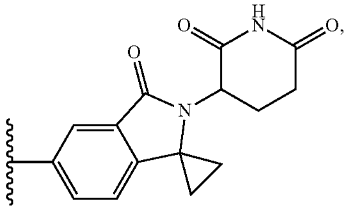
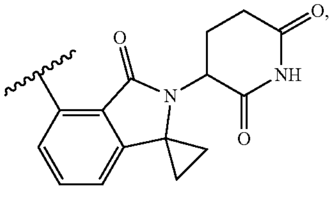

-continued
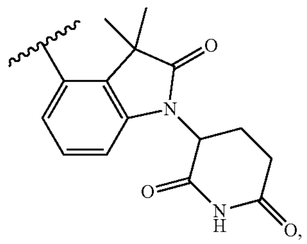
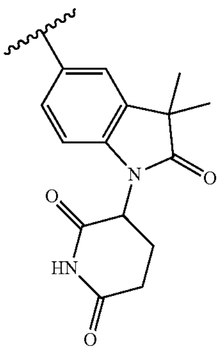
,
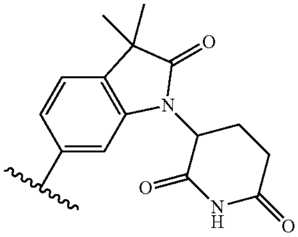
,
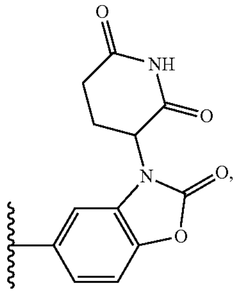
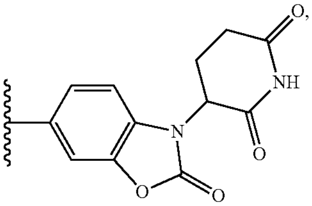
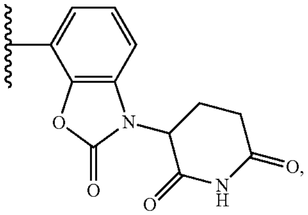
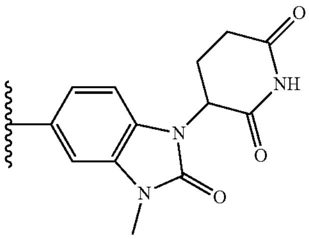
,
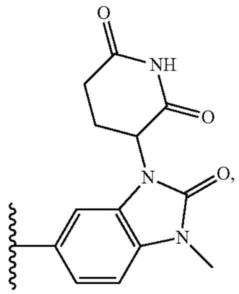
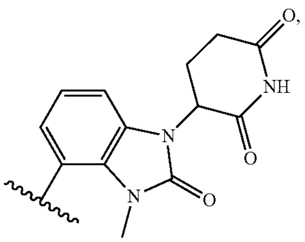
-continued
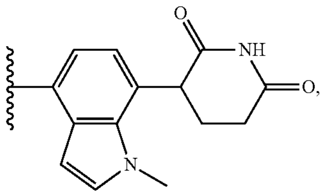
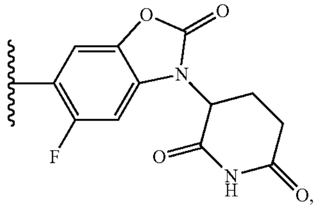
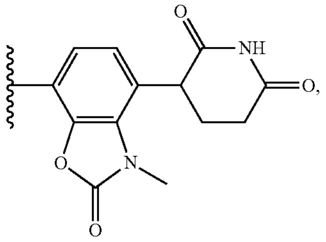
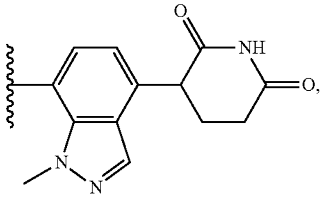
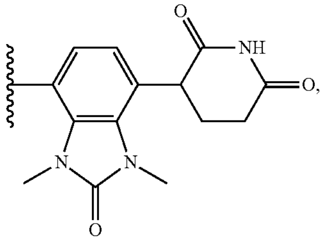
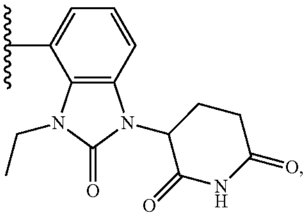
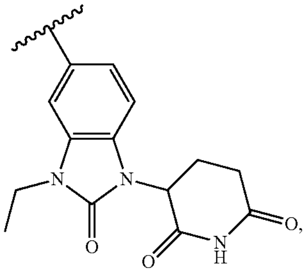

-continued
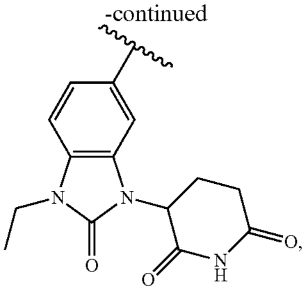
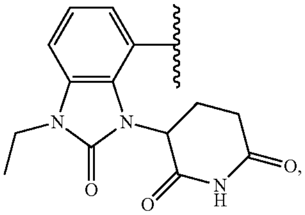
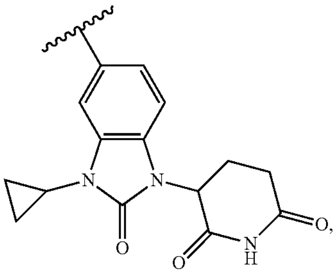
-continued
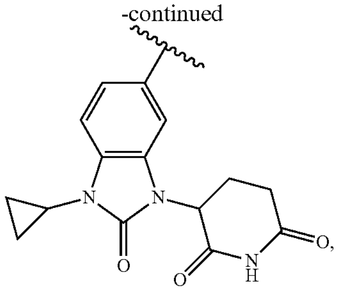
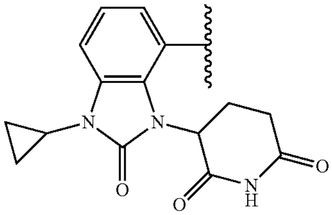 or
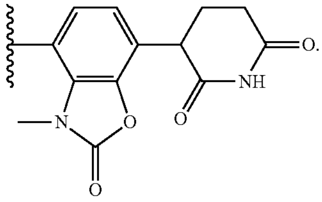
23. The compound of claim 1, wherein the compound is selected from
1
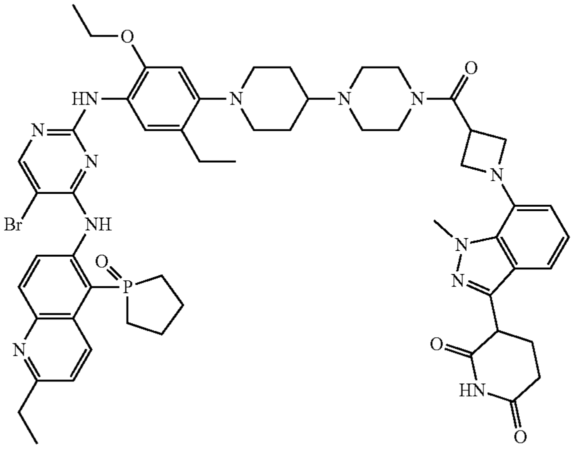

-continued
2
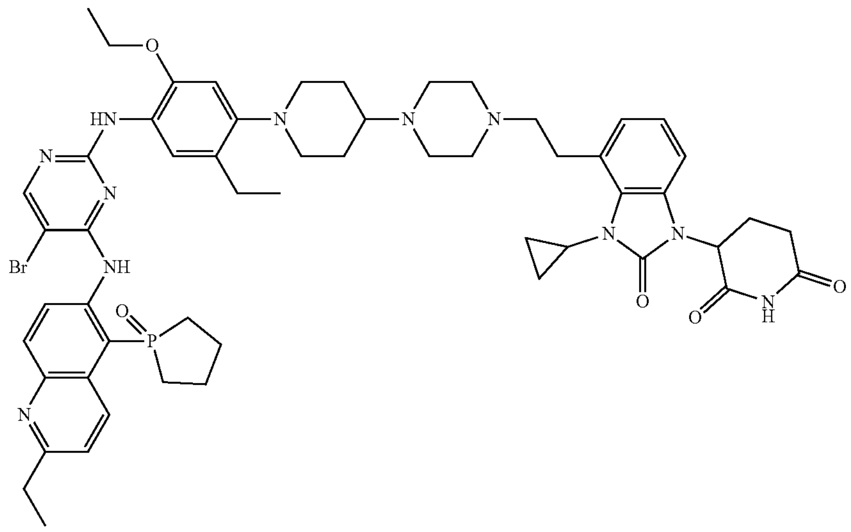
3
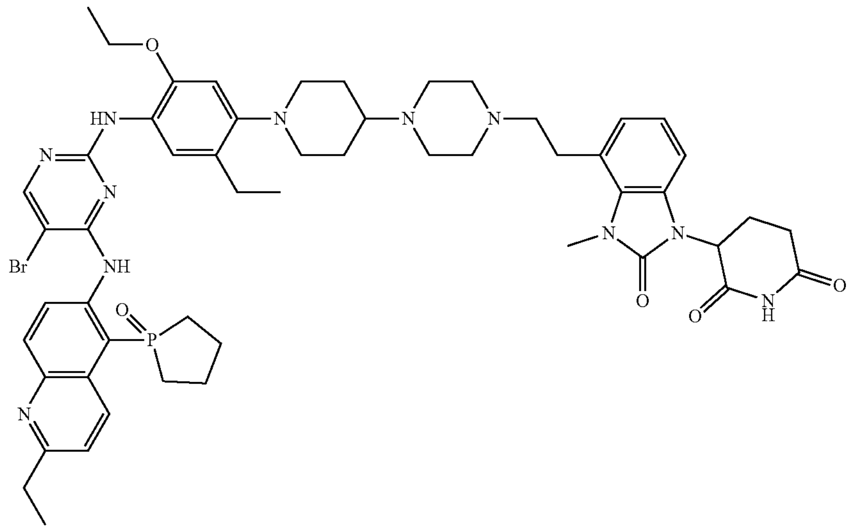
4
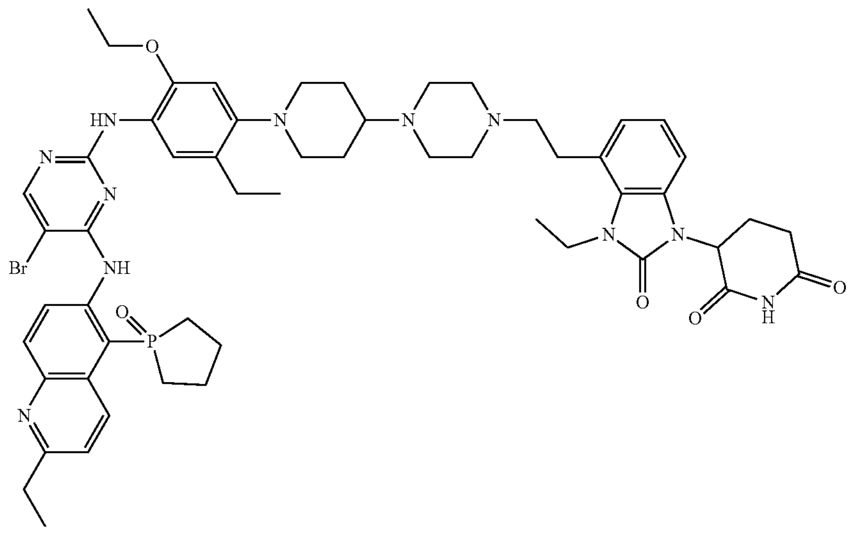

-continued
5
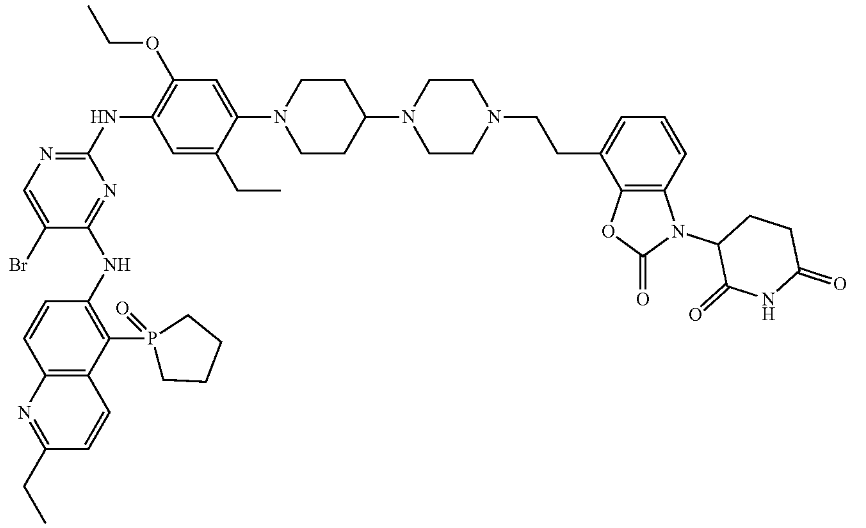
6
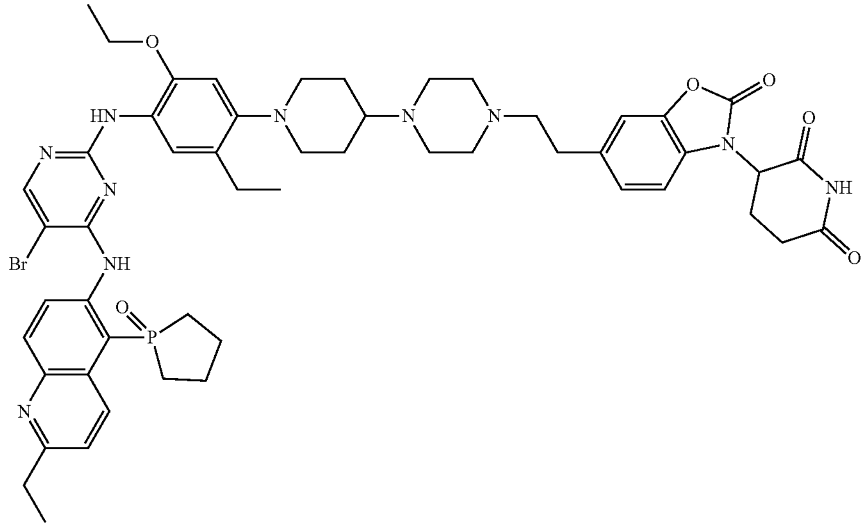
7
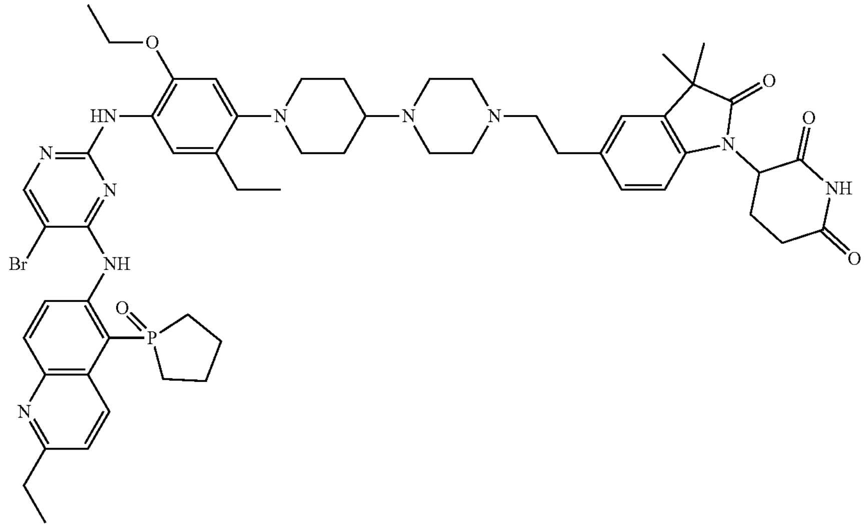

-continued
8
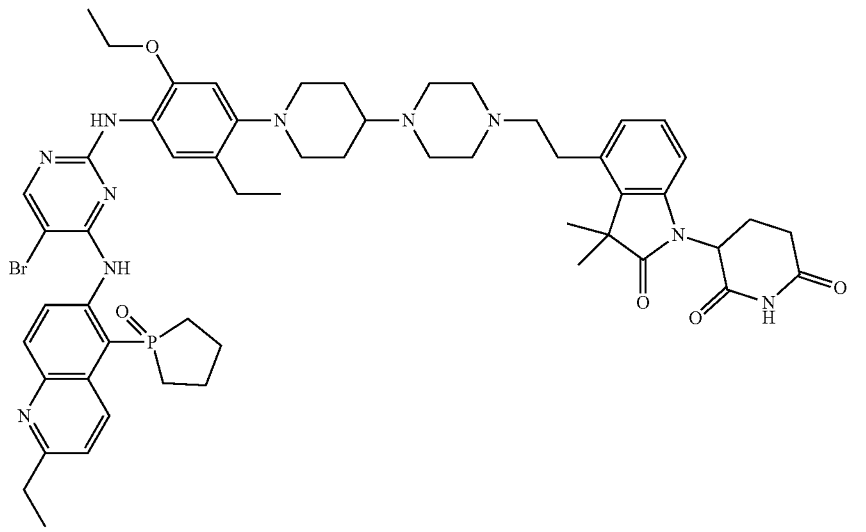
9
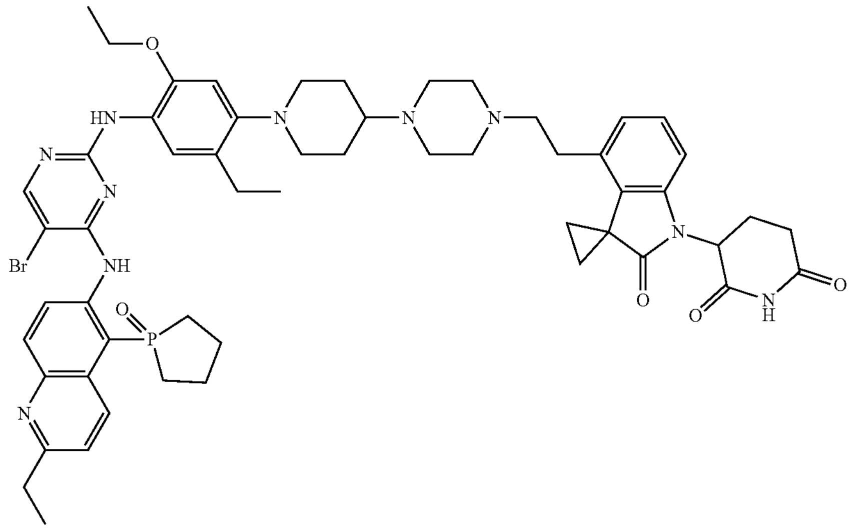
10
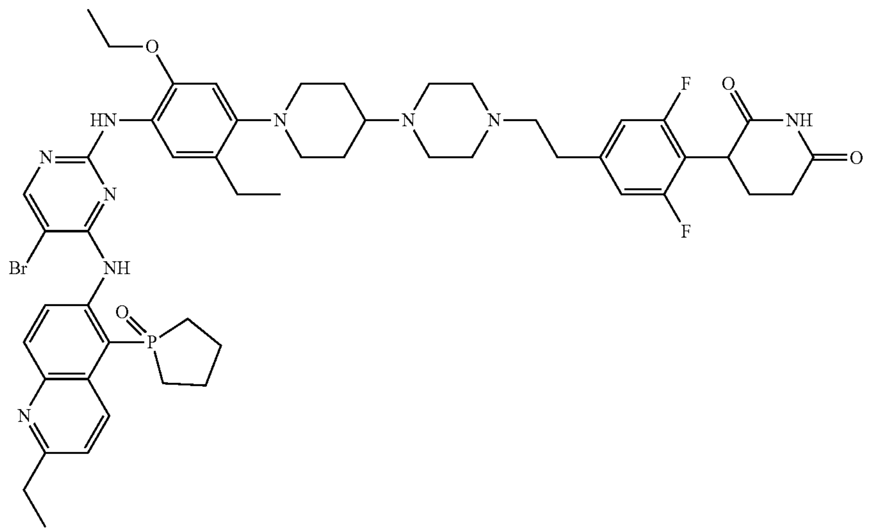

-continued
11
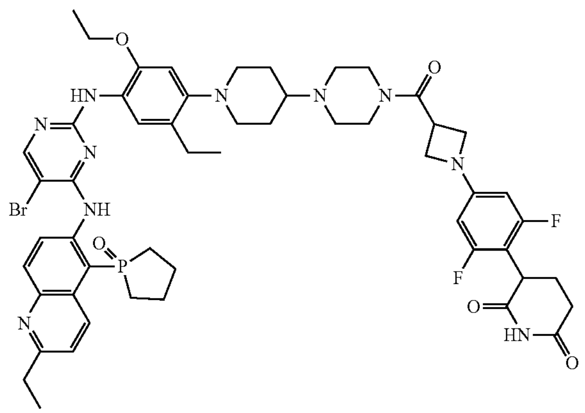
12
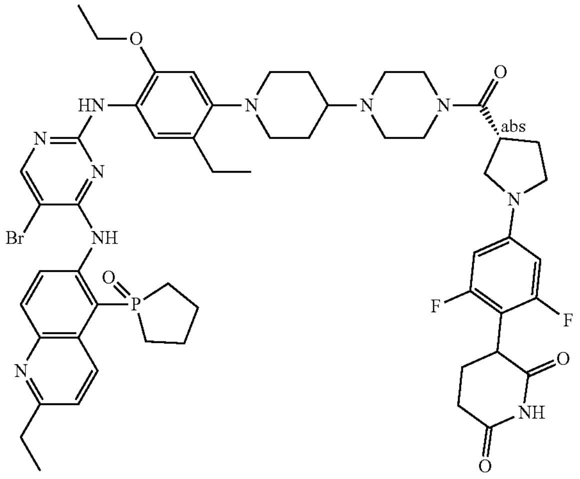
13
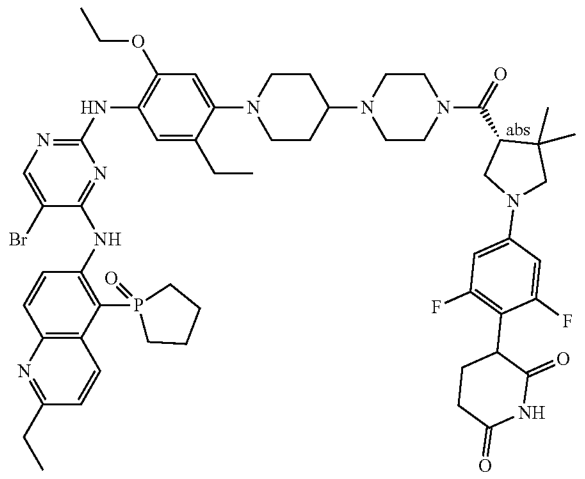
14
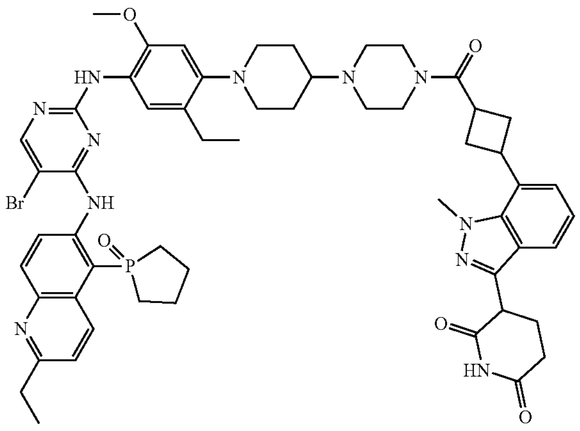
15
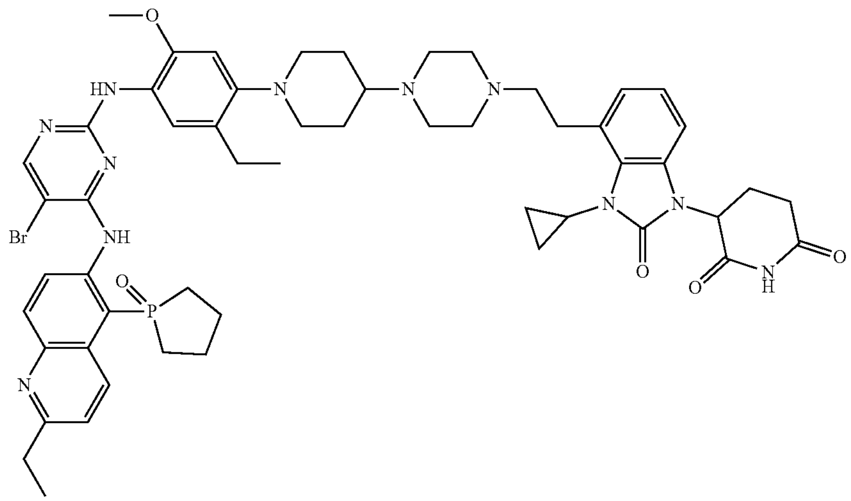

-continued
16
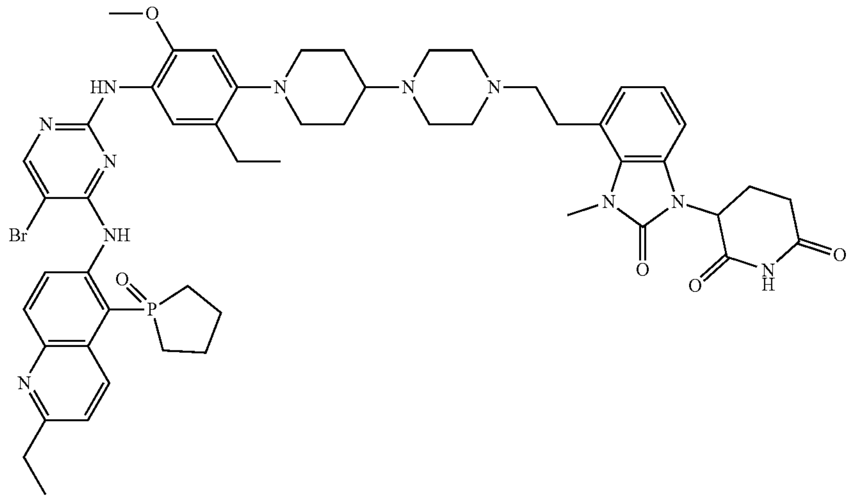
17
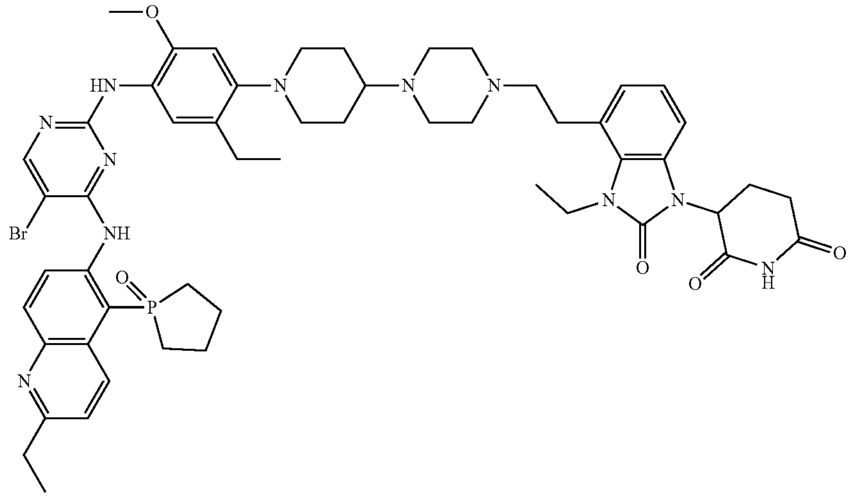
18
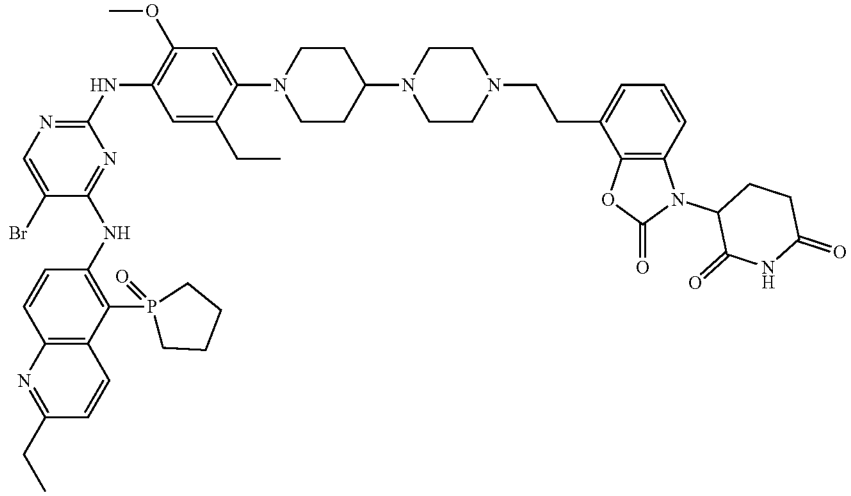

-continued
19
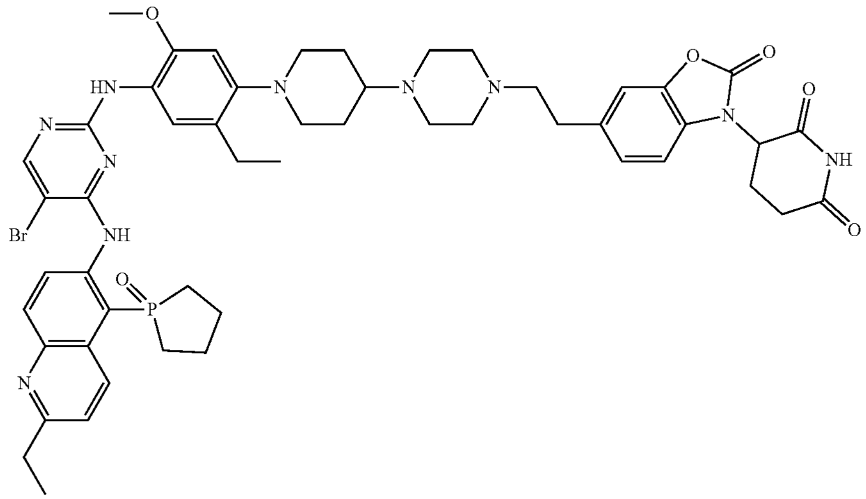
20
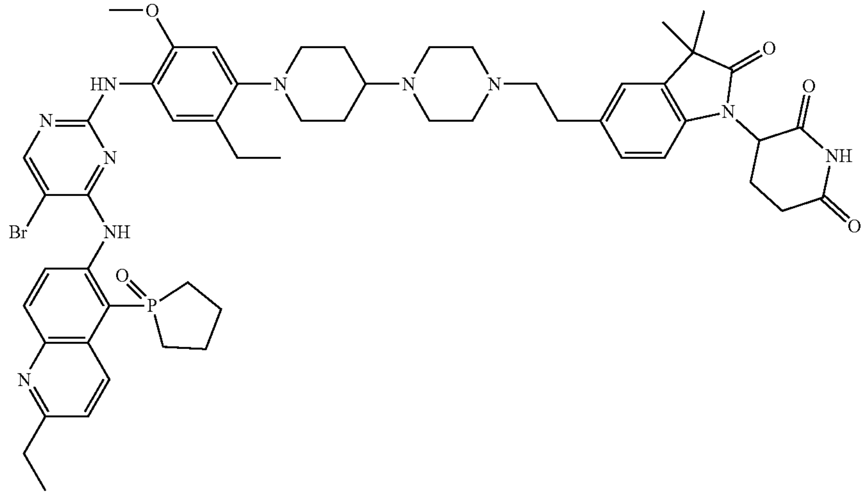
21
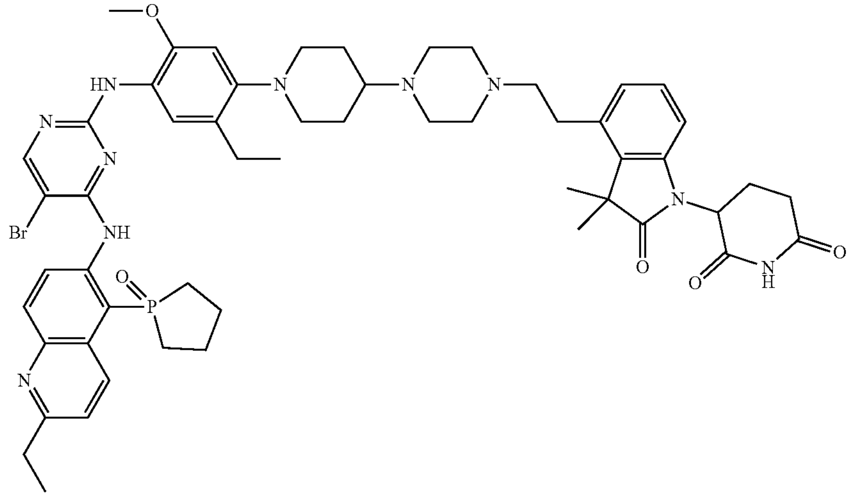

-continued
22
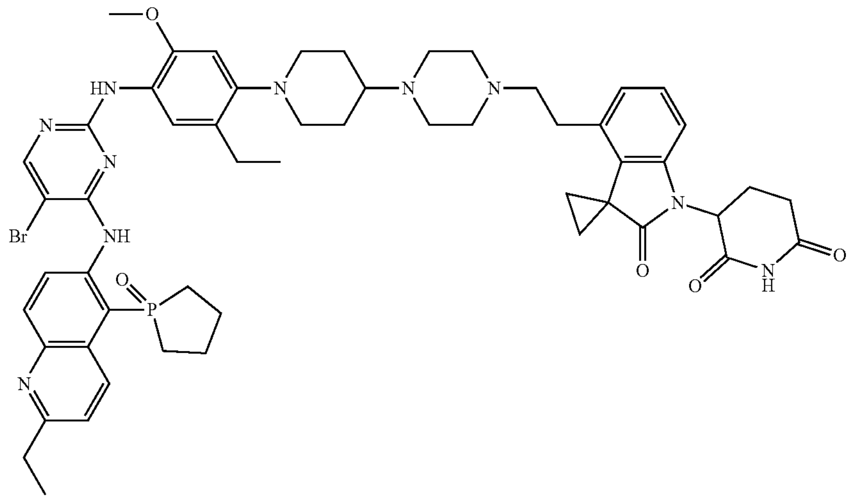
23
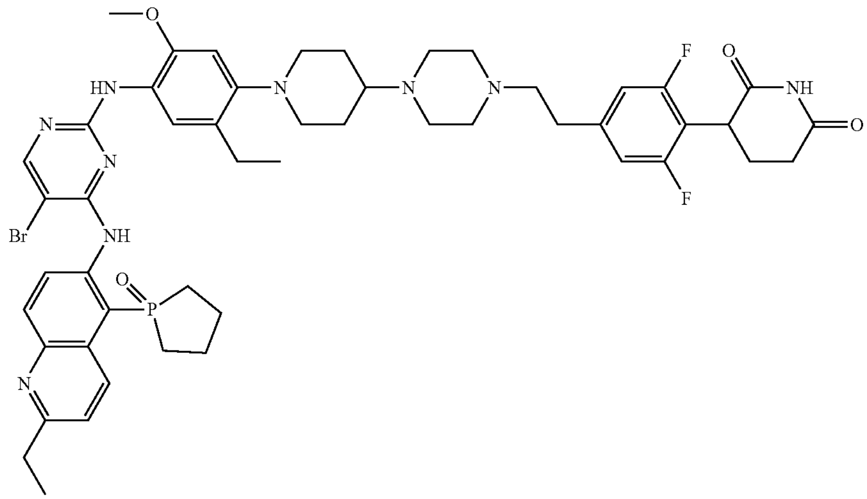
24
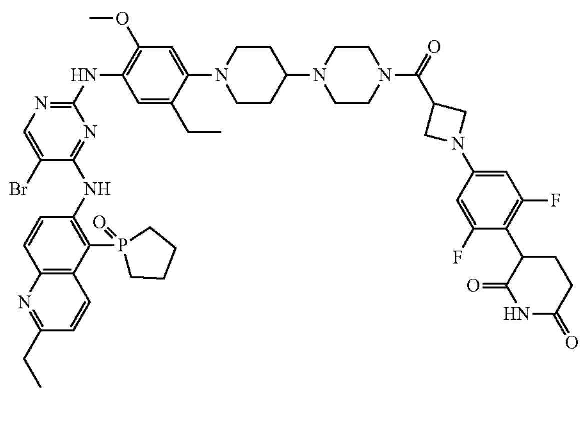
25
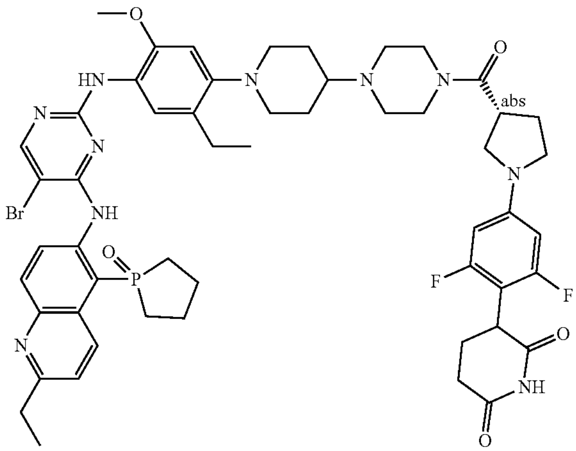

-continued
26
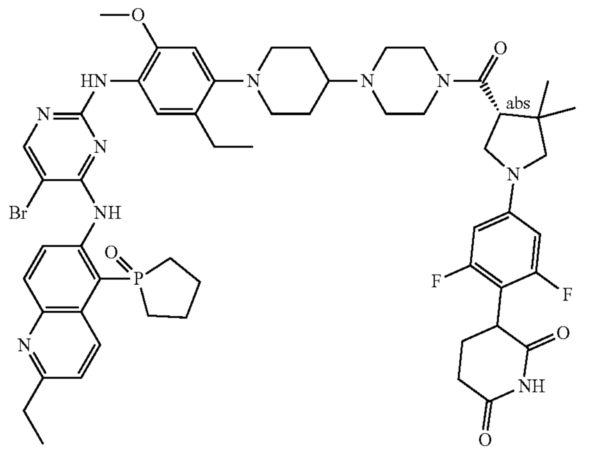
27
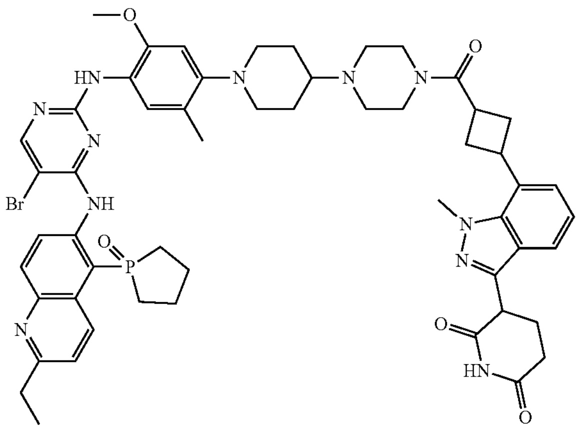
28
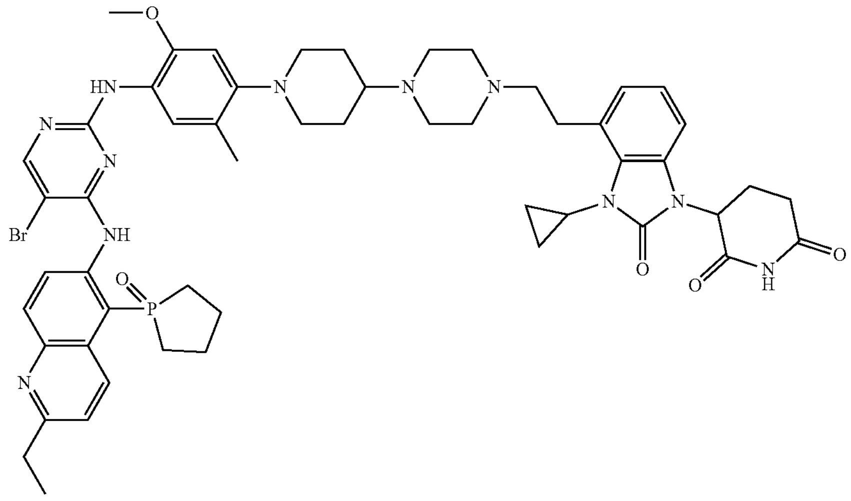
29
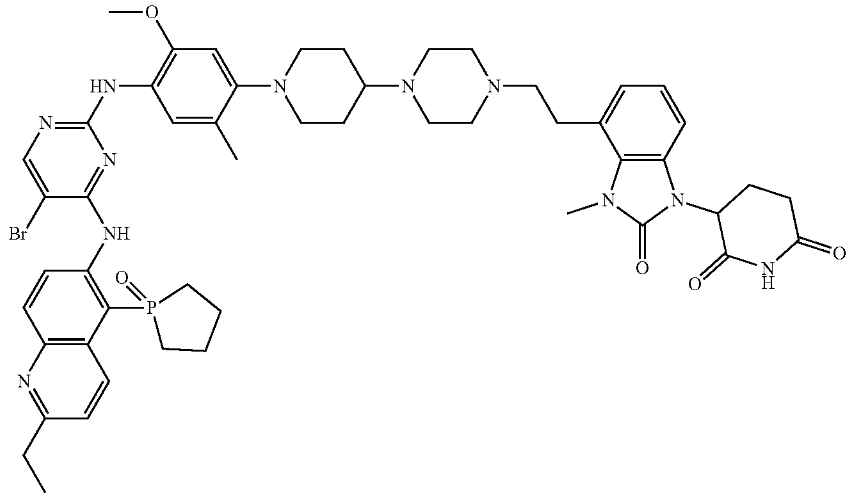

-continued
30
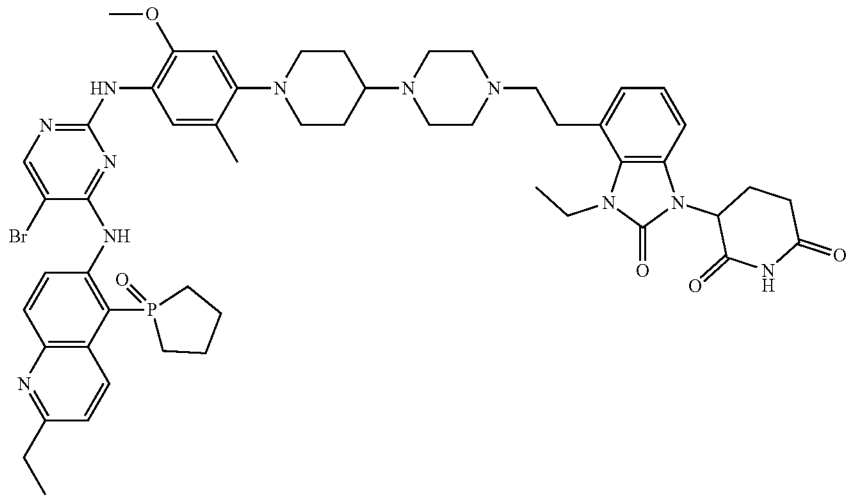
31
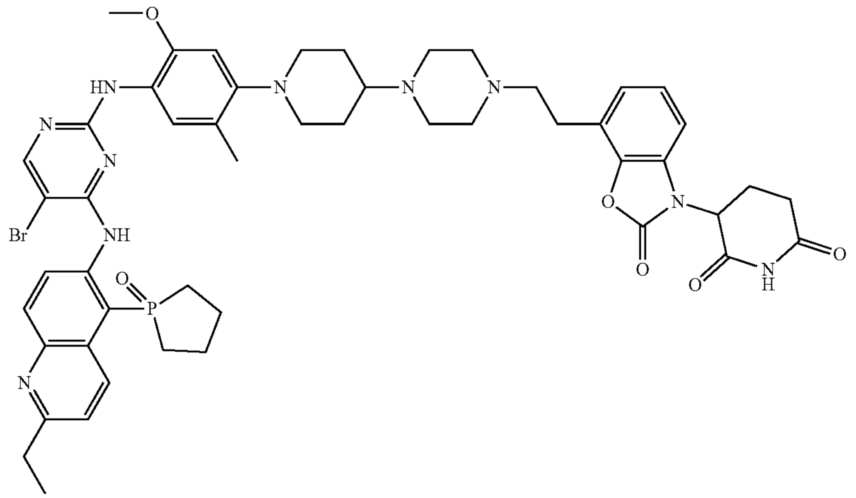
32
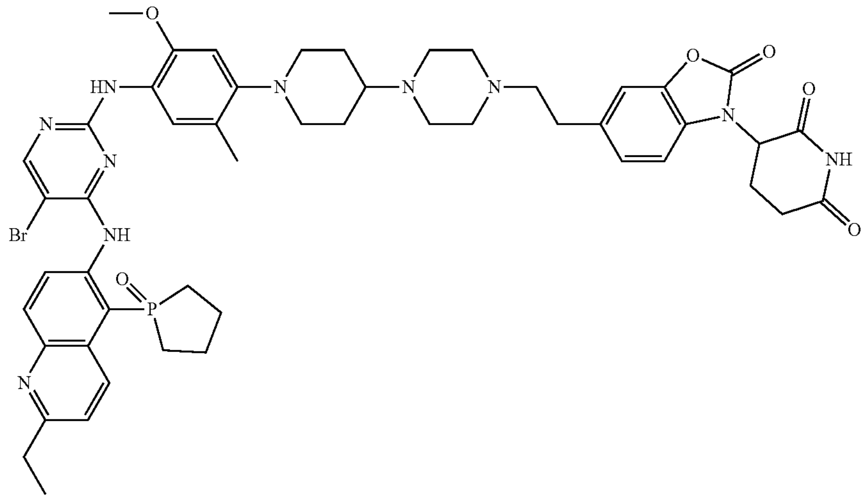

-continued
33
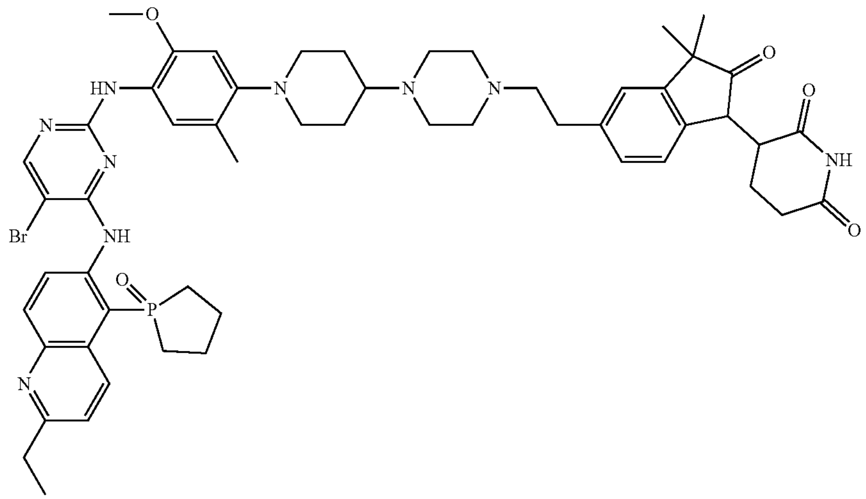
34
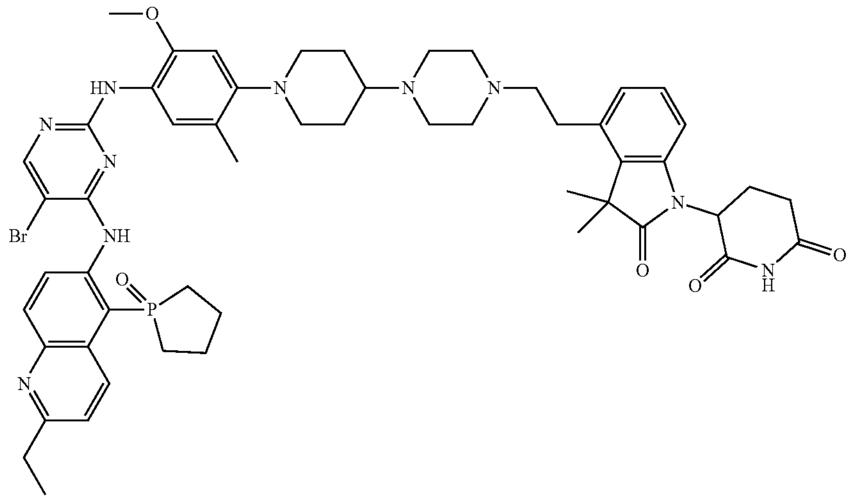
35
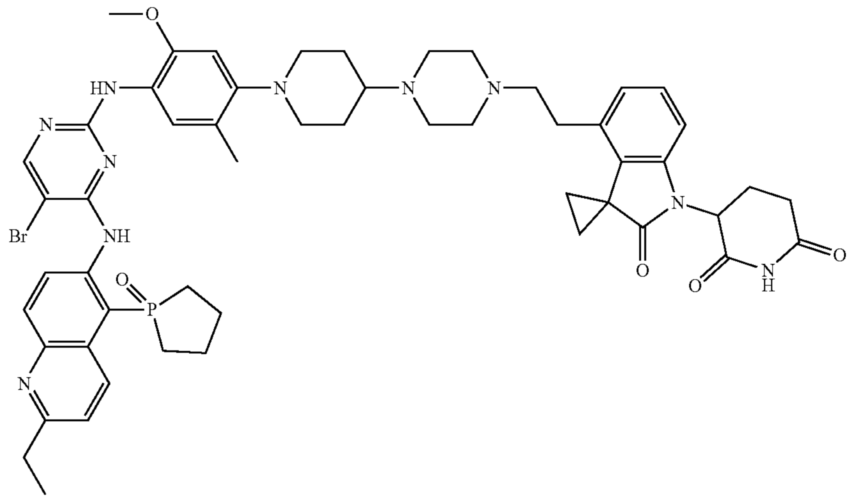

-continued
36
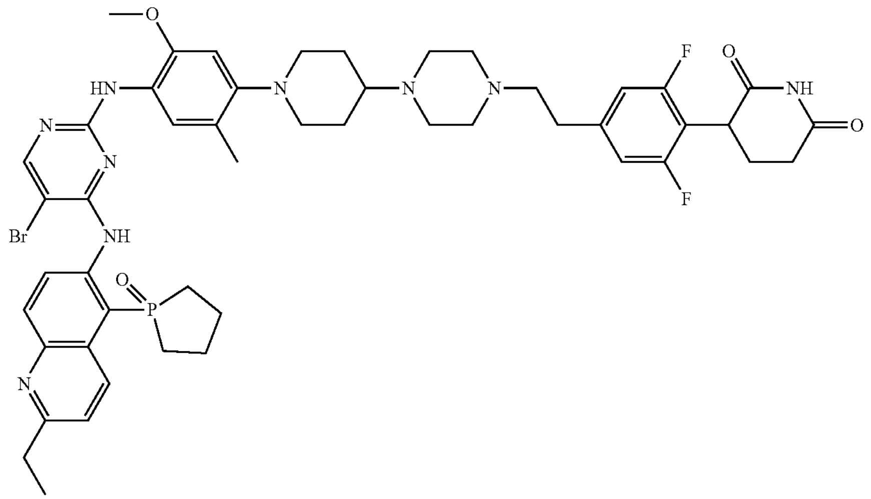
37
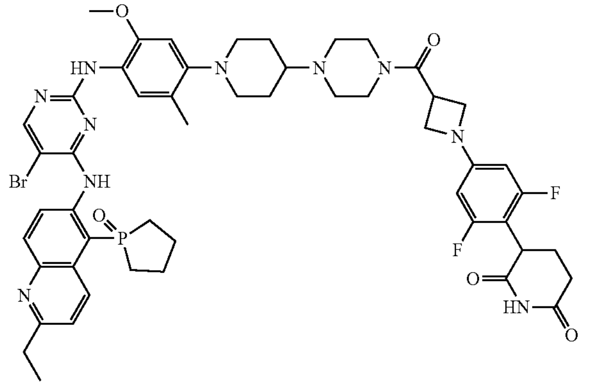
38
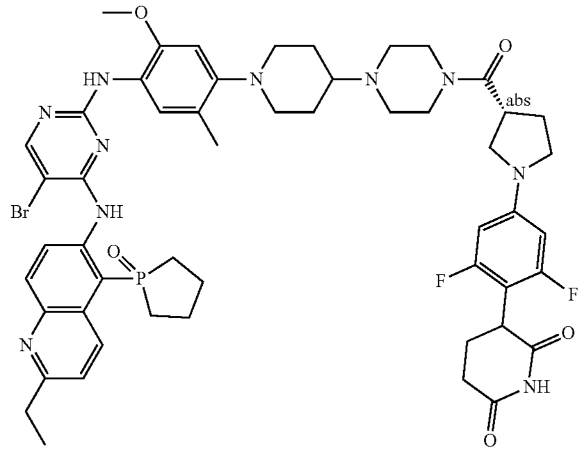
39
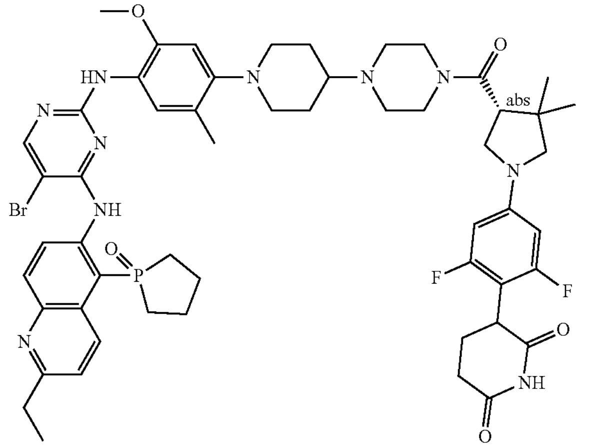
40
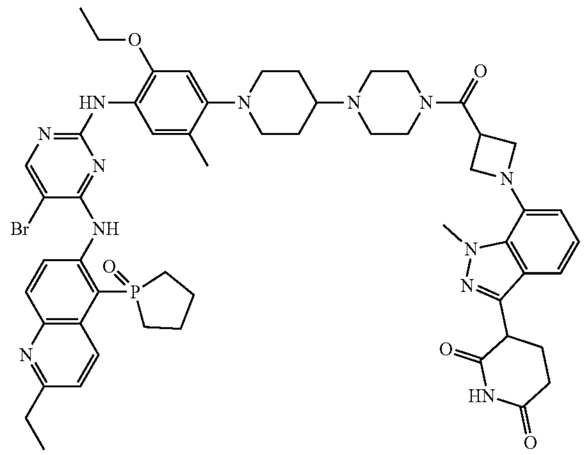

-continued
41
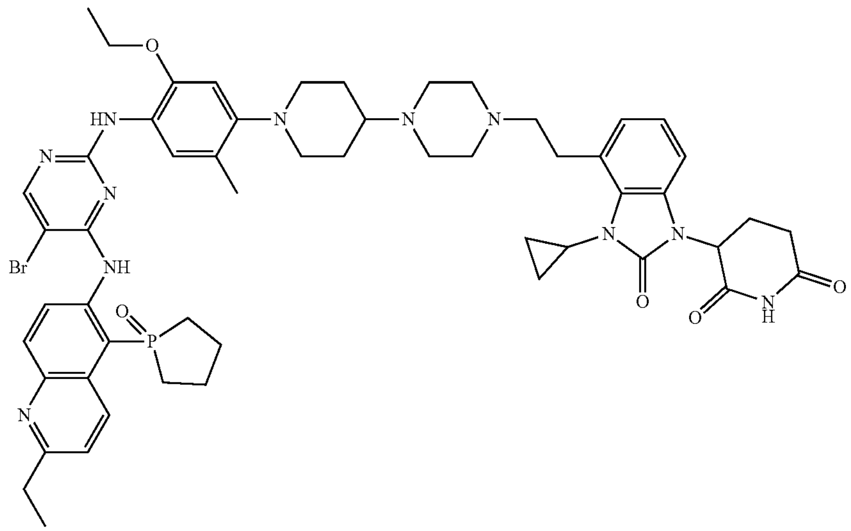
42
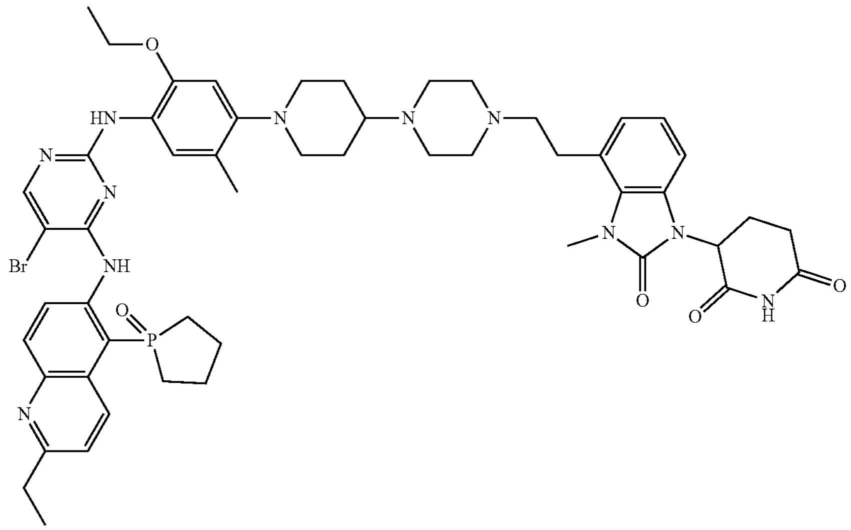
43
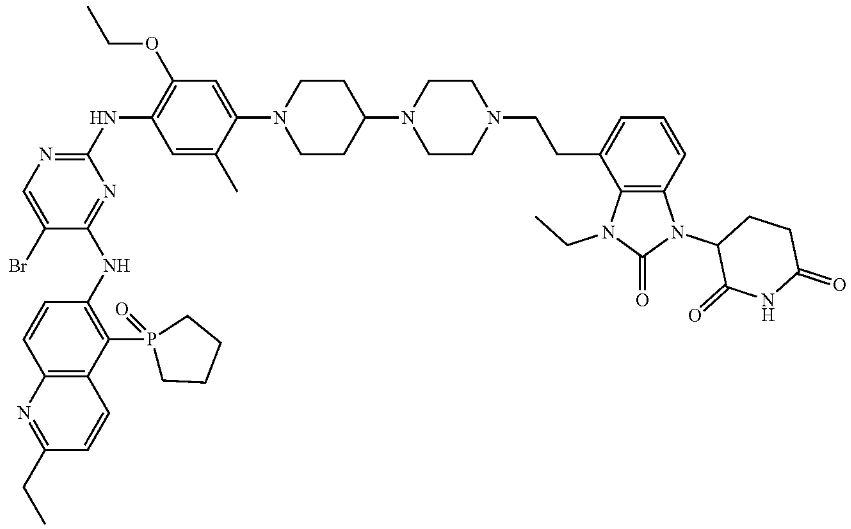

-continued
44
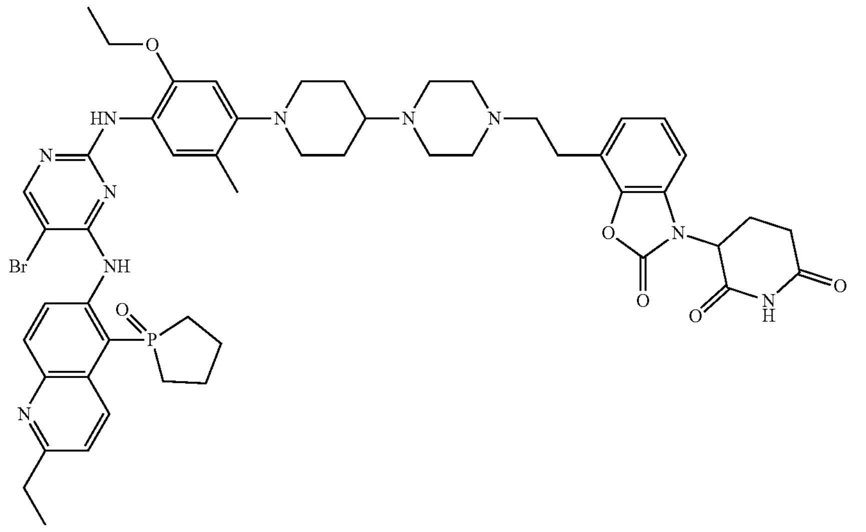
45
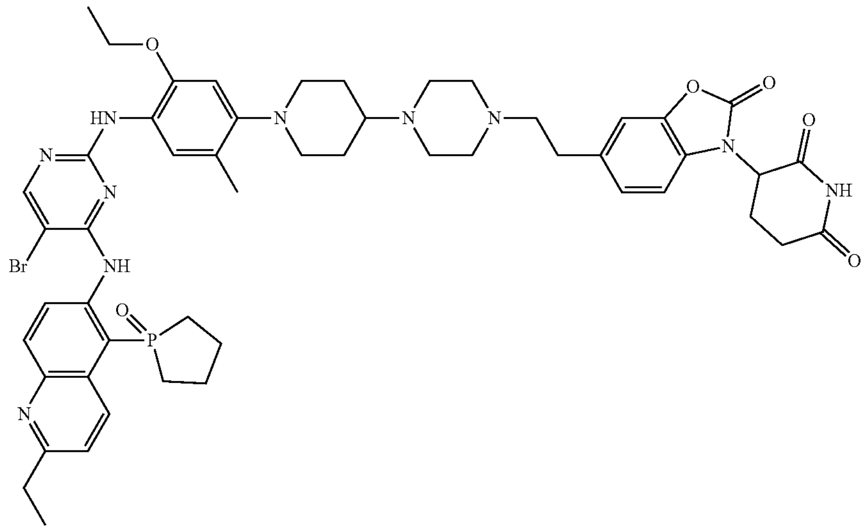
46
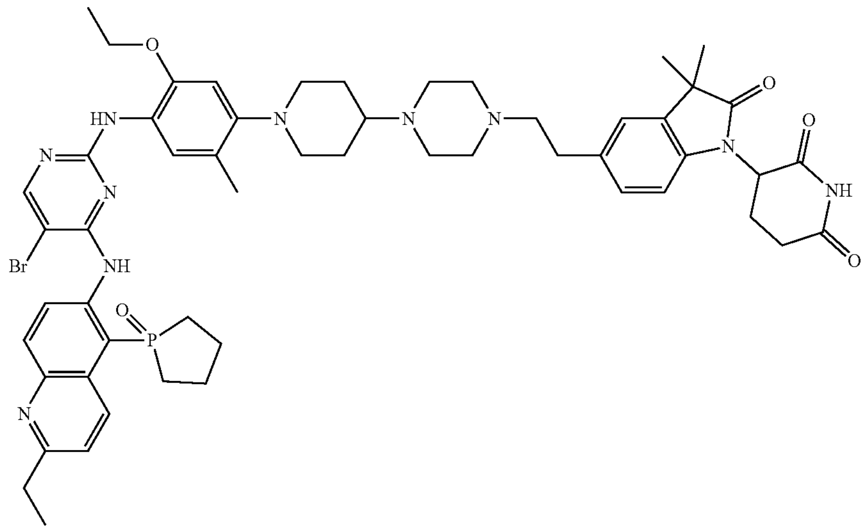

-continued
47
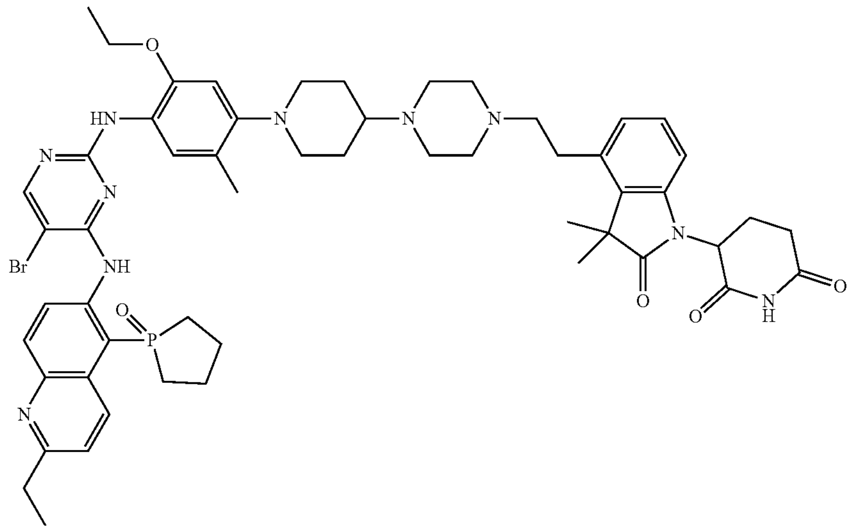
48
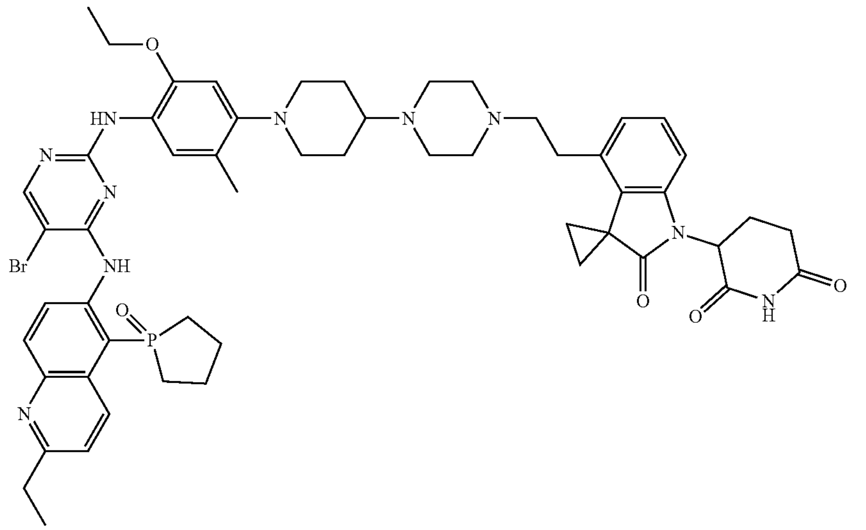
49
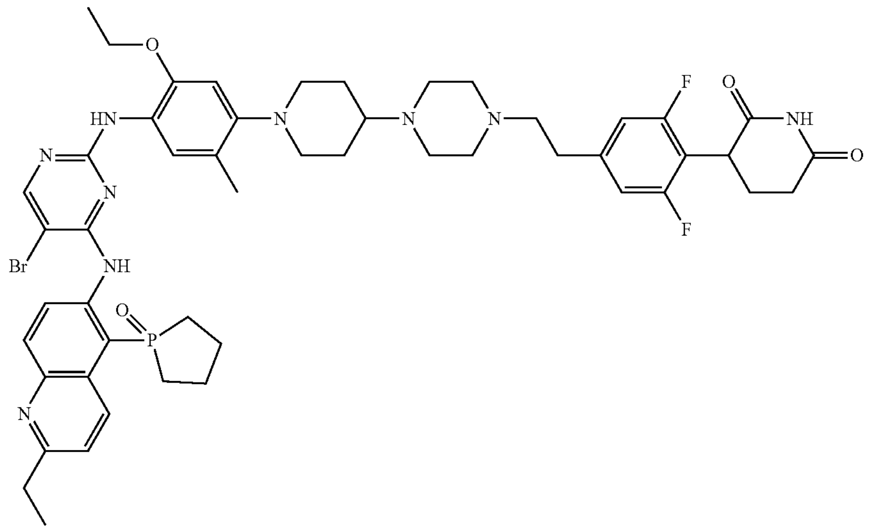

-continued
50
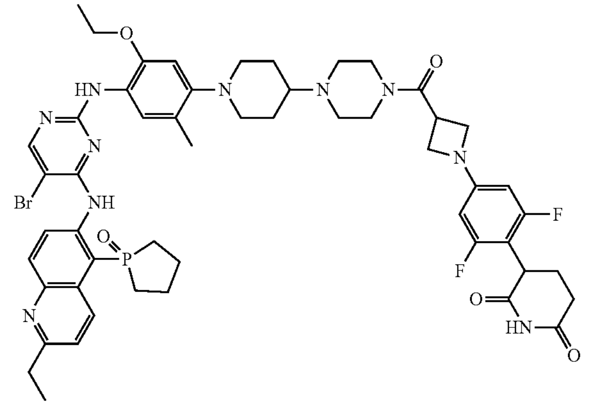
51
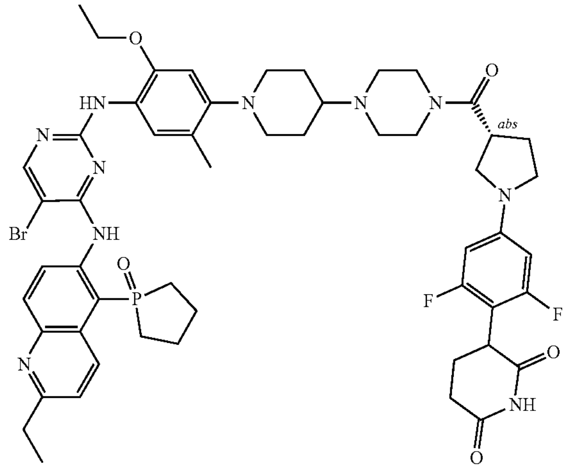
52
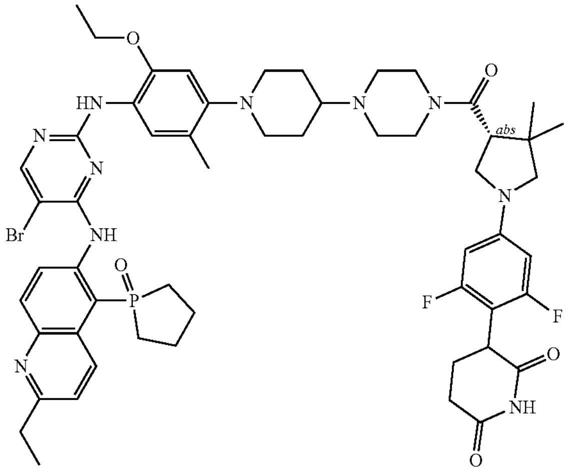
53
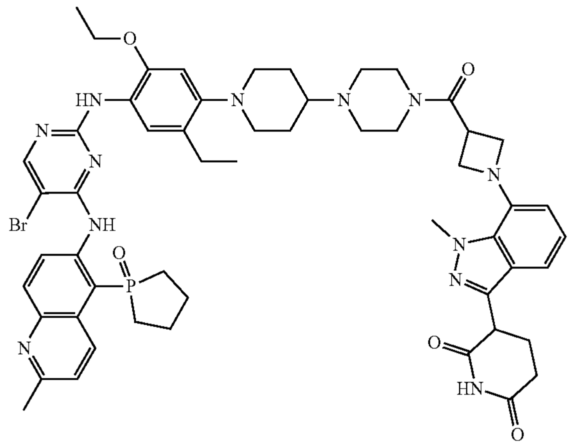

-continued
54
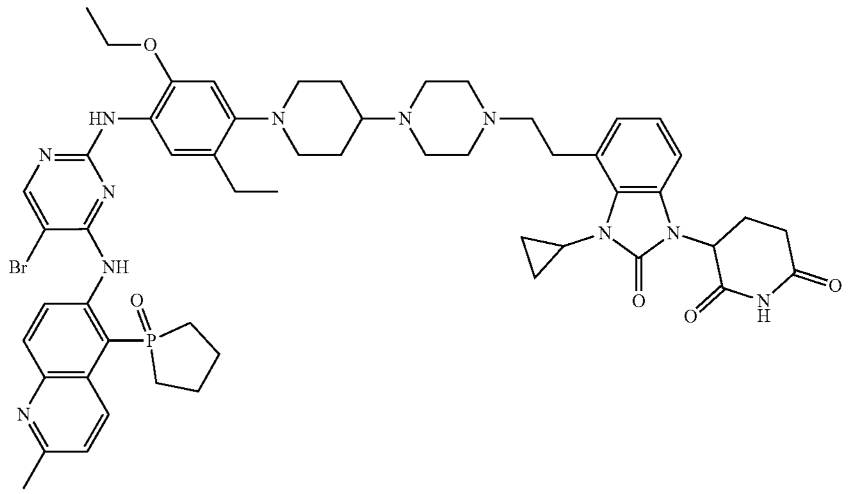
55
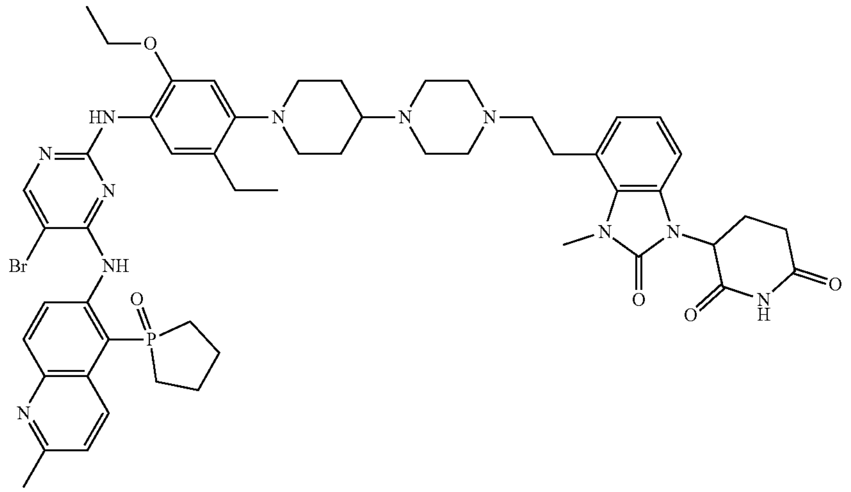
56
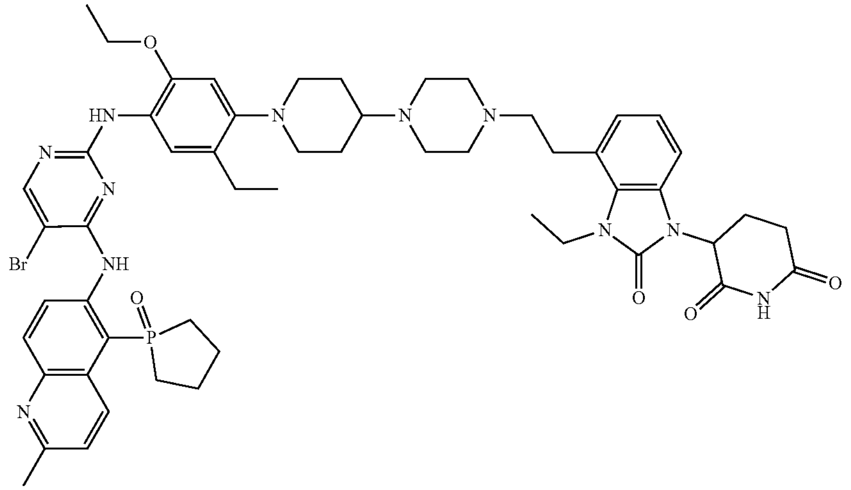

-continued
57
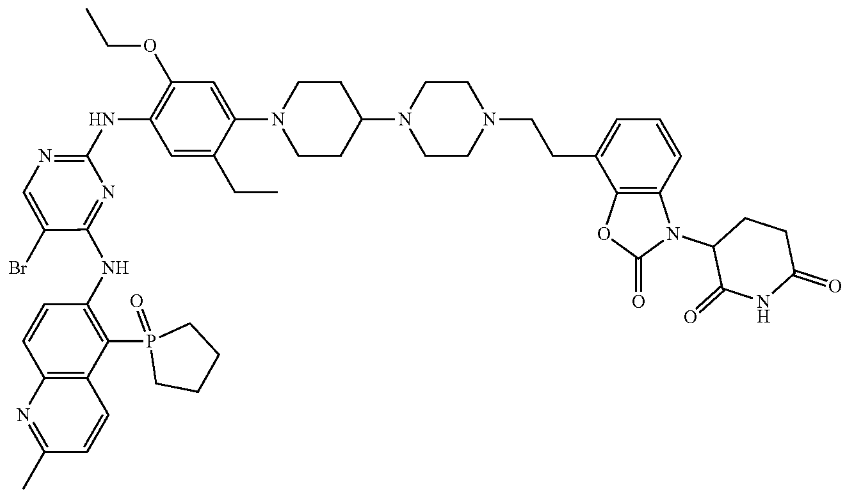
58
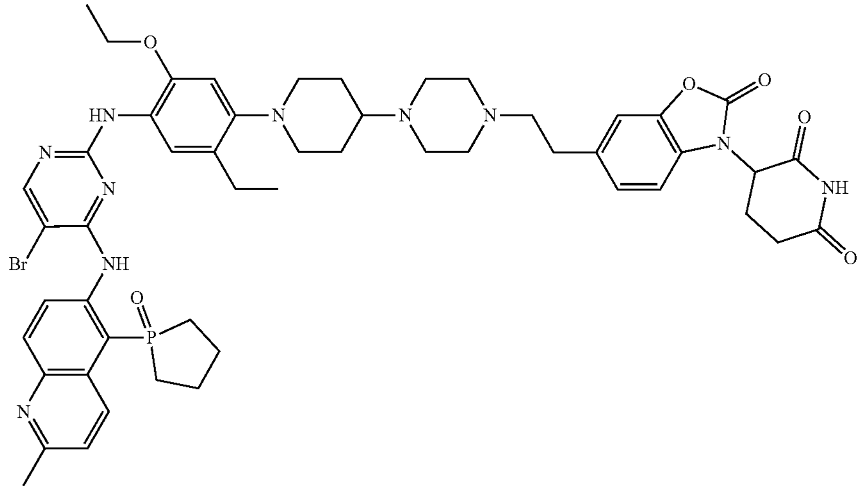
59
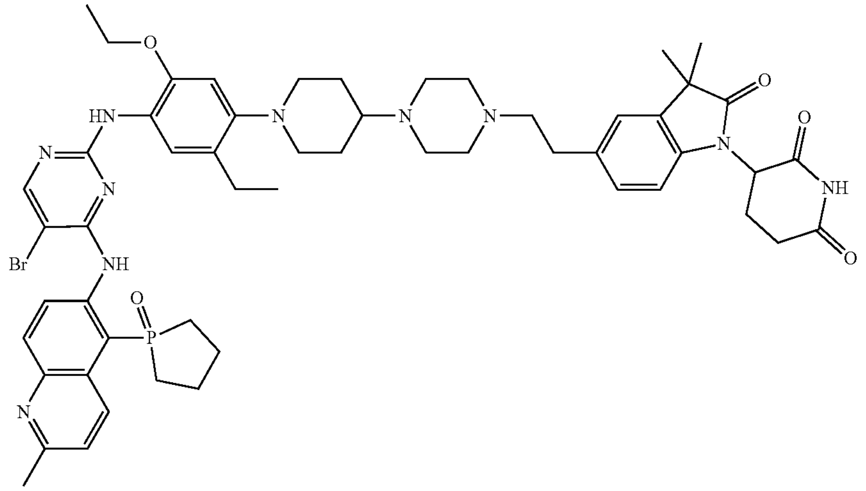

-continued
60
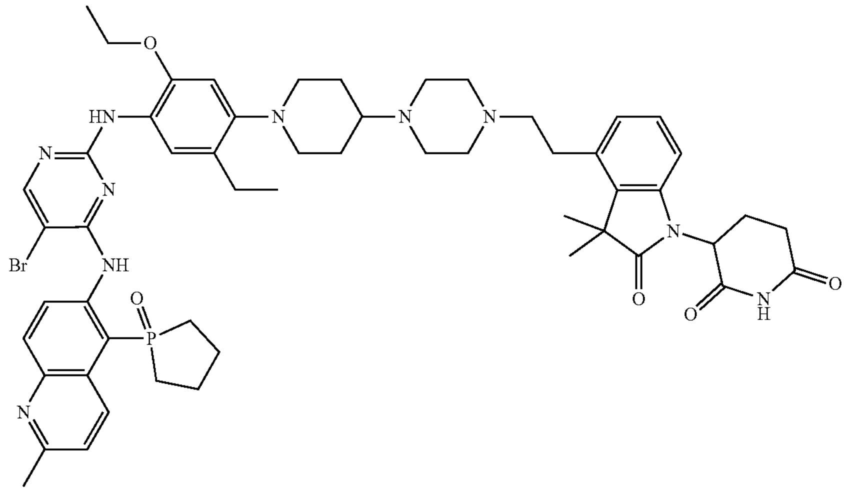
61
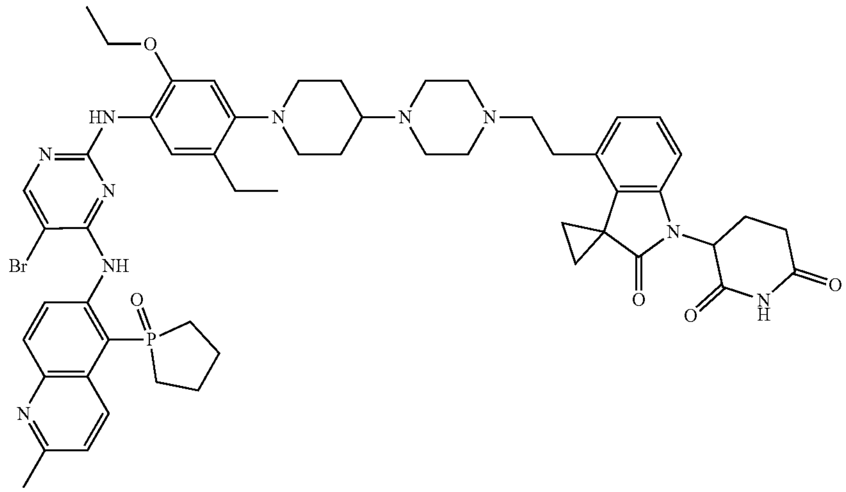
62
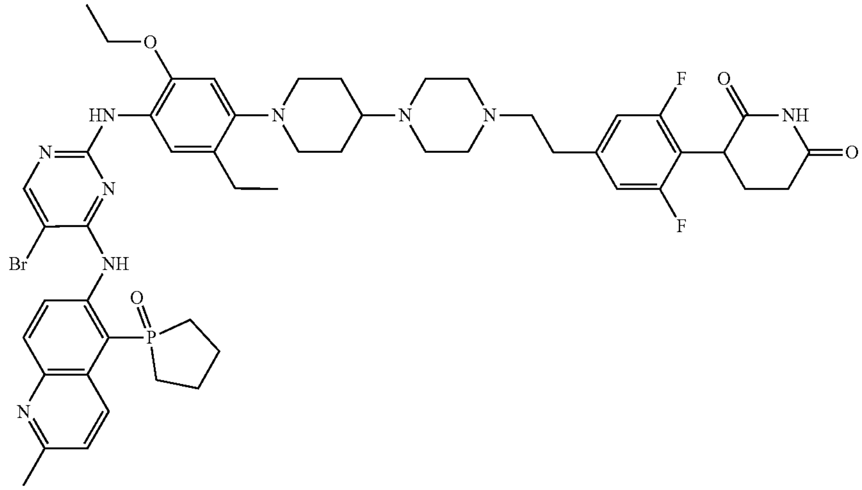

-continued
63
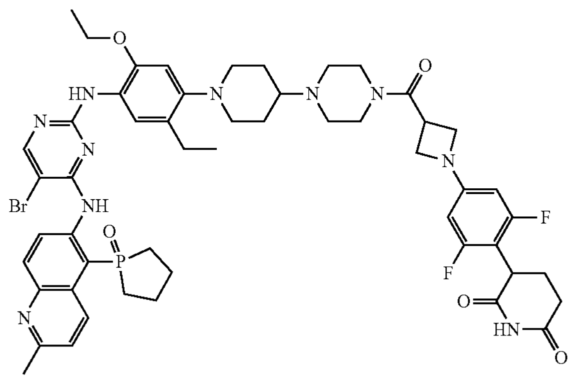
64
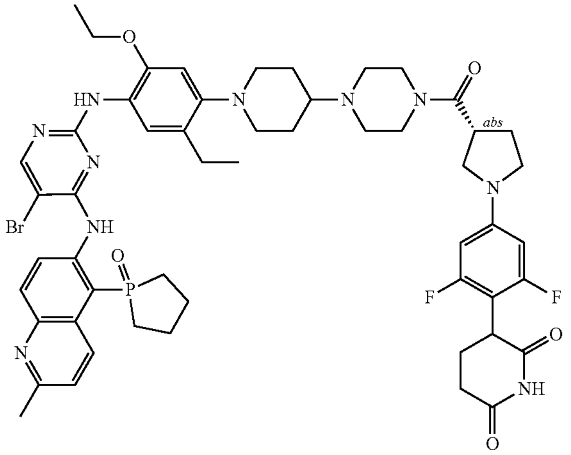
65
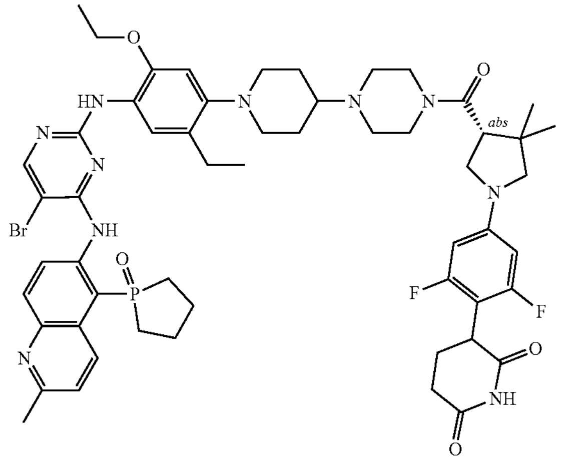
66
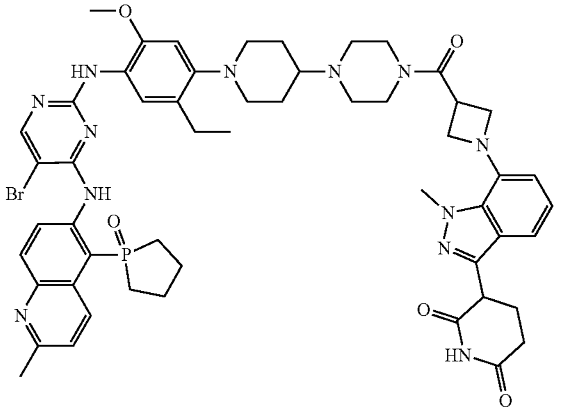
67
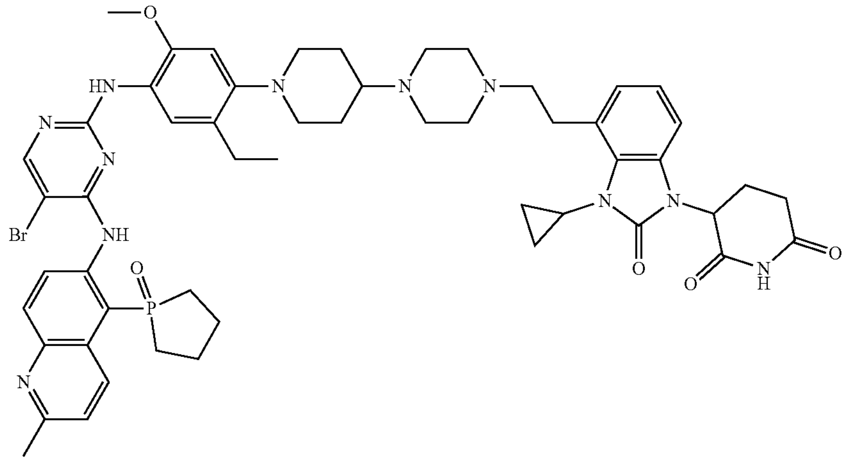

-continued
68
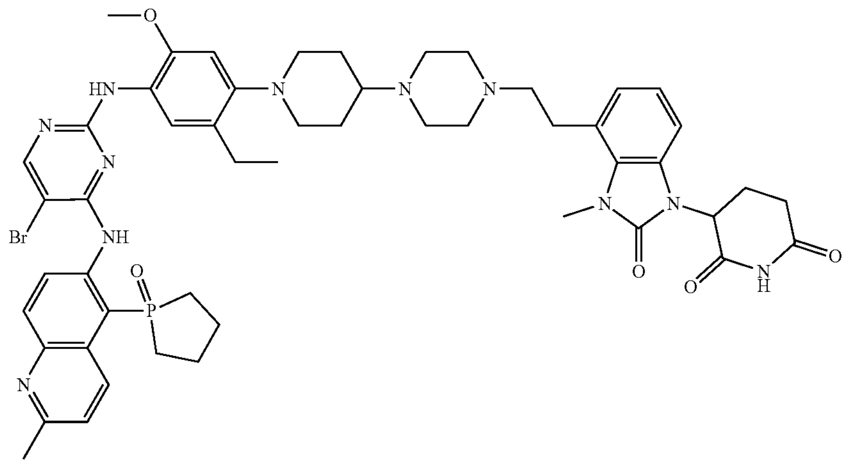
69
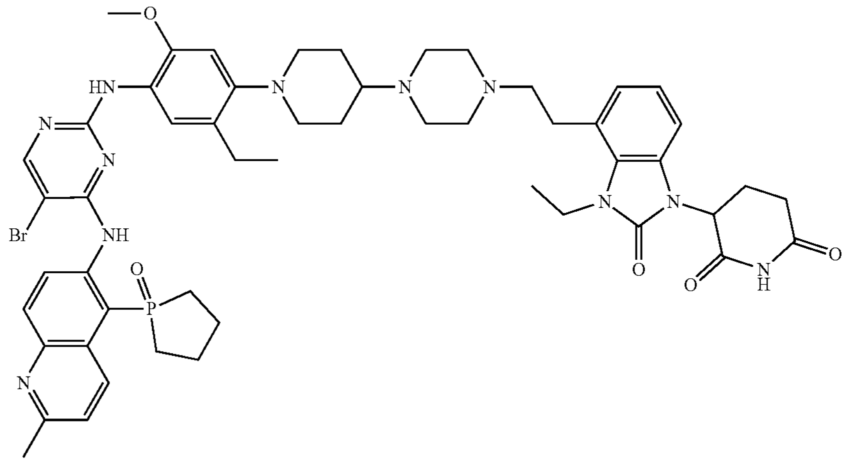
70
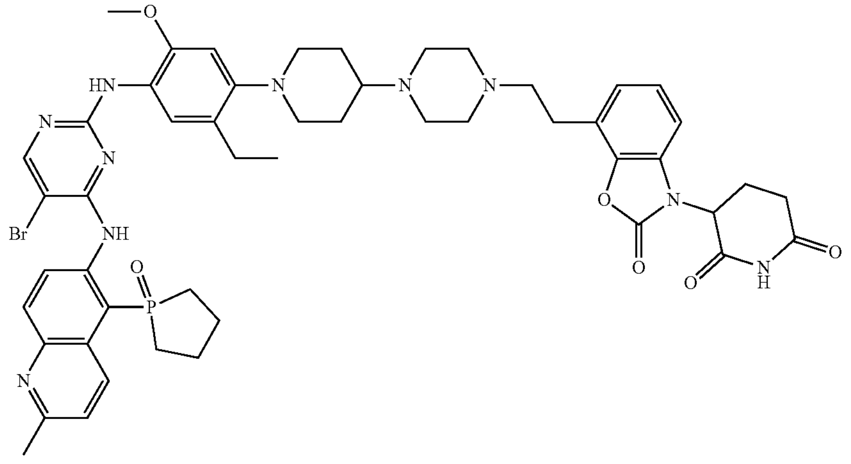

-continued
71
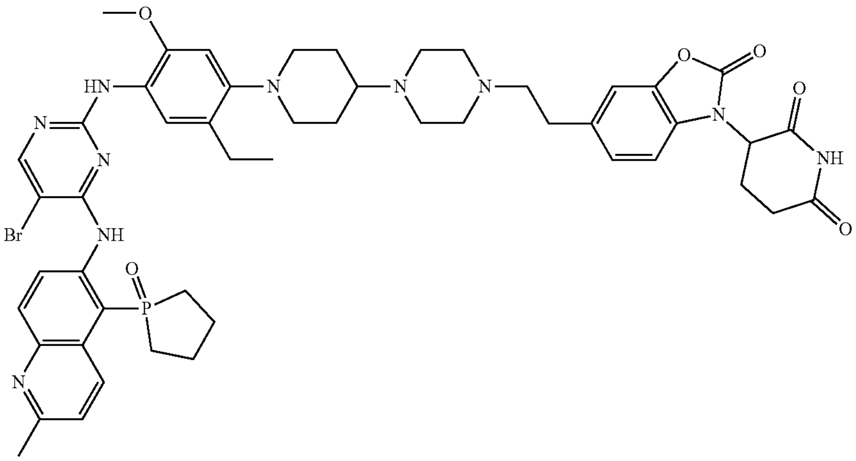
72
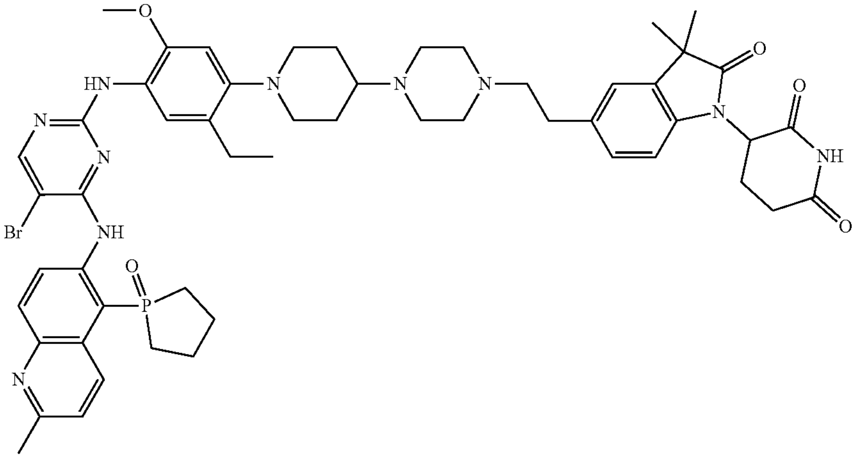
73
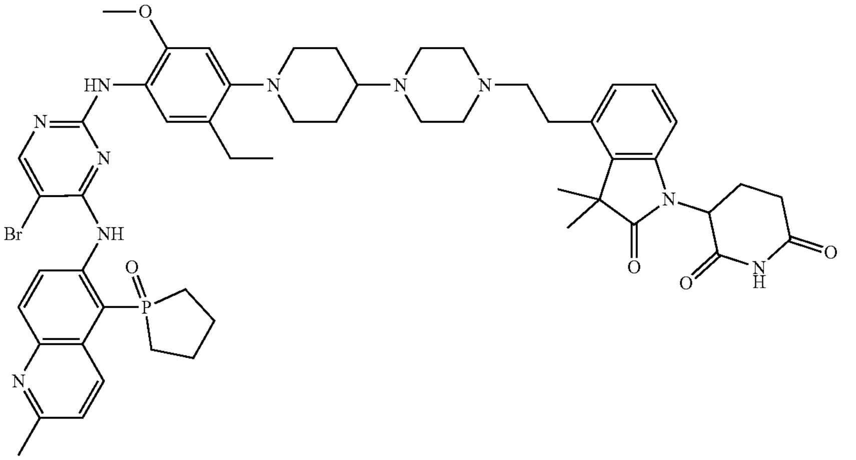

-continued
74
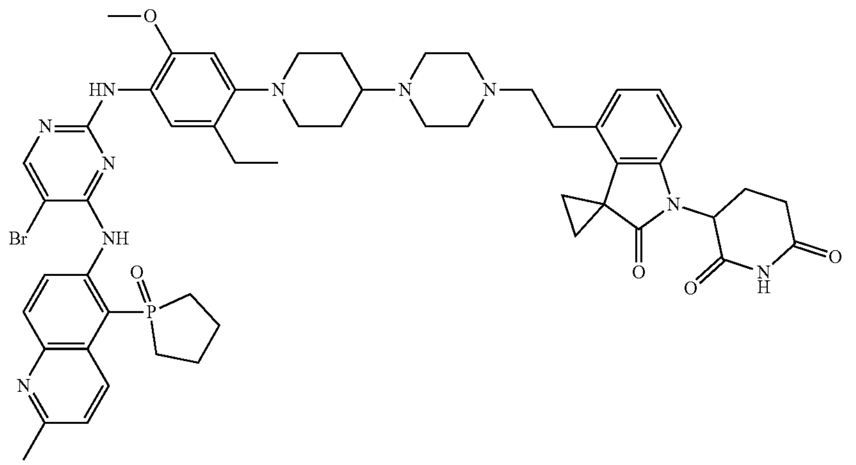
75
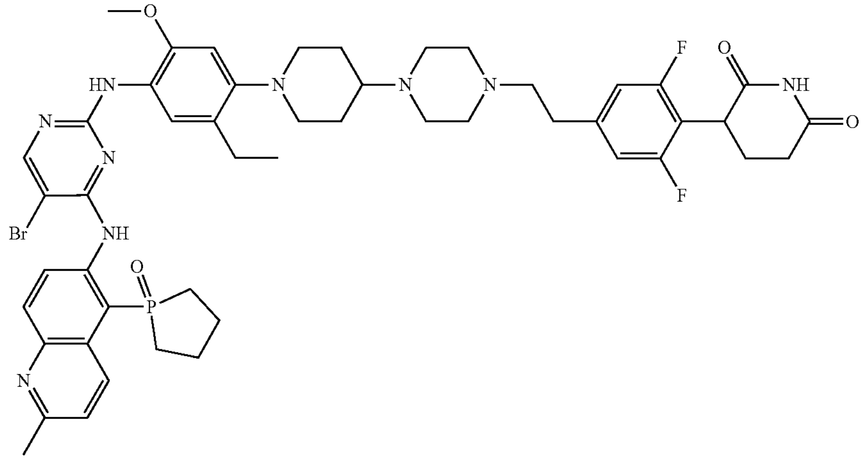
76
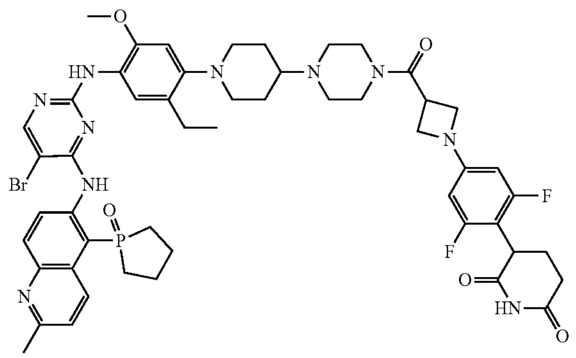
77
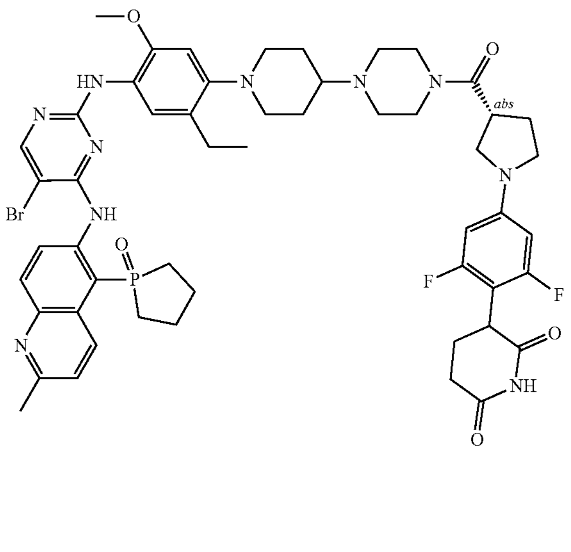

-continued
78
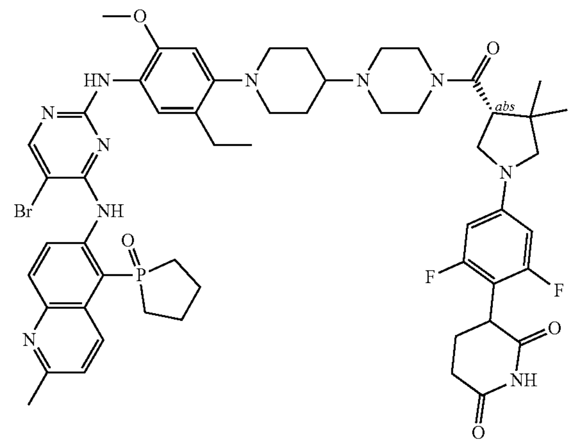
79
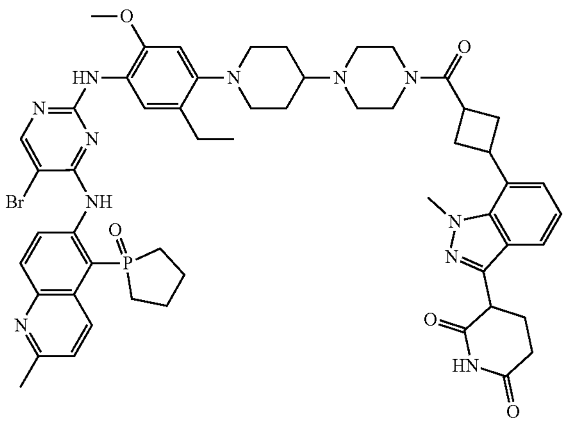
80
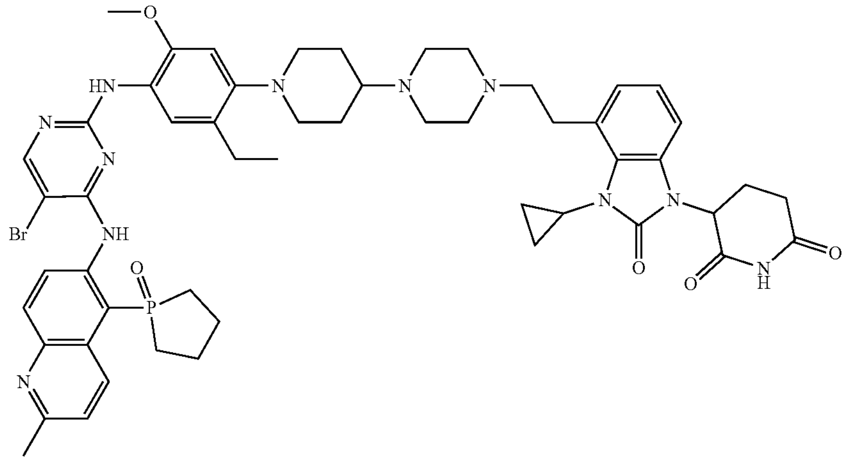
81
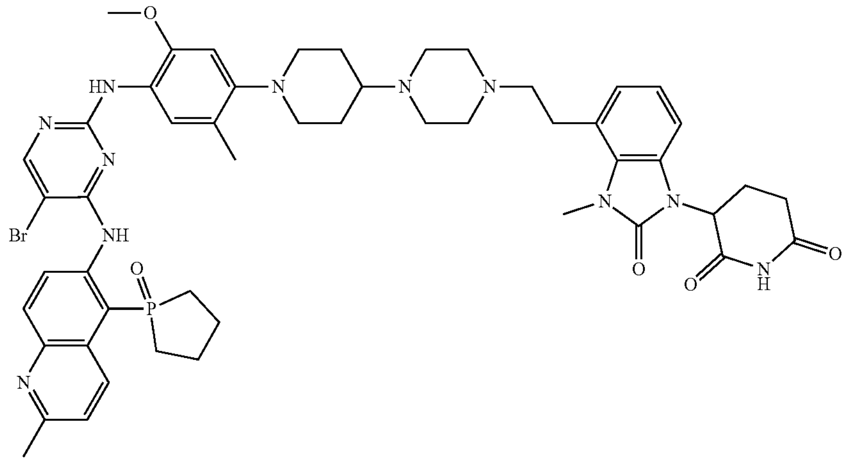

-continued
82
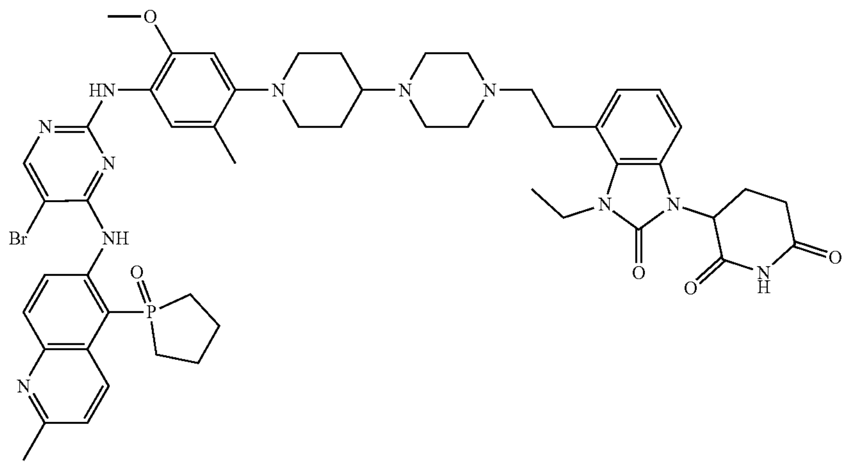
83
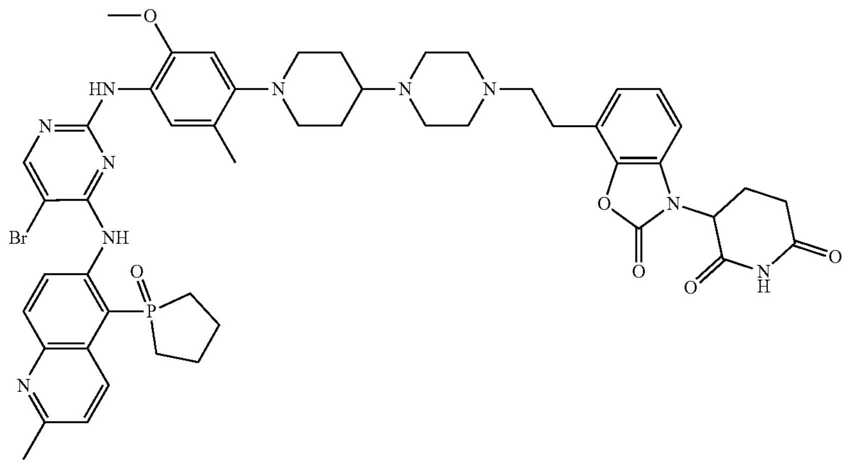
84
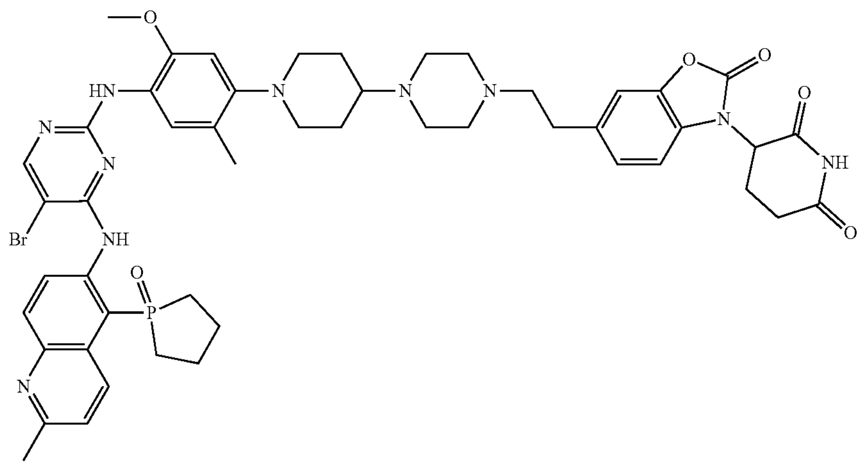

-continued
85
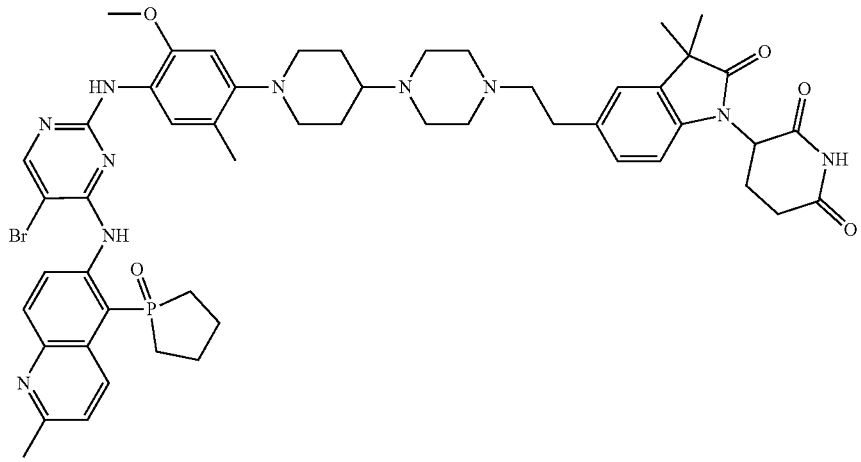
86
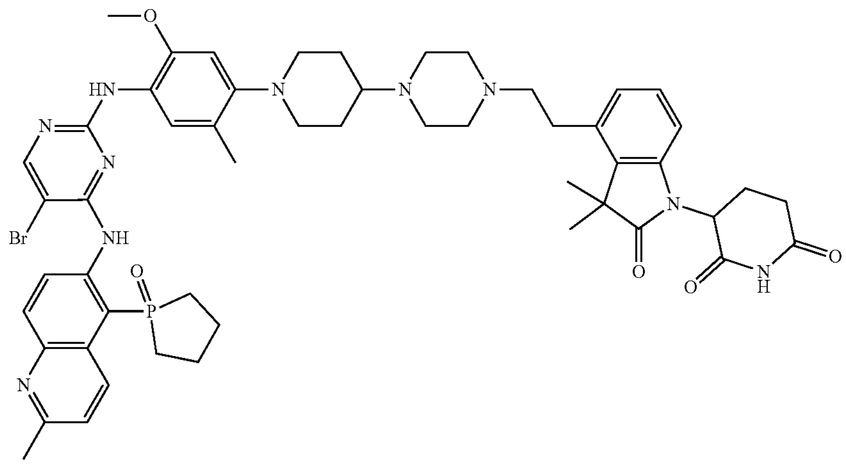
87
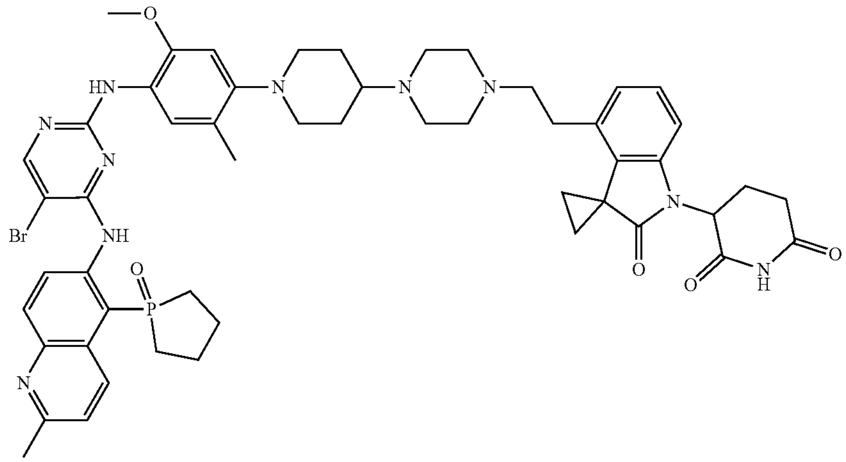

-continued
88
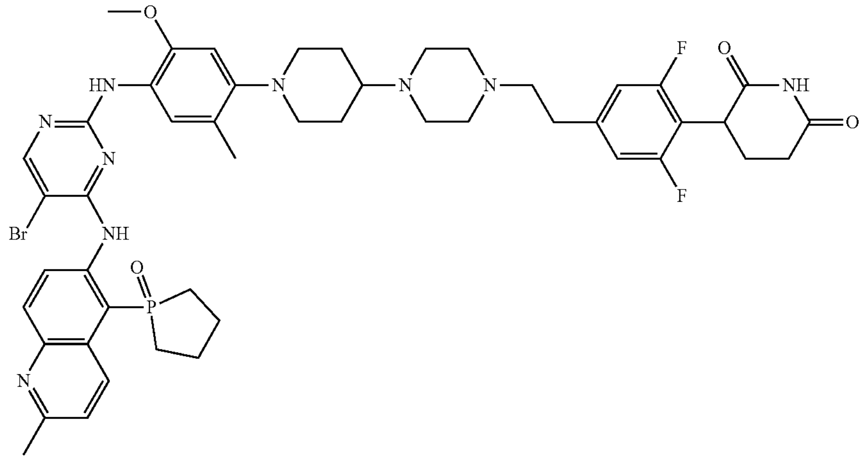
89
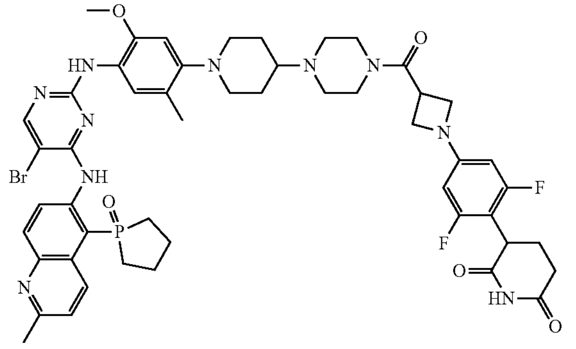
90
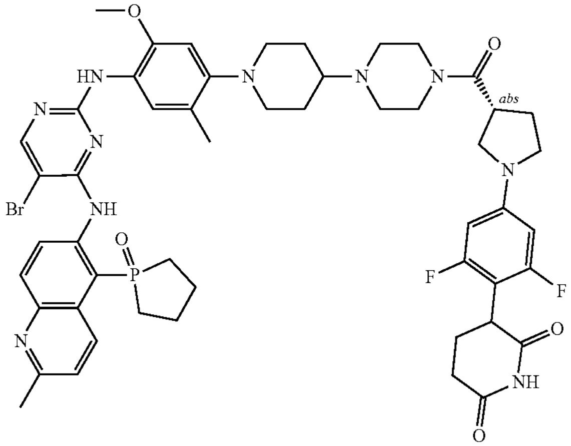
91
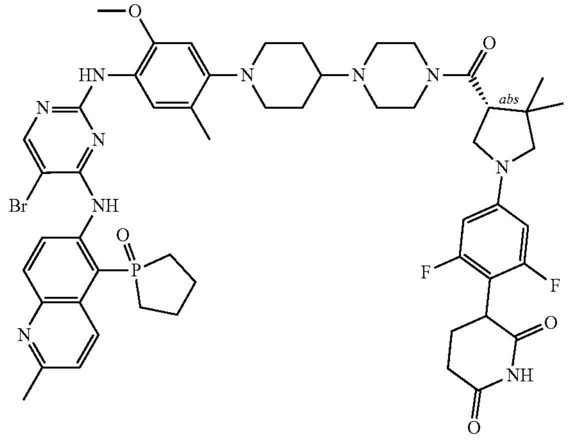
92
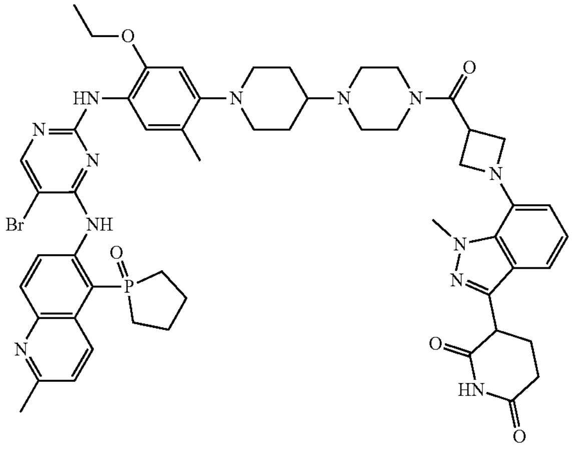

-continued
93
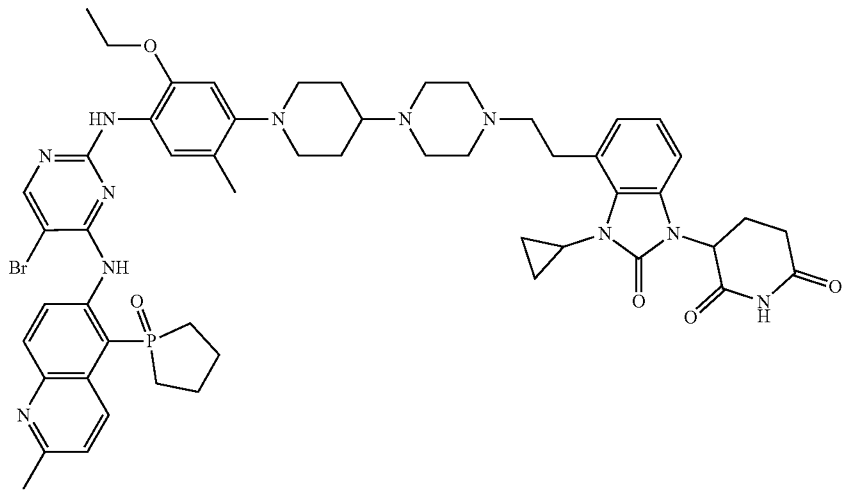
94
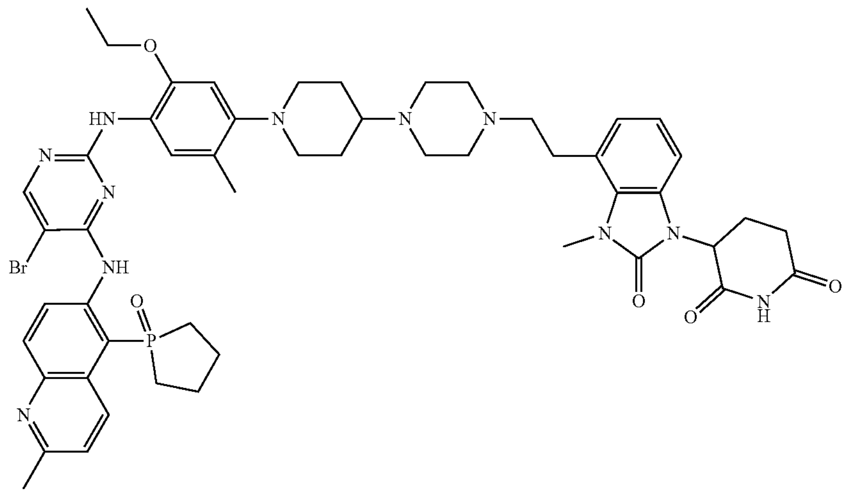
95
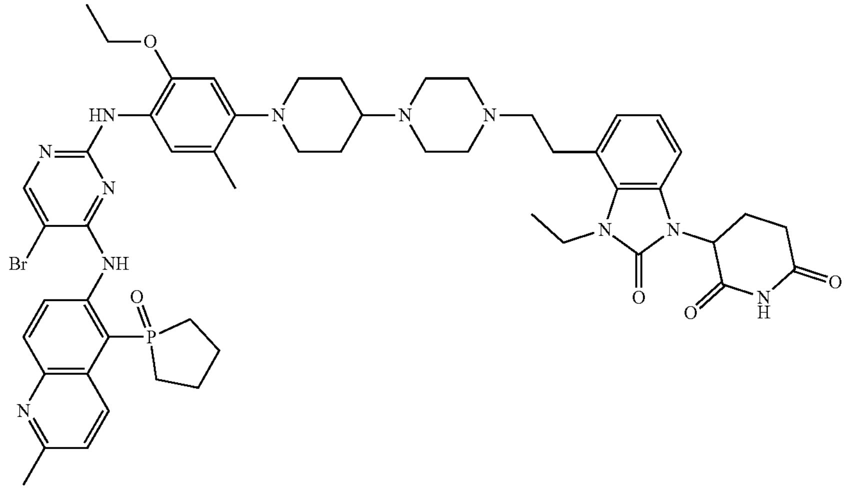

-continued
96
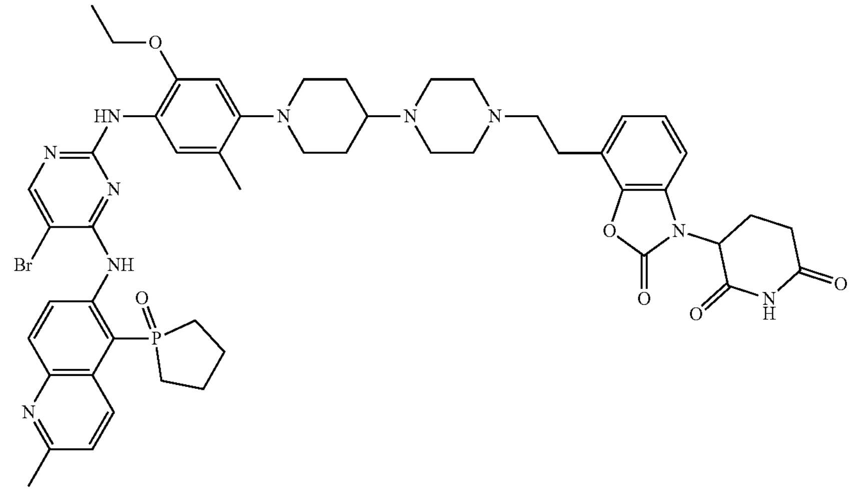
97
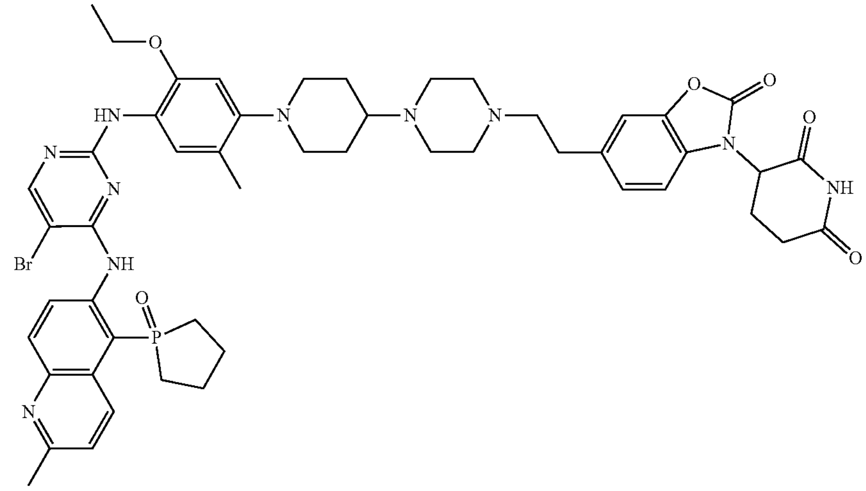
98
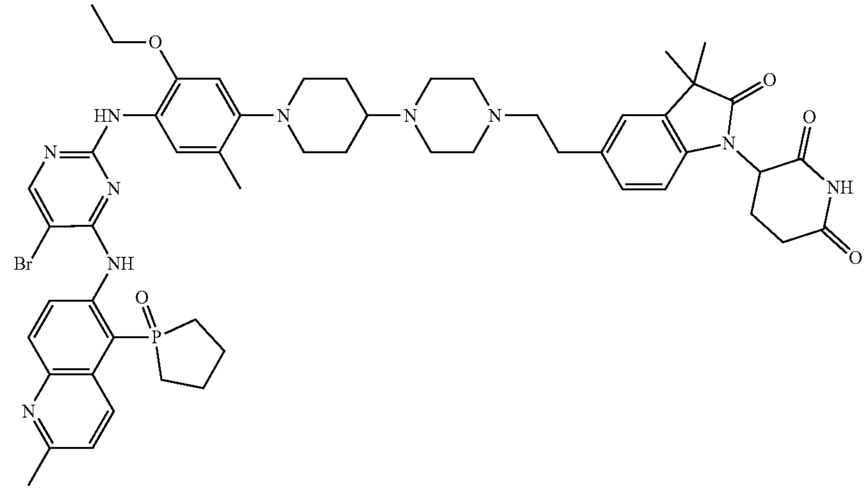

-continued
99
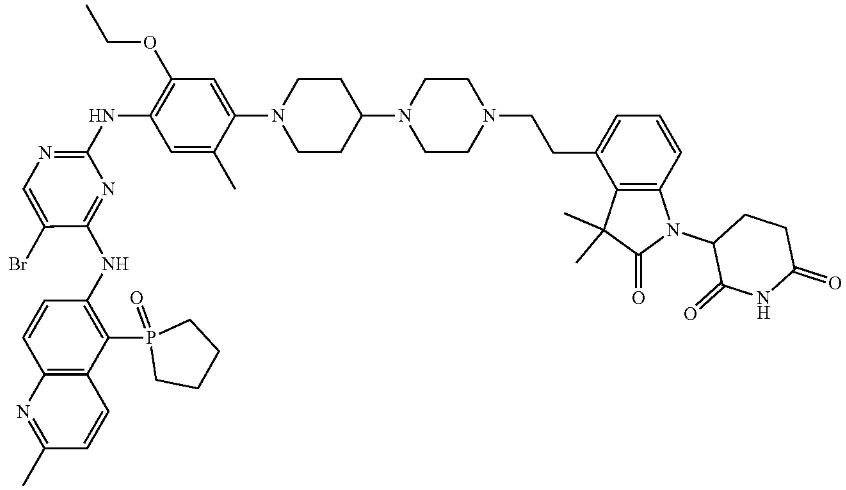
100
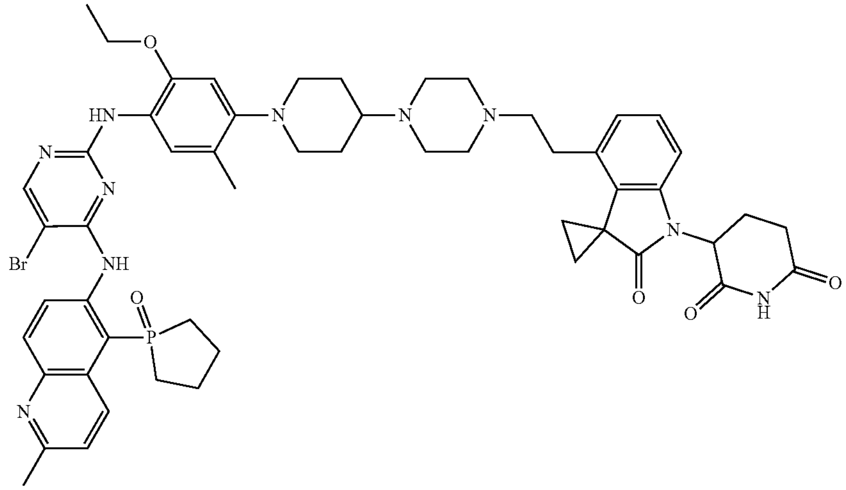
101
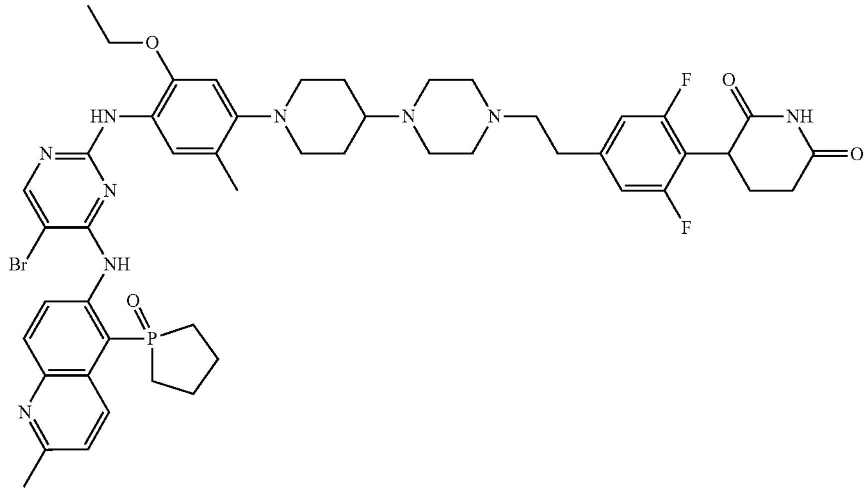

-continued
102
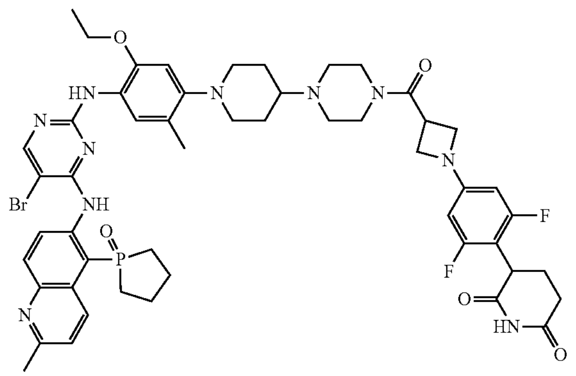
103
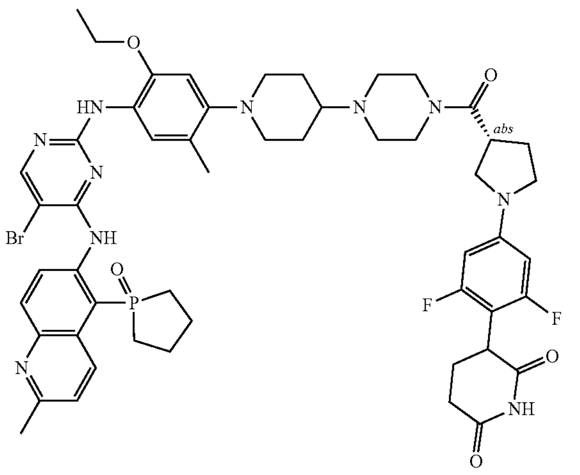
104
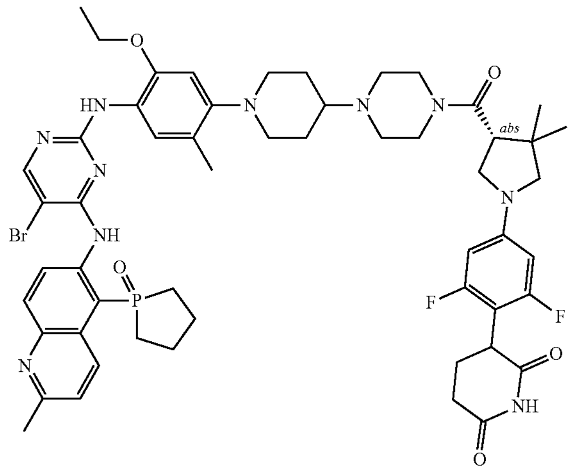
105
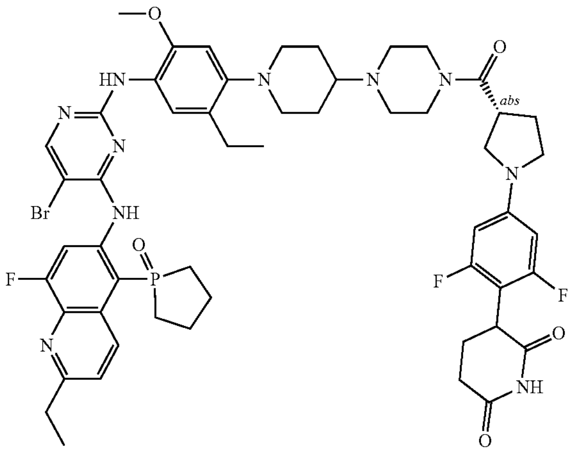
106
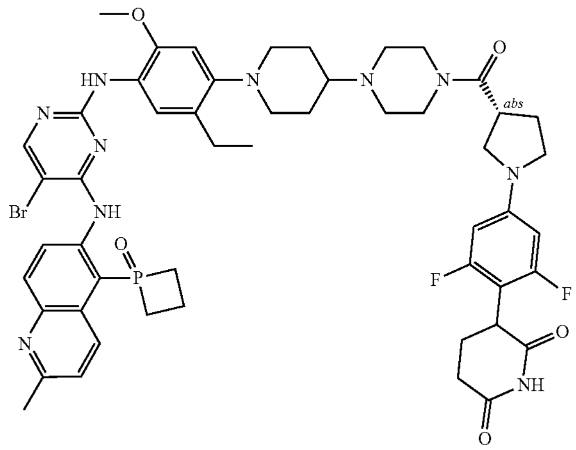
107
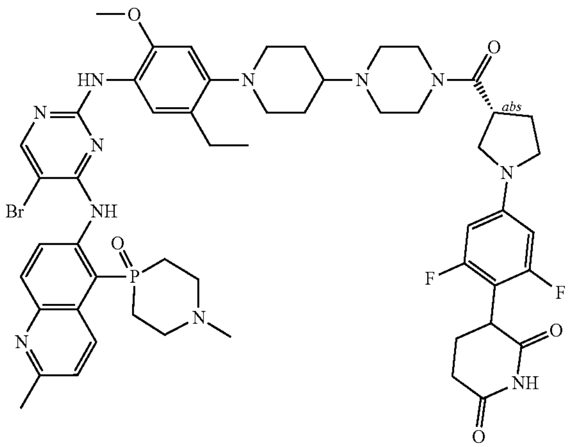

-continued
108
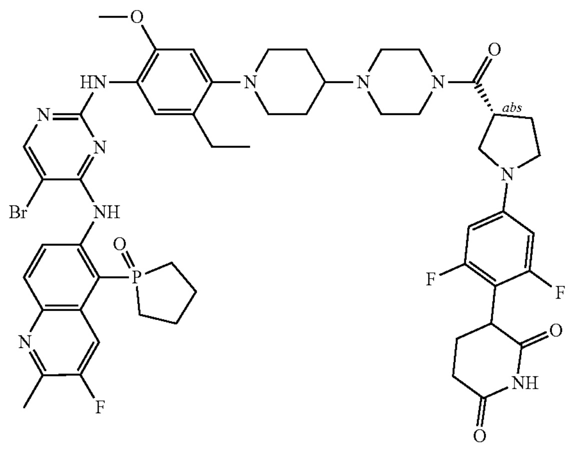
109
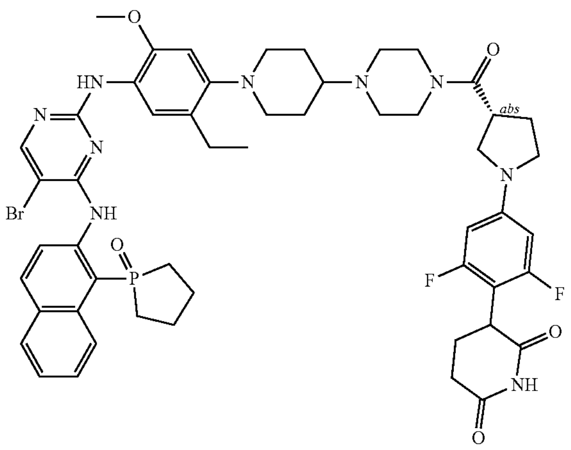
110
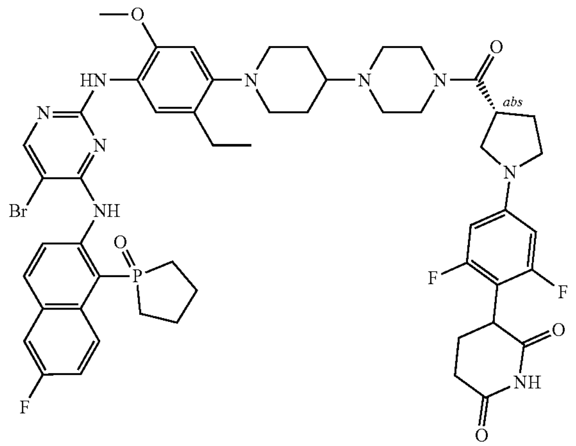
111
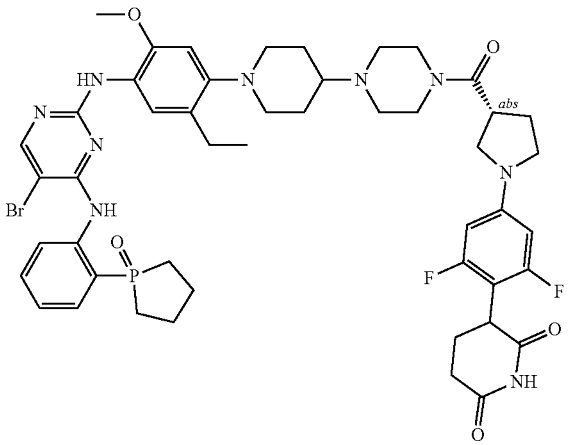
112
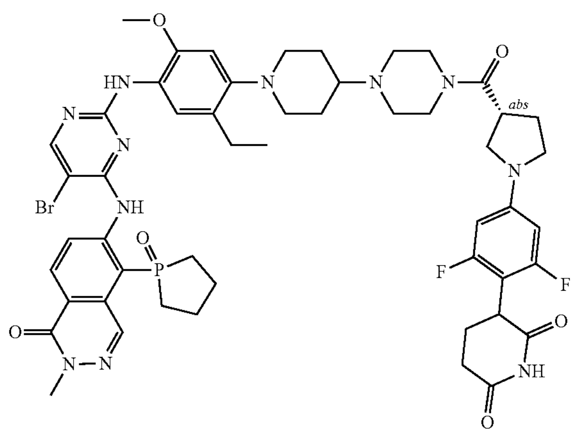
113
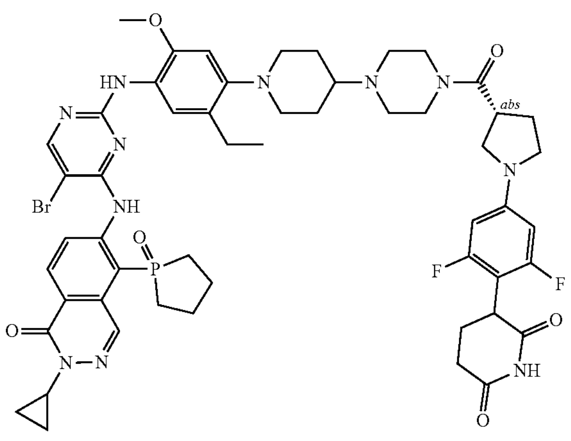

-continued
114
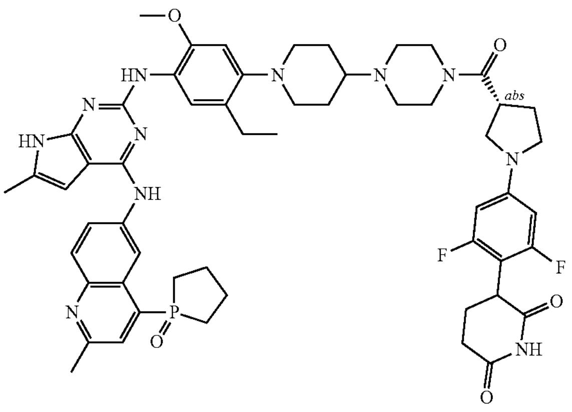
115
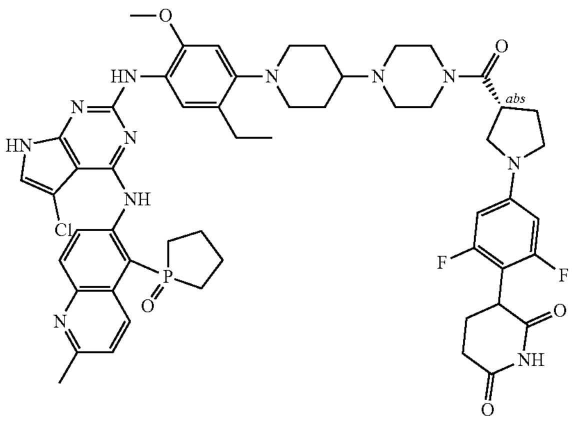
116
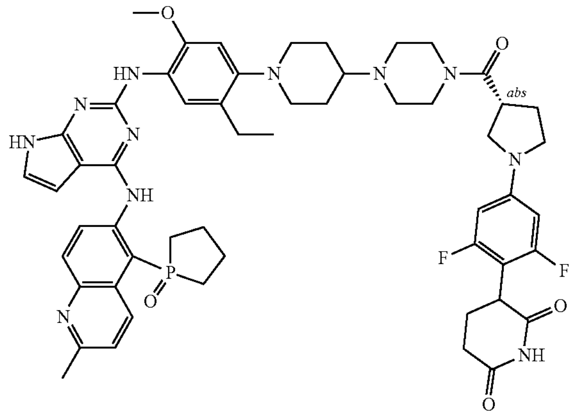
117
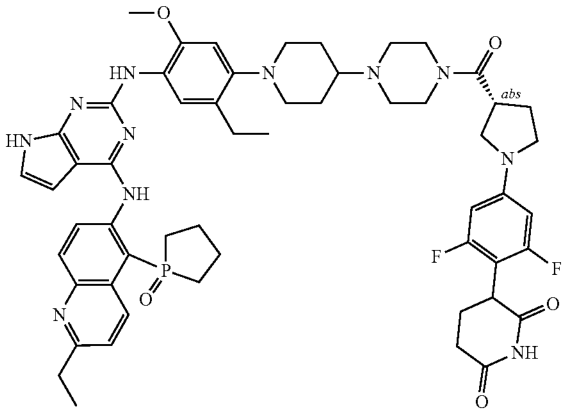
118
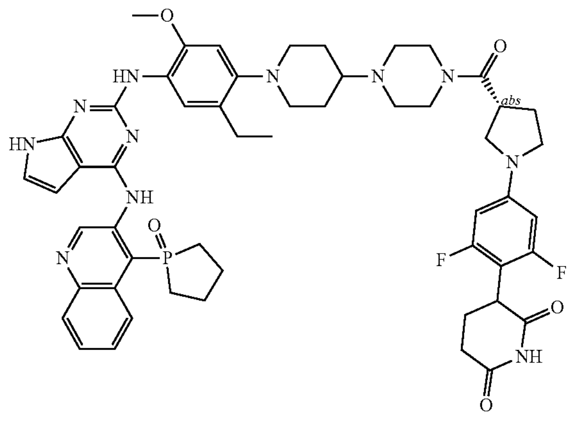
119
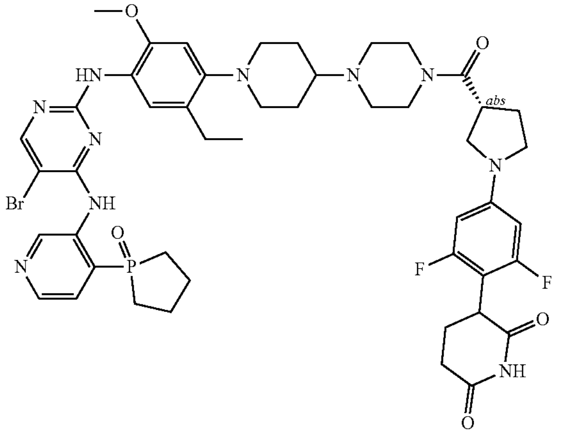

-continued
120
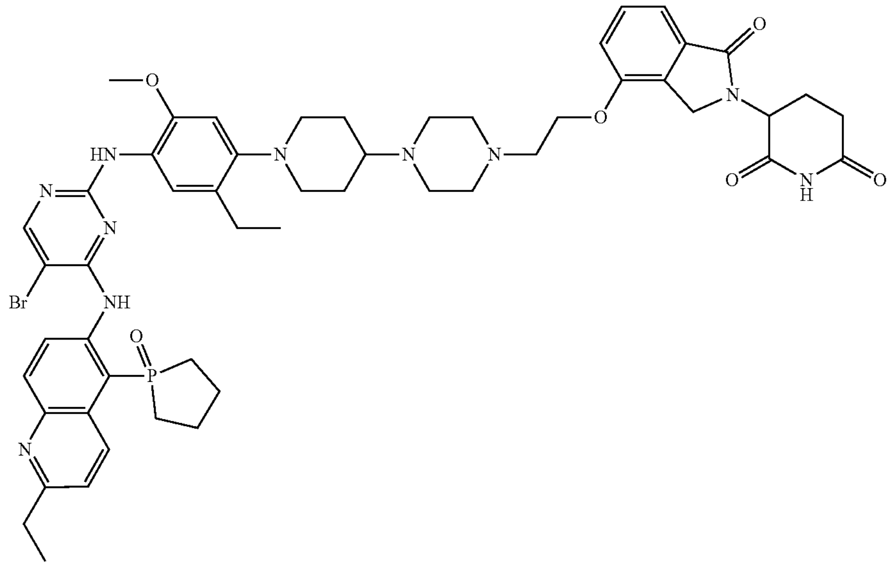
121
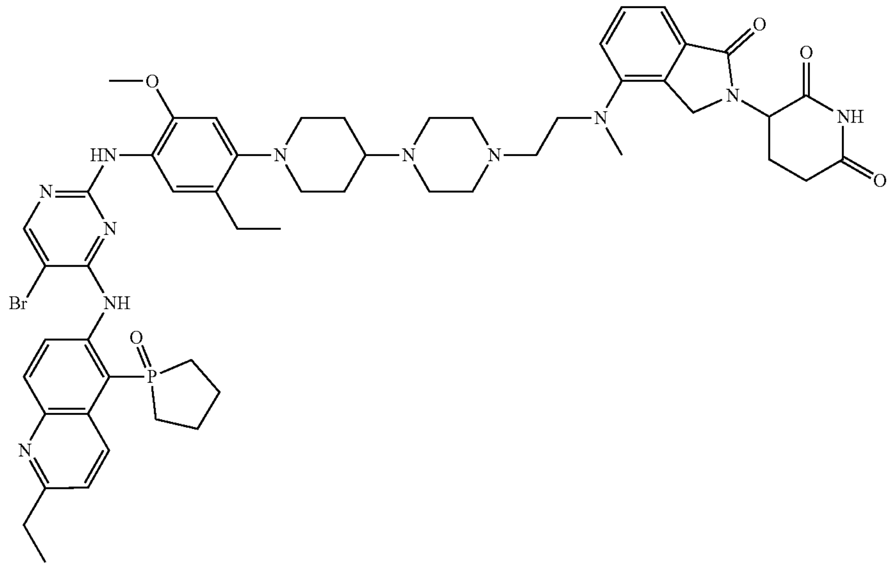
122
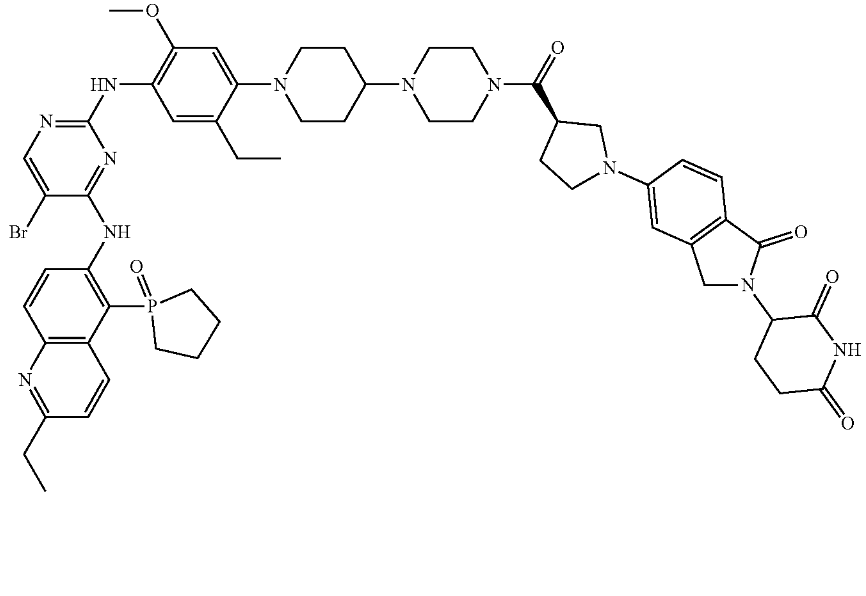

-continued
123
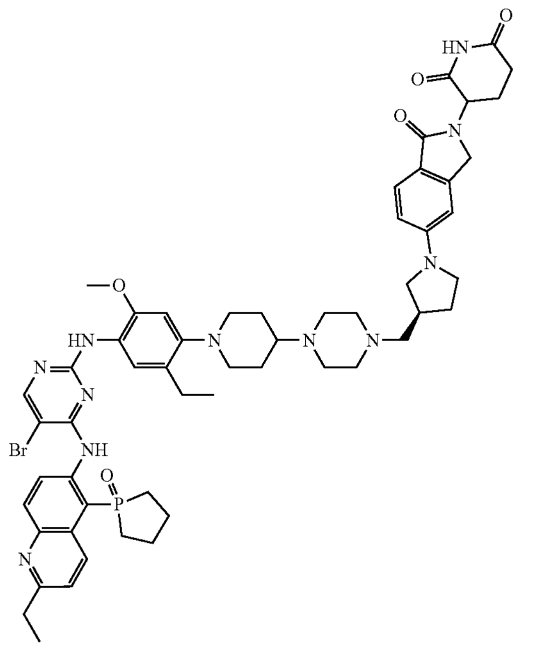
124
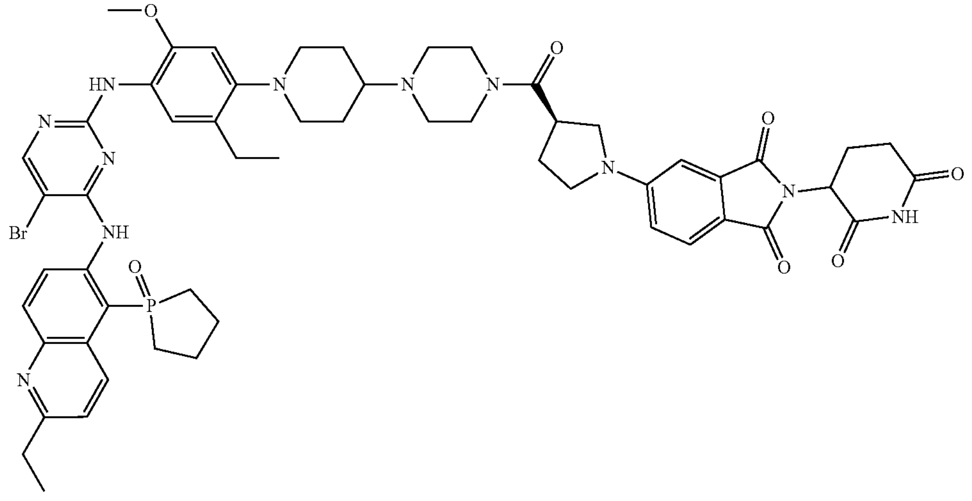
125
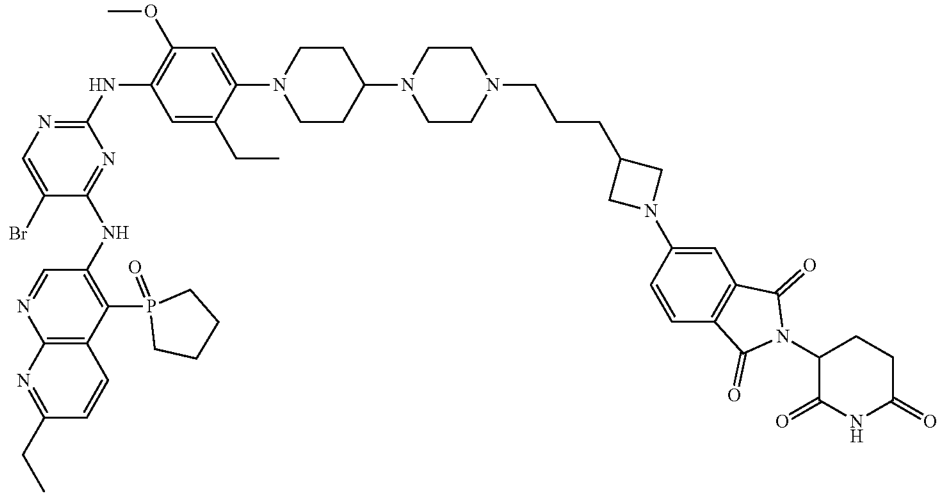

-continued
126
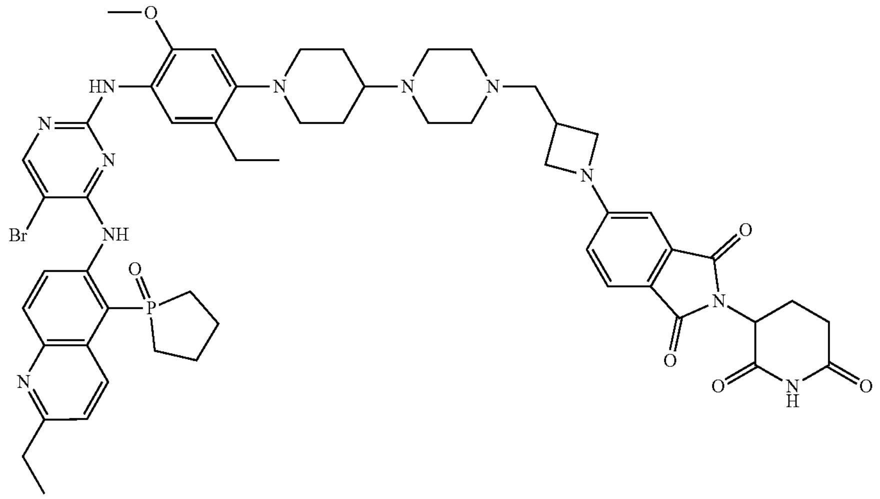
127
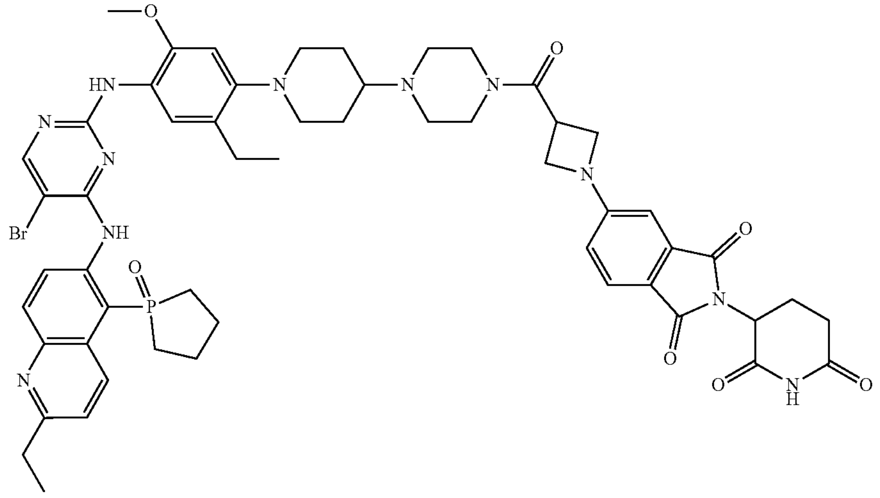
128
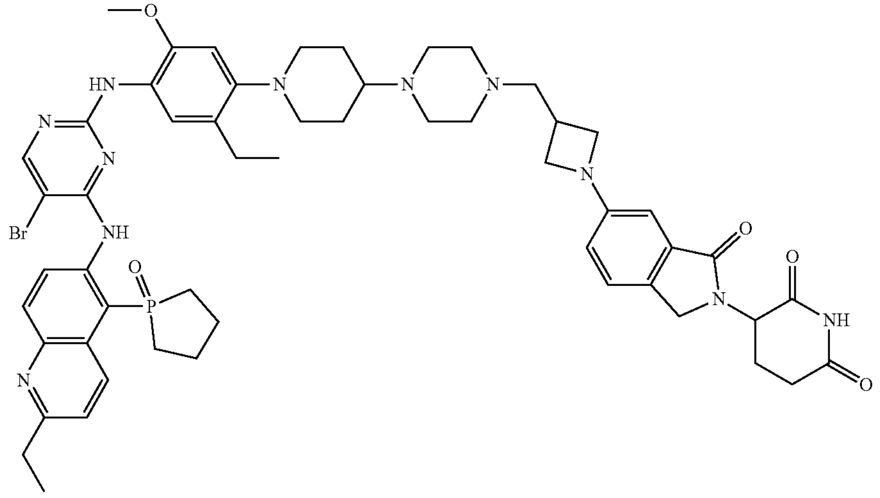

-continued
129
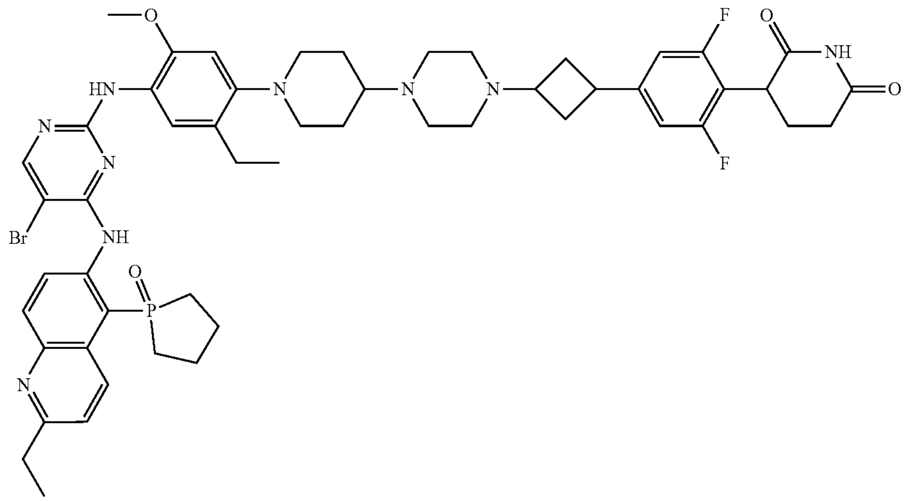
130
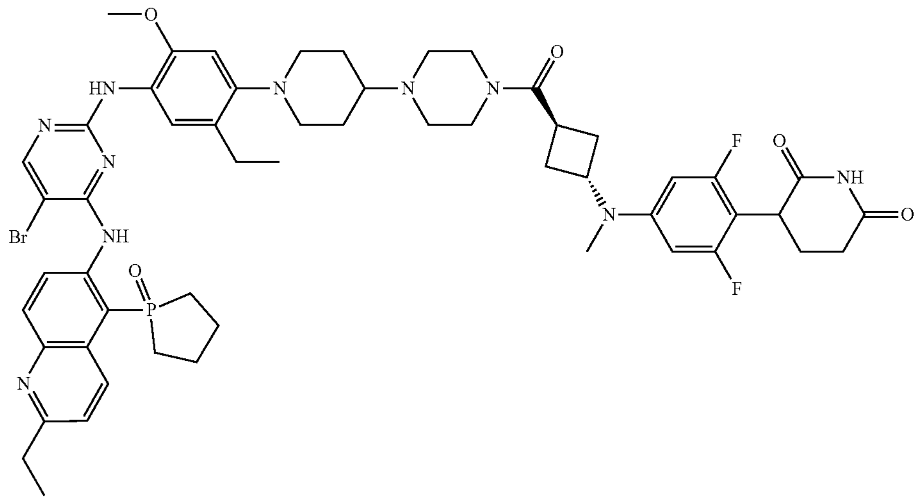
131
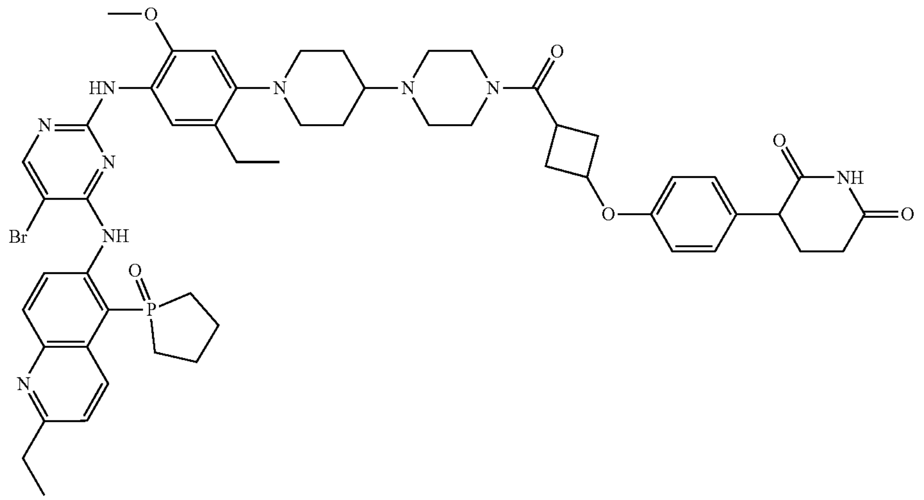

-continued
132
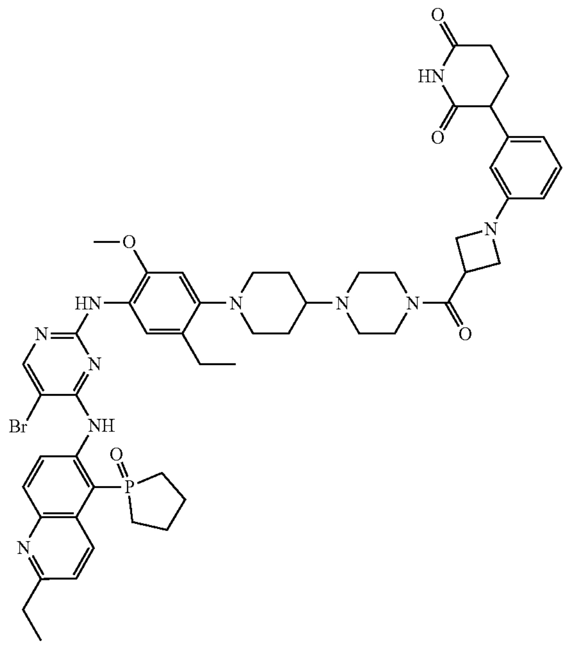
133
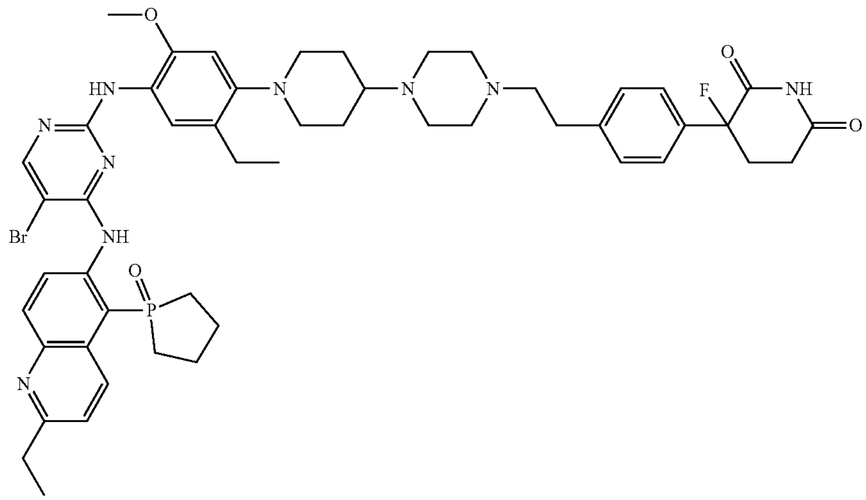

-continued
134
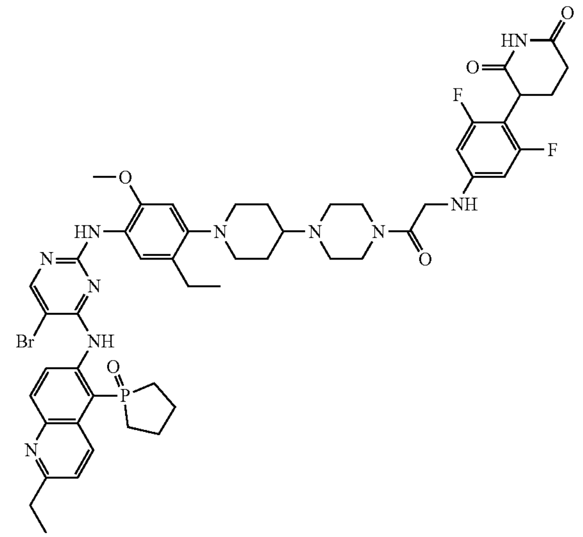
136
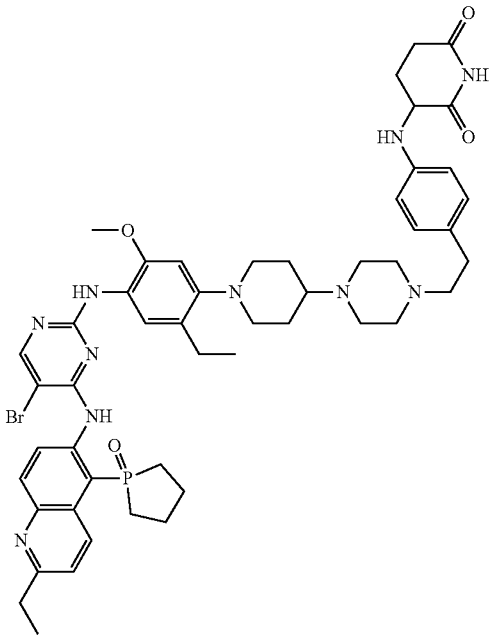
137
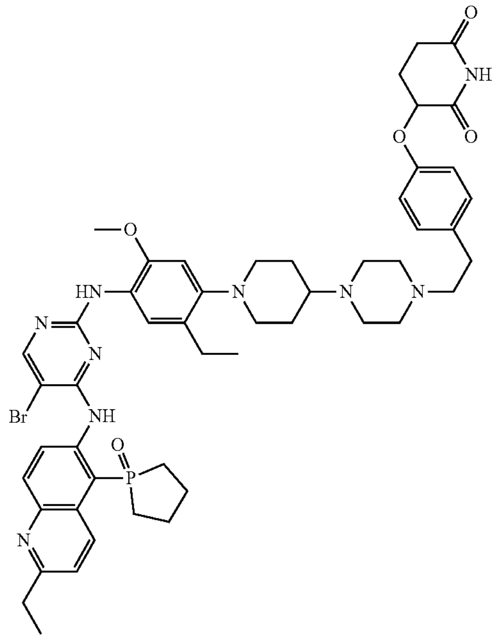

-continued
138
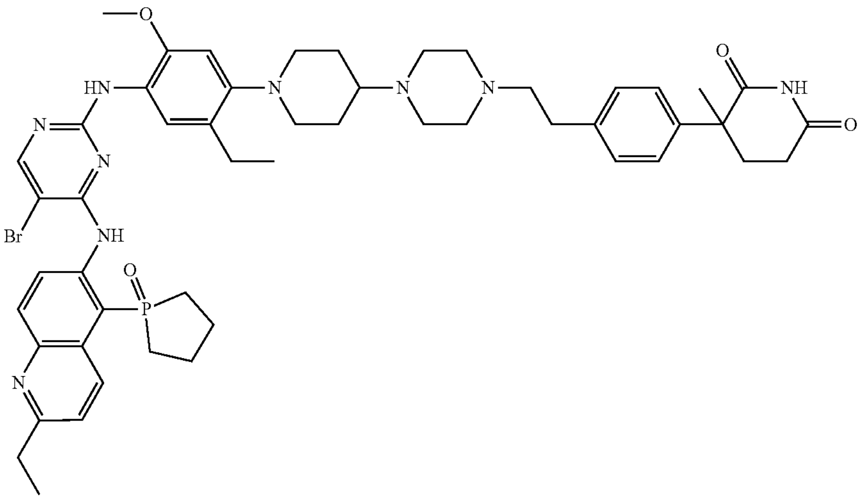
140
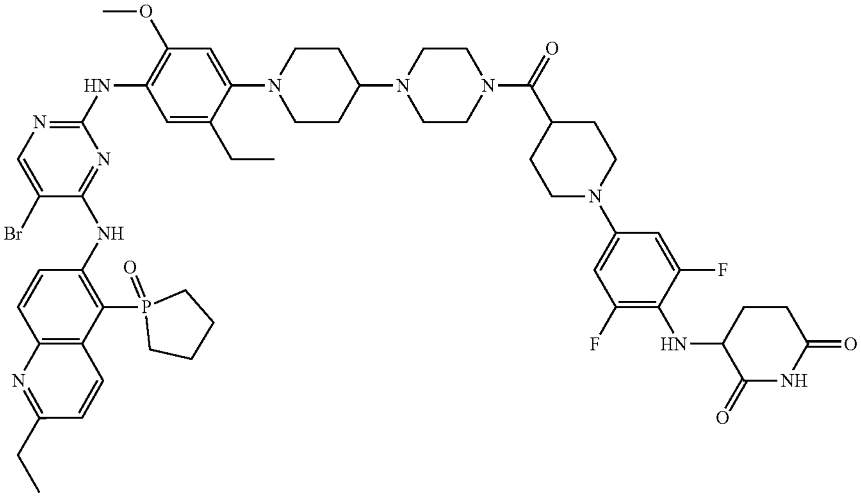
141
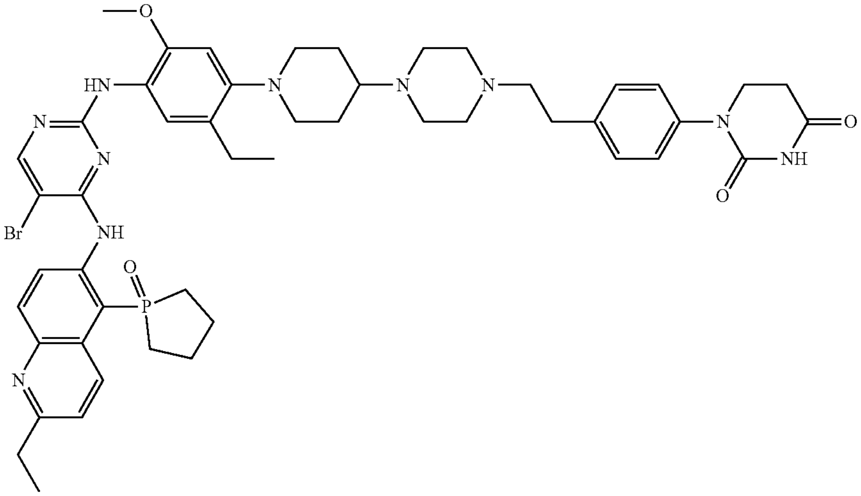

-continued
142
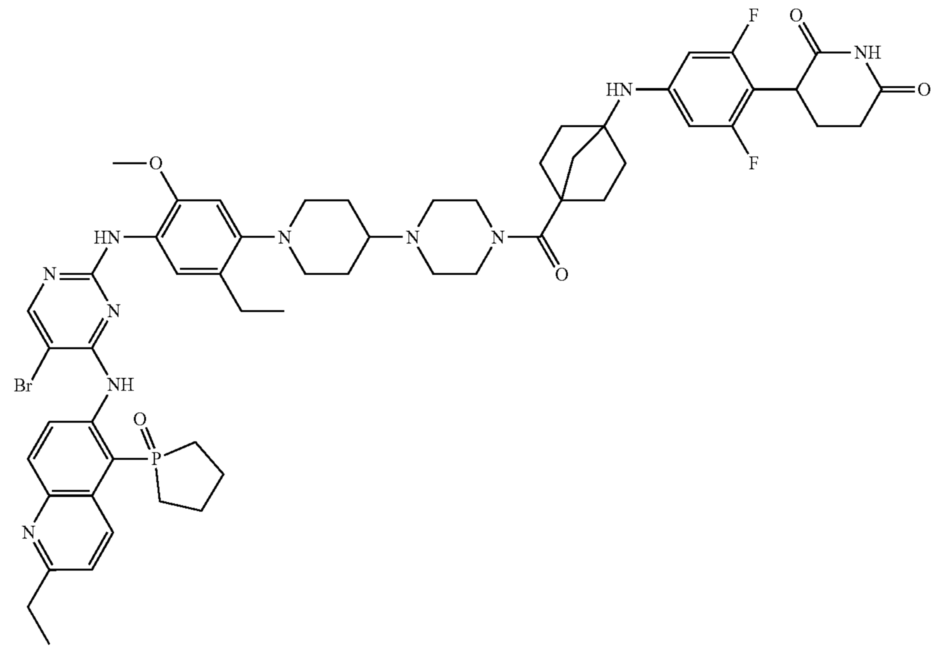
143
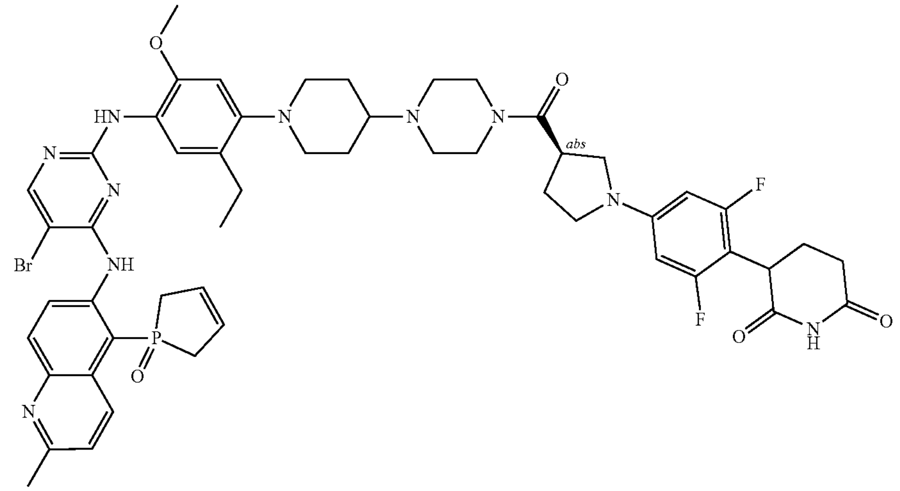
144
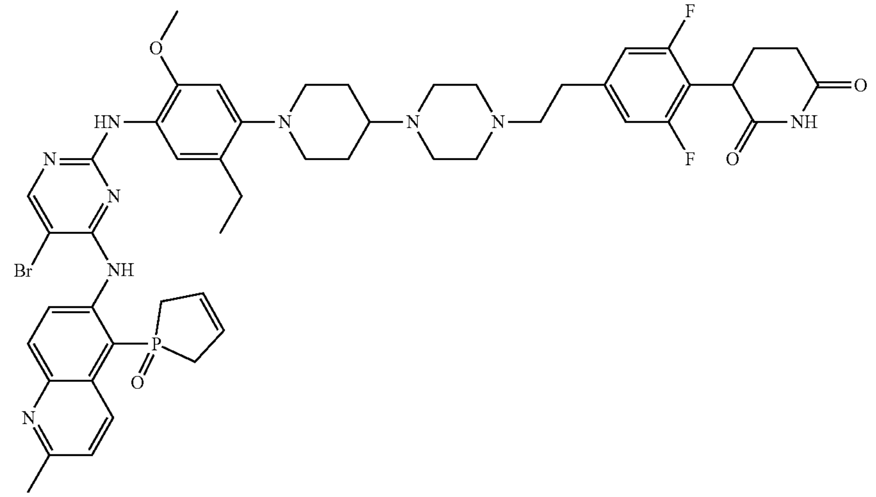

-continued
145
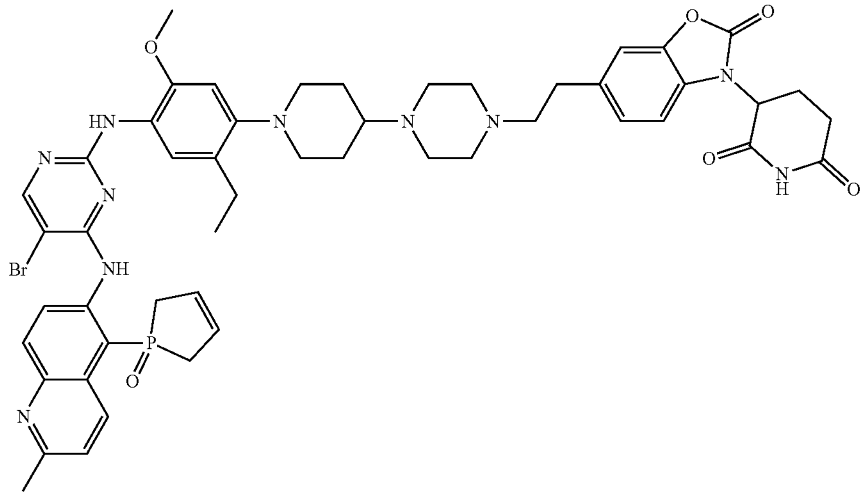
146
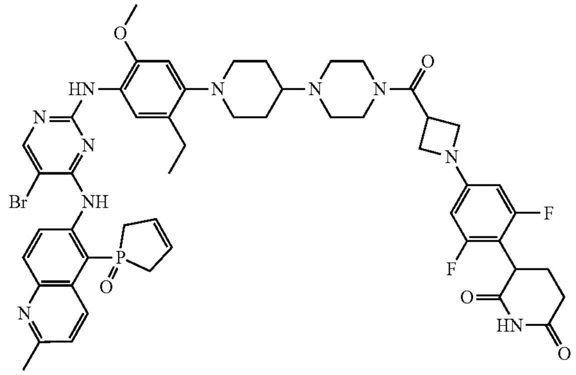
147
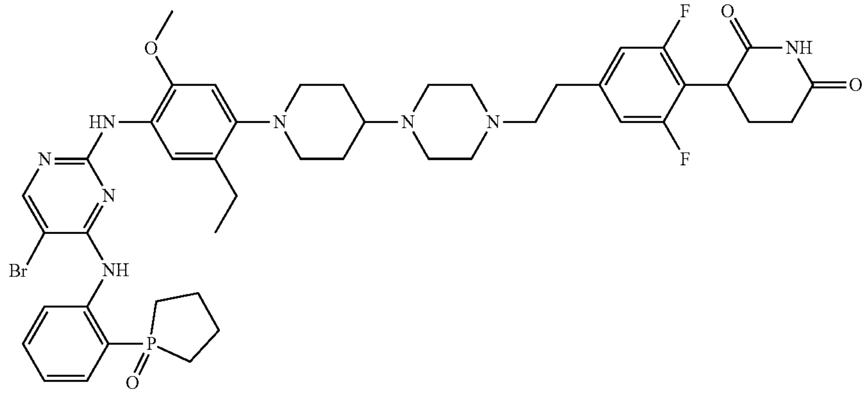
148
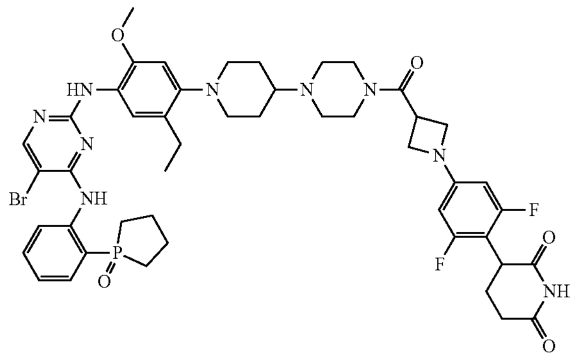

-continued
149
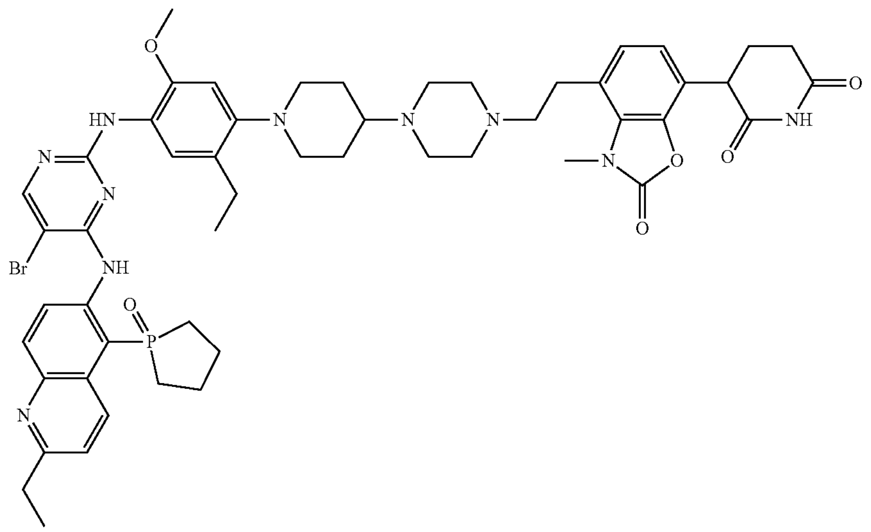
150
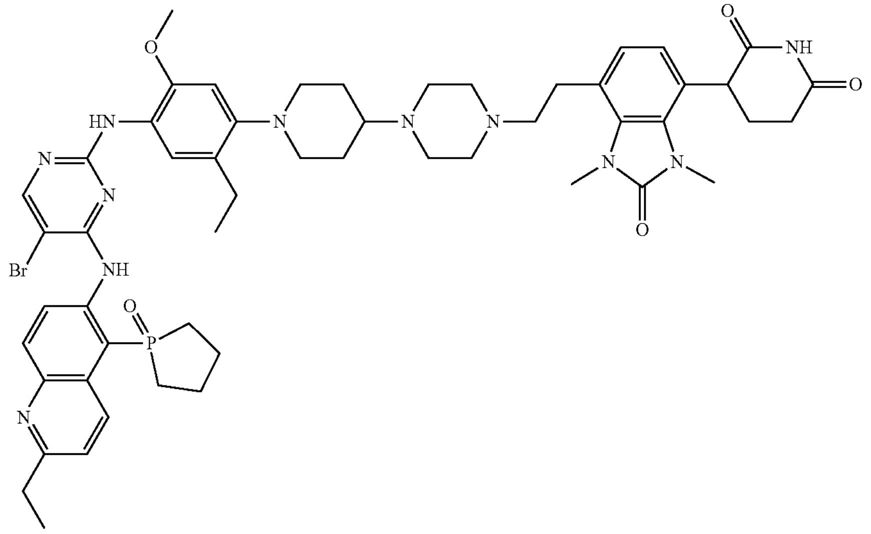
151
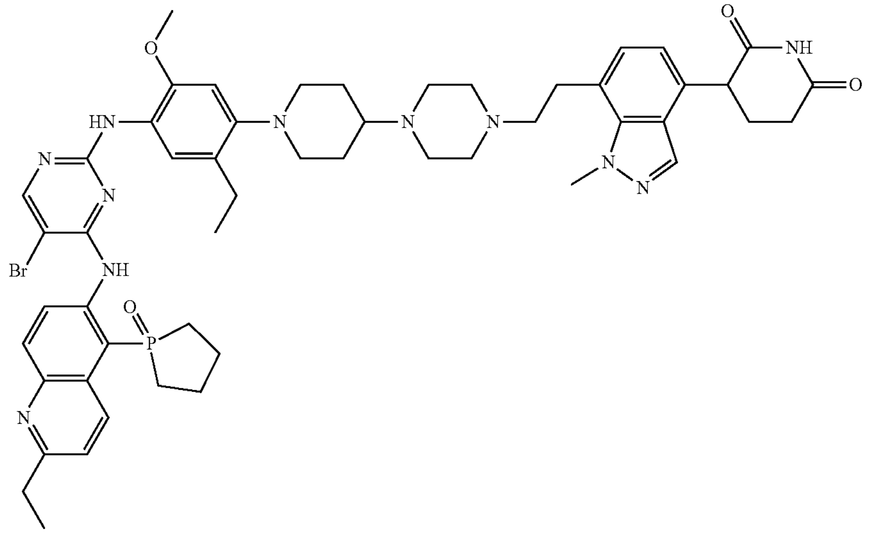

-continued
152
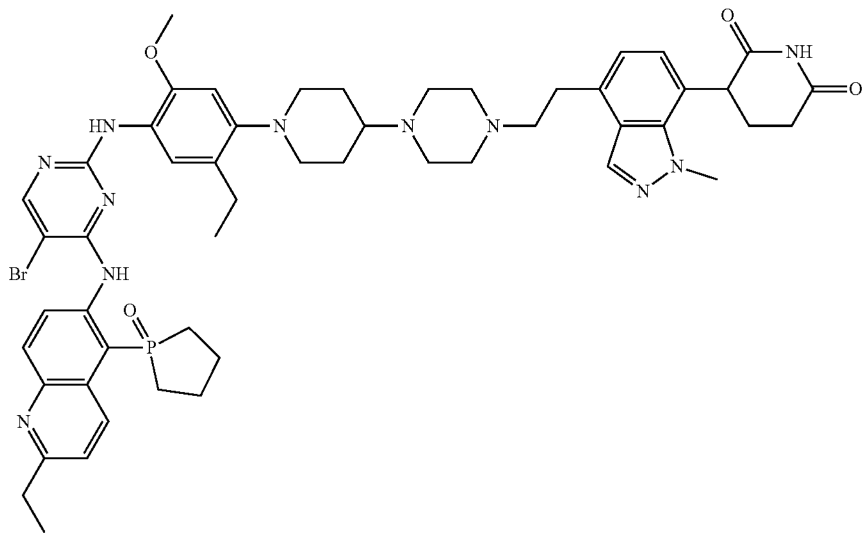
153
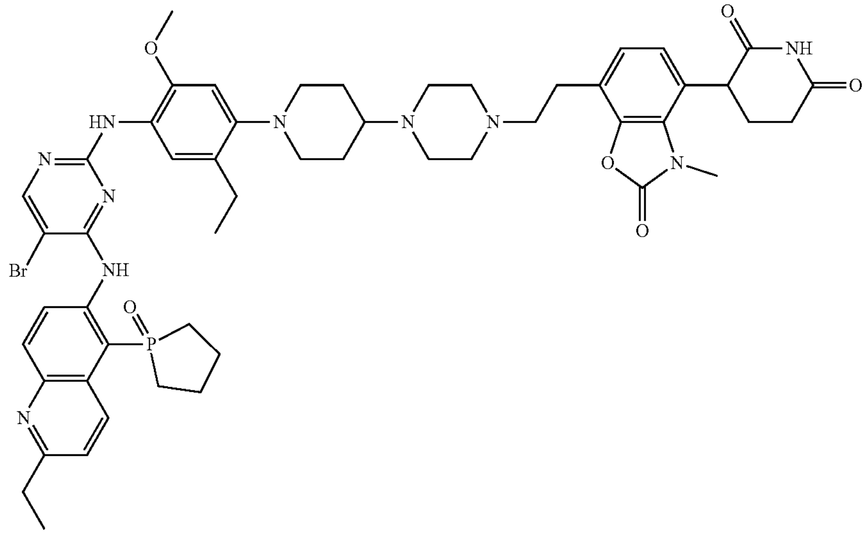
154
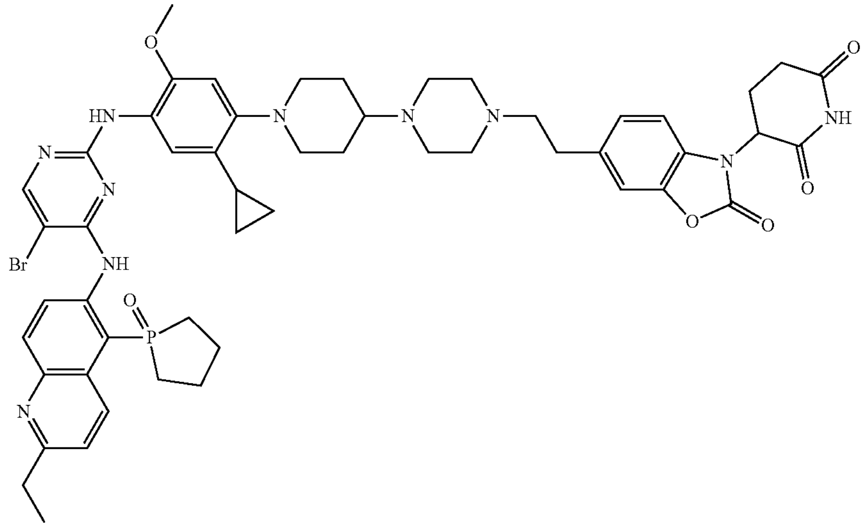

-continued
155
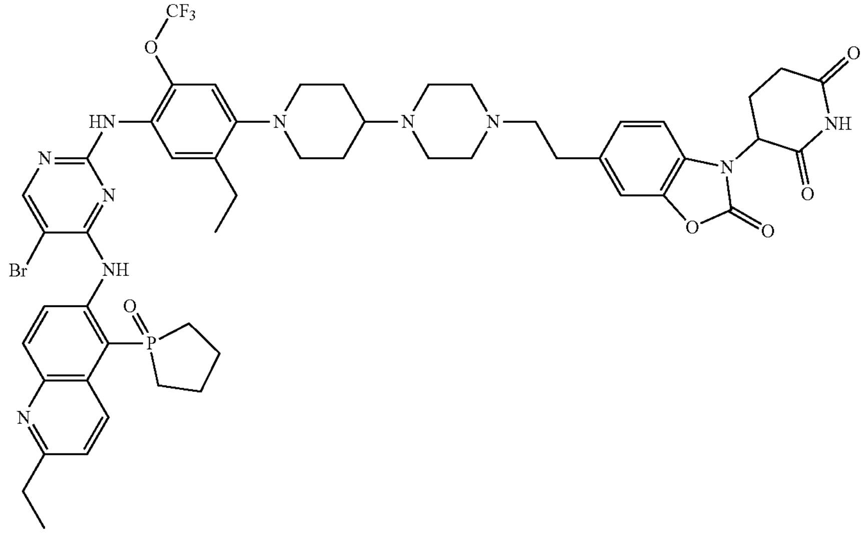
156
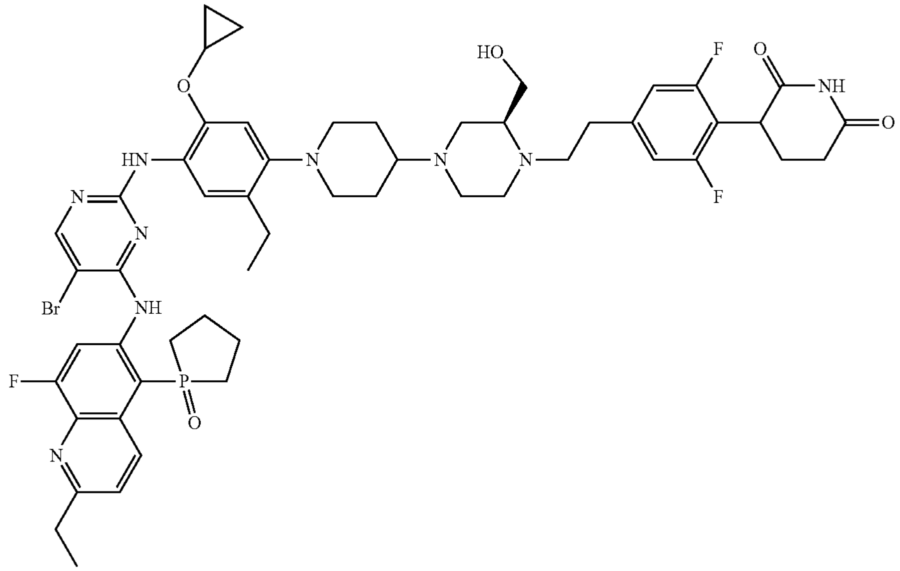
156
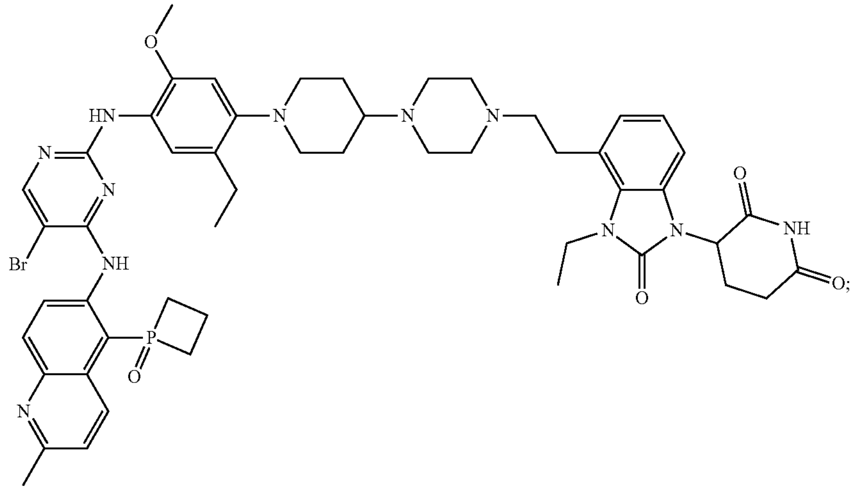
; and

-continued

157

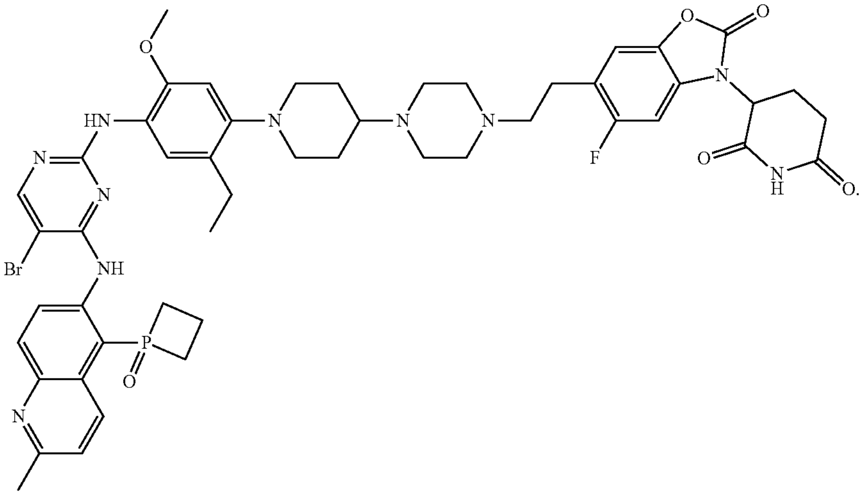

24. A pharmaceutical composition comprising a compound of claim 1 or a pharmaceutically acceptable salt, stereoisomer, tautomer or prodrug thereof, together with a pharmaceutically acceptable excipient.

25. A method of decreasing EGFR activity by inhibition and/or degradation, which comprises administering to an individual the compound according claim 1, or a pharmaceutically acceptable salt thereof, stereoisomer, tautomer or prodrug thereof, optionally wherein the individual has a cancer selected from pancreatic cancer, breast cancer, glioblastoma multiforme, head and neck cancer, and non-small cell lung cancer.

26. A method of treating a disease or disorder in a patient comprising administering to the patient a therapeutically effective amount of the compound of claim 1, or a pharmaceutically acceptable salt thereof, wherein the disease or disorder is associated with inhibition of EGFR, optionally wherein the disease is selected from cancer, pancreatic cancer, breast cancer, glioblastoma multiforme, head and neck cancer, or non-small cell lung cancer.

* * * * *